(12) United States Patent
Bartkovitz et al.

(10) Patent No.: US 8,354,444 B2
(45) Date of Patent: Jan. 15, 2013

(54) SUBSTITUTED PYRROLIDINE-2-CARBOXAMIDES

(75) Inventors: David Joseph Bartkovitz, Nutley, NJ (US); Xin-Jie Chu, Livingston, NJ (US); Qingjie Ding, Bridgewater, NJ (US); Nan Jiang, Pine Brook, NJ (US); Jin-Jun Liu, Warren Township, NJ (US); Tina Morgan Ross, Royersford, PA (US); Jing Zhang, Parsippany, NJ (US); Zhuming Zhang, Hillsborough, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 261 days.

(21) Appl. No.: 12/702,402

(22) Filed: Feb. 9, 2010

(65) Prior Publication Data
US 2010/0152190 A1    Jun. 17, 2010

Related U.S. Application Data

(63) Continuation-in-part of application No. 12/556,656, filed on Sep. 10, 2009.

(60) Provisional application No. 61/225,633, filed on Jul. 15, 2009, provisional application No. 61/097,884, filed on Sep. 18, 2008.

(51) Int. Cl.
*A61K 31/40* (2006.01)
*C07D 207/04* (2006.01)

(52) U.S. Cl. ......... 514/423; 548/530; 548/537; 514/408

(58) Field of Classification Search .............. 548/530, 548/537; 514/408, 423
See application file for complete search history.

(56) References Cited

U.S. PATENT DOCUMENTS

| 8,017,607 | B2 | 9/2011 | Bartkovitz et al. |
| 2010/0075948 | A1 | 3/2010 | Ding et al. |
| 2010/0152190 | A1 | 6/2010 | Bartkovitz et al. |

FOREIGN PATENT DOCUMENTS

| EP | 0641779 | 3/1995 |
| WO | 99/11606 | 3/1999 |
| WO | 00/44335 | 8/2000 |
| WO | 2006091646 A2 | 8/2006 |
| WO | 2006/135323 | 12/2006 |
| WO | 2008/067909 | 6/2008 |
| WO | 2008005268 A1 | 10/2008 |
| WO | 2009/004383 | 1/2009 |
| WO | 2009/146802 | 12/2009 |
| WO | 2009/157860 | 12/2009 |
| WO | 2010/031713 | 3/2010 |

OTHER PUBLICATIONS (Translation of Office Action in CR2011-0099 (Costa Rica) Jul. 22, 2011).
(Written Opinion of International Searching Authority Jun. 5, 2012).
Co-pending U.S. Appl. No. 13/172,916, filed Jun. 30, 2011.
Co-pending U.S. Appl. No. 13/226,523, filed Sep. 7, 2011.
U.S. Appl. No. 61/421,267, filed Dec. 9, 2010—Liu et al.

*Primary Examiner* — Golam M M Shameem
(74) *Attorney, Agent, or Firm* — George W. Johnston; Patricia S. Rocha-Tramaloni

(57) ABSTRACT

There are provided compounds of the formula

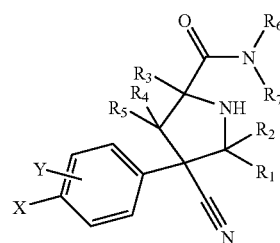

wherein X, Y, $R_1$, $R_2$, $R_3$, $R_3$, $R_4$, $R_5$, $R_6$ and $R_7$ are as described herein
and enantiomers and pharmaceutically acceptable salts and esters thereof. The compounds are useful as anticancer agents.

52 Claims, No Drawings

SUBSTITUTED PYRROLIDINE-2-CARBOXAMIDES

PRIORITY TO RELATED APPLICATION(S)

This application is a continuation-in-part of U.S. application Ser. No. 12/556,656, filed Sep. 10, 2009, which claims the benefit of U.S. Provisional Application No. 61/225,633, filed Jul. 15, 2009 and U.S. Provisional Application No. 61/097,884, filed Sep. 18, 2008. The entire contents of the above-identified applications are hereby incorporated by reference in its entirety.

BACKGROUND OF THE INVENTION p53 is a tumor suppresser protein that plays a central role in protection against development of cancer. It guards cellular integrity and prevents the propagation of permanently damaged clones of cells by the induction of growth arrest or apoptosis. At the molecular level, p53 is a transcription factor that can activate a panel of genes implicated in the regulation of cell cycle and apoptosis. p53 is a potent cell cycle inhibitor which is tightly regulated by MDM2 at the cellular level. MDM2 and p53 form a feedback control loop. MDM2 can bind p53 and inhibit its ability to transactivate p53-regulated genes. In addition, MDM2 mediates the ubiquitin-dependent degradation of p53. p53 can activate the expression of the MDM2 gene, thus raising the cellular level of MDM2 protein. This feedback control loop insures that both MDM2 and p53 are kept at a low level in normal proliferating cells. MDM2 is also a cofactor for E2F, which plays a central role in cell cycle regulation.

The ratio of MDM2 to p53 (E2F) is dysregulated in many cancers. Frequently occurring molecular defects in the p16INK4/p19ARF locus, for instance, have been shown to affect MDM2 protein degradation. Inhibition of MDM2-p53 interaction in tumor cells with wild-type p53 should lead to accumulation of p53, cell cycle arrest and/or apoptosis. MDM2 antagonists, therefore, can offer a novel approach to cancer therapy as single agents or in combination with a broad spectrum of other antitumor therapies. The feasibility of this strategy has been shown by the use of different macromolecular tools for inhibition of MDM2-p53 interaction (e.g. antibodies, antisense oligonucleotides, peptides). MDM2 also binds E2F through a conserved binding region as p53 and activates E2F-dependent transcription of cyclin A, suggesting that MDM2 antagonists might have effects in p53 mutant cells.

SUMMARY OF THE INVENTION

The present invention relates to pyrrolidine-2-carboxamide derivatives I which act as antagonists of mdm2 interactions and hence are useful as potent and selective anticancer agents. The present compounds are of the general formula I

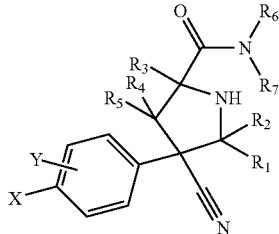

wherein X, Y, $R_1$, $R_2$, $R_3$, $R_3$, $R_4$, $R_5$, $R_6$ and $R_7$ are as described herein
and enantiomers and pharmaceutically acceptable salts and esters thereof.

DETAILED DESCRIPTION OF THE INVENTION

There are provided compounds of the formula

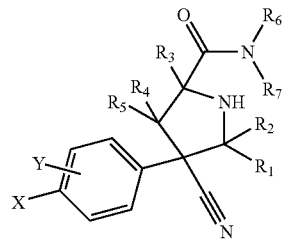

I wherein
X is selected from the group consisting of H, F, Cl, Br, I, cyano, nitro, ethynyl, cyclopropyl, methyl, ethyl, isopropyl, vinyl and methoxy, Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, hetereoaryl, hetereocycle, COOR', OCOR', CONR'R", NR'COR", NR"SO$_2$R', SO$_2$NR'R" and NR'R" wherein R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, hetereoaryl, substituted hetereoaryl, hetereocycle, or substituted hetereocycle.

and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, one of $R_1$ and $R_2$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen or lower alkyl, $R_3$ is H or lower alkyl, one of $R_4$ and $R_5$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, $R_6$ and $R_7$ are selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R", $(CH_2)_n$—SO$_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$—OR', $(CH_2CH_2O)_m$—$(CH_2)_n$—NR'R", $(CH_2CH_2O)_m$—$(CH_2)_n$—NR'COR", $(CH_2CH_2O)_m$—$(CH_2)_n$—NR'SO$_2$R", $(CH_2CH_2O)_m$—$(CH_2)_n$—COOH, $(CH_2CH_2O)_m$—$(CH_2)_n$—COOR', $(CH_2CH_2O)_m$—$(CH_2)_n$—CONR'R", $(CH_2CH_2O)_m$—$(CH_2)_n$—SO$_2$R', $(CH_2CH_2O)_m$—$(CH_2)_n$—COR', $(CH_2CH_2O)_m$—$(CH_2)_n$—SONR'R", $(CH_2CH_2O)_m$—

$(CH_2)_n$—$SO_2NR'R''$, $(CH_2)_p$—$(CH_2CH_2O)_m$—$(CH_2)_n$—$R'$, $(CH_2)_p$—$(CH_2CH_2O)_m$—$(CH_2)_n$—OH, $(CH_2)_p$—$(CH_2CH_2O)_m$—$(CH_2)_n$—$OR'$, $(CH_2)_p$—$(CH_2CH_2O)_m$—$(CH_2)_n$—$NR'R''$, $(CH_2)_p$—$(CH_2CH_2O)_m$—$(CH_2)_n$—$NR'COR''$, $(CH_2)_p$—$(CH_2CH_2O)_m$—$(CH_2)_n$—$NR'SO_2R''$, $(CH_2)_p$—$(CH_2CH_2O)_m$—$(CH_2)_n$—COOH, $(CH_2)_p$—$(CH_2CH_2O)_m$—$(CH_2)_n$—$COOR'$, $(CH_2)_p$—$(CH_2CH_2O)_m$—$(CH_2)_n$—$CONR'R''$, $(CH_2)_p$—$(CH_2CH_2O)_m$—$(CH_2)_n$—$SO_2R'$, $(CH_2)_p$—$(CH_2CH_2O)_m$—$(CH_2)_n$—$COR'$, $(CH_2)_p$—$(CH_2CH_2O)_m$—$(CH_2)_n$—$SONR'R''$, $(CH_2)_p$—$(CH_2CH_2O)_m$—$(CH_2)_n$—$SO_2NR'R''$, —$COR'$, —$SOR'$ and $SO_2R'$ wherein R' and R'' are as above, m, n and p are independently 0 to 6 and the pharmaceutically acceptable salts and esters thereof.

Preferred are compounds of formula I having a stereochemical structure as shown as formula II

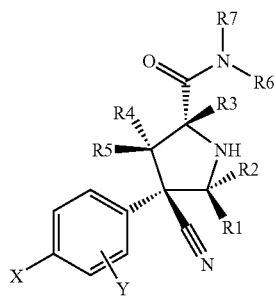

II wherein

X is selected from the group consisting of H, F, Cl, Br, I, cyano, nitro, ethynyl, cyclopropyl, methyl, ethyl, isopropyl, vinyl and methoxy, Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, hetereoaryl, hetereocycle, $COOR'$, $OCOR'$, $CONR'R''$, $NR'COR''$, $NR''SO_2R'$, $SO_2NR'R''$ and $NR'R''$ wherein R' and R'' are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, hetereocycle, or substituted hetereocycle, and wherein R' and R'' may independently link to form a cyclic structure selected from substituted or unsubstituted cycloalkyl, substituted or unsubstituted cycloalkenyl, substituted or unsubstituted heteroaryl or substituted or unsubstituted heterocycle, $R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl, $R_2$ is hydrogen or lower alkyl, $R_3$ is H or lower alkyl, $R_5$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, $R_4$ is hydrogen, $R_6$ and $R_7$ are selected from the group consisting of $(CH_2)_n$—$R'$, $(CH_2)_n$—$NR'R''$, $(CH_2)_n$—$NR'COR''$, $(CH_2)_n$—$NR'SO_2R''$, $(CH_2)_n$—COOH, $(CH_2)_n$—$COOR'$, $(CH_2)_n$—$CONR'R''$, $(CH_2)_n$—$OR'$, $(CH_2)_n$—$SR'$, $(CH_2)_n$—$SOR'$, $(CH_2)_n$—$SO_2R'$, $(CH_2)_n$—$COR'$, $(CH_2)_n$—$SO_3H$, $(CH_2)_n$—$SONR'R''$, $(CH_2)_n$—$SO_2NR'R''$, $(CH_2CH_2O)_m$—$(CH_2)_n$—$R'$, $(CH_2CH_2O)_m$—$(CH_2)_n$—OH, $(CH_2CH_2O)_m$—$(CH_2)_n$—$OR'$, $(CH_2CH_2O)_m$—$(CH_2)_n$—$NR'R''$, $(CH_2CH_2O)_m$—$(CH_2)_n$—$NR'COR''$, $(CH_2CH_2O)_m$—$(CH_2)_n$—$NR'SO_2R''$, $(CH_2CH_2O)_m$—$(CH_2)_n$—COOH, $(CH_2CH_2O)_m$—$(CH_2)_n$—$COOR'$, $(CH_2CH_2O)_m$—$(CH_2)_n$—$CONR'R''$, $(CH_2CH_2O)_m$—$(CH_2)_n$—$SO_2R'$, $(CH_2CH_2O)_m$—$(CH_2)_n$—$COR'$, $(CH_2CH_2O)_m$—$(CH_2)_n$—$SONR'R''$, $(CH_2CH_2O)_m$—$(CH_2)_n$—$SO_2NR'R''$, $(CH_2)_p$—$(CH_2CH_2O)_m$—$(CH_2)_n$—$R'$, $(CH_2)_p$—$(CH_2CH_2O)_m$—$(CH_2)_n$—OH, $(CH_2)_p$—$(CH_2CH_2O)_m$—$(CH_2)_n$—$OR'$, $(CH_2)_p$—$(CH_2CH_2O)_m$—$(CH_2)_n$—$NR'R''$, $(CH_2)_p$—$(CH_2CH_2O)_m$—$(CH_2)_n$—$NR'COR''$, $(CH_2)_p$—$(CH_2CH_2O)_m$—$(CH_2)_n$—$NR'SO_2R''$, $(CH_2)_p$—$(CH_2CH_2O)_m$—$(CH_2)_n$—COOH, $(CH_2)_p$—$(CH_2CH_2O)_m$—$(CH_2)_n$—$COOR'$, $(CH_2)_p(CH_2CH_2O)_m$—$(CH_2)_n$—$CONR'R''$, $(CH_2)_p$—$(CH_2CH_2O)_m$—$(CH_2)_n$—$SO_2R'$, $(CH_2)_p$—$(CH_2CH_2O)_m$—$(CH_2)_n$—$COR'$, $(CH_2)_p$—$(CH_2CH_2O)_m$—$(CH_2)_n$—$SONR'R''$, $(CH_2)_p$—$(CH_2CH_2O)_m$—$(CH_2)_n$—$SO_2NR'R''$, —$COR'$, —$SOR'$ and $SO_2R'$ wherein R' and R'' are as above, m, n, and p are independently 0 to 6 and the pharmaceutically acceptable salts and esters thereof.

Especially preferred are compounds of formula II wherein X is F, Cl or Br,

Y is one to two group(s) independently selected from the group consisting of H, F, Cl, Br, I, CN, OH, nitro, lower alkyl, cycloalkyl, lower alkoxy, lower alkenyl, lower cycloalkenyl and lower alkynyl, $R_1$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, $R_2$ is hydrogen, $R_3$ is H, $R_5$ is selected from the group consisting of aryl, substituted aryl, heteroaryl and substituted heteroaryl, $R_4$ is hydrogen, $R_6$ and $R_7$ are selected from the group consisting of $(CH_2)_n$—$R'$, $(CH_2)_n$—$NR'R''$, $(CH_2)_n$—$NR'COR''$, $(CH_2)_n$—$NR'SO_2R''$, $(CH_2)_n$—COOH, $(CH_2)_n$—$COOR'$, $(CH_2)_n$—$CONR'R''$, $(CH_2)_n$—$OR'$, $(CH_2)_n$—$SR'$, $(CH_2)_n$—$SOR'$, $(CH_2)_n$—$SO_2R'$, $(CH_2)_n$—$COR'$, $(CH_2)_n$—$SO_3H$, $(CH_2)_n$—$SONR'R''$, $(CH_2)_n$—$SO_2NR'R''$, $(CH_2CH_2O)_m$—$(CH_2)_n$—$R'$, $(CH_2CH_2O)_m$—$(CH_2)_n$—OH, $(CH_2CH_2O)_m$—$(CH_2)_n$—$OR'$, $(CH_2CH_2O)_m$—$(CH_2)_n$—$NR'R''$, $(CH_2CH_2O)_m$—$(CH_2)_n$—$NR'COR''$, $(CH_2CH_2O)_m$—$(CH_2)_n$—$NR'SO_2R''$, $(CH_2CH_2O)_m$—$(CH_2)_n$—COOH, $(CH_2CH_2O)_m$—$(CH_2)_n$—$COOR'$, $(CH_2CH_2O)_m$—$(CH_2)_n$—$CONR'R''$, $(CH_2CH_2O)_m$—$(CH_2)_n$—$SO_2R'$, $(CH_2CH_2O)_m$—$(CH_2)_n$—$COR'$, $(CH_2CH_2O)_m$—$(CH_2)_n$—$SONR'R''$, $(CH_2)_p$—$(CH_2CH_2O)_m$—$(CH_2)_n$—$SO_2NR'R''$, $(CH_2)_p$—$(CH_2CH_2O)_m$—$(CH_2)_n$—$R'$, $(CH_2)_p$—$(CH_2CH_2O)_m$—$(CH_2)_n$—OH, $(CH_2)_p$—$(CH_2CH_2O)_m$—$(CH_2)_n$—$OR'$, $(CH_2)_p$—$(CH_2CH_2O)_m$—$(CH_2)_n$—$NR'R''$, $(CH_2)_p$—$(CH_2CH_2O)_m$—$(CH_2)_n$—$NR'COR''$, $(CH_2)_p$—$(CH_2CH_2O)_m$—$(CH_2)_n$—$NR'SO_2R''$, $(CH_2)_p$—$(CH_2CH_2O)_m$—$(CH_2)_n$—COOH, $(CH_2)_p$—$(CH_2CH_2O)_m$—$(CH_2)_n$—$COOR'$, $(CH_2)_p$—$(CH_2CH_2O)_m$—$(CH_2)_n$—$CONR'R''$, $(CH_2)_p$—$(CH_2CH_2O)_m$—$(CH_2)_n$—$SO_2R'$, $(CH_2)_p$—$(CH_2CH_2O)_m$—$(CH_2)_n$—$COR'$, $(CH_2)_p$—$(CH_2CH_2O)_m$—$(CH_2)_n$—$SONR'R''$, $(CH_2)_p$—$(CH_2CH_2O)_m$—$(CH_2)_n$—$SO_2NR'R''$, —$COR'$, —$SOR'$ and $SO_2R'$ wherein R' and R" are independently selected from H, lower alkyl, substituted lower alkyl, lower cycloalkyl, substituted lower cycloalkyl, lower alkenyl, substituted lower alkenyl, lower cycloalkenyl, substituted lower cycloalkenyl, aryl, substituted aryl, heteroaryl, substituted heteroaryl, hetereocycle, or substituted hetereocycle, and wherein R' and R" may also independently link to form a cyclic structure selected from substituted or unsubstituted cycloalkyl, substituted or unsubstituted cycloalkenyl, substituted or unsubstituted heteroaryl or substituted or unsubstituted heterocycle, m, n and p are independently 0 to 6 and the pharmaceutically acceptable salts and esters thereof.

Further preferred are compounds of formula II wherein:

X is F, Cl or Br,

Y is a mono-substituting group selected from H or F and $R_1$ is selected from the group consisting of lower alkyl, substituted lower alkyl, lower alkenyl, substituted lower alkenyl, heterocycle, substituted heterocycle, cycloalkyl, substituted cycloalkyl, cycloalkenyl and substituted cycloalkenyl.

Further preferred $R_1$ is a substituted lower alkyl selected from:

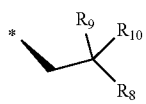

where $R_8$, $R_9$ are both methyl, or linked to form a cyclopropyl, cyclobutyl, cyclopentyl or acyclohexyl group, $R_{10}$ is $(CH_2)_m$—$R_{11}$, m is 0, 1 or 2, $R_{11}$ is selected from hydrogen, hydroxyl, lower alkyl, lower alkoxy, aryl, substituted aryl, hetereoaryl, substituted heteroaryl, heterocycle or substituted heterocycle, $R_2$ is H, $R_3$ is H, $R_5$ is a substituted phenyl selected from:

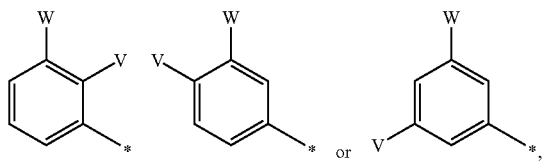

W is F, Cl or Br,

V is H or F, $R_4$ is hydrogen, one of $R_6$ and $R_7$ is hydrogen and the other is $(CH_2)$—R', n is 0 or 1 and R' is selected from aryl, substituted aryl, hetereoaryl, substituted heteroaryl, heterocycle or substituted heterocycle.

Especially preferred are compounds selected from the group consisting of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-morpholin-4-yl-ethyl)-amide, (2R,3R,4R,5S)-3-(3-chloro-phenyl)-4-(4-chloro-phenyl)-4-cyano-5-(2,2-dimethyl-propyl)-pyrrolidine-2-carboxylic acid (2-morpholin-4-yl-ethyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid dimethylamide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide, (2R,3R,4R,5S)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide, rac-(2S,3R,4R,5R)-4-(3-chloro-phenyl)-3-(4-chloro-phenyl)-2-(2,2-dimethyl-propyl)-5-[4-(2-morpholin-4-yl-2-oxo-ethyl)-piperazine-1-carbonyl]-pyrrolidine-3-carbonitrile, rac-(2S,3R,4R,5R)-4-(3-chloro-phenyl)-3-(4-chloro-phenyl)-2-(2,2-dimethyl-propyl)-5-[4-(2-oxo-2-pyrrolidin-1-yl-ethyl)-piperazine-1-carbonyl]-pyrrolidine-3-carbonitrile, rac-(2S,3R,4R,5R)-4-(3-chloro-phenyl)-3-(4-chloro-phenyl)-2-(2,2-dimethyl-propyl)-5-[4-(2-hydroxy-ethyl)-piperazine-1-carbonyl]-pyrrolidine-3-carbonitrile, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (4-hydroxy-butyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-pyrrolidin-1-yl-ethyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-piperazin-1-yl-ethyl)-amide, (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid methyl ester, (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (1-hydroxymethyl-cyclopropylmethyl)-amide, rac-(2R,3R,4R,5S)-3-(3-Chloro-phenyl)-4-(4-chloro-phenyl)-4-cyano-5-(2,2-dimethyl-propyl)-pyrrolidine-2-carboxylic acid (1-hydroxymethyl-cyclobutylmethyl)-amide, rac-(2R,3R,4R,5S)-3-(3-chloro-phenyl)-4-(4-chloro-phenyl)-4-cyano-5-(2,2-dimethyl-propyl)pyrrolidine-2-carboxylic acid (3,3-dimethyl-butyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2,2-dimethyl-propyl)-amide, (2S,3R,4R,5R)-4-(3-chloro-phenyl)-3-(4-chloro-phenyl)-2-(2,2-dimethyl-propyl)-5-((S)-2-hydroxymethyl-pyrrolidine-1-carbonyl)pyrrolidine-3-carbonitrile, rac-(2R,3R,4R,5S)-3-(3-chloro-phenyl)-4-(4-chloro-phenyl)-4-cyano-5-(2,2-dimethyl-propyl)-pyrrolidine-2-carboxylic acid 2-(3,4-dimethoxy-phenyl)ethyl amide, (2S,3S,4S,5R)-3-(3-chloro-phenyl)-4-(4-chloro-phenyl)-4-cyano-5-(2,2-dimethyl-propyl)-pyrrolidine-2-carboxylic acid ((R)-1-hydroxymethyl-3-methyl-butyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-propyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid [2-(cis-2,6-dimethyl-morpholin-4-yl)-ethyl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-cyclopropyl-ethyl)-amide, rac-(3-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-propyl)-carbamic acid tert-butyl ester, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-amino-propyl)-amide,
rac-(2R,3R,4R,5S)-3-(3-chloro-phenyl)-4-(4-chloro-phenyl)-4-cyano-5-(2,2-dimethyl-propyl)-pyrrolidine-2-carboxylic acid [3-(1-acetyl-piperidin-4-ylamino)-propyl]-amide,
rac-(2R,3R,4R,5S)-3-(3-chloro-phenyl)-4-(4-chloro-phenyl)-4-cyano-5-isobutyl-pyrrolidine-2-carboxylic acid (3-hydroxy-propyl)-amide,
rac-(2R,3R,4R,5R)-5-(3-chloro-phenyl)-4-(4-chloro-phenyl)-4-cyano-3-(2,2-dimethyl-propyl)-pyrrolidine-2-carboxylic acid (3-hydroxy-propyl)-amide,
rac-(2R,3R,4R,5S)-3-(3-chloro-phenyl)-4-(4-chloro-phenyl)-4-cyano-5-(2,2-dimethyl-propyl)-2-methyl-pyrrolidine-2-carboxylic acid (3-hydroxy-propyl)-amide,
rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid ((S)-3,4-dihydroxy-butyl)-amide,
rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (2-hydroxy-1,1-dimethyl-ethyl)-amide,
rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (3-hydroxy-2,2-dimethyl-propyl)-amide,
rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid [2-(2-hydroxy-ethoxy)-ethyl]-amide,
rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (2-acetylamino-ethyl)-amide,
rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (3-imidazol-1-yl-propyl)-amide,
rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((R)-4-hydroxy-3-methyl-butyl)-amide,
rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid cyclopropylmethoxy-amide,
rac-(2R,3R,4R,5S)-3,5-bis-(3-chloro-phenyl)-4-(4-chloro-phenyl)-4-cyano-pyrrolidine-2-carboxylic acid [2-((S)-2,2-dimethyl-[1,3]dioxolan-4-yl)-ethyl]-amide,
rac-(2R,3R,4R,5S)-3,5-bis-(3-chloro-phenyl)-4-(4-chloro-phenyl)-4-cyano-pyrrolidine-2-carboxylic acid ((S)-3,4-dihydroxy-butyl)-amide,
rac-(2R,3R,4R,5S)-3-(3-chloro-phenyl)-4-(4-chloro-phenyl)-4-cyano-5-(1-ethyl-propyl)-pyrrolidine-2-carboxylic acid ((S)-3,4-dihydroxy-butyl)-amide,
rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide,
(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide,
rac-(2R,3R,4R,5S)-3-(3-chloro-phenyl)-4-(4-chloro-phenyl)-4-cyano-5-isobutyl-pyrrolidine-2-carboxylic acid ((S)-3,4-dihydroxy-butyl)-amide,
rac-(2R,3R,4R,5R)-3-(3-chloro-phenyl)-4-(4-chloro-phenyl)-4-cyano-5-isobutyl-pyrrolidine-2-carboxylic acid ((S)-3,4-dihydroxy-butyl)-amide,
rac-(2R,3R,4R,5R)-3-(3-chloro-phenyl)-4-(4-chloro-phenyl)-4-cyano-5-(1-ethyl-propyl)-pyrrolidine-2-carboxylic acid ((S)-3,4-dihydroxy-butyl)-amide,
rac-(2R,3R,4R)-3-(3-chloro-phenyl)-4-(4-chloro-phenyl)-4-cyano-5,5-diethyl-pyrrolidine-2-carboxylic acid ((S)-3,4-dihydroxy-butyl)-amide,
rac-(2R,3R,4R,5S)-3-(3-chloro-phenyl)-4-(4-chloro-phenyl)-4-cyano-5-isopropyl-pyrrolidine-2-carboxylic acid ((S)-3,4-dihydroxy-butyl)-amide,
rac-(2R,3R,4R,5S)-3-(3-chloro-phenyl)-4-(4-chloro-phenyl)-4-cyano-5-cyclohexyl-pyrrolidine-2-carboxylic acid ((S)-3,4-dihydroxy-butyl)-amide,
rac-(2R,3S,4R,5S)-5-tert-butyl-3-(3-chloro-2-fluoro-phenyl)-4-(4-chloro-phenyl)-4-cyano-pyrrolidine-2-carboxylic acid ((S)-3,4-dihydroxy-butyl)-amide,
rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide,
(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide,
rac-(2S,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide,
rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid ((S)-3,4-dihydroxy-butyl)-amide,
rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid ((S)-3,4-dihydroxy-butyl)-amide rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide,
(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide,
rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid ((S)-3,4-dihydroxy-butyl)-amide,
rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid ((S)-3,4-dihydroxy-butyl)-amide,
rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid ((S)-3,4-dihydroxy-butyl)-amide,
rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide,
(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide,
rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide,
(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide,
rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide
(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid ((S)-3,4-dihydroxy-butyl)-amide, rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid ((S)-3,4-dihydroxy-butyl)-amide, rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, (2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, (2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((R)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((R)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide, (2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-dimethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid ((S)-3,4-dihydroxy-butyl)-amide, rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3S,4R,5S)-4-(4-chloro-2-fluoro-phenyl)-3-[5-chloro-2-(2-hydroxy-ethoxy)-phenyl]-4-cyano-5-(2,2-dimethyl-propyl)-pyrrolidine-2-carboxylic acid ((S)-3,4-dihydroxy-butyl)-amide, rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid ((S)-3,4-dihydroxy-butyl)-amide, rac(2R,3R,4R,5S)-3-(3-chloro-phenyl)-4-(4-chloro-phenyl)-4-cyano-5-(2,2-dimethyl-propyl)-pyrrolidine-2-carboxylic acid (quinolin-3-ylmethyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-hydroxy-benzylamide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-ethyl-butyl)-amide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-carboxylic acid tert-butyl ester, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid piperidin-4-ylamide trifluoroacetic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methanesulfonylpiperidin-4-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-carbonyl-piperidin-4-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-benzoyl-piperidin-4-yl)-amide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-carboxylic acid isopropylamide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide, chiral 2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide, rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((R)-1-oxiranylmethoxy)-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((R)-3-amino-2-hydroxy-propoxy)-2-methyl-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-{2-[(R)-2-hydroxy-3-(3-hydroxy-propylamino)-propoxy]-2-methyl-propyl}-1H-pyrazol-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-{2-[(R)-2-hydroxy-3-(2-hydroxy-1-hydroxymethyl-ethylamino)-propoxy]-2-methyl-propyl}-1H-pyrazol-3-yl)-amide, rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((S)-1-oxiranylmethoxy)-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-amino-2-hydroxy-propoxy)-2-methyl-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-2,3-dihydroxy-propoxy)-2-methyl-propyl]-1H-pyrazol-3-yl}-amide, of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl)-amide, rac-{(S)-3-[2-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-1,1-dimethyl-ethoxy]-2-hydroxy-propylamino}-acetic acid, rac-(2R,3S,4R,5S)-3-(3-chloro-2-fluoro-phenyl)-4-(4-chloro-2-fluoro-phenyl)-4-cyano-5-(2,2-dimethyl-propyl) pyrrolidine-2-carboxylic acid {1-[2-((S)-2-hydroxy-3-methylamino-propoxy)-2-methyl-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((R)-3-dimethylamino-2-hydroxy-propoxy)-2-methyl-propyl]-1H-pyrazol-3-yl}-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,3-dihydroxy-propyl)-1H-pyrazol-3-yl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-(2-hydroxy-ethyl)-1H-pyrazol-3-yl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((S)-2,3-dihydroxy-propyl)-amide, rac-(2S,3S,4S,5R)-3-(3-chloro-phenyl)-4-(4-chloro-phenyl)-4-cyano-5-(2,2-dimethyl-propyl)-pyrrolidine-2-carboxylic acid ((S)-2,3-dihydroxy-propyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,2-dimethyl-[1,3]dioxolan-4-ylmethyl)-1H-pyrazol-3-yl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid 2-trifluoromethyl-benzylamide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-(2-oxo-pyrrolidin-1-yl)-benzylamide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (tetrahydro-pyran-4-ylmethyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-2-hydroxymethyl-propyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [2-(2-amino-ethoxy)-ethyl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methanesulfonyl-propyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-methanesulfonyl-ethyl)-amide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-cyclohexylamino-1-carboxylic acid tert-butyl ester, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoro acetic acid salt, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-N-methanesulfonamide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-N-methanesulfonamide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-(1,1-dioxo)-2-isothiazolidine, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-urea, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid N-[1-(2-hydroxy ethyl)-piperidin-4-yl]amide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-sulfonic acid amide, rac 3-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetic acid, rac 3-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N,N-bis-(2-methoxy-ethyl)-acetamide, rac 3-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N,N-bis-(2-hydroxy-ethyl)-acetamide, rac 3-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N-(3-methoxy-propyl)-acetamide, rac 2-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetamide, rac (2S,3R,4S,5R)-4-(3-chloro-2-fluoro-phenyl)-3-(4-chloro-2-fluoro-phenyl)-2-(2,2-dimethyl-propyl)-5-[4-(2-morpholin-4-yl-2-oxo-ethyl)-piperazine-1-carbonyl]-pyrrolidine-3-carbonitrile, rac 2-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N-[2-((S)-2,2-dimethyl-[1,3]dioxolan-4-yl)-ethyl]-acetamide, rac 2-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N—((S)-3,4-dihydroxy-butyl)-acetamide, rac {1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid methyl ester, rac {1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid hydrochloride salt, rac 2-{1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetamide, rac 2-{1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-N,N-bis-(2-hydroxy-ethyl)-acetamide, rac 2-{1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-N-(2-hydroxy-ethyl)-N-methyl-acetamide, rac 2-{1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-N-(2-hydroxy-propyl)-acetamide, rac {[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-acetic acid tert-butyl ester, rac {[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-acetic aid trifluoro acetic acid salt, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid carbamoylmethyl-amide, {[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-acetic aid trifluoro acetic acid salt, rac 3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-carbamoyl-phenyl)-amide, rac 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester, rac 3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-hydroxymethyl-phenyl)-amide, rac (3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-propyl)-carbamic acid tert-butyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-amino-propyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-(aminosulfonyl-amino)-propyl)-amide, rac 2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-carbamoyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide, rac 2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac 2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-cyano-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-hydroxy-2-methyl-propyl)-amide, rac 3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid 2-hydroxy-2-methyl-propyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-methanesulfonylamino-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1H-tetrazol-5-ylmethyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-ureado-propyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-methylsulfanyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-methanesulfonyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-methanesulfinyl-phenyl)-amide, 3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-carbamoyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-amino-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide, rac 2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiazole-4-carboxylic acid ethyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1,3-dioxo-2,3-dihydro-1H-isoindol-5-yl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methylsulfanyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide, 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester, 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, 4-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylamino-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-trifluoro-methanesulfonylamino-phenyl)-amide, rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [3-(1-methyl-1H-tetrazol-5-yl)-phenyl]-amide, rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [3-(2-methyl-1H-tetrazol-5-yl)-phenyl]-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide, rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [4-(2-methyl-1H-tetrazol-5-yl)-phenyl]-amide, rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [4-(1-methyl-1H-tetrazol-5-yl)-phenyl]-amide, rac 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid ethyl ester, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-3-chloro-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-chloro-4-(1H-tetrazol-5-yl)-phenyl]-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-fluoro-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-fluoro-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-chloro-phenyl)-amide, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid tert-butyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-methoxy-pyridin-3-yl)-amide, rac 3-({[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid methyl ester, rac 4-({[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid methyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid methyl ester, rac 3-({[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid, rac 4-({[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid, rac 5-bromo-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid methyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methyl-benzoic acid methyl ester, rac 2-Chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-trifluoromethyl-benzoic acid methyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methyl-benzoic acid, rac 2-Chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2H-[1,2,4]triazol-3-yl)-phenyl]-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(5-oxo-2,5-dihydro-1H-[1,2,4]thiazol-3-yl)-phenyl]-amide, rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide, rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2-methoxycarbonyl-2-methyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid ((S)-3,4-dihydroxy-butyl)-amide, rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2-ethyl-2-hydroxymethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(1-hydroxymethyl-cyclohexylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-[4-(2-hydroxy-ethoxy)-2,2-dimethyl-butyl]-pyrrolidine-2-carboxylic acid ((S)-3,4-dihydroxy-butyl)-amide, rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-5-(4-acetylamino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(4-methanesulfonylamino-2,2-dimethyl-butyl)-pyrrolidine-2-carboxylic acid ((S)-3,4-dihydroxy-butyl)-amide, rac-(2R,3S,4R,5S)-5-(4-benzoylamino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid ((S)-3,4-dihydroxy-butyl)-amide, rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-5-[2-(1-benzyl-piperidin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-[2-methyl-2-(tetrahydro-pyran-4-yl)-propyl]-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide, (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide, rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide, (2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide, rac-(2S,3R,4S,5R)-4-(3-chloro-2-fluoro-phenyl)-3-(4-chloro-2-fluoro-phenyl)-2-(2,2-dimethyl-propyl)-5-(3-hydroxy-azetidine-1-carbonyl)-pyrrolidine-3-carbonitrile, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1-pyrazol-3-yl]-amide, (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1-pyrazol-3-yl]-amide, rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide, (2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid amide, rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-nicotinic acid methyl ester, of rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-N-(2-hydroxy-1,1-dimethyl-ethyl)-nicotinamide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-acetylamino-pyridin-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [5-((S)-1,2-dihydroxy-ethyl)-pyrazin-2-yl]-amide, rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid (1-methyl-2-oxo-1,2-dihydro-pyridin-4-yl)-amide, rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid methyl ester, rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid, rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-chloro-pyridazin-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-methyl-pyridin-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide, rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid methyl ester, rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid, 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-methoxy-pyridin-4-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-hydroxy-pyridin-4-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetyl-phenyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-bromo-acetyl)-phenyl]-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-dimethylamino-acetyl)-phenyl]-amide, rac-(5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-4H-[1,2,4]triazol-3-yl)-acetic acid, rac-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-acetic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1H-imidazol-4-ylmethyl)-amide, rac-(2S,3R,4S,5R)-4-(3-chloro-2-fluoro-phenyl)-3-(4-chloro-2-fluoro-phenyl)-2-(2,2-dimethyl-propyl)-5-(2-oxa-6-aza-spiro[3.3]heptane-6-carbonyl)-pyrrolidine-3-carbonitrile, rac-1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-azetidine-3-carboxylic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-[1,2,3]triazol-1-yl-ethyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-carbamoylmethyl-1H-pyrazol-3-yl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-(2-hydroxy-2-methyl-propyl)-1H-pyrazol-3-yl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methanesulfonylamino-propyl)-amide, chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide, rac-1-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-cyclopropane carboxylic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(4-hydroxy-piperidin-4-ylmethyl)-1H-pyrazol-3-yl]-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-acetyl-thiophen-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-carbamoyl-thiophen-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-((S)-3-dimethylamino-2-hydroxy-propyl)-1H-pyrazol-3-yl]-amide, rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid, rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester, rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac-4-{[(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester, rac-4-{[(2R,3R,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid methyl ester, of rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid, rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid methyl ester, rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid, rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid methyl ester, rac-[4-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-ylmethyl)-4-hydroxy-piperidin-1-yl]-acetic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (5-iodo-pyridin-2-yl)-amide, rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-ethylcarbamoyl-phenyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-trifluoromethyl-phenyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-acetyl)-phenyl]-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylaminocarbonyl-phenyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-ethyl)-2-oxo-1,2-dihydro-pyridin-4-yl]-amide, 4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid, 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid, chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid, chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid methyl ester, 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid methyl ester, 2-((2R,3S,4R,5S)-3-(3-chloro-2-fluorophenyl)-4-(4-chloro-2-fluorophenyl)-4-cyano-5-neopentylpyrrolidine-2-carboxamido)thiazole-5-carboxylic acid triethylamine salt, rac 6-((2R,3S,4R,5S)-3-(3-chloro-2-fluorophenyl)-4-(4-chloro-2-fluorophenyl)-4-cyano-5-neopentylpyrrolidine-2-carboxamido)-2-naphthoic acid, rac 6-((2R,3S,4R,5S)-3-(3-chloro-2-fluorophenyl)-4-(4-chloro-2-fluorophenyl)-4-cyano-5-neopentylpyrrolidine-2-carboxamido)-2-naphthoic acid methyl ester, rac methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methylbenzoate, rac 14-((2R,3S,4R,5S)-3-(3-chloro-2-fluorophenyl)-4-(4-chloro-2-fluorophenyl)-4-cyano-5-neopentylpyrrolidine-2-carboxamido)-3-methylbenzoic acid, rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-3,5-dimethyl-phenyl)-amide, rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,6-dimethyl-benzoic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-methoxy-benzoic acid, rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-trifluoromethyl-benzoic acid, rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-bromo-2-methoxy-phenyl)-amide, rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylcarbamoyl-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-methyl-benzoic acid, rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,5-dimethyl-benzoic acid, rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-fluoro-benzoic acid, rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (6-iodo-pyridin-3-yl)-amide, 2-Chloro-4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-benzoic acid methyl ester, chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid, chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid ethyl ester, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid methyl ester, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid methyl ester, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid methyl ester, rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid, chiral 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid methyl ester, chiral 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid, chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid ethyl ester, chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid, rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-ethoxy-benzoic acid, chiral (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-hydrazinocarbonyl-phenyl)-amide, chiral [2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-ethyl]-carbamic acid tent-butyl ester, chiral (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-amino-ethyl)-phenyl]-amide, chiral 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyrazine-2-carboxylic acid, chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-methoxybenzoic acid, chiral-4-({[(2S,3R,4S,5R)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid, chiral methyl 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoate, chiral 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoic acid, chiral-4-(((2S,3R,4S,5R)-3-(3-chloro-2-fluorophenyl)-4-(4-chloro-2-fluorophenyl)-4-cyano-5-neopentylpyrrolidine-2-carboxamido)methyl)-2-fluorobenzoic acid, chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-fluorobenzoic acid, chiral (2R,3S,4R,5S)-3-(3-chloro-2-fluorophenyl)-4-(4-chloro-2-fluorophenyl)-4-cyano-N-(2-morpholinopyrimidin-5-yl)-5-neopentylpyrrolidine-2-carboxamide, chiral (2R,3S,4R,5S)-3-(3-chloro-2-fluorophenyl)-4-(4-chloro-2-fluorophenyl)-4-cyano-5-neopentyl-N-(pyrimidin-5-yl)pyrrolidine-2-carboxamide, chiral (2S,3R,4S,5R)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide, chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylate, chiral-5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylic acid, chiral-methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylate, chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylic acid, chiral-methyl 4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoate, chiral-4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoic acid, chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylate, chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylic acid, chiral-(2R,3S,4R,5S)—N-(benzo[d]oxazol-5-yl)-3-(3-chloro-2-fluorophenyl)-4-(4-chloro-2-fluorophenyl)-4-cyano-5-neopentylpyrrolidine-2-carboxamide, rac-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-benzyl)-carbamic acid tert-butyl ester, rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-aminomethyl-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(methanesulfonylamino-methyl)-phenyl]-amide, 1-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid ethyl ester, 1-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid, rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide, rac-5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-pyrrolidin-1-yl-benzoic acid, rac-4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-4-methyl-piperidine-1-carboxylic acid tert-butyl ester, rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-methyl-piperidin-4-yl)-amide, rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (1-methanesulfonyl-4-methyl-piperidin-4-yl)-amide, methyl 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylate, 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylic acid, chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid, chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid ethyl ester, chiral (R)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid, chiral (S)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid, chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester, chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester, chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid, chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid, chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid, rac (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (5-iodo-pyridin-2-yl)-amide, 2-chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, 6-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-2-ylamide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-4-ylamide, 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-3-ylamide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-3,5-dimethyl-phenyl)-amide, 4-{[(2R,3S,4R,5S)-4-(4-Chloro-2-fluoro-phenyl)-3-(3-chloro-2 fluoro-phenyl)-4-cyano-5-(2,2-dimethyl-propyl)-pyrrolidine-2-carbonyl]-amino}-2-fluoro-benzoic acid tert-butyl ester, 4-{[(2R,3S,4R,5S)-4-(4-Chloro-2-fluoro-phenyl)-3-(3-chloro-2 fluoro-phenyl)-4-cyano-5-(2,2-dimethyl-propyl)-pyrrolidine-2-carbonyl]-amino}-2-fluoro-benzoic acid, 4-{[(2R,3S,4R,5S)-4-(4-Chloro-2-fluoro-phenyl)-3-(3-chloro-2 fluoro-phenyl)-4-cyano-5-(2,2-dimethyl-propyl)-pyrrolidine-2-carbonyl]-amino}-3-fluoro-benzoic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-trifluoromethyl-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-2-trifluoromethoxy-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-trifluoromethoxy-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-trifluoromethoxy-benzoic acid, 6-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid, 6-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid methyl ester, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (6-iodo-pyridin-3-yl)-amide, 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid methyl ester, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (6-carbamoyl-naphthalen-2-yl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-chloro-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-trifluoromethyl-phenyl)-amide, 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-fluoro-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-fluoro-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-methoxy-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,5-difluoro-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,5-difluoro-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (3,5-difluoro-4-iodo-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,6-difluoro-benzoic acid, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-hydroxy-benzoic acid, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-methoxy-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-trifluoromethoxy-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-fluoro-phenyl)-amide, (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-chloro-phenyl)-amide, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-fluoro-5-methoxy-benzoic acid methyl ester, 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-fluoro-5-methoxy-benzoic acid, 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-4-methyl-pentanoic acid, chiral 2-(4-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid methyl ester, chiral 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-methyl-1-methylcarbamoyl-ethyl)-phenyl]-amide, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {4-[1-(3-hydroxy-propylcarbamoyl)-1-methyl-ethyl]-phenyl}amide and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-carbamoyl-1-methyl-ethyl)-phenyl]-amide.

In the specification where indicated the various groups may be substituted by 1-5 or, preferably, 1-3 substituents independently selected from the group consisting of lower alkyl, lower-alkenyl, lower-alkynyl, dioxo-lower-alkylene (forming e.g. a benzodioxyl group), halogen, hydroxy, CN, $CF_3$, $NH_2$, N(H, lower-alkyl), N(lower-alkyl)$_2$, aminocarbonyl, carboxy, $NO_2$, lower-alkoxy, thio-lower-alkoxy, lower-alkylsulfonyl, aminosulfonyl, lower-alkylcarbonyl, lower-alkylcarbonyloxy, lower-alkoxycarbonyl, lower-alkyl-carbonyl-NH, fluoro-lower-alkyl, fluoro-lower-alkoxy, lower-alkoxycarbonyl-lower-alkoxy, carboxy-lower-alkoxy, carbamoyl-lower-alkoxy, hydroxy-lower-alkoxy, $NH_2$-lower-alkoxy, N(H, lower-alkyl)-lower-alkoxy, N(lower-alkyl)$_2$-lower-alkoxy, lower-alkyl-1-oxiranyl-lower-alkoxy-lower-alkyl, 2-oxo-pyrrolidin-1-yl, (1,1-dioxo)-2-isothiazolidine, 3-lower-alkyl sulfinyl, a substituted or unsubstituted heterocyclic ring, a substituted or unsubstituted aryl ring, a substituted or unsubstituted heteroaryl ring, trifluoro-lower-alkylsulfonylamino-aryl, lower-alkyl sulfonylaminocarbonyl, lower-alkyl sulfonylaminocarbonyl-aryl, hydroxycarbamoyl-phenyl, benzyloxy-lower-alkoxy, mono- or lower-alkyl substituted amino-sulfonyl and lower-alkyl which can optionally be substituted with halogen, hydroxy, $NH_2$, N(H, lower-alkyl) or N(lower-alkyl)$_2$. Preferred substituents for the cycloalkyl, cycloalkenyl, aryl, heteroaryl and heterocycle rings are halogen, lower alkoxy, lower alkyl, hydroxycarbonyl, carboxy, carboxy lower alkoxy, oxo and CN. Preferred substituents for alkyl are alkoxy and N(lower alkyl)$_2$.

The term "alkyl" refers to straight- or branched-chain saturated hydrocarbon groups having from 1 to about 20 carbon atoms, including groups having from 1 to about 7 carbon atoms. In certain embodiments, alkyl substituents may be lower alkyl substituents. The term "lower alkyl" refers to alkyl groups having from 1 to 6 carbon atoms, and in certain embodiments from 1 to 4 carbon atoms. Examples of alkyl groups include, but are not limited to, methyl, ethyl, n-propyl, i-propyl, n-butyl, s-butyl, t-butyl, n-pentyl, and s-pentyl.

As used herein, "cycloalkyl" is intended to refer to any stable monocyclic or polycyclic system which consists of carbon atoms only, any ring of which being saturated, and the term "cycloalkenyl" is intended to refer to any stable monocyclic or polycyclic system which consists of carbon atoms only, with at least one ring thereof being partially unsaturated.

Examples of cycloalkyls include, but are not limited to, cyclopropyl, cyclobutyl, cyclopentyl, cyclohexyl, cycloheptyl, adamantyl, cyclooctyl, bicycloalkyls, including bicyclooctanes such as [2.2.2]bicyclooctane or [3.3.0]bicyclooctane, bicyclononanes such as [4.3.0]bicyclononane, and bicyclodecanes such as [4.4.0]bicyclodecane (decalin), or spiro compounds. Examples of cycloalkenyls include, but are not limited to, cyclopentenyl or cyclohexenyl.

The term "alkenyl" as used herein means an unsaturated straight-chain or branched aliphatic hydrocarbon group containing one double bond and having 2 to 6, preferably 2 to 4 carbon atoms. Examples of such "alkenyl group" are vinyl ethenyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl and 5-hexenyl.

The term "alkynyl" as used herein means an unsaturated straight-chain or branched aliphatic hydrocarbon group containing one triple bond and having 2 to 6, preferably 2 to 4 carbon atoms. Examples of such "alkynyl group" are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl.

The term "halogen" as used in the definitions means fluorine, chlorine, bromine, or iodine, preferably fluorine and chlorine.

"Aryl" means a monovalent, monocyclic or bicyclic, aromatic carbocyclic hydrocarbon radical, preferably a 6-10 member aromatic ring system. Preferred aryl groups include, but are not limited to, phenyl, naphthyl, tolyl, and xylyl. Where the aryl group is bicyclic a preferred group is 1,3-dioxo-2,3-dihydro-1H-isoindol-5-yl group.

"Heteroaryl" means an aromatic heterocyclic ring system containing up to two rings. Preferred heteroaryl groups include, but are not limited to, thienyl, furyl, indolyl, pyrrolyl, pyridinyl, pyrazinyl, oxazolyl, thiaxolyl, quinolinyl, pyrimidinyl, imidazole substituted or unsubstituted triazolyl and substituted or unsubstituted tetrazolyl.

In the case of aryl or heteroaryl which are bicyclic it should be understood that one ring may be aryl while the other is heteroaryl and both being substituted or unsubstituted.

"Heterocycle" or "heterocyclic ring" means a substituted or unsubstituted 5 to 8 membered, mono- or bicyclic, non-aromatic hydrocarbon, wherein 1 to 3 carbon atoms are replaced by a hetero atom selected from nitrogen, oxygen or sulfur atom. Examples include pyrrolidin-2-yl; pyrrolidin-3-yl; piperidinyl; morpholin-4-yl and the like which in turn can be substituted. "Hetero atom" means an atom selected from N, O and S.

"Alkoxy, alkoxyl or lower alkoxy" refers to any of the above lower alkyl groups attached to an oxygen atom. Typical lower alkoxy groups include methoxy, ethoxy, isopropoxy or propoxy, butyloxy and the like. Further included within the meaning of alkoxy are multiple alkoxy side chains, e.g. ethoxy ethoxy, methoxy ethoxy, methoxy ethoxy ethoxy and the like and substituted alkoxy side chains, e.g., dimethylamino ethoxy, diethylamino ethoxy, dimethoxy-phosphoryl methoxy and the like.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoro acetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (6th Ed. 1995) at pp. 196 and 1456-1457.

The compounds of formula I and II as well as their salts that have at least one asymmetric carbon atom may be present as racemic mixtures or different stereoisomers. The various isomers can be isolated by known separation methods, e.g., chromatography.

Compounds disclosed herein and covered by formula I and II above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

The compounds of the present invention are useful in the treatment or control of cell proliferative disorders, in particular oncological disorders. These compounds and formulations containing said compounds may be particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration; it may be given as continuous infusion.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, sachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

"Effective amount" means an amount that is effective to prevent, alleviate or ameliorate symptoms of disease or prolong the survival of the subject being treated.

"IC50" refers to the concentration of a particular compound required to inhibit 50% of a specific measured activity. $IC_{50}$ can be measured, inter alia, as is described subsequently.

Synthetic Methods

The present invention provides methods for the synthesis of pyrrolidine-2-carboxamide. The compounds of the invention can be prepared by processes known in the art. Suitable processes for synthesizing these compounds are provided in the examples.

Compounds of this invention can be synthesized according to the following general schemes. The key transformation is a convergent [2+3] cylcoaddition of emine II and activated olefin III to generate pyrrolidine-3-carbonitrile compounds IV in a stereoselective and efficient manner.

The starting materials are either commercially available or can be synthesized by methods known to those of ordinary skill in the art. Preparations of intermediates II and III are illustrated in Scheme 1 and 2. In general an appropriately selected aldehyde or ketonecan be reacted with glycine tert-butyl ester or glycine methyl ester to generate imine II and were used as a crude product (Scheme 1).

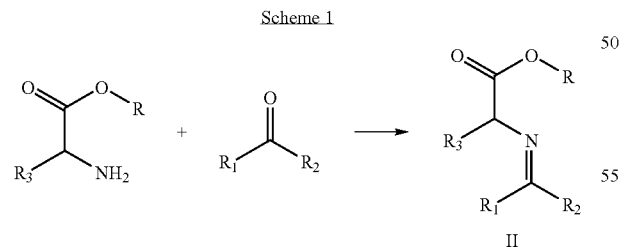

Reagents and conditions: R is tert-butyl or methyl
(1) If R1 or R2 is H, CH2Cl2, room temperature, overnight;
(2) If R1 and R2 are both not H, ethanol, 100° C., 48 h;

An intermediate of formula III can be made from a base-catalyzed condensation reaction of appropriately selected substituted-phenyl acetonitrile and aldehyde The reaction proceeds in a highly stereoselective manner with Z-isomer as the major or exclusive product.

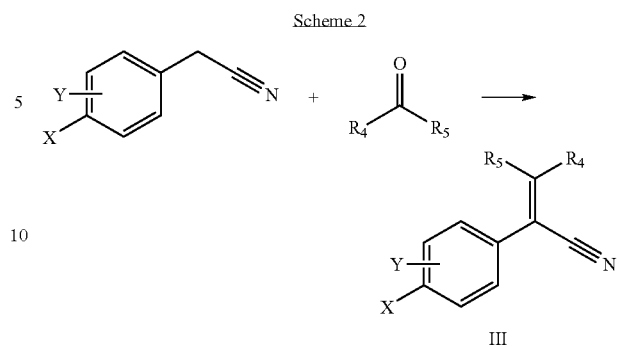

Reagents and conditions:
If $R_5$ is H, aq. NaOH, iPrOH, room temperature, 5 min or NaOMe, MeOH, 50° C., 3 h As illustrated in Scheme 3, pyrrolidine of formula IV can be made from intermediates II and III by a convergent 1,3-dipolar cylcoaddition reaction mediated by lewis acid AgF and triethylamine. The [2+3] cycloaddition reactions of azomethine ylides 1,3-dipoles with olefinic dipolarphiles to form pyrrolidine ring formation have been described in published procedures including Jorgensen, K. A. et al (*Org. Lett.* 2005, Vol 7, No. 21, 4569-4572), Grigg, R. et al (*Tetrahedron,* 1992, Vol 48, No. 47, 10431-10442; *Tetrahedron,* 2002, Vol 58, 1719-1737), Schreiber, S. L. et al (*J. Am. Chem. Soc.,* 2003, 125, 10174-10175), and Carretero, J. C. et al (*Tetrahedron,* 2007, 63, 6587-6602). Compounds IV is subsequently converted to acid V followed by amide formation with various amines using HATU as the coupling reagent to give the compounds of formula I. The amide formation from V to I can also be achieved under other conditions using EDCI and HOBt or oxalyl chloride as the coupling reagent to activate the acid V.

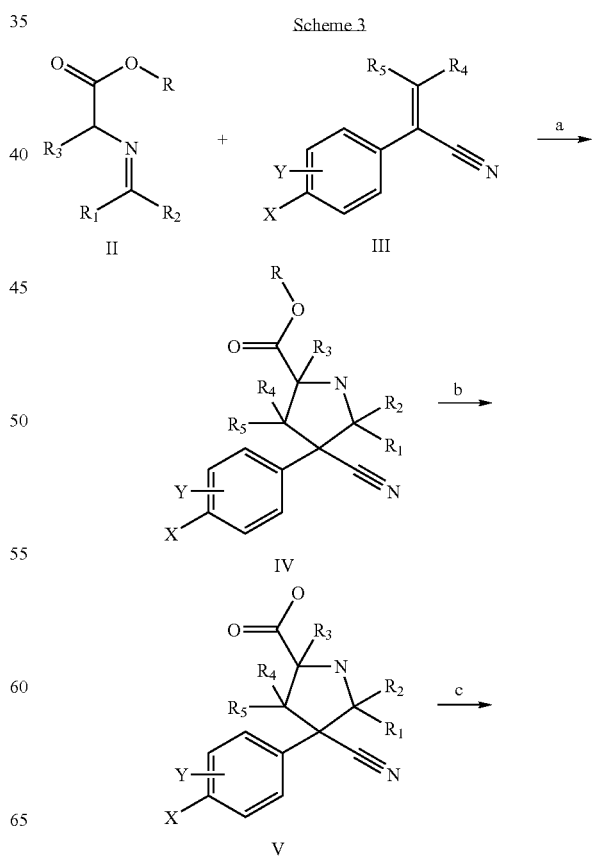

-continued

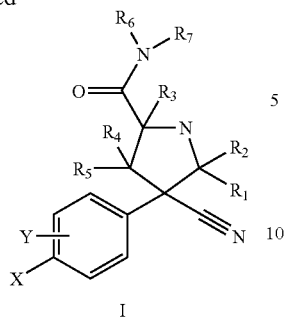

Reagents and conditions:
a. AgF, NEt₃, CH₂Cl₂ or ClCH₂CH₂Cl, rt, 18 h;
b. 1) If R is tert-butyl, conc. H₂SO₄; or TFA, CH₂Cl₂, rt, 18 h;
or 2) If R is methyl, NaOH or LiOH, H₂O and MeOH and THF, rt, 18 h;
c. HNR₆R₇, HATU, iPr₂NEt, CH₂Cl₂, rt, 18 h The pyrrolidine compounds I, IV, V are prepared initially as a racemic mixture and can be chirally separated using chiral Super Fluid Chromatography (SFC) or chiral HPLC or chiral column chromatography. For example, racemic mixture of compound Ia and Ia' can be readily resolved into two optically pure or enriched chiral enantiomers by separation using chiral Super Fluid Chromatography (SFC). (Scheme 4).

EXAMPLES

The compounds of the present invention may be synthesized according to known techniques. The following examples and references are provided to aid the understanding of the present invention, the true scope of which is set forth in the appended claims.

Example 1a

Preparation of intermediate [3,3-dimethyl-but-(E)-ylideneamino]-acetic acid tert-butyl ester

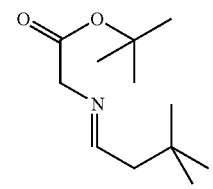

M.W. 213.32
C₁₂H₂₃NO₂

A mixture of glycine tert-butyl ester (Alfa) (2.71 g, 20.0 mmol) and 3,3-dimethyl-butyraldehyde (Alfa) (2.21 g, 21.0 mmol) in CH₂Cl₂ (50 mL) was stirred at rt overnight. The reaction mixture was concentrated and the residue was dried in vacuo to give [3,3-dimethyl-but-(E)-ylideneamino]-acetic acid tert-butyl ester (4.29 g, 100%) as colorless oil which was used in the next step without further purification.

Scheme 4

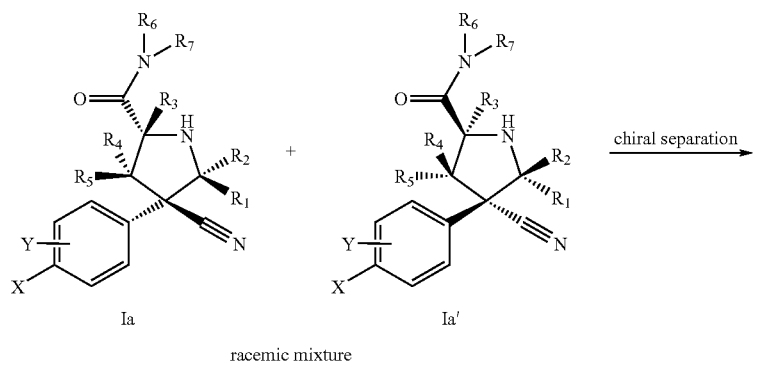

racemic mixture

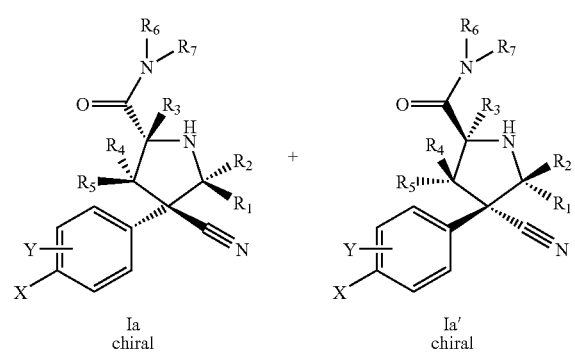

Example 1b

Preparation of intermediate (Z)-3-(3-chloro-phenyl)-2-(4-chloro-phenyl)-acrylonitrile

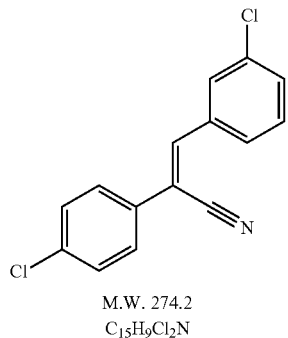 [SMILES: N#C/C(=C\c1cccc(Cl)c1)c1ccc(Cl)cc1]

M.W. 274.2
$C_{15}H_9Cl_2N$

Method A To a solution of 4-chlorobenzyl cyanide (5.62 g, 4.00 mmol) and 3-chloro-benzaldehyde (Aldrich) (6.06 g, 4.00 mmol) in iPrOH (250 mL) was added 4 N NaOH (5 mL) dropwise at rt and the reaction mixture was stirred at rt for 10 min to give a white suspension. The solid was filtered and washed with water and iPrOH and then dried overnight in vacuum to give (Z)-3-(3-chloro-phenyl)-2-(4-chloro-phenyl)-acrylonitrile (9.33 g, 85.1%) as a white powder which was used in the next step without further purification.

Method B To a solution of 4-chlorobenzyl cyanide (Aldrich) (4.5 g, 30 mmol) and 3-chloro-benzaldehyde (Aldrich) (4 g, 29 mmol) in methanol (150 mL) was slowly added a methanolic solution (Aldrich, 25 wt. %) of sodium methoxide (10 mL, 44 mmol). The reaction mixture was heated and stirred at 50° C. for 3 h. The mixture became cloudy, and was cooled to room temperature and filtered. The white precipitate was washed with water, cold methanol, and then dried in vacuo to give the first batch of desired product (5.5 g). The filtrate was concentrated, diluted with water, neutralized by aqueous HCl solution to "pH" 7, then extracted with ethyl acetate. The organic layer was separated, dried over $MgSO_4$, and concentrated. The residue was purified by chromatography (EtOAc:hexanes=1:20, then 1:10) to give the second batch of the desired product (1.6 g). The two batches were combined to give (Z)-3-(3-chloro-phenyl)-2-(4-chloro-phenyl)-acrylonitrile as a white powder (7.1 g, 88%).

HRMS ($ES^+$), m/z Calcd for $C_{15}H_9Cl_2N$ [M+]: 273.0112. found: 273.0113.

Example 1c

Preparation of intermediate rac-(2R,3R,4R,5S)-3-(3-chloro-phenyl)-4-(4-chloro-phenyl)-4-cyano-5-(2,2-dimethyl-propyl)-pyrrolidine-2-carboxylic acid tert-butyl ester

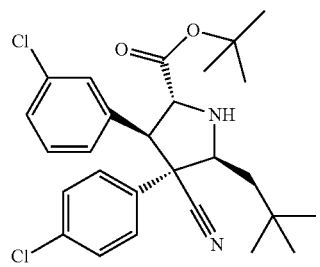

M.W. 487.5
$C_{27}H_{32}Cl_2N_2O_2$

To a solution of [3,3-dimethyl-but-(E)-ylideneamino]-acetic acid tert-butyl ester (4.26 g, 20.00 mmol) and (Z)-3-(3-chloro-phenyl)-2-(4-chloro-phenyl)-acrylonitrile (5.48 g, 20.00 mmol) in $ClCH_2CH_2Cl$ (100 mL) were added triethyl amine (4.2 g, 40.00 mmol) and AgF (2.53 g, 20.00 mmol) in one portion. The mixture was stirred at rt overnight. The mixture was then quenched with sat. $NH_4Cl$ and extracted with $CH_2Cl_2$. The organic phase was separated, filtered through Celite and dried over $Na_2SO_4$. The mixture was then separated and concentrated. The residue was triturated with EtOAc and nHexane, and the precipitates were collected by filtration and the mother liquid was concentrated and further purified by flash column ($SiO_2$, 1-20% of EtOAc in hexanes) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid tert-butyl ester (6.65 g, 68.2%; HRMS ($ES^+$) m/z Calcd for $C_{27}H_{32}Cl_2N_2O_2$+H [(M+H)$^+$]: 487.1914. found: 487.1910.) and rac-(2R,3R,4R,5R)-3-(3-chloro-phenyl)-4-(4-chloro-phenyl)-4-cyano-5-(2,2-dimethyl-propyl)-pyrrolidine-2-carboxylic acid tert-butyl ester (0.86 g, 8.8%).

HRMS ($ES^+$) m/z Calcd for $C_{27}H_{32}Cl_2N_2O_2$+H [(M+H)$^+$]: 487.1914. found: 487.1910.).

Example 1d

Preparation of intermediate rac-(2R,3R,4R,5S)-3-(3-chloro-phenyl)-4-(4-chloro-phenyl)-4-cyano-5-(2,2-dimethyl-propyl)-pyrrolidine-2-carboxylic acid

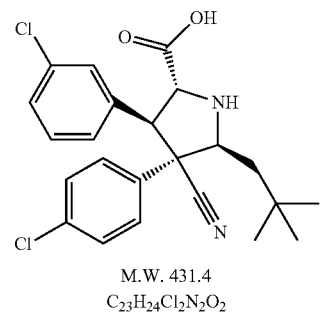 [SMILES: CC(C)(C)C[C@@H]1N[C@@H](C(=O)O)[C@H](c2cccc(Cl)c2)[C@@]1(C#N)c1ccc(Cl)cc1]

M.W. 431.4
$C_{23}H_{24}Cl_2N_2O_2$

A solution of rac-(2R,3R,4R,5S)-3-(3-chloro-phenyl)-4-(4-chloro-phenyl)-4-cyano-5-(2,2-dimethyl-propyl)-pyrrolidine-2-carboxylic acid tert-butyl ester (3.78 g, 7.75 mmol) in conc. $H_2SO_4$ (20 mL) was stirred at rt for 2 hrs. The mixture was then poured into ice and extracted with EtOAc. The organic phase was separated, dried over $Na_2SO_4$, and concentrated. The residue was then triturated with EtOAc and nHexane and the precipitates were collected by filtration and washed with ether to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3.60 g, 100%) as a white solid which was used in the next step without further purification: HRMS ($ES^+$) m/z Calcd for $C_{23}H_{24}Cl_2N_2O_2$+H [(M+H)$^+$]: 431.1288. found: 431.1287.

Example 1e

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-morpholin-4-yl-ethyl)-amide

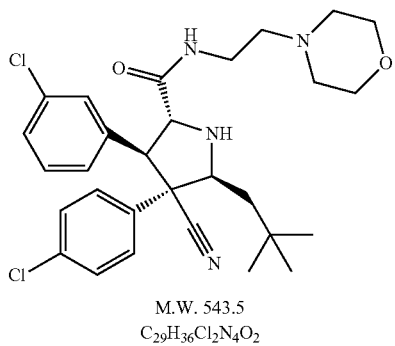 [SMILES: CC(C)(C)C[C@@H]1N[C@@H](C(=O)NCCN2CCOCC2)[C@H](c2cccc(Cl)c2)[C@@]1(C#N)c1ccc(Cl)cc1]

M.W. 543.5
$C_{29}H_{36}Cl_2N_4O_2$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (61.0 mg, 0.14 mmol), 2-morpholin-4-yl-ethylamine (36.0 mg, 0.28 mmol), 2-(7-azabenzotriazol-1-yl)-N,N,N',N'-tetramethyluronium hexafluorophosphate (HATU, 106.0 mg, 0.28 mmol) and iPr$_2$NEt (38.8 mg, 0.30 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by SiO$_2$ flash column (20-100% of EtOAc in Hexanes) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-morpholin-4-yl-ethyl)-amide (60.5 mg, 86.4%) as a white amorphous.

HRMS (ES$^+$) m/z Calcd for $C_{29}H_{36}Cl_2N_4O_2$+H [(M+H)$^+$]: 543.2288. found: 543.2284.

Example 1f

Preparation of (2R,3R,4R,5S)-3-(3-chloro-phenyl)-4-(4-chloro-phenyl)-4-cyano-5-(2,2-dimethyl-propyl)-pyrrolidine-2-carboxylic acid (2-morpholin-4-yl-ethyl)-amide

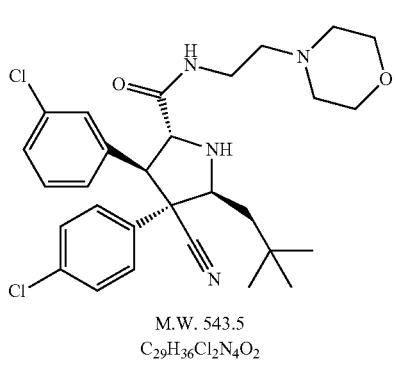 [SMILES: CC(C)(C)C[C@@H]1N[C@@H](C(=O)NCCN2CCOCC2)[C@H](c2cccc(Cl)c2)[C@@]1(C#N)c1ccc(Cl)cc1]

M.W. 543.5
$C_{29}H_{36}Cl_2N_4O_2$

The racemic product obtained above (Example 1e, 45 mg) was further separated by SFC chiral column to give-(2R,3R, 4R,5S)-3-(3-chloro-phenyl)-4-(4-chloro-phenyl)-4-cyano-5-(2,2-dimethyl-propyl)-pyrrolidine-2-carboxylic acid (2-morpholin-4-yl-ethyl)-amide (13.1 mg, 29.1%) and (2S, 3S,4S,5R)-3-(3-chloro-phenyl)-4-(4-chloro-phenyl)-4-cyano-5-(2,2-dimethylpropyl)-pyrrolidine-2-carboxylic acid (2-morpholin-4-yl-ethyl)-amide (14.6 mg, 32.4%).

Example 2

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid dimethylamide

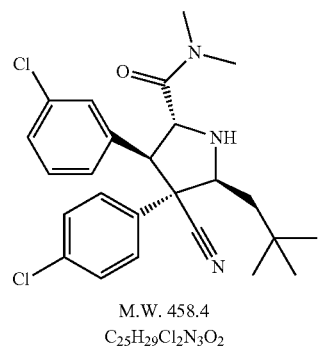 [SMILES: CN(C)C(=O)[C@@H]1N[C@@H](CC(C)(C)C)[C@](C#N)(c2ccc(Cl)cc2)[C@H]1c1cccc(Cl)c1]

M.W. 458.4
$C_{25}H_{29}Cl_2N_3O_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (61.0 mg, 0.14 mmol) prepared in Example 1d was reacted with dimethylamine (1.0 M in THF, 2 mL), HATU (106.0 mg, 0.28 mmol) and iPr$_2$NEt (38.8 mg, 0.30 mmol) in CH$_2$Cl$_2$ (2 mL) at rt overnight to give rac-(2R,3R, 4R,5S)-3-(3-chloro-phenyl)-4-(4-chloro-phenyl)-4-cyano-5-(2,2-dimethyl-propyl)-pyrrolidine-2-carboxylic acid dimethyl amide (57.8 mg, 90.0%).

HRMS (ES$^+$) m/z Calcd for $C_{25}H_{29}Cl_2N_3O_2$+H [(M+H)$^+$]: 458.1761. found: 458.1757.

Example 3a

Preparation of intermediate 2-((S)-2,2-dimethyl-[1,3]dioxolan-4-yl)-ethylamine

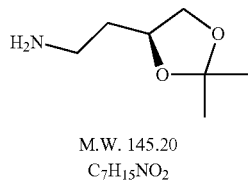

M.W. 145.20
$C_7H_{15}NO_2$

Step A To a solution of (4S)-(+)-4-(2-hydroxyethyl)-2,2-dimethyl-1,3-dioxolane (Aldrich) (21.1 g, 0.14 mol) and triethylamine (40 mL, 0.28 mol) in dichloromethane (250 mL) at 0° C. was added methanesulfonyl chloride (13.4 mL, 0.17 mol) dropwise. The reaction mixture was stirred at 0° C. for 1.5 h, then water was added. The organic layer was separated, washed with water, brine, dried over MgSO$_4$, concentrated to give methanesulfonic acid 2-((S)-2,2-dimethyl-[1,3]dioxolan-4-yl)-ethyl ester as a yellow oil (31.7 g, 98%).

Step B To a solution of methanesulfonic acid 2-((S)-2,2-dimethyl-[1,3]dioxolan-4-yl)-ethyl ester (31.7 g, 0.14 mol) in N,N-dimethylformamide (200 mL) was added NaN$_3$ (46 g, 0.71 mol). The reaction mixture was stirred at room temperature for 70 h. Then the mixture was partitioned between ethyl acetate and water. The organic layer was separated, washed with water, brine several times, dried over MgSO$_4$, concentrated to give (S)-4-(2-azido-ethyl)-2,2-dimethyl-[1,3]dioxolane as a yellow oil (21.3 g, 88%).

Step C A suspension of (S)-4-(2-azido-ethyl)-2,2-dimethyl-[1,3]dioxolane as a yellow oil (18.7 g, 0.11 mol) and PtO$_2$ (2.5 g) in ethyl acetate (100 mL) was vigorously shaken in a Parr under atmosphere of H$_2$ (50 psi) for 18 h. The mixture was filtered through a short pad of celite. The filtrate was concentrated to give 2-((S)-2,2-dimethyl-[1,3]dioxolan-4-yl)-ethylamine as a colorless oil (14 g, 88%).

Example 3b

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide

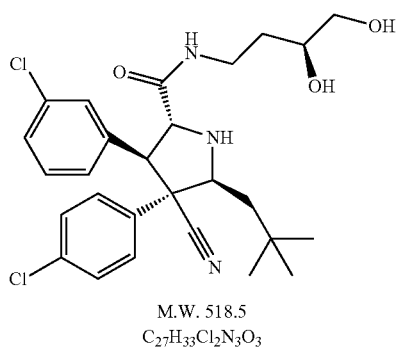 [SMILES: CC(C)(C)C[C@@H]1N[C@@H](C(=O)NCC[C@H](O)CO)[C@H](c2cccc(Cl)c2)[C@@]1(C#N)c1ccc(Cl)cc1]

M.W. 518.5
$C_{27}H_{33}Cl_2N_3O_3$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (431.4 mg, 1.00 mmol) prepared in Example 1d, 2-((S)-2,2-dimethyl-[1,3]dioxolan-4-yl)-ethylamine (217.5 mg, 1.5 mmol), HATU (570.30 mg, 1.50 mmol) and iPr$_2$NEt (258.6 mg, 2.00 mmol) in CH$_2$Cl$_2$ (20 mL) was stirred at rt for 1 hour. The mixture was then diluted with CH$_2$Cl$_2$ and washed with water, brine. The organic phase was separated, filtered and dried over Na$_2$SO$_4$. The mixture was then concentrated and the residue was treated with PPTS (cat) in MeOH (20 mL) at 120° C. for 5 min with CEM microwave reactor. The reaction mixture was concentrated and the residue was diluted with EtOAc and washed with water, brine. The organic phase was separated, filtered and dried over Na$_2$SO$_4$. The mixture was then concentrated and purified by SiO$_2$ flash column (5% of MeOH in EtOAc) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide (450.0 mg, 86.7%) as a white amorphous.

HRMS (ES$^+$) m/z Calcd for $C_{27}H_{33}Cl_2N_3O_3$+H[(M+H)$^+$]: 518.1972. found: 518.1970.

Example 3c

Preparation of (2R,3R,4R,5S)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide

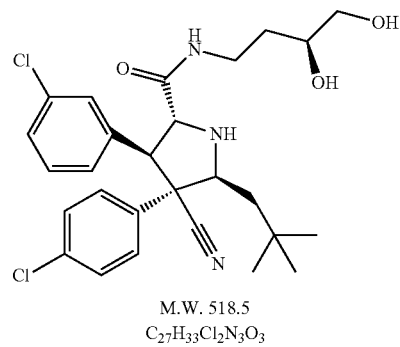 [SMILES: CC(C)(C)C[C@@H]1N[C@@H](C(=O)NCC[C@H](O)CO)[C@H](c2cccc(Cl)c2)[C@@]1(C#N)c1ccc(Cl)cc1]

M.W. 518.5
$C_{27}H_{33}Cl_2N_3O_3$

The racemic product obtained above (Example 3b, 450.0 mg) was further separated by SFC chiral column to give (2R,3R,4R,5S)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide (178.6 mg, 34.4%) and (2S,3S,4S,5R)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide (159.8 mg, 30.8%).

Example 4

Preparation of rac-(2S,3R,4R,5R)-4-(3-chloro-phenyl)-3-(4-chloro-phenyl)-2-(2,2-dimethyl-propyl)-5-[4-(2-morpholin-4-yl-2-oxo-ethyl)-piperazine-1-carbonyl]-pyrrolidine-3-carbonitrile

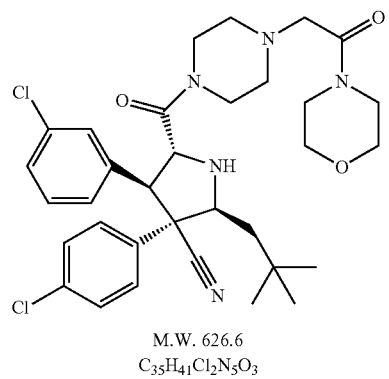 [SMILES: CC(C)(C)C[C@@H]1N[C@@H](C(=O)N2CCN(CC(=O)N3CCOCC3)CC2)[C@H](c2cccc(Cl)c2)[C@@]1(C#N)c1ccc(Cl)cc1]

M.W. 626.6
$C_{35}H_{41}Cl_2N_5O_3$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (61.0 mg, 0.14 mmol) prepared in Example 1d was reacted with 1-morpholin-4-yl-2-piperazin-1-yl-ethanone (65.0 mg, 0.30 mmol), HATU (106.0 mg, 0.28 mmol) and iPr$_2$NEt (38.8 mg, 0.30 mmol) in CH$_2$Cl$_2$ (2 mL) at rt overnight to give rac-(2S,3R,4R,5R)-4-(3-chloro-phenyl)-3-(4-chloro-phenyl)-2-(2,2-dimethyl-propyl)-5-[4-(2-morpholin-4-yl-2-oxo-ethyl)-piperazine-1-carbonyl]-pyrrolidine-3-carbonitrile (45.5 mg, 51.9%).
HRMS (ES$^+$) m/z Calcd for C$_{35}$H$_{41}$Cl$_2$N$_5$O$_3$+H [(M+H)$^+$]: 626,2659. found: 626.2654.

Example 5

Preparation of rac-(2S,3R,4R,5R)-4-(3-chloro-phenyl)-3-(4-chloro-phenyl)-2-(2,2-dimethyl-propyl)-5-[4-(2-oxo-2-pyrrolidin-1-yl-ethyl)-piperazine-1-carbonyl]-pyrrolidine-3-carbonitrile

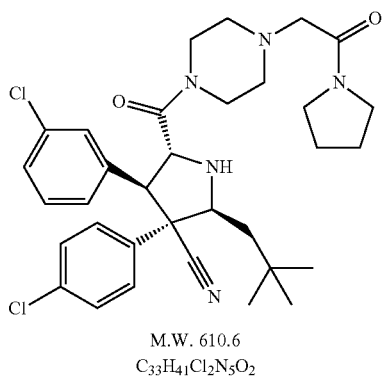 [SMILES: CC(C)(C)C[C@@H]1N[C@@H](C(=O)N2CCN(CC(=O)N3CCCC3)CC2)[C@H](c2cccc(Cl)c2)[C@@]1(C#N)c1ccc(Cl)cc1]

M.W. 610.6
C$_{33}$H$_{41}$Cl$_2$N$_5$O$_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (61.0 mg, 0.14 mmol) prepared in Example 1d was reacted with 2-piperazin-1-yl-1-pyrrolidin-1-yl-ethanone (65.0 mg, 0.33 mmol), HATU (106.0 mg, 0.28 mmol) and iPr$_2$NEt (38.8 mg, 0.30 mmol) in CH$_2$Cl$_2$ (2 mL) at rt overnight to give rac-(2S,3R,4R,5R)-4-(3-Chloro-phenyl)-3-(4-chloro-phenyl)-2-(2,2-dimethyl-propyl)-5-[4-(2-oxo-2-pyrrolidin-1-yl-ethyl)-piperazine-1-carbonyl]-pyrrolidine-3-carbonitrile (60.5 mg, 70.8%).
HRMS (ES$^+$) m/z Calcd for C$_{33}$H$_{41}$Cl$_2$N$_5$O$_2$+H [(M+H)$^+$]: 610.2710. found: 610.2708.

Example 6

Preparation of rac-(2S,3R,4R,5R)-4-(3-chloro-phenyl)-3-(4-chloro-phenyl)-2-(2,2-dimethyl-propyl)-5-[4-(2-hydroxy-ethyl)-piperazine-1-carbonyl]-pyrrolidine-3-carbonitrile

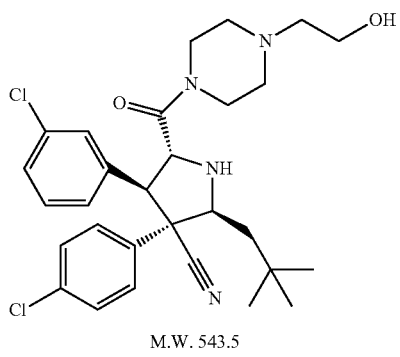

M.W. 543.5
C$_{29}$H$_{36}$Cl$_2$N$_4$O$_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (61.0 mg, 0.14 mmol) prepared in Example 1d was reacted with 2-piperazin-1-yl-ethanol (65.0 mg, 0.50 mmol), HATU (106.0 mg, 0.28 mmol) and iPr$_2$NEt (38.8 mg, 0.30 mmol) in CH$_2$Cl$_2$ (2 mL) at rt overnight to give rac-(2S,3R,4R,5R)-4-(3-chloro-phenyl)-3-(4-chloro-phenyl)-2-(2,2-dimethyl-propyl)-5-[4-(2-hydroxy-ethyl)-piperazine-1-carbonyl]-pyrrolidine-3-carbonitrile (48.3 mg, 63.5%).
HRMS (ES$^+$) m/z Calcd for C$_{29}$H$_{36}$Cl$_2$N$_4$O$_2$+H [(M+H)$^+$]: 543.2288. found: 543.2284.

Example 7

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (4-hydroxy-butyl)-amide

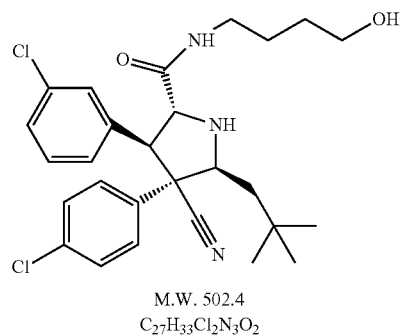 [SMILES: CC(C)(C)C[C@@H]1N[C@@H](C(=O)NCCCCO)[C@H](c2cccc(Cl)c2)[C@@]1(C#N)c1ccc(Cl)cc1]

M.W. 502.4
C$_{27}$H$_{33}$Cl$_2$N$_3$O$_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (61.0 mg, 0.14 mmol) prepared in Example 1d was reacted with 4-methylamino-butan-1-ol (44.5 mg, 0.50 mmol), HATU (106.0 mg, 0.28 mmol) and iPr$_2$NEt (38.8 mg, 0.30 mmol) in CH$_2$Cl$_2$ (2 mL) at rt overnight to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (4-hydroxy-butyl)-amide (30.5 mg, 43.4%). HRMS (ES$^+$) m/z Calcd for C$_{27}$H$_{33}$Cl$_2$N$_3$O$_2$+H [(M+H)$^+$]: 502,2023. found: 502.2020.

Example 8

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-pyrrolidin-1-yl-ethyl)-amide

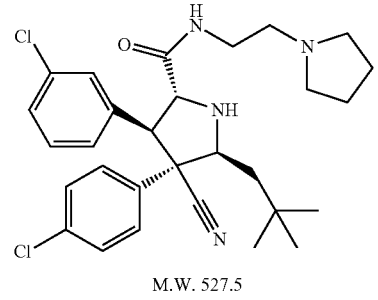

M.W. 527.5
C$_{29}$H$_{36}$Cl$_2$N$_4$O

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (82.2 mg, 0.20 mmol) prepared in Example 1d was reacted with 2-pyrrolidin-1-yl-ethylamine (34.2 mg, 0.30 mmol), HATU (76.0 mg, 0.20 mmol) and iPr$_2$NEt (38.8 mg, 0.30 mmol) in CH$_2$Cl$_2$ (2 mL) at rt overnight to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-pyrrolidin-1-yl-ethyl)-amide (50.6 mg, 64.0%). HRMS (ES$^+$) m/z Calcd for C$_{29}$H$_{36}$Cl$_2$N$_4$O+H [(M+H)$^+$]: 527.2339. found: 5277338.

Example 9

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-piperazin-1-yl-ethyl)-amide

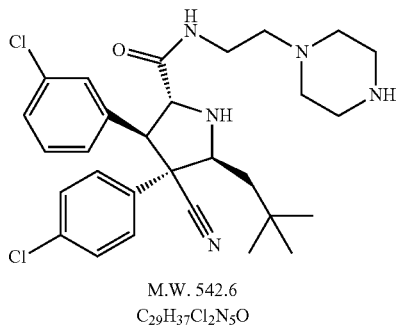 [SMILES: CC(C)(C)C[C@@H]1N[C@@H](C(=O)NCCN2CCNCC2)[C@H](c2cccc(Cl)c2)[C@@]1(C#N)c1ccc(Cl)cc1]

M.W. 542.6
C$_{29}$H$_{37}$Cl$_2$N$_5$O

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (82.2 mg, 0.20 mmol) prepared in Example 1d was reacted with 2-piperazin-1-yl-ethylamine (38.7 mg, 0.30 mmol), HATU (76.0 mg, 0.20 mmol) and iPr$_2$NEt (38.8 mg, 0.30 mmol) in CH$_2$Cl$_2$ (2 mL) at rt overnight to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-piperazin-1-yl-ethyl)-amide (45.9 mg, 58.0%). HRMS (ES$^+$) m/z Calcd for C$_{29}$H$_{37}$Cl$_2$N$_5$O+H [(M+H)$^+$]: 542.2448. found: 542.2445.

Example 10a

Preparation of (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester

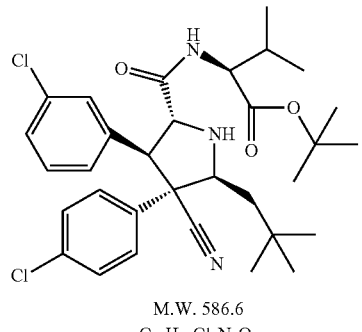

M.W. 586.6
C$_{32}$H$_{41}$Cl$_2$N$_3$O$_3$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (215.7 mg, 0.50 mmol) prepared in Example 1d was reacted with (S)-2-amino-3-methyl-butyric acid tert-butyl ester (125.4 mg, 0.60 mmol), HATU (210.1.0 mg, 0.60 mmol) and iPr$_2$NEt (129.3 mg, 1.00 mmol) in CH$_2$Cl$_2$ (5 mL) at rt overnight to give (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester (95.0 mg, 32.4%) after column separation. HRMS (ES$^+$) m/z Calcd for C$_{32}$H$_{41}$Cl$_2$N$_3$O$_3$+H [(M+H)$^+$]: 586.2602. found: 586.2598.

Example 10b

Preparation of (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester

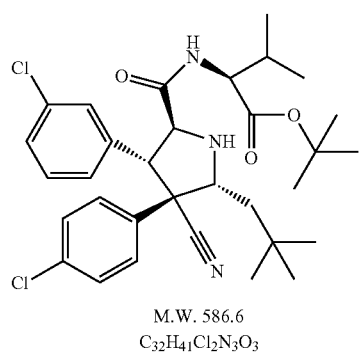 [SMILES: CC(C)[C@H](NC(=O)[C@H]1N[C@H](CC(C)(C)C)[C@@](C#N)(c2ccc(Cl)cc2)[C@@H]1c1cccc(Cl)c1)C(=O)OC(C)(C)C]

M.W. 586.6
C$_{32}$H$_{41}$Cl$_2$N$_3$O$_3$

Column separation from the above example (Example 10a) gave (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester (98.0 mg, 33.4%).
HRMS (ES$^+$) m/z Calcd for C$_{32}$H$_{41}$Cl$_2$N$_3$O$_3$+H [(M+H)$^+$]: 586.2601. found: 586.2598.

Example 10c

Preparation of (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid methyl ester

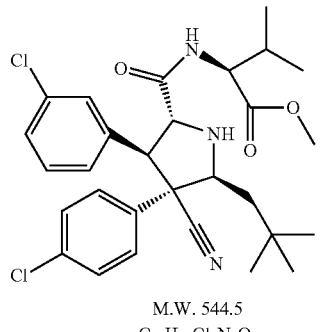

M.W. 544.5
C$_{29}$H$_{35}$Cl$_2$N$_3$O$_3$

Column separation from the above example (Example 10a) gave a mixture of (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester and (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester (45.8 mg, 15.6%). The mixture was treated with $2NH_2SO_4$ (catalytic) in MeOH (1 mL) at 120° C. for 10 min using CEM microwave reactor to give after purification by PR-HPLC: (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid methyl ester (15.5 mg, 36.5%).

HRMS (ES$^+$) m/z, Calcd for $C_{29}H_{35}Cl_2N_3O_3$+H [(M+H)$^+$]: 544.2128. found: 544.2127.

Example 10d

Preparation of (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid methyl ester

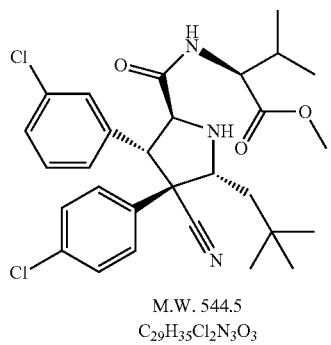 [SMILES: COC(=O)[C@@H](NC(=O)[C@H]1N[C@H](CC(C)(C)C)[C@@](C#N)(c2ccc(Cl)cc2)[C@@H]1c1cccc(Cl)c1)C(C)C]

M.W. 544.5
$C_{29}H_{35}Cl_2N_3O_3$

Column separation from the above example (Example 10a) gave a mixture of (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester and (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester (45.8 mg, 15.6%). The mixture was treated with $2NH_2SO_4$ (catalytic) in MeOH (1 mL) at 120° C. for 10 min using CEM microwave reactor to give after purification by reverse phase chromatography (20-95% of MeCN/water): (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid methyl ester (13.5 mg, 31.8%).

HRMS (ES$^+$) m/z Calcd for $C_{29}H_{35}Cl_2N_3O_3$+H [(M+H)$^+$]: 544.2128. found: 544.2126.

Example 11

Preparation of (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid

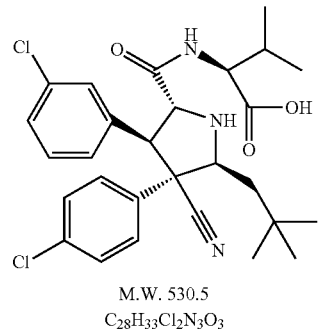 [SMILES: CC(C)[C@H](NC(=O)[C@@H]1N[C@@H](CC(C)(C)C)[C@](C#N)(c2ccc(Cl)cc2)[C@H]1c1cccc(Cl)c1)C(=O)O]

M.W. 530.5
$C_{28}H_{33}Cl_2N_3O_3$

A mixture of (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester (86.0 mg, 0.15 mmol) prepared in Example 10a and 2 $NH_2SO_4$ (0.5 mL) in MeCN (1 mL) was heated to 120° C. for 10 min with CEM microwave reactor. The mixture was then concentrated and the residue was purified by reverse phase chromatography (20-95% of MECN/water) to give: (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid (45.1 mg, 58.0%).

HRMS (ES$^+$) m/z Calcd for $C_{28}H_{33}Cl_2N_3O_3$+H [(M+H)$^+$]: 530.1972. found: 530.1971.

Example 12

Preparation of (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid

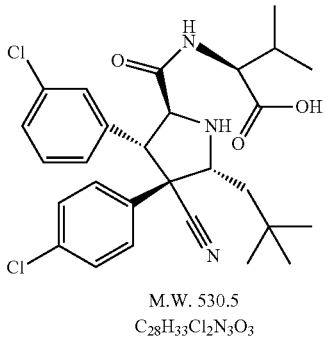 [SMILES: CC(C)[C@H](NC(=O)[C@H]1N[C@H](CC(C)(C)C)[C@@](C#N)(c2ccc(Cl)cc2)[C@@H]1c1cccc(Cl)c1)C(=O)O]

M.W. 530.5
$C_{28}H_{33}Cl_2N_3O_3$

A mixture of (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid tert-butyl ester (90 mg, 0.15 mmol) prepared in Example 10b and 2 $NH_2SO_4$ (0.5 mL) in MeCN (1 mL) was heated to 120° C. for 10 min with CEM microwave reactor. The mixture was then concentrated and the residue was purified by reverse phase chromatography (20-95% of MeCN/water) to give: (S)-2-{[(2S,3S,4S,5R)-3-(3-chloro-phenyl)-4-(4-chloro-phenyl)-4-cyano-5-(2,2-dimethyl-propyl)-pyrrolidine-2-carbonyl]-amino}-3-methyl-butyric acid (45.8 mg, 56.3%).

HRMS (ES$^+$) m/z Calcd for $C_{28}H_{33}Cl_2N_3O_3$+H [(M+H)$^+$]: 530.1972 found: 530.1971.

Example 13

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (1-hydroxymethyl-cyclopropylmethyl)-amide

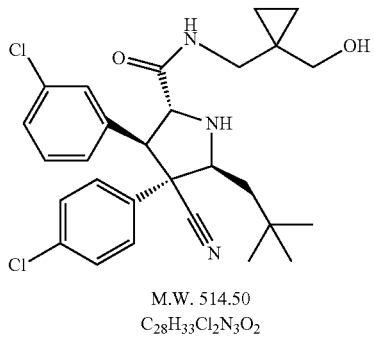 [SMILES: CC(C)(C)C[C@@H]1N[C@@H](C(=O)NCC2(CO)CC2)[C@H](c2cccc(Cl)c2)[C@@]1(C#N)c1ccc(Cl)cc1]

M.W. 514.50
$C_{28}H_{33}Cl_2N_3O_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol) prepared in Example 1d, (1-aminomethyl-cyclopropyl)-methanol (30.3 mg, 0.3 mmol), HATU (76.0 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of MeCN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (1-hydroxymethyl-cyclopropylmethyl)-amide (23.9 mg, 24.7%) as a white powder.

HRMS (ES$^+$) m/z Calcd for $C_{28}H_{33}Cl_2N_3O_2$+H [(M+H)$^+$]: 514.2023. found: 514.2024.

Example 14

Preparation of rac-(2R,3R,4R,5S)-3-(3-Chloro-phenyl)-4-(4-chloro-phenyl)-4-cyano-5-(2,2-dimethyl-propyl)-pyrrolidine-2-carboxylic acid (1-hydroxymethyl-cyclobutylmethyl)-amide

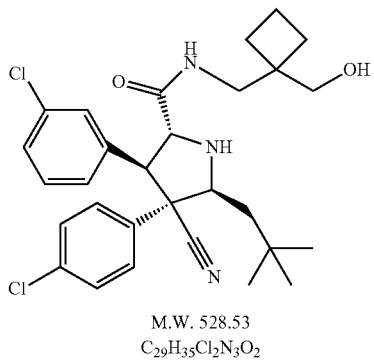 [SMILES: CC(C)(C)C[C@@H]1N[C@@H](C(=O)NCC2(CO)CCC2)[C@H](c2cccc(Cl)c2)[C@@]1(C#N)c1ccc(Cl)cc1]

M.W. 528.53
$C_{29}H_{35}Cl_2N_3O_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with (1-aminomethyl-cyclobutyl)-methanol (34.5 mg, 0.3 mmol), HATU (76 mg, 0.2 mmol) and iPr$_2$NEt (0.1 mL, 0.55 mmol) in CH$_2$Cl$_2$ (2 mL) at rt overnight to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (1-hydroxymethyl-cyclopropylmethyl)-amide (11.2 mg, 10.6%).

HRMS (ES$^+$) m/z Calcd for $C_{29}H_{35}Cl_2N_3O_2$+H [(M+H)$^+$]: 528.2179. found: 528.2179.

Example 15

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-tert-butyl benzylamide

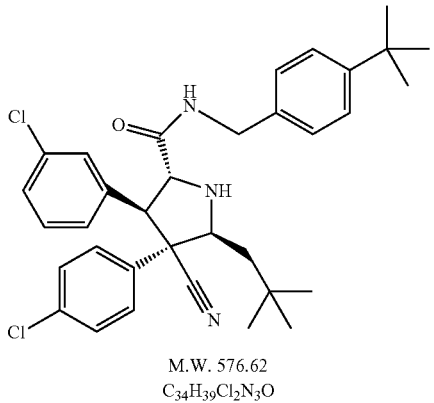 [SMILES: CC(C)(C)C[C@@H]1N[C@@H](C(=O)NCc2ccc(C(C)(C)C)cc2)[C@H](c2cccc(Cl)c2)[C@@]1(C#N)c1ccc(Cl)cc1]

M.W. 576.62
$C_{34}H_{39}Cl_2N_3O$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 4-tert-butylbenzylamine (48.98 mg, 0.3 mmol), HATU (76 mg, 0.2 mmol) and iPr$_2$NEt (0.1 mL, 0.55 mmol) in CH$_2$Cl$_2$ (2 mL) at rt overnight to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-tert-butyl-benzylamide (41.8 mg, 36.25%).

HRMS (ES$^+$) m/z Calcd for $C_{34}H_{39}Cl_2N_3O$+H [(M+H)$^+$]: 576.2543. found: 576.2541.

Example 16

Preparation of rac-(2R,3R,4R,5S)-3-(3-chloro-phenyl)-4-(4-chloro-phenyl)-4-cyano-5-(2,2-dimethyl-propyl)pyrrolidine-2-carboxylic acid (3,3-dimethyl-butyl)-amide

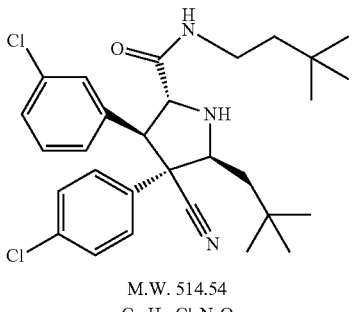

M.W. 514.54
$C_{29}H_{37}Cl_2N_3O$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 3,3-dimethylbutylamine (30.36 mg, 0.3 mmol), HATU (76 mg, 0.2 mmol) and iPr$_2$NEt (0.1 mL, 0.55 mmol) in CH$_2$Cl$_2$ (2 mL) at rt overnight to give rac-(2R,3R,4R,5S)-3-(3-chloro-phenyl)-4-(4-chloro-phenyl)-4-cyano-5-(2,2-dimethyl-propyl)pyrrolidine-2-carboxylic acid (3,3-dimethyl-butyl)-amide (30.4 mg, 29.5%).

HRMS (ES$^+$) m/z Calcd for C$_{29}$H$_{37}$Cl$_2$N$_3$O+H [(M+H)$^+$]: 514.2387. found: 514.2384.

Example 17

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2,2-dimethyl-propyl)-amide

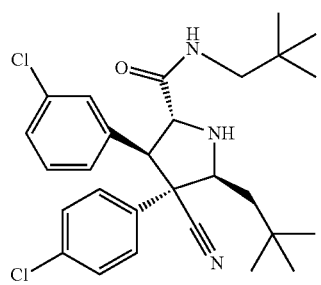

M.W. 500.52
C$_{28}$H$_{35}$Cl$_2$N$_3$O

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 2,2-dimethyl-propylamine (34.2 mg, 0.3 mmol), HATU (76 mg, 0.2 mmol) and iPr$_2$NEt (0.1 mL, 0.55 mmol) in CH$_2$Cl$_2$ (2 mL) at rt overnight to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2,2-dimethyl-propyl)-amide (24.6 mg, 24.6%).

HRMS (ES$^+$) m/z Calcd for C$_{28}$H$_{35}$Cl$_2$N$_3$O+H [(M+H)$^+$]: 500.2230. found: 500.2229.

Example 18

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2,2,2-trifluoro-ethyl)-amide

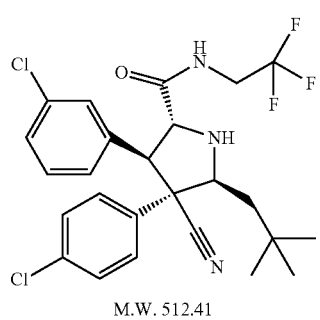

M.W. 512.41
C$_{25}$H$_{26}$Cl$_2$F$_3$N$_3$O

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d, 2,2,2-trifluoroethylamine (29.7 mg, 0.3 mmol), HATU (76 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was concentrated then purified by flash column (SiO$_2$, 1-20% of EtOAc in Heptane) to afford rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2,2,2-trifluoro-ethyl)-amide (2,2-dimethyl-propyl)-amide (48.1 mg, 46.9%).

HRMS (ES$^+$) m/z Calcd for C$_{25}$H$_{26}$Cl$_2$F$_3$N$_3$O+H [(M+H)$^+$]: 512.1478. found: 512.1478.

Example 19a

Preparation of (2R,3S,4S,5S)-4-(3-chloro-phenyl)-3-(4-chloro-phenyl)-2-(2,2-dimethyl-propyl)-54S)-2-hydroxymethyl-pyrrolidine-1-carbonyl)-pyrrolidine-3-carbonitrile

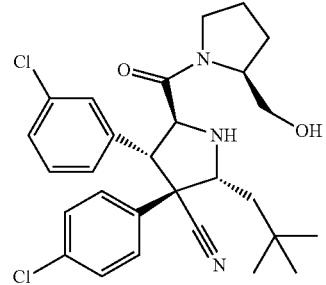

M.W. 514.494
C$_{28}$H$_{33}$Cl$_2$N$_3$O$_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with (S)-1-pyrrolidin-2-yl-methanol (30.3 mg, 0.3 mmol), HATU (76 mg, 0.2 mmol) and iPr$_2$NEt (0.1 mL, 0.55 mmol) in CH$_2$Cl$_2$ (2 mL) at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (30-95% of MeCN/water) to give (2R,3S,4S,5S)-4-(3-chloro-phenyl)-3-(4-chloro-phenyl)-2-(2,2-dimethyl-propyl)-5-((S)-2-hydroxymethyl-pyrrolidine-1-carbonyl)-pyrrolidine-3-carbonitrile (12.0 mg, 11.7%).

HRMS (ES$^+$) m/z Calcd for C$_{28}$H$_{33}$Cl$_2$N$_3$O$_2$+H [(M+H)$^+$]: 514.2023. found: 514.2023.

Example 19b

Preparation of (2S,3R,4R,5R)-4-(3-chloro-phenyl)-3-(4-chloro-phenyl)-2-(2,2-dimethyl-propyl)-54S)-2-hydroxymethyl-pyrrolidine-1-carbonyl)pyrrolidine-3-carbonitrile

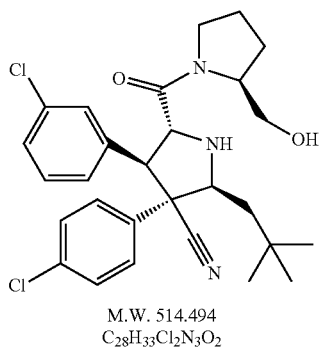 [SMILES: CC(C)(C)C[C@@H]1N[C@@H](C(=O)N2CCC[C@H]2CO)[C@H](c2cccc(Cl)c2)[C@@]1(C#N)c1ccc(Cl)cc1]

M.W. 514.494
$C_{28}H_{33}Cl_2N_3O_2$

Reverse phase chromatography separation from the above example (Example 19a) gave (2S,3R,4R,5R)-4-(3-chloro-phenyl)-3-(4-chloro-phenyl)-2-(2,2-dimethyl-propyl)-5-((S)-2-hydroxymethyl-pyrrolidine-1-carbonyl)pyrrolidine-3-carbonitrile (18.1 mg, 17.6%).

HRMS (ES$^+$) m/z Calcd for $C_{28}H_{33}Cl_2N_3O_2$+H [(M+H)$^+$]: 514.2023. found: 514.2023.

Example 20

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [2-(3,4-dimethoxy-phenyl)-ethyl]-methyl-amide

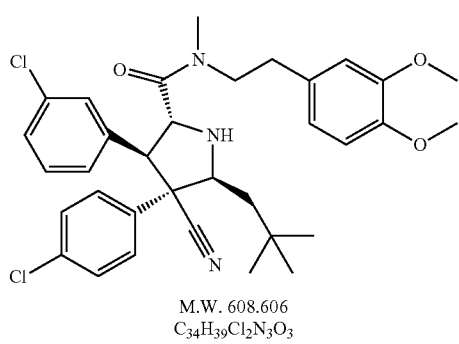 [SMILES: COc1ccc(CCN(C)C(=O)[C@@H]2N[C@@H](CC(C)(C)C)[C@](C#N)(c3ccc(Cl)cc3)[C@H]2c2cccc(Cl)c2)cc1OC]

M.W. 608.606
$C_{34}H_{39}Cl_2N_3O_3$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol) prepared in Example 1d was reacted with [2-(3,4-dimethoxy-phenyl)-ethyl]-methyl-amine (58.6 mg, 0.3 mmol), HATU (76.0 mg, 0.2 mmol) and iPr$_2$NEt (0.1 mL, 0.55 mmol) in CH$_2$Cl$_2$ (2 mL) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid [2-(3,4-dimethoxy-phenyl)-ethyl]-methyl-amide (57.3 mg, 48.26%) as a white powder.

HRMS (ES$^+$) m/z Calcd for $C_{34}H_{39}Cl_2N_3O_3$+H [(M+H)$^+$]: 608.2441. found: 608.2437.

Example 21

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 2-(3,4-dimethoxy-phenyl)ethyl amide

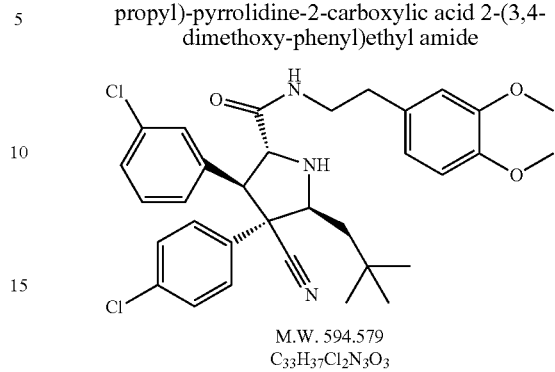

M.W. 594.579
$C_{33}H_{37}Cl_2N_3O_3$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 2-(3,4-dimethoxy-phenyl)ethyl amine (30.3 mg, 0.3 mmol), HATU (76 mg, 0.2 mmol) and iPr$_2$NEt (0.1 mL, 0.55 mmol) in CH$_2$Cl$_2$ (2 mL) to at rt overnight to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid 2-(3,4-dimethoxy-phenyl)ethyl amide (53.6 mg, 45.07%).

HRMS (ES$^+$) m/z. Calcd for $C_{33}H_{37}Cl_2N_3O_3$+H [(M+H)$^+$]: 594.2285. found: 594.2283.

Example 22

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 3-chloro-2-fluoro-benzylamide

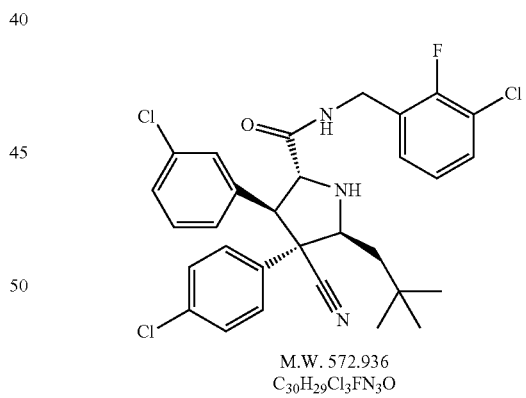

M.W. 572.936
$C_{30}H_{29}Cl_3FN_3O$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 3-chloro-2-fluoro-benzyl amine (47.9 mg, 0.3 mmol), HATU (76 mg, 0.2 mmol) and iPr$_2$NEt (0.1 mL, 0.55 mmol) in CH$_2$Cl$_2$ (2 mL) at rt overnight to rac-(2R,3R,4R,5S)-3-(3-chloro-phenyl)-4-(4-chloro-phenyl)-4-cyano-5-(2,2-dimethyl-propyl)-pyrrolidine-2-carboxylic acid 3-chloro-2-fluoro-benzylamide (24.5 mg, 21.4%).

HRMS (ES$^+$) m/z Calcd for $C_{30}H_{29}Cl_3FN_3O$+H [(M+H)$^+$]: 572.1433. found: 572.1431.

Example 23a

Preparation of (2R,3R,4R,5S)-3-(3-chloro-phenyl)-4-(4-chloro-phenyl)-4-cyano-5-(2,2-dimethyl-propyl)-pyrrolidine-2-carboxylic acid ((R)-1-hydroxymethyl-3-methyl-butyl)-amide

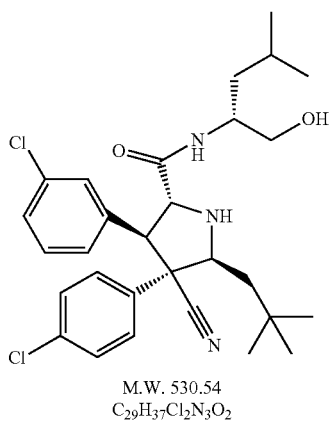 [SMILES: CC(C)C[C@H](CO)NC(=O)[C@@H]1N[C@@H](CC(C)(C)C)[C@](C#N)(c2ccc(Cl)cc2)[C@H]1c1cccc(Cl)c1]

M.W. 530.54
$C_{29}H_{37}Cl_2N_3O_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d, (R)-2-amino-4-methyl-pentan-1-ol (35.16 mg, 0.3 mmol), HATU (76 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (30-95% of MeCN/water) to give (2R,3R,4R,5S)-3-(3-chloro-phenyl)-4-(4-chloro-phenyl)-4-cyano-5-(2,2-dimethyl-propyl)-pyrrolidine-2-carboxylic acid ((R)-1-hydroxymethyl-3-methyl-butyl)-amide (26.2 mg, 24.7%).

HRMS (ES$^+$) m/z Calcd for $C_{29}H_{37}Cl_2N_3O_2$+H [(M+H)$^+$]: 530.2336. found: 530.2333.

Example 23b

Preparation of (2S,3S,4S,5R)-3-(3-chloro-phenyl)-4-(4-chloro-phenyl)-4-cyano-5-(2,2-dimethyl-propyl)-pyrrolidine-2-carboxylic acid ((R)-1-hydroxymethyl-3-methyl-butyl)-amide

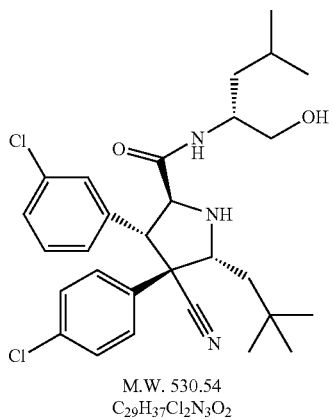 [SMILES: CC(C)C[C@H](CO)NC(=O)[C@H]1N[C@H](CC(C)(C)C)[C@@](C#N)(c2ccc(Cl)cc2)[C@@H]1c1cccc(Cl)c1]

M.W. 530.54
$C_{29}H_{37}Cl_2N_3O_2$

Reverse phase chromatography separation from the above example (Example 23a) gave (2S,3S,4S,5R)-3-(3-chloro-phenyl)-4-(4-chloro-phenyl)-4-cyano-5-(2,2-dimethyl-propyl)-pyrrolidine-2-carboxylic acid ((R)-1-hydroxymethyl-3-methyl-butyl)-amide (23.3 mg, 21.9%).

HRMS (ES$^+$) m/z Calcd for $C_{29}H_{37}Cl_2N_3O_2$+H [(M+H)$^+$]: 530.2336. found: 530.2336.

Example 24

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 3,4-difluoro-benzylamide

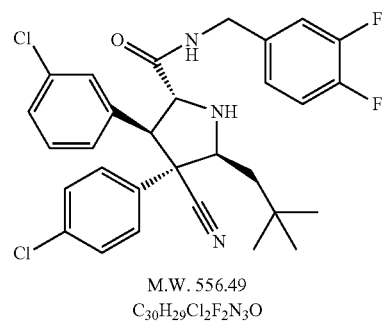 [SMILES: CC(C)(C)C[C@@H]1N[C@@H](C(=O)NCc2ccc(F)c(F)c2)[C@H](c2cccc(Cl)c2)[C@@]1(C#N)c1ccc(Cl)cc1]

M.W. 556.49
$C_{30}H_{29}Cl_2F_2N_3O$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 3,4-difluoro-benzyl amine (42.94 mg, 0.3 mmol), HATU (76 mg, 0.2 mmol) and iPr$_2$NEt (0.1 mL, 0.55 mmol) in CH$_2$Cl$_2$ (2 mL) at rt overnight to rac-(2R,3R,4R,5S)-3-(3-chloro-phenyl)-4-(4-chloro-phenyl)-4-cyano-5-(2,2-dimethyl-propyl)-pyrrolidine-2-carboxylic acid 3,4-difluoro-benzyl amide (53.5 mg, 48.1%).

HRMS (ES$^+$) m/z Calcd for $C_{30}H_{29}Cl_2F_2N_3O$+H [(M+H)$^+$]: 556.1729. found: 556.1728.

Example 25a

Preparation of intermediate rac-(2R,3R,4R,5S)-3-(3-chloro-phenyl)-4-(4-chloro-phenyl)-4-cyano-5-(2,2-dimethyl-propyl)-pyrrolidine-2-carboxylic acid trifluoroacetic acid

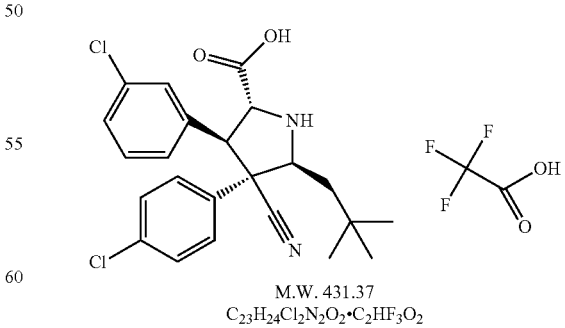

M.W. 431.37
$C_{23}H_{24}Cl_2N_2O_2 \cdot C_2HF_3O_2$

To a solution of rac-(2R,3R,4R,5S)-3-(3-chloro-phenyl)-4-(4-chloro-phenyl)-4-cyano-5-(2,2-dimethyl-propyl)-pyrrolidine-2-carboxylic acid tert-butyl ester prepared in Example 1c (2 g, 4.12 mmol) in dichloromethane (30 mL)

was added trifluoroacetic acid (10 mL). The reaction mixture was stirred at room temperature for 18 h, and concentrated. The residue was then triturated with ethyl ether hexanes, concentrated, dried under reduced pressure to give rac-(2R, 3R,4R,5S)-3-(3-chloro-phenyl)-4-(4-chloro-phenyl)-4-cyano-5-(2,2-dimethyl-propyl)-pyrrolidine-2-carboxylic acid trifluoroacetic acid as a white solid (2.1 g, 94%)

HRMS (ES$^+$) m/z Calcd for $C_{23}H_{24}Cl_2N_2O_2$+H [(M+H)$^+$]: 431.1288. found: 431.1287.

Example 25b

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-propyl)-amide

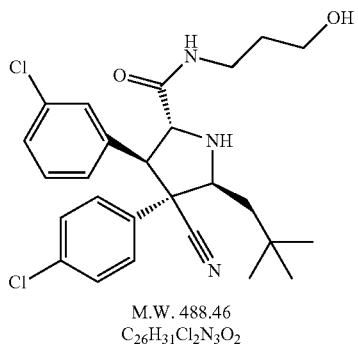 [SMILES: CC(C)(C)C[C@@H]1N[C@@H](C(=O)NCCCO)[C@H](c2cccc(Cl)c2)[C@@]1(C#N)c1ccc(Cl)cc1]

M.W. 488.46
$C_{26}H_{31}Cl_2N_3O_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid trifluoroacetic acid prepared in Example 25a (0.5 g, 1.1 mmol) was reacted with 3-amino-1-propanol (Aldrich) (0.4 g, 5.3 mmol), HATU (0.5 g, 1.31 mmol) and iPr$_2$NEt (1 g, 7.7 mmol) in CH$_2$Cl$_2$ (30 mL) at room temperature for 24 h to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-propyl)-amide as a white solid (0.56 g, 93%).

HRMS (ES$^+$) m/z Calcd for $C_{26}H_{31}Cl_2N_3O_2$+H [(M+H)$^+$]: 488.1866. found: 488.1864.

Example 26a

Preparation of intermediate (Z)-3-(3-chloro-2-fluoro-phenyl)-2-(4-chloro-phenyl)-acrylonitrile

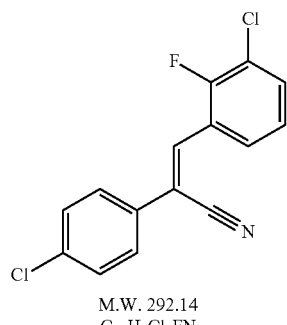

M.W. 292.14
$C_{15}H_8Cl_2FN$

In a manner similar to the method described in Example 1b, 4-chlorobenzyl cyanide (8.9 g, 59 mmol) was reacted with 3-chloro-2-fluorobenzaldehyde (Oakwood) (10 g, 63 mmol), methanolic solution (25 wt %) of sodium methoxide (15 mL, 66 mmol) in methanol (300 mL) at 40° C. for 5 h to give (Z)-3-(3-chloro-2-fluoro-phenyl)-2-(4-chloro-phenyl)-acrylonitrile as a white powder (16 g, 92%).

Example 26b

Preparation of intermediate rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid tert-butyl ester

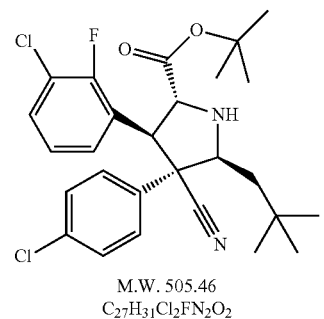 [SMILES: CC(C)(C)C[C@@H]1N[C@@H](C(=O)OC(C)(C)C)[C@H](c2cccc(Cl)c2F)[C@@]1(C#N)c1ccc(Cl)cc1]

M.W. 505.46
$C_{27}H_{31}Cl_2FN_2O_2$

In a manner similar to the method described in Example 1c, [3,3-dimethyl-but-(E)-ylideneamino]-acetic acid tert-butyl ester prepared in Example 1a (2.1 g, 10 mmol) was reacted with (Z)-3-(3-chloro-2-fluoro-phenyl)-2-(4-chloro-phenyl)-acrylonitrile (2.3 g, 7.9 mmol) prepared in Example 26a, AgF (1.5 g, 12 mmol), and triethylamine (2 g, 20 mmol) in 1,2-dichloroethane (130 mL) at room temperature for 18 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid tert-butyl ester as a white foam (2.7 g, 68%).

Example 26c

Preparation of intermediate rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid

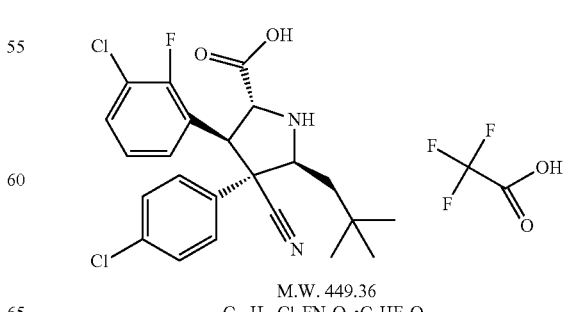

M.W. 449.36
$C_{23}H_{23}Cl_2FN_2O_2 \cdot C_2HF_3O_2$

In a manner similar to the method described in Example 25a, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid tert-butyl ester prepared in Example 26b (0.8 g, 1.6 mmol) was reacted with trifluoroacetic acid in dichloromethane at room temperature to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid as a white solid (0.9 g, 100%).

HRMS (ES⁺) m/z Calcd for $C_{23}H_{23}Cl_2FN_2O_2$+H [(M+H)⁺]: 449.1194 found: 449.1194.

Example 26d

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid [2-(cis-2,6-dimethyl-morpholin-4-yl)-ethyl]-amide

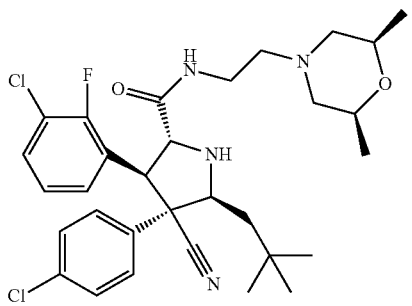

M.W. 589.58
$C_{31}H_{39}Cl_2FN_4O_2$

In a manner similar to the method described in Example 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.20 g, 0.36 mmol) was reacted with 4-(2-aminoethyl)-cis-2,6-dimethylmorpholine (Oakwood) (0.20 g, 1.2 mmol), HATU (0.3 g, 0.78 mmol) and iPr₂NEt (0.60 g, 4.6 mmol) in CH₂Cl₂ (20 mL) at room temperature for 20 hrs to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid [2-(cis-2,6-dimethyl-morpholin-4-yl)-ethyl]-amide as a white solid (0.20 g, 94%). HRMS (ES⁺) m/z Calcd for $C_{31}H_{39}Cl_2FN_4O_2$+H [(M+H)⁺]: 589.2507. found: 589.2507.

Example 27

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-cyclopropyl-ethyl)-amide

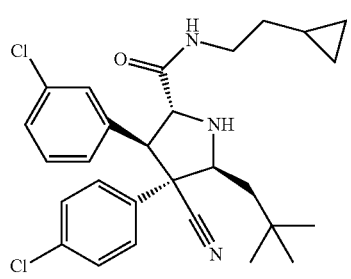

M.W. 498.50
$C_{28}H_{33}Cl_2N_3O$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid trifluoroacetic acid prepared in Example 25a (0.16 g, 0.37 mmol) was reacted with 2-cyclopropylethylamine (Bridge Organics) (0.1 g, 1.1 mmol), HATU (0.2 g, 0.5 mmol) and iPr₂NEt (0.3 g, 2 mmol) in CH₂Cl₂ (20 mL) at room temperature for 20 h to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-cyclopropyl-ethyl)-amide as a white solid (0.11 g, 37%).

HRMS (ES⁺) m/z Calcd for $C_{28}H_{33}Cl_2N_3O$+H [(M+H)⁺]: 498.2074. found: 498.2075.

Example 28

Preparation of rac-(3-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-propyl)-carbamic acid tert-butyl ester

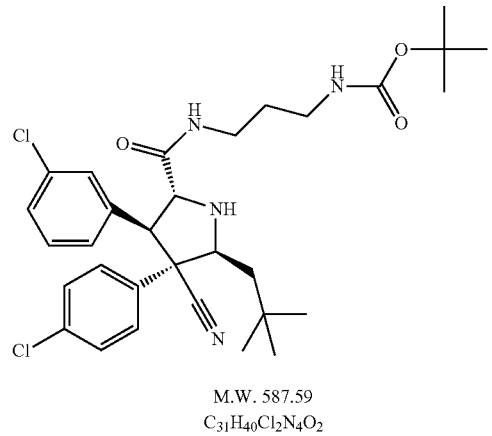 [SMILES: CC(C)(C)C[C@@H]1N[C@@H](C(=O)NCCCNC(=O)OC(C)(C)C)[C@H](c2cccc(Cl)c2)[C@@]1(C#N)c1ccc(Cl)cc1]

M.W. 587.59
$C_{31}H_{40}Cl_2N_4O_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid prepared in Example 25a (1 g, 1.8 mmol) was reacted with N-Boc-1,3-diaminopropane (Aldrich) (0.7 g, 4 mmol), HATU (1.4 g, 3.7 mmol) and iPr₂NEt (2.8 g, 21 mmol) in CH₂Cl₂ (100 mL) at room temperature for 60 h to give rac-(3-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-propyl)-carbamic acid tert-butyl ester as a white solid (0.92 g, 87%).

HRMS (ES⁺) m/z Calcd for $C_{31}H_{40}Cl_2N_4O_2$+H [(M+H)⁺]: 587.2550. found: 587.2551.

Example 29

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-amino-propyl)-amide

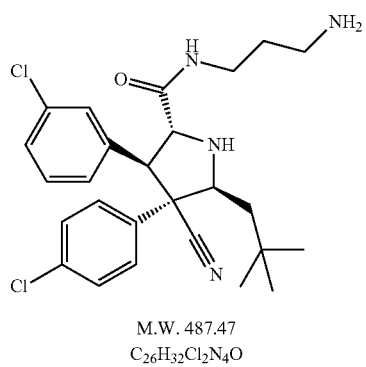 [SMILES: CC(C)(C)C[C@@H]1N[C@@H](C(=O)NCCCN)[C@H](c2cccc(Cl)c2)[C@@]1(C#N)c1ccc(Cl)cc1]

M.W. 487.47
$C_{26}H_{32}Cl_2N_4O$

To a solution of rac-(3-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-propyl)-carbamic acid tert-butyl ester prepared in Example 28 (0.9 g, 1.5 mmol) in dichloromethane (30 mL) was added trifluoroacetic acid (5 mL). The reaction mixture was stirred at room temperature for 1 h, and concentrated. The residue was then neutralized with saturated aqueous NaHCO$_3$ solution, and then extracted with ethyl acetate. The organic layer was separated, dried over MgSO$_4$, concentrated, dried under reduced pressure to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-amino-propyl)-amide as a white solid (0.8 g, 100%)

HRMS (ES$^+$) m/z Calcd for $C_{26}H_{32}Cl_2N_4O+H$ [(M+H)$^+$]: 487.2026. found: 487.2027.

Example 30

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [3-(1-acetyl-piperidin-4-ylamino)-propyl]-amide

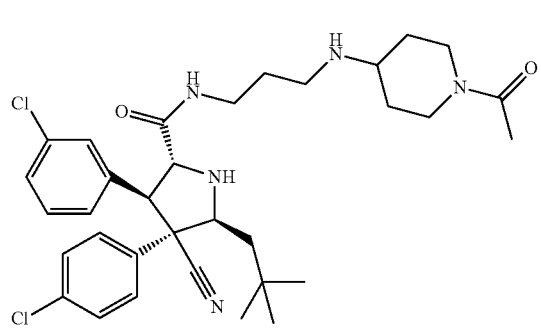

M.W. 640.65
$C_{34}H_{43}Cl_2N_5O_3$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-amino-propyl)-amide prepared in Example 29 (0.18 g, 0.37 mmol) was reacted with 1-acetylpiperidine-4-carboxylic acid (Lancaster) (0.7 g, 0.58 mmol), HATU (0.3 g, 0.78 mmol) and iPr$_2$NEt (0.5 g, 3.9 mmol) in CH$_2$Cl$_2$ (20 mL) at room temperature for 20 h to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid [3-(1-acetyl-piperidin-4-ylamino)-propyl]-amide as a white solid (0.16 g, 67%).

HRMS (ES$^+$) m/z Calcd for $C_{34}H_{43}Cl_2N_5O_3+H$ [(M+H)$^+$]: 640.2816. found: 640.2818.

Example 31a

Preparation of intermediate [3-Methyl-but-(E)-ylideneamino]-acetic acid tert-butyl ester

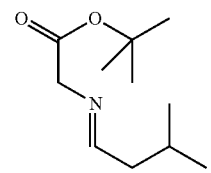

M.W. 199.16
$C_{11}H_{21}NO_2$

In a manner similar to the method described in Example 1a, glycine tert-butyl ester (0.65 g, 5 mmol) was reacted with isovaleraldehyde (Alfa) (0.43 g, 5 mmol) in CH$_2$Cl$_2$ at room temperature for 18 h to give [3-methyl-but-(E)-ylideneamino]-acetic acid tert-butyl ester as a colorless oil (0.98 g, 98%).

Example 31b

Preparation of intermediate rac-(2R,3R,4R,5S)-3-(3-chloro-phenyl)-4-(4-chloro-phenyl)-4-cyano-5-isobutyl-pyrrolidine-2-carboxylic acid tert-butyl ester

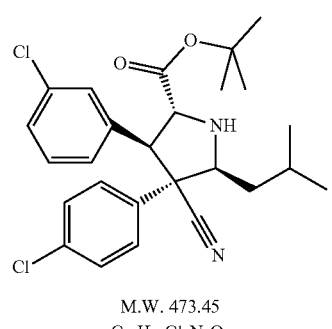

M.W. 473.45
$C_{26}H_{30}Cl_2N_2O_2$

In a manner similar to the method described in Example 1c, [3-methyl-but-(E)-ylideneamino]-acetic acid tert-butyl ester prepared in Example 31a (2 g, 10 mmol) was reacted with (Z)-3-(3-chloro-phenyl)-2-(4-chloro-phenyl)-acrylonitrile (2 g, 7.3 mmol) prepared in Example 1b, AgF (1.3 g, 10 mmol), and triethylamine (2 g, 20 mmol) in dichloromethane (100 mL) at room temperature for 18 h to give rac-(2R,3R,4R,5S)-3-(3-chloro-phenyl)-4-(4-chloro-phenyl)-4-cyano-5-isobutyl-pyrrolidine-2-carboxylic acid tert-butyl ester as a white foam (0.7 g, 20%).

Example 31c

Preparation of intermediate rac-(2R,3R,4R,5S)-3-(3-chloro-phenyl)-4-(4-chloro-phenyl)-4-cyano-5-isobutyl-pyrrolidine-2-carboxylic acid trifluoroacetic acid

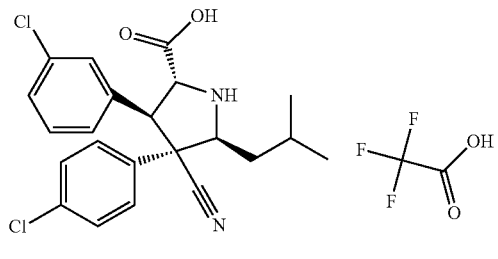

M.W. 417.34
$C_{22}H_{22}Cl_2N_2O_2 \cdot C_2HF_3O_2$

In a manner similar to the method described in Example 25a, rac-(2R,3R,4R,5S)-3-(3-chloro-phenyl)-4-(4-chloro-phenyl)-4-cyano-5-isobutyl-pyrrolidine-2-carboxylic acid tert-butyl ester prepared in Example 31b (0.4 g, 0.85 mmol) was reacted with trifluoroacetic acid in dichloromethane at room temperature to give rac-(2R,3R,4R,5S)-3-(3-chloro-phenyl)-4-(4-chloro-phenyl)-4-cyano-5-isobutyl-pyrrolidine-2-carboxylic acid trifluoroacetic acid as a off white solid (0.4 g, 89%).

HRMS (ES$^+$) m/z Calcd for $C_{22}H_{22}Cl_2N_2O_2+H [(M+H)^+]$: 417.1131. found: 417.1131.

Example 31d

Preparation of rac-(2R,3R,4R,5S)-3-(3-chloro-phenyl)-4-(4-chloro-phenyl)-4-cyano-5-isobutyl-pyrrolidine-2-carboxylic acid (3-hydroxy-propyl)-amide

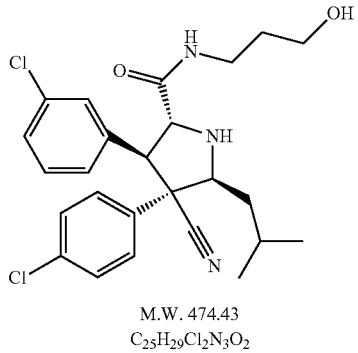 [SMILES: CC(C)C[C@@H]1N[C@@H](C(=O)NCCCO)[C@H](c2cccc(Cl)c2)[C@@]1(C#N)c1ccc(Cl)cc1]

M.W. 474.43
$C_{25}H_{29}Cl_2N_3O_2$

In a manner similar to the method described in Example 1e, rac-(2R,3R,4R,5S)-3-(3-chloro-phenyl)-4-(4-chloro-phenyl)-4-cyano-5-isobutyl-pyrrolidine-2-carboxylic acid trifluoroacetic acid prepared in Example 31c (0.6 g, 1.1 mmol) was reacted with 3-amino-1-propanol (Aldrich) (0.4 g, 5.3 mmol), HATU and iPr$_2$NEt in CH$_2$Cl$_2$ at room temperature to give rac-(2R,3R,4R,5S)-3-(3-chloro-phenyl)-4-(4-chloro-phenyl)-4-cyano-5-isobutyl-pyrrolidine-2-carboxylic acid (3-hydroxy-propyl)-amide as a white solid (0.21 g, 40%).

HRMS (ES$^+$) m/z Calcd for $C_{25}H_{29}Cl_2N_3O_2+H [(M+H)^+]$: 474.1710. found: 474.1710.

Example 32a

Preparation of intermediate {[1-(3-Chloro-phenyl)-meth-(E)-ylidene]-amino}-acetic acid tert-butyl ester

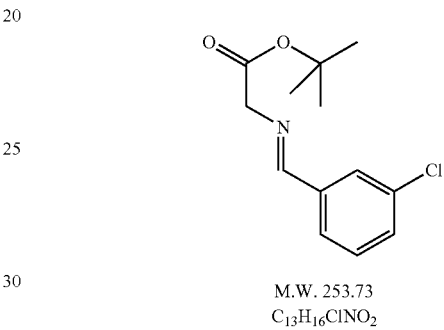

M.W. 253.73
$C_{13}H_{16}ClNO_2$

In a manner similar to the method described in Example 1a, glycine tert-butyl ester (1.31 g, 10 mmol) was reacted with 3-chlorobenzaldehyde (Aldrich) (1.4 g, 10 mmol) in CH$_2$Cl$_2$ at room temperature for 18 h to give {[1-(3-chloro-phenyl)-meth-(E)-ylidene]-amino}-acetic acid tert-butyl ester as a pale yellow oil (2.4 g, 95%).

Example 32b

Preparation of intermediate (Z)-2-(4-chloro-phenyl)-5,5-dimethyl-hex-2-enenitrile

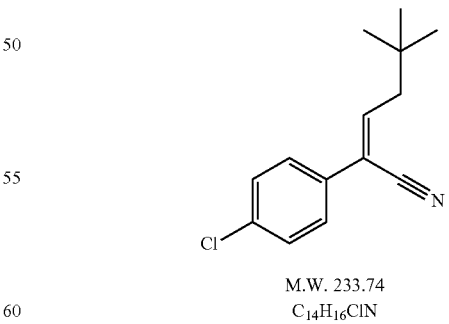

M.W. 233.74
$C_{14}H_{16}ClN$

In a manner similar to the method described in Example 1b, 4-chlorobenzyl cyanide (4.5 g, 30 mmol) was reacted with 3,3-dimethyl-butyraldehyde (Aldrich) (3 g, 30 mmol), methanolic solution (25 wt %) of sodium methoxide (7 mL, 30 mmol) in methanol (130 mL) at room temperature for 3 h to give (Z)-2-(4-chloro-phenyl)-5,5-dimethyl-hex-2-enenitrile as a colorless oil (5 g, 71%).

Example 32c

Preparation of intermediate rac-(2R,3R,4R,5S)-5-(3-Chloro-phenyl)-4-(4-chloro-phenyl)-4-cyano-3-(2,2-dimethyl-propyl)-pyrrolidine-2-carboxylic acid tert-butyl ester

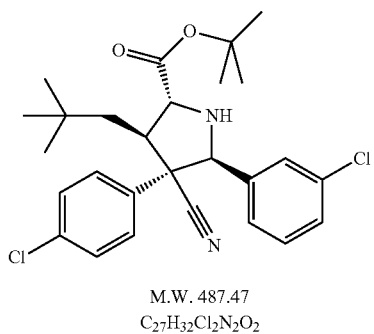 [SMILES: CC(C)(C)C[C@H]1[C@H](C(=O)OC(C)(C)C)N[C@@H](c2cccc(Cl)c2)[C@]1(C#N)c1ccc(Cl)cc1]

M.W. 487.47
$C_{27}H_{32}Cl_2N_2O_2$

In a manner similar to the method described in Example 1c, {[1-(3-chloro-phenyl)-meth-(E)-ylidene]-amino}-acetic acid tert-butyl ester prepared in Example 32a (2.6 g, 11 mmol) was reacted with (Z)-2-(4-chloro-phenyl)-5,5-dimethyl-hex-2-enenitrile (2 g, 7.9 mmol) prepared in Example 32b, AgF (1.3 g, 10 mmol), and triethylamine (2.2 g, 22 mmol) in 1,2-dichloroethane (100 mL) at room temperature for 24 h to give rac-(2R,3R,4R,5S)-5-(3-Chloro-phenyl)-4-(4-chloro-phenyl)-4-cyano-3-(2,2-dimethyl-propyl)-pyrrolidine-2-carboxylic acid tert-butyl ester as a white foam (1.2 g, 31%).

HRMS (ES$^+$) m/z Calcd for $C_{27}H_{32}Cl_2N_2O_2$+H [(M+H)$^+$]: 487.1914. found: 487.1912.

Example 32d

Preparation of intermediate rac-(2R,3R,4R,5S)-5-(3-Chloro-phenyl)-4-(4-chloro-phenyl)-4-cyano-3-(2,2-dimethyl-propyl)-pyrrolidine-2-carboxylic acid trifluoroacetic acid

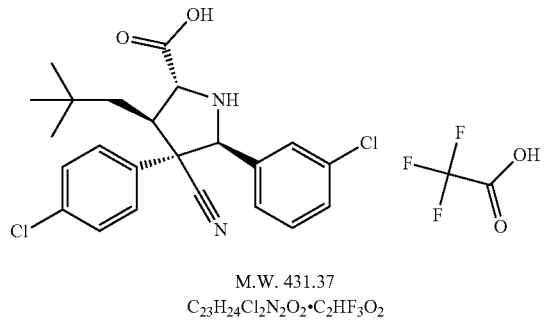

M.W. 431.37
$C_{23}H_{24}Cl_2N_2O_2 \cdot C_2HF_3O_2$

In a manner similar to the method described in Example 25a, rac-(2R,3R,4R,5S)-5-(3-Chloro-phenyl)-4-(4-chloro-phenyl)-4-cyano-3-(2,2-dimethyl-propyl)-pyrrolidine-2-carboxylic acid tert-butyl ester prepared in Example 32c (1.2 g, 2.5 mmol) was reacted with trifluoroacetic acid in dichloromethane at room temperature to give rac-(2R,3R,4R,5S)-5-(3-Chloro-phenyl)-4-(4-chloro-phenyl)-4-cyano-3-(2,2-dimethyl-propyl)-pyrrolidine-2-carboxylic acid trifluoroacetic acid as a yellow solid (1.0 g, 76%).

HRMS (ES$^+$) m/z Calcd for $C_{23}H_{24}Cl_2N_2O_2$+H [(M+H)$^+$]: 431.1288. found: 431.1288.

Example 32e

Preparation of rac-(2R,3R,4R,5R)-5-(3-chloro-phenyl)-4-(4-chloro-phenyl)-4-cyano-3-(2,2-dimethyl-propyl)-pyrrolidine-2-carboxylic acid (3-hydroxy-propyl)-amide

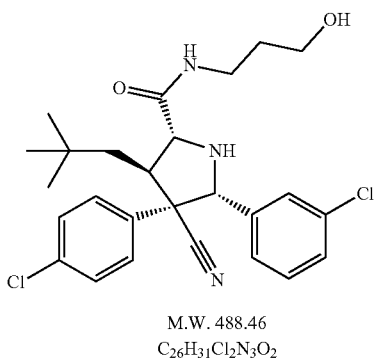 [SMILES: CC(C)(C)C[C@H]1[C@H](C(=O)NCCCO)N[C@H](c2cccc(Cl)c2)[C@]1(C#N)c1ccc(Cl)cc1]

M.W. 488.46
$C_{26}H_{31}Cl_2N_3O_2$

In a manner similar to the method described in Example 1e, rac-(2R,3R,4R,5R)-5-(3-chloro-phenyl)-4-(4-chloro-phenyl)-4-cyano-3-(2,2-dimethyl-propyl)-pyrrolidine-2-carboxylic acid trifluoroacetic acid prepared in Example 32d (0.6 g, 1.1 mmol) was reacted with 3-amino-1-propanol (Aldrich) (0.6 g, 8 mmol), HATU and iPr$_2$NEt in CH$_2$Cl$_2$ at room temperature to give rac-(2R,3R,4R,5R)-5-(3-chloro-phenyl)-4-(4-chloro-phenyl)-4-cyano-3-(2,2-dimethyl-propyl)-pyrrolidine-2-carboxylic acid (3-hydroxy-propyl)-amide as a yellow solid (0.12 g, 22%).

HRMS (ES$^+$) m/z Calcd for $C_{26}H_{31}Cl_2N_3O_2$+H [(M+H)$^+$]: 488.1866. found: 488.1864.

Example 33a

Preparation of intermediate (S)-2-[3,3-Dimethyl-but-(E)-ylideneamino]-propionic acid tert-butyl ester

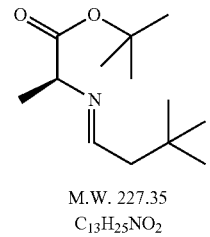 [SMILES: C[C@H](/N=C/CC(C)(C)C)C(=O)OC(C)(C)C]

M.W. 227.35
$C_{13}H_{25}NO_2$

A mixture of L-alanine tert-butyl ester hydrochloride (Bachem) (1.8 g, 10 mmol) and MgSO$_4$ in CH$_2$Cl$_2$ (100 mL) was added triethylamine (1.5 g, 15 mmol). The mixture was stirred at room temperature for 1 h, and 3,3-dimethyl-butyraldehyde (1 g, 10 mmol) was added. The reaction mixture was stirred at room temperature for 18 h. The mixture was filtered, and the filtrate was washed with water, brine, and concentrated. The residue was dried under reduced pressure to give (S)-2-[3,3-dimethyl-but-(E)-ylideneamino]-propionic acid tert-butyl ester as colorless oil (2.3 g, 100%) which was used without further purification.

Example 33b

Preparation of intermediate rac-(2R,3R,4R,5S)-3-(3-Chloro-phenyl)-4-(4-chloro-phenyl)-4-cyano-5-(2,2-dimethyl-propyl)-2-methyl-pyrrolidine-2-carboxylic acid tert-butyl ester

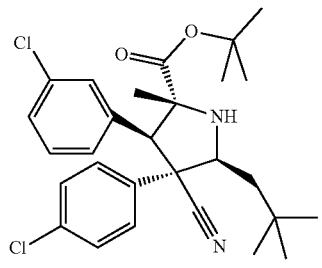

M.W. 501.50
$C_{28}H_{34}Cl_2N_2O_2$

In a manner similar to the method described in Example 1c, (S)-2-[3,3-dimethyl-but-(E)-ylideneamino]-propionic acid tert-butyl ester prepared in Example 33a (2.4 g, 11 mmol) was reacted with (Z)-3-(3-chloro-phenyl)-2-(4-chloro-phenyl)-acrylonitrile (2.4 g, 8.8 mmol) prepared in Example 1b, AgF (1.6 g, 13 mmol), and triethylamine (2.4 g, 24 mmol) in 1,2-dichloroethane (150 mL) at room temperature for 20 h to give rac-(2R,3R,4R,5S)-3-(3-Chloro-phenyl)-4-(4-chloro-phenyl)-4-cyano-5-(2,2-dimethyl-propyl)-2-methyl-pyrrolidine-2-carboxylic acid tert-butyl ester as a white foam (2.4 g, 54%).

HRMS (ES$^+$) in Calcd for $C_{28}H_{34}Cl_2N_2O_2$+H [(M+H)$^+$]: 501.2070. found: 501.2066.

Example 33c

Preparation of intermediate rac-(2R,3R,4R,5S)-3-(3-chloro-phenyl)-4-(4-chloro-phenyl)-4-cyano-5-(2,2-dimethyl-propyl)-2-methyl-pyrrolidine-2-carboxylic acid trifluoroacetic acid

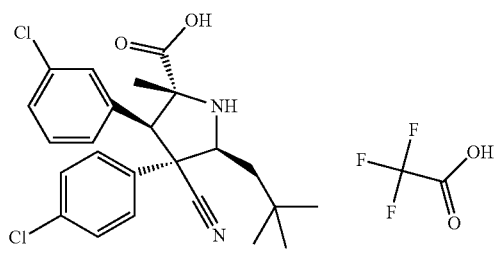

M.W. 445.39
$C_{24}H_{26}Cl_2N_2O_2 \cdot C_2HF_3O_2$

In a manner similar to the method described in Example 25a, rac-(2R,3R,4R,5S)-3-(3-chloro-phenyl)-4-(4-chloro-phenyl)-4-cyano-5-(2,2-dimethyl-propyl)-2-methyl-pyrrolidine-2-carboxylic acid tert-butyl ester prepared in Example 33b (1 g, 2 mmol) was reacted with trifluoroacetic acid in dichloromethane at room temperature to give rac-(2R,3R,4R,5S)-3-(3-chloro-phenyl)-4-(4-chloro-phenyl)-4-cyano-5-(2,2-dimethyl-propyl)-2-methyl-pyrrolidine-2-carboxylic acid trifluoroacetic acid as a white solid (1.1 g, 98%).

HRMS (ES$^+$) m/z Calcd for $C_{24}H_{26}Cl_2N_2O_2$+H [(M+H)$^+$]: 445.1444. found: 445.1443.

Example 33d

Preparation of rac-(2R,3R,4R,5S)-3-(3-chloro-phenyl)-4-(4-chloro-phenyl)-4-cyano-5-(2,2-dimethyl-propyl)-2-methyl-pyrrolidine-2-carboxylic acid (3-hydroxy-propyl)-amide

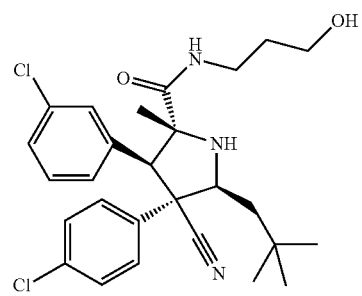

M.W. 502.48
$C_{27}H_{33}Cl_2N_3O_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-2-methyl-pyrrolidine-2-carboxylic acid trifluoroacetic acid prepared in Example 33c (0.4 g, 0.7 mmol) was reacted with 3-amino-1-propanol (Aldrich) (0.4 g, 5.3 mmol), HATU (0.5 g, 1.3 mmol) and iPr$_2$NEt (1 g, 7.7 mmol) in CH$_2$Cl$_2$ (30 mL) at room temperature for 24 h to give rac-(2R,3R,4R,5S)-3-(3-chloro-phenyl)-4-(4-chloro-phenyl)-4-cyano-5-(2,2-dimethyl-propyl)-2-methyl-pyrrolidine-2-carboxylic acid (3-hydroxy-propyl)-amide as a white solid (0.21 g, 60%).

HRMS (ES$^+$) m/z Calcd for $C_{27}H_{33}Cl_2N_3O_2$+H [(M+H)$^+$]: 502.2023. found: 502.2021.

Example 34a

Preparation of intermediate [2-Cyclopentyl-eth-(E)-ylideneamino]-acetic acid tert-butyl ester

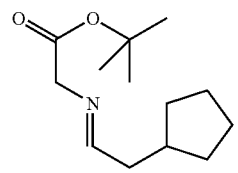

M.W. 225.33
$C_{13}H_{23}NO_2$

In a manner similar to the method described in Example 1a, glycine tert-butyl ester (0.7 g, 5 mmol) was reacted with 2-cyclopentylacetaldehyde (Betapharma) (0.9 g, 8 mmol) in $CH_2Cl_2$ at room temperature for 20 h to give [2-cyclopentyl-eth-(E)-ylideneamino]-acetic acid tert-butyl ester as a colorless oil (1 g, 90%).

Example 34b

Preparation of intermediate rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid tert-butyl ester

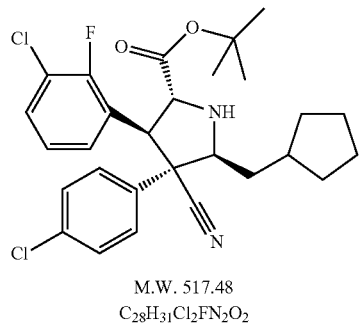 [SMILES: CC(C)(C)OC(=O)[C@@H]1N[C@@H](CC2CCCC2)[C@](C#N)(c2ccc(Cl)cc2)[C@H]1c1cccc(Cl)c1F]

M.W. 517.48
$C_{28}H_{31}Cl_2FN_2O_2$

In a manner similar to the method described in Example 1c, [2-cyclopentyl-eth-(E)-ylideneamino]-acetic acid tert-butyl ester prepared in Example 34a (1 g, 4.4 mmol) was vented with (Z)-3-(3-chloro-2-fluoro-phenyl)-2-(4-chloro-phenyl)-acrylonitrile (0.9 g, 3 mmol) prepared in Example 26a, AgF (1.3 g, 10 mmol), and triethylamine (2 g, 20 mmol) in dichloromethane (150 mL) at room temperature for 24 h to give rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid tert-butyl ester as a white foam (0.4 g, 26%).

Example 34c

Preparation of intermediate rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid trifluoroacetic acid

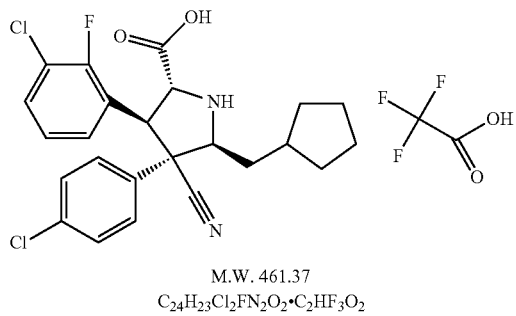

M.W. 461.37
$C_{24}H_{23}Cl_2FN_2O_2 \cdot C_2HF_3O_2$

In a manner similar to the method described in Example 25a, rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid tert-butyl ester prepared in Example 34b (0.4 g, 0.77 mmol) was reacted with trifluoroacetic acid in dichloromethane at room temperature to give rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid trifluoroacetic acid as a off white solid (0.5 g, 100%).

Example 34d

Preparation of rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid ((S)-3,4-dihydroxy-butyl)-amide

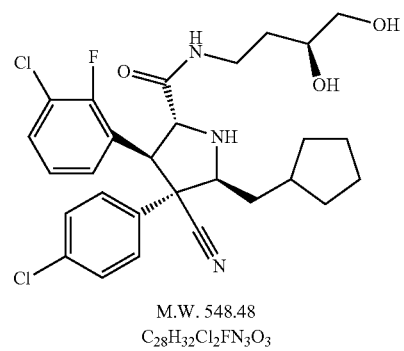 [SMILES: N#C[C@]1(c2ccc(Cl)cc2)[C@H](CC2CCCC2)N[C@@H](C(=O)NCC[C@H](O)CO)[C@@H]1c1cccc(Cl)c1F]

M.W. 548.48
$C_{28}H_{32}Cl_2FN_3O_3$

In a manner similar to the method described in Example 3b, rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid trifluoroacetic acid prepared in Example 34c (0.4 g, 0.71 mmol) was reacted with 2-((S)-2,2-dimethyl-[1,3]dioxolan-4-yl)-ethylamine (0.2 g, 1.4 mmol), HATU (0.4 g, 1.1 mmol) and $iPr_2NEt$ (0.6 g, 4.7 mmol) in $CH_2Cl_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid ((S)-3,4-dihydroxy-butyl)-amide as a white solid (0.14 g, 36%).

HRMS (ES$^+$) m/z Calcd for $C_{28}H_{32}Cl_2FN_3O_3$+H [(M+H)$^+$]: 548.1878. found: 548.1880.

Example 35

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (2-hydroxy-1,1-dimethyl-ethyl)-amide

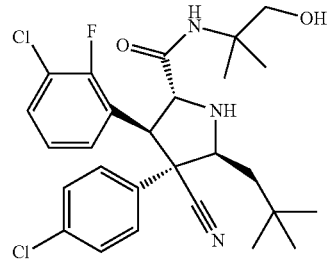

M.W. 520.47
$C_{27}H_{32}Cl_2FN_3O_2$

In a manner similar to the method described in Example 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.2 g, 0.36 mmol) was reacted with 2-amino-2-methyl-1-propanol (Fluka) (0.2 g, 2.2 mmol), HATU (0.3 g, 0.78 mmol) and iPr$_2$NEt (0.5 g, 3.8 mmol) in CH$_2$Cl$_2$ (10 mL) at room temperature for 24 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (2-hydroxy-1,1-dimethyl-ethyl)-amide as a white solid (0.17 g, 91%).

HRMS (ES$^+$) m/z Calcd for C$_{27}$H$_{32}$Cl$_2$FN$_3$O$_2$+H [(M+H)$^+$]: 520.1929. found: 590.1929.

Example 36

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (3-hydroxy-2,2-dimethyl-propyl)-amide

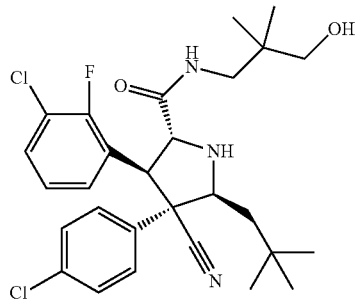

M.W. 534.5
C$_{28}$H$_{34}$Cl$_2$FN$_3$O$_2$

In a manner similar to the method described in Example 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.2 g, 0.36 mmol) was reacted with 3-amino-2,2-dimethyl-1-propanol (TCI-US) (0.2 g, 2 mmol), HATU (0.2 g, 0.5 mmol) and iPr$_2$NEt (0.2 g, 1.6 mmol) in CH$_2$Cl$_2$ (20 mL) at room temperature for 20 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (3-hydroxy-2,2-dimethyl-propyl)-amide as a white solid (0.16 g, 83%).

HRMS (ES$^+$) m/z Calcd for C$_{28}$H$_{34}$Cl$_2$FN$_3$O$_2$+H [(M+H)$^+$]: 534.2085. found: 534.2084.

Example 37

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid [2-(2-hydroxy-ethoxy)-ethyl]-amide

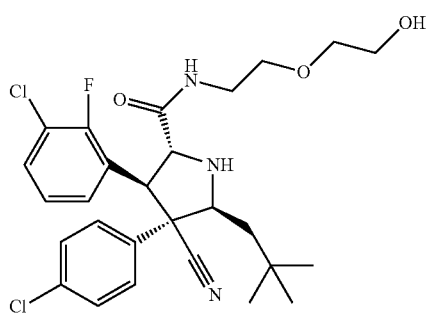

M.W. 536.47
C$_{27}$H$_{32}$Cl$_2$FN$_3$O$_3$

In a manner similar to the method described in Example 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.3 g, 0.54 mmol) was reacted with 2-(2-aminoethyl)ethanol (Aldrich) (0.15 g, 1.4 mmol), HATU (0.3 g, 0.75 mmol) and iPr$_2$NEt (0.6 g, 4.8 mmol) in CH$_2$Cl$_2$ (20 mL) at room temperature for 24 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid [2-(2-hydroxy-ethoxy)-ethyl]-amide as a white solid (0.18 g, 62%).

HRMS (ES$^+$) m/z Calcd for C$_{27}$H$_{32}$Cl$_2$FN$_3$O$_3$+H [(M+H)$^+$]: 536.1878. found: 536.1877.

Example 38

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (2-acetylamino-ethyl)-amide

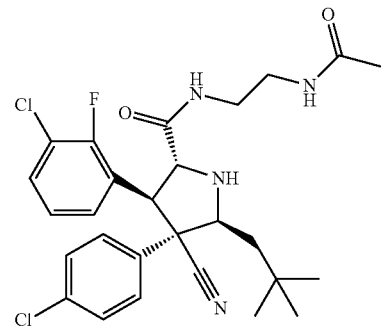

M.W. 533.47
C$_{27}$H$_{31}$Cl$_2$FN$_4$O$_2$

In a manner similar to the method described in Example 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.3 g, 0.54 mmol) was reacted with N-acetyl-ethylenediamine (Aldrich) (0.15 g, 1.5 mmol), HATU (0.3 g, 0.75 mmol) and iPr$_2$NEt (0.6 g, 4.8 mmol) in CH$_2$Cl$_2$ (20 mL) at room temperature for 24 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (2-acetylamino-ethyl)-amide as a white solid (0.24 g, 83%).

HRMS (ES$^+$) m/z Calcd for C$_{27}$H$_{31}$Cl$_2$FN$_4$O$_2$+H [(M+H)$^+$]: 533.1881 found: 533.1882.

Example 39

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (3-imidazol-1-yl-propyl)-amide

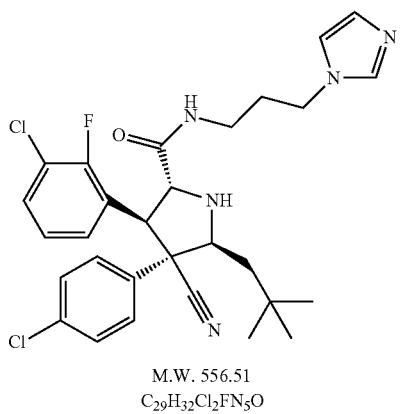 [SMILES: CC(C)(C)C[C@@H]1N[C@@H](C(=O)NCCCn2ccnc2)[C@H](c2cccc(Cl)c2F)[C@@]1(C#N)c1ccc(Cl)cc1]

M.W. 556.51
$C_{29}H_{32}Cl_2FN_5O$

In a manner similar to the method described in Example 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.2 g, 0.36 mmol) was reacted with 1-(3-aminopropyl)imidazole (Aldrich) (0.15 g, 1.2 mmol), HATU (0.3 g, 0.75 mmol) and iPr$_2$NEt (0.5 g, 3.6 mmol) in CH$_2$Cl$_2$ (20 mL) at room temperature for 24 h to give rac-(2R,3S,4R,5S)-3-(3-chloro-2-fluoro-phenyl)-4-(4-chlorophenyl)-4-cyano-5-(2,2-dimethyl-propyl)-pyrrolidine-2-carboxylic acid (3-imidazol-1-yl-propyl)-amide as a white solid (0.19 g, 94%).

HRMS (ES$^+$) m/z Calcd for $C_{29}H_{32}Cl_2FN_5O$+H [(M+H)$^+$]: 556.2041. found: 556.2040.

Example 40

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((R)-4-hydroxy-3-methyl-butyl)-amide

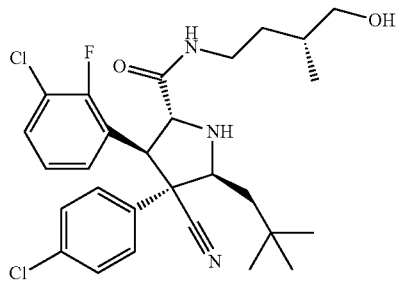

M.W. 534.5
$C_{28}H_{34}Cl_2FN_3O_2$

In a manner similar to the method described in Example 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.16 g, 0.29 mmol) was reacted with (R)-4-amino-2-methyl-1-butanol (TCI-US) (0.1 g, 1 mmol), HATU (0.2 g, 0.5 mmol) and iPr$_2$NEt (0.3 g, 2 mmol) in CH$_2$Cl$_2$ (20 mL) at room temperature for 20 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((R)-4-hydroxy-3-methyl-butyl)-amide as a white solid (0.1 g, 65%).

HRMS (ES$^+$) m/z Calcd for $C_{28}H_{34}Cl_2FN_3O_2$+H [(M+H)$^+$]: 534.2085. found: 534.2084.

Example 41

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid cyclopropylmethoxy-amide

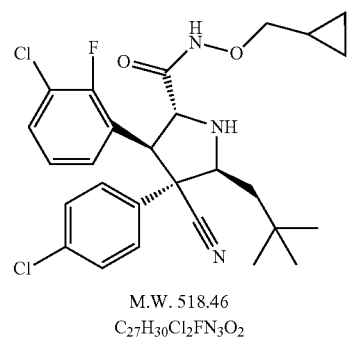 [SMILES: CC(C)(C)C[C@@H]1N[C@@H](C(=O)NOCC2CC2)[C@H](c2cccc(Cl)c2F)[C@@]1(C#N)c1ccc(Cl)cc1]

M.W. 518.46
$C_{27}H_{30}Cl_2FN_3O_2$

In a manner similar to the method described in Example 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.15 g, 0.27 mmol) was reacted with O-cyclopropylmethylhydroxyamine (HUHU Tech) (0.1 g, 1.1 mmol), HATU (0.2 g, 0.5 mmol) and iPr$_2$NEt (0.3 g, 2 mmol) in CH$_2$Cl$_2$ (20 mL) at room temperature for 20 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid cyclopropylmethoxy-amide as a white solid (30 mg, 21%).

HRMS (ES$^+$) m/z Calcd for $C_{27}H_{30}Cl_2FN_3O_2$+H [(M+H)$^+$]: 518.1772. found: 518.1773.

Example 42a

Preparation of intermediate rac-(2R,3R,4R,5S)-3,5-bis-(3-chloro-phenyl)-4-(4-chloro-phenyl)-4-cyano-pyrrolidine-2-carboxylic acid tert-butyl ester

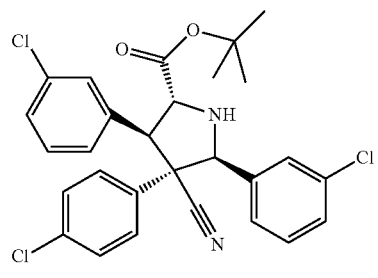

M.W. 527.88
$C_{28}H_{25}Cl_3N_2O_2$

In a manner similar to the method described in Example 1c, {[1-(3-Chloro-phenyl)-meth-(E)-ylidene]-amino}-acetic acid tert-butyl ester prepared in Example 32a (2 g, 7.6 mmol) was reacted with (Z)-3-(3-chloro-phenyl)-2-(4-chloro-phenyl)-acrylonitrile (0.55 g, 2 mmol) prepared in Example 1b, AgF (1.3 g, 10 mmol), and triethylamine (1.9 g, 19 mmol) in dichloromethane (30 mL) at 50° C. for 20 h to give rac-(2R,3R,4R,5S)-3,5-bis-(3-chloro-phenyl)-4-(4-chloro-phenyl)-4-cyano-pyrrolidine-2-carboxylic acid tert-butyl ester as a white foam (0.45 g, 44%).

HRMS (ES$^+$) m/z Calcd for C$_{28}$H$_{25}$Cl$_3$N$_2$O$_2$+H [(M+H)$^+$]: 527.1055. found: 527.1051.

Example 42b

Preparation of intermediate rac-(2R,3R,4R,5S)-3,5-bis-(3-chloro-phenyl)-4-(4-chloro-phenyl)-4-cyano-pyrrolidine-2-carboxylic acid trifluoroacetic acid

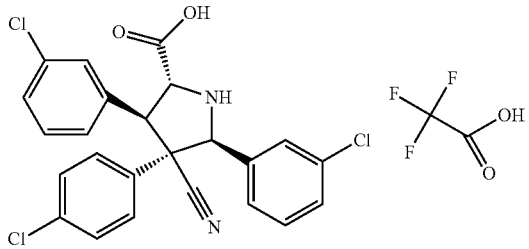

M.W. 471.77
C$_{24}$H$_{17}$Cl$_3$N$_2$O$_2$·C$_2$HF$_3$O$_2$

In a manner similar to the method described in Example 25a, rac-(2R,3R,4R,5S)-3,5-bis-(3-chloro-phenyl)-4-(4-chloro-phenyl)-4-cyano-pyrrolidine-2-carboxylic acid tert-butyl ester prepared in Example 42a (0.45 g, 0.85 mmol) was reacted with trifluoroacetic acid in dichloromethane at room temperature to give rac-(2R,3R,4R,5S)-3,5-bis-(3-chloro-phenyl)-4-(4-chloro-phenyl)-4-cyano-pyrrolidine-2-carboxylic acid trifluoroacetic acid as a off white solid (0.49 g, 98%).

HRMS (ES$^+$) m/z Calcd for C$_{24}$H$_{17}$Cl$_3$N$_2$O$_2$+H [(M+H)$^+$]: 471.0429. found: 471.0429.

Example 42c

Preparation of rac-(2R,3R,4R,5S)-3,5-bis-(3-chloro-phenyl)-4-(4-chloro-phenyl)-4-cyano-pyrrolidine-2-carboxylic acid [2-((S)-2,2-dimethyl-[1,3]dioxolan-4-yl)-ethyl]-amide

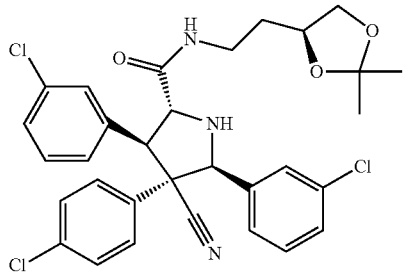

M.W. 598.96
C$_{31}$H$_{30}$Cl$_3$N$_3$O$_3$

In a manner similar to the method described in Example 1e, rac-(2R,3R,4R,5S)-3,5-bis-(3-chloro-phenyl)-4-(4-chloro-phenyl)-4-cyano-pyrrolidine-2-carboxylic acid trifluoroacetic acid prepared in Example 42b (0.3 g, 0.5 mmol) was reacted with 2-((S)-2,2-dimethyl-[1,3]dioxolan-4-yl)-ethylamine (0.3 g, 2 mmol), HATU (0.3 g, 0.75 mmol) and iPr$_2$NEt (0.6 g, 4 mmol) in CH$_2$Cl$_2$ (30 mL) at room temperature for 20 h to give rac-(2R,3R,4R,5S)-3,5-bis-(3-chloro-phenyl)-4-(4-chloro-phenyl)-4-cyano-pyrrolidine-2-carboxylic acid [2-((S)-2,2-dimethyl-[1,3]dioxolan-4-yl)-ethyl]-amide as a off white solid (0.25 g, 83%).

HRMS (ES$^+$) m/z Calcd for C$_{31}$H$_{30}$Cl$_3$N$_3$O$_3$+H [(M+H)$^+$]: 598.1426. found: 598.1424.

Example 42d

Preparation of rac-(2R,3R,4R,5S)-3,5-bis-(3-chloro-phenyl)-4-(4-chloro-phenyl)-4-cyano-pyrrolidine-2-carboxylic acid ((S)-3,4-dihydroxy-butyl)-amide

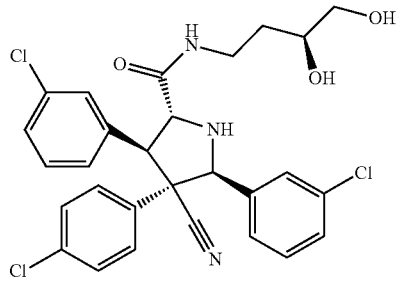

M.W. 558.89
C$_{28}$H$_{26}$Cl$_3$N$_3$O$_3$

To a solution of rac-(2R,3R,4R,5S)-3,5-bis-(3-chloro-phenyl)-4-(4-chloro-phenyl)-4-cyano-pyrrolidine-2-carboxylic acid [2-((S)-2,2-dimethyl-[1,3]dioxolan-4-yl)-ethyl]-amide prepared in Example 42c (0.4 g, 0.66 mol) in tetrahydrofuran (10 mL) was added aqueous HCl solution (1N, 10 mL). The reaction mixture was stirred at room temperature for 2 h, then concentrated. Then the residue was partitioned between ethyl acetate and water. The organic layer was separated, washed with water, aqueous saturated NaHCO$_3$, brine, dried over MgSO$_4$, concentrated, dried under reduced pressure to give rac-(2R,3R,4R,5S)-3,5-bis-(3-chloro-phenyl)-4-(4-chloro-phenyl)-4-cyano-pyrrolidine-2-carboxylic acid ((S)-3,4-dihydroxy-butyl)-amide as a white solid (0.2 g, 89%).

HRMS (ES$^+$) m/z Calcd for C$_{28}$H$_{26}$Cl$_3$N$_3$O$_3$+H [(M+H)$^+$]: 558.1113. found: 558.1110.

Example 43a

Preparation of intermediate [2-ethyl-but-(E)-ylideneamino]-acetic acid tert-butyl ester

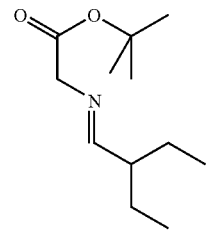

M.W. 213.32
C$_{12}$H$_{23}$NO$_2$

In a manner similar to the method described in Example 1a, glycine tert-butyl ester (0.65 g, 5 mmol) was reacted with 2-ethylbutyraldehyde (Aldrich) (0.55 g, 5 mmol) in CH$_2$Cl$_2$ at room temperature for 18 h to give [2-ethyl-but-(E)-ylideneamino]-acetic acid tert-butyl ester as a colorless oil (1 g, 94%).

Example 43b

Preparation of intermediate rac-(2R,3R,4R,5S)-3-(3-chloro-phenyl)-4-(4-chloro-phenyl)-4-cyano-5-(1-ethyl-propyl)-pyrrolidine-2-carboxylic acid tert-butyl ester

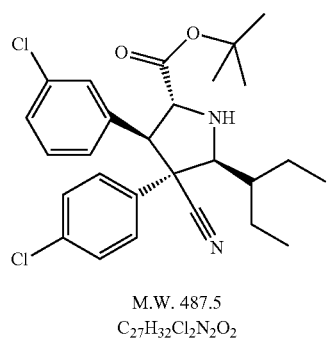 [SMILES: CCC(CC)[C@@H]1N[C@@H](C(=O)OC(C)(C)C)[C@H](c2cccc(Cl)c2)[C@@]1(C#N)c1ccc(Cl)cc1]

M.W. 487.5
C$_{27}$H$_{32}$Cl$_2$N$_2$O$_2$

In a manner similar to the method described in Example 1c, [2-ethyl-but-(E)-ylideneamino]-acetic acid tert-butyl ester prepared in Example 43a (1 g, 4.7 mmol) was reacted with (Z)-3-(3-chloro-phenyl)-2-(4-chloro-phenyl)-acrylonitrile (0.91 g, 3.3 mmol) prepared in Example 1b, AgF (1.5 g, 12 mmol), and triethylamine (1.9 g, 19 mmol) in 1,2-dichloroethane (50 mL) at room temperature for 18 h to give rac-(2R,3R,4R,5S)-3-(3-chloro-phenyl)-4-(4-chloro-phenyl)-4-cyano-5-(1-ethyl-propyl)-pyrrolidine-2-carboxylic acid tert-butyl ester as a white foam (1.1 g, 68%).

Example 43c

Preparation of intermediate rac-(2R,3R,4R,5S)-3-(3-chloro-phenyl)-4-(4-chloro-phenyl)-4-cyano-5-(1-ethyl-propyl)-pyrrolidine-2-carboxylic acid trifluoroacetic acid

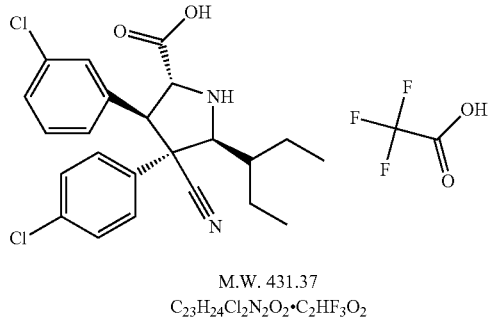

M.W. 431.37
C$_{23}$H$_{24}$Cl$_2$N$_2$O$_2$·C$_2$HF$_3$O$_2$

In a manner similar to the method described in Example 25a, rac-(2R,3R,4R,5S)-3-(3-chloro-phenyl)-4-(4-chloro-phenyl)-4-cyano-5-(1-ethyl-propyl)-pyrrolidine-2-carboxylic acid tert-butyl ester prepared in Example 43b (1.1 g, 2.3 mmol) was reacted with trifluoroacetic acid in dichloromethane at room temperature to give rac-(2R,3R,4R,5S)-3-(3-chloro-phenyl)-4-(4-chloro-phenyl)-4-cyano-5-(1-ethyl-propyl)-pyrrolidine-2-carboxylic acid trifluoroacetic acid as a white solid (1.2 g, 98%).

HRMS (ES$^+$) m/z Calcd for C$_{23}$H$_{24}$Cl$_2$N$_2$O$_2$+H [(M+H)$^+$]: 431.1288. found: 431.1286.

Example 43d

Preparation of rac-(2R,3R,4R,5S)-3-(3-chloro-phenyl)-4-(4-chloro-phenyl)-4-cyano-5-(1-ethyl-propyl)-pyrrolidine-2-carboxylic acid ((S)-3,4-dihydroxy-butyl)-amide

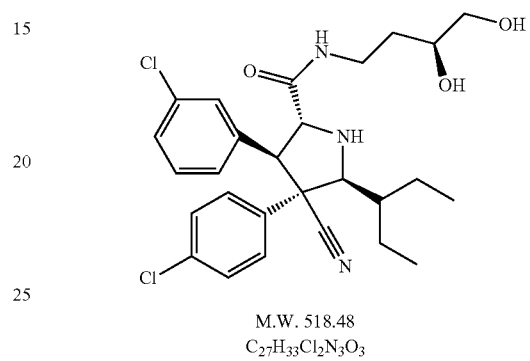

M.W. 518.48
C$_{27}$H$_{33}$Cl$_2$N$_3$O$_3$

In a manner similar to the method described in Examples 42c, 42d, rac-(2R,3R,4R,5S)-3-(3-chloro-phenyl)-4-(4-chloro-phenyl)-4-cyano-5-(1-ethyl-propyl)-pyrrolidine-2-carboxylic acid trifluoroacetic acid prepared in Example 43c (0.55 g, 1 mmol) was reacted with 2-((S)-2,2-dimethyl-[1,3]dioxolan-4-yl)-ethylamine (0.2 g, 1.3 mmol), HATU (0.4 g, 1.1 mmol) and iPr$_2$NEt (0.2 g, 1.5 mmol) in CH$_2$Cl$_2$ at room temperature for 20 h, then reacted with aqueous HCl solution in tetrahydrofuran at room temperature for 2 h to give rac-(2R,3R,4R,5S)-3-(3-chloro-phenyl)-4-(4-chloro-phenyl)-4-cyano-5-(1-ethyl-propyl)-pyrrolidine-2-carboxylic acid ((S)-3,4-dihydroxy-butyl)-amide as a white solid (0.5 g, 96%).

HRMS (ES$^+$) m/z Calcd for C$_{27}$H$_{33}$Cl$_2$N$_3$O$_3$+H [(M+H)$^+$]: 518.1972. found: 518.1970.

Example 44a

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide

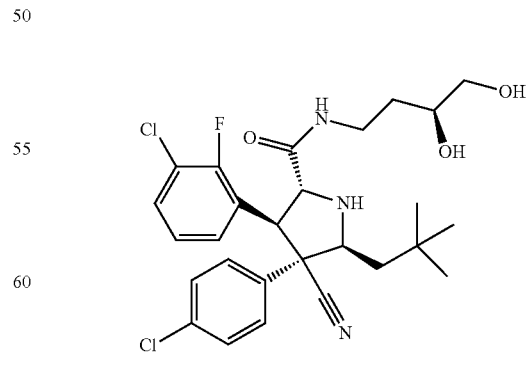

M.W. 536.47
C$_{27}$H$_{32}$Cl$_2$FN$_3$O$_3$

In a manner similar to the method described in Examples 42c, 42d, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.25 g, 0.44 mmol) was reacted with 2-((S)-2,2-dimethyl-[1,3]dioxolan-4-yl)-ethylamine (0.2 g, 1.3 mmol), HATU (0.3 g, 0.79 mmol) and iPr$_2$NEt (0.5 g, 3.9 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide as a white solid (0.21 g, 89%).

HRMS (ES$^+$) m/z Calcd for C$_{27}$H$_{32}$Cl$_2$FN$_3$O$_3$+H [(M+H)$^+$]: 536.1878. found: 536.1875.

Example 44b

Preparation of (2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide

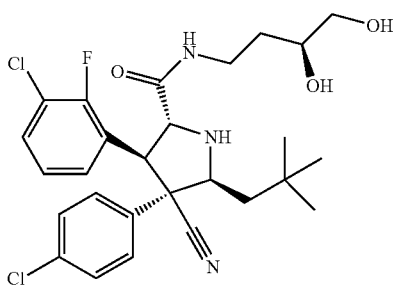

M.W. 536.47
C$_{27}$H$_{32}$Cl$_2$FN$_3$O$_3$

Rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide (0.19 g) was separated by chiral SFC chromatography to provide chiral-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide as a white solid (85 mg, 45%) and chiral-(2S,3R,4SR,5R)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide as a white solid (81 mg, 43%).

Example 45

Preparation of rac-(2R,3R,4R,5S)-3-(3-chloro-phenyl)-4-(4-chloro-phenyl)-4-cyano-5-isobutyl-pyrrolidine-2-carboxylic acid ((S)-3,4-dihydroxy-butyl)-amide

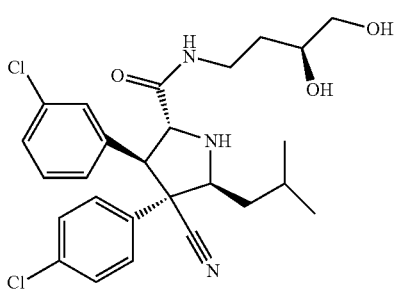

M.W. 504.46
C$_{26}$H$_{31}$Cl$_2$N$_3$O$_3$

In a manner similar to the method described in Examples 42c, 42d, rac-(2R,3R,4R,5S)-3-(3-chloro-phenyl)-4-(4-chloro-phenyl)-4-cyano-5-isobutyl-pyrrolidine-2-carboxylic acid trifluoroacetic acid prepared in Example 31c (0.4 g, 0.75 mmol) was reacted with 2-((S)-2,2-dimethyl-[1,3]dioxolan-4-yl)-ethylamine (0.25 g, 1.6 mmol), HATU (0.4 g, 1.1 mmol) and iPr$_2$NEt (1 g, 7.8 mmol) in CH$_2$Cl$_2$ at room temperature for 20 h, then reacted with aqueous HCl solution in tetrahydrofuran at room temperature for 2 h to give rac-(2R,3R,4R,5S)-3-(3-chloro-phenyl)-4-(4-chloro-phenyl)-4-cyano-5-isobutyl-pyrrolidine-2-carboxylic acid ((S)-3,4-dihydroxy-butyl)-amide as a white solid (0.4 g, 95%).

HRMS (ES$^+$) m/z Calcd for C$_{26}$H$_{31}$Cl$_2$N$_3$O$_3$+H [(M+H)$^+$]: 504.1815. found: 504.1815.

Example 46a

Preparation of intermediate rac-(2R,3R,4R,5R)-3-(3-chloro-phenyl)-4-(4-chloro-phenyl)-4-cyano-5-isobutyl-pyrrolidine-2-carboxylic acid tert-butyl ester

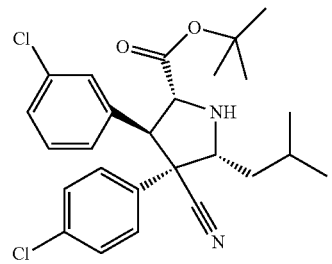

M.W. 473.45
C$_{26}$H$_{30}$Cl$_2$N$_2$O$_2$

In the preparation of rac-(2R,3R,4R,5S)-3-(3-chloro-phenyl)-4-(4-chloro-phenyl)-4-cyano-5-isobutyl-pyrrolidine-2-carboxylic acid tert-butyl ester as described in Example 31b, rac-(2R,3R,4R,5R)-3-(3-chloro-phenyl)-4-(4-chloro-phenyl)-4-cyano-5-isobutyl-pyrrolidine-2-carboxylic acid tert-butyl ester was obtained as the second product: white powder, Yield: 0.82 g, 24%.

HRMS (ES$^+$) m/z Calcd for C$_{26}$H$_{30}$Cl$_2$N$_2$O$_2$+H [(M+H)$^+$]: 473.1757. found: 473.1756.

Example 46b

Preparation of intermediate rac-(2R,3R,4R,5R)-3-(3-chloro-phenyl)-4-(4-chloro-phenyl)-4-cyano-5-isobutyl-pyrrolidine-2-carboxylic acid trifluoroacetic acid

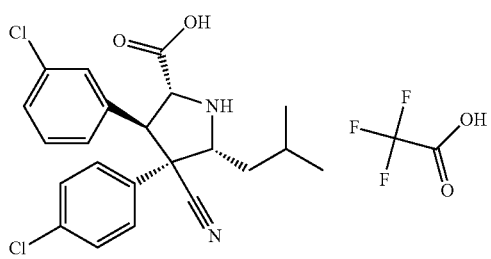

M.W. 417.34
C$_{22}$H$_{22}$Cl$_2$N$_2$O$_2$·C$_2$HF$_3$O$_2$

In a manner similar to the method described in Example 25a, rac-(2R,3R,4R,5R)-3-(3-chloro-phenyl)-4-(4-chloro-phenyl)-4-cyano-5-isobutyl-pyrrolidine-2-carboxylic acid tert-butyl ester prepared in Example 46a (0.6 g, 1.3 mmol) was reacted with trifluoroacetic acid in dichloromethane at room temperature to give rac-(2R,3R,4R,5R)-3-(3-chloro-phenyl)-4-(4-chloro-phenyl)-4-cyano-5-isobutyl-pyrrolidine-2-carboxylic acid trifluoroacetic acid as a off white solid (0.6 g, 89%).

Example 46c

Preparation of rac-(2R,3R,4R,5R)-3-(3-chloro-phenyl)-4-(4-chloro-phenyl)-4-cyano-5-isobutyl-pyrrolidine-2-carboxylic acid ((S)-3,4-dihydroxy-butyl)-amide

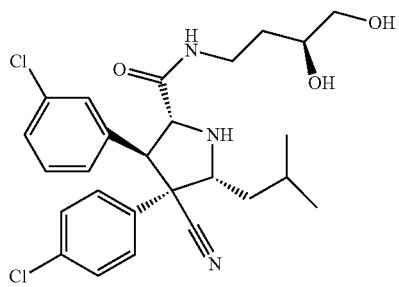

M.W. 504.46
$C_{26}H_{31}Cl_2N_3O_3$

In a manner similar to the method described in Examples 42c, 42d, rac-(2R,3R,4R,5R)-3-(3-chloro-phenyl)-4-(4-chloro-phenyl)-4-cyano-5-isobutyl-pyrrolidine-2-carboxylic acid trifluoroacetic acid prepared in Example 46b (0.6 g, 1.1 mmol) was reacted with 2-((S)-2,2-dimethyl-[1,3]dioxolan-4-yl)-ethylamine (0.3 g, 2 mmol), HATU (0.5 g, 1.3 mmol) and iPr$_2$NEt (1.2 g, 9.3 mmol) in CH$_2$Cl$_2$ at room temperature for 20 h, then reacted with aqueous HCl solution in tetrahydrofuran at room temperature for 2 h to give rac-(2R,3R,4R,5R)-3-(3-chloro-phenyl)-4-(4-chloro-phenyl)-4-cyano-5-isobutyl-pyrrolidine-2-carboxylic acid ((S)-3,4-dihydroxy-butyl)-amide as a white solid (0.6 g, 95%).
HRMS (ES$^+$) m/z Calcd for $C_{26}H_{31}Cl_2N_3O_3$+H [(M+H)$^+$]: 504.1815. found: 504.1816.

Example 47a

Preparation of intermediate rac-(2R,3R,4R,5R)-3-(3-chloro-phenyl)-4-(4-chloro-phenyl)-4-cyano-5-(1-ethyl-propyl)-pyrrolidine-2-carboxylic acid tert-butyl ester

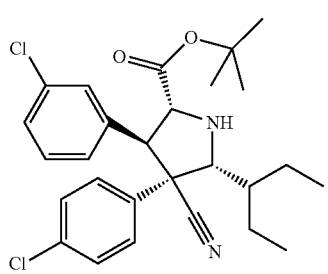

M.W. 487.5
$C_{27}H_{32}Cl_2N_2O_2$

In the preparation of rac-(2R,3R,4R,5S)-3-(3-chloro-phenyl)-4-(4-chloro-phenyl)-4-cyano-5-(1-ethyl-propyl)-pyrrolidine-2-carboxylic acid tert-butyl ester as described in Example 43b, rac-(2R,3R,4R,5R)-3-(3-chloro-phenyl)-4-(4-chloro-phenyl)-4-cyano-5-(1-ethyl-propyl)-pyrrolidine-2-carboxylic acid tert-butyl ester was obtained as the second product: white foam, Yield, 0.26 g, 16%.

Example 47b

Preparation of intermediate rac-(2R,3R,4R,5R)-3-(3-chloro-phenyl)-4-(4-chloro-phenyl)-4-cyano-5-(1-ethyl-propyl)-pyrrolidine-2-carboxylic acid trifluoroacetic acid

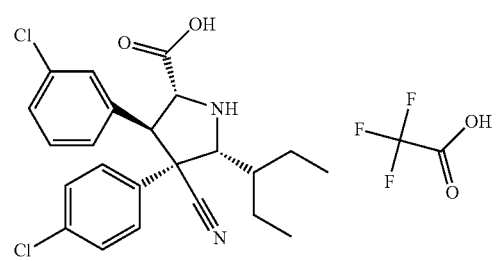

M.W. 431.37
$C_{23}H_{24}Cl_2N_2O_2 \cdot C_2HF_3O_2$

In a manner similar to the method described in Example 25a, rac-(2R,3R,4R,5R)-3-(3-chloro-phenyl)-4-(4-chloro-phenyl)-4-cyano-5-(1-ethyl-propyl)-pyrrolidine-2-carboxylic acid tert-butyl ester prepared in Example 47a (0.25 g, 0.5 mmol) was reacted with trifluoroacetic acid in dichloromethane at room temperature to give rac-(2R,3R,4R,5R)-3-(3-chloro-phenyl)-4-(4-chloro-phenyl)-4-cyano-5-(1-ethyl-propyl)-pyrrolidine-2-carboxylic acid trifluoroacetic acid as a off white solid (0.2 g, 73%).
HRMS (ES$^+$) m/z Calcd for $C_{23}H_{24}Cl_2N_2O_2$+H [(M+H)$^+$]: 431.1288. found: 431.1285.

Example 47c

Preparation of rac-(2R,3R,4R,5R)-3-(3-chloro-phenyl)-4-(4-chloro-phenyl)-4-cyano-5-(1-ethyl-propyl)-pyrrolidine-2-carboxylic acid ((S)-3,4-dihydroxy-butyl)-amide

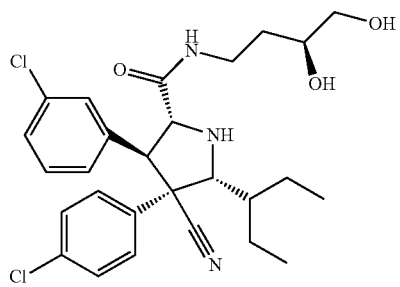

M.W. 518.48
$C_{27}H_{33}Cl_2N_3O_3$

In a manner similar to the method described in Example 42e, rac-(2R,3R,4R,5S)-3-(3-chloro-phenyl)-4-(4-chloro-phenyl)-4-cyano-5-(1-ethyl-propyl)-pyrrolidine-2-carboxylic acid trifluoroacetic acid prepared in Example 47b (0.27 g, 0.5 mmol) was reacted with 2-((S)-2,2-dimethyl-[1,3]dioxolan-4-yl)-ethylamine (0.2 g, 1.3 mmol), HATU (0.4 g, 1.1 mmol) and iPr₂NEt (0.4 g, 3 mmol) in CH₂Cl₂ at room temperature for 20 h, then reacted with aqueous HCl solution in tetrahydrofuran at room temperature for 2 h to give rac-(2R, 3R,4R,5R)-3-(3-chloro-phenyl)-4-(4-chloro-phenyl)-4-cyano-5-(1-ethyl-propyl)-pyrrolidine-2-carboxylic acid ((8)-3, 4-dihydroxy-butyl)-amide as a white solid (0.23 g, 88%).

HRMS (ES⁺) m/z Calcd for $C_{27}H_{33}Cl_2N_3O_3$+H [(M+H)⁺]: 518.1972. found: 518.1971.

Example 48a

Preparation of intermediate (1-ethyl-propylideneamino)-acetic acid tert-butyl ester

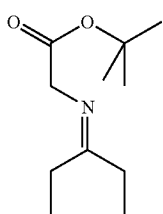

M.W. 199.16
$C_{11}H_{21}NO_2$

A mixture of glycine tert-butyl ester (Alfa) (0.66 g, 10 mmol) and 3-pentanone (6 g, 70 mmol) in ethanol (6 mL) was heated at 110° C. in a sealed tube for 48 h. The reaction mixture was concentrated and dried in vacuo to give crude (1-ethyl-propylideneamino)-acetic acid tert-butyl ester as a colorless oil (1.0 g). The crude product contains unreacted glycine tert-butyl ester and was used without further purification.

Example 48b

Preparation of intermediate rac-(2R,3R,4R)-3-(3-chloro-phenyl)-4-(4-chloro-phenyl)-4-cyano-5,5-diethyl-pyrrolidine-2-carboxylic acid tert-butyl ester

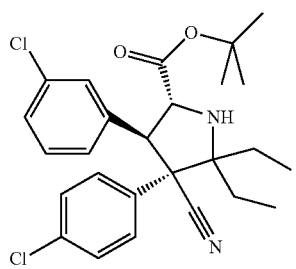

M.W. 473.45
$C_{26}H_{30}Cl_2N_2O_2$

In a manner similar to the method described in Example 1c, crude (1-ethyl-propylideneamino)-acetic acid tert-butyl ester prepared in Example 48a (1.2 g, 6 mmol) was reacted with (Z)-3-(3-chloro-phenyl)-2-(4-chloro-phenyl)-acrylonitrile (0.7 g, 2.5 mmol) prepared in Example 1b, AgF (1.9 g, 15 mmol), and triethylamine (2.5 g, 25 mmol) in 1,2-dichloroethane (130 mL) at room temperature for 10 h to give rac-(2R,3R,4R)-3-(3-chloro-phenyl)-4-(4-chloro-phenyl)-4-cyano-5,5-diethyl-pyrrolidine-2-carboxylic acid tert-butyl ester as a yellow gum (0.33 g, 28%).

Example 48c

Preparation of intermediate rac-(2R,3R,4R)-3-(3-chloro-phenyl)-4-(4-chloro-phenyl)-4-cyano-5,5-diethyl-pyrrolidine-2-carboxylic acid trifluoroacetic acid

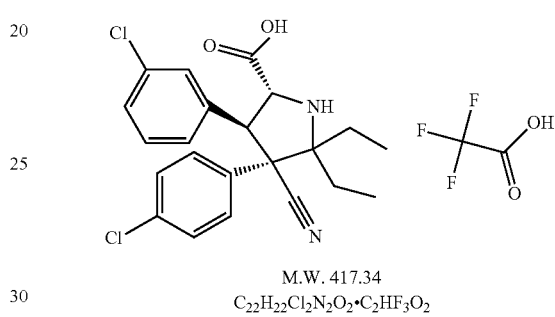

M.W. 417.34
$C_{22}H_{22}Cl_2N_2O_2 \cdot C_2HF_3O_2$

In a manner similar to the method described in Example 25a, rac-(2R,3R,4R)-3-(3-chloro-phenyl)-4-(4-chloro-phenyl)-4-cyano-5,5-diethyl-pyrrolidine-2-carboxylic acid tert-butyl ester prepared in Example 48c (0.33 g, 0.7 mmol) was reacted with trifluoroacetic acid in dichloromethane at room temperature to give rac-(2R,3R,4R)-3-(3-chloro-phenyl)-4-(4-chloro-phenyl)-4-cyano-5,5-diethyl-pyrrolidine-2-carboxylic acid trifluoroacetic acid as a off white foam (0.35 g, 96%).

HRMS (ES⁺) m/z Calcd for $C_{22}H_{22}Cl_2N_2O_2$+H [(M+H)⁺]: 417.1131.0429. found: 417.1132.

Example 48d

Preparation of rac-(2R,3R,4R)-3-(3-chloro-phenyl)-4-(4-chloro-phenyl)-4-cyano-5,5-diethyl-pyrrolidine-2-carboxylic acid ((S)-3,4-dihydroxy-butyl)-amide

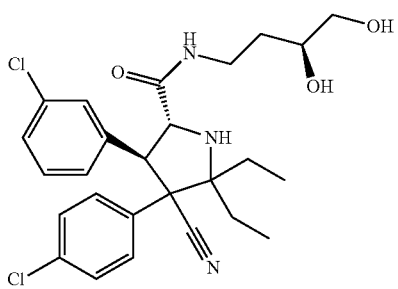

M.W. 504.46
$C_{26}H_{31}Cl_2N_3O_3$

In a manner similar to the method described in Examples 42c, 42d, rac-(2R,3R,4R)-3-(3-chloro-phenyl)-4-(4-chloro-phenyl)-4-cyano-5,5-diethyl-pyrrolidine-2-carboxylic acid trifluoroacetic acid prepared in Example 48c (0.33 g, 0.62 mmol) was reacted with 2-((S)-2,2-dimethyl-[1,3]dioxolan-4-yl)-ethylamine (0.15 g, 1 mmol), HATU (0.34 g, 0.89 mmol) and iPr$_2$NEt (1 g, 7.8 mmol) in CH$_2$Cl$_2$ at room temperature for 20 h, then reacted with aqueous HCl solution in tetrahydrofuran at room temperature for 2 h to give rac-(2R,3R,4R)-3-(3-chloro-phenyl)-4-(4-chloro-phenyl)-4-cyano-5,5-diethyl-pyrrolidine-2-carboxylic acid ((S)-3,4-dihydroxy-butyl)-amide as a off white solid (0.4 g, 95%).

HRMS (ES$^+$) m/z Calcd for C$_{26}$H$_{31}$Cl$_2$N$_3$O$_3$+H [(M+H)$^+$]: 504.1815. found: 504.1815.

Example 49a

Preparation of intermediate [2-methyl-prop-(E)-ylideneamino]-acetic acid tert-butyl ester

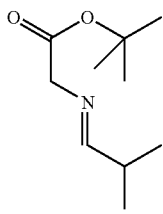

M.W. 185.27
C$_{10}$H$_{19}$NO$_2$

In a manner similar to the method described in Example 1a, glycine tert-butyl ester (0.65 g, 5 mmol) was reacted with isobutyraldehyde (Aldrich) (0.4 g, 5 mmol) in CH$_2$Cl$_2$ at room temperature for 20 h to give [2-methyl-prop-(E)-ylideneamino]-acetic acid tert-butyl ester as a colorless oil (0.9 g, 97%).

Example 49b

Preparation of intermediate rac-(2R,3R,4R,5S)-3-(3-chloro-phenyl)-4-(4-chloro-phenyl)-4-cyano-5-isopropyl-pyrrolidine-2-carboxylic acid tert-butyl ester

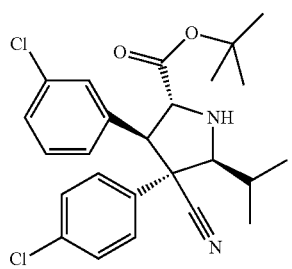

M.W. 459.42
C$_{25}$H$_{28}$Cl$_2$N$_2$O$_2$

In a manner similar to the method described in Example 1c, [2-methyl-prop-(E)-ylideneamino]-acetic acid tert-butyl ester prepared in Example 49a (1 g, 5.4 mmol) was reacted with (Z)-3-(3-chloro-phenyl)-2-(4-chloro-phenyl)-acrylonitrile (0.85 g, 3.1 mmol) prepared in Example 1b, AgF (1.5 g, 12 mmol), and triethylamine (2 g, 20 mmol) in dichloromethane (100 mL) at room temperature for 20 h to give rac-(2R,3R,4R,5S)-3-(3-chloro-phenyl)-4-(4-chloro-phenyl)-4-cyano-5-isopropyl-pyrrolidine-2-carboxylic acid tert-butyl ester as a white foam (0.64 g, 45%).

Example 49c

Preparation of intermediate rac-(2R,3R,4R,5S)-3-(3-chloro-phenyl)-4-(4-chloro-phenyl)-4-cyano-5-isopropyl-pyrrolidine-2-carboxylic acid trifluoroacetic acid

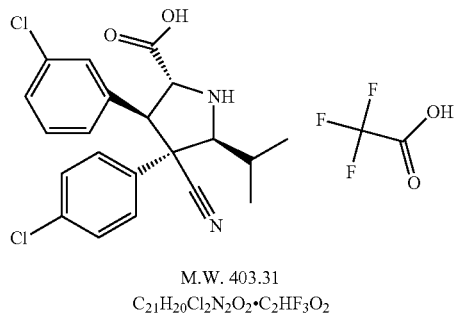

M.W. 403.31
C$_{21}$H$_{20}$Cl$_2$N$_2$O$_2$·C$_2$HF$_3$O$_2$

In a manner similar to the method described in Example 25a, rac-(2R,3R,4R,5S)-3-(3-chloro-phenyl)-4-(4-chloro-phenyl)-4-cyano-5-isopropyl-pyrrolidine-2-carboxylic acid tert-butyl ester prepared in Example 49b (0.64 g, 1.4 mmol) was reacted with trifluoroacetic acid in dichloromethane at room temperature to give rac-(2R,3R,4R,5S)-3-(3-chloro-phenyl)-4-(4-chloro-phenyl)-4-cyano-5-isopropyl-pyrrolidine-2-carboxylic acid trifluoroacetic acid as a off white solid (0.7 g, 100%).

HRMS (ES$^+$) m/z Calcd for C$_{21}$H$_{20}$Cl$_2$N$_2$O$_2$+H [(M+H)$^+$]: 403.0975. found: 403.0974.

Example 49d

Preparation of rac-(2R,3R,4R,5S)-3-(3-chloro-phenyl)-4-(4-chloro-phenyl)-4-cyano-5-isopropyl-pyrrolidine-2-carboxylic acid ((S)-3,4-dihydroxy-butyl)-amide

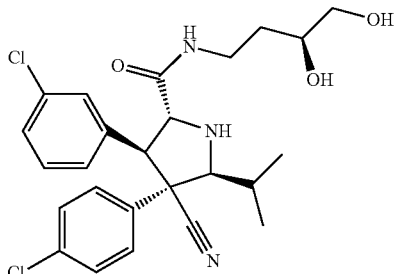

M.W. 490.43
C$_{25}$H$_{29}$Cl$_2$N$_3$O$_3$

In a manner similar to the method described in Examples 42c, 42d, rac-(2R,3R,4R,5S)-3-(3-chloro-phenyl)-4-(4-chloro-phenyl)-4-cyano-5-isopropyl-pyrrolidine-2-carboxylic acid trifluoroacetic acid prepared in Example 49c (0.5 g, 0.97 mmol) was reacted with 2-((S)-2,2-dimethyl-[1,3]dioxolan-4-yl)-ethylamine (0.25 g, 1.7 mmol), HATU (0.5 g, 1.3 mmol) and iPr$_2$NEt (1 g, 7.8 mmol) in CH$_2$Cl$_2$ at room temperature for 20 h, then reacted with aqueous HCl solution in tetrahydrofuran at room temperature for 2 h to give rac-(2R,3R,4R,5S)-3-(3-chloro-phenyl)-4-(4-chloro-phenyl)-4-cyano-5-isopropyl-pyrrolidine-2-carboxylic acid ((S)-3,4-dihydroxy-butyl)-amide as a white solid (0.25 g, 52%).

HRMS (ES$^+$) m/z Calcd for C$_{25}$H$_{29}$Cl$_2$N$_3$O$_3$+H [(M+H)$^+$]: 490.1659. found: 490.1657.

Example 50a

Preparation of intermediate {[1-cyclohexyl-meth-(E)-ylidene]-amino}-acetic acid tert-butyl ester

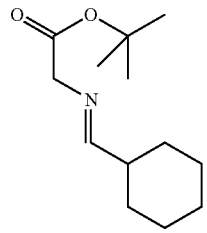

M.W. 225.33
C$_{13}$H$_{23}$NO$_2$

In a manner similar to the method described in Example 1a, glycine tert-butyl ester (0.65 g, 5 mmol) was reacted with cyclohexanecarbaldehyde (Aldrich) (0.6 g, 5 mmol) in CH$_2$Cl$_2$ at room temperature for 20 h to give {[1-cyclohexyl-meth-(E)-ylidene]-amino}-acetic acid tert-butyl ester as a colorless oil (1.2 g, 100%).

Example 50b

Preparation of intermediate rac-(2R,3R,4R,5S)-3-(3-chloro-phenyl)-4-(4-chloro-phenyl)-4-cyano-5-cyclohexyl-pyrrolidine-2-carboxylic acid tert-butyl ester

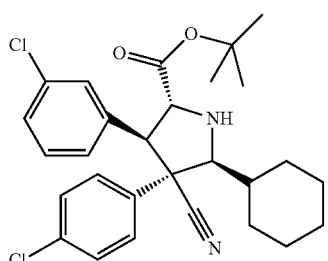

M.W. 499.49
C$_{28}$H$_{32}$Cl$_2$N$_2$O$_2$

In a manner similar to the method described in Example 1c, {[1-cyclohexyl-meth-(E)-ylidene]-amino}-acetic acid tert-butyl ester prepared in Example 50a (1.2 g, 5.3 mmol) was reacted with (Z)-3-(3-chloro-phenyl)-2-(4-chloro-phenyl)-acrylonitrile (1 g, 3.7 mmol) prepared in Example 1b, AgF (1.5 g, 12 mmol), and triethylamine (2 g, 20 mmol) in dichloromethane (100 mL) at room temperature for 20 h to give rac-(2R,3R,4R,5S)-3-(3-chloro-phenyl)-4-(4-chloro-phenyl)-4-cyano-5-cyclohexyl-pyrrolidine-2-carboxylic acid tert-butyl ester as a white foam (0.69 g, 38%).

Example 50c

Preparation of intermediate rac-(2R,3R,4R,5S)-3-(3-chloro-phenyl)-4-(4-chloro-phenyl)-4-cyano-5-cyclohexyl-pyrrolidine-2-carboxylic acid trifluoroacetic acid

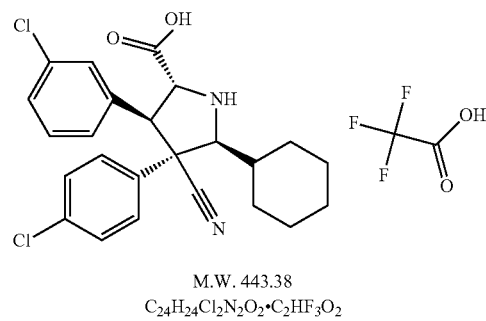

M.W. 443.38
C$_{24}$H$_{24}$Cl$_2$N$_2$O$_2$·C$_2$HF$_3$O$_2$

In a manner similar to the method described in Example 25a, rac-(2R,3R,4R,5S)-3-(3-chloro-phenyl)-4-(4-chloro-phenyl)-4-cyano-5-cyclohexyl-pyrrolidine-2-carboxylic acid tert-butyl ester prepared in Example 50b (0.69 g, 1.4 mmol) was reacted with trifluoroacetic acid in dichloromethane at room temperature to give rac-(2R,3R,4R,5S)-3-(3-chloro-phenyl)-4-(4-chloro-phenyl)-4-cyano-5-cyclohexyl-pyrrolidine-2-carboxylic acid trifluoroacetic acid as a off white solid (0.8 g, 100%).

HRMS (ES$^+$) m/z Calcd for C$_{24}$H$_{24}$Cl$_2$N$_2$O$_2$+H [(M+H)$^+$]: 443.1288. found: 443.1286.

Example 50d

Preparation of rac-(2R,3R,4R,5S)-3-(3-chloro-phenyl)-4-(4-chloro-phenyl)-4-cyano-5-cyclohexyl-pyrrolidine-2-carboxylic acid ((S)-3,4-dihydroxy-butyl)-amide

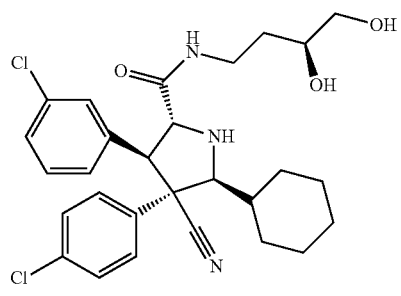

M.W. 530.49
C$_{28}$H$_{33}$Cl$_2$N$_3$O$_3$

In a manner similar to the method described in Examples 42c, 42d, rac-(2R,3R,4R,5S)-3-(3-chloro-phenyl)-4-(4-chloro-phenyl)-4-cyano-5-cyclohexyl-pyrrolidine-2-carboxylic acid trifluoroacetic acid prepared in Example 50c (0.5 g, 0.76 mmol) was reacted with 2-((S)-2,2-dimethyl-[1,3]dioxolan-4-yl)-ethylamine (0.3 g, 2 mmol), HATU (0.4 g, 1.1 mmol) and iPr$_2$NEt (0.9 g, 7 mmol) in CH$_2$Cl$_2$ at room temperature for 20 h, then reacted with aqueous HCl solution in tetrahydrofuran at room temperature for 2 h to give rac-(2R,3R,4R,5S)-3-(3-chloro-phenyl)-4-(4-chloro-phenyl)-4-cyano-5-cyclohexyl-pyrrolidine-2-carboxylic acid ((S)-3,4-dihydroxy-butyl)-amide as a white solid (0.25 g, 62%).

HRMS (ES$^+$) m/z Calcd for C$_{28}$H$_{33}$Cl$_2$N$_3$O$_3$+H [(M+H)$^+$]: 530.1972. found: 530.1971.

Example 51a

Preparation of intermediate [2,2-dimethyl-prop-(E)-ylideneamino]-acetic acid tert-butyl ester

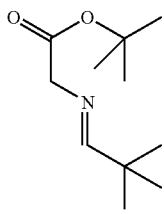

M.W. 199.16
C$_{11}$H$_{21}$NO$_2$

In a manner similar to the method described in Example 1a, glycine tert-butyl ester (0.65 g, 5 mmol) was reacted with trimethylacetaldehyde (Aldrich) (0.42 g, 5 mmol) in CH$_2$Cl$_2$ at room temperature for 20 h to give [2,2-dimethyl-prop-(E)-ylideneamino]-acetic acid tert-butyl ester as a colorless oil (1.0 g, 100%).

Example 51b

Preparation of intermediate rac-(2R,3S,4R,5S)-5-tert-butyl-3-(3-chloro-2-fluoro-phenyl)-4-(4-chloro-phenyl)-4-cyano-pyrrolidine-2-carboxylic acid tert-butyl ester

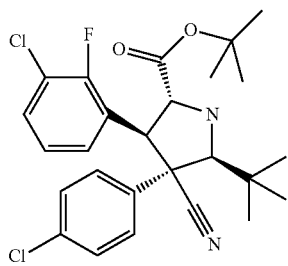

M.W. 491.44
C$_{26}$H$_{29}$Cl$_2$FN$_2$O$_2$

In a manner similar to the method described in Example 1c, [2,2-dimethyl-prop-(E)-ylideneamino]-acetic acid tert-butyl ester prepared in Example 51a (1 g, 5 mmol) was reacted with (Z)-3-(3-chloro-2-fluoro-phenyl)-2-(4-chloro-phenyl)-acrylonitrile (0.8 g, 2.7 mmol) prepared in Example 26a, AgF (1.5 g, 12 mmol), and triethylamine (2 g, 20 mmol) in dichloromethane (50 mL) at room temperature for 24 h to give (2R,3S,4R,5S)-5-tert-Butyl-3-(3-chloro-2-fluoro-phenyl)-4-(4-chloro-phenyl)-4-cyano-pyrrolidine-2-carboxylic acid tert-butyl ester as a white foam (0.4 g, 30%).

Example 51c

Preparation of intermediate rac-(2R,3S,4R,5S)-5-tert-butyl-3-(3-chloro-2-fluoro-phenyl)-4-(4-chloro-phenyl)-4-cyano-pyrrolidine-2-carboxylic acid trifluoroacetic acid

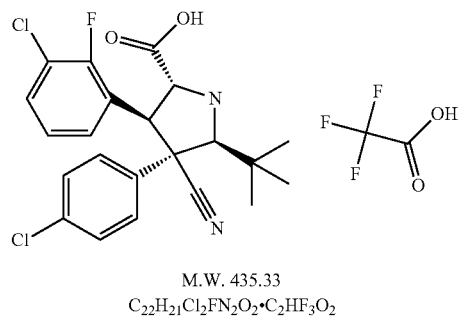

M.W. 435.33
C$_{22}$H$_{21}$Cl$_2$FN$_2$O$_2$·C$_2$HF$_3$O$_2$

In a manner similar to the method described in Example 25a, rac-(2R,3S,4R,5S)-5-tert-Butyl-3-(3-chloro-2-fluoro-phenyl)-4-(4-chloro-phenyl)-4-cyano-pyrrolidine-2-carboxylic acid tert-butyl ester prepared in Example 51b (0.3 g, 0.6 mmol) was reacted with trifluoroacetic acid in dichloromethane at room temperature to give rac-(2R,3S,4R,5S)-5-tert-Butyl-3-(3-chloro-2-fluoro-phenyl)-4-(4-chloro-phenyl)-4-cyano-pyrrolidine-2-carboxylic acid trifluoroacetic acid as a off white solid (0.4 g, 100%).

HRMS (ES$^+$) m/z Calcd for C$_{22}$H$_{21}$Cl$_2$FN$_2$O$_2$+H [(M+H)$^+$]: 435.1037. found: 435.1036.

Example 51d

Preparation of rac-(2R,3S,4R,5S)-5-tert-butyl-3-(3-chloro-2-fluoro-phenyl)-4-(4-chloro-phenyl)-4-cyano-pyrrolidine-2-carboxylic acid ((S)-3,4-dihydroxy-butyl)-amide

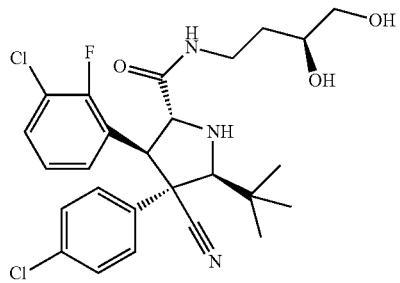

M.W. 522.45
C$_{26}$H$_{30}$Cl$_2$FN$_3$O$_3$

In a manner similar to the method described in Examples 42c, 42d, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 51c (0.4 g, 0.73 mmol) was reacted with 2-((S)-2,2-dimethyl-[1,3]dioxolan-4-yl)-ethylamine (0.2 g, 1.3 mmol), HATU (0.3 g, 0.79 mmol) and iPr$_2$NEt (0.6 g, 4.7 mmol) in CH$_2$Cl$_2$ at room temperature for 20 h, then reacted with aqueous HCl solution in tetrahydrofuran at room temperature for 2 h to give rac-(2R,3S,4R,5S)-5-tert-butyl-3-(3-chloro-2-fluoro-phenyl)-4-(4-chloro-phenyl)-4-cyano-pyrrolidine-2-carboxylic acid ((S)-3,4-dihydroxy-butyl)-amide as a white solid (0.22 g, 58%).

HRMS (ES$^+$) m/z Calcd for C$_{26}$H$_{30}$Cl$_2$FN$_3$O$_3$+H [(M+H)$^+$]: 522,1721. found: 522.1719.

Example 52a

Preparation of intermediate (Z)-3-(3-chloro-2-fluoro-phenyl)-2-(4-chloro-2-fluoro-phenyl)-acrylonitrile

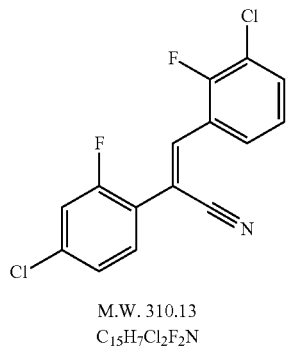 [SMILES: N#C/C(=C\c1cccc(Cl)c1F)c1ccc(Cl)cc1F]

M.W. 310.13
C$_{15}$H$_7$Cl$_2$F$_2$N

In a manner similar to the method described in Example 1b, 4-chloro-2-fluorophenylacetonitrile (5 g, 30 mmol) was reacted with 3-chloro-2-fluorobenzaldehyde (5 g, 32 mmol), methanolic solution (25 wt %) of sodium methoxide (21 mL, 92 mmol) in methanol (200 mL) at 45° C. for 5 h to give (Z)-3-(3-chloro-2-fluoro-phenyl)-2-(4-chloro-2-fluoro-phenyl)-acrylonitrile as a white powder (9 g, 97%).

Example 52b

Preparation of intermediate rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid tert-butyl ester

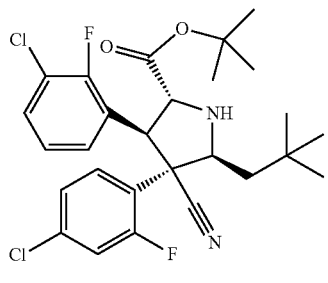

M.W. 523.46
C$_{27}$H$_{30}$Cl$_2$F$_2$N$_2$O$_2$

In a manner similar to the method described in Example 1c, [3-methyl-but-(E)-ylideneamino]-acetic acid tert-butyl ester prepared in Example 1a (2.3 g, 11 mmol) was reacted with (Z)-3-(3-chloro-2-fluoro-phenyl)-2-(4-chloro-2-fluoro-phenyl)-acrylonitrile (2.5 g, 8 mmol) prepared in Example 52a, AgF (0.7 g, 5.5 mmol), and triethylamine (2.9 g, 29 mmol) in dichloromethane (200 mL) at room temperature for 18 h to give rac-(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid tert-butyl ester as a white foam (3 g, 64%).

Example 52c

Preparation of intermediate rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid

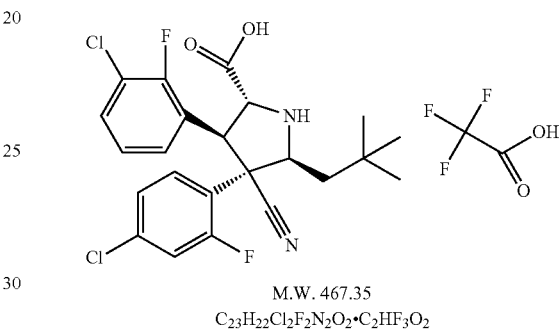

M.W. 467.35
C$_{23}$H$_{22}$Cl$_2$F$_2$N$_2$O$_2$•C$_2$HF$_3$O$_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid tert-butyl ester prepared in Example 52b (0.4 g, 0.8 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid as a white solid (0.5 g, 100%).

HRMS (ES$^+$) m/z Calcd for C$_{23}$H$_{22}$Cl$_2$F$_2$N$_2$O$_2$+H [(M+H)$^+$]: 467.1099. found: 467.1098.

Example 52d

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

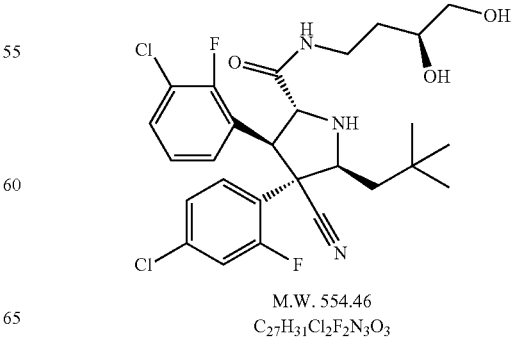

M.W. 554.46
C$_{27}$H$_{31}$Cl$_2$F$_2$N$_3$O$_3$

In a manner similar to the method described in Examples 42c, 42d, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.4 g, 0.69 mmol) was reacted with 2-((S)-2,2-dimethyl-[1,3]dioxolan-4-yl)-ethylamine (0.25 g, 1.7 mmol), HATU (0.35 g, 0.92 mmol) and iPr$_2$NEt (0.75 g, 5.8 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2, 2-dimethyl-propyl)-pyrrolidine-2-carboxylic acid ((S)-3,4-dihydroxy-butyl)-amide as a white solid (0.26 g, 84%).

HRMS (ES$^+$) m/z Calcd for $C_{27}H_{31}Cl_2F_2N_3O_3$+H [(M+H)$^+$]: 554.1784 found: 554.1783.

Example 52e

Preparation of (2R,3S,4R,5S)-3-(3-chloro-2-fluoro-phenyl)-4-(4-chloro-2-fluoro-phenyl)-4-cyano-5-(2, 2-dimethyl-propyl)-pyrrolidine-2-carboxylic acid ((S)-3,4-dihydroxy-butyl)-amide

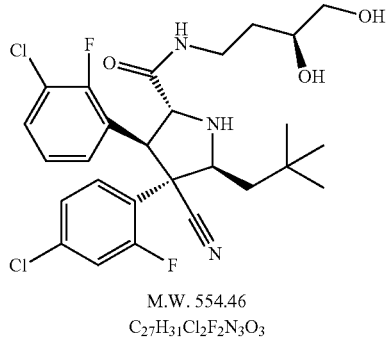 [SMILES: CC(C)(C)C[C@@H]1N[C@@H](C(=O)NCC[C@H](O)CO)[C@H](c2cccc(Cl)c2F)[C@@]1(C#N)c1ccc(Cl)cc1F]

M.W. 554.46
$C_{27}H_{31}Cl_2F_2N_3O_3$

Rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide (0.3 g) was separated by chiral SFC chromatography to provide chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (120 mg, 40%) and chiral-(2S,3R, 4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (121 mg, 40%).

Example 53a

Preparation of intermediate rac-(2S,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid tert-butyl ester

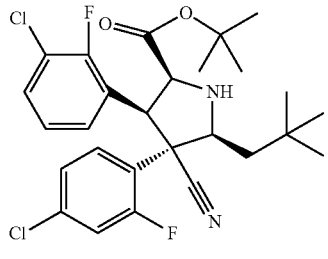

M.W. 523.46
$C_{27}H_{30}Cl_2F_2N_2O_2$

In preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid tert-butyl ester as described in Example 52b, rac-(2S,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid tert-butyl ester was obtained as the second product: a white foam (0.98 g, 21%).

Example 53b

Preparation of intermediate rac-(2S,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid

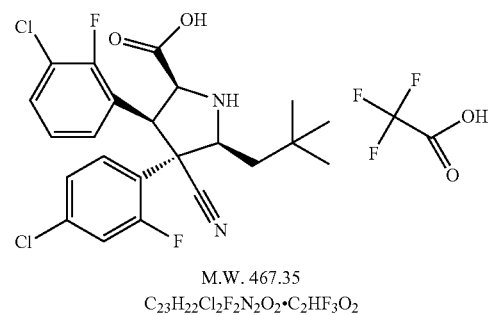

M.W. 467.35
$C_{23}H_{22}Cl_2F_2N_2O_2 \cdot C_2HF_3O_2$

In a manner similar to the method described in Example 25a, rac-(2S,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid tert-butyl ester prepared in Example 53a (0.4 g, 0.8 mmol) was reacted trifluoroacetic acid in dichloromethane at room temperature to give rac-(2S, 3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid as a white solid (0.5 g, 100%).

HRMS (ES$^+$) m/z Calcd for $C_{23}H_{22}Cl_2F_2N_2O_2$+H [(M+H)$^+$]: 467.1099. found: 467.1099.

Example 53c

Preparation of rac-(2S,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

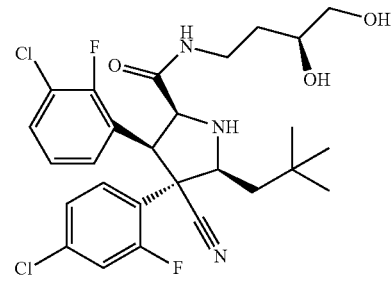

M.W. 554.46
$C_{27}H_{31}Cl_2F_2N_3O_3$

In a manner similar to the method described in Examples 42c, 42d, rac-(2S,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 53b (0.3 g, 0.5 mmol) was reacted with 2-((S)-2,2-dimethyl-[1,3]dioxolan-4-yl)-ethylamine (0.15 g, 1 mmol), HATU (0.3 g, 0.79 mmol) and iPr$_2$NEt (0.4 g, 3.1 mmol) in CH$_2$Cl$_2$ at room temperature for 20 h, then reacted with aqueous HCl solution in tetrahydrofuran at room temperature for 2 h to give rac-(2S,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.26 g, 94%).

HRMS (ES$^+$) m/z Calcd for C$_{27}$H$_{31}$Cl$_2$F$_2$N$_3$O$_3$+H [(M+H)$^+$]: 554.1784. found: 554.1782.

Example 54a

Preparation of intermediate (Z)-2-(4-bromo-phenyl)-3-(3-chloro-2-fluoro-phenyl)-acrylonitrile

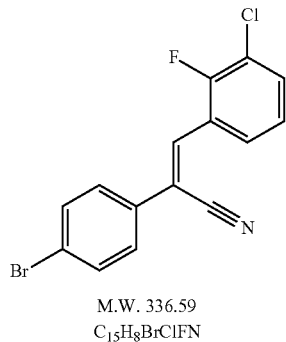 [SMILES: N#C/C(=C\c1cccc(Cl)c1F)c1ccc(Br)cc1]

M.W. 336.59
C$_{15}$H$_8$BrClFN

In a manner similar to the method described in Example 1b, 4-bromophenylacetonitrile (Aldrich) (4.5 g, 23 mmol) was reacted with 3-chloro-2-fluorobenzaldehyde (5.2 g, 33 mmol), methanolic solution (25 wt %) of sodium methoxide (15 mL, 66 mmol) in methanol (150 mL) at 50° C. for 3 h to give (Z)-2-(4-bromo-phenyl)-3-(3-chloro-2-fluoro-phenyl)-acrylonitrile as a white powder (7.8 g, 100%).

Example 54b

Preparation of intermediate rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid tert-butyl ester

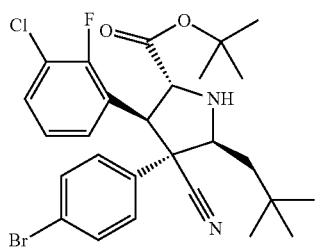

M.W. 549.92
C$_{27}$H$_{31}$BrClFN$_2$O$_2$

In a manner similar to the method described in Example 1c, [3,3-dimethyl-but-(E)-ylideneamino]-acetic acid tert-butyl ester prepared in Example 1a (1.1 g, 5 mmol) was reacted with (Z)-2-(4-bromo-phenyl)-3-(3-chloro-2-fluoro-phenyl)-acrylonitrile (1.2 g, 3.6 mmol) prepared in Example 54a, AgF (1.3 g, 10 mmol), and triethylamine (2 g, 20 mmol) in dichloromethane (100 mL) at room temperature for 3 h to give rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid tert-butyl ester as a white foam (1.1 g, 56%).

Example 54c

Preparation of intermediate rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid trifluoroacetic acid

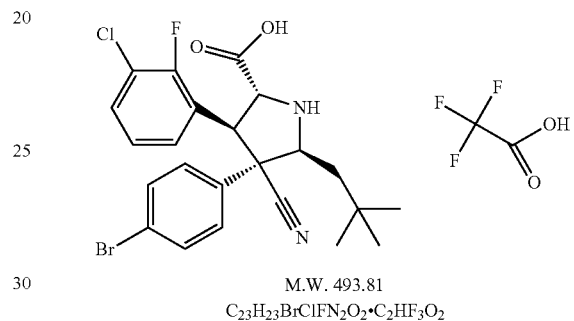

M.W. 493.81
C$_{23}$H$_{23}$BrClFN$_2$O$_2$·C$_2$HF$_3$O$_2$

In a manner similar to the method described in Example 25a, rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid tert-butyl ester prepared in Example 54b (1.1 g, 2 mmol) was reacted with trifluoroacetic acid in dichloromethane at room temperature to give rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid trifluoroacetic acid as a off white solid (1.2 g, 99%).

HRMS (ES$^+$) m/z Calcd for C$_{23}$H$_{23}$BrClFN$_2$O$_2$+H [(M+H)$^+$]: 493.0688. found: 493.0689.

Example 54d

Preparation of rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid ((S)-3,4-dihydroxy-butyl)-amide

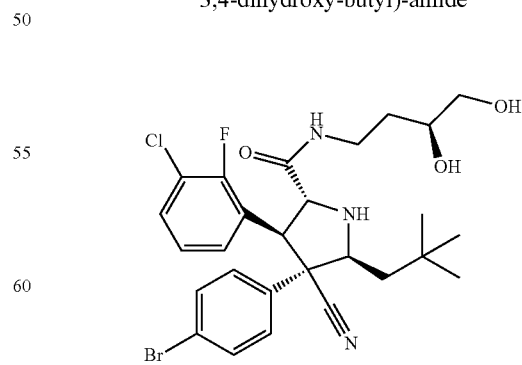

M.W. 580.92
C$_{27}$H$_{32}$BrClFN$_3$O$_3$

In a manner similar to the method described in Examples 42c, 42d, rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid trifluoroacetic acid prepared in Example Mc (0.3 g, 0.49 mmol) was reacted with 2-4S)-2,2-dimethyl-[1,3]dioxolan-4-yl)-ethylamine (0.15 g, 1 mmol), HATU (0.23 g, 0.6 mmol) and iPr$_2$NEt (0.4 g, 3.1 mmol) in CH$_2$Cl$_2$ at room temperature for 20 h, then reacted with aqueous HCl solution in tetrahydrofuran at room temperature for 2 h to give rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.18 g, 63%).

HRMS (ES$^+$) m/z Calcd for C$_{27}$H$_{32}$BrClFN$_3$O$_3$+H [(M+H)$^+$]: 580.1373. found: 580.1372.

Example 55a

Preparation of intermediate (Z)-3-(3-chloro-2-fluoro-phenyl)-2-(4-fluoro-phenyl)-acrylonitrile

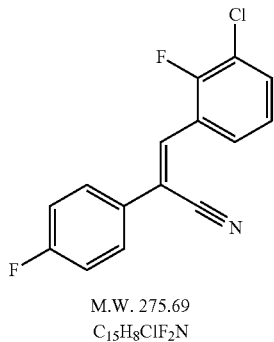 [SMILES: N#C/C(=C\c1cccc(Cl)c1F)c1ccc(F)cc1]

M.W. 275.69
C$_{15}$H$_8$ClF$_2$N

In a manner similar to the method described in Example 1b, 4-fluorophenylacetonitrile (Aldrich) (3.5 g, 26 mmol) was reacted with 3-chloro-2-fluorobenzaldehyde (5.3 g, 34 mmol), methanolic solution (25 wt %) of sodium methoxide (15 mL, 66 mmol) in methanol (200 mL) at 50° C. for 3 h to give (Z)-3-(3-chloro-2-fluoro-phenyl)-2-(4-fluoro-phenyl)-acrylonitrile as a white powder (5.7 g, 80%).

Example 55b

Preparation of intermediate rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid tert-butyl ester

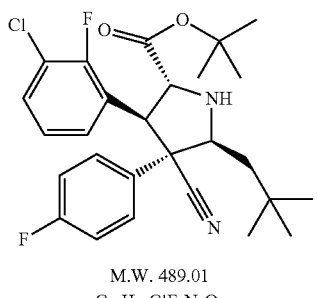

M.W. 489.01
C$_{27}$H$_{31}$ClF$_2$N$_2$O$_2$

In a manner similar to the method described in Example 1c, [3,3-dimethyl-but-(E)-ylideneamino]-acetic acid tert-butyl ester prepared in Example 1a (1.1 g, 5 mmol) was reacted with (Z)-3-(3-chloro-2-fluoro-phenyl)-2-(4-fluoro-phenyl)-acrylonitrile (1.25 g, 4.5 mmol) prepared in Example 55a, AgF (1.6 g, 13 mmol), and triethylamine (1.6 g, 16 mmol) in dichloromethane (100 mL) at room temperature for 5 h to give rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid tert-butyl ester as a white foam (1.6 g, 72%).

Example 55c

Preparation of intermediate rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid trifluoroacetic acid

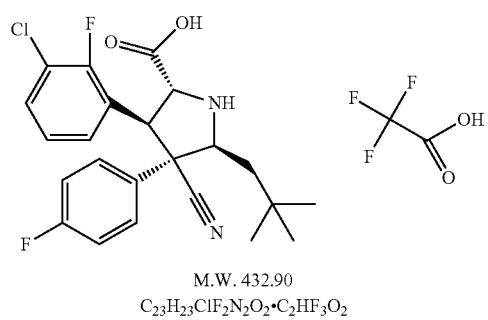 [SMILES: CC(C)(C)C[C@@H]1N[C@@H](C(=O)O)[C@H](c2cccc(Cl)c2F)[C@@]1(C#N)c1ccc(F)cc1 ; O=C(O)C(F)(F)F]

M.W. 432.90
C$_{23}$H$_{23}$ClF$_2$N$_2$O$_2$·C$_2$HF$_3$O$_2$

In a manner similar to the method described in Example 25a, rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid tert-butyl ester prepared in Example 55b (1.6 g, 3.3 mmol) was reacted with trifluoroacetic acid in dichloromethane at room temperature to give rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid trifluoroacetic acid as a white solid (1.7 g, 94%).

Example 55d

Preparation of rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid ((S)-3,4-dihydroxy-butyl)-amide

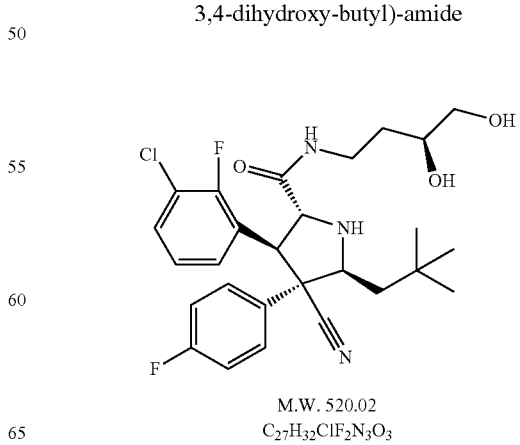

M.W. 520.02
C$_{27}$H$_{32}$ClF$_2$N$_3$O$_3$

In a manner similar to the method described in Example 42e, rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid trifluoroacetic acid prepared in Example 55c (0.4 g, 0.73 mmol) was reacted with 2-((S)-2,2-dimethyl-[1,3]dioxolan-4-yl)-ethylamine (0.2 g, 1.4 mmol), HATU (0.3 g, 0.8 mmol) and iPr$_2$NEt (0.6 g, 4.6 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid ((S)-3,4-dihydroxy-butyl)-amide as a white solid (0.21 g, 55%).

HRMS (ES$^+$) m/z Calcd for C$_{27}$H$_{32}$ClF$_2$N$_3$O$_3$+H [(M+H)$^+$]: 520.2173. found: 520.2175.

Example 56a

Preparation of intermediate (Z)-3-(3-Chloro-2-fluoro-phenyl)-2-(2,4-dichloro-phenyl)-acrylonitrile

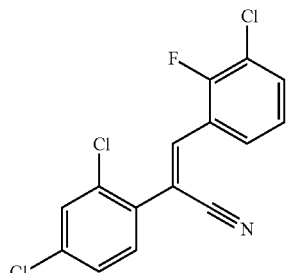

M.W. 326.59
C$_{15}$H$_7$Cl$_3$FN

In a manner similar to the method described in Example 1b, 2,4-dichlorobenzyl cyanide (6 g, 32 mmol) was reacted with 3-chloro-2-fluorobenzaldehyde (6 g, 38 mmol), methanolic solution (25 wt %) of sodium methoxide (30 mL, 131 mmol) in methanol (200 mL) at 50° C. for 3 h to give (Z)-3-(3-chloro-2-fluoro-phenyl)-2-(2,4-dichloro-phenyl)-acrylonitrile as a white powder (7 g, 67%).

Example 56b

Preparation of intermediate rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid tert-butyl ester

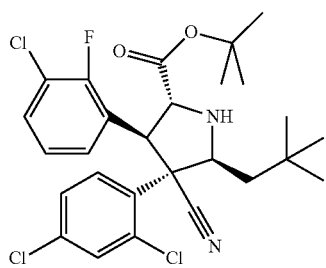

M.W. 539.91
C$_{27}$H$_{30}$Cl$_3$FN$_2$O$_2$

In a manner similar to the method described in Example 1c, [3-methyl-but-(E)-ylideneamino]-acetic acid tert-butyl ester prepared in Example 1a (2.1 g, 10 mmol) was reacted with (Z)-3-(3-chloro-2-fluoro-phenyl)-2-(2,4-dichloro-phenyl)-acrylonitrile (2.2 g, 6.7 mmol) prepared in Example 56a, AgF (2 g, 16 mmol), and triethylamine (5 g, 50 mmol) in dichloromethane (200 mL) at room temperature for 20 h to give rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid tert-butyl ester as a white foam (2.4 g, 66%).

Example 56c

Preparation of intermediate rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid trifluoroacetic acid

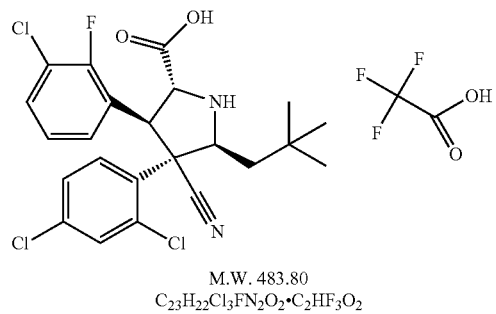

M.W. 483.80
C$_{23}$H$_{22}$Cl$_3$FN$_2$O$_2$·C$_2$HF$_3$O$_2$

In a manner similar to the method described in Example 25a, rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid tert-butyl ester prepared in Example 56b (2.4 g, 7.4 mmol) was reacted with trifluoroacetic acid in dichloromethane at room temperature to give rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid trifluoroacetic acid as a white solid (2.7 g, 100%).

Example 56d

Preparation of rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide

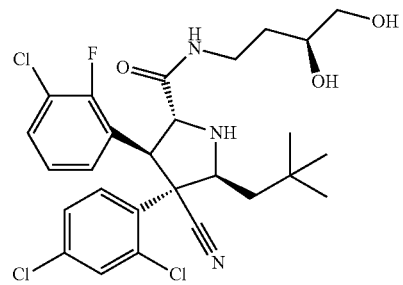

M.W. 570.92
C$_{27}$H$_{31}$Cl$_3$FN$_3$O$_3$

In a manner similar to the method described in Examples 42c, 42d, rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid trifluoroacetic acid prepared in Example 56c (0.6 g, 1 mmol) was reacted with 2-((S)-2,2-dimethyl-[1,3]dioxolan-4-yl)-ethylamine (0.3 g, 2 mmol), HATU (0.5 g, 1.3 mmol) and iPr$_2$NEt (0.9 g, 7 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide as a white solid (0.5 g, 88%).

HRMS (ES$^+$) m/z Calcd for C$_{27}$H$_{31}$Cl$_3$FN$_3$O$_3$+H [(M+H)$^+$]: 570.1488. found: 570.1487.

Example 56e

Preparation of (2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide

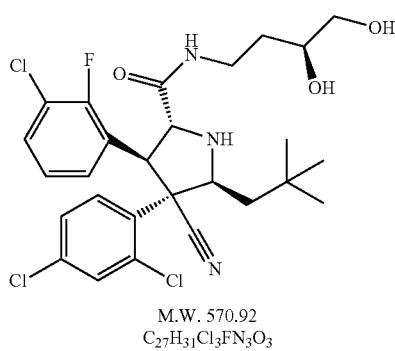

M.W. 570.92
C$_{27}$H$_{31}$Cl$_3$FN$_3$O$_3$

Rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide (0.5 g) was separated by chiral SFC chromatography to provide chiral-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide as a white solid (200 mg, 40%) and chiral-(2S,3R,4S,5R)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide as a white solid (220 mg, 44%).

Example 57a

Preparation of intermediate (Z)-3-(3-chloro-2-fluoro-phenyl)-2-(4-chloro-2-methyl-phenyl)-acrylonitrile

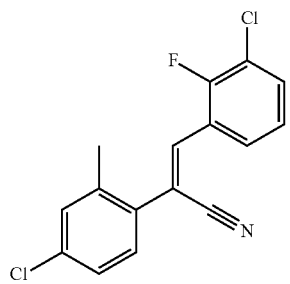

M.W. 306.17
C$_{16}$H$_{10}$Cl$_2$FN

Step A A mixture of 4-chloro-2-methylbenzyl alcohol (Aldrich) (5 g, 32 mmol) in thionyl chloride (20 mL) was heated at refluxing (100° C.) for 30 min. The mixture was cooled to room temperature and concentrated. The residue was diluted with ethyl acetate, washed with saturated aqueous NaHCO$_3$ solution, water, brine, dried over MgSO$_4$, and concentrated to give 4-chloro-2-methylbenzyl chloride as a light yellow oil (5.2 g, 93%).

Step B To a solution of 4-chloro-2-methylbenzyl chloride (5.2 g, 30 mmol) in ethanol (40 mL) was added an aqueous solution (30 mL) of KCN (5 g, 77 mmol) at room temperature. The reaction mixture was then heated at 100° C. for 2 h. The mixture was cooled to room temperature and concentrated. The residue was partitioned between ethyl acetate and water. The organic layer was separated, concentrated. The residue was purified by chromatography (EtOAc:hexanes=1:10, then 1:4) to give 4-chloro-2-methylbenzyl cyanide as a yellow oil (3.5 g, 66%).

Step C In a manner similar to the method described in Example 1b, 4-chloro-2-methylbenzyl cyanide (3.5 g, 21 mmol) was reacted with 3-chloro-2-fluorobenzaldehyde (5 g, 32 mmol), methanolic solution (25 wt %) of sodium methoxide (15 mL, 66 mmol) in methanol (100 mL) at 50° C. for 5 h to give (Z)-3-(3-chloro-2-fluoro-phenyl)-2-(4-chloro-2-methyl-phenyl)-acrylonitrile as a white powder (4 g, 62%).

Example 57b

Preparation of intermediate rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid tert-butyl ester

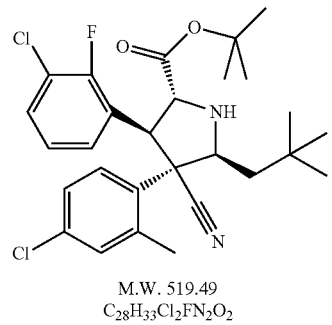 [SMILES: Cc1cc(Cl)ccc1[C@@]1(C#N)[C@H](CC(C)(C)C)N[C@@H](C(=O)OC(C)(C)C)[C@@H]1c1cccc(Cl)c1F]

M.W. 519.49
C$_{28}$H$_{33}$Cl$_2$FN$_2$O$_2$

In a manner similar to the method described in Example 1c, [3-methyl-but-(E)-ylideneamino]-acetic acid tert-butyl ester prepared in Example 1a (2.1 g, 10 mmol) was reacted with (Z)-3-(3-chloro-2-fluoro-phenyl)-2-(4-chloro-2-methyl-phenyl)-acrylonitrile (2.3 g, 7.5 mmol) prepared in Example 57a, AgF (1.3 g, 10 mmol), and triethylamine (2.8 g, 28 mmol) in dichloromethane (100 mL) at room temperature for 20 h to give rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid tert-butyl ester as a white foam (1.9 g, 49%).

Example 57c

Preparation of intermediate rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid trifluoroacetic acid

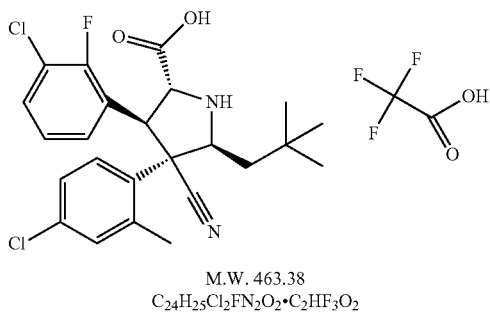

M.W. 463.38
$C_{24}H_{25}Cl_2FN_2O_2 \cdot C_2HF_3O_2$

In a manner similar to the method described in Example 25a, rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid tert-butyl ester prepared in Example 57b (1.9 g, 3.7 mmol) was reacted with trifluoroacetic acid in dichloromethane at room temperature to give rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid trifluoroacetic acid as a white solid (2.1 g, 98%).

Example 57d

Preparation of rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid ((S)-3,4-dihydroxy-butyl)-amide

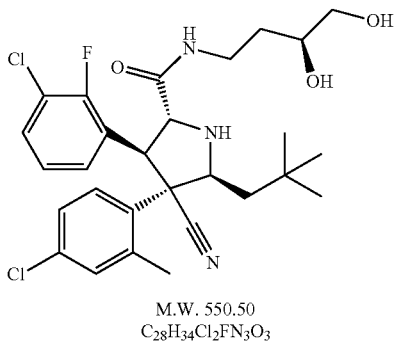 [SMILES: Cc1cc(Cl)ccc1[C@@]1(C#N)[C@H](CC(C)(C)C)N[C@@H](C(=O)NCC[C@H](O)CO)[C@@H]1c1cccc(Cl)c1F]

M.W. 550.50
$C_{28}H_{34}Cl_2FN_3O_3$

In a manner similar to the method described in Examples 42c, 42d, rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid trifluoroacetic acid prepared in Example 57c (0.4 g, 0.69 mmol) was reacted with 2-((S)-2,2-dimethyl-[1,3]dioxolan-4-yl)-ethylamine (0.2 g, 1.4 mmol), HATU (0.4 g, 1.1 mmol) and iPr$_2$NEt (0.8 g, 6.2 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid ((S)-3,4-dihydroxy-butyl)-amide as a white solid (0.29 g, 76%).

HRMS (ES$^+$) m/z Calcd for $C_{28}H_{34}Cl_2FN_3O_3$+H [(M+H)$^+$]: 550.2034. found: 550.2036.

Example 58a

Preparation of intermediate (Z)-3-(3-chloro-2-fluoro-phenyl)-2-(4-chloro-2-methoxy-phenyl)-acrylonitrile

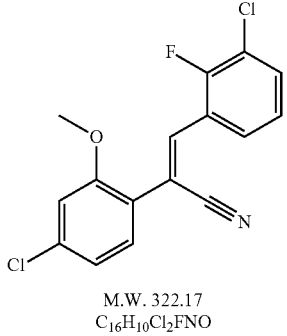 [SMILES: COc1cc(Cl)ccc1/C(C#N)=C/c1cccc(Cl)c1F]

M.W. 322.17
$C_{16}H_{10}Cl_2FNO$

Step A In a manner similar to the method described in Example 57 Step A, 4-chloro-2-methoxybenzyl alcohol (Aldrich) (4.9 g, 28 mmol) was reacted with thionyl chloride (20 mL) to give 4-chloro-2-methoxybenzyl chloride as a white solid (5.1 g, 95%).

Step B In a manner similar to the method described in Example 57 Step B, 4-chloro-2-methoxybenzyl chloride (5.1 g, 27 mmol) was reacted with NaCN (3 g, 61 mmol) in ethanol (40 mL) and water (20 mL) at 100° C. for 8 h to give 4-chloro-2-methoxybenzyl cyanide as a colorless oil (1.8 g, 36%)

Step C In a manner similar to the method described in Example 1b, 4-chloro-2-methoxybenzyl cyanide (1.8 g, 10 mmol) was reacted with 3-chloro-2-fluorobenzaldehyde (2 g, 13 mmol), methanolic solution (25 wt %) of sodium methoxide (15 mL, 66 mmol) in methanol (50 mL) at 50° C. for 2 h to give (Z)-3-(3-chloro-2-fluoro-phenyl)-2-(4-chloro-2-methoxy-phenyl)-acrylonitrile as a white powder (2.1 g, 65%).

Example 58b

Preparation of intermediate rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid tert-butyl ester

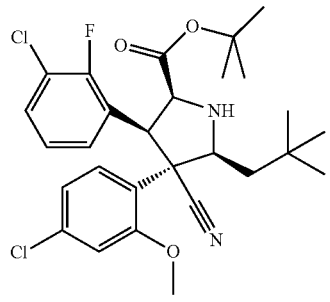

M.W. 535.49
$C_{28}H_{33}Cl_2FN_2O_3$

In a manner similar to the method described in Example 1c, [3-methyl-but-(E)-ylideneamino]-acetic acid tert-butyl ester prepared in Example 1a (2.1 g, 10 mmol) was reacted with (Z)-3-(3-chloro-2-fluoro-phenyl)-2-(4-chloro-2-methoxy-phenyl)-acrylonitrile (1.8 g, 5.6 mmol) prepared in Example 58a, AgF (1.7 g, 13 mmol), and triethylamine (2.8 g, 28 mmol) in dichloromethane (100 mL) at room temperature for 24 h to give rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid tert-butyl ester as a white foam (1.8 g, 60%).

Example 58c

Preparation of intermediate rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid trifluoroacetic acid

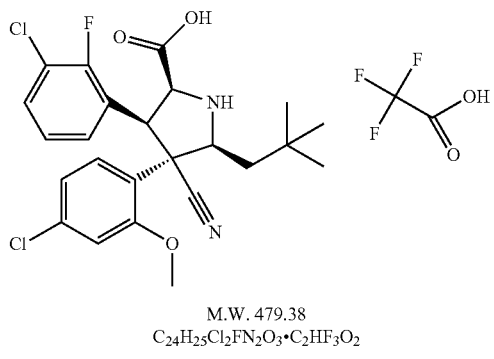

M.W. 479.38
$C_{24}H_{25}Cl_2FN_2O_3 \cdot C_2HF_3O_2$

In a manner similar to the method described in Example 25a, rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid tert-butyl ester prepared in Example 58b (1.3 g, 2.4 mmol) was reacted with trifluoroacetic acid in dichloromethane at room temperature to give rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid trifluoroacetic acid as a white solid (1.5 g, 100%).

Example 58d

Preparation of rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid ((S)-3,4-dihydroxy-butyl)-amide

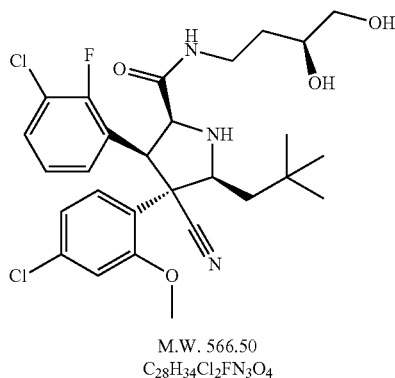 [SMILES: COc1cc(Cl)ccc1[C@@]1(C#N)[C@H](CC(C)(C)C)N[C@H](C(=O)NCC[C@H](O)CO)[C@@H]1c1cccc(Cl)c1F]

M.W. 566.50
$C_{28}H_{34}Cl_2FN_3O_4$

In a manner similar to the method described in Examples 42c, 42d, rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid trifluoroacetic acid prepared in Example 58c (0.4 g, 0.67 mmol) was reacted with 2-((S)-2,2-dimethyl-[1,3]dioxolan-4-yl)-ethylamine (0.25 g, 1.7 mmol), HATU (0.4 g, 1.1 mmol) and iPr₂NEt (0.6 g, 4.7 mmol) in CH₂Cl₂ at room temperature for 20 h, then reacted with aqueous HCl solution in tetrahydrofuran at room temperature for 2 h to give rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid ((S)-3,4-dihydroxy-butyl)-amide as a white solid (0.23 g, 61%).

HRMS (ES⁺) m/z Calcd for $C_{28}H_{34}Cl_2FN_3O_4$+H [(M+H)⁺]: 566.1983. found: 566.1983.

Example 59a

Preparation of intermediate [2-cyclohexyl-eth-(E)-ylideneamino]-acetic acid tert-butyl ester

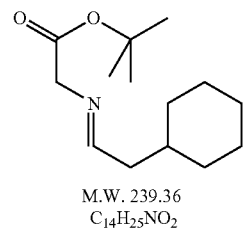 [SMILES: CC(C)(C)OC(=O)C/N=C/CC1CCCCC1]

M.W. 239.36
$C_{14}H_{25}NO_2$

In a manner similar to the method described in Example 1a, glycine tert-butyl ester (1.3 g, 10 mmol) was reacted with 2-cyclohexylacetaldehyde (Betapharma) (1.3 g, 10 mmol) in CH₂Cl₂ at room temperature for 5 h to give [2-cyclohexyl-eth-(E)-ylideneamino]-acetic acid tert-butyl ester as a colorless oil (2.3 g, 96%).

Example 59b

Preparation of intermediate rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid tert-butyl ester

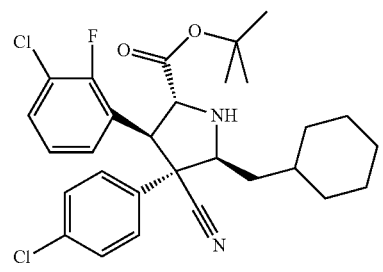

M.W. 531.50
$C_{29}H_{33}Cl_2FN_2O_2$

In a manner similar to the method described in Example 1c, [2-cyclohexyl-eth-(E)-ylideneamino]-acetic acid tert-butyl ester prepared in Example 59a (2.3 g, 10 mmol) was reacted with (Z)-3-(3-chloro-2-fluoro-phenyl)-2-(4-chloro-phenyl)-acrylonitrile (1.9 g, 6.5 mmol) prepared in Example 26a, AgF (1.7 g, 13 mmol), and triethylamine (2.6 g, 26 mmol) in dichloromethane (100 mL) at room temperature for 18 h to give rac-(2R,3S,4R,5S)-3-(3-chloro-2-fluoro-phenyl)-4-(4- chloro-phenyl)-4-cyano-5-cyclohexylmethyl-pyrrolidine-2-carboxylic acid tert-butyl ester as a white foam (1.9 g, 55%).

Example 59c

Preparation of intermediate rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid trifluoroacetic acid

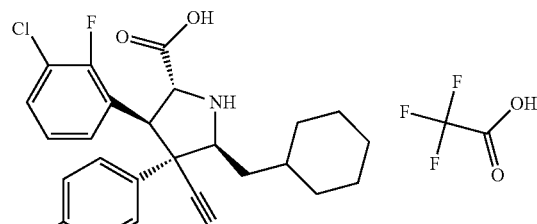

M.W. 475.39
$C_{25}H_{25}Cl_2FN_2O_2 \cdot C_2HF_3O_2$

In a manner similar to the method described in Example 25a, rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid tert-butyl ester prepared in Example 59b (1.9 g, 3.6 mmol) was reacted with trifluoroacetic acid in dichloromethane at room temperature to give rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid trifluoroacetic acid as a white solid (2.1 g, 99%).

Example 59d

Preparation of rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid ((S)-3,4-dihydroxy-butyl)-amide

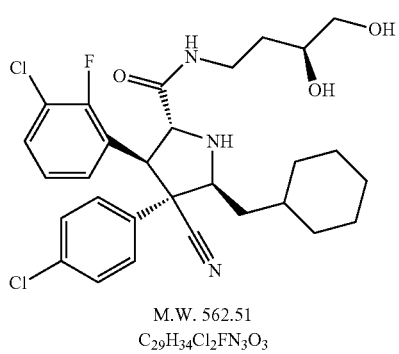 [SMILES: N#C[C@]1(c2ccc(Cl)cc2)[C@H](CC2CCCCC2)N[C@@H](C(=O)NCC[C@H](O)CO)[C@@H]1c1cccc(Cl)c1F]

M.W. 562.51
$C_{29}H_{34}Cl_2FN_3O_3$

In a manner similar to the method described in Examples 42c, 42d, rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid trifluoroacetic acid prepared in Example 59c (0.6 g, 1 mmol) was reacted with 2-((S)-2,2-dimethyl-[1,3]dioxolan-4-yl)-ethylamine (0.3 g, 2 mmol), HATU (0.6 g, 1.6 mmol) and iPr₂NEt (0.9 g, 7 mmol) in CH₂Cl₂ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid ((S)-3,4-dihydroxy-butyl)-amide as a white solid (0.4 g, 71%).

HRMS (ES⁺) m/z Calcd for $C_{29}H_{34}Cl_2FN_3O_3+H$ [(M+H)⁺]: 562.2034 found: 562.2033.

Example 60a

Preparation of intermediate rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid tert-butyl ester

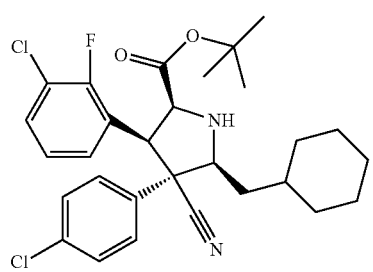

M.W. 531.50
$C_{29}H_{33}Cl_2FN_2O_2$

In preparation of rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid tert-butyl ester as described in Example 59b, rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid tert-butyl ester was obtained as the second product: a white foam, Yield, 1 g, 29%.

Example 60b

Preparation of intermediate rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid trifluoroacetic acid

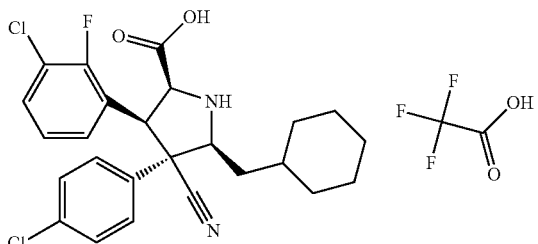

M.W. 475.39
$C_{25}H_{25}Cl_2FN_2O_2 \cdot C_2HF_3O_2$

In a manner similar to the method described in Example 25a, rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid tert-butyl ester prepared in Example 60a (0.4 g, 0.75 mmol) was reacted with trifluoroacetic acid in dichloromethane at room temperature to give rac-(2S,3S,4R,5S)-3-

(3-chloro-2-fluoro-phenyl)-4-(4-chloro-phenyl)-4-cyano-5-cyclohexylmethyl-pyrrolidine-2-carboxylic acid trifluoroacetic acid as a white solid (0.46 g, 100%).

Example 60c

Preparation of rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid ((S)-3,4-dihydroxy-butyl)-amide

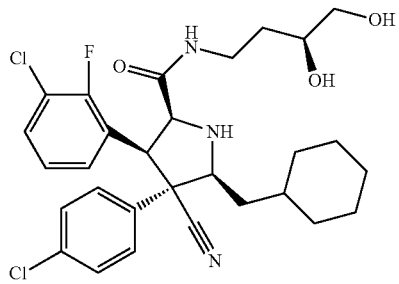

M.W. 562.51
$C_{29}H_{34}Cl_2FN_3O_3$

In a manner similar to the method described in Example 42e, rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid trifluoroacetic acid prepared in Example 60b (0.45 g, 0.75 mmol) was reacted with 2-((S)-2,2-dimethyl-[1,3]dioxolan-4-yl)-ethylamine (0.23 g, 1.6 mmol), HATU (0.45 g, 1.2 mmol) and iPr$_2$NEt (0.9 g, 7 mmol) in CH$_2$Cl$_2$ at room temperature for 20 h, then reacted with aqueous HCl solution in tetrahydrofuran at room temperature for 2 h to give rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid ((S)-3,4-dihydroxy-butyl)-amide as a white solid (0.4 g, 95%).

HRMS (ES$^+$) m/z Calcd for $C_{29}H_{34}Cl_2FN_3O_3$+H [(M+H)$^+$]: 562.2034 found: 562.2033.

Example 61a

Preparation of intermediate (Z)-2-(4-chloro-2-methoxy-phenyl)-3-(3-chloro-phenyl)-acrylonitrile

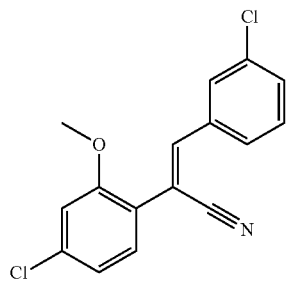

M.W. 304.18
$C_{16}H_{11}Cl_2NO$

In a manner similar to the method described in Example 1b, 4-chloro-2-methoxybenzyl cyanide (2 g, 10 mmol) prepared in Example 58a Step B was reacted with 3-chlorobenzaldehyde (2 g, 14 mmol), methanolic solution (25 wt %) of sodium methoxide (15 mL, 66 mmol) in methanol (50 mL) at 50° C. for 5 h to give (Z)-2-(4-chloro-2-methoxy-phenyl)-3-(3-chloro-phenyl)-acrylonitrile as a white powder (1.9 g, 63%).

Example 61b

Preparation of intermediate rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid tert-butyl ester

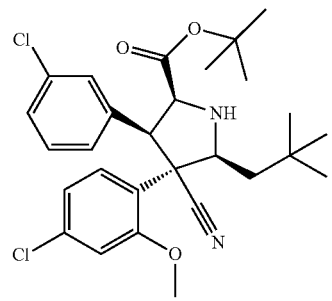

M.W. 517.50
$C_{28}H_{34}Cl_2N_2O_3$

In a manner similar to the method described in Example 1c, [3-methyl-but-(E)-ylideneamino]-acetic acid tert-butyl ester prepared in Example 1a (2.1 g, 10 mmol) was reacted with (Z)-2-(4-chloro-2-methoxy-phenyl)-3-(3-chloro-phenyl)-acrylonitrile (1.8 g, 5.9 mmol) prepared in Example 61a, AgF (1.7 g, 13 mmol), and triethylamine (2.8 g, 28 mmol) in dichloromethane (100 mL) at room temperature for 24 h to give rac-(2S,3S,4R,5S)-3-(3-chloro-2-fluoro-phenyl)-4-(4-chloro-2-methoxy-phenyl)-4-cyano-5-(2,2-dimethyl-propyl)-pyrrolidine-2-carboxylic acid tert-butyl ester as a white foam (1.8 g, 60%).

Example 61c

Preparation of intermediate rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid trifluoroacetic acid

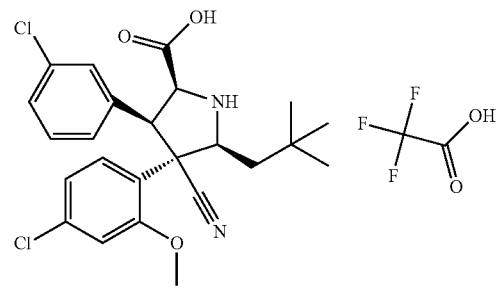

M.W. 461.39
$C_{24}H_{26}Cl_2N_2O_3 \cdot C_2HF_3O_2$

In a manner similar to the method described in Example 25a, rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid tert-butyl ester prepared in Example 61b (2 g, 3.9 mmol) was reacted with trifluoroacetic acid in dichloromethane at room temperature to give rac-(2S,3R,4R, 5S)-4-(4-chloro-2-methoxy-phenyl)-3-(3-chloro-phenyl)-4-cyano-5-(2,2-dimethyl-propyl)-pyrrolidine-2-carboxylic acid trifluoroacetic acid as a white solid (2.2 g, 98%).

Example 61d

Preparation of rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid ((S)-3,4-dihydroxy-butyl)-amide

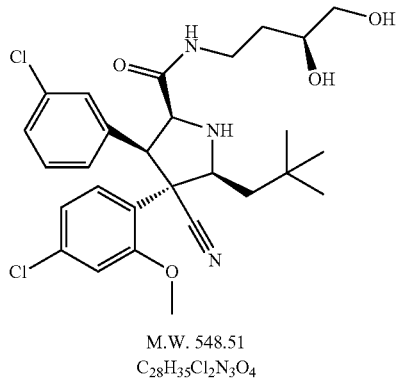 [SMILES: COc1cc(Cl)ccc1[C@@]1(C#N)[C@H](CC(C)(C)C)N[C@H](C(=O)NCC[C@H](O)CO)[C@@H]1c1cccc(Cl)c1]

M.W. 548.51
$C_{28}H_{35}Cl_2N_3O_4$

In a manner similar to the method described in Examples 42c, 42d, rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid trifluoroacetic acid prepared in Example 61c (0.2 g, 0.35 mmol) was reacted with 2-4S)-2,2-dimethyl-[1,3]dioxolan-4-yl)-ethylamine (0.15 g, 1.0 mmol), HATU (0.24 g, 0.63 mmol) and iPr$_2$NEt (0.3 mL, 1.7 mmol) in CH$_2$Cl$_2$ at room temperature for 20 h, then reacted with aqueous HCl solution in tetrahydrofuran at room temperature for 2 h to give rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid ((S)-3,4-dihydroxy-butyl)-amide as a white solid (0.15 g, 84%).

HRMS (ES$^+$) m/z Calcd for $C_{28}H_{35}Cl_2N_3O_4$+H [(M+H)$^+$]: 548.2078. found: 548.2077.

Example 62a

Preparation of intermediate (Z)-2-(4-chloro-2-fluoro-phenyl)-3-(2,3-difluoro-phenyl)-acrylonitrile

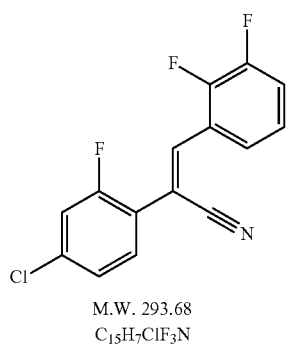 [SMILES: N#C/C(=C\c1cccc(F)c1F)c1ccc(Cl)cc1F]

M.W. 293.68
$C_{15}H_7ClF_3N$

In a manner similar to the method described in Example 1b, 4-chloro-2-fluorophenylacetonitrile (4.5 g, 26 mmol) was reacted with 2,3-difluorobenzaldehyde (Aldrich) (4.5 g, 32 mmol), methanolic solution (25 wt %) of sodium methoxide (6.3 g, 29 mmol) in methanol (135 mL) at 50° C. for 3 h to give (Z)-2-(4-chloro-2-fluoro-phenyl)-3-(2,3-difluoro-phenyl)-acrylonitrile as a white powder (6.85 g, 88%).

Example 62b

Preparation of intermediate rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid tert-butyl ester

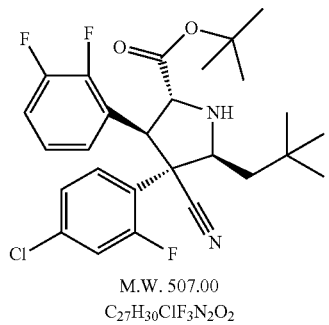 [SMILES: CC(C)(C)C[C@@H]1N[C@@H](C(=O)OC(C)(C)C)[C@H](c2cccc(F)c2F)[C@@]1(C#N)c1ccc(Cl)cc1F]

M.W. 507.00
$C_{27}H_{30}ClF_3N_2O_2$

In a manner similar to the method described in Example 1c, [3-methyl-but-(E)-ylideneamino]-acetic acid tert-butyl ester prepared in Example 1a (2.1 g, 10 mmol) was reacted with (Z)-2-(4-chloro-2-fluoro-phenyl)-3-(2,3-difluoro-phenyl)-acrylonitrile (2.3 g, 8 mmol) prepared in Example 62a, AgF (1.5 g, 12 mmol), and triethylamine (2.7 mL, 20 mmol) in dichloromethane (120 mL) at room temperature for 18 h to give rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid tert-butyl ester as a white foam (1.8 g, 44%).

Example 62c

Preparation of intermediate rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid trifluoroacetic acid

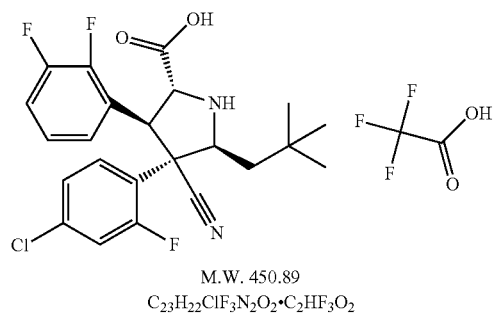

M.W. 450.89
$C_{23}H_{22}ClF_3N_2O_2 \cdot C_2HF_3O_2$

In a manner similar to the method described in Example 25a, rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid tert-butyl ester prepared in Example 62b (1.8 g, 3.6 mmol) was reacted with trifluoroacetic acid in dichloromethane at room temperature to give rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid trifluoroacetic acid as a white solid (2 g, 100%).

HRMS (ES+) m/z Calcd for $C_{23}H_{22}ClF_3N_2O_2$+H [(M+H)+]: 451.1395. found: 451.1394.

Example 62d

Preparation of rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide

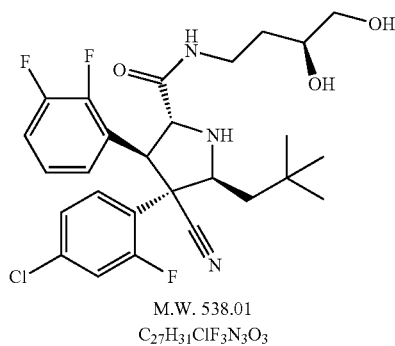 [SMILES: CC(C)(C)C[C@@H]1N[C@@H](C(=O)NCC[C@H](O)CO)[C@H](c2cccc(F)c2F)[C@@]1(C#N)c1ccc(Cl)cc1F]

M.W. 538.01
$C_{27}H_{31}ClF_3N_3O_3$

In a manner similar to the method described in Examples 42c, 42d, rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid trifluoroacetic acid prepared in Example 62c (0.47 g, 0.83 mmol) was reacted with 2-((S)-2,2-dimethyl-[1,3]dioxolan-4-yl)-ethylamine (0.36 g, 2.5 mmol), HATU (0.57 g, 1.49 mmol) and iPr$_2$NEt (0.72 mL, 4.2 mmol) in CH$_2$Cl$_2$ at room temperature for 20 h, then reacted with aqueous HCl solution in tetrahydrofuran at room temperature for 2 h to give rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide as a white solid (0.26 g, 58%).

HRMS (ES+) m/z Calcd for $C_{27}H_{31}Cl_2F_2N_3O_3$+H [(M+H)+]: 538.2079. found: 538.2077.

Example 62e

Preparation of (2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide

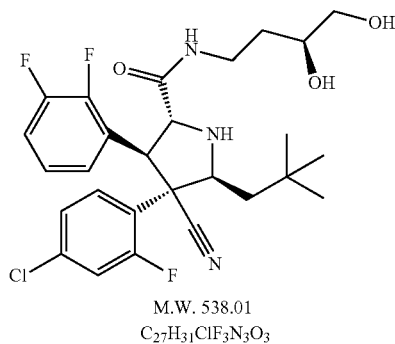

M.W. 538.01
$C_{27}H_{31}ClF_3N_3O_3$

Rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide (0.22 g) was separated by chiral SFC chromatography to provide chiral-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide as a white solid (87 mg, 40%) and chiral-(2S,3R,4S,5R)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide as a white solid (87 mg, 40%).

Example 63a

Preparation of intermediate (Z)-3-(3-bromo-2-fluoro-phenyl)-2-(4-chloro-2-fluoro-phenyl)-acrylonitrile

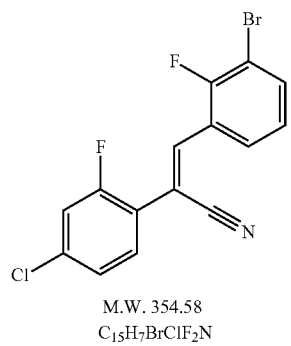 [SMILES: N#C/C(=C\c1cccc(Br)c1F)c1ccc(Cl)cc1F]

M.W. 354.58
$C_{15}H_7BrClF_2N$

In a manner similar to the method described in Example 1b, 4-chloro-2-fluorophenylacetonitrile (1.39 g, 8.2 mmol) was reacted with 3-bromo-2-fluorobenzaldehyde (Apollo) (2 g, 9.9 mmol), methanolic solution (25 wt %) of sodium methoxide (2 g, 9 mmol) in methanol (40 mL) at 50° C. for 3 h to give (Z)-3-(3-bromo-2-fluoro-phenyl)-2-(4-chloro-2-fluoro-phenyl)-acrylonitrile as a white powder (2.3 g, 79%).

Example 63b

Preparation of intermediate rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid tert-butyl ester

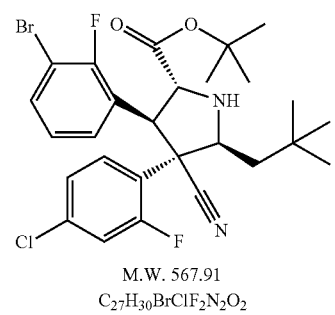 [SMILES: CC(C)(C)C[C@@H]1N[C@@H](C(=O)OC(C)(C)C)[C@H](c2cccc(Br)c2F)[C@@]1(C#N)c1ccc(Cl)cc1F]

M.W. 567.91
$C_{27}H_{30}BrClF_2N_2O_2$

In a manner similar to the method described in Example 1c, [3-methyl-but-(E)-ylideneamino]-acetic acid tert-butyl ester prepared in Example 1a (2.1 g, 10 mmol) was reacted with (Z)-3-(3-bromo-2-fluoro-phenyl)-2-(4-chloro-2-fluoro-phenyl)-acrylonitrile (2.3 g, 6.5 mmol) prepared in Example 63a, AgF (1.5 g, 12 mmol), and triethylamine (2.7 mL, 20 mmol) in dichloromethane (120 mL) at room temperature for 18 h to give rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid tert-butyl ester as a white foam (2 g, 54%).

Example 63c

Preparation of intermediate rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid trifluoroacetic acid

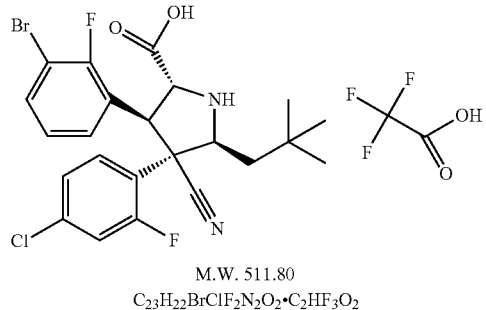

M.W. 511.80
$C_{23}H_{22}BrClF_2N_2O_2 \cdot C_2HF_3O_2$

In a manner similar to the method described in Example 1d, rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid tert-butyl ester prepared in Example 63b (2 g, 3.5 mmol) was reacted with trifluoroacetic acid in dichloromethane at room temperature to give rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid trifluoroacetic acid as a white solid (2.1 g, 95%).

HRMS (ES$^+$) m/z Calcd for $C_{23}H_{22}BrClF_2N_2O_2$+H [(M+H)$^+$]: 511.0594. found: 511.0595.

Example 63d

Preparation of rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

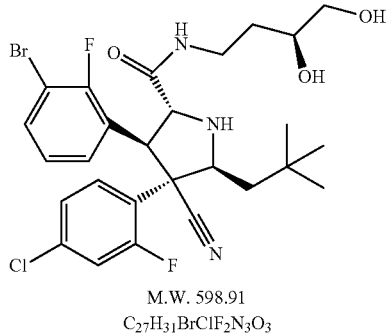

M.W. 598.91
$C_{27}H_{31}BrClF_2N_3O_3$

In a manner similar to the method described in Examples 42c, 42d, rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 63c (0.51 g, 0.83 mmol) was reacted with 2-((S)-2,2-dimethyl-[1,3]dioxolan-4-yl)-ethylamine (0.36 g, 2.5 mmol), HATU (0.57 g, 1.49 mmol) and iPr$_2$NEt (0.72 mL, 4.2 mmol) in CH$_2$Cl$_2$ at room temperature for 20 h, then reacted with aqueous HCl solution in tetrahydrofuran at room temperature for 2 h to give rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.2 g, 40%).

HRMS (ES$^+$) m/z Calcd for $C_{27}H_{31}BrClF_2N_3O_3$+H [(M+H)$^+$]: 598.1278. found: 598.1278.

Example 63e

Preparation of (2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

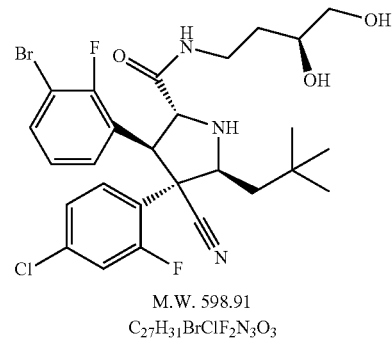 [SMILES: CC(C)(C)C[C@@H]1N[C@@H](C(=O)NCC[C@H](O)CO)[C@H](c2cccc(Br)c2F)[C@@]1(C#N)c1ccc(Cl)cc1F]

M.W. 598.91
$C_{27}H_{31}BrClF_2N_3O_3$

Rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide (0.15 g) was separated by chiral SFC chromatography to provide chiral (2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (66 mg, 44%) and chiral (2S,3R,4S,5R)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (70 mg, 47%).

Example 64a

Preparation of intermediate (Z)-2-(4-chloro-2-fluoro-phenyl)-3-(3-chloro-phenyl)-acrylonitrile

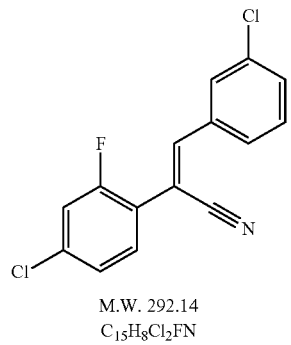 [SMILES: N#C/C(=C\c1cccc(Cl)c1)c1ccc(Cl)cc1F]

M.W. 292.14
$C_{15}H_8Cl_2FN$

In a manner similar to the method described in Example 1b, 4-chloro-2-fluorophenylacetonitrile (4.5 g, 26 mmol) was reacted with 3-chlorobenzaldehyde (Aldrich) (4.4 g, 32 mmol), methanolic solution (25 wt %) of sodium methoxide (6.6 mL, 29 mmol) in methanol (150 mL) at 50° C. for 3 h to give (Z)-2-(4-Chloro-2-fluoro-phenyl)-3-(3-chloro-phenyl)-acrylonitrile as a white powder (6.5 g, 84%).

Example 64b

Preparation of intermediate rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid tert-butyl ester

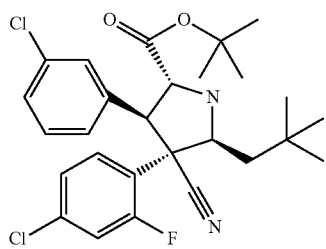

M.W. 505.46
$C_{27}H_{31}Cl_2FN_2O_2$

In a manner similar to the method described in Example 1c, [3-methyl-but-(E)-ylideneamino]-acetic acid tert-butyl ester prepared in Example 1a (2.1 g, 10 mmol) was reacted with (Z)-2-(4-chloro-2-fluoro-phenyl)-3-(3-chloro-phenyl)-acrylonitrile (2.3 g, 8 mmol) prepared in Example 64a, AgF (1.5 g, 12 mmol), and triethylamine (2.7 mL, 20 mmol) in dichloromethane (120 mL) at room temperature for 18 h to give rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid tert-butyl ester as a white foam (1.02 g, 25%).

Example 64c

Preparation of intermediate rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid trifluoroacetic acid

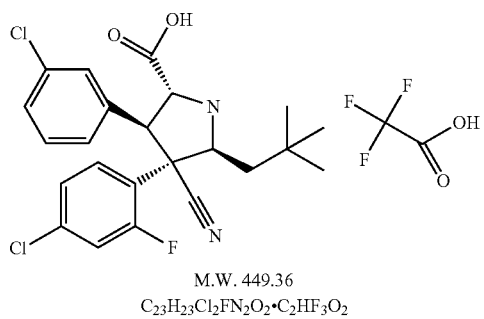

M.W. 449.36
$C_{23}H_{23}Cl_2FN_2O_2 \cdot C_2HF_3O_2$

In a manner similar to the method described in Example 1d, rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid tert-butyl ester prepared in Example 64b (1 g, 2 mmol) was reacted with trifluoroacetic acid in dichloromethane at room temperature to give rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid trifluoroacetic acid as a white solid (0.88 g, 79%).

HRMS (ES$^+$) m/z Calcd for $C_{23}H_{23}Cl_2FN_2O_2$+H [(M+H)$^+$]: 449.1194 found: 449.1194.

Example 64d

Preparation of rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide

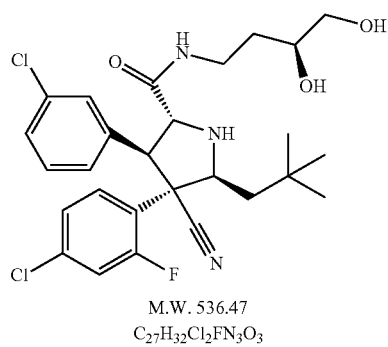 [SMILES: CC(C)(C)C[C@@H]1N[C@@H](C(=O)NCC[C@H](O)CO)[C@H](c2cccc(Cl)c2)[C@@]1(C#N)c1ccc(Cl)cc1F]

M.W. 536.47
$C_{27}H_{32}Cl_2FN_3O_3$

In a manner similar to the method described in Examples 42c, 42d, rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid trifluoroacetic acid prepared in Example 64c (0.46 g, 0.83 mmol) was reacted with 2-((S)-2,2-dimethyl-[1,3]dioxolan-4-yl)-ethylamine (0.36 g, 2.5 mmol), HATU (0.57 g, 1.5 mmol) and iPr$_2$NEt (0.72 mL, 4.2 mmol) in CH$_2$Cl$_2$ at room temperature for 20 h, then reacted with aqueous HCl solution in tetrahydrofuran at room temperature for 2 h to give rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide as a white solid (0.21 g, 48%).

HRMS (ES$^+$) m/z Calcd for $C_{27}H_{32}Cl_2FN_3O_3$+H [(M+H)$^+$]: 536.1878. found: 536.1877.

Example 64e

Preparation of (2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide

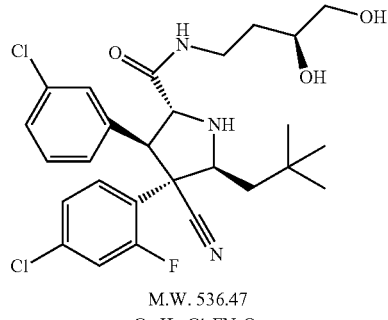

M.W. 536.47
$C_{27}H_{32}Cl_2FN_3O_3$

Rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide (0.15 g) was separated by chiral SFC chromatography to provide chiral (2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide as a white solid (71 mg, 47%) and chiral-(2S,3S,4S,5R)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide as a white solid (70 mg, 47%).

Example 65a

Preparation of intermediate (Z)-2-(4-chloro-2-fluoro-phenyl)-3-(3-fluoro-phenyl)-acrylonitrile

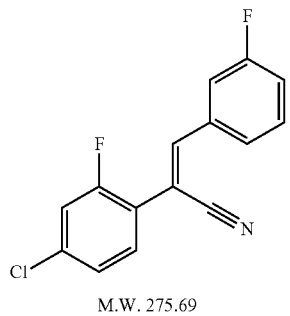

M.W. 275.69
$C_{15}H_8ClF_2N$

In a manner similar to the method described in Example 1b, 4-chloro-2-fluorophenylacetonitrile (3.27 g, 19 mmol) was reacted with 3-fluorobenzaldehyde (Aldrich) (2.87 g, 23 mmol), methanolic solution (25 wt %) of sodium methoxide (4.83 mL, 21 mmol) in methanol (90 mL) at 50° C. for 3 h to give (Z)-2-(4-chloro-2-fluoro-phenyl)-3-(3-fluoro-phenyl)-acrylonitrile as a white powder (5.2 g, 98%).

Example 65b

Preparation of intermediate rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid tert-butyl ester

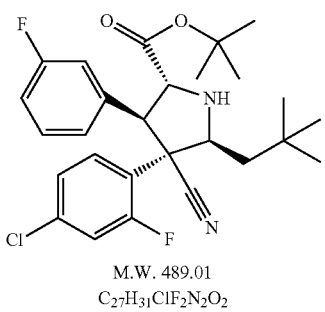 [SMILES: CC(C)(C)C[C@@H]1N[C@@H](C(=O)OC(C)(C)C)[C@H](c2cccc(F)c2)[C@@]1(C#N)c1ccc(Cl)cc1F]

M.W. 489.01
$C_{27}H_{31}ClF_2N_2O_2$

In a manner similar to the method described in Example 1c, [3-methyl-but-(E)-ylideneamino]-acetic acid tert-butyl ester prepared in Example 1a (2.1 g, 10 mmol) was reacted with (Z)-2-(4-chloro-2-fluoro-phenyl)-3-(3-fluoro-phenyl)-acrylonitrile (2.2 g, 8 mmol) prepared in Example 65a, AgF (1.5 g, 12 mmol), and triethylamine (2.7 mL, 20 mmol) in dichloromethane (120 mL) at room temperature for 18 h to give rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid tert-butyl ester as a white foam (1.02 g, 26%).

Example 65c

Preparation of intermediate rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid trifluoroacetic acid

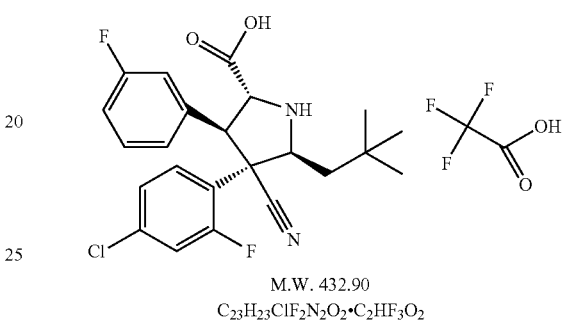

M.W. 432.90
$C_{23}H_{23}ClF_2N_2O_2 \cdot C_2HF_3O_2$

In a manner similar to the method described in Example 1d, rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid tert-butyl ester prepared in Example 65b (1 g, 2.1 mmol) was reacted with trifluoroacetic acid in dichloromethane at room temperature to give rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid trifluoroacetic acid as a white solid (1 g, 88%).

HRMS (ES$^+$) m/z Calcd for $C_{23}H_{23}ClF_2N_2O_2$+H [(M+H)$^+$]: 433.1489. found: 433.1487.

Example 65d

Preparation of rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid ((S)-3,4-dihydroxy-butyl)-amide

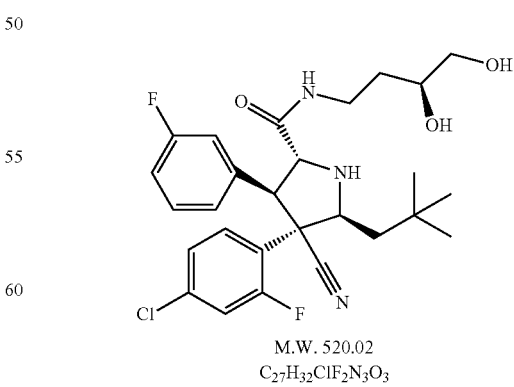

M.W. 520.02
$C_{27}H_{32}ClF_2N_3O_3$

In a manner similar to the method described in Examples 42c, 42d, rac-(2R,3R,4R,5S)-4-(4-chloro-2-fluoro-phenyl)-

4-cyano-5-(2,2-dimethyl-propyl)-3-(3-fluoro-phenyl)-pyrrolidine-2-carboxylic acid trifluoroacetic acid prepared in Example 65c (0.46 g, 0.83 mmol) was reacted with 2-((S)-2,2-dimethyl-[1,3]dioxolan-4-yl)-ethylamine (0.36 g, 2.5 mmol), HATU (0.57 g, 1.5 mmol) and iPr$_2$NEt (0.72 mL, 4.2 mmol) in CH$_2$Cl$_2$ at room temperature for 20 h, then reacted with aqueous HCl solution in tetrahydrofuran at room temperature for 2 h to give rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid ((S)-3,4-dihydroxy-butyl)-amide as a white solid (0.21 g, 48%).

HRMS (ES$^+$) m/z Calcd for C$_{27}$H$_{32}$ClF$_2$N$_3$O$_3$+H [(M+H)$^+$]: 520.2173. found: 520.2171.

Example 66a

Preparation of intermediate (Z)-3-(3-bromo-phenyl)-2-(4-chloro-2-fluoro-phenyl)-acrylonitrile

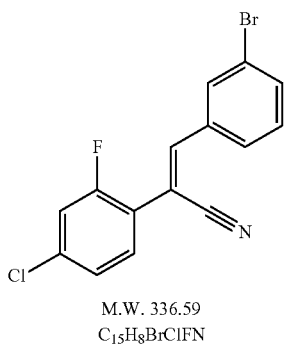 [SMILES: N#C/C(=C\c1cccc(Br)c1)c1ccc(Cl)cc1F]

M.W. 336.59
C$_{15}$H$_8$BrClFN

In a manner similar to the method described in Example 1b, 4-chloro-2-fluorophenylacetonitrile (1.9 g, 11 mmol) was reacted with 3-bromobenzaldehyde (Aldrich) (1.57 mL, 13.4 mmol), methanolic solution (25 wt %) of sodium methoxide (2.8 mL, 12 mmol) in methanol (50 mL) at 50° C. for 3 h to give (Z)-3-(3-bromo-phenyl)-2-(4-chloro-2-fluoro-phenyl)-acrylonitrile as a white powder (2.3 g, 60%).

Example 66b

Preparation of intermediate rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid tert-butyl ester

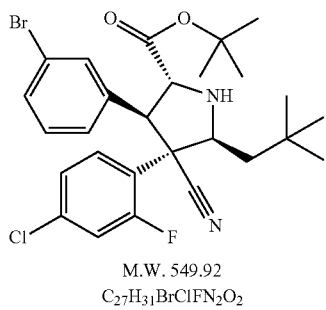 [SMILES: CC(C)(C)C[C@@H]1N[C@@H](C(=O)OC(C)(C)C)[C@H](c2cccc(Br)c2)[C@@]1(C#N)c1ccc(Cl)cc1F]

M.W. 549.92
C$_{27}$H$_{31}$BrClFN$_2$O$_2$

In a manner similar to the method described in Example 1c, [3-methyl-but-(E)-ylideneamino]-acetic acid tert-butyl ester prepared in Example 1a (2.1 g, 10 mmol) was reacted with (Z)-3-(3-bromo-phenyl)-2-(4-chloro-2-fluoro-phenyl)-acrylonitrile (2 g, 5.9 mmol) prepared in Example 66a, AgF (1.5 g, 12 mmol), and triethylamine (2.7 mL, 20 mmol) in dichloromethane (120 mL) at room temperature for 18 h to give rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid tert-butyl ester as a white foam (1.3 g, 40%).

Example 66c

Preparation of intermediate rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid trifluoroacetic acid

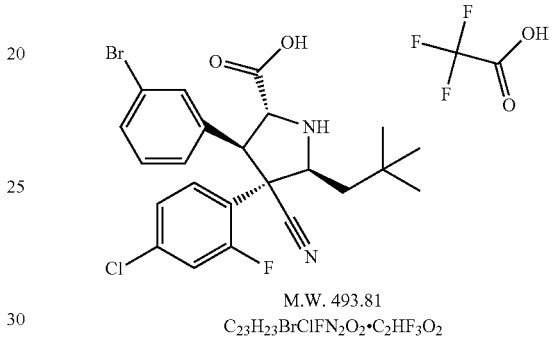

M.W. 493.81
C$_{23}$H$_{23}$BrClFN$_2$O$_2$·C$_2$HF$_3$O$_2$

In a manner similar to the method described in Example 25a, rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid tert-butyl ester prepared in Example 66b (1.2 g, 2.2 mmol) was reacted with trifluoroacetic acid in dichloromethane at room temperature to give rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid trifluoroacetic acid as a white solid (1.1 g, 83%).

HRMS (ES$^+$) m/z Calcd for C$_{23}$H$_{23}$BrClFN$_2$O$_2$+H [(M+H)$^+$]: 493.0688. found: 493.0688.

Example 66d

Preparation of rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

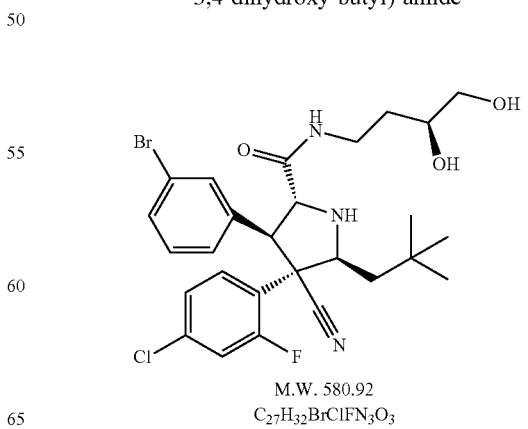

M.W. 580.92
C$_{27}$H$_{32}$BrClFN$_3$O$_3$

In a manner similar to the method described in Examples 42c, 42d, rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid trifluoroacetic acid prepared in Example 66c (0.5 g, 0.83 mmol) was reacted with 2-((S)-2,2-dimethyl-[1,3]dioxolan-4-yl)-ethylamine (0.36 g, 2.5 mmol), HATU (0.57 g, 1.49 mmol) and iPr$_2$NEt (0.72 mL, 4.2 mmol) in CH$_2$Cl$_2$ at room temperature for 20 h, then reacted with aqueous HCl solution in tetrahydrofuran at room temperature for 2 h to give rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.26 g, 55%).

HRMS (ES$^+$) m/z Calcd for C$_{27}$H$_{32}$BrClFN$_3$O$_3$+H [(M+H)$^+$]: 580.1373, found: 580.1372.

Example 67a

Preparation of intermediate rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid tert-butyl ester

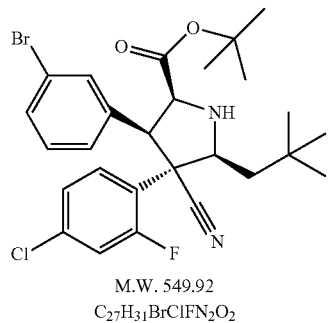 [SMILES: CC(C)(C)C[C@@H]1N[C@H](C(=O)OC(C)(C)C)[C@H](c2cccc(Br)c2)[C@@]1(C#N)c1ccc(Cl)cc1F]

M.W. 549.92
C$_{27}$H$_{31}$BrClFN$_2$O$_2$

In preparation of rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid tert-butyl ester as described in Example 66b, rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid tert-butyl ester was obtained as the second product: a white foam (1.2 g, 37%).

Example 67b

Preparation of intermediate rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid trifluoroacetic acid

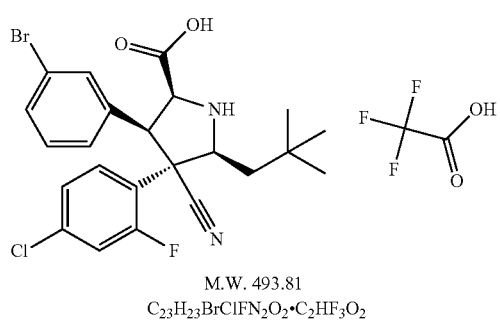

M.W. 493.81
C$_{23}$H$_{23}$BrClFN$_2$O$_2$·C$_2$HF$_3$O$_2$

In a manner similar to the method described in Example 25a, rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid tert-butyl ester prepared in Example 67a (1.3 g, 2.4 mmol) was reacted with trifluoroacetic acid in dichloromethane at room temperature to give rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid trifluoroacetic acid as a white solid (1.2 g, 83%).

HRMS (ES$^+$) m/z Calcd for C$_{23}$H$_{23}$BrClFN$_2$O$_2$+H [(M+H)$^+$]: 493.0688. found: 493.0689.

Example 67c

Preparation of rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

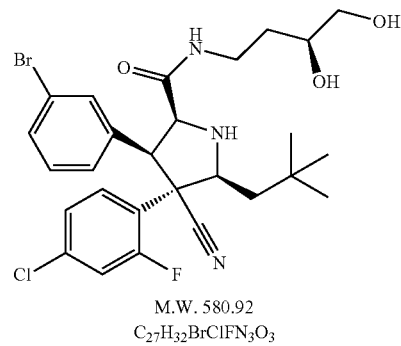 [SMILES: CC(C)(C)C[C@@H]1N[C@H](C(=O)NCC[C@H](O)CO)[C@H](c2cccc(Br)c2)[C@@]1(C#N)c1ccc(Cl)cc1F]

M.W. 580.92
C$_{27}$H$_{32}$BrClFN$_3$O$_3$

In a manner similar to the method described in Examples 42c, 42d, rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid trifluoroacetic acid prepared in Example 67b (0.5 g, 0.83 mmol) was reacted with 2-((S)-2,2-dimethyl-[1,3]dioxolan-4-yl)-ethylamine (0.36 g, 2.5 mmol), HATU (0.57 g, 1.49 mmol) and iPr$_2$NEt (0.72 mL, 4.2 mmol) in CH$_2$Cl$_2$ at room temperature for 20 h, then reacted with aqueous HCl solution in tetrahydrofuran at room temperature for 2 h to give rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.21 g, 44%).

HRMS (ES$^+$) m/z Calcd for C$_{27}$H$_{32}$BrClFN$_3$O$_3$+H [(M+H)$^+$]: 580.1373. found: 580.1372.

Example 68a

Preparation of intermediate (Z)-2-(4-Chloro-2-fluoro-phenyl)-3-(3,4-dichloro-phenyl)-acrylonitrile

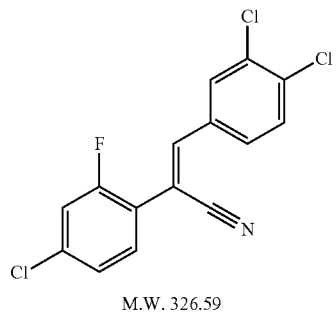

M.W. 326.59
C$_{15}$H$_7$Cl$_3$FN

In a manner similar to the method described in Example 1b, 4-chloro-2-fluorophenyl acetonitrile (4.5 g, 26 mmol) was reacted with 3,4-dichlorobenzaldehyde (Aldrich) (5.5 g, 32 mmol), methanolic solution (25 wt %) of sodium methoxide (6.6 mL, 29 mmol) in methanol (150 mL) at 50° C. for 3 h to give (Z)-2-(4-chloro-2-fluoro-phenyl)-3-(3,4-dichloro-phenyl)-acrylonitrile as a white powder (6.5 g, 76%).

Example 68b

Preparation of intermediate rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid tert-butyl ester

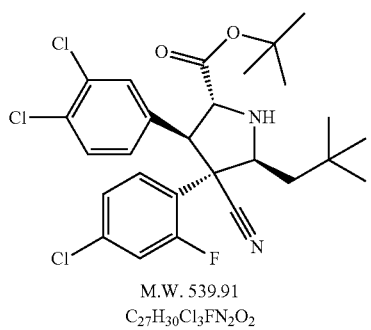 [SMILES: CC(C)(C)C[C@@H]1N[C@@H](C(=O)OC(C)(C)C)[C@H](c2ccc(Cl)c(Cl)c2)[C@@]1(C#N)c1ccc(Cl)cc1F]

M.W. 539.91
$C_{27}H_{30}Cl_3FN_2O_2$

In a manner similar to the method described in Example 1c, [3-methyl-but-(E)-ylideneamino]-acetic acid tert-butyl ester prepared in Example 1a (2.1 g, 10 mmol) was reacted with (Z)-2-(4-chloro-2-fluoro-phenyl)-3-(3,4-dichloro-phenyl)-acrylonitrile (2.6 g, 8 mmol) prepared in Example 68a, AgF (1.5 g, 12 mmol), and triethylamine (2.7 mL, 20 mmol) in dichloromethane (120 mL) at room temperature for 18 h to give rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid tert-butyl ester as a white foam (1.7 g, 39%).

Example 68c

Preparation of intermediate rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid trifluoroacetic acid

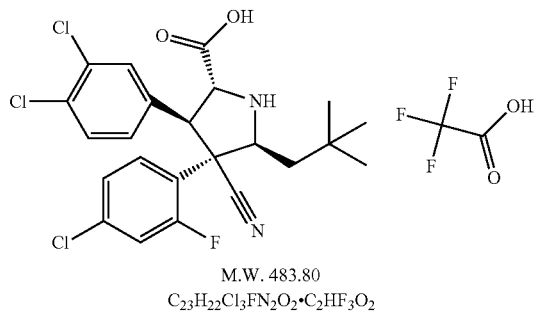

M.W. 483.80
$C_{23}H_{22}Cl_3FN_2O_2 \cdot C_2HF_3O_2$

In a manner similar to the method described in Example 25a, rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid tert-butyl ester prepared in Example 68b (1.7 g, 3.1 mmol) was reacted with trifluoroacetic acid in dichloromethane at room temperature to give rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid trifluoroacetic acid as a white solid (1.8 g, 96%).

Example 68d

Preparation of rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid ((S)-3,4-dihydroxy-butyl)-amide

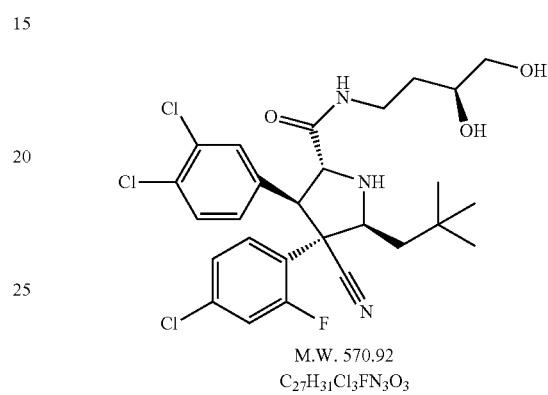

M.W. 570.92
$C_{27}H_{31}Cl_3FN_3O_3$

In a manner similar to the method described in Examples 42c, 42d, rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid trifluoroacetic acid prepared in Example 68c (0.5 g, 0.84 mmol) was reacted with 2-((S)-2,2-dimethyl-[1,3]dioxolan-4-yl)-ethylamine (0.36 g, 2.5 mmol), HATU (0.57 g, 1.5 mmol) and iPr$_2$NEt (0.72 mL, 4.2 mmol) in CH$_2$Cl$_2$ at room temperature for 20 h, then reacted with aqueous HCl solution in tetrahydrofuran at room temperature for 2 h to give rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid ((S)-3,4-dihydroxy-butyl)-amide as a white solid (0.28 g, 59%).

HRMS (ES$^+$) m/z Calcd for $C_{27}H_{31}Cl_3FN_3O_3$+H [(M+H)$^+$]: 570.1488. found: 570.1489.

Example 69a

Preparation of intermediate (Z)-3-(3-chloro-4-fluoro-phenyl)-2-(4-chloro-2-fluoro-phenyl)-acrylonitrile

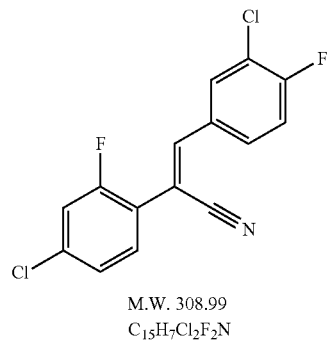 [SMILES: N#C/C(=C\c1ccc(F)c(Cl)c1)c1ccc(Cl)cc1F]

M.W. 308.99
$C_{15}H_7Cl_2F_2N$

In a manner similar to the method described in Example 1b, 4-chloro-2-fluorophenylacetonitrile (3.3 g, 19 mmol) was reacted with 4-chloro-3-fluoro-benzaldehyde (Aldrich) (3.65 g, 23 mmol), methanolic solution (25 wt %) of sodium methoxide (4.8 mL, 21 mmol) in methanol (90 mL) at 50° C. for 3 h to give (Z)-3-(3-chloro-4-fluoro-phenyl)-2-(4-chloro-2-fluoro-phenyl)-acrylonitrile as a white powder (3 g, 50%).

Example 69b

Preparation of intermediate rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid tert-butyl ester

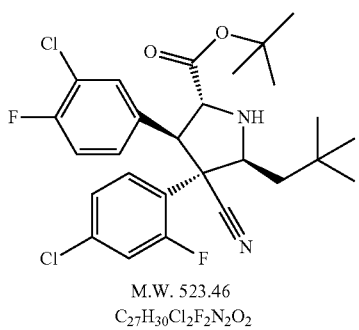 [SMILES: CC(C)(C)C[C@@H]1N[C@@H](C(=O)OC(C)(C)C)[C@H](c2ccc(F)c(Cl)c2)[C@@]1(C#N)c1ccc(Cl)cc1F]

M.W. 523.46
$C_{27}H_{30}Cl_2F_2N_2O_2$

In a manner similar to the method described in Example 1c, [3-methyl-but-(E)-ylideneamino]-acetic acid tert-butyl ester prepared in Example 1a (2.1 g, 10 mmol) was reacted with (Z)-3-(3-chloro-4-fluoro-phenyl)-2-(4-chloro-2-fluoro-phenyl)-acrylonitrile (2.5 g, 8 mmol) prepared in Example 69a, AgF (1.5 g, 12 mmol), and triethylamine (2.7 mL, 20 mmol) in dichloromethane (120 mL) at room temperature for 18 h to give rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid tert-butyl ester as a white foam (1 g, 24%).

Example 69c

Preparation of intermediate rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid trifluoroacetic acid

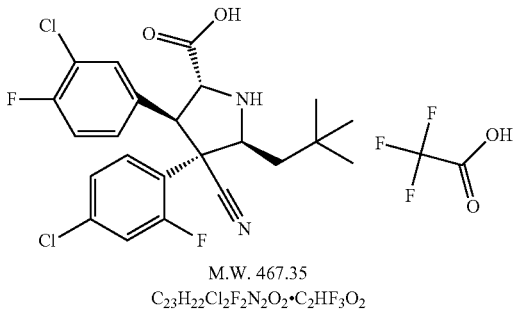

M.W. 467.35
$C_{23}H_{22}Cl_2F_2N_2O_2 \cdot C_2HF_3O_2$

In a manner similar to the method described in Example 25a, rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid tert-butyl ester prepared in Example 69b (1 g, 1.9 mmol) was reacted with trifluoroacetic acid in dichloromethane at room temperature to give rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid trifluoroacetic acid as a white solid (1 g, 90%).

Example 69d

Preparation of rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

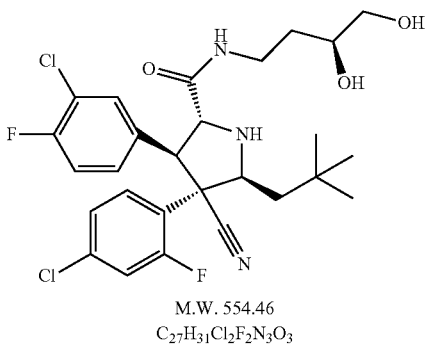 [SMILES: CC(C)(C)C[C@@H]1N[C@@H](C(=O)NCC[C@H](O)CO)[C@H](c2ccc(F)c(Cl)c2)[C@@]1(C#N)c1ccc(Cl)cc1F]

M.W. 554.46
$C_{27}H_{31}Cl_2F_2N_3O_3$

In a manner similar to the method described in Examples 42c, 42d, rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 69c (0.28 g, 0.48 mmol) was reacted with 2-((S)-2,2-dimethyl-[1,3]dioxolan-4-yl)-ethylamine (0.21 g, 1.44 mmol), HATU (0.33 g, 0.87 mmol) and iPr₂NEt (0.42 mL, 2.4 mmol) in CH₂Cl₂ at room temperature for 20 h, then reacted with aqueous HCl solution in tetrahydrofuran at room temperature for 2 h to give rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.18 g, 77%).

HRMS (ES⁺) m/z Calcd for $C_{27}H_{31}Cl_3FN_3O_3$+H [(M+H)⁺]: 554.1784. found: 554.1785.

Example 69e

Preparation of (2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

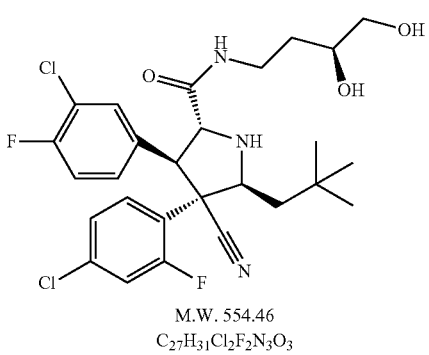 [SMILES: CC(C)(C)C[C@@H]1N[C@@H](C(=O)NCC[C@H](O)CO)[C@H](c2ccc(F)c(Cl)c2)[C@@]1(C#N)c1ccc(Cl)cc1F]

M.W. 554.46
$C_{27}H_{31}Cl_2F_2N_3O_3$

Rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide (0.14 g) was separated by chiral SFC chromatography to provide chiral (2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (61 mg, 44%) and chiral-(2S,3S,4S,5R)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (61 mg, 44%).

Example 70a

Preparation of intermediate (Z)-3-(4-bromo-thiophen-2-yl)-2-(4-chloro-2-fluoro-phenyl)-acrylonitrile

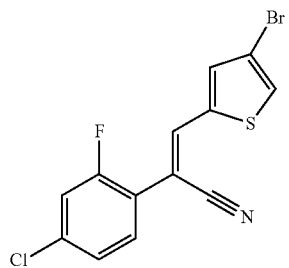

M.W. 342.62
$C_{13}H_6BrClFNS$

In a manner similar to the method described in Example 1b, 4-chloro-2-fluorophenylacetonitrile (4.05 g, 24 mmol) was reacted with 4-bromo-2-thiophenecarboxaldehyde (Aldrich) (6.08 g, 29 mmol), methanolic solution (25 wt %) of sodium methoxide (6 mL, 26 mmol) in methanol (90 mL) at 50° C. for 3 h to give (Z)-3-(4-bromo-thiophen-2-yl)-2-(4-chloro-2-fluoro-phenyl)-acrylonitrile as a light yellow solid (5.2 g, 64%).

Example 70b

Preparation of intermediate rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid tert-butyl ester

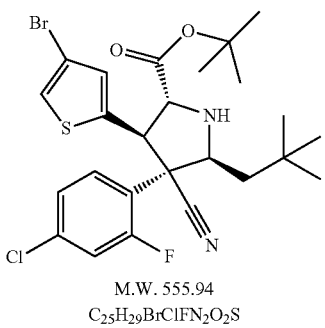 [SMILES: CC(C)(C)C[C@@H]1N[C@@H](C(=O)OC(C)(C)C)[C@H](c2cc(Br)cs2)[C@@]1(C#N)c1ccc(Cl)cc1F]

M.W. 555.94
$C_{25}H_{29}BrClFN_2O_2S$

In a manner similar to the method described in Example 1c, [3-methyl-but-(E)-ylideneamino]-acetic acid tert-butyl ester prepared in Example 1a (2.1 g, 10 mmol) was reacted with (Z)-3-(4-bromo-thiophen-2-yl)-2-(4-chloro-2-fluoro-phenyl)-acrylonitrile (2.7 g, 8 mmol) prepared in Example 70a, AgF (1.5 g, 12 mmol), and triethylamine (2.7 mL, 20 mmol) in dichloromethane (120 mL) at room temperature for 18 h to give rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid tert-butyl ester as a white foam (0.9 g, 20%).

Example 70c

Preparation of intermediate rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid trifluoroacetic acid

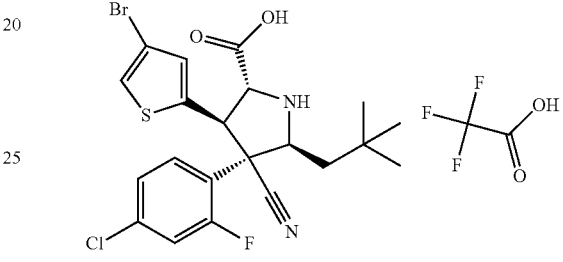

M.W. 499.83
$C_{21}H_{21}BrClFN_2O_2S \cdot C_2HF_3O_2$

In a manner similar to the method described in Example 25a, rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid tert-butyl ester prepared in Example 70b (0.9 g, 1.6 mmol) was reacted with trifluoroacetic acid in dichloromethane at room temperature to give rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid trifluoroacetic acid as a light blue solid (0.9 g, 92%).

Example 70d

Preparation of rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

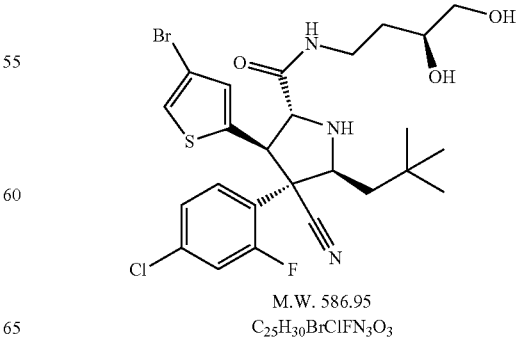

M.W. 586.95
$C_{25}H_{30}BrClFN_3O_3$

In a manner similar to the method described in Examples 42c, 42d, rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid trifluoroacetic acid prepared in Example 70c (0.2 g, 0.33 mmol) was reacted with 2-4S)-2,2-dimethyl-[1,3]dioxolan-4-yl)-ethylamine (0.14 g, 1 mmol), HATU (0.22 g, 0.58 mmol) and iPr₂NEt (0.28 mL, 1.63 mmol) in CH₂Cl₂ at room temperature for 20 h, then reacted with aqueous HCl solution in tetrahydrofuran at room temperature for 2 h to give rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.15 g, 80%).

HRMS (ES⁺) m/z Calcd for $C_{25}H_{30}BrClFN_3O_3$+H [(M+H)⁺]: 586.0937. found: 586.0935.

Example 71a

Preparation of intermediate (Z)-2-(4-Chloro-2-fluoro-phenyl)-3-(3-chloro-4-trifluoromethyl-phenyl)-acrylonitrile

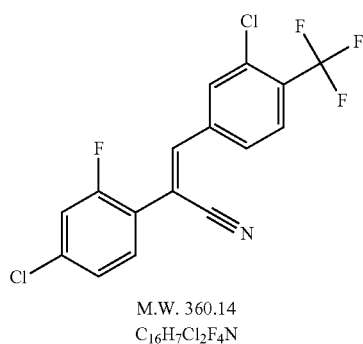 [SMILES: N#C/C(=C\c1ccc(C(F)(F)F)c(Cl)c1)c1ccc(Cl)cc1F]

M.W. 360.14
$C_{16}H_7Cl_2F_4N$

Step A A mixture of 3-chloro-4-(trifluoromethyl)benzyl alcohol (Synquest) (4.77 g, 23 mmol) and activated MnO₂ (19.5 g, 230 mmol) in 1,2-dichlorethane (80 mL) was heated and stirred at 80° C. for 3 h. The mixture was cooled to room temperature and filtered through a short pad of celite. The celite was washed with dichloromethane, and ethyl acetate. The filtrates were combined, concentrated, dried under reduced pressure to give 3-chloro-4-(trifluoromethyl)benzaldehyde as a light yellow oil (2.8 g, 60%).

Step B In a manner similar to the method described in Example 1b, 4-chloro-2-methylbenzyl cyanide (1.9 g, 11 mmol) was reacted with 3-chloro-4-(trifluoromethyl)benzaldehyde (2.8 g, 14 mmol), methanolic solution (25 wt %) of sodium methoxide (2.8 mL, 12 mmol) in methanol (50 mL) at 50° C. for 5 h to give (Z)-2-(4-chloro-2-fluoro-phenyl)-3-(3-chloro-4-trifluoromethyl-phenyl)-acrylonitrile as a yellow solid (2.45 g, 61%).

Example 71b

Preparation of intermediate rac-(2R,3R,4R,5S)-4-(4-chloro-2-fluoro-phenyl)-3-(3-chloro-4-trifluoromethyl-phenyl)-4-cyano-5-(2,2-dimethyl-propyl)-pyrrolidine-2-carboxylic acid tert-butyl ester

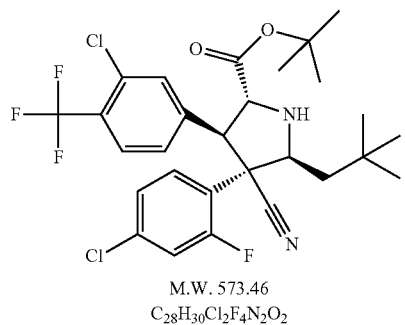 [SMILES: CC(C)(C)C[C@@H]1N[C@@H](C(=O)OC(C)(C)C)[C@H](c2ccc(C(F)(F)F)c(Cl)c2)[C@@]1(C#N)c1ccc(Cl)cc1F]

M.W. 573.46
$C_{28}H_{30}Cl_2F_4N_2O_2$

In a manner similar to the method described in Example 1c, [3-methyl-but-(E)-ylideneamino]-acetic acid tert-butyl ester prepared in Example 1a (2.1 g, 10 mmol) was reacted with (Z)-2-(4-chloro-2-fluoro-phenyl)-3-(3-chloro-4-trifluoromethyl-phenyl)-acrylonitrile (2.5 g, 6.9 mmol) prepared in Example 71a, AgF (1 g, 8 mmol), and triethylamine (2.4 mL, 17 mmol) in dichloromethane (120 mL) at room temperature for 18 h to give rac-(2R,3R,4R,5S)-4-(4-chloro-2-fluoro-phenyl)-3-(3-chloro-4-trifluoromethyl-phenyl)-4-cyano-5-(2,2-dimethyl-propyl)-pyrrolidine-2-carboxylic acid tert-butyl ester as a white foam (1.2 g, 30%).

Example 70c

Preparation of intermediate rac-(2R,3R,4R,5S)-4-(4-chloro-2-fluoro-phenyl)-3-(3-chloro-4-trifluoromethyl-phenyl)-4-cyano-5-(2,2-dimethyl-propyl)-pyrrolidine-2-carboxylic acid trifluoroacetic acid

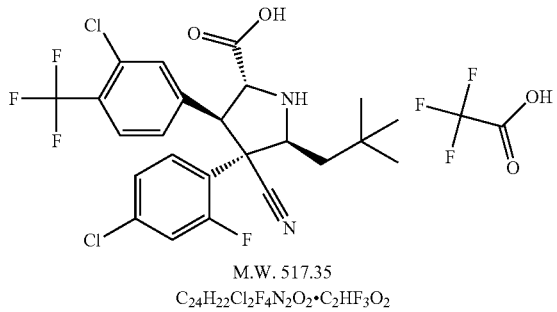

M.W. 517.35
$C_{24}H_{22}Cl_2F_4N_2O_2 \cdot C_2HF_3O_2$

In a manner similar to the method described in Example 25a, rac-(2R,3R,4R,5S)-4-(4-chloro-2-fluoro-phenyl)-3-(3-chloro-4-trifluoromethyl-phenyl)-4-cyano-5-(2,2-dimethyl-propyl)-pyrrolidine-2-carboxylic acid tert-butyl ester prepared in Example 70b (1.2 g, 2.1 mmol) was reacted with trifluoroacetic acid in dichloromethane at room temperature to give rac-(2R,3R,4R,5S)-4-(4-chloro-2-fluoro-phenyl)-3-(3-chloro-4-trifluoromethyl-phenyl)-4-cyano-5-(2,2-dimethyl-propyl)-pyrrolidine-2-carboxylic acid trifluoroacetic acid as solid (1.1 g, 83%).

Example 71d

Preparation of (2R,3R,4R,5S)-4-(4-chloro-2-fluoro-phenyl)-3-(3-chloro-4-trifluoromethyl-phenyl)-4-cyano-5-(2,2-dimethyl-propyl)-pyrrolidine-2-carboxylic acid ((S)-3,4-dihydroxy-butyl)-amide

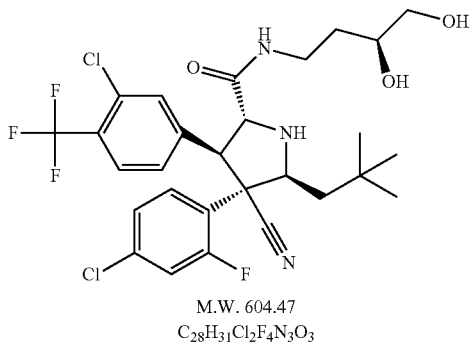 [SMILES: CC(C)(C)C[C@@H]1N[C@@H](C(=O)NCC[C@H](O)CO)[C@H](c2ccc(C(F)(F)F)c(Cl)c2)[C@@]1(C#N)c1ccc(Cl)cc1F]

M.W. 604.47
$C_{28}H_{31}Cl_2F_4N_3O_3$

In a manner similar to the method described in Examples 42c, 42d, rac-(2R,3R,4R,5S)-4-(4-chloro-2-fluoro-phenyl)-3-(3-chloro-4-trifluoromethyl-phenyl)-4-cyano-5-(2,2-dimethyl-propyl)-pyrrolidine-2-carboxylic acid trifluoroacetic acid prepared in Example 71c (0.22 g, 0.35 mmol) was reacted with 2-((S)-2,2-dimethyl-[1,3]dioxolan-4-yl)-ethylamine (0.15 g, 1.05 mmol), HATU (0.24 g, 0.63 mmol) and iPr$_2$NEt (0.3 mL, 1.74 mmol) in CH$_2$Cl$_2$ at room temperature for 20 h, then reacted with aqueous HCl solution in tetrahydrofuran at room temperature for 2 h to give rac-(2R,3R,4R,5S)-3-(3-chloro-4-fluoro-phenyl)-4-(4-chloro-2-trifluoromethyl-phenyl)-4-cyano-5-(2,2-dimethyl-propyl)-pyrrolidine-2-carboxylic acid ((S)-3,4-dihydroxy-butyl)-amide as a white solid (0.14 g, 73%).

HRMS (ES$^+$) m/z Calcd for $C_{28}H_{31}Cl_2F_4N_3O_3$+H [(M+H)$^+$]: 604.1752. found: 604.1748.

Example 72a

Preparation of rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide

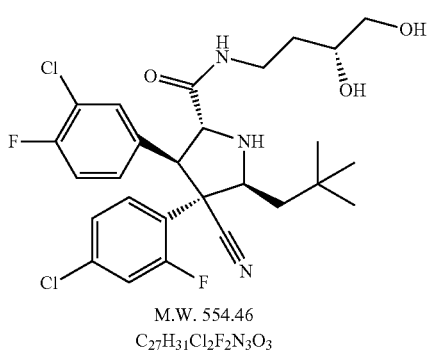 [SMILES: CC(C)(C)C[C@@H]1N[C@@H](C(=O)NCC[C@@H](O)CO)[C@H](c2ccc(F)c(Cl)c2)[C@@]1(C#N)c1ccc(Cl)cc1F]

M.W. 554.46
$C_{27}H_{31}Cl_2F_2N_3O_3$

Step A In a manner similar to the method described in Example 3a Step A to C, (4R)-(−)-4-(2-hydroxyethyl)-2,2-dimethyl-1,3-dioxolane (Aldrich) (4.91 g, 33.6 mmol) was reacted with methanesulfonyl chloride (3.12 mL, 40.3 mmol) and triethylamine (9.34 mL, 67 mmol) in dichloromethane, then reacted with NaN$_3$ (10.7 g, 0.16 mol) in N,N-dimethylformamide, then treated with PtO$_2$ and H$_2$ (50 psi) in ethyl acetate to give 2-((R)-2,2-dimethyl-[1,3]dioxolan-4-yl)-ethylamine as a brown oil (4.4 g, 90% for three steps).

Step B In a manner similar to the method described in Examples 42c, 42d, rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 69c (0.2 g, 0.48 mmol) was reacted with 2-((R)-2,2-dimethyl-[1,3]dioxolan-4-yl)-ethylamine (0.15 g, 1.0 mmol), HATU (0.23 g, 0.62 mmol) and iPr$_2$NEt (0.3 mL, 1.72 mmol) in CH$_2$Cl$_2$ at room temperature for 20 h, then reacted with aqueous HCl solution in tetrahydrofuran at room temperature for 2 h to give rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide as a white solid (0.11 g, 74%).

HRMS (ES$^+$) m/z Calcd for $C_{27}H_{31}Cl_3FN_3O_3$+H [(M+H)$^+$]: 554.1784. found: 554.1786.

Example 72b

Preparation of (2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide

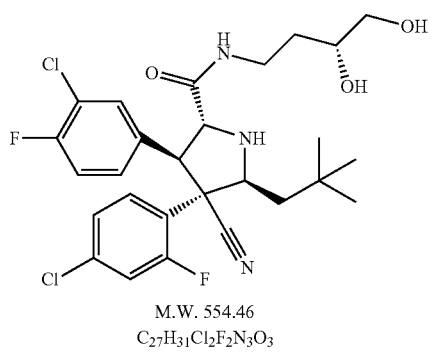 [SMILES: CC(C)(C)C[C@@H]1N[C@@H](C(=O)NCC[C@@H](O)CO)[C@H](c2ccc(F)c(Cl)c2)[C@@]1(C#N)c1ccc(Cl)cc1F]

M.W. 554.46
$C_{27}H_{31}Cl_2F_2N_3O_3$

Rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide (80 mg) was separated by chiral SFC chromatography to provide chiral (2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide as a white solid (35 mg, 44%) and chiral (2S,3S,4S,5R)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide as a white solid (35 mg, 44%).

Example 73a

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide

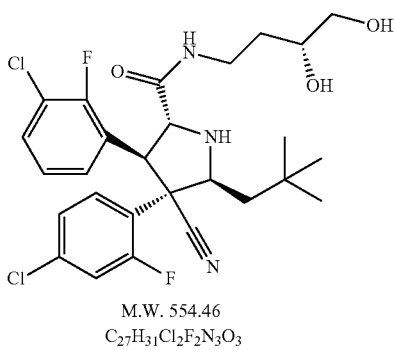 [SMILES: CC(C)(C)C[C@@H]1N[C@@H](C(=O)NCC[C@@H](O)CO)[C@H](c2cccc(Cl)c2F)[C@@]1(C#N)c1ccc(Cl)cc1F]

M.W. 554.46
$C_{27}H_{31}Cl_2F_2N_3O_3$

In a manner similar to the method described in Example 72a, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 53b (0.44 g, 0.769 mmol) was reacted with 2-((R)-2,2-dimethyl-[1,3]dioxolan-4-yl)-ethylamine (0.33 g, 2.3 mmol), HATU (0.52 g, 1.36 mmol) and iPr$_2$NEt (0.66 mL, 3.8 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide as a white solid (0.29 g, 68%).

HRMS (ES$^+$) m/z Calcd for $C_{27}H_{31}Cl_2F_2N_3O_3$+H [(M+H)$^+$]: 554.1784 found: 554.1783.

Example 73b

Preparation of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide

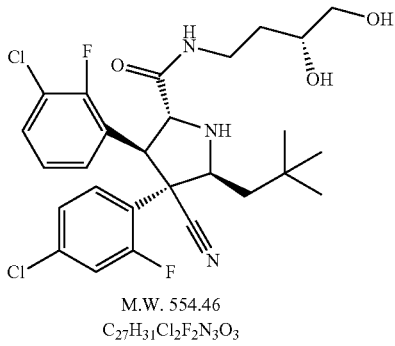 [SMILES: CC(C)(C)C[C@@H]1N[C@@H](C(=O)NCC[C@@H](O)CO)[C@H](c2cccc(Cl)c2F)[C@@]1(C#N)c1ccc(Cl)cc1F]

M.W. 554.46
$C_{27}H_{31}Cl_2F_2N_3O_3$

Rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide (0.28 g) was separated by chiral SFC chromatography to provide chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide as a white solid (109 mg, 39%) and chiral-(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide as a white solid (109 mg, 39%).

Example 74

Preparation of rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((R)-3,4-dihydroxy-butyl)-amide

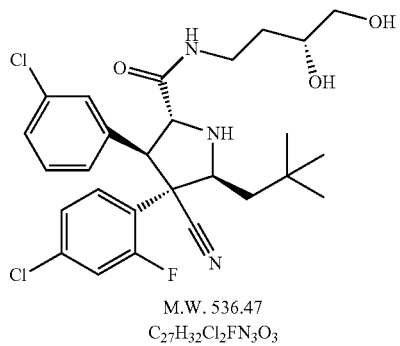 [SMILES: CC(C)(C)C[C@@H]1N[C@@H](C(=O)NCC[C@@H](O)CO)[C@H](c2cccc(Cl)c2)[C@@]1(C#N)c1ccc(Cl)cc1F]

M.W. 536.47
$C_{27}H_{32}Cl_2FN_3O_3$

In a manner similar to the method described in Example 72a, rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid trifluoroacetic acid (0.2 g, 0.36 mmol) was reacted with 2-((R)-2,2-dimethyl-[1,3]dioxolan-4-yl)-ethylamine (0.15 g, 1.07 mmol), HATU (0.24 g, 0.64 mmol) and iPr$_2$NEt (0.31 mL, 1.78 mmol) in CH$_2$Cl$_2$ at room temperature for 20 h, then reacted with aqueous HCl solution in tetrahydrofuran at room temperature for 2 h to give rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((R)-3,4-dihydroxy-butyl)-amide as a white solid (0.1 g, 54%).

HRMS (ES$^+$) m/z Calcd for $C_{27}H_{32}Cl_2FN_3O_3$+H [(M+H)$^+$]: 536.1878. found: 536.1880.

Example 75

Preparation of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((R)-3,4-dihydroxy-butyl)-amide

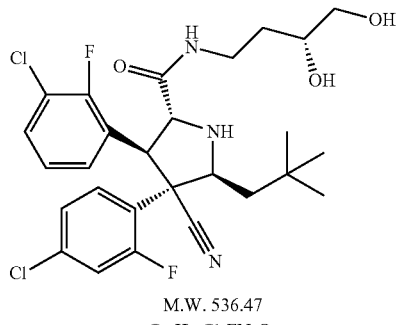

M.W. 536.47
$C_{27}H_{32}Cl_2FN_3O_3$

In a manner similar to the method described in Example 72a, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid (0.2 g, 0.36 mmol) was reacted with 2-((R)-2,2-dimethyl-[1,3]dioxolan-4-yl)-ethylamine (0.15 g, 1.07 mmol), HATU (0.24 g, 0.64 mmol) and iPr$_2$NEt (0.31 g, 1.78 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((R)-3,4-dihydroxy-butyl)-amide as a white solid (0.1 g, 54%).

HRMS (ES$^+$) m/z Calcd for C$_{27}$H$_{32}$Cl$_2$FN$_3$O$_3$+H [(M+H)$^+$]: 536.1878. found: 536.1880.

Example 76

Preparation of rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid ((R)-3,4-dihydroxy-butyl)-amide

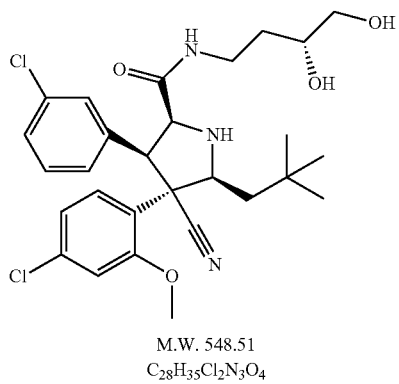 [SMILES: COc1cc(Cl)ccc1[C@@]1(C#N)[C@H](CC(C)(C)C)N[C@H](C(=O)NCC[C@@H](O)CO)[C@@H]1c1cccc(Cl)c1]

M.W. 548.51
C$_{28}$H$_{35}$Cl$_2$N$_3$O$_4$

In a manner similar to the method described in Example 72a, rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid trifluoroacetic acid (0.2 g, 0.35 mmol) was reacted with 2-((R)-2,2-dimethyl-[1,3]dioxolan-4-yl)-ethylamine (0.15 g, 1.0 mmol), HATU (0.24 g, 0.63 mmol) and iPr$_2$NEt (0.3 mL, 1.7 mmol) in CH$_2$Cl$_2$ at room temperature for 20 h, then reacted with aqueous HCl solution in tetrahydrofuran at room temperature for 2 h to give rac-(2S,3R,4R,5S)-4-(4-chloro-2-methoxy-phenyl)-3-(3-chloro-phenyl)-4-cyano-5-(2,2-dimethyl-propyl)-pyrrolidine-2-carboxylic acid ((R)-3,4-dihydroxy-butyl)-amide as a white solid (0.1 g, 57%).

HRMS (ES$^+$) m/z Calcd for C$_{28}$H$_{35}$Cl$_2$N$_3$O$_4$+H [(M+H)$^+$]: 548.2078. found: 548.2074.

Example 77

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((R)-3,4-dihydroxy-butyl)-amide

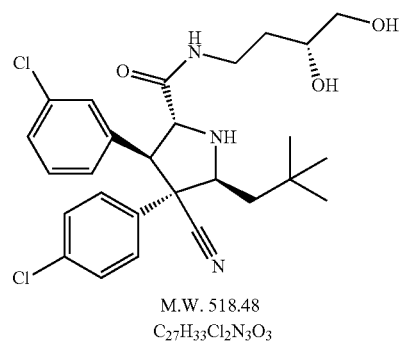 [SMILES: CC(C)(C)C[C@@H]1N[C@@H](C(=O)NCC[C@@H](O)CO)[C@H](c2cccc(Cl)c2)[C@@]1(C#N)c1ccc(Cl)cc1]

M.W. 518.48
C$_{27}$H$_{33}$Cl$_2$N$_3$O$_3$

In a manner similar to the method described in Example 72a, rac-(2R,3R,4R,5S)-3-(3-chloro-phenyl)-4-(4-chloro-phenyl)-4-cyano-5-(2,2-dimethyl-propyl)-pyrrolidine-2-carboxylic acid trifluoroacetic acid (0.2 g, 0.37 mmol) was reacted with 2-((R)-2,2-dimethyl-[1,3]dioxolan-4-yl)-ethylamine (0.159 g, 1.1 mmol), HATU (0.25 g, 0.66 mmol) and iPr$_2$NEt (0.32 mL, 1.8 mmol) in CH$_2$Cl$_2$ at room temperature for 20 h, then reacted with aqueous HCl solution in tetrahydrofuran at room temperature for 2 h to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((R)-3,4-dihydroxy-butyl)-amide as a white solid (0.15 g, 81%).

HRMS (ES$^+$) m/z Calcd for C$_{27}$H$_{33}$Cl$_2$N$_3$O$_3$+H [(M+H)$^+$]: 518.1972. found: 518.1972.

Example 78a

Preparation of intermediate [3,3,4-trimethyl-pent-(E)-ylideneamino]-acetic acid tert-butyl ester

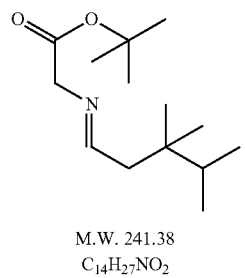 [SMILES: CC(C)C(C)(C)C/C=N/CC(=O)OC(C)(C)C]

M.W. 241.38
C$_{14}$H$_{27}$NO$_2$

Step A To a solution of ethyl 3,3-dimethylacrylate (Aldrich) (6.98 g, 54 mmol) in anhydrous tetrahydrofuran (60 mL) was added chlorotrimethylsilane (12 mL, 70 mmol), CuI (1.5 g, 8 mmol) under nitrogen. The mixture was stirred and the temperature was cooled to −20° C. To the stirring mixture was slowly added a tetrahydrofuran solution (2 N) if isopropyl-magnesium chloride (40 mL, 80 mmol) during a period of 30 min while maintaining the temperature below −10° C. After the addition was finished, the reaction mixture was gradually warmed to 0° C. and stirred at 0° C. for 3 h. Aqueous saturated NH$_4$Cl solution was added to quench the reaction, and the mixture was extracted with ethyl acetate and ethyl ether. The organic layers were combined, concentrated. The residue was purified by chromatography (EtOAc:hexanes=1:20, 1:10) to give 3,3,4-trimethyl-pentanoic acid ethyl ester as a colorless oil (7 g, 75%).

Step B To a solution of 3,3,4-trimethyl-pentanoic acid ethyl ester (7 g, 41 mmol) in anhydrous ethyl ether (100 mL) at 0° C. was added a ethyl ether solution (1 M) of LiAlH$_4$ (67 mL, 67 mmol) under nitrogen. The reaction mixture was stirred at 0° C. for 1 h, then poured into a ice-water. The mixture was extracted with ethyl acetate. The organic layer were separated, washed with water, aqueous HCl solution, brine, dried over MgSO$_4$, and concentrated to give 3,3,4-trimethyl-pentan-1-ol as a colorless oil (5.4 g, 100%).

Step C To a solution of 3,3,4-trimethyl-pentan-1-ol (5.4 g, 41 mmol) in dichloromethane (100 mL) was added Dess-Martin periodinane (22 g 52 mmol) The reaction mixture was stirred at room temperature for 3 h. Aqueous Na$_2$SO$_3$ solution was added to quench the reaction. The organic layers were separated, washed with saturated NaHCO$_3$, brine, dried over MgSO$_4$, and concentrated. The residue was purified by chromatography (EtOAc:hexanes=1:30) to give 3,3,4-trimethyl-pentanal as a colorless oil (Yield: 1.1 g, 21%).

Step D In a manner similar to the method described in Example 1a, glycine tert-butyl ester (1 g, 7.7 mmol) was reacted with 3,3,4-trimethyl-pentanal (1.1 g, 8 mmol) in CH$_2$Cl$_2$ at room temperature for 5 h to give [3,3,4-trimethyl-pent-(E)-ylideneamino]-acetic acid tert-butyl ester as a colorless oil (1.5 g, 80%).

Example 78b

Preparation of intermediate rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid tert-butyl ester

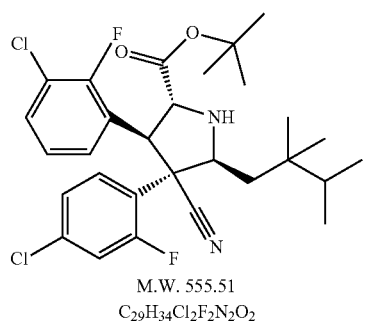 [SMILES: CC(C)C(C)(C)C[C@@H]1N[C@@H](C(=O)OC(C)(C)C)[C@H](c2cccc(Cl)c2F)[C@@]1(C#N)c1ccc(Cl)cc1F]

M.W. 555.51
C$_{29}$H$_{34}$Cl$_2$F$_2$N$_2$O$_2$

In a manner similar to the method described in Example 1c, [3,3,4-trimethyl-pent-(E)-ylideneamino]-acetic acid tert-butyl ester prepared in Example 78a (1.5 g, 6.2 mmol) was reacted with (Z)-3-(3-chloro-2-fluoro-phenyl)-2-(4-chloro-2-fluoro-phenyl)-acrylonitrile (1.1 g, 3.5 mmol) prepared in Example 52a, AgF (1.2 g, 9.5 mmol), and triethylamine (2 g, 20 mmol) in dichloromethane (150 mL) at room temperature for 18 h to give rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid tert-butyl ester as a white foam (1.1 g, 56%).

Example 78c

Preparation of intermediate rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid trifluoroacetic acid

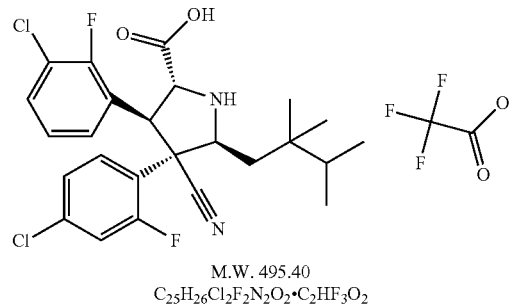

M.W. 495.40
C$_{25}$H$_{26}$Cl$_2$F$_2$N$_2$O$_2$·C$_2$HF$_3$O$_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid tert-butyl ester prepared in Example 78b (1.1 g, 2 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid trifluoroacetic acid as a off white solid (1.1 g, 91%).

Example 78d

Preparation of rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide

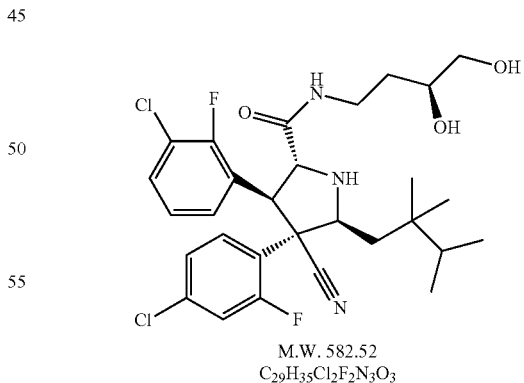

M.W. 582.52
C$_{29}$H$_{35}$Cl$_2$F$_2$N$_3$O$_3$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid trifluoroacetic acid prepared in Example 78c (0.55 g, 0.9 mmol) was reacted with 2-((S)-2,2-dimethyl-[1,3]dioxolan-4-yl)-ethylamine (0.39 g, 2.7 mmol), HATU (0.62 g, 1.6 mmol) and iPr$_2$NEt (0.78 mL, 4.5 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide as a white solid (0.32 g, 62%).

HRMS (ES$^+$) m/z Calcd for C$_{29}$H$_{35}$Cl$_2$F$_2$N$_3$O$_3$+H [(M+H)$^+$]: 582.2097. found: 582.2095.

Example 78e

Preparation of (2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide

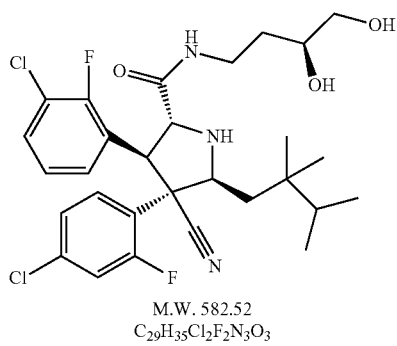 [SMILES: CC(C)C(C)(C)C[C@@H]1N[C@@H](C(=O)NCC[C@H](O)CO)[C@H](c2cccc(Cl)c2F)[C@@]1(C#N)c1ccc(Cl)cc1F]

M.W. 582.52
C$_{29}$H$_{35}$Cl$_2$F$_2$N$_3$O$_3$

Rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide (0.25 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide as a white solid (0.1 g, 40%) and chiral (2S,3R,4S,5R)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide as a white solid (0.1 g, 40%).

Example 79a

Preparation of rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide

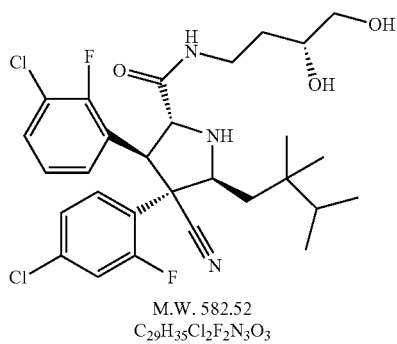 [SMILES: CC(C)C(C)(C)C[C@@H]1N[C@@H](C(=O)NCC[C@@H](O)CO)[C@H](c2cccc(Cl)c2F)[C@@]1(C#N)c1ccc(Cl)cc1F]

M.W. 582.52
C$_{29}$H$_{35}$Cl$_2$F$_2$N$_3$O$_3$

In a manner similar to the method described in Example 72a rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid trifluoroacetic acid prepared in Example 78c (0.55 g, 0.9 mmol) was reacted with 2-((R)-2,2-dimethyl-[1,3]dioxolan-4-yl)-ethylamine (0.39 g, 2.7 mmol), HATU (0.62 g, 1.6 mmol) and iPr$_2$NEt (0.78 mL, 4.5 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide as a white solid (0.3 g, 58%).

HRMS (ES$^+$) m/z Calcd for C$_{29}$H$_{35}$Cl$_2$F$_2$N$_3$O$_3$+H [(M+H)$^+$]: 582.2097. found: 582.2094.

Example 79b

Preparation of (2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide

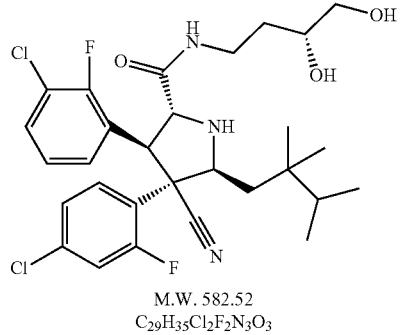 [SMILES: CC(C)C(C)(C)C[C@@H]1N[C@@H](C(=O)NCC[C@@H](O)CO)[C@H](c2cccc(Cl)c2F)[C@@]1(C#N)c1ccc(Cl)cc1F]

M.W. 582.52
C$_{29}$H$_{35}$Cl$_2$F$_2$N$_3$O$_3$

Rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide (0.29 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide as a white solid (0.12 g, 41%) and chiral (2S,3R,4S,5R)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide as a white solid (0.12 g, 41%).

Example 80a

Preparation of intermediate [3,3-dimethyl-pent-4-en-(E)-ylideneamino]-acetic acid tert-butyl ester

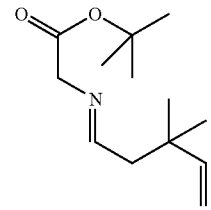

M.W. 225.33
C$_{13}$H$_{23}$NO$_2$

Step A To a solution of methyl 3,3-dimethyl-4-pentenoate (Aldrich) (6.1 g, 43 mmol) in anhydrous ethyl ether (100 mL) at 0° C. was added a tetrahydrofuran solution (2 M) of LiAlH$_4$ (32 mL, 64 mmol) under nitrogen. The reaction mixture was stirred at 0° C. for 1 h, then poured into a ice-water. The mixture was extracted with ethyl acetate. The organic layer were separated, washed with water, aqueous HCl solution, brine, dried over MgSO$_4$, and concentrated to give 3,3-dimethyl-pent-4-en-1-ol as a colorless oil (4.8 g, 98%).

Step B To a solution of oxalyl chloride (5.9 g, 46 mmol) (Aldrich) in dichloromethane (60 mL) at −78° C. was added the solution of dimethyl sulfoxide (6.6 mL, 92 mmol) in dichloromethane dropwise. After 5 mins, the solution of 3,3-dimethyl-pent-4-en-1-ol (4.8 g, 42 mmol) in dichloromethane (10 mL) was added dropwise. The reaction mixture was stirred at −78° C. for 15 min. Triethylamine (21 mL, 0.15 mol) was added and the reaction mixture was slowly warmed up to room temperature and stirred at room temperature for 45 min. The water was added. The organic layers were separated, and the aqueous layer was extracted with dichloromethane. The organic layers were combined, washed with 10% of HCl, saturated NaHCO$_3$, brine, dried over MgSO$_4$, and concentrated to give 3,3-dimethyl-pent-4-enal as a colorless oil (Yield: 3.2 g, 68%).

Step C. In a manner similar to the method described in Example 1a, glycine tert-butyl ester (1.3 g, 10 mmol) was reacted with 3,3-dimethyl-pent-4-enal (1.2 g, 11 mmol) in CH$_2$Cl$_2$ at room temperature for 18 h to give [3,3-dimethyl-pent-4-en-(E)-ylideneamino]-acetic acid tert-butyl ester as a colorless oil (2.1 g, 93%).

Example 80b

Preparation of intermediate rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid tert-butyl ester

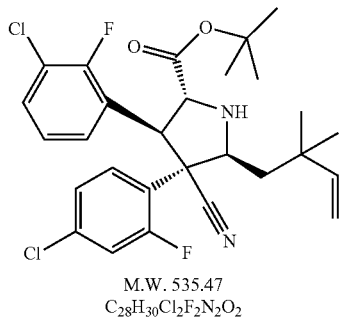 [SMILES: C=CC(C)(C)C[C@@H]1N[C@@H](C(=O)OC(C)(C)C)[C@H](c2cccc(Cl)c2F)[C@@]1(C#N)c1ccc(Cl)cc1F]

M.W. 535.47
C$_{28}$H$_{30}$Cl$_2$F$_2$N$_2$O$_2$

In a manner similar to the method described in Example 1c, [3,3-dimethyl-pent-4-en-(E)-ylideneamino]-acetic acid tert-butyl ester prepared in Example 80a (2.1 g, 9.3 mmol) was reacted with (Z)-3-(3-chloro-2-fluoro-phenyl)-2-(4-chloro-2-fluoro-phenyl)-acrylonitrile (2 g, 6.4 mmol) prepared in Example 52a, AgF (0.9 g, 7.1 mmol), and triethylamine (1.5 g, 15 mmol) in dichloromethane (150 mL) at room temperature for 18 h to give rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid tert-butyl ester as a white foam (0.98 g, 56%).

Example 80c

Preparation of intermediate rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid trifluoroacetic acid

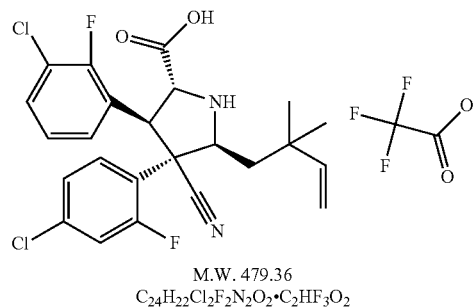

M.W. 479.36
C$_{24}$H$_{22}$Cl$_2$F$_2$N$_2$O$_2$·C$_2$HF$_3$O$_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid tert-butyl ester prepared in Example 80b (1.0 g, 1.7 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid trifluoroacetic acid as a white solid (1.0 g, 91%).

Example 80d

Preparation of intermediate rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid [2-((S)-2,2-dimethyl-[1,3]dioxolan-4-yl)-ethyl]-amide

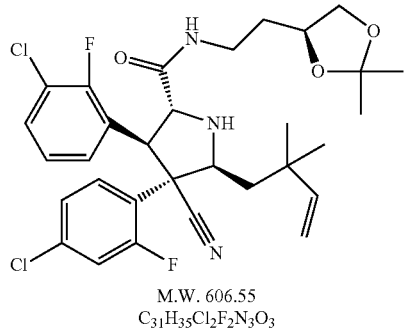 [SMILES: C=CC(C)(C)C[C@@H]1N[C@@H](C(=O)NCC[C@H]2COC(C)(C)O2)[C@H](c2cccc(Cl)c2F)[C@@]1(C#N)c1ccc(Cl)cc1F]

M.W. 606.55
C$_{31}$H$_{35}$Cl$_2$F$_2$N$_3$O$_3$

In a manner similar to the method described in Example 42c, rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid prepared in Example 80c (1.0 g, 1.69 mmol) was reacted with 2-((S)-2,2-dimethyl-[1,3]dioxolan-4-yl)-ethylamine (0.73 g, 5.0 mmol), HATU (1.15 g, 3 mmol) and iPr$_2$NEt (1.46 mL, 8.4 mmol) in CH$_2$Cl$_2$ at room temperature for 20 h to give rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid [2-((S)-2,2-dimethyl-[1,3]dioxolan-4-yl)-ethyl]-amide as a white solid (0.82 g, 80%).

Example 80e

Preparation of rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid ((S)-3,4-dihydroxy-butyl)-amide

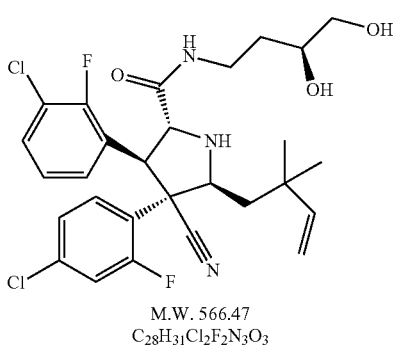 [SMILES: C=CC(C)(C)C[C@@H]1N[C@@H](C(=O)NCC[C@H](O)CO)[C@H](c2cccc(Cl)c2F)[C@@]1(C#N)c1ccc(Cl)cc1F]

M.W. 566.47
C$_{28}$H$_{31}$Cl$_2$F$_2$N$_3$O$_3$

In a manner similar to the method described in Example 42d, rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid [2-((S)-2,2-dimethyl-[1,3]dioxolan-4-yl)-ethyl]-amide prepared in Example 80d (0.36 g, 0.59 mmol) was reacted with aqueous HCl solution (1 N, 1 mL) in tetrahydrofuran (10 mL) at room temperature for 2 h to give rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid ((S)-3,4-dihydroxy-butyl)-amide as a white solid (0.32 g, 95%).

HRMS (ES$^+$) m/z Calcd for C$_{28}$H$_{31}$Cl$_2$F$_2$N$_3$O$_3$+H [(M+H)$^+$]: 566.1784. found: 566.1786.

Example 81a

Preparation of intermediate rac-(2R,3S,4R,5S)-3-(3-chloro-2-fluoro-phenyl)-4-(4-chloro-2-fluoro-phenyl)-4-cyano-5-(2,2-dimethyl-butyl)-pyrrolidine-2-carboxylic acid [2-((S)-2,2-dimethyl-[1,3]dioxolan-4-yl)-ethyl]-amide

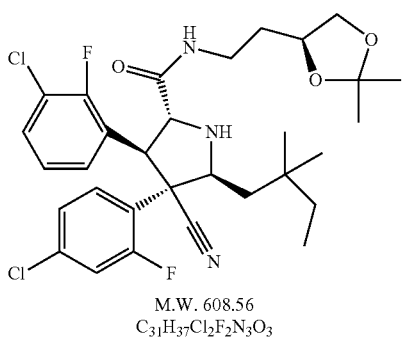 [SMILES: CCC(C)(C)C[C@@H]1N[C@@H](C(=O)NCC[C@H]2COC(C)(C)O2)[C@H](c2cccc(Cl)c2F)[C@@]1(C#N)c1ccc(Cl)cc1F]

M.W. 608.56
C$_{31}$H$_{37}$Cl$_2$F$_2$N$_3$O$_3$

A suspension of rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid [2-((S)-2,2-dimethyl-[1,3]dioxolan-4-yl)-ethyl]-amide prepared in Example 80d (0.4 g, 0.65 mmol) and PtO$_2$ (0.2 g) in ethyl acetate (15 mL) was vigorously shaken under H$_2$ atmosphere (30 psi) for 1 h. The mixture was filtered through a short pad of celite, and the filtrate was concentrated to give rac-(2R,3S,4R,5S)-3-(3-chloro-2-fluoro-phenyl)-4-(4-chloro-2-fluoro-phenyl)-4-cyano-5-(2,2-dimethyl-butyl)-pyrrolidine-2-carboxylic acid [2-((S)-2,2-dimethyl-[1,3]dioxolan-4-yl)-ethyl]-amide as a white gum (0.33 g, 83%).

Example 81b

Preparation of rac-(2R,3S,4R,5S)-3-(3-chloro-2-fluoro-phenyl)-4-(4-chloro-2-fluoro-phenyl)-4-cyano-5-(2,2-dimethyl-butyl)-pyrrolidine-2-carboxylic acid ((S)-3,4-dihydroxy-butyl)-amide

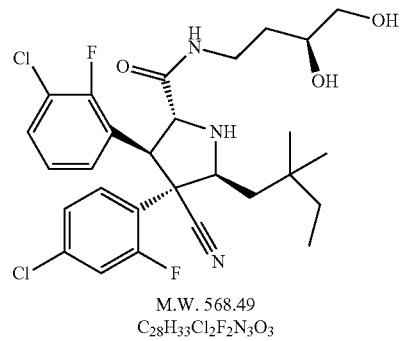 [SMILES: CCC(C)(C)C[C@@H]1N[C@@H](C(=O)NCC[C@H](O)CO)[C@H](c2cccc(Cl)c2F)[C@@]1(C#N)c1ccc(Cl)cc1F]

M.W. 568.49
C$_{28}$H$_{33}$Cl$_2$F$_2$N$_3$O$_3$

In a manner similar to the method described in Example 42d, rac-(2R,3S,4R,5S)-3-(3-chloro-2-fluoro-phenyl)-4-(4-chloro-2-fluoro-phenyl)-4-cyano-5-(2,2-dimethyl-butyl)-pyrrolidine-2-carboxylic acid [2-((S)-2,2-dimethyl-[1,3]dioxolan-4-yl)-ethyl]-amide prepared in Example 81a (0.41 g, 0.67 mmol) was reacted with aqueous HCl solution (1 N, 1 mL) in tetrahydrofuran (10 mL) at room temperature for 2 h to give rac-(2R,3S,4R,5S)-3-(3-chloro-2-fluoro-phenyl)-4-(4-chloro-2-fluoro-phenyl)-4-cyano-5-(2,2-dimethyl-butyl)-pyrrolidine-2-carboxylic acid ((S)-3,4-dihydroxy-butyl)-amide as a white solid (0.38 g, 99%).

HRMS (ES$^+$) m/z Calcd for C$_{28}$H$_{33}$Cl$_2$F$_2$N$_3$O$_3$+H [(M+H)$^+$]: 568.1940. found: 568.1942.

Example 82a

Preparation of intermediate [3-methyl-3-phenyl-but-(E)-ylideneamino]-acetic acid tert-butyl ester

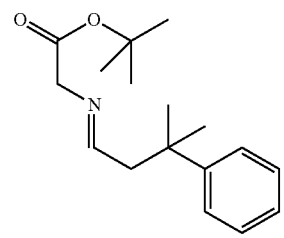

M.W. 275.39
C$_{17}$H$_{25}$NO$_2$

Step A To a solution of 3-methyl-3-phenylbutanoic acid (ChemBridge) (4.46 g, 25 mmol) in anhydrous tetrahydrofuran (150 mL) at 0° C. was added a tetrahydrofuran solution (1 M) of $BH_3$·THF (Aldrich, 50 mL, 50 mmol) under nitrogen. The reaction mixture was stirred at room temperature for 3 h, then concentrated. The residue was partitioned between ethyl acetate and water. The organic layer were separated, washed with water, aqueous HCl solution, brine, dried over $MgSO_4$, and concentrated to give 3-methyl-3-phenyl-butan-1-ol as a colorless oil (4.1 g, 100%).

Step B To a solution of oxalyl chloride (1.7 g, 13 mmol) (Aldrich) in dichloromethane (50 mL) at −78° C. was added the solution of dimethyl sulfoxide (1.9 mL, 27 mmol) in dichloromethane (10 mL) dropwise. After 5 mins, the solution of 3-methyl-3-phenyl-butan-1-ol (2 g, 12 mmol) in dichloromethane (10 mL) was added dropwise. The reaction mixture was stirred at −78° C. for 15 min. Triethylamine (6.1 mL, 44 mol) was added and the reaction mixture was slowly warmed up to room temperature and stirred at room temperature for 45 min. The water was added. The organic layers were separated, and the aqueous layer was extracted with dichloromethane. The organic layers were combined, washed with 10% of HCl, saturated $NaHCO_3$, brine, dried over $MgSO_4$, and concentrated to give 3-methyl-3-phenyl-butyraldehyde as a colorless oil (Yield: 1.8 g, 90%).

Step C In a manner similar to the method described in Example 1a, glycine tert-butyl ester (1.3 g, 10 mmol) was reacted with 3-methyl-3-phenyl-butyraldehyde (1.8 g, 11 mmol) in $CH_2Cl_2$ at room temperature for 18 h to give [[3-methyl-3-phenyl-but-(E)-ylideneamino]-acetic acid tert-butyl ester as a colorless oil (2.3 g, 93%).

Example 82b

Preparation of intermediate rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid tert-butyl ester

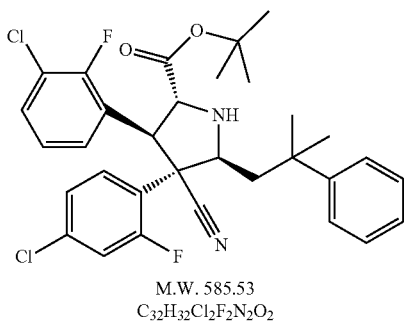 [SMILES: CC(C)(C)OC(=O)[C@@H]1N[C@@H](CC(C)(C)c2ccccc2)[C@](C#N)(c2ccc(Cl)cc2F)[C@H]1c1cccc(Cl)c1F]

M.W. 585.53
$C_{32}H_{32}Cl_2F_2N_2O_2$

In a manner similar to the method described in Example 1c, [[3-methyl-3-phenyl-but-(E)-ylideneamino]-acetic acid tert-butyl ester prepared in Example 82a (2.3 g, 8.3 mmol) was reacted with (Z)-3-(3-chloro-2-fluoro-phenyl)-2-(4-chloro-2-fluoro-phenyl)-acrylonitrile (2.4 g, 7.7 mmol) prepared in Example 52a, AgF (0.7 g, 5.5 mmol), and triethylamine (2.1 g, 21 mmol) in dichloromethane (150 mL) at room temperature for 18 h to give rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid tert-butyl ester as a white foam (1 g, 22%).

Example 82c

Preparation of intermediate rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid trifluoroacetic acid

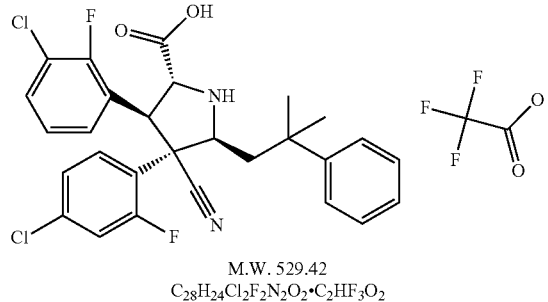

M.W. 529.42
$C_{28}H_{24}Cl_2F_2N_2O_2$·$C_2HF_3O_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid tert-butyl ester prepared in Example 82b (1.0 g, 1.7 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid trifluoroacetic acid as a white solid (1.0 g, 91%).

Example 82d

Preparation of rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid ((S)-3,4-dihydroxy-butyl)-amide

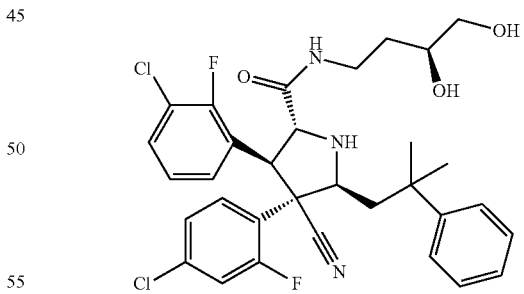

M.W. 616.53
$C_{32}H_{33}Cl_2F_2N_3O_3$

In a manner similar to the method described in Examples 42c, 42d, rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid trifluoroacetic acid prepared in Example 82c (0.35 g, 0.54 mmol) was reacted with 2-((S)-2,2-dimethyl-[1,3]dioxolan-4-yl)-ethylamine (0.24 g, 1.62 mmol), HATU (0.37 g, 0.98 mmol) and iPr$_2$NEt (0.47 mL, 2.7 mmol) in CH$_2$Cl$_2$ at room temperature for 20 h, then reacted with aqueous HCl solution in tetrahydrofuran at room temperature to give rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid ((S)-3,4-dihydroxy-butyl)-amide as a white solid (0.21 g, 66%).

HRMS (ES$^+$) m/z Calcd for C$_{32}$H$_{33}$Cl$_2$F$_2$N$_3$O$_3$+H [(M+H)$^+$]: 616.1940. found: 616.1039.

Example 83a

Preparation of intermediate (Z)-3-(3-chloro-5-fluoro-phenyl)-2-(4-chloro-2-fluoro-phenyl)-acrylonitrile

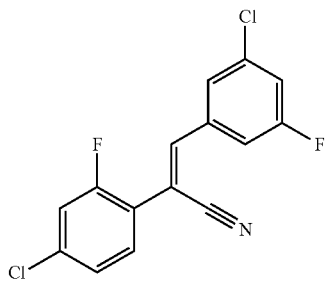

M.W. 308.99
C$_{15}$H$_7$Cl$_2$F$_2$N

In a manner similar to the method described in Example 1b, 4-chloro-2-fluorophenylacetonitrile (3.4 g, 20 mmol) was reacted with 3-chloro-5-fluoro-benzaldehyde (Aldrich) (3.77 g, 24 mmol), methanolic solution (25 wt %) of sodium methoxide (4.99 mL, 22 mmol) in methanol (90 mL) at 50° C. for 3 h to give (Z)-3-(3-chloro-5-fluoro-phenyl)-2-(4-chloro-2-fluoro-phenyl)-acrylonitrile as a white powder (5.5 g, 90%).

Example 83b

Preparation of intermediate rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid tert-butyl ester

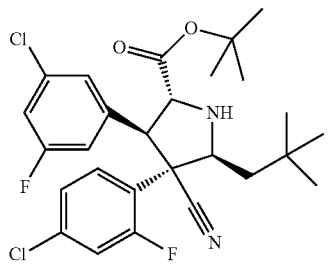

M.W. 523.46
C$_{27}$H$_{30}$Cl$_2$F$_2$N$_2$O$_2$

In a manner similar to the method described in Example 1c, [3-methyl-but-(E)-ylideneamino]-acetic acid tert-butyl ester prepared in Example 1a (2.1 g, 10 mmol) was reacted with (Z)-3-(3-chloro-5-fluoro-phenyl)-2-(4-chloro-2-fluoro-phenyl)-acrylonitrile (2.5 g, 8 mmol) prepared in Example 83a, AgF (1.0 g, 8 mmol), and triethylamine (2.8 mL, 20 mmol) in dichloromethane (120 mL) at room temperature for 18 h to give rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid tert-butyl ester as a white foam (1.2 g, 29%).

Example 83c

Preparation of intermediate rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid trifluoroacetic acid

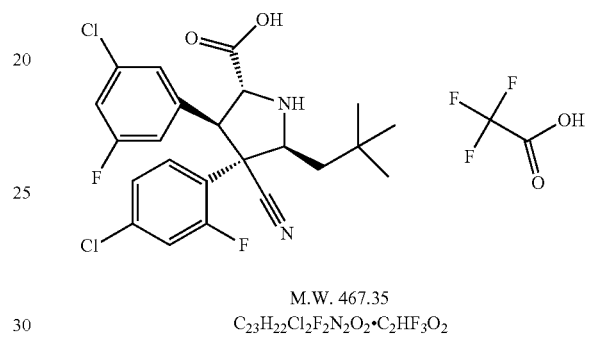

M.W. 467.35
C$_{23}$H$_{22}$Cl$_2$F$_2$N$_2$O$_2$•C$_2$HF$_3$O$_2$

In a manner similar to the method described in Example 25a, rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid tert-butyl ester prepared in Example 83b (1.2 g, 2.2 mmol) was reacted with trifluoroacetic acid in dichloromethane at room temperature to give rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid trifluoroacetic acid as a white solid (1.3 g, 97%).

Example 83d

Preparation of rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

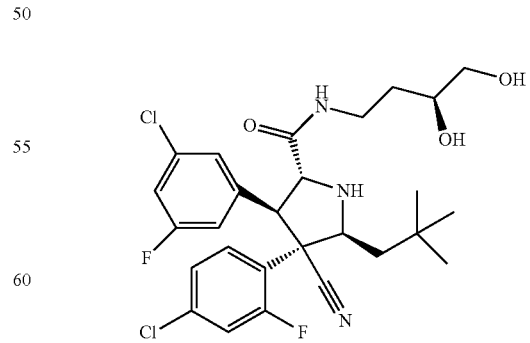

M.W. 554.46
C$_{27}$H$_{31}$Cl$_2$F$_2$N$_3$O$_3$

In a manner similar to the method described in Examples 42c, 42d, rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 83c (0.4 g, 0.69 mmol) was reacted with 2-((S)-2,2-dimethyl-[1,3]dioxolan-4-yl)-ethylamine (0.3 g, 2.06 mmol), HATU (0.47 g, 1.24 mmol) and iPr₂NEt (0.6 mL, 3.44 mmol) in CH₂Cl₂ at room temperature for 20 h, then reacted with aqueous HCl solution in tetrahydrofuran at room temperature to give rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.13 g, 35%).

HRMS (ES⁺) m/z Calcd for $C_{27}H_{31}Cl_3FN_3O_3$+H [(M+H)⁺]: 554.1784. found: 554.1782.

Example 84a

Preparation of intermediate (Z)-3-{2-[2-(tert-butyl-dimethyl-silanyloxy)-ethoxy]-5-chloro-phenyl}-2-(4-chloro-2-fluoro-phenyl)-acrylonitrile

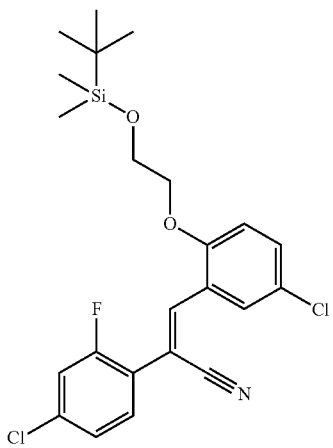

M.W. 466.46
$C_{23}H_{26}Cl_2FNO_2Si$

Step A To a solution of 5-chlorosalicylaldehyde (2 g, 12.8 mmol) (Aldrich) in N,N-dimethylformamide (40 mL) was added K₂CO₃ (5.3 g, 38 mmol), and (2-bromo-ethoxy)-tert-butyl-dimethyl-silane (3.67 g, 15 mmol, Aldrich). The reaction mixture was heated at 60° C. for 18 h. The crude was cooled to room temperature, diluted with ethyl acetate, washed with water, brine. The organic layer was separated, concentrated, and the residue was purified by chromatography (EtOAc:Hexanes=1:8, then 1:4) to give 2-[2-(tert-butyl-dimethyl-silanyloxy)-ethoxy]-5-chloro-benzaldehyde as a brown oil (Yield 3.8 g, 91%).

Step B In a manner similar to the method described in Example 1b, 4-chloro-2-fluorophenylacetonitrile (1.7 g, 10 mmol) was reacted with 2-[2-(tert-butyl-dimethyl-silanyloxy)-ethoxy]-5-chloro-benzaldehyde (3.8 g, 12.5 mmol), methanolic solution (25 wt %) of sodium methoxide (2.5 mL, 11 mmol) in methanol (60 mL) at 50° C. for 3 h to give (Z)-3-{2-[2-(tert-butyl-dimethyl-silanyloxy)-ethoxy]-5-chloro-phenyl}-2-(4-chloro-2-fluoro-phenyl)-acrylonitrile as a yellow oil (4.5 g, 80%).

Example 84b

Preparation of intermediate rac-(2R,3S,4R,5S)-3-{2-[2-(tert-butyl-dimethyl-silanyloxy)-ethoxy]-5-chloro-phenyl}-4-(4-chloro-2-fluoro-phenyl)-4-cyano-5-(2,2-dimethyl-propyl)-pyrrolidine-2-carboxylic acid tert-butyl ester

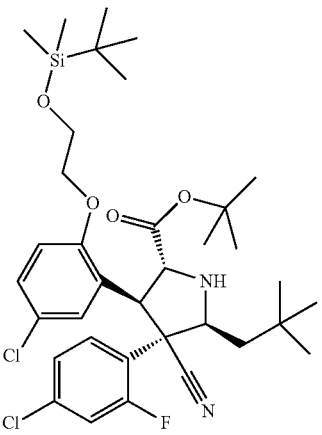

M.W. 679.78
$C_{35}H_{49}Cl_2FN_2O_4Si$

In a manner similar to the method described in Example 1c, [3-methyl-but-(E)-ylideneamino]-acetic acid tert-butyl ester prepared in Example 1a (2.1 g, 10 mmol) was reacted with (Z)-3-{2-[2-(tert-butyl-dimethyl-silanyloxy)-ethoxy]-5-chloro-phenyl}-2-(4-chloro-2-fluoro-phenyl)-acrylonitrile (3.7 g, 8 mmol) prepared in Example 84a, AgF (1.0 g, 8 mmol), and triethylamine (2.8 mL, 20 mmol) in dichloromethane (120 mL) at room temperature for 18 h to give rac-(2R,3S,4R,5S)-3-{2-[2-(tert-butyl-dimethyl-silanyloxy)-ethoxy]-5-chloro-phenyl}-4-(4-chloro-2-fluoro-phenyl)-4-cyano-5-(2,2-dimethyl-propyl)-pyrrolidine-2-carboxylic acid tert-butyl ester as a white foam (1.0 g, 18%).

Example 84c

Preparation of intermediate rac-(2R,3S,4R,5S)-4-(4-chloro-2-fluoro-phenyl)-3-[5-chloro-2-(2-hydroxy-ethoxy)-phenyl]-4-cyano-5-(2,2-dimethyl-propyl)-pyrrolidine-2-carboxylic acid trifluoroacetic acid

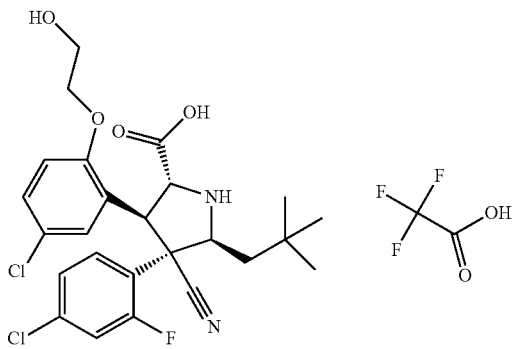

M.W. 509.47
$C_{25}H_{27}Cl_2FN_2O_4 \cdot C_2HF_3O_2$

In a manner similar to the method described in Example 25a, rac-(2R,3S,4R,5S)-3-{2-[2-(tert-butyl-dimethyl-silanyloxy)-ethoxy]-5-chloro-phenyl}-4-(4-chloro-2-fluoro-phenyl)-4-cyano-5-(2,2-dimethyl-propyl)-pyrrolidine-2-carboxylic acid tert-butyl ester prepared in Example 84b (1.0 g, 1.5 mmol) was reacted with trifluoroacetic acid in dichloromethane at room temperature to give rac-(2R,3S,4R,5S)-4-(4-chloro-2-fluoro-phenyl)-3-[5-chloro-2-(2-hydroxy-ethoxy)-phenyl]-4-cyano-5-(2,2-dimethyl-propyl)-pyrrolidine-2-carboxylic acid trifluoroacetic acid as a white solid (0.9 g, 98%).

Example 84d

Preparation of rac-(2R,3S,4R,5S)-4-(4-chloro-2-fluoro-phenyl)-3-[5-chloro-2-(2-hydroxy-ethoxy)-phenyl]-4-cyano-5-(2,2-dimethyl-propyl)-pyrrolidine-2-carboxylic acid ((S)-3,4-dihydroxy-butyl)-amide

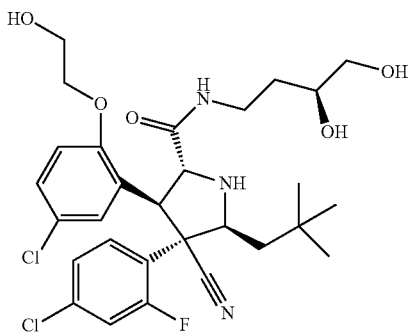

M.W. 596.53
$C_{29}H_{36}Cl_2FN_3O_5$

In a manner similar to the method described in Examples 42c, 42d, rac-(2R,3S,4R,5S)-4-(4-chloro-2-fluoro-phenyl)-3-[5-chloro-2-(2-hydroxy-ethoxy)-phenyl]-4-cyano-5-(2,2-dimethyl-propyl)-pyrrolidine-2-carboxylic acid trifluoroacetic acid prepared in Example 84c (0.4 g, 0.64 mmol) was reacted with 2-((S)-2,2-dimethyl-[1,3]dioxolan-4-yl)-ethylamine (0.28 g, 1.93 mmol), HATU (0.44 g, 1.15 mmol) and iPr$_2$NEt (0.56 mL, 3.21 mmol) in CH$_2$Cl$_2$ at room temperature for 20 h, then reacted with aqueous HCl solution in tetrahydrofuran at room temperature to give rac-(2R,3S,4R,5S)-4-(4-chloro-2-fluoro-phenyl)-3-[5-chloro-2-(2-hydroxy-ethoxy)-phenyl]-4-cyano-5-(2,2-dimethyl-propyl)-pyrrolidine-2-carboxylic acid ((S)-3,4-dihydroxy-butyl)-amide as a white solid (50 mg, 13%).

HRMS (ES$^+$) m/z Calcd for $C_{29}H_{36}Cl_2FN_3O_5$+H [(M+H)$^+$]: 596.2089. found: 596.2087.

Example 85a

Preparation of intermediate (Z)-2-(4-chloro-2-fluoro-phenyl)-3-(5-chloro-2-methoxy-phenyl)-acrylonitrile

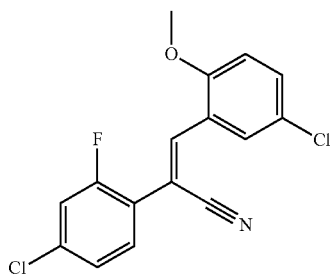

M.W. 322.17
$C_{16}H_{10}Cl_2FNO$

In a manner similar to the method described in Example 1b, 4-chloro-2-fluorophenylacetonitrile (2.8 g, 16.6 mmol) was reacted with 5-chloro-2-methoxybenzaldehyde (Matrix) (3.4 g, 19.9 mmol), methanolic solution (25 wt %) of sodium methoxide (4.17 mL, 18 mmol) in methanol (100 mL) at 50° C. for 3 h to give (Z)-2-(4-chloro-2-fluoro-phenyl)-3-(5-chloro-2-methoxy-phenyl)-acrylonitrile as a white solid (2.0 g, 37%).

Example 85b

Preparation of intermediate rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid tert-butyl ester

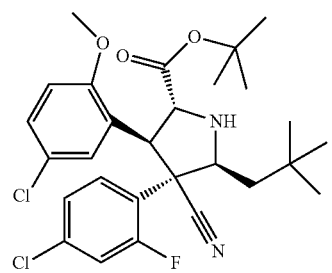

M.W. 535.49
$C_{28}H_{33}Cl_2FN_2O_3$

In a manner similar to the method described in Example 1c, [3-methyl-but-(E)-ylideneamino]-acetic acid tert-butyl ester prepared in Example 1a (1.1 g, 5 mmol) was reacted with (Z)-2-(4-chloro-2-fluoro-phenyl)-3-(5-chloro-2-methoxy-phenyl)-acrylonitrile (1.28 g, 4 mmol) prepared in Example 85a, AgF (0.76 g, 6 mmol), and triethylamine (1.38 mL, 10 mmol) in dichloromethane (100 mL) at room temperature for 18 h to give rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid tert-butyl ester as a white foam (0.3 g, 14%).

Example 85c

Preparation of intermediate rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid trifluoroacetic acid

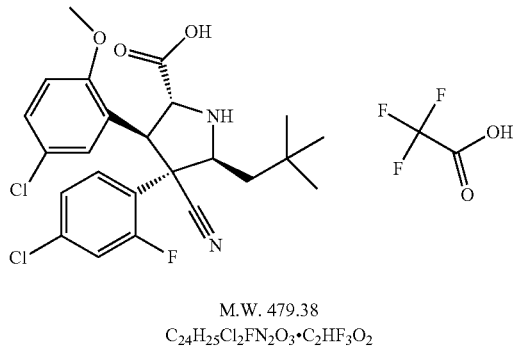 [SMILES: COc1ccc(Cl)cc1[C@H]1[C@H](C(=O)O)N[C@@H](CC(C)(C)C)[C@]1(C#N)c1ccc(Cl)cc1F ; O=C(O)C(F)(F)F]

M.W. 479.38
$C_{24}H_{25}Cl_2FN_2O_3 \cdot C_2HF_3O_2$

In a manner similar to the method described in Example 25a, rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid tert-butyl ester prepared in Example 85b (0.3 g, 0.56 mmol) was reacted with trifluoroacetic acid in dichloromethane at room temperature to give rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid trifluoroacetic acid as a white solid (0.32 g, 97%).

Example 85d

Preparation of rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid ((S)-3,4-dihydroxy-butyl)-amide

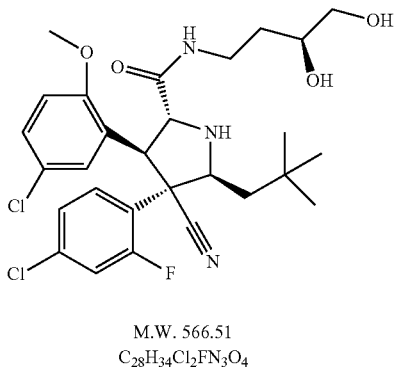 [SMILES: COc1ccc(Cl)cc1[C@H]1[C@H](C(=O)NCC[C@H](O)CO)N[C@@H](CC(C)(C)C)[C@]1(C#N)c1ccc(Cl)cc1F]

M.W. 566.51
$C_{28}H_{34}Cl_2FN_3O_4$

In a manner similar to the method described in Examples 42c, 42d, rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid trifluoroacetic acid prepared in Example 85c (0.32 g, 0.54 mmol) was reacted with 2-((S)-2,2-dimethyl-[1,3]dioxolan-4-yl)-ethylamine (0.23 g, 1.62 mmol), HATU (0.37 g, 0.98 mmol) and iPr$_2$NEt (0.47 mL, 2.7 mmol) in CH$_2$Cl$_2$ at room temperature for 20 h, then reacted with aqueous HCl solution in tetrahydrofuran at room temperature to give rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid ((S)-3,4-dihydroxy-butyl)-amide as a white solid (65 mg, 21%).

HRMS (ES$^+$) m/z Calcd for $C_{28}H_{34}Cl_2FN_3O_4$+H [(M+H)$^+$]: 566.1983. found: 566.1984.

Example 86

Preparation of rac(2R,3R,4R,5S)-3-(3-chloro-phenyl)-4-(4-chloro-phenyl)-4-cyano-5-(2,2-dimethyl-propyl)-pyrrolidine-2-carboxylic acid (quinolin-3-ylmethyl)-amide

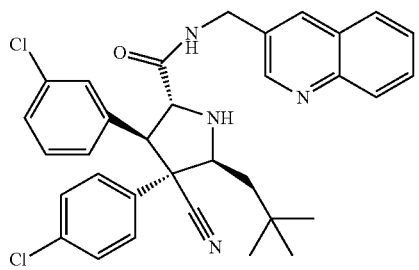

M.W. 571.56
$C_{33}H_{32}Cl_2N_4O$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol) prepared in Example 1d was reacted with quinolin-3-yl-methylamine (47.5 mg, 0.3 mmol), HATU (76.0 mg, 0.2 mmol) and iPr$_2$NEt (0.1 mL, 0.55 mmol) in CH$_2$Cl$_2$ (2 mL) at rt overnight. to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (quinolin-3-ylmethyl)-amide (54.4 mg, 47.5%) as a white powder.

HRMS (ES$^+$) m/z Calcd for $C_{33}H_{32}Cl_2N_4$+H [(M+H)$^+$]: 571.2026. found: 571.2027.

Example 87

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-trifluoromethyl-benzylamide

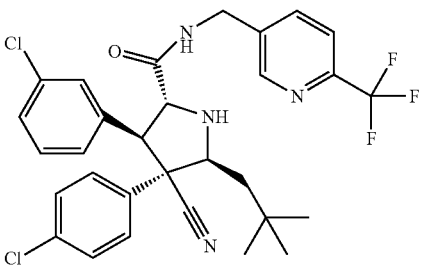

M.W. 588.498
$C_{31}H_{30}Cl_2F_3N_3O$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 4-trifluoromethylbenzyl amine (52.5 mg, 0.3 mmol), HATU (76 mg, 0.2 mmol) and iPr$_2$NEt (0.1 mL, 0.55 mmol) in CH$_2$Cl$_2$ (2 mL) was stirred at rt overnight to rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-trifluoromethyl-benzylamide (58.1 mg, 58.04%).

HRMS (ES$^+$) m/z Calcd for C$_{31}$H$_{30}$Cl$_2$F$_3$N$_3$O+H [(M+H)$^+$]: 588.1791. found: 588.1788.

Example 88

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 3-trifluoromethyl-benzyl amide

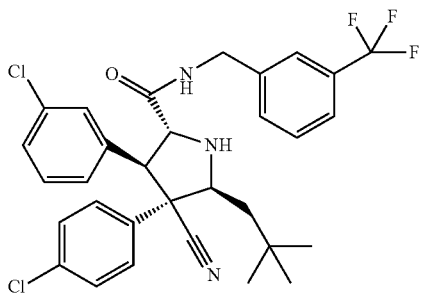

M.W. 588.498
C$_{31}$H$_{30}$Cl$_2$F$_3$N$_3$O

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 3-trifluoromethylbenzyl amine (52.55 mg, 0.3 mmol), HATU (76 mg, 0.2 mmol) and iPr$_2$NEt (0.1 mL, 0.55 mmol) in CH$_2$Cl$_2$ (2 mL) was stirred at rt overnight to rac-(2R,3R,4R,5S)-3-(3-chloro-phenyl)-4-(4-chloro-phenyl)-4-cyano-5-(2,2-dimethyl-propyl)-pyrrolidine-2-carboxylic acid 3-trifluoromethyl-benzyl amide (26.2 mg, 26.2%).

HRMS (ES$^+$) m/z Calcd for C$_{31}$H$_{30}$Cl$_2$F$_3$N$_3$O+H [(M+H)$^+$]: 588.1791. found: 588.1788.

Example 89

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-hydroxy-benzylamide

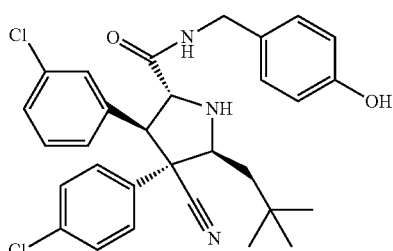

M.W. 536.51
C$_{30}$H$_{31}$Cl$_2$N$_3$O$_2$

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 4-hydroxybenzyl amine (36.9 mg, 0.3 mmol), HATU (76 mg, 0.2 mmol) and iPr$_2$NEt (0.1 mL, 0.55 mmol) in CH$_2$Cl$_2$ (2 mL) was stirred at rt overnight to rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-hydroxy-benzylamide (45.1 mg, 45.0%).

HRMS (ES$^+$) m/z Calcd for C$_{30}$H$_{31}$Cl$_2$N$_3$O$_2$+H [(M+H)$^+$]: 536.1866. found: 536.1866.

Example 90

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 3-iodo-benzylamide

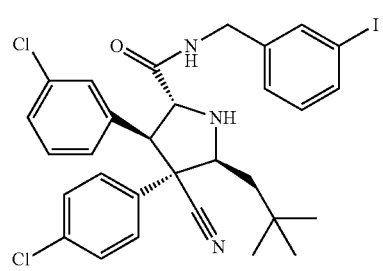

M.W. 646.393
C$_{30}$H$_{30}$Cl$_2$IN$_3$O

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 3-iodobenzyl amine (68.92 mg, 0.3 mmol), HATU (76 mg, 0.2 mmol) and iPr$_2$NEt (0.1 mL, 0.55 mmol) in CH$_2$Cl$_2$ (2 mL) was stirred at rt overnight to rac-(2R,3R,4R,5S)-3-(3-chloro-phenyl)-4-(4-chloro-phenyl)-4-cyano-5-(2,2-dimethyl-propyl)-pyrrolidine-2-carboxylic acid 3-iodo-benzylamide (44.1 mg, 34.1%).

HRMS (ES$^+$) m/z Calcd for C$_{30}$H$_{30}$Cl$_2$IN$_3$O+H [(M+H)$^+$]: 646.0884. found: 646.0881.

Example 91

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-ethyl-butyl)-amide

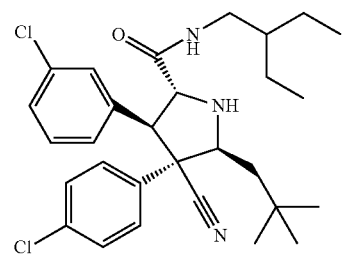

M.W. 514.54
C$_{29}$H$_{37}$Cl$_2$N$_3$O

In a manner similar to the method described in Example 1e, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.2 mmol) prepared in Example 1d was reacted with 2-ethyl butyl amine (30.3 mg, 0.3 mmol), HATU (76 mg, 0.2 mmol) and iPr₂NEt (0.1 mL, 0.55 mmol) in CH₂Cl₂ (2 mL) was stirred at rt overnight to rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-ethyl-butyl)-amide (34 mg, 33.04%).

HRMS (ES⁺) m/z Calcd for $C_{29}H_{37}Cl_2N_3O+H$ [(M+H)⁺]: 514.2387. found: 514.2385.

Example 92

Preparation of rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-carboxylic acid tert-butyl ester

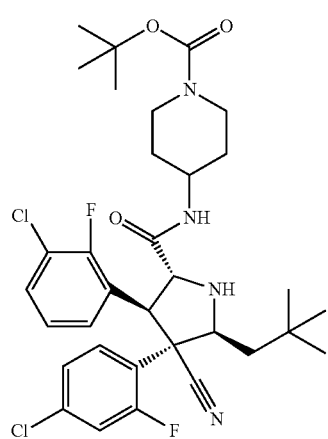

M.W. 649.61
$C_{33}H_{40}Cl_2F_2N_4O_3$

In a manner similar to the method described in Examples 42c, 42d, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (1.8 g, 3.1 mmol) was reacted with 4-Amino-piperidine-1-carboxylic acid tert-butyl ester(Aldrich, 931 mg, 4.65 g, 4.65 mmol), HATU (2.12 g, 0.92 mmol) and iPr₂NEt (2.7 mL, 15.5 mmol) in CH₂Cl₂ at room temperature overnight, then reacted with aqueous HCl solution in tetrahydrofuran at room temperature for 2 h to give a white solid (0.758 g, 38%).

HRMS (ES⁺) m/z Calcd for $C_{33}H_{40}Cl_2F_2N_4O_3+H$ [(M+H)⁺]: 649.2519. found: 649.2518.

Example 93

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid piperidin-4-ylamide trifluoroacetic acid

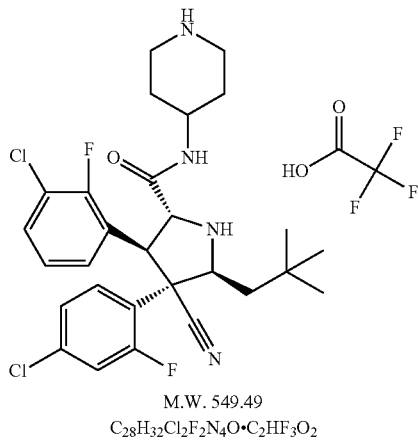

M.W. 549.49
$C_{28}H_{32}Cl_2F_2N_4O \cdot C_2HF_3O_2$

To a stirred solution of a mixture of TFA/CH₂Cl₂ (5 mL/10 mL), rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-carboxylic acid tert-butyl ester (example 92, 510 mg, 0.79 mmol) was added and the mixture was stirred at rt for 15 min. The solvent was removed and the residue dried to give a white solid after precipitation from methylene chloride and ethyl acetate. 492 mg.

HRMS (ES⁺) m/z Calcd for $C_{28}H_{32}Cl_2F_2N_4O+H$ [(M+H)⁺]: 549.1994. found: 549.1994.

Example 94

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methanesulfonylpiperidin-4-yl)-amide

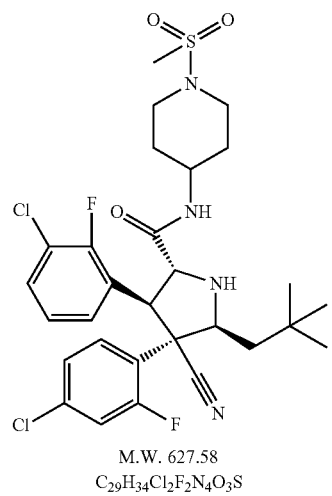 [SMILES: CC(C)(C)C[C@@H]1N[C@@H](C(=O)NC2CCN(S(C)(=O)=O)CC2)[C@H](c2cccc(Cl)c2F)[C@@]1(C#N)c1ccc(Cl)cc1F]

M.W. 627.58
$C_{29}H_{34}Cl_2F_2N_4O_3S$

To a stirred solution of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid piperidin-4-ylamide trifluoroacetic acid (80 mg, 0.10 mmol) in methylene chloride (10 mL), methanesulfonyl chloride (14 uL, 0.18 mmol) and triethylamine (84 uL, 0.61 mmol) were added and the mixture was stirred at rt for 1 hr. The reaction was quenched with water and the organic layer was separated and dried with sodium sulfate. Removal of solvent gave the crude which was chromatographed on an ISCO machine (0-10% EtOAc/CH$_2$Cl$_2$) to give a white solid. 53 mg.

HRMS (ES$^+$) m/z Calcd for C$_{29}$H$_{34}$Cl$_2$F$_2$N$_4$O$_3$S+H [(M+H)$^+$]: 627.1770. found: 627.1766.

Example 95

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-carbonyl-piperidin-4-yl)-amide

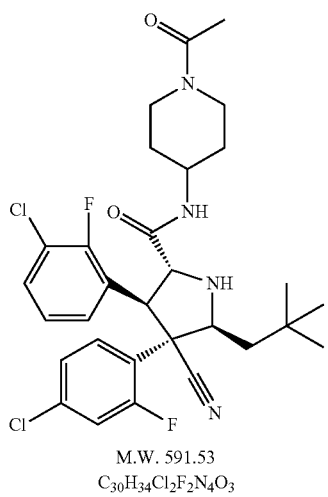 [SMILES: CC(=O)N1CCC(NC(=O)[C@@H]2N[C@@H](CC(C)(C)C)[C@](C#N)(c3ccc(Cl)cc3F)[C@H]2c2cccc(Cl)c2F)CC1]

M.W. 591.53
C$_{30}$H$_{34}$Cl$_2$F$_2$N$_4$O$_3$

To a stirred solution of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid piperidin-4-ylamide trifluoroacetic acid (80 mg, 0.10 mmol) in methylene chloride (10 mL), acetic anhydride (18 uL, 0.18 mmol) and triethylamine (84 uL, 0.61 mmol) were added and the mixture was stirred at rt for 1.5 hr. The reaction was quenched with water and the organic layer was separated and dried with sodium sulfate. Removal of solvent gave the crude which was chromatographed on an ISCO machine (0-10% EtOAc/CH$_2$Cl$_2$) to give a white solid. 58 mg.

HRMS (ES$^+$) m/z Calcd for C$_{30}$H$_{34}$Cl$_2$F$_2$N$_4$O$_3$+H [(M+H)$^+$]: 591.2100. found: 591.2099.

Example 96

Preparation of rac-(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (1-benzoyl-piperidin-4-yl)-amide

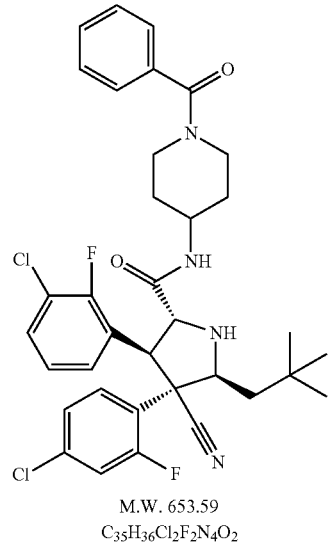 [SMILES: CC(C)(C)C[C@@H]1N[C@@H](C(=O)NC2CCN(C(=O)c3ccccc3)CC2)[C@H](c2cccc(Cl)c2F)[C@@]1(C#N)c1ccc(Cl)cc1F]

M.W. 653.59
C$_{35}$H$_{36}$Cl$_2$F$_2$N$_4$O$_2$

To a stirred solution of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid piperidin-4-ylamide trifluoroacetic acid (80 mg, 0.10 mmol) in methylene chloride (10 mL), benzoyl chloride (21 uL, 0.18 mmol) and triethylamine (84 uL, 0.61 mmol) were added and the mixture was stirred at rt for 1 hr. The reaction was quenched with water and the organic layer was separated and dried with sodium sulfate. Removal of solvent gave the crude which was chromatographed on an ISCO machine (0-10% EtOAc/CH$_2$Cl$_2$) to give a white solid. 36 mg.

HRMS (ES$^+$) m/z Calcd for C$_{35}$H$_{36}$Cl$_2$F$_2$N$_4$O$_2$+H [(M+H)$^+$]: 653.2256. found: 653.2253.

Example 97

Preparation of rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-carboxylic acid isopropylamide

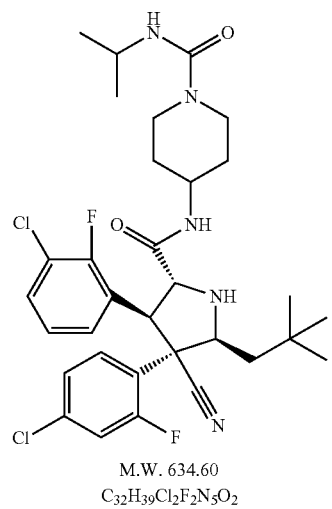 [SMILES: CC(C)NC(=O)N1CCC(NC(=O)[C@@H]2N[C@@H](CC(C)(C)C)[C@](C#N)(c3ccc(Cl)cc3F)[C@H]2c2cccc(Cl)c2F)CC1]

M.W. 634.60
C$_{32}$H$_{39}$Cl$_2$F$_2$N$_5$O$_2$

To a stirred solution of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid piperidin-4-ylamide trifluoroacetic (80 mg, 0.10 mmol) in methylene chloride (10 mL), 2-propyl isocyante (18 uL, 0.18 mmol) and triethylamine (84 uL, 0.61 mmol) were added and the mixture was stirred at rt for 1 h. The reaction was quenched with water and the organic layer was separated and dried with sodium sulfate. Removal of solvent gave the crude which was chromatographed on an ISCO machine (0-10% EtOAc/CH$_2$Cl$_2$) to give a white solid.

HRMS (ES$^+$) m/z Calcd for C$_{32}$H$_{39}$Cl$_2$F$_2$N$_5$O$_2$+H [(M+H)$^+$]: 634.2520. found: 634.2522.

Example 98a

Preparation of intermediate (Z)-3-(5-chloro-2-fluoro-phenyl)-2-(4-chloro-2-fluoro-phenyl)-acrylonitrile

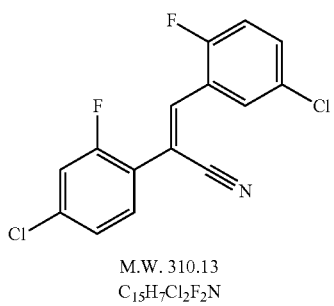 [SMILES: N#C/C(=C\c1cc(Cl)ccc1F)c1ccc(Cl)cc1F]

M.W. 310.13
C$_{15}$H$_7$Cl$_2$F$_2$N

In a manner similar to the method described in Example 1b, 4-chloro-2-fluorophenylacetonitrile (2.8 g, 16.6 mmol) was reacted with 5-chloro-2-fluorobenzaldehyde (Alfa) (3.2 g, 19.9 mmol), methanolic solution (25 wt %) of sodium methoxide (4.17 mL, 18 mmol) in methanol (100 mL) at 50° C. for 3 h to give (Z)-2-(4-chloro-2-fluoro-phenyl)-3-(5-chloro-2-methoxy-phenyl)-acrylonitrile as a off white solid (3.5 g, 68.6%).

Example 98b

Preparation of intermediate rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid tert-butyl ester

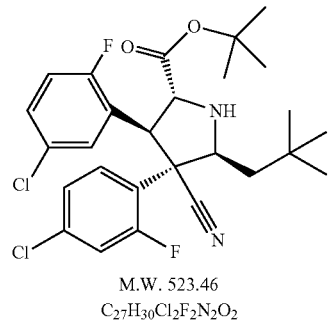 [SMILES: CC(C)(C)C[C@@H]1N[C@@H](C(=O)OC(C)(C)C)[C@H](c2cc(Cl)ccc2F)[C@@]1(C#N)c1ccc(Cl)cc1F]

M.W. 523.46
C$_{27}$H$_{30}$Cl$_2$F$_2$N$_2$O$_2$

In a manner similar to the method described in Example 1c, [3-methyl-but-(E)-ylideneamino]-acetic acid tert-butyl ester prepared in Example 1a (2.2 g, 10 mmol) was reacted with (Z)-2-(4-chloro-2-fluoro-phenyl)-3-(5-chloro-2-methoxy-phenyl)-acrylonitrile (2.46 g, 8 mmol) prepared in Example 98a, AgF (1.52 g, 12 mmol), and triethylamine (2.78 mL, 20 mmol) in dichloromethane (1500 mL) at room temperature for 18 h to give rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid tert-butyl ester as a white foam (1.1 g, 26%).

Example 98c

Preparation of intermediate rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid

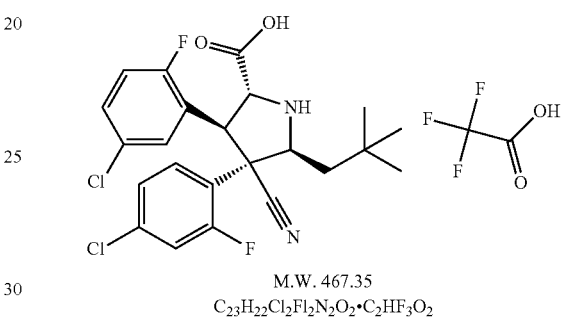

M.W. 467.35
C$_{23}$H$_{22}$Cl$_2$Fl$_2$N$_2$O$_2$·C$_2$HF$_3$O$_2$

In a manner similar to the method described in Example 25a, rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid tert-butyl ester prepared in Example 98b (1.1 g, 2.1 mmol) was reacted with trifluoroacetic acid in dichloromethane at room temperature to give rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid as a white solid (1.1 g, 90%).

Example 98d

Preparation of rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide

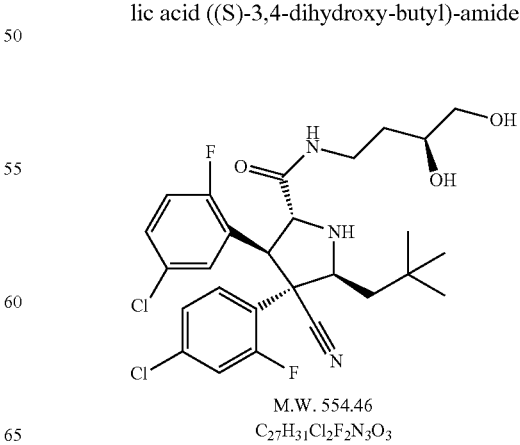

M.W. 554.46
C$_{27}$H$_{31}$Cl$_2$F$_2$N$_3$O$_3$

In a manner similar to the method described in Examples 42c, 42d, rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 98c (0.4 g, 0.68 mmol) was reacted with 2-((S)-2,2-dimethyl-[1,3]dioxolan-4-yl)-ethylamine (0.3 g, 2.06 mmol), HATU (0.47 g, 1.24 mmol) and iPr$_2$NEt (0.6 mL, 3.44 mmol) in CH$_2$Cl$_2$ at room temperature for 20 h, then reacted with aqueous HCl solution in tetrahydrofuran at room temperature to give rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide as a white solid (0.36 g, 80%).

HRMS (ES$^+$) m/z Calcd for C$_{27}$H$_{31}$Cl$_2$F$_2$N$_3$O$_3$+H [(M+H)$^+$]: 554.1784 found: 554.1782.

Example 99a

Preparation of intermediate [3-cyclopropyl-3-methyl-but-(E)-ylideneamino]-acetic acid tert-butyl ester

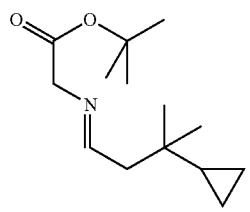

M.W. 239.36
C$_{14}$H$_{25}$NO$_2$

Step A To a suspension of CuI (7.61 g, 40 mmol) in anhydrous tetrahydrofuran (100 mL) at −50° C. was added cyclopropylmagnesium bromide (0.5 M, 160 mL, 80 mmol) during a period of 15 min. After the addition was finished, the reaction mixture was gradually warmed room temperature and stirred for 20 min. Then the temperature of the mixture was lowered to −50° C., a tetrahydrofuran solution (50 mL) of diethyl isopropylidenemalonate (Aldrich) (4 g, 20 mmol) was added. The reaction mixture was allowed to slowly warmed to room temperature and stirred for 3 h. Aqueous saturated NH$_4$Cl solution was added to quench the reaction. The mixture was filtered, and the filtrate was concentrated to remove most of tetrahydrofuran. The residue was extracted with ethyl acetate twice. The organic layers were combined, concentrated. The residue was purified by chromatography (EtOAc:hexanes=1:20, 1:10) to give 2-(1-cyclopropyl-1-methyl-ethyl)-malonic acid diethyl ester as a colorless oil (4.3 g, 89%).

Step B To a solution of 2-(1-cyclopropyl-1-methyl-ethyl)-malonic acid diethyl ester (4.3 g, 17.8 mmol) in DMSO (30 mL) was added LiCl (1.5 g, 35.6 mmol) and H$_2$O (0.3 mL, 17.8 mmol). The reaction mixture was heated at 170° C. for 4 h, then poured into a ice-water, extracted with ethyl acetate. The organic layer were separated, washed with water, brine, dried over MgSO$_4$, and concentrated to give 3-cyclopropyl-3-methyl-butyric acid ethyl ester as a colorless oil (2 g, 66%).

Step C To a solution of 3-cyclopropyl-3-methyl-butyric acid ethyl ester (2 g, 11.75 mmol) in anhydrous tetrahydrofuran (40 mL) at 0° C. was added a tetrhydrofuran solution (1 M) of LiAlH$_4$ (23.5 mL, 23.5 mmol) under nitrogen. The reaction mixture was stirred at 0° C. for 1 h, then poured into a ice-water. The mixture was extracted with ethyl acetate. The organic layer were separated, washed with water, aqueous HCl solution, brine, dried over MgSO$_4$, and concentrated. The residue was purified by chromatography (EtOAc:hexanes=1:10, 1:5) to give 3-cyclopropyl-3-methyl-butan-1-ol as a colorless oil (0.7 g, 46%).

Step D To a solution of oxalyl chloride (0.75 g, 5.9 mmol) (Aldrich) in dichloromethane (30 mL) at −78° C. was added the solution of dimethyl sulfoxide (0.84 mL, 11.8 mmol) in dichloromethane (5 mL) dropwise. After 5 mins, the solution of 3-cyclopropyl-3-methyl-butan-1-ol (0.69 g, 5.4 mmol) in dichloromethane (10 mL) was added dropwise. The reaction mixture was stirred at −78° C. for 15 min. Triethylamine (2.7 mL, 19.4 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO$_3$, brine, dried over MgSO$_4$, and concentrated to give 3-cyclopropyl-3-methyl-butyraldehyde as a light yellow oil (Yield: 0.68 g, 98%).

Step E In a manner similar to the method described in Example 1a, glycine tert-butyl ester (0.65 g, 5 mmol) was reacted with 3-cyclopropyl-3-methyl-butyraldehyde (0.68 g, 5.3 mmol) in CH$_2$Cl$_2$ at room temperature for 5 h to give [3-cyclopropyl-3-methyl-but-(E)-ylideneamino]-acetic acid tert-butyl ester as a colorless oil (0.9 g, 75%).

Example 99b

Preparation of intermediate rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid methyl ester

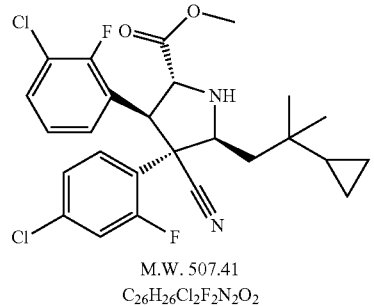 [SMILES: COC(=O)[C@@H]1N[C@@H](CC(C)(C)C2CC2)[C@](C#N)(c2ccc(Cl)cc2F)[C@H]1c1cccc(Cl)c1F]

M.W. 507.41
C$_{26}$H$_{26}$Cl$_2$F$_2$N$_2$O$_2$

To a solution of [3-cyclopropyl-3-methyl-but-(E)-ylideneamino]-acetic acid tert-butyl ester prepared in Example 99a (0.9 g, 3.76 mmol) and (Z)-3-(3-chloro-2-fluoro-phenyl)-2-(4-chloro-2-fluoro-phenyl)-acrylonitrile (1.16 g, 3.76 mmol) prepared in Example 52a in dichloromethane (100 mL) were added triethylamine (0.76 g, 7.5 mmol) and AgF (0.47 g, 3.76 mmol), in one portion. The mixture was stirred at room temperature for overnight. The mixture was then quenched with sat. NH$_4$Cl and extracted with CH$_2$Cl$_2$. The organic phase was separated, filtered through celite and dried over Na$_2$SO$_4$, and concentrated. The residue was dissolved into methanol (40 mL), and DBU (3 mL) was added. The mixture was heated at 100° C. for 5 h, then cooled to room temperature, and concentrated. The residue was partitioned between ethyl acetate and water. The organic layer were separated, dried over MgSO$_4$, and concentrated. The residue was purified by chromatography (EtOAc:hexanes=1:5, 1:3) to give rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid methyl ester as a white foam (0.95 g, 50%).

Example 99c

Preparation of intermediate rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid

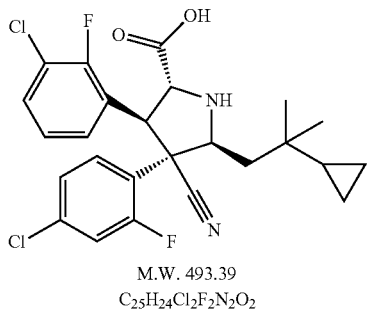 [SMILES: CC(C)(C[C@@H]1N[C@@H](C(=O)O)[C@H](c2cccc(Cl)c2F)[C@@]1(C#N)c1ccc(Cl)cc1F)C1CC1]

M.W. 493.39
$C_{25}H_{24}Cl_2F_2N_2O_2$

To rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid methyl ester prepared in Example 99b (0.95 g, 1.87 mmol) in tetrahydrofuran (40 mL) was added an aqueous solution (20 mL) of NaOH (0.15 g, 3.7 mmol) and methanol (20 mL). The reaction mixture was stirred at room temperature for 18 h. The "pH" of the mixture was adjusted to 5 by aqueous HCl solution. The mixture was concentrated. The residue was partitioned between ethyl acetate and water. The organic layer was separated, washed with water, brine, dried over MgSO$_4$, concentrated, and triturated with dichloromethane and hexanes to give rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid as a white solid (0.78 g, 80%)

Example 99d

Preparation of rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide

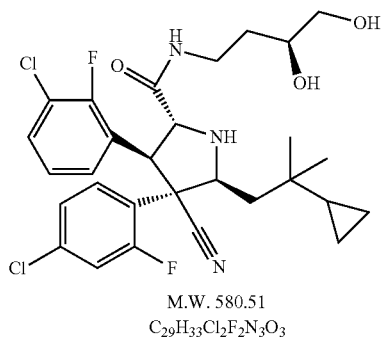 [SMILES: CC(C)(C[C@@H]1N[C@@H](C(=O)NCC[C@H](O)CO)[C@H](c2cccc(Cl)c2F)[C@@]1(C#N)c1ccc(Cl)cc1F)C1CC1]

M.W. 580.51
$C_{29}H_{33}Cl_2F_2N_3O_3$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid prepared in Example 99c (0.41 g, 0.83 mmol) was reacted with 2-((S)-2,2-dimethyl-[1,3]dioxolan-4-yl)-ethylamine (0.36 g, 2.5 mmol), HATU (0.57 g, 1.5 mmol) and iPr$_2$NEt (0.43 mL, 2.5 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide as a white solid (0.33 g, 70%).

HRMS (ES$^+$) m/z Calcd for $C_{29}H_{33}Cl_2F_2N_3O_3$+H [(M+H)$^+$]: 580.1940. found: 580.1936.

Example 99e

Preparation of (2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide

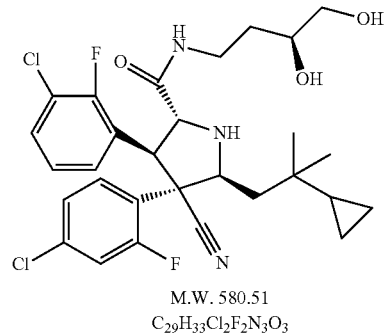 [SMILES: CC(C)(C[C@@H]1N[C@@H](C(=O)NCC[C@H](O)CO)[C@H](c2cccc(Cl)c2F)[C@@]1(C#N)c1ccc(Cl)cc1F)C1CC1]

M.W. 580.51
$C_{29}H_{33}Cl_2F_2N_3O_3$

Rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide (0.3 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide as a white solid (0.11 g, 37%) and chiral (2S,3R,4S,5R)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide as a white solid (0.11 g, 37%).

HRMS (ES$^+$) m/z Calcd for $C_{29}H_{33}Cl_2F_2N_3O_3$+H [(M+H)$^+$]: 580.1940. found: 580.1941.

Example 100a

Preparation of intermediate (Z)-3-(3-chloro-2-fluoro-phenyl)-2-(4-chloro-3-methyl-phenyl)-acrylonitrile

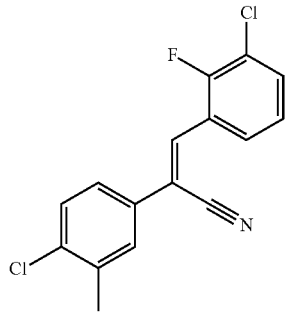

M.W. 306.17
$C_{16}H_{10}Cl_2FN$

Step A In a manner similar to the method described in Example 57 Step A, 4-chloro-2-methylbenzyl alcohol (PLATTE) (1.69 g, 11 mmol) was reacted with thionyl chloride (20 mL) to give 4-chloro-2-methylbenzyl chloride as a colorless oil (1.83 g, 97%).

Step B In a manner similar to the method described in Example 57 Step B, 4-chloro-2-methylbenzyl chloride (1.83 g, 10 mmol) was reacted with KCN (1.76 g, 27 mmol) in ethanol (13 mL) and water (10 mL) at 100° C. for 1 h to give 4-chloro-2-methylbenzyl cyanide as a yellow oil (1.2 g, 69%)

Step C In a manner similar to the method described in Example 1b, 4-chloro-2-methylbenzyl cyanide (1.2 g, 7.2 mmol) was reacted with 3-chloro-2-fluorobenzaldehyde (1.38 g, 8.7 mmol), methanolic solution (25 wt %) of sodium methoxide (1.82 mL, 8 mmol) in methanol (50 mL) at 50° C. for 3 h to give (Z)-3-(3-chloro-2-fluoro-phenyl)-2-(4-chloro-3-methyl-phenyl)-acrylonitrile as a white solid (2.0 g, 91%).

Example 100b

Preparation of intermediate rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid tert-butyl ester

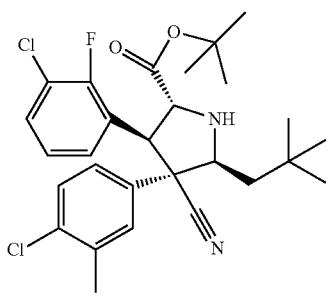

M.W. 519.49
C$_{28}$H$_{33}$Cl$_2$N$_2$O$_2$

To a solution of [3-cyclopropyl-3-methyl-but-(E)-ylideneamino]-acetic acid tert-butyl ester prepared in Example 1a (0.93 g, 7.3 mmol) and To a solution of [3-cyclopropyl-3-methyl-but-(E)-ylideneamino]-acetic acid tert-butyl ester prepared in Example 99a (1.6 g, 7.3 mmol) and (Z)-3-(3-chloro-2-fluoro-phenyl)-2-(4-chloro-2-fluoro-phenyl)-acrylonitrile (1.5 g, 4.9 mmol) prepared in Example 100a in dichloromethane (100 mL) were added triethylamine (1.7 g, 12 mmol) and AgF (0.9 g, 7.3 mmol), in one portion. The mixture was stirred at room temperature for 18 h. The mixture was then quenched with sat. NH$_4$Cl and extracted with CH$_2$Cl$_2$. The organic phase was separated, filtered through celite and dried over Na$_2$SO$_4$, and concentrated. The residue was dissolved into tert-butanol (30 mL), and DBU (5 mL) was added. The mixture was heated at 100° C. for 18 h, then cooled to room temperature, and concentrated. The residue was partitioned between ethyl acetate and water. The organic layer were separated, dried over MgSO$_4$, and concentrated. The residue was purified by chromatography (EtOAc:hexanes=1:10, 1:5) to give rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid tert-butyl ester as a white foam (2 g, 80%).

Example 100c

Preparation of intermediate rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid trifluoroacetic acid

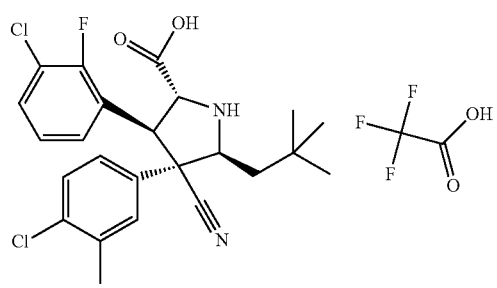

M.W. 463.38
C$_{24}$H$_{25}$Cl$_2$FN$_2$O$_2$·C$_2$HF$_3$O$_2$

In a manner similar to the method described in Example 25a, rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid tert-butyl ester prepared in Example 100b (2.0 g, 3.8 mmol) was reacted with trifluoroacetic acid in dichloromethane at room temperature to give rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid trifluoroacetic acid as a white solid (1.88 g, 85%).

Example 100d

Preparation of rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid ((S)-3,4-dihydroxy-butyl)-amide

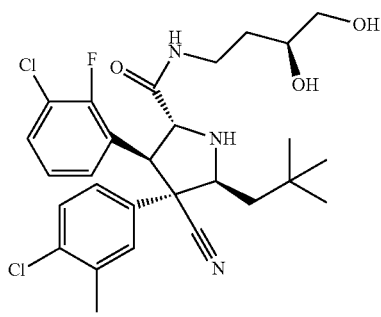

M.W. 550.50
C$_{28}$H$_{34}$Cl$_2$FN$_3$O$_3$

In a manner similar to the method described in Examples 42c, 42d, rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid trifluoroacetic acid prepared in Example 100c (0.44 g, 0.76 mmol) was reacted with 2-((S)-2,2-dimethyl-[1,3]dioxolan-4-yl)-ethylamine (0.33 g, 2.3 mmol), HATU (0.52 g, 1.37 mmol) and iPr₂NEt (0.66 mL, 3.8 mmol) in CH₂Cl₂ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid ((S)-3,4-dihydroxy-butyl)-amide as a white solid (0.26 g, 64%).

HRMS (ES⁺) m/z Calcd for C₂₈H₃₄Cl₂FN₃O₃+H [(M+H)⁺]: 550.2034. found: 550.2034.

Example 101a

Preparation of intermediate [2-(tetrahydro-pyran-4-yl)-eth-(E)-ylideneamino]-acetic acid tert-butyl ester

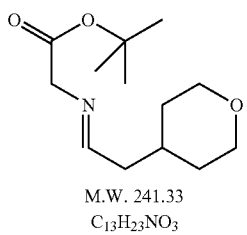

M.W. 241.33
C₁₃H₂₃NO₃

In a manner similar to the method described in Example 1a, glycine tert-butyl ester (0.65 g, 5 mmol) was reacted with (tetrahydro-pyran-4-yl)-acetaldehyde (Pharmacore) (0.64 g, 5 mmol) in CH₂Cl₂ at room temperature for 5 h to give [2-(tetrahydro-pyran-4-yl)-eth-(E)-ylideneamino]-acetic acid tert-butyl ester as a colorless oil (0.43 g, 33%).

Example 101b

Preparation of intermediate rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid tert-butyl ester

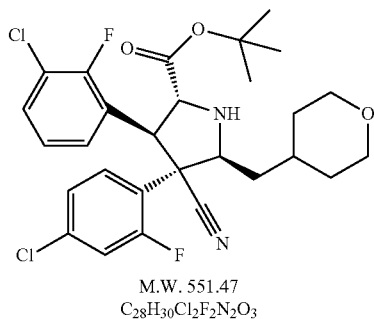 [SMILES: CC(C)(C)OC(=O)[C@@H]1N[C@@H](CC2CCOCC2)[C@](C#N)(c2ccc(Cl)cc2F)[C@H]1c1cccc(Cl)c1F]

M.W. 551.47
C₂₈H₃₀Cl₂F₂N₂O₃

In a manner similar to the method described in Example 100b, [2-(tetrahydro-pyran-4-yl)-eth-(E)-ylideneamino]-acetic acid tert-butyl ester prepared in Example 100a (0.43 g, 1.8 mmol) was reacted with (Z)-3-(3-chloro-2-fluoro-phenyl)-2-(4-chloro-2-fluoro-phenyl)-acrylonitrile (0.31 g, 1 mmol) prepared in Example 52a, AgF (0.19 g, 1.5 mmol), and triethylamine (0.46 g, 4.5 mmol) in dichloromethane (50 mL) at room temperature for 18 h, followed by reaction with DBU in tert-butanol at 100° C. for 8 h to give rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid tert-butyl ester as a white solid (0.45 g, 82%).

Example 101c

Preparation of intermediate rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid trifluoroacetic acid

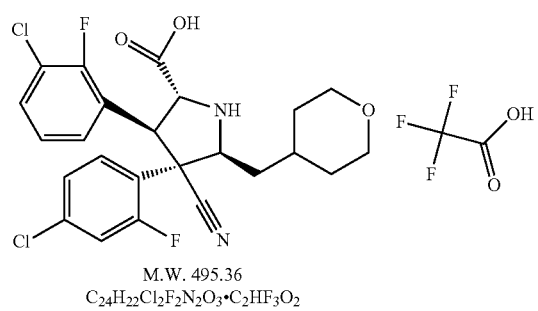

M.W. 495.36
C₂₄H₂₂Cl₂F₂N₂O₃·C₂HF₃O₂

In a manner similar to the method described in Example 25a, rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid tert-butyl ester prepared in Example 101b (0.45 g, 0.81 mmol) was vented with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid trifluoroacetic acid as a white solid (0.4 g, 80%).

Example 101d

Preparation of rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid ((S)-3,4-dihydroxy-butyl)-amide

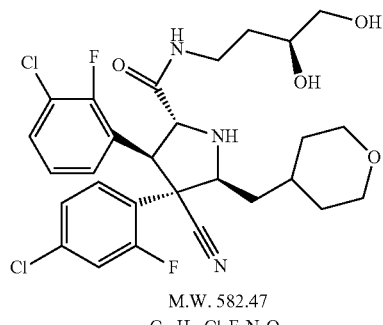

M.W. 582.47
C₂₈H₃₁Cl₂F₂N₃O₄

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid trifluoroacetic acid prepared in Example 101c (0.15 g, 0.25 mmol) was reacted with 2-((S)-2,2-dimethyl-[1,3]dioxolan-4-yl)- ethylamine (0.11 g, 0.74 mmol), HATU (0.17 g, 0.44 mmol) and iPr$_2$NEt (0.21 mL, 1.2 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid ((S)-3,4-dihydroxy-butyl)-amide as a white solid (0.25 g, 80%).

HRMS (ES$^+$) m/z Calcd for C$_{28}$H$_{31}$Cl$_2$F$_2$N$_3$O$_4$+H [(M+H)$^+$]: 582.1733. found: 582.1731.

Example 102a

Preparation of intermediate [2-(1-methyl-cyclohexyl)-eth-(E)-ylideneamino]-acetic acid tert-butyl ester

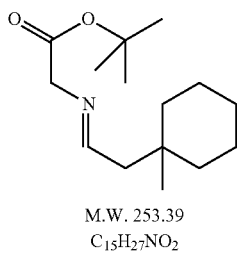

M.W. 253.39
C$_{15}$H$_{27}$NO$_2$

Step A To a suspension of NaH (60%, 3 g, 74 mmol) in DME (100 mL) was added methyl (dimethoxyphosphonyl) acetate (Aldrich) (11.3 g, 61.8 mmol). The mixture was stirred at room temperature for 40 min, then cyclohexanone (6.07 g, 61.8 mmol) was added. The reaction mixture was stirred at room temperature for 18 h. Aqueous saturated NH$_4$Cl solution was added and the mixture was extracted with ethyl acetate twice. The organic layers were combined, dried over MgSO$_4$, concentrated. The residue was purified by chromatography (EtOAc:hexanes=1:10) to give cyclohexylidene-acetic acid methyl ester as a colorless oil (6.4 g, 67%). Similar transformation was reported by Bruckner, R. et al in *Eur. J. Org. Chem.* 2006, 2119-2133 and the described procedures were used without modification.

Step B To a suspension of CuI (7.61 g, 40 mmol) in anhydrous ethyl ether (20 mL) at 0° C. was added an ethyl ether solution (1.6 M) of MeLi (50 mL, 80 mmol) The reaction mixture was stirred at 0° C. for 10 min. The solvent was evaporated under reduced pressure, then dichloromethane (20 mL) was added under nitrogen at 0° C. The mixture was stirred for 5 min. The solvent was evaporated again. To the residue was added dichlormethane (20 mL), and the temperature of the mixture was lowered to -78° C. To the mixture was added chlorotrimethylsilane (4.3 g, 40 mmol) and a dichloromethane solution (20 mL) of cyclohexylidene-acetic acid methyl ester (3.1 g, 20 mmol). The reaction mixture was allowed to slowly warmed to 0° C. and stirred for 1 h. Aqueous saturated NH$_4$Cl solution was added to quench the reaction. The mixture was extracted with ethyl ether twice. The organic layers were combined, dried over MgSO$_4$, concentrated. The residue was purified by chromatography (EtOAc: hexanes=1:5) to give (1-methyl-cyclohexyl)-acetic acid methyl ester as a colorless oil (3.3 g, 97%). Similar transformation was reported by Yamamoto, Y. et al in *Tetrahedron Letter* 44 (2003), 4265-4266 and the described procedures were used without modification.

Step C To a solution of (1-methyl-cyclohexyl)-acetic acid methyl ester (3.3 g, 19.4 mmol) in anhydrous tetrahydrofuran (50 mL) at 0° C. was added a tetrahydrofuran solution (1 M) of LiAlH$_4$ (29 mL, 29 mmol) under nitrogen. The reaction mixture was stirred at 0° C. for 1 h, then poured into a ice-water. The mixture was extracted with ethyl acetate. The organic layer were separated, washed with water, aqueous HCl solution, brine, dried over MgSO$_4$, and concentrated. The residue was purified by chromatography (EtOAc:hexanes=1:4) to give 2-(1-methyl-cyclohexyl)-ethanol as a colorless oil (2.2 g, 80%).

Step D To a solution of oxalyl chloride (2.18 g, 17.2 mmol) (Aldrich) in dichloromethane (12 mL) at -78° C. was added the solution of dimethyl sulfoxide (2.44 mL, 34.3 mmol) in dichloromethane (8 mL) dropwise. After 5 mins, the solution of 2-(1-methyl-cyclohexyl)-ethanol (2.2 g, 15.6 mmol) in dichloromethane (10 mL) was added dropwise. The reaction mixture was stirred at -78° C. for 15 min. Triethylamine (7.8 mL, 56 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO$_3$, brine, dried over MgSO$_4$, and concentrated to give (1-methyl-cyclohexyl)-acetaldehyde as a light yellow oil (Yield: 2 g, 91%).

Step E In a manner similar to the method described in Example 1a, glycine tert-butyl ester (1.87 g, 14.3 mmol) was reacted with (1-methyl-cyclohexyl)-acetaldehyde (2.9 g, 14.3 mmol) in CH$_2$Cl$_2$ at room temperature for 18 h to give [2-(1-methyl-cyclohexyl)-eth-(E)-ylideneamino]-acetic acid tert-butyl ester as a colorless oil (3.4 g, 95%).

Example 102b

Preparation of intermediate rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid tert-butyl ester

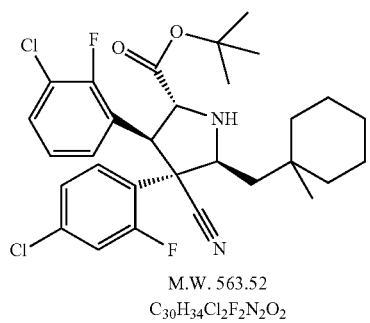 [SMILES: CC1(C[C@@H]2N[C@@H](C(=O)OC(C)(C)C)[C@H](c3cccc(Cl)c3F)[C@@]2(C#N)c2ccc(Cl)cc2F)CCCCC1]

M.W. 563.52
C$_{30}$H$_{34}$Cl$_2$F$_2$N$_2$O$_2$

In a manner similar to the method described in Example 100b, [2-(1-methyl-cyclohexyl)-eth-(E)-ylideneamino]-acetic acid tert-butyl ester prepared in Example 101a (2.55 g, 10 mmol) was reacted with (Z)-3-(3-chloro-2-fluoro-phenyl)-2-(4-chloro-2-fluoro-phenyl)-acrylonitrile (2.5 g, 8 mmol) prepared in Example 52a, AgF (1.55 g, 12.3 mmol), and triethylamine (2.8 mL, 20 mmol) in dichloromethane (150 mL) at room temperature for 18 h, followed by the reaction with DBU (10 ml) in tert-butanol (50 mL) at 100° C. for 18 h to give rac-(2R,3S,4R,5S)-3-(3-chloro-2-fluoro-phenyl)-4-(4- chloro-2-fluoro-phenyl)-4-cyano-5-(1-methyl-cyclohexylmethyl)-pyrrolidine-2-carboxylic acid tert-butyl ester as a light yellow solid (3 g, 66%).

Example 102c

Preparation of intermediate rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid trifluoroacetic acid

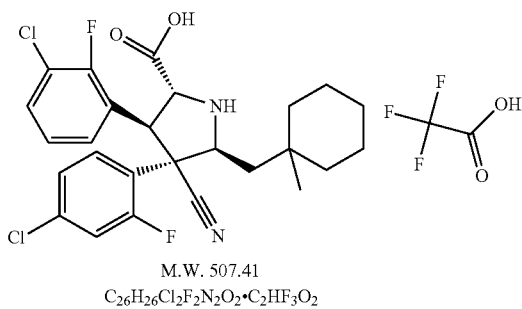

M.W. 507.41
$C_{26}H_{26}Cl_2F_2N_2O_2 \cdot C_2HF_3O_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid tert-butyl ester prepared in Example 102b (3 g, 5.3 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid trifluoroacetic acid as a off white solid (3.3 g, 100%).

Example 102d

Preparation of rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide

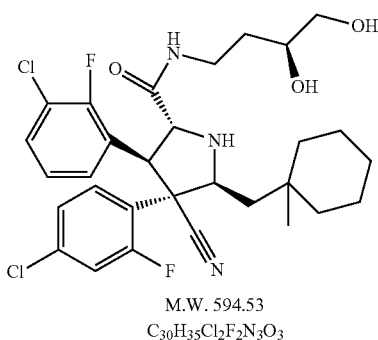 [SMILES: CC1(C[C@@H]2N[C@@H](C(=O)NCC[C@H](O)CO)[C@H](c3cccc(Cl)c3F)[C@@]2(C#N)c2ccc(Cl)cc2F)CCCCC1]

M.W. 594.53
$C_{30}H_{35}Cl_2F_2N_3O_3$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid trifluoroacetic acid prepared in Example 102c (0.5 g, 0.8 mmol) was reacted with 2-((S)-2,2-dimethyl-[1,3]dioxolan-4-yl)-ethylamine (0.35 g, 2.41 mmol), HATU (0.55 g, 1.45 mmol) and iPr$_2$NEt (0.70 mL, 4.0 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide as a white solid (0.22 g, 46%).

HRMS (ES$^+$) m/z Calcd for $C_{30}H_{35}Cl_2F_2N_3O_3$+H [(M+H)$^+$]: 594.2097. found: 594.2094.

Example 102e

Preparation of (2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide

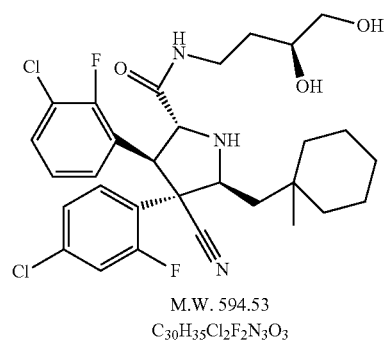 [SMILES: CC1(C[C@@H]2N[C@@H](C(=O)NCC[C@H](O)CO)[C@H](c3cccc(Cl)c3F)[C@@]2(C#N)c2ccc(Cl)cc2F)CCCCC1]

M.W. 594.53
$C_{30}H_{35}Cl_2F_2N_3O_3$

Rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide (0.18 g) was separated by chiral SFC chromatography to provide chiral (2R,3S,4R,5S)-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide as a white solid (78 mg, 71%) and chiral (2S,3R,4S,5R)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide as a white solid (80 mg, 73%).

HRMS (ES$^+$) m/z Calcd for $C_{30}H_{35}Cl_2F_2N_3O_3$+H [(M+H)$^+$]: 594.2097. found: 594.2094.

Example 103a

Preparation of intermediate 4-[(E)-tert-butoxycarbonylmethylimino]-2,2-dimethyl-butyric acid benzyl ester

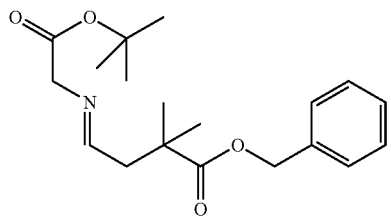

M.W. 333.43
$C_{19}H_{27}NO_4$

Step A A mixture of 2,2-dimethylbutyrolactone (6.84 g, 60 mmol) and KOH (3.36 mmol) in H₂O (60 mL) was heated at reflux for 2 h. The solution was cooled to room temperature and concentrated to dryness to give 4-hydroxy-2,2-dimethyl-butanoic acid monopotassium salt as a white solid (10.2 g, 100%).

Step B To the mixture of 4-hydroxy-2,2-dimethyl-butanoic acid monopotassium salt (60 mmol) and benzyl bromide (8.55 mL, 72 mmol) were added NaI (10.8 g, 72 mmol) and K₂CO₃ (8.29 g, 60 mmol). The reaction mixture was stirred at reflux for 18 h. The precipitate was filtered off and the filtrate was evaporated. The residue was purified by flash column chromatography (EtOAc: hexanes=1:2) to give 4-hydroxy-2,2-dimethyl-butyric acid benzyl ester as a colorless oil (9 g, 67%)

The same transformations were reported in EP246529 and the described procedures were used without modification.

Step C To a solution of oxalyl chloride (2.8 mL, 22 mmol) (Aldrich) in dichloromethane (40 mL) at −78° C. was added the solution of dimethyl sulfoxide (3.1 mL, 44 mmol) in dichloromethane (5 mL) dropwise. After 5 mins, the solution of 4-hydroxy-2,2-dimethyl-butyric acid benzyl ester (4.5 g, 20 mmol) in dichloromethane (5 mL) was added dropwise. The reaction mixture was stirred at −78° C. for 15 min. Triethylamine (10 mL, 72 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO₃, brine, dried over MgSO₄, and concentrated to give 2,2-dimethyl-4-oxo-butyric acid benzyl ester as a colorless oil (Yield: 2.9 g, 66%).

Step D In a manner similar to the method described in Example 1a, glycine tert-butyl ester (1.72 g, 13.2 mmol) was reacted with 2,2-dimethyl-4-oxo-butyric acid benzyl ester (4.1 g, 132 mmol) in CH₂Cl₂ at room temperature for 18 h to give 4-[(E)-tert-butoxycarbonylmethylimino]-2,2-dimethyl-butyric acid benzyl ester as a colorless oil (4.1 g, 93%).

Example 103b

Preparation of intermediate rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid tert-butyl ester

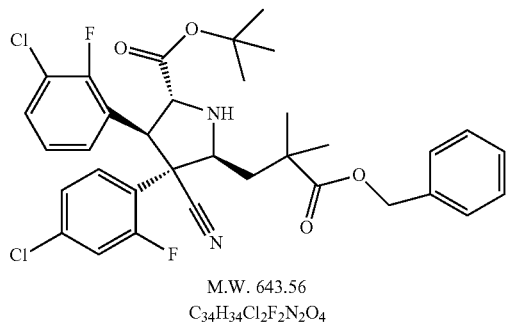 [SMILES: CC(C)(C)OC(=O)[C@@H]1N[C@@H](CC(C)(C)C(=O)OCc2ccccc2)[C@](C#N)(c2ccc(Cl)cc2F)[C@H]1c1cccc(Cl)c1F]

M.W. 643.56
C₃₄H₃₄Cl₂F₂N₂O₄

In a manner similar to the method described in Example 100b, 4-[(E)-tert-butoxycarbonylmethylimino]-2,2-dimethyl-butyric acid benzyl ester prepared in Example 103a (4.1 g, 12.3 mmol) was reacted with (Z)-3-(3-chloro-2-fluoro-phenyl)-2-(4-chloro-2-fluoro-phenyl)-acrylonitrile (2.5 g, 8 mmol) prepared in Example 52a, AgF (1.55 g, 12.3 mmol), and triethylamine (2.5 g, 24 mmol) in dichloromethane (150 mL) at room temperature for 18 h, followed by the reaction with DBU (4 ml) in tert-butanol (40 mL) at 100° C. for 4 h to give rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid tert-butyl ester as a light yellow gum (0.98 g, 19%).

Example 103c

Preparation of intermediate rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid trifluoroacetic acid

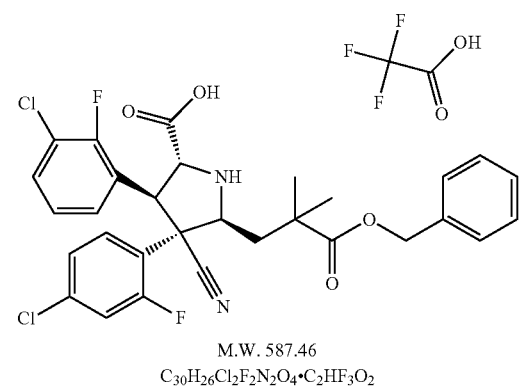

M.W. 587.46
C₃₀H₂₆Cl₂F₂N₂O₄·C₂HF₃O₂

In a manner similar to the method described in Example 25a, rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid tert-butyl ester prepared in Example 103b (0.98 g, 1.6 mmol) was reacted with trifluoroacetic acid in dichloromethane at room temperature to give rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid trifluoroacetic acid as a white gum (0.94 g, 86%).

Example 103d

Preparation of rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide

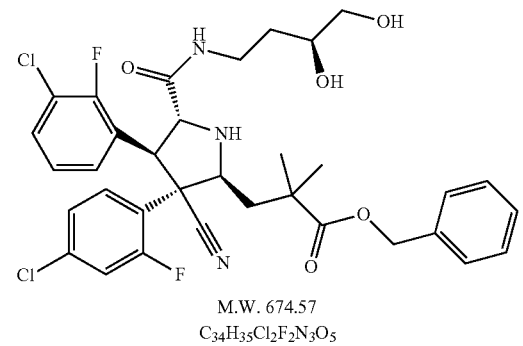 [SMILES: CC(C)(C[C@@H]1N[C@@H](C(=O)NCC[C@H](O)CO)[C@H](c2cccc(Cl)c2F)[C@@]1(C#N)c1ccc(Cl)cc1F)C(=O)OCc1ccccc1]

M.W. 674.57
C₃₄H₃₅Cl₂F₂N₃O₅

In a manner similar to the method described in Examples 42c and 42d, rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid trifluoroacetic acid prepared in Example 103c (0.94 g, 1.34 mmol) was reacted with 2-((S)-2,2-dimethyl-[1,3]dioxolan-4-yl)-ethylamine (0.58 g, 4.0 mmol), HATU (0.92 g, 2.41 mmol) and iPr₂NEt (1.17 mL, 6.7 mmol) in CH₂Cl₂ at room temperature for 20 h, then reacted with aqueous HCl solution in tetrahydrofuran at room temperature for 2 h to give rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide as a white solid (0.2 g, 22%).

HRMS (ES⁺) m/z Calcd for C₃₄H₃₅Cl₂F₂N₃O+H [(M+H)⁺]: 674.1995. found: 674.1991.

Example 104a

Preparation of intermediate 4-[(E)-tert-butoxycarbonylmethylimino]-2,2-dimethyl-butyric acid methyl ester

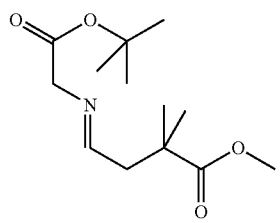

M.W. 257.33
C₁₃H₂₃NO₄

Step A A mixture of 2,2-dimethylbutyrolactone (6.84 g, 60 mmol) and KOH (3.36 g) in H₂O (60 mL) was heated at reflux for 2 h. The solution was cooled to room temperature, and acidified to "pH" 5 with aqueous HCl solution. The mixture was then extracted with ethyl acetate three times. The combined organic layers were washed with brine, dried over MgSO₄, concentrated under reduced pressure to give 4-hydroxy-2,2-dimethyl-butanoic acid as a colorless oil (4 g, 51%).

Step B To the mixture of 4-hydroxy-2,2-dimethyl-butanoic acid (2.2 g, 16.6 mmol) in ethyl ether (16 mL) and methanol (24 mL) at 0° C. was added a hexane solution (2.0 M) of trimethylsilyldiazomethane (Aldrich) (12.5 mL, 25 mmol). The reaction mixture was stirred at 0° C. for 1 h. The solvents were evaporated. The residue was taken up in ethyl acetate, washed with diluted aqueous HCl solution, saturated aqueous NaHCO₃ solution, brine, dried over MgSO₄, and concentrated to give 4-hydroxy-2,2-dimethyl-butyric acid methyl ester as a colorless oil (1.5 g, 62%).

Step C To a solution of oxalyl chloride (1.09 mL, 12.5 mmol) (Aldrich) in dichloromethane (20 mL) at −78° C. was added the solution of dimethyl sulfoxide (1.77 mL, 25 mmol) in dichloromethane (5 mL) dropwise. After 5 mins, the solution of 4-hydroxy-2,2-dimethyl-butyric acid methyl ester (1.5 g, 11.3 mmol) in dichloromethane (5 mL) was added dropwise. The reaction mixture was stirred at −78° C. for 15 min. Triethylamine (5.7 mL, 41 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO₃, brine, dried over MgSO₄, and concentrated to give 2,2-dimethyl-4-oxo-butyric acid methyl ester as a light yellow oil (Yield: 1.2 g, 81%).

Step D In a manner similar to the method described in Example 1a, glycine tert-butyl ester (1.09 g, 8.32 mmol) was reacted with 2,2-dimethyl-4-oxo-butyric acid methyl ester (1.2 g, 8.32 mmol) in CH₂Cl₂ at room temperature for 18 h to give 4-[(E)-tert-butoxycarbonylmethylimino]-2,2-dimethyl-butyric acid methyl ester as a colorless oil (2.1 g, 100%).

Example 104b

Preparation of intermediate rac-(2R,3S,4R,5S)-3-(3-chloro-2-fluoro-phenyl)-4-(4-chloro-2-fluoro-phenyl)-4-cyano-5-(2-methoxycarbonyl-2-methyl-propyl)-pyrrolidine-2-carboxylic acid tert-butyl ester

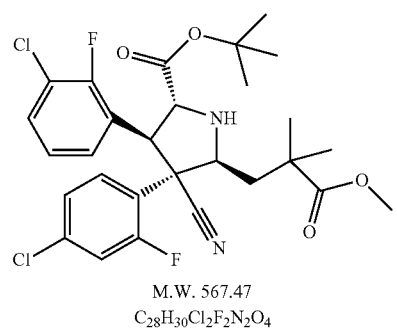 [SMILES: COC(=O)C(C)(C)C[C@@H]1N[C@@H](C(=O)OC(C)(C)C)[C@H](c2cccc(Cl)c2F)[C@@]1(C#N)c1ccc(Cl)cc1F]

M.W. 567.47
C₂₈H₃₀Cl₂F₂N₂O₄

In a manner similar to the method described in Example 100b, 4-[(E)-tert-butoxycarbonylmethylimino]-2,2-dimethyl-butyric acid methyl ester prepared in Example 104a (2.1 g, 8.3 mmol) was reacted with (Z)-3-(3-chloro-2-fluoro-phenyl)-2-(4-chloro-2-fluoro-phenyl)-acrylonitrile (2.05 g, 6.7 mmol) prepared in Example 52a, AgF (1.27 g, 10 mmol), and triethylamine (2.3 mL, 17 mmol) in dichloromethane (150 mL) at room temperature for 18 h, followed by the reaction with DBU (2 ml) in tert-butanol (10 mL) at 100° C. for 2 h to give rac-(2R,3S,4R,5S)-3-(3-chloro-2-fluoro-phenyl)-4-(4-chloro-2-fluoro-phenyl)-4-cyano-5-(2-methoxycarbonyl-2-methyl-propyl)-pyrrolidine-2-carboxylic acid tert-butyl ester as a white solid (0.75 g, 20%).

Example 104c

Preparation of intermediate rac-(2R,3S,4R,5S)-3-(3-chloro-2-fluoro-phenyl)-4-(4-chloro-2-fluoro-phenyl)-4-cyano-5-(2-methoxycarbonyl-2-methyl-propyl)-pyrrolidine-2-carboxylic acid trifluoroacetic acid

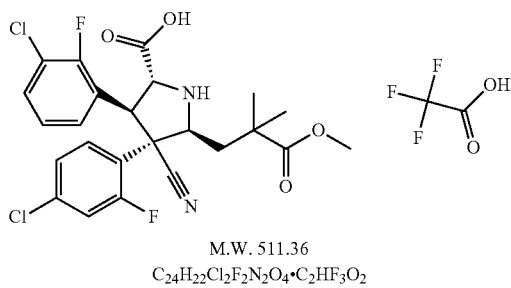 [SMILES: COC(=O)C(C)(C)C[C@@H]1N[C@@H](C(=O)O)[C@H](c2cccc(Cl)c2F)[C@@]1(C#N)c1ccc(Cl)cc1F ; O=C(O)C(F)(F)F]

M.W. 511.36
C₂₄H₂₂Cl₂F₂N₂O₄·C₂HF₃O₂

In a manner similar to the method described in Example 25a, rac-(2R,3S,4R,5S)-3-(3-chloro-2-fluoro-phenyl)-4-(4-chloro-2-fluoro-phenyl)-4-cyano-5-(2-methoxycarbonyl-2-methyl-propyl)-pyrrolidine-2-carboxylic acid tert-butyl ester prepared in Example 104b (0.7 g, 1.23 mmol) was reacted trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(2-methoxycarbonyl-2-methyl-propyl)-pyrrolidine-2-carboxylic acid trifluoroacetic acid as a white solid (0.75 g, 97%).

Example 104d

Preparation of rac-(2R,3S,4R,5S)-3-(3-chloro-2-fluoro-phenyl)-4-(4-chloro-2-fluoro-phenyl)-4-cyano-5-(2-methoxycarbonyl-2-methyl-propyl)-pyrrolidine-2-carboxylic acid ((S)-3,4-dihydroxy-butyl)-amide

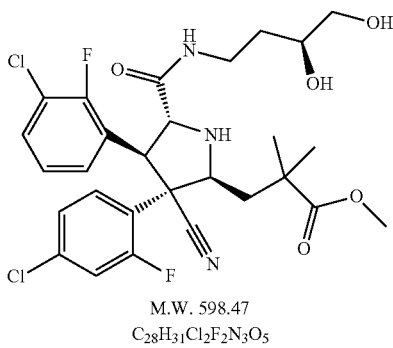 [SMILES: COC(=O)C(C)(C)C[C@@H]1N[C@@H](C(=O)NCC[C@H](O)CO)[C@H](c2cccc(Cl)c2F)[C@@]1(C#N)c1ccc(Cl)cc1F]

M.W. 598.47
$C_{28}H_{31}Cl_2F_2N_3O_5$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(2-methyl-2-phenoxycarbonyl-propyl)-pyrrolidine-2-carboxylic acid trifluoroacetic acid prepared in Example 104c (0.75 g, 1.26 mmol) was reacted with 2-((S)-2,2-dimethyl-[1,3]dioxolan-4-yl)-ethylamine (0.52 g, 3.6 mmol), HATU (0.82 g, 2.16 mmol) and iPr$_2$NEt (1.04 mL, 6 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2-methyl-2-phenoxycarbonyl-propyl)-pyrrolidine-2-carboxylic acid ((S)-3,4-dihydroxy-butyl)-amide as a white solid (0.45 g, 56%).

HRMS (ES$^+$) m/z Calcd for $C_{28}H_{31}Cl_2F_2N_3O_5$+H [(M+H)$^+$]: 598.1682. found: 598.1679.

Example 105a

Preparation of intermediate [4-(tert-butyl-dimethyl-silanyloxy)-3,3-dimethyl-but-(E)-ylideneamino]-acetic acid tert-butyl ester

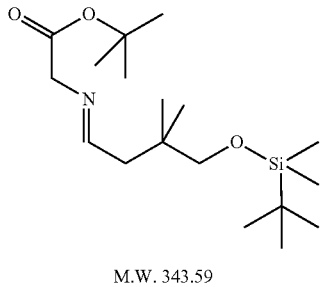

M.W. 343.59
$C_{18}H_{37}NO_3Si$

Step A A mixture of 2,2-dimethyl-propane-1,3-diol (Aldrich) (10 g, 96 mmol) and imidazole (9.8 g, 140 mmol) in dichloromethane (200 mL) was added tert-butyldimethylchlorosilane (15.9 g, 10.6 mmol). The reaction mixture was stirred at room temperature for 0.5 h. Water was added. The organic layer was separated, the aqueous layer was then extracted with dichloromethane. The combined organic layers were washed with brine, dried over MgSO$_4$, concentrated to give 3-(tert-butyl-dimethyl-silanyloxy)-2,2-dimethyl-propan-1-ol as a colorless oil (20.4 g, 97%).

Step B To the solution of 3-(tert-butyl-dimethyl-silanyloxy)-2,2-dimethyl-propan-1-ol (20.4 g, 93 mmol) and triethylamine (26 g, 186 mmol) in dichloromethane (200 mL) at 0° C. was added a dichlormethane solution (20 mL) of methanesulfonyl chloride (Aldrich) (8.69 mL, 112 mmol). The reaction mixture was stirred at 0° C. for 2 h. Water was added. Organic layer was separated, the aqueous layer was extracted with dichlormethane. The combined organic layers were washed with diluted aqueous HCl solution, saturated aqueous NaHCO$_3$ solution, brine, dried over MgSO$_4$, and concentrated to give methanesulfonic acid 3-(tert-butyl-dimethyl-silanyloxy)-2,2-dimethyl-propyl ester as a yellow oil (24 g, 87%).

Step C To the solution of methanesulfonic acid 3-(tert-butyl-dimethyl-silanyloxy)-2,2-dimethyl-propyl ester (5 g, 16.8 mmol) in anhydrous dimethyl sulfoxide (50 mL) was added KCN (2.85 g, 44 mmol). The reaction mixture was heated at 120° C. for 16 h. The mixture was cooled, and water was added. The mixture was extracted with ethyl acetate twice. The combined organic layers were washed with saturated aqueous NaHCO$_3$ solution, brine, dried over MgSO$_4$, and concentrated. The residue was purified by chromatography (EtOAc:hexanes=1:4) to give 4-(tert-butyl-dimethyl-silanyloxy)-3,3-dimethyl-butyronitrile as a yellow oil (2.2 g, 57%).

Step D To a solution of 4-(tert-butyl-dimethyl-silanyloxy)-3,3-dimethyl-butyronitrile (2.2 g, 9.67 mmol) (Aldrich) in dichloromethane (20 mL) at −78° C. was added a toluene solution (1 M) of DIBAL (10.6 mL, 10.6 mmol) dropwise. The reaction mixture was stirred at 0° C. for 3 h. The mixture was poured into aqueous saturated NH$_4$Cl solution. The organic layer was separated, and the aqueous layer was extracted with ethyl acetate. The organic layers were combined, washed with brine, dried over MgSO$_4$, and concentrated. The residue was purified by chromatography (EtOAc:hexanes=1:4) to give 4-(tert-butyl-dimethyl-silanyloxy)-3,3-dimethyl-butyraldehyde as a colorless oil (Yield: 0.84 g, 38%).

Step E In a manner similar to the method described in Example 1a, glycine tert-butyl ester (0.52 g, 3.64 mmol) was reacted with 4-(tert-butyl-dimethyl-silanyloxy)-3,3-dimethyl-butyraldehyde (0.84 g, 3.64 mmol) in CH$_2$Cl$_2$ at room temperature for 18 h to give [4-(tert-butyl-dimethyl-silanyloxy)-3,3-dimethyl-but-(E)-ylideneamino]-acetic acid tert-butyl ester as a colorless oil (1.25 g, 100%).

Example 105b

Preparation of intermediate rac-(2R,3S,4R,5S)-5-[3-(tert-butyl-dimethyl-silanyloxy)-2,2-dimethyl-propyl]-3-(3-chloro-2-fluoro-phenyl)-4-(4-chloro-2-fluoro-phenyl)-4-cyano-pyrrolidine-2-carboxylic acid tert-butyl ester

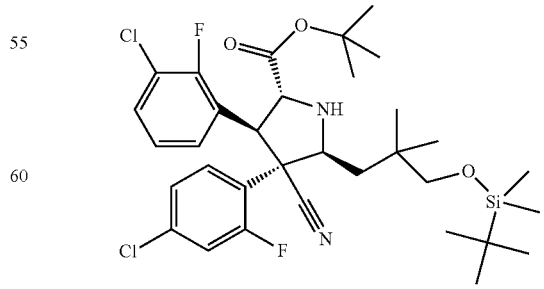

M.W. 653.72
$C_{33}H_{44}Cl_2F_2N_2O_3Si$

In a manner similar to the method described in Example 100b, [4-(tert-butyl-dimethyl-silanyloxy)-3,3-dimethyl-but-(E)-ylideneamino]-acetic acid tert-butyl ester prepared in Example 105a (1.25 g, 3.64 mmol) was reacted with (Z)-3-(3-chloro-2-fluoro-phenyl)-2-(4-chloro-2-fluoro-phenyl)-acrylonitrile (0.93 g, 3 mmol) prepared in Example 52a, AgF (0.57 g, 4.5 mmol), and triethylamine (1.05 mL, 7.5 mmol) in dichloromethane (100 mL) at room temperature for 18 h, followed by the reaction with DBU (3.6 ml) in tert-butanol (15 mL) at 100° C. for 2 h to give rac-(2R,3S,4R,5S)-5-[3-(tert-butyl-dimethyl-silanyloxy)-2,2-dimethyl-propyl]-3-(3-chloro-2-fluoro-phenyl)-4-(4-chloro-2-fluoro-phenyl)-4-cyano-pyrrolidine-2-carboxylic acid tert-butyl ester as a white solid (1.2 g, 61%).

Example 105c

Preparation of intermediate rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid trifluoroacetic acid

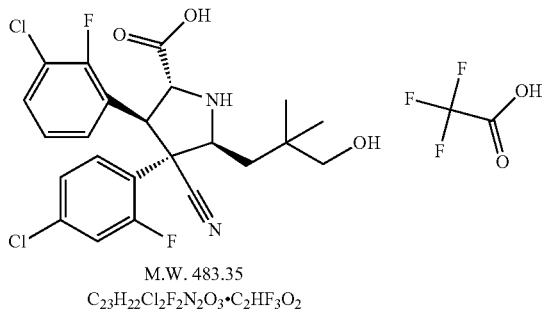 [SMILES: CC(C)(CO)C[C@@H]1N[C@@H](C(=O)O)[C@H](c2cccc(Cl)c2F)[C@@]1(C#N)c1ccc(Cl)cc1F ; O=C(O)C(F)(F)F]

M.W. 483.35
$C_{23}H_{22}Cl_2F_2N_2O_3 \cdot C_2HF_3O_2$

In a manner similar to the method described in Example 25a, rac-(2R,3S,4R,5S)-5-[3-(tert-butyl-dimethyl-silanyloxy)-2,2-dimethyl-propyl]-3-(3-chloro-2-fluoro-phenyl)-4-(4-chloro-2-fluoro-phenyl)-4-cyano-pyrrolidine-2-carboxylic acid tert-butyl ester prepared in Example 105b (1.1 g, 1.68 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid trifluoroacetic acid as a white solid (1 g, 100%).

Example 105d

Preparation of rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide

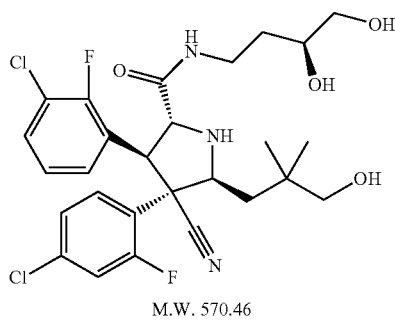

M.W. 570.46
$C_{27}H_{31}Cl_2F_2N_3O_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid trifluoroacetic acid prepared in Example 105c (1 g, 1.67 mmol) was reacted with 2-((S)-2,2-dimethyl-[1,3]dioxolan-4-yl)-ethylamine (0.73 g, 5 mmol), HATU (1.14 g, 3 mmol) and iPr₂NEt (1.46 mL, 8.4 mmol) in CH₂Cl₂ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide as a white solid (0.3 g, 64%).

HRMS (ES⁺) m/z Calcd for $C_{27}H_{31}Cl_2F_2N_3O$+H [(M+H)⁺]: 570.1733. found: 570.1731.

Example 105e

Preparation of (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide

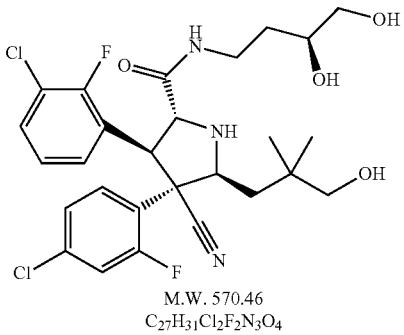

M.W. 570.46
$C_{27}H_{31}Cl_2F_2N_3O_4$

Rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide (0.24 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide as a white solid (102 mg, 43%) and chiral (2S,3R,4S,5R)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide as a white solid (93 mg, 39%).

HRMS (ES⁺) m/z Calcd for $C_{27}H_{31}Cl_2F_2N_3O_4$+H [(M+H)⁺]: 570.1733. found: 570.1730.

Example 106a

Preparation of intermediate [3,3-diethyl-pent-(E)-ylideneamino]-acetic acid tert-butyl ester

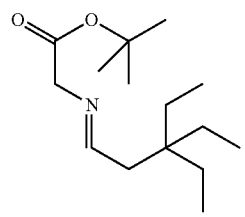

M.W. 255.40
$C_{15}H_{29}NO_2$

Step A To a solution of dimethyl malonate (10 g, 75 mmol), 3-pentanone (6.5 g, 75 mmol) and pyridine (7.9 g, 100 mmol) in anhydrous tetrahydrofuran (300 mL) at 0° C. was added a dichloromethane solution (1 M) of TiCl$_4$ (100 mL, 100 mmol) during a period of 1 h. After the addition was finished, the reaction mixture was gradually warmed room temperature and stirred for 18 h. Water was added to quench the reaction. The mixture was extracted with ethyl ether. The organic layer was separated, and the aqueous layer was extracted with ethyl acetate. The organic layers were combined, concentrated. The residue was purified by chromatography (EtOAc:hexanes=1:20) to give 2-(1-ethyl-propylidene)-malonic acid dimethyl ester as a light yellow oil (7 g, 46%).

Step B To a suspension of CuI (7.61 g, 40 mmol) in anhydrous tetrahydrofuran (100 mL) at −50° C. was added ethylmagnesium chloride (2 M, 40 mL, 80 mmol) during a period of 15 min. After the addition was finished, the reaction mixture was gradually warmed room temperature and stirred for 20 min. Then the temperature of the mixture was lowered to −50° C., a tetrahydrofuran solution (50 mL) of 2-(1-ethyl-propylidene)-malonic acid dimethyl ester (3.5 g, 17.5 mmol) was added. The reaction mixture was allowed to slowly warmed to room temperature and stirred for 3 h. Aqueous saturated NH$_4$Cl solution was added to quench the reaction. The mixture was filtered, and the filtrate was concentrated to remove most of tetrahydrofuran. The residue was extracted with ethyl acetate twice. The organic layers were combined, concentrated. The residue was purified by chromatography (EtOAc:hexanes=1:30) to give 2-(1,1-diethyl-propyl)-malonic acid dimethyl ester as a colorless oil (2.6 g, 57%).

Step C To a solution of 2-(1,1-diethyl-propyl)-malonic acid dimethyl ester (2.5 g, 11 mmol) in DMSO (30 mL) was added LiCl (0.91 g, 21.6 mmol) and H$_2$O (0.19 mL, 11 mmol). The reaction mixture was heated at 170° C. for 4 h, then poured into a ice-water, extracted with ethyl acetate. The organic layer were separated, washed with water, brine, dried over MgSO$_4$, and concentrated to give 3,3-diethyl-pentanoic acid methyl ester as a yellow oil (1.9 g, 100%).

Step D To a solution of 3,3-diethyl-pentanoic acid methyl ester (1.9 g, 11 mmol) in anhydrous tetrahydrofuran (50 mL) at 0° C. was added a tetrahydrofuran solution (2 M) of LiAlH$_4$ (9 mL, 18 mmol) under nitrogen. The reaction mixture was stirred at 0° C. for 1 h, then poured into a ice-water. The mixture was extracted with ethyl acetate. The organic layer were separated, washed with water, aqueous HCl solution, brine, dried over MgSO$_4$, and concentrated to give 3,3-diethyl-pentan-1-ol as a yellow oil (1.4 g, 90%).

Step E To a solution of oxalyl chloride (0.86 mL, 9.9 mmol) (Aldrich) in dichloromethane (20 mL) at −78° C. was added the solution of dimethyl sulfoxide (1.4 mL, 19.8 mmol) in dichloromethane (5 mL) dropwise. After 5 mins, the solution of 3,3-diethyl-pentan-1-ol (1.3 g, 9 mmol) in dichloromethane (5 mL) was added dropwise. The reaction mixture was stirred at −78° C. for 15 min. Triethylamine (4.5 mL, 32 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO$_3$, brine, dried over MgSO$_4$, and concentrated to give 3,3-diethyl-pentanal as a yellow oil (Yield: 1 g, 78%).

Step F In a manner similar to the method described in Example 1a, glycine tert-butyl ester (0.92 g, 7 mmol) was reacted with 3,3-diethyl-pentanal (1 g, 7 mmol) in CH$_2$Cl$_2$ at room temperature for 5 h to give [3,3-diethyl-pent-(E)-ylideneamino]-acetic acid tert-butyl ester as a colorless oil (1.8 g, 100%).

Example 106b

Preparation of intermediate rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid tert-butyl ester

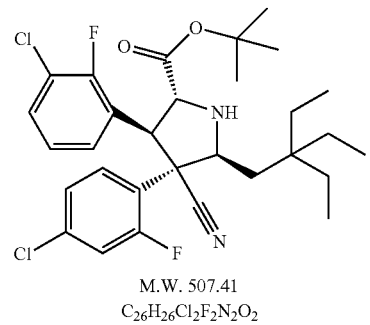 [SMILES: CCC(CC)(CC)C[C@@H]1N[C@@H](C(=O)OC(C)(C)C)[C@H](c2cccc(Cl)c2F)[C@@]1(C#N)c1ccc(Cl)cc1F]

M.W. 507.41
$C_{26}H_{26}Cl_2F_2N_2O_2$

In a manner similar to the method described in Example 100b, [3,3-diethyl-pent-(E)-ylideneamino]-acetic acid tert-butyl ester prepared in Example 106a (1.8 g, 7 mmol) was reacted with (Z)-3-(3-chloro-2-fluoro-phenyl)-2-(4-chloro-2-fluoro-phenyl)-acrylonitrile (1.74 g, 5.6 mmol) prepared in Example 52a, AgF (1.1 g, 8.6 mmol), and triethylamine (1.95 mL, 14 mmol) in dichloromethane (150 mL) at room temperature for 18 h, followed by the reaction with DBU (7 ml) in tert-butanol (30 mL) at 100° C. for 2 h to give rac-(2R,3S, 4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid tert-butyl ester as a white gum (1.8 g, 57%).

Example 106c

Preparation of intermediate rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid trifluoroacetic acid

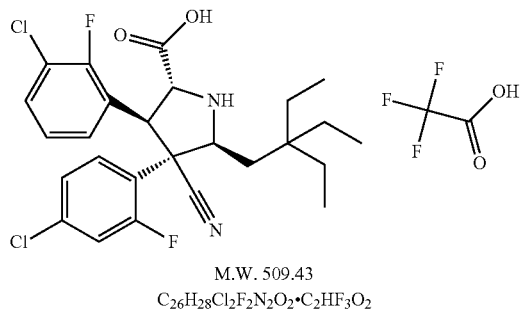

M.W. 509.43
$C_{26}H_{28}Cl_2F_2N_2O_2 \cdot C_2HF_3O_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid tert-butyl ester prepared in Example 106b (1.8 g, 3.2 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid trifluoroacetic acid as a light yellow solid (2 g, 100%).

Example 106d

Preparation of rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid ((S)-3,4-dihydroxy-butyl)-amide

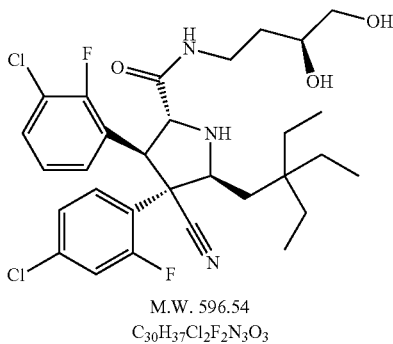 [SMILES: CCC(CC)(CC)C[C@@H]1N[C@@H](C(=O)NCC[C@H](O)CO)[C@H](c2cccc(Cl)c2F)[C@@]1(C#N)c1ccc(Cl)cc1F]

M.W. 596.54
$C_{30}H_{37}Cl_2F_2N_3O_3$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid trifluoroacetic acid prepared in Example 106c (0.5 g, 0.8 mmol) was reacted with 2-((S)-2,2-dimethyl-[1,3]dioxolan-4-yl)-ethylamine (0.35 g, 2.4 mmol), HATU (0.55 g, 1.4 mmol) and iPr$_2$NEt (0.7 mL, 4 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid ((S)-3,4-dihydroxy-butyl)-amide as a white solid (0.33 g, 70%).

HRMS (ES$^+$) m/z Calcd for $C_{30}H_{37}Cl_2F_2N_3O_3$+H [(M+H)$^+$]: 596.2253. found: 596.2254.

Example 107a

Preparation of intermediate [3-ethyl-3-methyl-pent-(E)-ylideneamino]-acetic acid tert-butyl ester

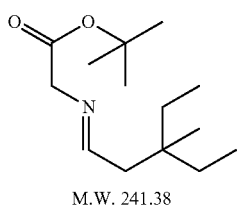

M.W. 241.38
$C_{14}H_{27}NO_2$

Step A To a suspension of CuI (5.7 g, 30 mmol) in anhydrous tetrahydrofuran (100 mL) at −50° C. was added methylmagnesium chloride (3 M, 20 mL, 60 mmol) during a period of 15 min. After the addition was finished, the reaction mixture was gradually warmed room temperature and stirred for 20 min. Then the temperature of the mixture was lowered to −50° C., a tetrahydrofuran solution (20 mL) of 2-(1-ethyl-propylidene)-malonic acid dimethyl ester (3 g, 15 mmol) prepared in Example 106a Step A was added. The reaction mixture was allowed to slowly warmed to room temperature and stirred for 1 h. Aqueous saturated NH$_4$Cl solution was added to quench the reaction. The mixture was filtered, and the filtrate was concentrated to remove most of tetrahydrofuran. The residue was extracted with ethyl acetate twice. The organic layers were combined, concentrated. The residue was purified by chromatography (EtOAc:hexanes=1:30) to give 2-(1-ethyl-1-methyl-propyl)-malonic acid dimethyl ester as a colorless oil (3 g, 93%).

Step B To a solution of 2-(1-ethyl-1-methyl-propyl)-malonic acid dimethyl ester (3 g, 14 mmol) in DMSO (30 mL) was added LiCl (1.2 g, 28 mmol) and H$_2$O (0.25 mL, 14 mmol). The reaction mixture was heated at 170° C. for 3 h, then poured into a ice-water, extracted with ethyl acetate. The organic layer were separated, washed with water, brine, dried over MgSO$_4$, and concentrated to give 3-ethyl-3-methyl-pentanoic acid methyl ester as a yellow oil (1.5 g, 68%).

Step C To a solution of 3-ethyl-3-methyl-pentanoic acid methyl ester (1.5 g, 9.4 mmol) in anhydrous tetrahydrofuran (30 mL) at 0° C. was added a tetrahydrofuran solution (2 M) of LiAlH$_4$ (5 mL, 10 mmol) under nitrogen. The reaction mixture was stirred at 0° C. for 1 h, then poured into a ice-water. The mixture was extracted with ethyl acetate. The organic layer were separated, washed with water, aqueous HCl solution, brine, dried over MgSO$_4$, and concentrated to give 3-ethyl-3-methyl-pentan-1-ol as a yellow oil (1.3 g, 100%).

Step D To a solution of oxalyl chloride (0.96 mL, 11 mmol) (Aldrich) in dichloromethane (20 mL) at −78° C. was added the solution of dimethyl sulfoxide (1.56 mL, 22 mmol) in dichloromethane (5 mL) dropwise. After 5 mins, the solution of 3-ethyl-3-methyl-pentan-1-ol (1.3 g, 10 mmol) in dichloromethane (5 mL) was added dropwise. The reaction mixture was stirred at −78° C. for 15 min. Triethylamine (5 mL, 36 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO$_3$, brine, dried over MgSO$_4$, and concentrated to give 3-ethyl-3-methyl-pentanal as a light yellow oil (Yield: 1 g, 78%).

Step E In a manner similar to the method described in Example 1a, glycine tert-butyl ester (1.0 g, 7.8 mmol) was reacted with 3-ethyl-3-methyl-pentanal (1 g, 7.8 mmol) in CH$_2$Cl$_2$ at room temperature for 5 h to give [3-ethyl-3-methyl-pent-(E)-ylideneamino]-acetic acid tert-butyl ester as a colorless oil (1.9 g, 100%).

Example 107b

Preparation of intermediate rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid tert-butyl ester

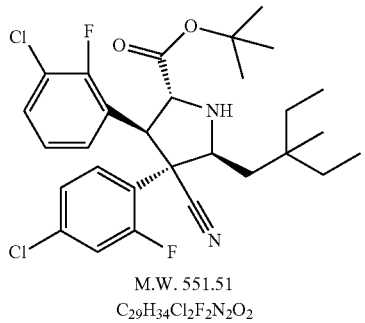 [SMILES: CCC(C)(CC)C[C@@H]1N[C@@H](C(=O)OC(C)(C)C)[C@H](c2cccc(Cl)c2F)[C@@]1(C#N)c1ccc(Cl)cc1F]

M.W. 551.51
$C_{29}H_{34}Cl_2F_2N_2O_2$

In a manner similar to the method described in Example 100b, [3-ethyl-3-methyl-pent-(E)-ylideneamino]-acetic acid tert-butyl ester prepared in Example 107a (1.9 g, 7.8 mmol) was reacted with (Z)-3-(3-chloro-2-fluoro-phenyl)-2-(4-chloro-2-fluoro-phenyl)-acrylonitrile (1.9 g, 6.2 mmol) prepared in Example 52a, AgF (1.2 g, 9.4 mmol), and triethylamine (2.1 mL, 15 mmol) in dichloromethane (150 mL) at room temperature for 18 h, followed by the reaction with DBU (7 ml) in tert-butanol (30 mL) at 100° C. for 2 h to give rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid tert-butyl ester as a light yellow gum (2.5 g, 74%).

Example 107c

Preparation of intermediate rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid trifluoroacetic acid

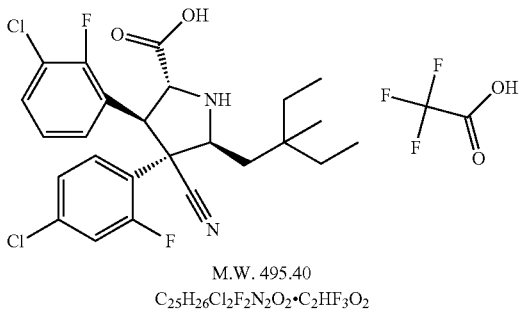

M.W. 495.40
$C_{25}H_{26}Cl_2F_2N_2O_2 \cdot C_2HF_3O_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid tert-butyl ester prepared in Example 107b (1.8 g, 3.2 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid trifluoroacetic acid as a light yellow solid (2.5 g, 91%).

Example 107d

Preparation of rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid ((S)-3,4-dihydroxy-butyl)-amide

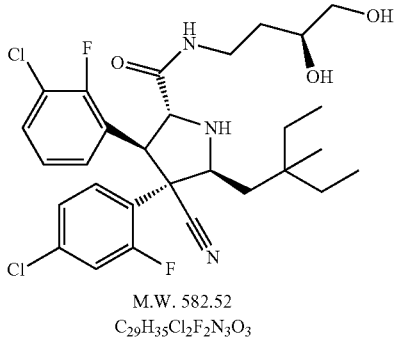 [SMILES: CCC(C)(CC)C[C@@H]1N[C@@H](C(=O)NCC[C@H](O)CO)[C@H](c2cccc(Cl)c2F)[C@@]1(C#N)c1ccc(Cl)cc1F]

M.W. 582.52
$C_{29}H_{35}Cl_2F_2N_3O_3$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid trifluoroacetic acid prepared in Example 106c (0.6 g, 1 mmol) was reacted with 2-((S)-2,2-dimethyl-[1,3]dioxolan-4-yl)-ethylamine (0.43 g, 3 mmol), HATU (0.67 g, 1.8 mmol) and iPr$_2$NEt (0.86 mL, 4.9 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid ((S)-3,4-dihydroxy-butyl)-amide as a white solid (0.3 g, 53%).

HRMS (ES$^+$) m/z Calcd for $C_{29}H_{35}Cl_2F_2N_3O_3$+H [(M+H)$^+$]: 582.2097 found: 582.2096.

Example 108a

Preparation of intermediate (Z)-2-(4-chloro-2,6-difluoro-phenyl)-3-(3-chloro-2-fluoro-phenyl)-acrylonitrile

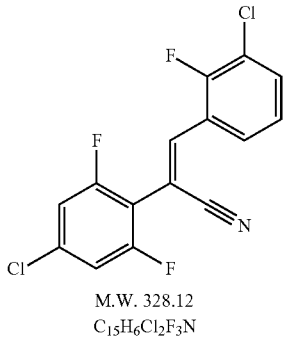 [SMILES: N#C/C(=C\c1cccc(Cl)c1F)c1c(F)cc(Cl)cc1F]

M.W. 328.12
$C_{15}H_6Cl_2F_3N$

Step A To the solution of 4-chloro-2,6-difluorobenzyl bromide (Alfa) (2.5 g, 10 mmol) in ethanol (13 mL) and H$_2$O (10 mL) was added KCN (1.75 g, 27 mmol). The reaction mixture was heated at 100° C. for 1 h. The mixture was cooled, and extracted with ethyl acetate. The organic layer was separated, washed with saturated aqueous NaHCO$_3$ solution, brine, dried over MgSO$_4$, and concentrated. The residue was purified by chromatography (EtOAc:hexanes=1:4) to give (4-chloro-2,6-difluoro-phenyl)-acetonitrile as a yellow oil (1.1 g, 57%).

Step B In a manner similar to the method described in Example 1b, (4-chloro-2,6-difluoro-phenyl)-acetonitrile (1.1 g, 6 mmol) was reacted with 2-fluoro-3-chlorobenzaldehyde (1.2 g, 7 mmol), methanolic solution (25 wt %) of sodium methoxide (1.5 mL, 7 mmol) in methanol (40 mL) at 50° C. for 3 h to give (Z)-2-(4-chloro-2,6-difluoro-phenyl)-3-(3-chloro-2-fluoro-phenyl)-acrylonitrile as a white solid (1.5 g, 75%).

Example 108b

Preparation of intermediate rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid tert-butyl ester

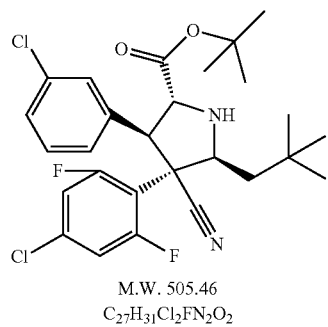 [SMILES: CC(C)(C)C[C@@H]1N[C@@H](C(=O)OC(C)(C)C)[C@H](c2cccc(Cl)c2)[C@@]1(C#N)c1c(F)cc(Cl)cc1F]

M.W. 505.46
C$_{27}$H$_{31}$Cl$_2$FN$_2$O$_2$

In a manner similar to the method described in Example 1c, [3-methyl-but-(E)-ylideneamino]-acetic acid tert-butyl ester prepared in Example 1a (1 g, 5 mmol) was reacted with (Z)-2-(4-chloro-2,6-difluoro-phenyl)-3-(3-chloro-2-fluoro-phenyl)-acrylonitrile (1.3 g, 4 mmol) prepared in Example 109a, AgF (0.77 g, 6 mmol), and triethylamine (1.4 mL, 10 mmol) in dichloromethane (120 mL) at room temperature for 18 h, followed by the reaction with DBU (4.8 ml) in tert-butanol (20 mL) at 100° C. for 2 h to give rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid tert-butyl ester as a white gum (0.9 g, 41%).

Example 108c

Preparation of intermediate rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid trifluoroacetic acid

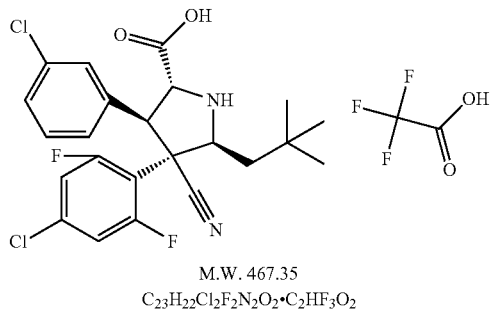

M.W. 467.35
C$_{23}$H$_{22}$Cl$_2$F$_2$N$_2$O$_2$·C$_2$HF$_3$O$_2$

In a manner similar to the method described in Example 25a, rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid tert-butyl ester prepared in Example 108b (0.9 g, 1.7 mmol) was reacted with trifluoroacetic acid in dichloromethane at room temperature to give rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid trifluoroacetic acid as a white solid (0.9 g, 91%).

Example 108d

Preparation of rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid ((S)-3,4-dihydroxy-butyl)-amide

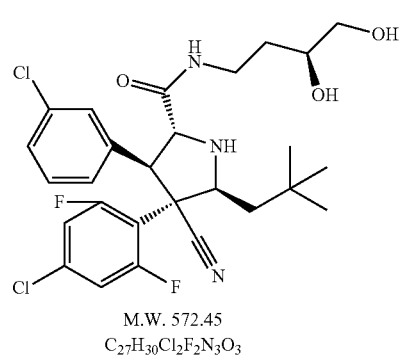 [SMILES: CC(C)(C)C[C@@H]1N[C@@H](C(=O)NCC[C@H](O)CO)[C@H](c2cccc(Cl)c2)[C@@]1(C#N)c1c(F)cc(Cl)cc1F]

M.W. 572.45
C$_{27}$H$_{30}$Cl$_2$F$_2$N$_3$O$_3$

In a manner similar to the method described in Examples 42c, 42d, rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid trifluoroacetic acid prepared in Example 108c (0.4 g, 0.67 mmol) was reacted with 2-((S)-2,2-dimethyl-[1,3]dioxolan-4-yl)-ethylamine (0.29 g, 2 mmol), HATU (0.46 g, 1.2 mmol) and iPr$_2$NEt (0.58 mL, 3.3 mmol) in CH$_2$Cl$_2$ at room temperature for 20 h, then reacted with aqueous HCl solution in tetrahydrofuran at room temperature for 2 h to give rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid ((S)-3,4-dihydroxy-butyl)-amide as a white solid (0.3 g, 77%).

HRMS (ES$^+$) m/z Calcd for C$_{27}$H$_{30}$Cl$_2$F$_2$N$_3$O$_3$+H [(M+H)$^+$]: 572.1689. found: 572.1691.

Example 109a

Preparation of intermediate (Z)-2-(4-chloro-2,5-difluoro-phenyl)-3-(3-chloro-2-fluoro-phenyl)-acrylonitrile

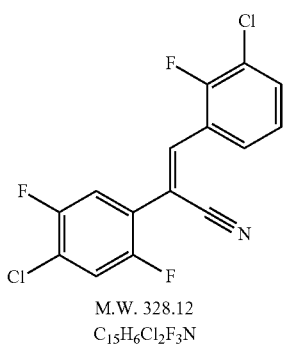 [SMILES: N#C/C(=C\c1cccc(Cl)c1F)c1cc(F)c(Cl)cc1F]

M.W. 328.12
C$_{15}$H$_6$Cl$_2$F$_3$N

Step A To the solution of 4-chloro-2,5-difluorobenzoic acid (Oakwood) (6.08 g, 31 mmol) in anhydrous tetrahydrofuran (75 mL) at 0° C. was added a solution of BH₃.THF (1 M, 62 mL, 62 mmol). The reaction mixture was stirred at room temperature for 18 h. Aqueous HCl solution was added, and the mixture was extracted with ethyl acetate. The organic layer was separated, washed with saturated aqueous NaHCO₃ solution, brine, dried over MgSO₄, and concentrated to give (4-chloro-2,5-difluoro-phenyl)-methanol as a colorless oil (5.5 g, 98%).

Step B A mixture of (4-chloro-2,5-difluoro-phenyl)-methanol (5.5 g, 32 mmol) in thionyl chloride (25 mL) was heated at refluxing (100° C.) for 30 min. The mixture was cooled to room temperature and concentrated. The residue was diluted with ethyl acetate, washed with saturated aqueous NaHCO₃ solution, water, brine, dried over MgSO₄, and concentrated to give 1-chloro-4-chloromethyl-2,5-difluoro-benzene as a yellow oil (2.1 g, 34%).

Step C To the solution of 1-chloro-4-chloromethyl-2,5-difluoro-benzene (2.1 g, 11 mmol) in ethanol (13 mL) and H₂O (10 mL) was added KCN (1.8 g, 28 mmol). The reaction mixture was heated at 100° C. for 1 h. The mixture was cooled, and extracted with ethyl acetate. The organic layer was separated, washed with saturated aqueous NaHCO₃ solution, brine, dried over MgSO₄, and concentrated. The residue was purified by chromatography (EtOAc:hexanes=1:4) to give 4-chloro-2,5-difluoro-phenyl)-acetonitrile as a light yellow oil (1.0 g, 50%).

Step D In a manner similar to the method described in Example 1b, 4-chloro-2,5-difluoro-phenyl)-acetonitrile (1.0 g, 5 mmol) was reacted with 2-fluoro-3-chlorobenzaldehyde (1.0 g, 6 mmol), methanolic solution (25 wt %) of sodium methoxide (1.3 mL, 5.9 mmol) in methanol (40 mL) at 50° C. for 3 h to give (Z)-2-(4-chloro-2,5-difluoro-phenyl)-3-(3-chloro-2-fluoro-phenyl)-acrylonitrile as a white solid (1.3 g, 75%).

Example 109b

Preparation of intermediate rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid tert-butyl ester

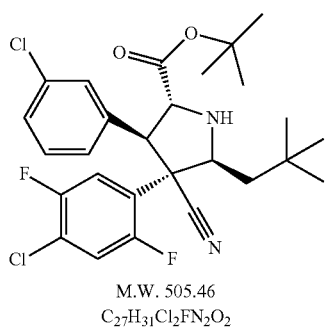 [SMILES: CC(C)(C)C[C@@H]1N[C@@H](C(=O)OC(C)(C)C)[C@H](c2cccc(Cl)c2)[C@@]1(C#N)c1cc(F)c(Cl)cc1F]

M.W. 505.46
C₂₇H₃₁Cl₂FN₂O₂

In a manner similar to the method described in Example 1c, [3-methyl-but-(E)-ylideneamino]-acetic acid tert-butyl ester prepared in Example 1a (5 mmol) was reacted with give (Z)-2-(4-chloro-2,5-difluoro-phenyl)-3-(3-chloro-2-fluoro-phenyl)-acrylonitrile (1.3 g, 3 mmol) prepared in Example 109a, AgF (0.77 g, 6 mmol), and triethylamine (1.4 mL, 10 mmol) in dichloromethane (120 mL) at room temperature for 18 h, followed by the reaction with DBU (4.8 ml) in tert-butanol (20 mL) at 100° C. for 2 h to give rac-(2R,3R,4R,5S)- 4-(4-chloro-2,5-difluoro-phenyl)-3-(3-chloro-phenyl)-4-cyano-5-(2,2-dimethyl-propyl)-pyrrolidine-2-carboxylic acid tert-butyl ester as a light yellow gum (1.5 g, 69%).

Example 109c

Preparation of intermediate rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid trifluoroacetic acid

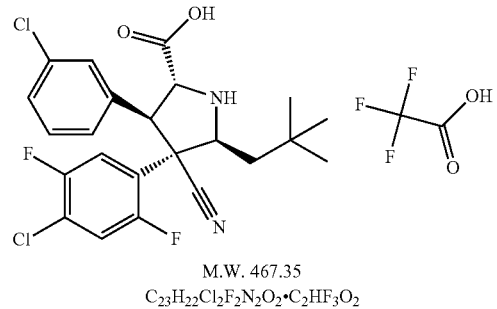

M.W. 467.35
C₂₃H₂₂Cl₂F₂N₂O₂·C₂HF₃O₂

In a manner similar to the method described in Example 25a, rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid tert-butyl ester prepared in Example 109b (1.5 g, 2.8 mmol) was reacted with trifluoroacetic acid in dichloromethane at room temperature to give rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid trifluoroacetic acid as a off white solid (1.5 g, 91%).

Example 109d

Preparation of rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid ((S)-3,4-dihydroxy-butyl)-amide

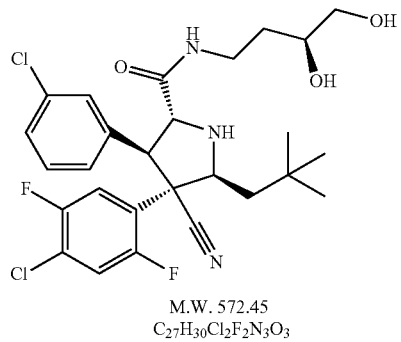 [SMILES: CC(C)(C)C[C@@H]1N[C@@H](C(=O)NCC[C@H](O)CO)[C@H](c2cccc(Cl)c2)[C@@]1(C#N)c1cc(F)c(Cl)cc1F]

M.W. 572.45
C₂₇H₃₀Cl₂F₂N₃O₃

In a manner similar to the method described in Examples 42c, 42d, rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid trifluoroacetic acid prepared in Example 108c (0.5 g, 0.84 mmol) was reacted with 2-((S)-2,2-dimethyl-[1,3]dioxolan-4-yl)-ethylamine (0.36 g, 2.5 mmol), HATU (0.57 g, 1.5 mmol) and iPr₂NEt (0.73 mL, 4.2 mmol) in CH$_2$Cl$_2$ at room temperature for 20 h, then reacted with aqueous HCl solution in tetrahydrofuran at room temperature for 2 h to give rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid ((S)-3,4-dihydroxy-butyl)-amide as a white solid (0.3 g, 50%).

HRMS (ES$^+$) m/z Calcd for C$_{27}$H$_{30}$Cl$_2$F$_2$N$_3$O$_3$+H [(M+H)$^+$]: 572.1689. found: 572.1680.

Example 110a

Preparation of intermediate [4-methoxy-3,3-dimethyl-but-(E)-ylideneamino]-acetic acid tert-butyl ester

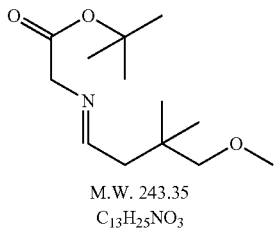 [SMILES: COCC(C)(C)C/C=N/CC(=O)OC(C)(C)C]

M.W. 243.35
C$_{13}$H$_{25}$NO$_3$

Step A A mixture of 2,2-dimethyl-propane-1,3-diol (Aldrich) (5 g, 48 mmol) in anhydrous ethyl ether (100 mL) at 0° C. was added thionyl chloride (8.7 mL, 120 mmol). The reaction mixture was stirred at 0° C. for 2 h. Water was added. The organic layer was separated, the aqueous layer was then extracted with ethyl ether. The combined organic layers were washed with saturated aqueous NaHCO$_3$ solution, brine, dried over MgSO$_4$, concentrated to give 5,5-dimethyl-[1,3,2]dioxathiane 2-oxide as a light pink oil (4.8 g, 82%).

Step B To the solution of 5,5-dimethyl-[1,3,2]dioxathiane 2-oxide (4.8 g, 39 mmol) in anhydrous dimethyl sulfoxide (50 mL) was added NaCN (5.8 g, 118 mmol). The reaction mixture was heated at 120° C. for 5 h. The mixture was cooled, and water was added. The mixture was extracted with ethyl acetate twice. The combined organic layers were washed with saturated aqueous NaHCO$_3$ solution, brine, dried over MgSO$_4$, and concentrated. The residue was purified by chromatography (EtOAc:hexanes=1:4) to give 4-hydroxy-3,3-dimethyl-butyronitrile as a yellow oil (1.6 g, 38%).

Step C To the solution of 4-hydroxy-3,3-dimethyl-butyronitrile (0.8 g, 7 mmol) in anhydrous dimethylformamide (5 mL) was added NaH (60%, 0.42 g, 11 mmol). The mixture was stirred at room temperature for 15 min, then iodomethane (0.88 mL, 14 mmol) was added. The mixture was stirred at room temperature for 1 h. Water was added. The mixture was extracted with ethyl acetate twice. The combined organic layers were washed with brine, dried over MgSO$_4$, and concentrated to give 4-methoxy-3,3-dimethyl-butyronitrile as a yellow oil (0.85 g, 94%).

Step D To a solution of 4-methoxy-3,3-dimethyl-butyronitrile (0.85 g, 6.7 mmol) in dichloromethane (20 mL) at –78° C. was added a toluene solution (1 M) of DIBAL (7.4 mL, 7.4 mmol) dropwise. The reaction mixture was stirred at 0° C. for 1 h. The mixture was poured into aqueous saturated NH$_4$Cl solution. The organic layer was separated, and the aqueous layer was extracted with ethyl acetate. The organic layers were combined, washed with brine, dried over MgSO$_4$, and concentrated to give 4-methoxy-3,3-dimethyl-butyraldehyde as a colorless oil (Yield: 0.3 g, 34%).

Step E In a manner similar to the method described in Example 1a, glycine tert-butyl ester (0.3 g, 2.3 mmol) was reacted with 4-methoxy-3,3-dimethyl-butyraldehyde (0.3 g, 2.3 mmol) in CH$_2$Cl$_2$ at room temperature for 18 h to give [4-methoxy-3,3-dimethyl-but-(E)-ylideneamino]-acetic acid tert-butyl ester as a colorless oil (0.56 g, 100%).

Example 110b

Preparation of intermediate rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid tert-butyl ester

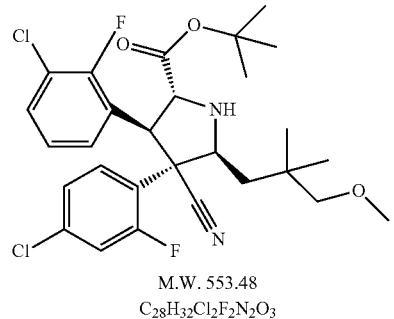 [SMILES: COCC(C)(C)C[C@@H]1N[C@@H](C(=O)OC(C)(C)C)[C@H](c2cccc(Cl)c2F)[C@@]1(C#N)c1ccc(Cl)cc1F]

M.W. 553.48
C$_{28}$H$_{32}$Cl$_2$F$_2$N$_2$O$_3$

In a manner similar to the method described in Example 100b, [4-methoxy-3,3-dimethyl-but-(E)-ylideneamino]-acetic acid tert-butyl ester prepared in Example 110a (3.8 mmol) was reacted with (Z)-3-(3-chloro-2-fluoro-phenyl)-2-(4-chloro-2-fluoro-phenyl)-acrylonitrile (0.94 g, 3 mmol) prepared in Example 52a, AgF (0.58 g, 4.6 mmol), and triethylamine (1.06 mL, 7.6 mmol) in dichloromethane (100 mL) at room temperature for 18 h, followed by the reaction with DBU (3.6 ml) in tert-butanol (20 mL) at 100° C. for 2 h to give rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid tert-butyl ester as a light yellow solid (1 g, 59%).

Example 110c

Preparation of intermediate rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid trifluoroacetic acid

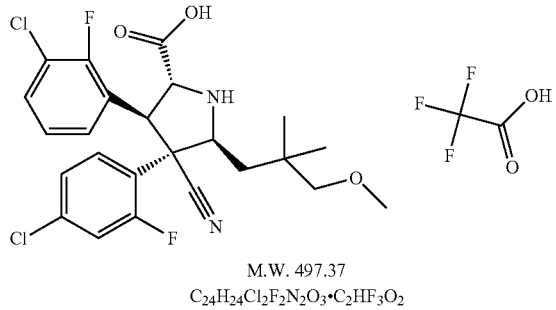 [SMILES: COCC(C)(C)C[C@@H]1N[C@@H](C(=O)O)[C@H](c2cccc(Cl)c2F)[C@@]1(C#N)c1ccc(Cl)cc1F ; O=C(O)C(F)(F)F]

M.W. 497.37
C$_{24}$H$_{24}$Cl$_2$F$_2$N$_2$O$_3$·C$_2$HF$_3$O$_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid tert-butyl ester prepared in Example 105b (1.0 g, 1.8 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid trifluoroacetic acid as a yellow solid (0.9 g, 82%).

Example 110d

Preparation of rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide

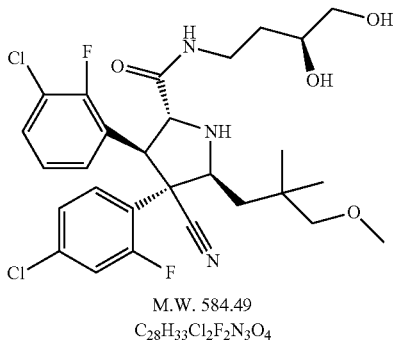 [SMILES: COCC(C)(C)C[C@@H]1N[C@@H](C(=O)NCC[C@H](O)CO)[C@H](c2cccc(Cl)c2F)[C@@]1(C#N)c1ccc(Cl)cc1F]

M.W. 584.49
$C_{28}H_{33}Cl_2F_2N_3O_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid trifluoroacetic acid prepared in Example 110c (0.45 g, 0.74 mmol) was reacted with 2-((S)-2,2-dimethyl-[1,3]dioxolan-4-yl)-ethylamine (0.32 g, 2.2 mmol), HATU (0.5 g, 1.3 mmol) and iPr$_2$NEt (0.64 mL, 3.7 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide as a white solid (0.28 g, 65%).

HRMS (ES$^+$) m/z Calcd for $C_{28}H_{33}Cl_2F_2N_3O_4$+H [(M+H)$^+$]: 584.1889. found: 584.1890.

Example 110e

Preparation of (2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide

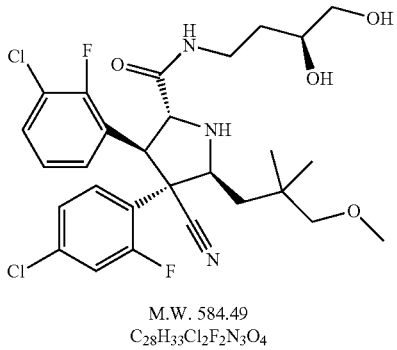 [SMILES: COCC(C)(C)C[C@@H]1N[C@@H](C(=O)NCC[C@H](O)CO)[C@H](c2cccc(Cl)c2F)[C@@]1(C#N)c1ccc(Cl)cc1F]

M.W. 584.49
$C_{28}H_{33}Cl_2F_2N_3O_4$

Rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide (0.24 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide as a white solid (114 mg, 48%) and chiral (2S,3R,4S,5R)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide as a white solid (114 mg, 48%).

HRMS (ES$^+$) m/z Calcd for $C_{28}H_{33}Cl_2F_2N_3O_4$+H [(M+H)$^+$]: 584.1889. found: 584.1892.

Example 111a

Preparation of intermediate 3-(tert-butyl-dimethyl-silanyloxymethyl)-3-ethyl-pent-(E)-ylideneamino]-acetic acid tert-butyl ester

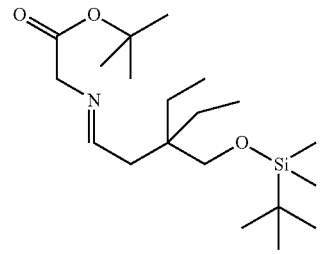

M.W. 371.64
$C_{20}H_{41}NO_3Si$

Step A A mixture of 2,2-diethyl-propane-1,3-diol (Aldrich) (5.5 g, 40 mmol) in anhydrous ethyl ether (100 mL) at 0° C. was added thionyl chloride (10.6 g, 90 mmol). The reaction mixture was stirred at 0° C. for 2 h. Water was added. The organic layer was separated, the aqueous layer was then extracted with ethyl ether. The combined organic layers were washed with saturated aqueous NaHCO$_3$ solution, brine, dried over MgSO$_4$, concentrated to give 5,5-diethyl-[1,3,2]dioxathiane 2-oxide as a colorless oil (7 g, 98%).

Step B To the solution of 5,5-diethyl-[1,3,2]dioxathiane 2-oxide (7 g, 39 mmol) in anhydrous dimethyl sulfoxide (40 mL) was added NaCN (3.9 g, 80 mmol). The reaction mixture was heated at 120° C. for 20 h. The mixture was cooled, and water was added. The mixture was extracted with ethyl acetate twice. The combined organic layers were washed with saturated aqueous NaHCO$_3$ solution, brine, dried over MgSO$_4$, and concentrated. The residue was purified by chromatography (EtOAc:hexanes=1:2) to give 3-ethyl-3-hydroxymethyl-pentanenitrile as a yellow oil (1.7 g, 31%).

Step C To the solution of 3-ethyl-3-hydroxymethyl-pentanenitrile (1.7 g, 12 mmol) and imidazole (1.2 g, 18 mmol) in dichloromethane (80 mL) was added tert-butyldimethylchlorosilane (2 g, 13 mmol). The reaction mixture was stirred at room temperature for 2 h. Water was added. The organic layer was separated, the aqueous layer was then extracted with dichloromethane. The combined organic layers were washed with brine, dried over MgSO$_4$, concentrated to give 3-(tert-butyl-dimethyl-silanyloxymethyl)-3-ethyl-pentanenitrile as a colorless oil (2.28 g, 74%).

Step D To a solution of 3-(tert-butyl-dimethyl-silanyloxymethyl)-3-ethyl-pentanenitrile (2.28 g, 8.9 mmol) in dichloromethane (20 mL) at −78° C. was added a toluene solution (1 M) of DIBAL (9.8 mL, 9.8 mmol) dropwise. The reaction mixture was stirred at 0° C. for 1 h. The mixture was poured into aqueous saturated NH$_4$Cl solution. The organic layer was separated, and the aqueous layer was extracted with ethyl acetate. The organic layers were combined, washed with brine, dried over MgSO$_4$, and concentrated to give 3-(tert-butyl-dimethyl-silanyloxymethyl)-3-ethyl-pentanal as a colorless oil (Yield: 1.5 g, 65%).

Step E In a manner similar to the method described in Example 1a, glycine tert-butyl ester (0.78 g, 5.8 mmol) was reacted with 3-(tert-butyl-dimethyl-silanyloxymethyl)-3-ethyl-pentanal (1.5 g, 5.8 mmol) in CH$_2$Cl$_2$ at room temperature for 18 h to give [4-methoxy-3,3-dimethyl-but-(E)-ylideneamino]-acetic acid tert-butyl ester as a colorless oil (2.2 g, 100%).

Example 111b

Preparation of intermediate rac-(2R,3S,4R,5S)-5-[2-(tert-butyl-dimethyl-silanyloxymethyl)-2-ethyl-butyl]-3-(3-chloro-2-fluoro-phenyl)-4-(4-chloro-2-fluoro-phenyl)-4-cyano-pyrrolidine-2-carboxylic acid tert-butyl ester

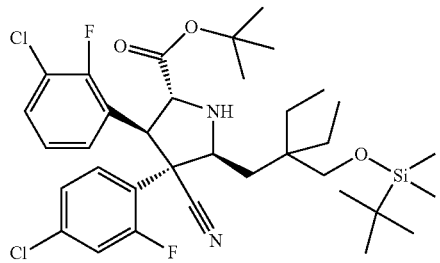

M.W. 681.77
C$_{35}$H$_{48}$Cl$_2$F$_2$N$_2$O$_3$Si

In a manner similar to the method described in Example 100b, give [4-(tert-butyl-dimethyl-silanyloxy)-3,3-dimethyl-but-(E)-ylideneamino]-acetic acid tert-butyl ester prepared in Example 111a (2.2 g, 5.8 mmol) was reacted with (Z)-3-(3-chloro-2-fluoro-phenyl)-2-(4-chloro-2-fluoro-phenyl)-acrylonitrile (1.43 g, 4.6 mmol) prepared in Example 52a, AgF (0.89 g, 7 mmol), and triethylamine (1.6 mL, 12 mmol) in dichloromethane (100 mL) at room temperature for 18 h, followed by the reaction with DBU (7 ml) in tert-butanol (20 mL) at 100° C. for 2 h to give rac-(2R,3S,4R,5S)-5-[2-(tert-butyl-dimethyl-silanyloxymethyl)-2-ethyl-butyl]-3-(3-chloro-2-fluoro-phenyl)-4-(4-chloro-2-fluoro-phenyl)-4-cyano-pyrrolidine-2-carboxylic acid tert-butyl ester as a light yellow solid (1.8 g, 58%).

Example 111c

Preparation of intermediate rac-(2R,3S,4R,5S)-3-(3-chloro-2-fluoro-phenyl)-4-(4-chloro-2-fluoro-phenyl)-4-cyano-5-(2-ethyl-2-hydroxymethyl-butyl)-pyrrolidine-2-carboxylic acid trifluoroacetic acid

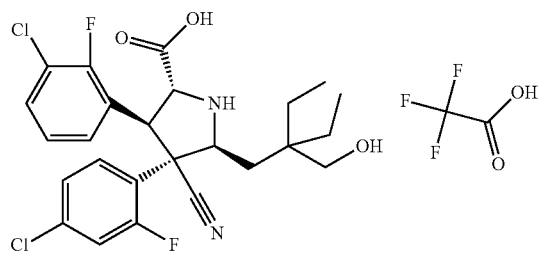

M.W. 511.40
C$_{25}$H$_{26}$Cl$_2$F$_2$N$_2$O$_3$·C$_2$HF$_3$O$_2$

In a manner similar to the method described in Example 25a, rac-(2R,3S,4R,5S)-5-[2-(tert-butyl-dimethyl-silanyloxymethyl)-2-ethyl-butyl]-3-(3-chloro-2-fluoro-phenyl)-4-(4-chloro-2-fluoro-phenyl)-4-cyano-pyrrolidine-2-carboxylic acid tert-butyl ester prepared in Example 111b (1.8 g, 2.6 mmol) was reacted trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(2-ethyl-2-hydroxymethyl-butyl)-pyrrolidine-2-carboxylic acid trifluoroacetic acid as a light yellow solid (1.5 g, 94%).

Example 111d

Preparation of rac-(2R,3S,4R,5S)-3-(3-chloro-2-fluoro-phenyl)-4-(4-chloro-2-fluoro-phenyl)-4-cyano-5-(2-ethyl-2-hydroxymethyl-butyl)-pyrrolidine-2-carboxylic acid ((S)-3,4-dihydroxy-butyl)-amide

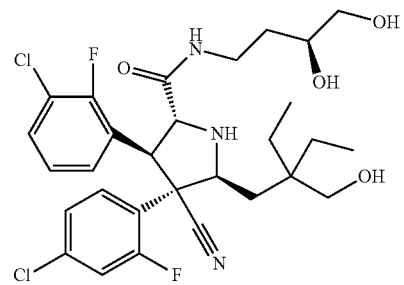

M.W. 598.51
C$_{29}$H$_{35}$Cl$_2$F$_2$N$_3$O$_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(2-ethyl-2-hydroxymethyl-butyl)-pyrrolidine-2-carboxylic acid trifluoroacetic acid prepared in Example 111c (1.1 g, 1.8 mmol) was reacted with 2-((S)-2,2-dimethyl-[1,3]dioxolan-4-yl)-ethylamine (0.78 g, 5 mmol), HATU (1.2 g, 3 mmol) and iPr$_2$NEt (1.6 mL, 9 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(2-ethyl-2-hydroxymethyl-butyl)-pyrrolidine-2-carboxylic acid ((S)-3,4-dihydroxy-butyl)-amide as a white solid (0.11 g, 10%).

HRMS (ES$^+$) m/z Calcd for C$_{29}$H$_{35}$Cl$_2$F$_2$N$_3$O$_4$+H [(M+H)$^+$]: 598.2046. found: 598.2045.

Example 112a

Preparation of intermediate [2-(3-methyl-oxetan-3-yl)-eth-(E)-ylideneamino]-acetic acid tert-butyl ester

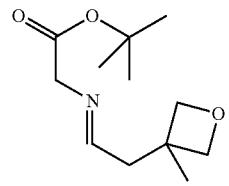

M.W. 227.31
C$_{12}$H$_{21}$NO$_3$

Step A To a solution of 3-methyl-3-oxetanemethanol (Aldrich) (3.5 g, 34 mmol) and triethylamine (10 g, 103 mmol) in dichloromethane (100 mL) at 0° C. was added a dichlormethane solution (20 mL) of methanesulfonyl chloride (Aldrich) (5.08 g, 45 mmol). The reaction mixture was stirred at 0° C. for 2 h. Water was added. Organic layer was separated, the aqueous layer was extracted with dichlormethane. The combined organic layers were washed with diluted aqueous HCl solution, saturated aqueous NaHCO$_3$ solution, brine, dried over MgSO$_4$, and concentrated to give methanesulfonic acid 3-methyl-oxetan-3-ylmethyl ester as a yellow oil (6 g, 97%).

Step B To the solution of methanesulfonic acid 3-methyl-oxetan-3-ylmethyl ester (6 g, 33 mmol) in anhydrous dimethyl sulfoxide (30 mL) was added NaCN (3.2 g, 67 mmol). The reaction mixture was heated at 130° C. for 3 h. The mixture was cooled, and water was added. The mixture was extracted with ethyl acetate twice. The combined organic layers were washed with saturated aqueous NaHCO$_3$ solution, brine, dried over MgSO$_4$, and concentrated to give (3-methyl-oxetan-3-yl)-acetonitrile as a yellow oil (2.5 g, 68%).

Step C To a solution of (3-methyl-oxetan-3-yl)-acetonitrile (2.5 g, 22.5 mmol) in dichloromethane (30 mL) at −78° C. was added a toluene solution (1 M) of DIBAL (24.7 mL, 24.7 mmol) dropwise. The reaction mixture was stirred at 0° C. for 3 h. The mixture was poured into aqueous saturated NH$_4$Cl solution. The organic layer was separated, and the aqueous layer was extracted with ethyl acetate. The organic layers were combined, washed with brine, dried over MgSO$_4$, and concentrated to give (3-methyl-oxetan-3-yl)-acetaldehyde as a colorless oil (Yield: 0.8 g, 31%).

Step D In a manner similar to the method described in Example 1a, glycine tert-butyl ester (0.92 g, 7 mmol) was reacted with (3-methyl-oxetan-3-yl)-acetaldehyde (0.8 g, 7 mmol) in CH$_2$Cl$_2$ at room temperature for 18 h to give [2-(3-methyl-oxetan-3-yl)-eth-(E)-ylideneamino]-acetic acid tert-butyl ester as a colorless oil (1.6 g, 100%).

Example 112b

Preparation of intermediate rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid tert-butyl ester

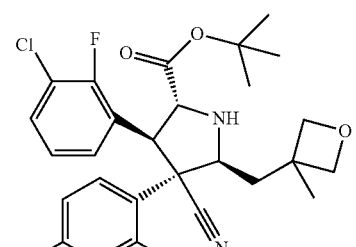

M.W. 537.44
C$_{27}$H$_{28}$Cl$_2$F$_2$N$_2$O$_3$

In a manner similar to the method described in Example 100b [2-(3-methyl-oxetan-3-yl)-eth-(E)-ylideneamino]-acetic acid tert-butyl ester prepared in Example 112a (1.6 g, 7 mmol) was reacted with (Z)-3-(3-chloro-2-fluoro-phenyl)-2-(4-chloro-2-fluoro-phenyl)-acrylonitrile (1.7 g, 5.6 mmol) prepared in Example 52a, AgF (1.1 g, 8.5 mmol), and triethylamine (1.9 mL, 14 mmol) in dichloromethane (100 mL) at room temperature for 18 h, followed by the reaction with DBU (6.7 ml) in tert-butanol (20 mL) at 100° C. for 2 h to rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid tert-butyl ester as a light yellow gum (1.0 g, 33%).

Example 112c

Preparation of intermediate rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid trifluoroacetic acid

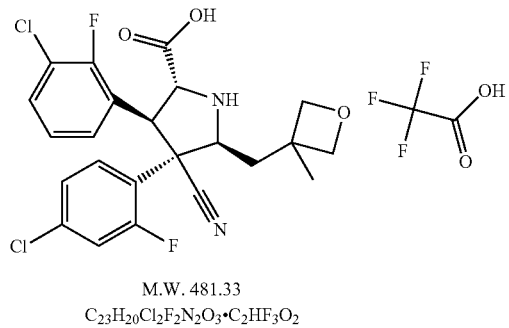

M.W. 481.33
C$_{23}$H$_{20}$Cl$_2$F$_2$N$_2$O$_3$·C$_2$HF$_3$O$_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid tert-butyl ester prepared in Example 112b (1.0 g, 1.9 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid trifluoroacetic acid as a white solid (1 g, 91%).

Example 112d

Preparation of rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid ((S)-3,4-dihydroxy-butyl)-amide

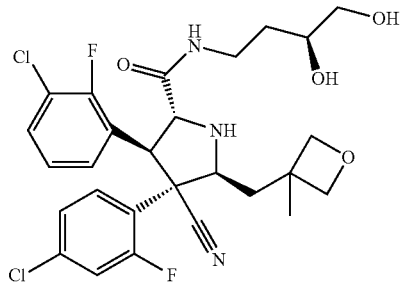

M.W. 568.45
C$_{27}$H$_{29}$Cl$_2$F$_2$N$_3$O$_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid trifluoroacetic acid prepared in Example 112c (0.5 g, 0.84 mmol) was reacted with 2-((S)-2,2-dimethyl-[1,3]dioxolan-4-yl)-ethylamine (0.36 g, 2.5 mmol), HATU (0.57 g, 1.5 mmol) and iPr$_2$NEt (0.73 mL, 4.2 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid ((S)-3,4-dihydroxy-butyl)-amide as a white solid (0.23 g, 48%).

HRMS (ES$^+$) m/z Calcd for C$_{27}$H$_{29}$Cl$_2$F$_2$N$_3$O$_4$+H [(M+H)$^+$]: 568.1576. found: 568.1579.

Example 113a

Preparation of intermediate [2-(3-ethyl-oxetan-3-yl)-eth-(E)-ylideneamino]-acetic acid tert-butyl ester

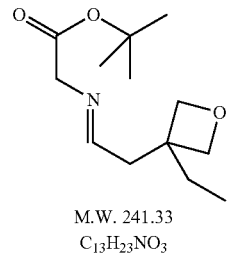 [SMILES: CCC1(C/C=N/CC(=O)OC(C)(C)C)COC1]

M.W. 241.33
C$_{13}$H$_{23}$NO$_3$

Step A In a manner similar to the methods described in Example 112a Step A. Step B., and Step C., 3-ethyl-3-oxetanemethanol (TCI-US) (3.5 g, 30 mmol) was reacted with triethylamine (6.6 g, 60 mmol) and treated with NaCN (2.2 g, 46 mmol) in anhydrous dimethyl sulfoxide at 130° C., followed by the reaction with DIBAL (1 M in heptane, 27 mL, 27 mmol) in dichloromethane at 0° C. to give (3-ethyl-oxetan-3-yl)-acetaldehyde as a light yellow oil (Yield: 2.5 g, 26% for three steps).

Step B In a manner similar to the method described in Example 1a, glycine tert-butyl ester (1 g, 7.8 mmol) was reacted with (3-ethyl-oxetan-3-yl)-acetaldehyde (1 g, 7.8 mmol) in CH$_2$Cl$_2$ at room temperature for 18 h to give [2-(3-ethyl-oxetan-3-yl)-eth-(E)-ylideneamino]-acetic acid tert-butyl ester as a yellow oil (1.9 g, 100%).

Example 113b

Preparation of intermediate rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid tert-butyl ester

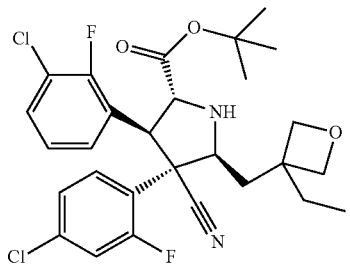

M.W. 551.41
C$_{28}$H$_{30}$Cl$_2$F$_2$N$_2$O$_3$

In a manner similar to the method described in Example 100b, [2-(3-ethyl-oxetan-3-yl)-eth-(E)-ylideneamino]-acetic acid tert-butyl ester prepared in Example 113a (1.9 g, 7.8 mmol) was reacted with (Z)-3-(3-chloro-2-fluoro-phenyl)-2-(4-chloro-2-fluoro-phenyl)-acrylonitrile (1.9 g, 6.2 mmol) prepared in Example 52a, AgF (1.2 g, 9.5 mmol), and triethylamine (2.2 mL, 16 mmol) in dichloromethane (100 mL) at room temperature for 18 h, followed by the reaction with DBU (7.5 ml) in tert-butanol (10 mL) at 100° C. for 2 h to give rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid tert-butyl ester as a white solid (2 g, 58%).

Example 113c

Preparation of intermediate rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid trifluoroacetic acid

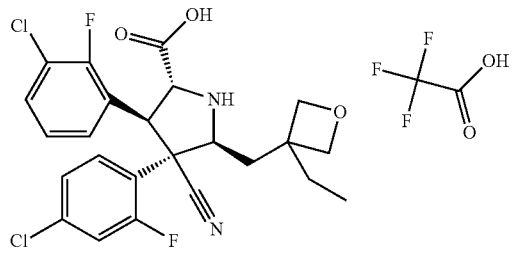

M.W. 495.36
C$_{24}$H$_{22}$Cl$_2$F$_2$N$_2$O$_3$·C$_2$HF$_3$O$_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid tert-butyl ester prepared in Example 113b (2 g, 3.6 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid trifluoroacetic acid as a white solid (2 g, 91%).

Example 113d

Preparation of rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid ((S)-3,4-dihydroxy-butyl)-amide

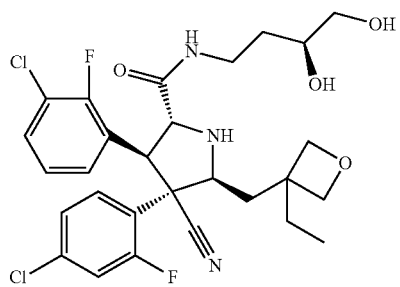

M.W. 582.47
C$_{28}$H$_{31}$Cl$_2$F$_2$N$_3$O$_4$

In a manner similar to the method described in Examples 42c and 42d rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid trifluoroacetic acid prepared in Example 105c (1 g, 1.6 mmol) was reacted with 2-((S)-2,2-dimethyl-[1,3]dioxolan-4-yl)-ethylamine (0.7 g, 5 mmol), HATU (1.1 g, 3 mmol) and iPr$_2$NEt (1.4 mL, 8 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid ((S)-3,4-dihydroxy-butyl)-amide as a white solid (0.56 g, 58%).

HRMS (ES$^+$) m/z Calcd for C$_{28}$H$_{31}$Cl$_2$F$_2$N$_3$O$_4$+H [(M+H)$^+$]: 582.1733. found: 582.1732.

Example 114a

Preparation of intermediate [2-[1-(tert-tutyl-dimethyl-silanyloxymethyl)-cyclopropyl]-eth-(E)-ylideneamino]-acetic acid tert-butyl ester

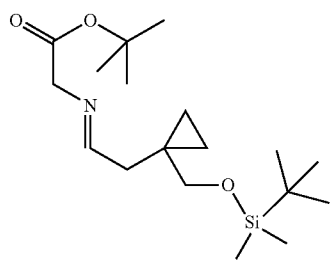

M.W. 341.57
C$_{18}$H$_{35}$NO$_3$Si

Step A In a manner similar to the methods described in Example 111a Step A. Step B., Step C., and Step D., 1,1-bis (hydroxymethyl)-cyclopropane (Aldrich) (4 g, 39 mmol) was reacted with thionyl chloride (14 g, 126 mmol) in anhydrous ethyl ether at 0° C., then reacted with NaCN (2.4 g, 49 mmol) in anhydrous dimethyl sulfoxide 120° C. for 18 h, then treated with tert-butyldimethylchlorosilane (1.4 g, 9 mmol) and imidazole (0.85 g, 13 mmol) in dichloromethane at room temperature, follone by the reaction with DIBAL (1 M in heptane, 8.3 mL, 8.3 mmol) at 0° C. to give [1-(tert-butyl-dimethyl-silanyloxymethyl)-cyclopropyl]-acetaldehyde as a colorless oil (Yield: 1.3 g, 15% for four steps).

Step B In a manner similar to the method described in Example 1a, glycine tert-butyl ester (0.75 g, 5.7 mmol) was reacted [1-(tert-butyl-dimethyl-silanyloxymethyl)-cyclopropyl]-acetaldehyde (1.3 g, 5.7 minor) in CH$_2$Cl$_2$ at room temperature for 18 h to give [2-[1-(tert-tutyl-dimethyl-silanyloxymethyl)-cyclopropyl]-eth-(E)-ylideneamino]-acetic acid tert-butyl ester as a colorless oil (1.9 g, 100%).

Example 114b

Preparation of intermediate rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid tert-butyl ester

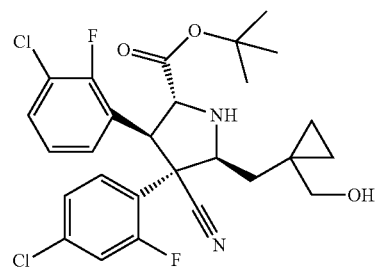

M.W. 537.44
C$_{27}$H$_{28}$Cl$_2$F$_2$N$_2$O$_3$

In a manner similar to the method described in Example 100b, [2-[1-(tert-tutyl-dimethyl-silanyloxymethyl)-cyclopropyl]-eth-(E)-ylideneamino]-acetic acid tert-butyl ester prepared in Example 114a (1.9 g, 5.7 mmol) was reacted with (Z)-3-(3-chloro-2-fluoro-phenyl)-2-(4-chloro-2-fluoro-phenyl)-acrylonitrile (1.4 g, 4.6 mmol) prepared in Example 52a, AgF (0.89 g, 7.1 mmol), and triethylamine (1.6 mL, 12 mmol) in dichloromethane (100 mL) at room temperature for 18 h, followed by the reaction with DBU (5 ml) in tert-butanol (20 mL) at 100° C. for 2 h to give rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid tert-butyl ester as a white solid (0.4 g, 30%).

Example 114c

Preparation of intermediate rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid trifluoroacetic acid

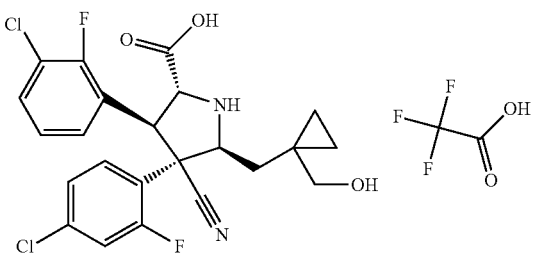

M.W. 481.33
C$_{23}$H$_{20}$Cl$_2$F$_2$N$_2$O$_3$·C$_2$HF$_3$O$_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid tert-butyl ester prepared in Example 114b (0.4 g, 0.74 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid trifluoroacetic acid as a white solid (0.4 g, 91%).

Example 114d

Preparation of rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide

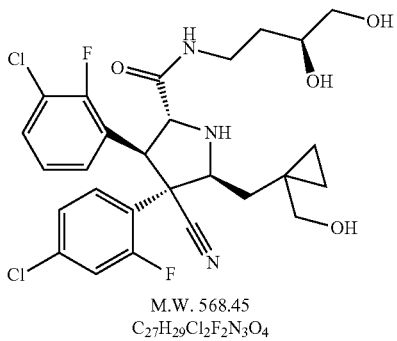 [SMILES: N#C[C@]1(c2ccc(Cl)cc2F)[C@H](CC2(CO)CC2)N[C@@H](C(=O)NCC[C@H](O)CO)[C@@H]1c1cccc(Cl)c1F]

M.W. 568.45
$C_{27}H_{29}Cl_2F_2N_3O_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid trifluoroacetic acid prepared in Example 114c (0.4 g, 0.67 mmol) was reacted with 2-((S)-2,2-dimethyl-[1,3]dioxolan-4-yl)-ethylamine (0.29 g, 2 mmol), HATU (0.46 g, 1.2 mmol) and iPr$_2$NEt (0.58 mL, 3.4 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide as a white solid (0.15 g, 40%).

HRMS (ES$^+$) m/z Calcd for $C_{27}H_{29}Cl_2F_2N_3O_4$+H [(M+H)$^+$]: 568.1576. found: 568.1578.

Example 114e

Preparation of (2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide

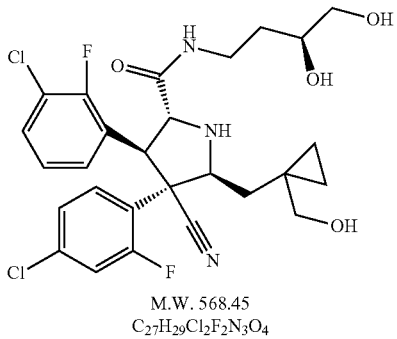 [SMILES: N#C[C@]1(c2ccc(Cl)cc2F)[C@H](CC2(CO)CC2)N[C@@H](C(=O)NCC[C@H](O)CO)[C@@H]1c1cccc(Cl)c1F]

M.W. 568.45
$C_{27}H_{29}Cl_2F_2N_3O_4$

Rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide (0.12 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide as a white solid (46 mg, 38%) and chiral (2S,3R,4S,5R)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide as a white solid (48 mg, 40%).

HRMS (ES$^+$) m/z Calcd for $C_{27}H_{29}Cl_2F_2N_3O_4$+H [(M+H)$^+$]: 568.1575. found: 568.1578.

Example 115a

Preparation of intermediate [2-[1-(tert-tutyl-dimethyl-silanyloxymethyl)-cyclobutyl]-eth-(E)-ylidene-amino]-acetic acid tert-butyl ester

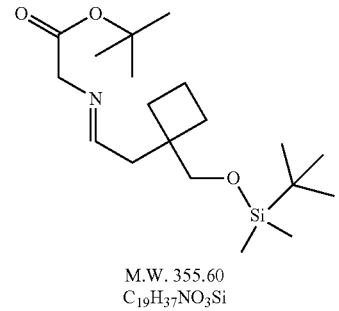 [SMILES: CC(C)(C)OC(=O)C/N=C/CC1(CO[Si](C)(C)C(C)(C)C)CCC1]

M.W. 355.60
$C_{19}H_{37}NO_3Si$

Step A In a manner similar to the methods described in Example 111a Step A. Step B., Step C., and Step D., 1,1-bis(hydroxymethyl)-cyclobutane (Waterstone) (3.8 g, 33 mmol) was reacted with thionyl chloride (8 g, 72 mmol) in anhydrous ethyl ether at 0° C., then reacted with NaCN (2 g, 41 mmol) in anhydrous dimethyl sulfoxide 120° C. for 18 h, then treated with tert-butyldimethylchlorosilane (1 g, 6 mmol) and imidazole (1 g, 15 mmol) in dichloromethane at room temperature, follone by the reaction with DIBAL (1 M in heptane, 6.4 mL, 6.4 mmol) at 0° C. to give [1-(tert-butyl-dimethyl-silanyloxymethyl)-cyclobutyl]-acetaldehyde as a colorless oil (Yield: 0.48 g, 6% for four steps).

Step B In a manner similar to the method described in Example 1a, glycine tert-butyl ester (0.26 g, 2 mmol) was reacted with [1-(tert-butyl-dimethyl-silanyloxymethyl)-cyclobutyl]-acetaldehyde (0.48 g, 2 mmol) in CH$_2$Cl$_2$ at room temperature for 18 h to give [2-[1-(tert-tutyl-dimethyl-silanyloxymethyl)-cyclopropyl]-eth-(E)-ylideneamino]-acetic acid tert-butyl ester as a colorless oil (0.71 g, 100%).

Example 115b

Preparation of intermediate rac-(2R,3S,4R,5S)-5-[1-(tert-butyl-dimethyl-silanyloxymethyl)-cyclobutylmethyl]-3-(3-chloro-2-fluoro-phenyl)-4-(4-chloro-2-fluoro-phenyl)-4-cyano-pyrrolidine-2-carboxylic acid tert-butyl ester

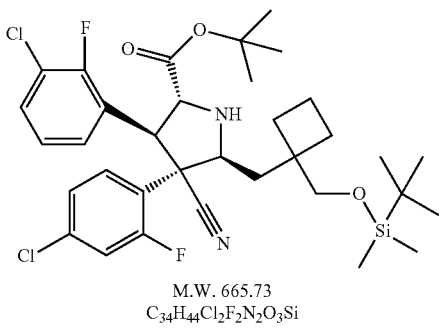 [SMILES: CC(C)(C)OC(=O)[C@@H]1N[C@@H](CC2(CO[Si](C)(C)C(C)(C)C)CCC2)[C@](C#N)(c2ccc(Cl)cc2F)[C@H]1c1cccc(Cl)c1F]

M.W. 665.73
$C_{34}H_{44}Cl_2F_2N_2O_3Si$

In a manner similar to the method described in Example 100b, [2-[1-(tert-tutyl-dimethyl-silanyloxymethyl)-cyclopropyl]-eth-(E)-ylideneamino]-acetic acid tert-butyl ester prepared in Example 115a (0.71 g, 2 mmol) was reacted with (Z)-3-(3-chloro-2-fluoro-phenyl)-2-(4-chloro-2-fluoro-phenyl)-acrylonitrile (0.49 g, 1.6 mmol) prepared in Example 52a, AgF (0.3 g, 2.4 mmol), and triethylamine (0.55 mL, 4 mmol) in dichloromethane (100 mL) at room temperature for 18 h, followed by the reaction with DBU (1 ml) in tert-butanol (15 mL) at 100° C. for 2 h to give rac-(2R,3S,4R,5S)-5-[1-(tert-butyl-dimethyl-silanyloxymethyl)-cyclobutylmethyl]-3-(3-chloro-2-fluoro-phenyl)-4-(4-chloro-2-fluoro-phenyl)-4-cyano-pyrrolidine-2-carboxylic acid tert-butyl ester as a yellow gum (0.7 g, 67%).

Example 115c

Preparation of intermediate rac-(2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid trifluoroacetic acid

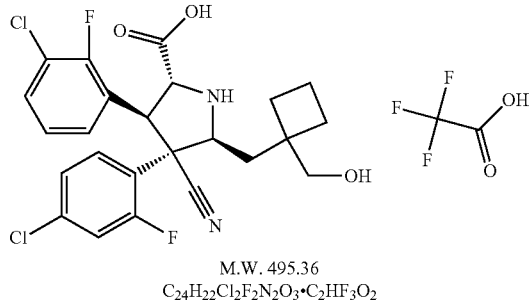 [SMILES: N#C[C@]1(c2ccc(Cl)cc2F)[C@H](CC2(CO)CCC2)N[C@@H](C(=O)O)[C@@H]1c1cccc(Cl)c1F ; O=C(O)C(F)(F)F]

M.W. 495.36
$C_{24}H_{22}Cl_2F_2N_2O_3 \cdot C_2HF_3O_2$

In a manner similar to the method described in Example 25a, rac-(2R,3S,4R,5S)-5-[1-(tert-butyl-dimethyl-silanyloxymethyl)-cyclobutylmethyl]-3-(3-chloro-2-fluoro-phenyl)-4-(4-chloro-2-fluoro-phenyl)-4-cyano-pyrrolidine-2-carboxylic acid tert-butyl ester prepared in Example 115b (0.7 g, 1 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid trifluoroacetic acid as a white solid (0.6 g, 100%).

Example 115d

Preparation of rac-(2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide

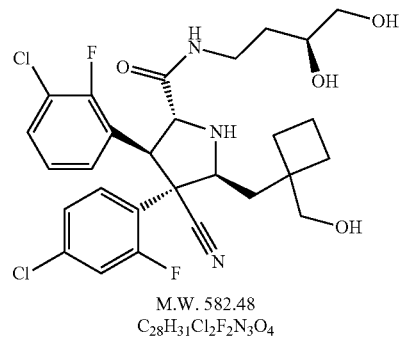 [SMILES: N#C[C@]1(c2ccc(Cl)cc2F)[C@H](CC2(CO)CCC2)N[C@@H](C(=O)NCC[C@H](O)CO)[C@@H]1c1cccc(Cl)c1F]

M.W. 582.48
$C_{28}H_{31}Cl_2F_2N_3O_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid trifluoroacetic acid prepared in Example 115c (0.6 g, 1 mmol) was reacted with 2-((S)-2,2-dimethyl-[1,3]dioxolan-4-yl)-ethylamine (0.43 g, 3 mmol), HATU (0.67 g, 1.8 mmol) and iPr$_2$NEt (0.86 mL, 4.9 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide as a white solid (0.32 g, 56%).

HRMS (ES$^+$) m/z Calcd for $C_{28}H_{31}Cl_2F_2N_3O_4$+H [(M+H)$^+$]: 582.1733. found: 582.1733.

Example 115e

Preparation of (2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide

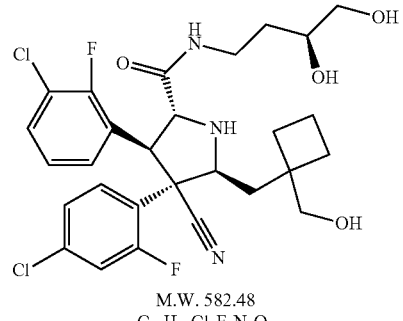

M.W. 582.48
$C_{28}H_{31}Cl_2F_2N_3O_4$

Rac-(2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide (0.25 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide as a white solid (104 mg, 41%) and chiral (2S,3R,4S,5R)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide as a white solid (103 mg, 41%).

HRMS (ES$^+$) m/z Calcd for $C_{28}H_{31}Cl_2F_2N_3O_4$+H [(M+H)$^+$]: 582.1733. found: 582.1733.

Example 116a

Preparation of intermediate [5-(tert-butyl-dimethyl-silanyloxy)-3,3-dimethyl-pent-(E)-ylideneamino]-acetic acid methyl ester

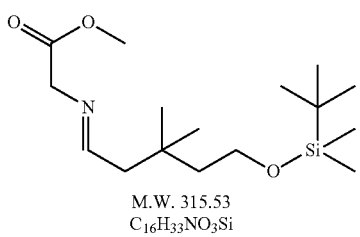 [SMILES: COC(=O)C/N=C/CC(C)(C)CCO[Si](C)(C)C(C)(C)C]

M.W. 315.53
$C_{16}H_{33}NO_3Si$

Step A To the solution of 3,3-dimethylglutaric acid (Aldrich) (5.1 g, 32 mmol) in anhydrous tetrahydrofuran (100 mL) at 0° C. was added a solution of BH$_3$.THF (1 M, 100 mL, 100 mmol). The reaction mixture was stirred at room temperature for 18 h. Aqueous HCl solution was added, and the mixture was extracted with ethyl acetate. The organic layer was separated, washed with saturated aqueous NaHCO$_3$ solution, brine, dried over MgSO$_4$, and concentrated. The residue was purified by chromatography (EtOAc) to give 3,3-dimethyl-pentane-1,5-diol as a colorless oil (1.5 g, 34%).

Step B A mixture of 3,3-dimethyl-pentane-1,5-diol (1.5 g, 11 mmol) and imidazole (1.4 g, 20 mmol) in dichloromethane (50 mL) was added tert-butyldimethylchlorosilane (1.7 g, 11 mmol). The reaction mixture was stirred at room temperature for 2 h. Water was added. The organic layer was separated, the aqueous layer was then extracted with dichloromethane. The combined organic layers were washed with brine, dried over MgSO$_4$, concentrated to give 5-(tert-butyl-dimethyl-silanyloxy)-3,3-dimethyl-penta-1-ol as a colorless oil (2.7 g, 100%).

Step C To a solution of oxalyl chloride (0.97 mL, 11 mmol) (Aldrich) in dichloromethane (20 mL) at −78° C. was added the solution of dimethyl sulfoxide (1.6 mL, 22 mmol) in dichloromethane (5 mL) dropwise. After 5 mins, the solution of 5-(tert-butyl-dimethyl-silanyloxy)-3,3-dimethyl-pentan-1-ol (2.5 g, 10 mmol) in dichloromethane (10 mL) was added dropwise. The reaction mixture was stirred at −78° C. for 15 min. Triethylamine (5 mL, 36 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO$_3$, brine, dried over MgSO$_4$, and concentrated to give 5-(tert-butyl-dimethyl-silanyloxy)-3,3-dimethyl-pentanal as a light yellow oil (Yield: 1.75 g, 71%).

Step D In a manner similar to the method described in Example 1a, glycine methyl ester hydrochloride (0.9 g, 7.2 mmol) was reacted with 5-(tert-butyl-dimethyl-silanyloxy)-3,3-dimethyl-pentanal (1.75 g, 7.2 mmol) and triethylamine (1.49 mL, 11 mmol) in CH$_2$Cl$_2$ at room temperature for 18 h to give [4-(tert-butyl-dimethyl-silanyloxy)-3,3-dimethyl-but-(E)-ylideneamino]-acetic acid methyl ester as a colorless oil (2.3 g, 100%).

Example 116b

Preparation of intermediate rac-(2R,3S,4R,5S)-5-[4-(tert-tutyl-dimethyl-silanyloxy)-2,2-dimethyl-butyl]-3-(3-chloro-2-fluoro-phenyl)-4-(4-chloro-2-fluoro-phenyl)-4-cyano-pyrrolidine-2-carboxylic acid methyl ester

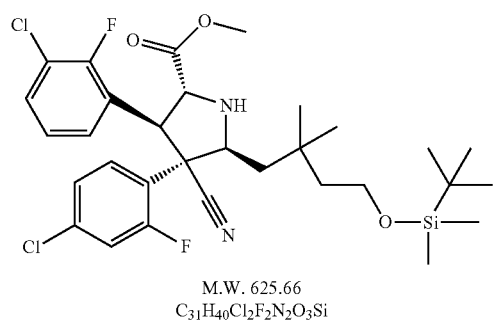 [SMILES: COC(=O)[C@@H]1N[C@@H](CC(C)(C)CCO[Si](C)(C)C(C)(C)C)[C@](C#N)(c2ccc(Cl)cc2F)[C@H]1c1cccc(Cl)c1F]

M.W. 625.66
$C_{31}H_{40}Cl_2F_2N_2O_3Si$

In a manner similar to the method described in Example 1c, [5-(tert-butyl-dimethyl-silanyloxy)-3,3-dimethyl-pent-(E)-ylideneamino]-acetic acid methyl ester prepared in Example 116a (6.4 mmol) was reacted with (Z)-3-(3-chloro-2-fluoro-phenyl)-2-(4-chloro-2-fluoro-phenyl)-acrylonitrile (1.58 g, 5.1 mmol) prepared in Example 52a, AgF (1 g, 7.8 mmol), and triethylamine (1.8 mL, 13 mmol) in dichloromethane (100 mL) at room temperature for 48 h to give rac-(2R,3S,4R,5S)-5-[4-(tert-tutyl-dimethyl-silanyloxy)-2,2-dimethyl-butyl]-3-(3-chloro-2-fluoro-phenyl)-4-(4-chloro-2-fluoro-phenyl)-4-cyano-pyrrolidine-2-carboxylic acid methyl ester as a yellow gum (1.6 g, 50%).

Example 116c

Preparation of intermediate rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid

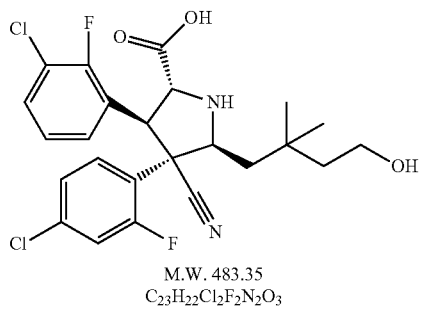 [SMILES: CC(C)(CCO)C[C@@H]1N[C@@H](C(=O)O)[C@H](c2cccc(Cl)c2F)[C@@]1(C#N)c1ccc(Cl)cc1F]

M.W. 483.35
$C_{23}H_{22}Cl_2F_2N_2O_3$

To rac-(2R,3S,4R,5S)-5-[4-(tert-tutyl-dimethyl-silanyloxy)-2,2-dimethyl-butyl]-3-(3-chloro-2-fluoro-phenyl)-4-(4-chloro-2-fluoro-phenyl)-4-cyano-pyrrolidine-2-carboxylic acid methyl ester prepared in Example 116b (0.7 g, 1.1 mmol) in tetrahydrofuran (10 mL) was added tetrahydrofuran solution (1 M, Aldrich) of TBAF (1.34 mL, 1.3 mmol). The reaction mixture was stirred at room temperature for 18 h. The mixture was concentrated, the residue was partitioned between ethyl acetate and water. The organic layer was separated, dried over MgSO$_4$, and concentrated. The residue was dissolved into tetrahydrofuran (10 mL), and an aqueous solution (1 M) of LiOH (10 mL, 10 mmol) was added. The reaction mixture was stirred at room temperature for 1 h. The "pH" of the mixture was adjusted to ~4-5 by aqueous HCl solution. The mixture was concentrated. The residue was partitioned between ethyl acetate and water. The organic layer was separated, washed with water, brine, dried over MgSO$_4$, concentrated to give intermediate rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid as a light yellow solid (0.3 g, 54%)

Example 116d

Preparation of rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide

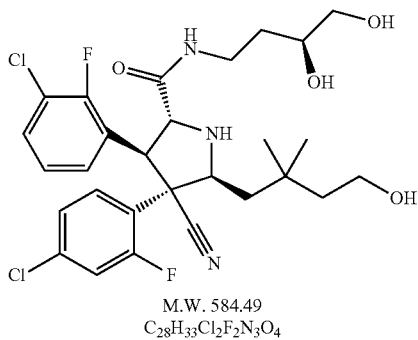 [SMILES: CC(C)(CCO)C[C@@H]1N[C@@H](C(=O)NCC[C@H](O)CO)[C@H](c2cccc(Cl)c2F)[C@@]1(C#N)c1ccc(Cl)cc1F]

M.W. 584.49
C$_{28}$H$_{33}$Cl$_2$F$_2$N$_3$O$_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid prepared in Example 116c (0.18 g, 0.36 mmol) was reacted with 2-((S)-2,2-dimethyl-[1,3]dioxolan-4-yl)-ethylamine (0.16 g, 1 mmol), HATU (0.25 g, 0.65 mmol) and iPr$_2$NEt (0.07 mL, 0.43 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide as a white solid (0.1 g, 54%).

HRMS (ES$^+$) m/z Calcd for C$_{28}$H$_{33}$Cl$_2$F$_2$N$_3$O$_4$+H [(M+H)$^+$]: 584.1889. found: 584.1889.

Example 116e

Preparation of (2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide

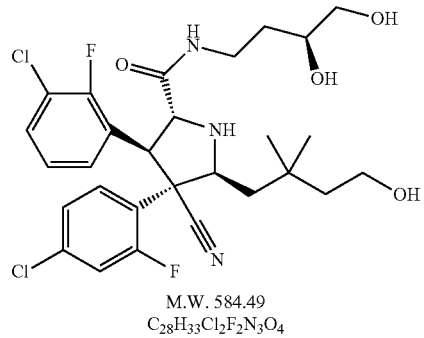 [SMILES: CC(C)(CCO)C[C@@H]1N[C@@H](C(=O)NCC[C@H](O)CO)[C@H](c2cccc(Cl)c2F)[C@@]1(C#N)c1ccc(Cl)cc1F]

M.W. 584.49
C$_{28}$H$_{33}$Cl$_2$F$_2$N$_3$O$_4$

Rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide (0.35 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide as a white solid (157 mg, 45%) and chiral (2S,3R,4S,5R)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide as a white solid (155 mg, 44%).

HRMS (ES$^+$) m/z Calcd for C$_{28}$H$_{33}$Cl$_2$F$_2$N$_3$O$_4$+H [(M+H)$^+$]: 584.1889. found: 584.1891.

Example 117a

Preparation of intermediate [2-[1-(tert-butyl-dimethyl-silanyloxymethyl)-cyclohex-3-enyl]-eth-(E)-ylideneamino]-acetic acid tert-butyl ester

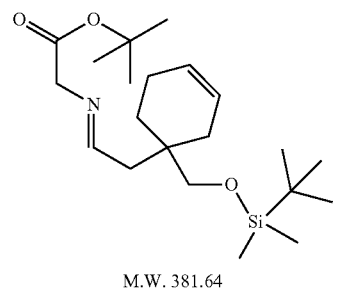

M.W. 381.64
C$_{21}$H$_{39}$NO$_3$Si

Step A In a manner similar to the methods described in Example 111a Step A. Step B., Step C., and Step D., 3-cyclohexene-1,1-dimethanol (Aldrich) (5.3 g, 37 mmol) was reacted with thionyl chloride (15 g, 135 mmol) in anhydrous ethyl ether at 0° C., then reacted with NaCN (3 g, 61 mmol) in anhydrous dimethyl sulfoxide 120° C. for 18 h, then treated with tert-butyldimethylchlorosilane (3.9 g, 26 mmol) and imidazole (2.4 g, 36 mmol) in dichloromethane at room temperature, follone by the reaction with DIBAL (1 M in heptane, 26 mL, 26 mmol) at 0° C. to give 1-(tert-butyl-dimethyl-silanyloxymethyl)-cyclohex-3-enecarbaldehyde as a light yellow oil (Yield: 6 g, 64% for four steps).

Step B In a manner similar to the method described in Example 1a, glycine tert-butyl ester (1.2 g, 9 mmol) was reacted with 1-(tert-butyl-dimethyl-silanyloxymethyl)-cyclohex-3-enecarbaldehyde (2.5 g, 9 mmol) in CH$_2$Cl$_2$ at room temperature for 18 h to give [2-[1-(tert-butyl-dimethyl-silanyloxymethyl)-cyclohex-3-enyl]-eth-(E)-ylideneamino]-acetic acid tert-butyl ester as a light yellow oil (3.5 g, 100%).

Example 117b

Preparation of intermediate rac-(2R,3S,4R,5S)-5-[1-(tert-butyl-dimethyl-silanyloxymethyl)-cyclohex-3-enylmethyl]-3-(3-chloro-2-fluoro-phenyl)-4-(4-chloro-2-fluoro-phenyl)-4-cyano-pyrrolidine-2-carboxylic acid tert-butyl ester

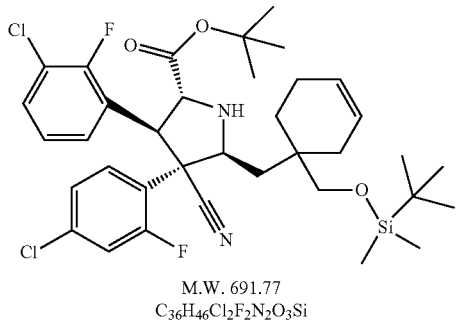 [SMILES: CC(C)(C)OC(=O)[C@@H]1N[C@@H](CC2(CO[Si](C)(C)C(C)(C)C)CC=CCC2)[C@](C#N)(c2ccc(Cl)cc2F)[C@H]1c1cccc(Cl)c1F]

M.W. 691.77
C$_{36}$H$_{46}$Cl$_2$F$_2$N$_2$O$_3$Si

In a manner similar to the method described in Example 100b, [2-[1-(tert-butyl-dimethyl-silanyloxymethyl)-cyclohex-3-enyl]-eth-(E)-ylideneamino]-acetic acid tert-butyl ester prepared in Example 117a (3.5 g, 9 mmol) was reacted with (Z)-3-(3-chloro-2-fluoro-phenyl)-2-(4-chloro-2-fluoro-phenyl)-acrylonitrile (2.3 g, 7 mmol) prepared in Example 52a, AgF (1.4 g, 11 mmol), and triethylamine (2.6 mL, 19 mmol) in dichloromethane (100 mL) at room temperature for 18 h, followed by the reaction with DBU (9 ml) in tert-butanol (10 mL) at 100° C. for 2 h to give rac-(2R,3S,4R,5S)-5-[1-(tert-butyl-dimethyl-silanyloxymethyl)-cyclohex-3-enylmethyl]-3-(3-chloro-2-fluoro-phenyl)-4-(4-chloro-2-fluoro-phenyl)-4-cyano-pyrrolidine-2-carboxylic acid tert-butyl ester as a white solid (2.6 g, 51%).

Example 117c

Preparation of intermediate rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid trifluoroacetic acid

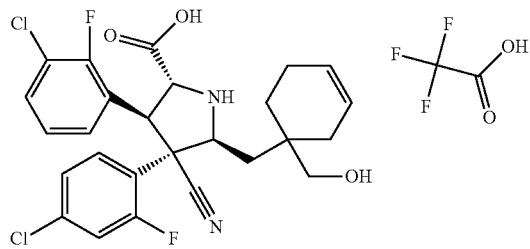

M. W.521.40
C$_{26}$H$_{24}$Cl$_2$F$_2$N$_2$O$_3$·C$_2$HF$_3$O$_2$

In a manner similar to the method described in Example 25a, rac-(2R,3S,4R,5S)-5-[1-(tert-butyl-dimethyl-silanyloxymethyl)-cyclohex-3-enylmethyl]-3-(3-chloro-2-fluoro-phenyl)-4-(4-chloro-2-fluoro-phenyl)-4-cyano-pyrrolidine-2-carboxylic acid tert-butyl ester prepared in Example 117b (2.6 g, 3.8 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid trifluoroacetic acid as a white solid (2.2 g, 92%).

Example 117d

Preparation of intermediate rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid [2-((S)-2,2-dimethyl-[1,3]dioxolan-4-yl)-ethyl]-amide

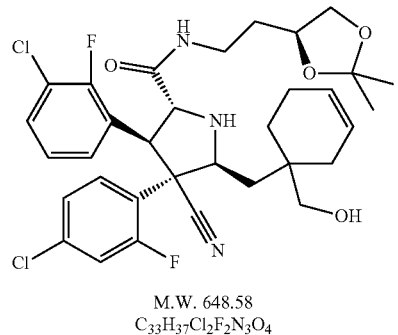 [SMILES: CC1(C)OC[C@H](CCNC(=O)[C@@H]2N[C@@H](CC3(CO)CC=CCC3)[C@](C#N)(c3ccc(Cl)cc3F)[C@H]2c2cccc(Cl)c2F)O1]

M.W. 648.58
C$_{33}$H$_{37}$Cl$_2$F$_2$N$_3$O$_4$

A mixture of rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid trifluoroacetic acid prepared in Example 117c (1 g, 1.6 mmol), HATU (1.07 g, 2.8 mmol) and iPr$_2$NEt (1.37 mL, 7.8 mmol) in CH$_2$Cl$_2$ (10 mL) was stirred at room temperature for 18 h. The mixture was then diluted with CH$_2$Cl$_2$ and washed with water, brine. The organic layer was separated, the aqueous layer was extracted with CH$_2$Cl$_2$. The organic layers were combined, and concentrated. The residue was dissolved into tetrahydrofuran (5 mL), and aqueous saturated K$_2$CO$_3$ (5 mL) was added. The mixture was stirred at room temperature for 30 min, then partitioned between ethyl acetate and water. The organic layer was separated, washed with water, brine, dried over MgSO$_4$ and concentrated. The residue was purified by flash chromatography (EtOAc) to give rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid [2-((S)-2,2-dimethyl-[1,3]dioxolan-4-yl)-ethyl]-amide as a white solid (0.48 g, 47%)

Example 117e

Preparation of rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid ((S)-3,4-dihydroxy-butyl)-amide

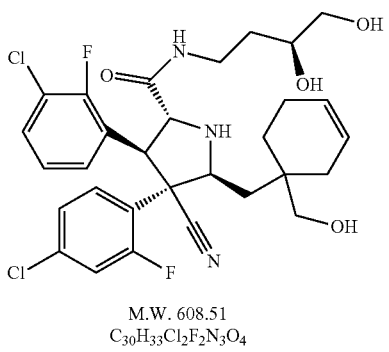 [SMILES: N#C[C@]1(c2ccc(Cl)cc2F)[C@H](CC2(CO)CC=CCC2)N[C@@H](C(=O)NCC[C@H](O)CO)[C@@H]1c1cccc(Cl)c1F]

M.W. 608.51
$C_{30}H_{33}Cl_2F_2N_3O_4$

In a manner similar to the method described in Examples 42d, rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid [2-((S)-2,2-dimethyl-[1,3]dioxolan-4-yl)-ethyl]-amide prepared in Example 117d (0.2 g, 0.3 mmol) was reacted with aqueous HCl solution (1 N, 1 mL, 1 mol) in tetrahydrofuran (9 mL) at room temperature for 2 h to give rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid ((S)-3,4-dihydroxy-butyl)-amide as a white solid (0.14 g, 75%).

HRMS (ES+) m/z Calcd for $C_{30}H_{33}Cl_2F_2N_3O_4$+H [(M+H)+]: 608.1889. found: 608.1888.

Example 118a

Preparation of intermediate rac-(2R,3S,4R,5S)-3-(3-chloro-2-fluoro-phenyl)-4-(4-chloro-2-fluoro-phenyl)-4-cyano-5-(1-hydroxymethyl-cyclohexylmethyl)-pyrrolidine-2-carboxylic acid [2-((S)-2,2-dimethyl-[1,3]dioxolan-4-yl)-ethyl]-amide

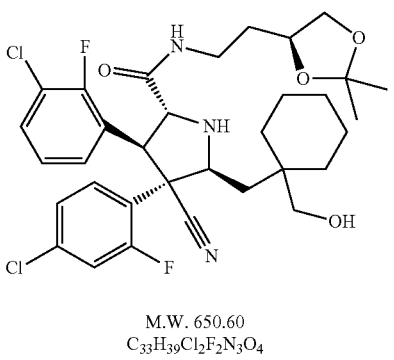 [SMILES: CC1(C)OC[C@H](CCNC(=O)[C@@H]2N[C@@H](CC3(CO)CCCCC3)[C@](C#N)(c3ccc(Cl)cc3F)[C@H]2c2cccc(Cl)c2F)O1]

M.W. 650.60
$C_{33}H_{39}Cl_2F_2N_3O_4$

To a solution of rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid [2-((S)-2,2-dimethyl-[1,3]dioxolan-4-yl)-ethyl]-amide (0.28 g, 0.43 mmol) prepared in Example 117d in ethyl acetate (10 mL) was added PtO₂ (0.1 g). The suspension was shaken vigorously under H₂ atmosphere (50 psi) for 1 h. The mixture was filtered through a short pad of celite. The filtrate was concentrated to give rac-(2R,3S,4R,5S)-3-(3-chloro-2-fluoro-phenyl)-4-(4-chloro-2-fluoro-phenyl)-4-cyano-5-(1-hydroxymethyl-cyclohexylmethyl)-pyrrolidine-2-carboxylic acid [2-((S)-2,2-dimethyl-[1,3]dioxolan-4-yl)-ethyl]-amide as a white solid (0.27 g, 96%)

Example 118b

Preparation of rac-(2R,3S,4R,5S)-3-(3-chloro-2-fluoro-phenyl)-4-(4-chloro-2-fluoro-phenyl)-4-cyano-5-(1-hydroxymethyl-cyclohexylmethyl)-pyrrolidine-2-carboxylic acid ((S)-3,4-dihydroxy-butyl)-amide

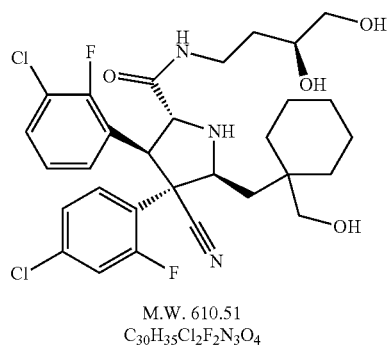 [SMILES: N#C[C@]1(c2ccc(Cl)cc2F)[C@H](CC2(CO)CCCCC2)N[C@@H](C(=O)NCC[C@H](O)CO)[C@@H]1c1cccc(Cl)c1F]

M.W. 610.51
$C_{30}H_{35}Cl_2F_2N_3O_4$

In a manner similar to the method described in Examples 42d, rac-(2R,3S,4R,5S)-3-(3-chloro-2-fluoro-phenyl)-4-(4-chloro-2-fluoro-phenyl)-4-cyano-5-(1-hydroxymethyl-cyclohexylmethyl)-pyrrolidine-2-carboxylic acid [2-((S)-2,2-dimethyl-[1,3]dioxolan-4-yl)-ethyl]-amide prepared in Example 118a (0.27 g, 0.4 mmol) was reacted with aqueous HCl solution (1 N, 1 mL, 1 mol) in tetrahydrofuran (9 mL) at room temperature for 2 h to give rac-(2R,3S,4R,5S)-3-(3-chloro-2-fluoro-phenyl)-4-(4-chloro-2-fluoro-phenyl)-4-cyano-5-(1-hydroxymethyl-cyclohexylmethyl)-pyrrolidine-2-carboxylic acid ((S)-3,4-dihydroxy-butyl)-amide as a white solid (0.23 g, 91%).

HRMS (ES+) m/z Calcd for $C_{30}H_{35}Cl_2F_2N_3O_4$+H [(M+H)+]: 610.2046. found: 610.2042.

Example 119a

Preparation of intermediate [5-[2-(tert-butyl-dimethyl-silanyloxy)-ethoxy]-3,3-dimethyl-pent-(E)-ylideneamino]-acetic acid tert-butyl ester

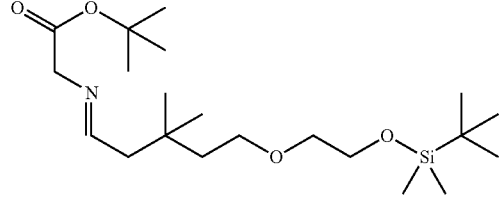

M.W. 401.67
$C_{21}H_{43}NO_4Si$

Step A To the solution of 3,3-dimethyl-pentane-1,5-diol (1.5 g, 11 mmol) prepared in Example 116a Step A. in anhydrous dimethylformamide (15 mL) was added NaH (60%, 0.68 g, 17 mmol). The mixture was stirred at room temperature for 15 min, then (2-bromoethoxy)-tert-butyldimethylsilane (3.3 g, 14 mmol) was added. The mixture was stirred at room temperature for 1 h. Water was added. The mixture was extracted with ethyl acetate twice. The combined organic layers were washed with brine, dried over $MgSO_4$, and concentrated. The residue was purified by chromatography (EtOAc:hexanes=1:3) to give 5-[2-(tert-butyl-dimethyl-silanyloxy)-ethoxy]-3,3-dimethyl-pentan-1-ol as a yellow oil (0.3 g, 9%).

Step B To a solution of oxalyl chloride (0.1 mL, 1 mmol) (Aldrich) in dichloromethane (5 mL) at −78° C. was added the solution of dimethyl sulfoxide (0.16 mL, 2.2 mmol) in dichloromethane (1 mL) dropwise. After 5 mins, the solution of 5-[2-(tert-butyl-dimethyl-silanyloxy)-ethoxy]-3,3-dimethyl-pentan-1-ol (0.3 g, 1 mmol) in dichloromethane (1 mL) was added dropwise. The reaction mixture was stirred at −78° C. for 15 min. Triethylamine (0.5 mL, 3.6 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated $NaHCO_3$, brine, dried over $MgSO_4$, and concentrated to give 5-[2-(tert-butyl-dimethyl-silanyloxy)-ethoxy]-3,3-dimethyl-pentanal as a yellow oil (Yield: 0.27 g, 94%).

Step C In a manner similar to the method described in Example 1a, glycine tert-butyl ester (0.13 g, 1 mmol) was reacted with 5-[2-(tert-butyl-dimethyl-silanyloxy)-ethoxy]-3,3-dimethyl-pentanal (0.27 g, 1 mmol) in $CH_2Cl_2$ at room temperature for 18 h to give [5-[2-(tert-butyl-dimethyl-silanyloxy)-ethoxy]-3,3-dimethyl-pent-(E)-ylideneamino]-acetic acid tert-butyl ester as a colorless oil (0.4 g, 100%).

Example 119b

Preparation of intermediate rac-(2R,3S,4R,5S)-5-{4-[2-(tert-butyl-dimethyl-silanyloxy)-ethoxy]-2,2-dimethyl-butyl}-3-(3-chloro-2-fluoro-phenyl)-4-(4-chloro-2-fluoro-phenyl)-4-cyano-pyrrolidine-2-carboxylic acid tert-butyl ester

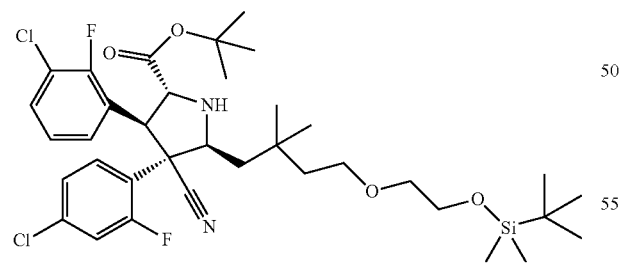

M.W. 711.80
$C_{36}H_{50}Cl_2F_2N_2O_4Si$

In a manner similar to the method described in Example 100b, [5-[2-(tert-butyl-dimethyl-silanyloxy)-ethoxy]-3,3-dimethyl-pent-(E)-ylideneamino]-acetic acid tert-butyl ester prepared in Example 119a (0.4 g, 1 mmol) was reacted with (Z)-3-(3-chloro-2-fluoro-phenyl)-2-(4-chloro-2-fluoro-phenyl)-acrylonitrile (0.3 g, 1 mmol) prepared in Example 52a, AgF (0.2 g, 1.5 mmol), and triethylamine (0.3 mL, 2.4 mmol) in dichloromethane (50 mL) at room temperature for 18 h, followed by the reaction with DBU (1 ml) in tert-butanol (2 mL) at 100° C. for 2 h to give rac-(2R,3S,4R,5S)-5-{4-[2-(tert-butyl-dimethyl-silanyloxy)-ethoxy]-2,2-dimethyl-butyl}-3-(3-chloro-2-fluoro-phenyl)-4-(4-chloro-2-fluoro-phenyl)-4-cyano-pyrrolidine-2-carboxylic acid tert-butyl ester as a white gum (0.49 g, 60%).

Example 119c

Preparation of intermediate rac-(2R,3S,4R,5S)-3-(3-chloro-2-fluoro-phenyl)-4-(4-chloro-2-fluoro-phenyl)-4-cyano-5-{2,2-dimethyl-4-[2-(2,2,2-trifluoro-acetoxy)-ethoxy]-butyl}-pyrrolidine-2-carboxylic acid trifluoroacetic acid

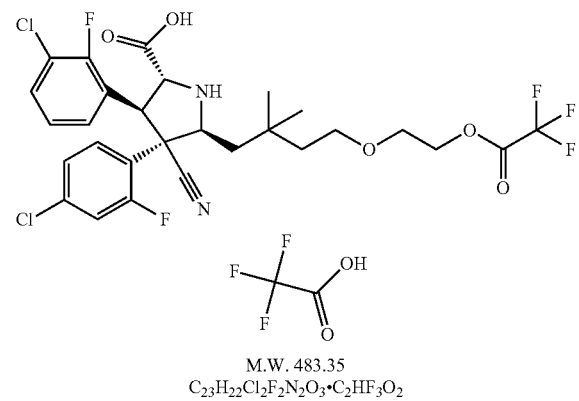

M.W. 483.35
$C_{23}H_{22}Cl_2F_2N_2O_3 \cdot C_2HF_3O_2$

To a solution of rac-(2R,3S,4R,5S)-5-{4-[2-(tert-butyl-dimethyl-silanyloxy)-ethoxy]-2,2-dimethyl-butyl}-3-(3-chloro-2-fluoro-phenyl)-4-(4-chloro-2-fluoro-phenyl)-4-cyano-pyrrolidine-2-carboxylic acid tert-butyl ester prepared in Example 119b (0.49 g, 0.55 mmol) in dichloromethane (3 mL) at room temperature was added trifluoroacetic acid (3 mL). The reaction mixture was stirred at room temperature for 18 h. The mixture was concentrated under reduced pressure to give rac-(2R,3S,4R,5S)-3-(3-chloro-2-fluoro-phenyl)-4-(4-chloro-2-fluoro-phenyl)-4-cyano-5-{2,2-dimethyl-4-[2-(2,2,2-trifluoro-acetoxy)-ethoxy]-butyl}-pyrrolidine-2-carboxylic acid trifluoroacetic acid as a yellow oil (0.37 g, 97%).

Example 119d

Preparation of rac-(2R,3S,4R,5S)-3-(3-chloro-2-fluoro-phenyl)-4-(4-chloro-2-fluoro-phenyl)-4-cyano-5-[4-(2-hydroxy-ethoxy)-2,2-dimethyl-butyl]-pyrrolidine-2-carboxylic acid ((S)-3,4-dihydroxy-butyl)-amide

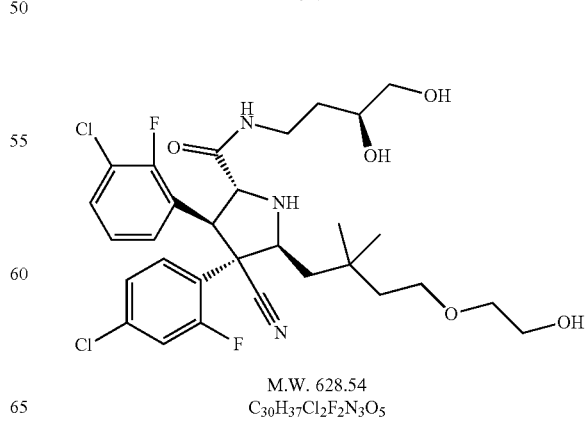

M.W. 628.54
$C_{30}H_{37}Cl_2F_2N_3O_5$

In a manner similar to the method described in Examples 117d and 117e, rac-(2R,3S,4R,5S)-3-(3-chloro-2-fluoro-phenyl)-4-(4-chloro-2-fluoro-phenyl)-4-cyano-5-{2,2-dimethyl-4-[2-(2,2,2-trifluoro-acetoxy)-ethoxy]-butyl}-pyrrolidine-2-carboxylic acid trifluoroacetic acid prepared in Example 119c (0.37 g, 0.58 mmol) was reacted with 2-((S)-2,2-dimethyl-[1,3]dioxolan-4-yl)-ethylamine (0.25 g, 1.7 mmol), HATU (0.4 g, 1 mmol) and iPr$_2$NEt (0.5 mL, 2.9 mmol) in CH$_2$Cl$_2$ at room temperature for 20 h, then treated with aqueous saturated K$_2$CO$_3$ solution in tetrahydrofuran, followed by reaction with aqueous HCl solution in tetrahydrofuran at room temperature to give rac-(2R,3S,4R,5S)-3-(3-chloro-2-fluoro-phenyl)-4-(4-chloro-2-fluoro-phenyl)-4-cyano-5-[4-(2-hydroxy-ethoxy)-2,2-dimethyl-butyl]-pyrrolidine-2-carboxylic acid ((S)-3,4-dihydroxy-butyl)-amide as a light yellow solid (90 mg, 25%).

HRMS (ES$^+$) m/z Calcd for C$_{30}$H$_{37}$Cl$_2$F$_2$N$_3$O$_5$+H [(M+H)$^+$]: 628.2151. found: 628.2150.

Example 120a

Preparation of intermediate [5-azido-3,3-dimethyl-pent-(E)-ylideneamino]-acetic acid tert-butyl ester

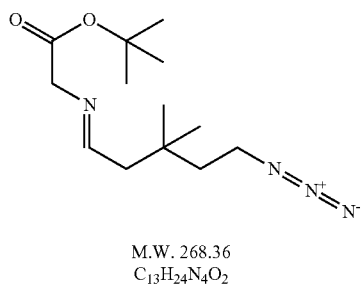 [SMILES: CC(C)(C/C=N/CC(=O)OC(C)(C)C)CCN=[N+]=[N-]]

M.W. 268.36
C$_{13}$H$_{24}$N$_4$O$_2$

Step A To the solution of 5-(tert-butyl-dimethyl-silanyloxy)-3,3-dimethyl-pentan-1-ol (1.1 g, 5 mmol) prepared in Example 116a Step B. and triethylamine (1.39 mL, 10 mmol) in dichloromethane (50 mL) at 0° C. was added a dichloromethane solution (10 mL) of methanesulfonyl chloride (Aldrich) (0.46 mL, 6 mmol). The reaction mixture was stirred at 0° C. for 1 h. Water was added. Organic layer was separated, the aqueous layer was extracted with dichlormethane. The combined organic layers were washed with diluted aqueous HCl solution, saturated aqueous NaHCO$_3$ solution, brine, dried over MgSO$_4$, and concentrated to give methanesulfonic acid 5-(tert-butyl-dimethyl-silanyloxy)-3,3-dimethyl-pentyl ester as a yellow oil (1.48 g, 99%).

Step B To the solution of methanesulfonic acid 5-(tert-butyl-dimethyl-silanyloxy)-3,3-dimethyl-pentyl ester (1.48 g, 4.96 mmol) in anhydrous dimethylformamide (10 mL) was added NaN$_3$ (1.6 g, 25 mmol). The reaction mixture was heated at 60° C. for 18 h. The mixture was cooled, and water was added. The mixture was extracted with ethyl acetate twice. The combined organic layers were washed with saturated aqueous NaHCO$_3$ solution, brine, dried over MgSO$_4$ to give (5-azido-3,3-dimethyl-pentyloxy)-tert-butyl-dimethyl-silane as a yellow oil (0.8 g, 67%).

Step C To a solution of (5-azido-3,3-dimethyl-pentyloxy)-tert-butyl-dimethyl-silane (0.8 g, 3 mmol) in tetrahydrofuran (5 mL) was added tetrahydrofuran solution (1 M, Aldrich) of TBAF (4.9 mL, 4.9 mmol). The reaction mixture was stirred at room temperature for 1 h. The mixture was concentrated, the residue was partitioned between ethyl acetate and water. The organic layer was separated, dried over MgSO$_4$, and concentrated. The residue was purified by chromatography (EtOAc:hexanes=1:3) to give 5-azido-3,3-dimethyl-pentan-1-ol as a colorless oil (0 g, 76%)

Step D To a solution of oxalyl chloride (0.24 mL, 2.7 mmol) (Aldrich) in dichloromethane (12 mL) at −78° C. was added the solution of dimethyl sulfoxide (0.38 mL, 5.5 mmol) in dichloromethane (1 mL) dropwise. After 5 mins, the solution of 5-azido-3,3-dimethyl-pentan-1-ol (0.39 g, 2.5 mmol) in dichloromethane (1 mL) was added dropwise. The reaction mixture was stirred at −78° C. for 15 min. Triethylamine (1.2 mL, 9 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO$_3$, brine, dried over MgSO$_4$, and concentrated to give 5-azido-3,3-dimethyl-pentanal as a yellow oil (Yield: 0.38 g, 99%).

Step C In a manner similar to the method described in Example 1a, glycine tert-butyl ester (0.32 g, 2.45 mmol) was reacted with 5-azido-3,3-dimethyl-pentanal (0.38 g, 2.45 mmol) in CH$_2$Cl$_2$ at room temperature for 18 h to give [5-azido-3,3-dimethyl-pent-(E)-ylideneamino]-acetic acid tert-butyl ester as a yellow oil (0.65 g, 100%).

Example 120b

Preparation of intermediate rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid tert-butyl ester

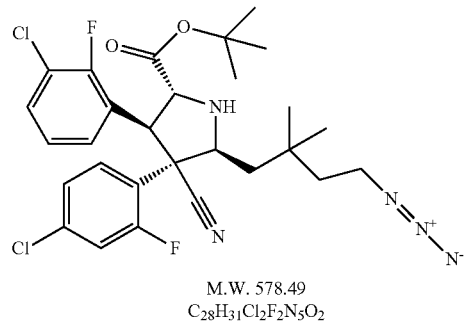 [SMILES: CC(C)(CCN=[NH+][NH-])C[C@@H]1N[C@@H](C(=O)OC(C)(C)C)[C@H](c2cccc(Cl)c2F)[C@@]1(C#N)c1ccc(Cl)cc1F]

M.W. 578.49
C$_{28}$H$_{31}$Cl$_2$F$_2$N$_5$O$_2$

In a manner similar to the method described in Example 100b, [5-azido-3,3-dimethyl-pent-(E)-ylideneamino]-acetic acid tert-butyl ester prepared in Example 120a (0.65 g, 2.45 mmol) was reacted with (Z)-3-(3-chloro-2-fluoro-phenyl)-2-(4-chloro-2-fluoro-phenyl)-acrylonitrile (0.76 g, 2.45 mmol) prepared in Example 52a, AgF (0.47 g, 3.7 mmol), and triethylamine (0.55 mL, 6 mmol) in dichloromethane (80 mL) at room temperature for 18 h, followed by the reaction with DBU (3 ml) in tert-butanol (3 mL) at 100° C. for 2 h to give rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid tert-butyl ester as a yellow gum (0.5 g, 36%).

Example 120c

Preparation of intermediate rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid trifluoroacetic acid

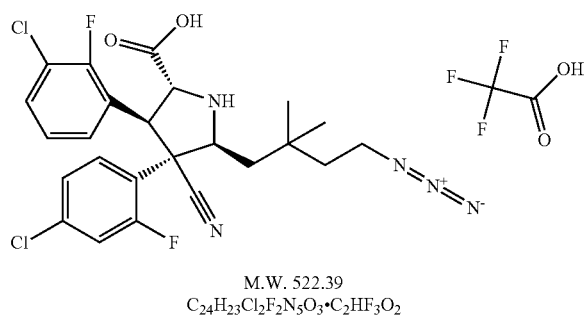 [SMILES: CC(C)(CCN=[N+]=[N-])C[C@@H]1N[C@@H](C(=O)O)[C@H](c2cccc(Cl)c2F)[C@@]1(C#N)c1ccc(Cl)cc1F ; O=C(O)C(F)(F)F]

M.W. 522.39
$C_{24}H_{23}Cl_2F_2N_5O_3 \cdot C_2HF_3O_2$

In a manner similar to the method described in Example 25a, rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid tert-butyl ester prepared in Example 120b (0.5 g, 0.86 mmol) was reacted with trifluoroacetic acid in dichloromethane at room temperature to give rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid trifluoroacetic acid as a yellow solid (0.54 g, 96%).

Example 120d

Preparation of intermediate rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide

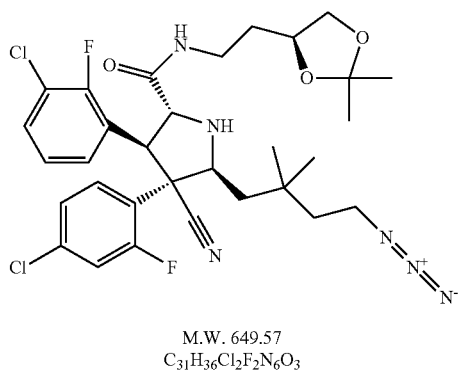 [SMILES: CC(C)(CCN=[N+]=[N-])C[C@@H]1N[C@@H](C(=O)NCC[C@H]2COC(C)(C)O2)[C@H](c2cccc(Cl)c2F)[C@@]1(C#N)c1ccc(Cl)cc1F]

M.W. 649.57
$C_{31}H_{36}Cl_2F_2N_6O_3$

In a manner similar to the method described in Examples 42c, rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid trifluoroacetic acid prepared in Example 120c (0.54 g, 0.85 mmol) was reacted with 2-((S)-2,2-dimethyl-[1,3]dioxolan-4-yl)-ethylamine (0.37 g, 2.54 mmol), HATU (0.58 g, 1.5 mmol) and iPr$_2$NEt (0.74 mL, 4.2 mmol) in CH$_2$Cl$_2$ at room temperature for 20 h, to give rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide as a light yellow solid (0.5 g, 91%).

Example 120e

Preparation of rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide

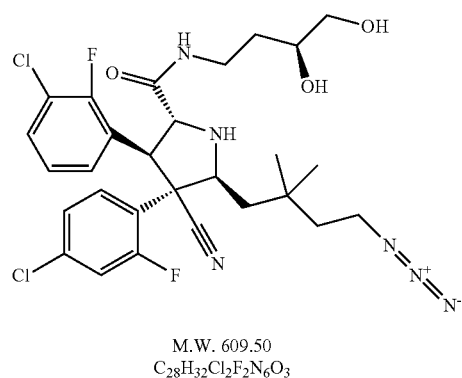 [SMILES: CC(C)(CCN=[N+]=[N-])C[C@@H]1N[C@@H](C(=O)NCC[C@H](O)CO)[C@H](c2cccc(Cl)c2F)[C@@]1(C#N)c1ccc(Cl)cc1F]

M.W. 609.50
$C_{28}H_{32}Cl_2F_2N_6O_3$

In a manner similar to the method described in Examples 42d, rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide prepared in Example 120d (40 mg, 0.06 mmol) was reacted with aqueous HCl solution (1 N, 3 mL, 3 mol) in tetrahydrofuran (7 mL) at room temperature for 2 h to give rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide as a off white solid (29 mg, 79%).

HRMS (ES$^+$) m/z Calcd for $C_{28}H_{32}Cl_2F_2N_6O_3$+H [(M+H)$^+$]: 609.1954. found: 609.1954.

Example 121a

Preparation of intermediate rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide

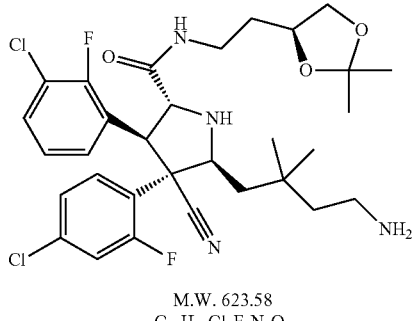

M.W. 623.58
$C_{31}H_{38}Cl_2F_2N_4O_3$

In a manner similar to the method described in Examples 118a, rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide prepared in Example 120d (0.5 g, 0.77 mmol) was treated with $PtO_2$ and $H_2$ in ethyl acetate to give rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide as a black gum (0.47 g, 98%)

Example 121b

Preparation of rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide

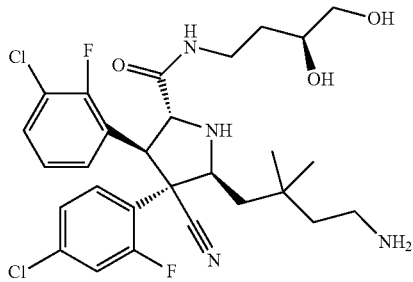

M.W. 583.50
$C_{28}H_{34}Cl_2F_2N_4O_3$

In a manner similar to the method described in Examples 42d, rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide prepared in Example 121a (50 mg, 0.08 mmol) was reacted with aqueous HCl solution (1 N, 3 mL, 3 mol) in tetrahydrofuran (7 mL) at room temperature for 2 h to give rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide as a off white solid (29 mg, 62%).

HRMS (ES$^+$) m/z Calcd for $C_{28}H_{34}Cl_2F_2N_4O_3$+H [(M+H)$^+$]: 583.2049. found: 583.2047.

Example 122a

Preparation of intermediate rac-(2R,3S,4R,5S)-5-(4-acetylamino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide

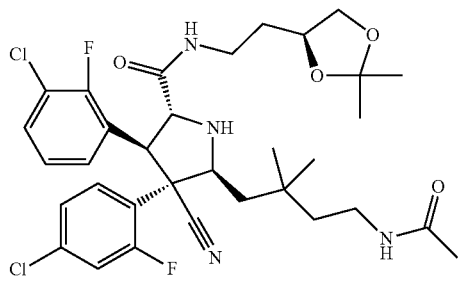

M.W. 665.61
$C_{33}H_{40}Cl_2F_2N_4O_4$

To a solution of rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide (60 mg, 0.096 mmol) prepared in Example 121a and triethylamine (0.033 mL, 0.24 mmol) in tetrahydrofuran (3 mL) was added acetyl chloride (0.08 mL, 0.11 mmol). The reaction mixture was stirred at room temperature for 30 min, then water was added. The mixture was partitioned between ethyl acetate and water. Organic layer was separated, washed with water, brine, dried over $MgSO_4$, and concentrated. The residue was purified by chromatography (2% MeOH in EtOAc) to give rac-(2R,3S,4R,5S)-5-(4-acetylamino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide as a off white gum (60 mg, 94%)

Example 122b

Preparation of rac-(2R,3S,4R,5S)-5-(4-acetylamino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide

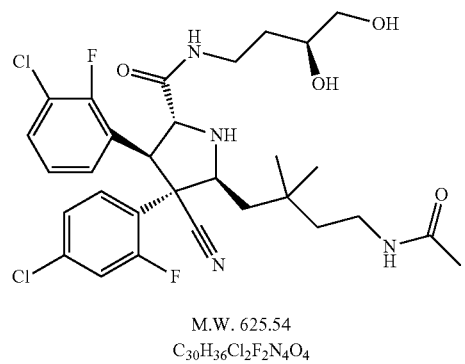 [SMILES: CC(=O)NCCC(C)(C)C[C@@H]1N[C@@H](C(=O)NCC[C@H](O)CO)[C@H](c2cccc(Cl)c2F)[C@@]1(C#N)c1ccc(Cl)cc1F]

M.W. 625.54
$C_{30}H_{36}Cl_2F_2N_4O_4$

In a manner similar to the method described in Examples 42d, rac-(2R,3S,4R,5S)-5-(4-acetylamino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide prepared in Example 122a (60 mg, 0.09 mmol) was reacted with aqueous HCl solution (1 N, 1 mL, 1 mol) in tetrahydrofuran (5 mL) at room temperature for 2 h to give rac-(2R,3S,4R,5S)-5-(4-acetylamino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide as a white solid (50 mg, 89%).

HRMS (ES$^+$) m/z Calcd for $C_{30}H_{36}Cl_2F_2N_4O_4$+H [(M+H)$^+$]: 625.2155. found: 625.2151.

Example 123

Preparation of rac-(2R,3S,4R,5S)-3-(3-chloro-2-fluoro-phenyl)-4-(4-chloro-2-fluoro-phenyl)-4-cyano-5-(4-methanesulfonylamino-2,2-dimethyl-butyl)-pyrrolidine-2-carboxylic acid ((S)-3,4-dihydroxy-butyl)-amide

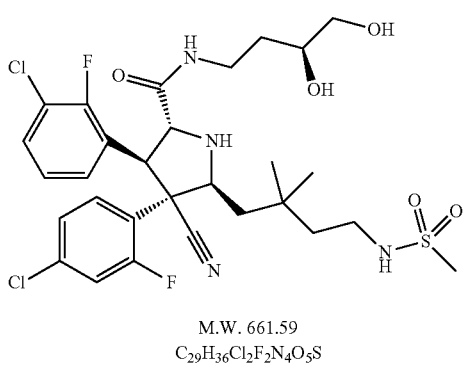 [SMILES: CC(C)(CCNS(C)(=O)=O)C[C@@H]1N[C@@H](C(=O)NCC[C@H](O)CO)[C@H](c2cccc(Cl)c2F)[C@@]1(C#N)c1ccc(Cl)cc1F]

M.W. 661.59
$C_{29}H_{36}Cl_2F_2N_4O_5S$

In a manner similar to the method described in Examples 122a and 122b, rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide (60 mg, 0.096 mmol) prepared in Example 121a was reacted with triethylamine and methanesulfonyl chloride (13 mg, 0.11 mmol) in dichloromethane, followed by the reaction with aqueous HCl solution in tetrahydrofuran to give rac-(2R,3S,4R,5S)-3-(3-chloro-2-fluoro-phenyl)-4-(4-chloro-2-fluoro-phenyl)-4-cyano-5-(4-methanesulfonylamino-2,2-dimethyl-butyl)-pyrrolidine-2-carboxylic acid ((S)-3,4-dihydroxy-butyl)-amide as a off white solid (57 mg, 90%)

HRMS (ES$^+$) m/z Calcd for $C_{29}H_{36}Cl_2F_2N_4O_5S$+H [(M+H)$^+$]: 661.1825. found: 661.1821.

Example 124

Preparation of rac-(2R,3S,4R,5S)-5-(4-benzoylamino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide

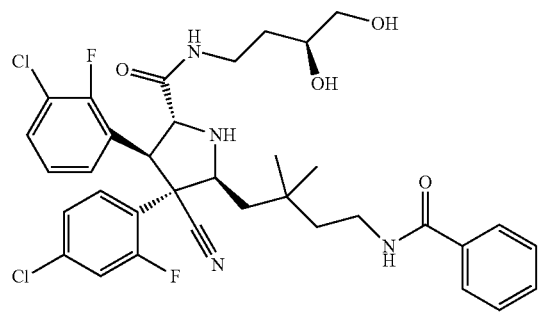

M.W. 687.61
$C_{35}H_{38}Cl_2F_2N_4O_4$

In a manner similar to the method described in Examples 122a and 122b, rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide (80 mg, 0.13 mmol) prepared in Example 121a was reacted with triethylamine and benzoyl chloride (22 mg, 0.16 mmol) in tetrahydrofuran, followed by the reaction with aqueous HCl solution in tetrahydrofuran to give rac-(2R,3S,4R,5S)-5-(4-benzoylamino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide as a off white solid (57 mg, 90%)

HRMS (ES$^+$) m/z Calcd for $C_{35}H_{38}Cl_2F_2N_4O_4$+H [(M+H)$^+$]: 687.2311. found: 687.2308.

Example 125a

Preparation of intermediate [3-methyl-3-(5-methyl-furan-2-yl)-but-(E)-ylideneamino]-acetic acid tert-butyl ester

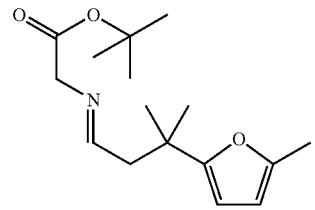

M.W. 279.38
$C_{16}H_{25}NO_3$

Step A To a solution of dimethyl malonate (6.5 g, 49 mmol), 2-acetyl-5-methylfuran (6.1 g, 49 mmol) and pyridine (16 g, 200 mmol) in anhydrous tetrahydrofuran (300 mL) at 0° C. was added a dichloromethane solution (1 M) of TiCl$_4$ (100 mL, 100 mmol) during a period of 1 h. After the addition was finished, the reaction mixture was gradually warmed room temperature and stirred for 18 h. Water was added to quench the reaction. The mixture was extracted with ethyl ether. The organic layer was separated, and the aqueous layer was extracted with ethyl acetate. The organic layers were combined, concentrated. The residue was purified by chromatography (EtOAc:hexanes=1:10) to give 2-[1-(5-methyl-furan-2-yl)-ethylidene]-malonic acid dimethyl ester as a yellow oil (3.7 g, 32%).

Step B To a suspension of CuI (7.61 g, 40 mmol) in anhydrous tetrahydrofuran (100 mL) at −50° C. was added methylmagnesium chloride (3 M, 27 mL, 80 mmol) during a period of 15 min. After the addition was finished, the reaction mixture was gradually warmed room temperature and stirred for 20 min. Then the temperature of the mixture was lowered to −50° C., a tetrahydrofuran solution (50 mL) of 2-[1-(5-methyl-furan-2-yl)-ethylidene]-malonic acid dimethyl ester (3.7 g, 15.5 mmol) was added. The reaction mixture was allowed to slowly warmed to room temperature and stirred for 3 h. Aqueous saturated NH$_4$Cl solution was added to quench the reaction. The mixture was filtered, and the filtrate was concentrated to remove most of tetrahydrofuran. The residue was extracted with ethyl acetate twice. The organic layers were combined, concentrated. The residue was purified by chromatography (EtOAc:hexanes=1:20, 1:10) to give 2-[1- methyl-1-(5-methyl-furan-2-yl)-ethyl]-malonic acid dimethyl ester as a colorless oil (2.5 g, 63%).

Step C To a solution of 2-[1-methyl-1-(5-methyl-furan-2-yl)-ethyl]-malonic acid dimethyl ester (2.5 g, 9.8 mmol) in DMSO (30 mL) was added LiCl (1 g, 23.7 mmol) and $H_2O$ (0.17 mL, 9.8 mmol). The reaction mixture was heated at 170° C. for 3 h, then poured into a ice-water, extracted with ethyl acetate. The organic layer were separated, washed with water, brine, dried over $MgSO_4$, and concentrated. The residue was purified by chromatography (EtOAc:hexanes=1:20, 1:20) to give 3-methyl-3-(5-methyl-furan-2-yl)-butyric acid methyl ester as a colorless oil (1.5 g, 78%).

Step D To a solution of 3-methyl-3-(5-methyl-furan-2-yl)-butyric acid methyl ester (1.5 g, 7.8 mmol) in anhydrous tetrahydrofuran (50 mL) at 0° C. was added a tetrahydrofuran solution (1 M) of $LiAlH_4$ (10 mL, 10 mmol) under nitrogen. The reaction mixture was stirred at 0° C. for 1 h, then poured into a ice-water. The mixture was extracted with ethyl acetate. The organic layer were separated, washed with water, aqueous HCl solution, brine, dried over $MgSO_4$, and concentrated to give 3-methyl-3-(5-methyl-furan-2-yl)-butan-1-ol as a yellow oil (1.2 g, 77%).

Step E To a solution of oxalyl chloride (0.91 g, 7.1 mmol) (Aldrich) in dichloromethane (20 mL) at −78° C. was added the solution of dimethyl sulfoxide (1 mL, 14.3 mmol) in dichloromethane (5 mL) dropwise. After 5 mins, the solution of 3-methyl-3-(5-methyl-furan-2-yl)-butan-1-ol (1.2 g, 7.1 mmol) in dichloromethane (5 mL) was added dropwise. The reaction mixture was stirred at −78° C. for 15 min. Triethylamine (3.6 mL, 26 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated $NaHCO_3$, brine, dried over $MgSO_4$, and concentrated to give 3-methyl-3-(5-methyl-furan-2-yl)-butyraldehyde as a yellow oil (Yield: 1 g, 83%).

Step F In a manner similar to the method described in Example 1a, glycine tert-butyl ester (0.79 g, 6 mmol) was reacted with 3-methyl-3-(5-methyl-furan-2-yl)-butyraldehyde 1 g, 6 mmol) in $CH_2Cl_2$ at room temperature for 5 h to give [3-methyl-3-(5-methyl-furan-2-yl)-but-(E)-ylideneamino]-acetic acid tert-butyl ester as a colorless oil (1.7 g, 100%).

Example 125b

Preparation of intermediate rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid tert-butyl ester

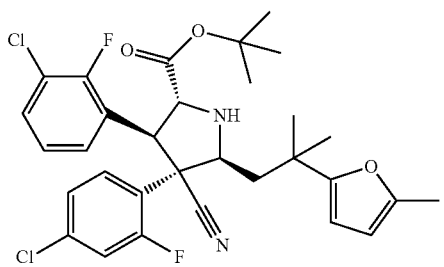

M.W. 589.52
$C_{31}H_{32}Cl_2F_2N_2O_3$

In a manner similar to the method described in Example 100b, [[3-methyl-3-(5-methyl-furan-2-yl)-but-(E)-ylideneamino]-acetic acid tert-butyl ester prepared in Example 125a (1.7 g, 6 mmol) was reacted with (Z)-3-(3-chloro-2-fluoro-phenyl)-2-(4-chloro-2-fluoro-phenyl)-acrylonitrile (1.48 g, 4.8 mmol) prepared in Example 52a, AgF (0.9 g, 7 mmol), and triethylamine (1.7 mL, 12 mmol) in dichloromethane (100 mL) at room temperature for 18 h, followed by the reaction with DBU (5.7 ml) in tert-butanol (10 mL) at 100° C. for 2 h to give rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid tert-butyl ester as a yellow solid (1.3 g, 46%).

Example 125c

Preparation of intermediate rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid trifluoroacetic acid

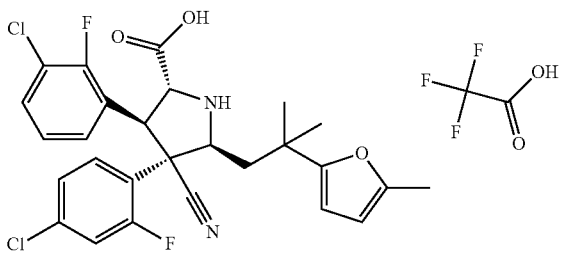

M.W. 533.41
$C_{27}H_{24}Cl_2F_2N_2O_3 \cdot C_2HF_3O_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid tert-butyl ester prepared in Example 125b (1.3 g, 2.2 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid trifluoroacetic acid as a brown solid (1.3 g, 92%).

Example 125d

Preparation of rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid ((S)-3,4-dihydroxy-butyl)-amide

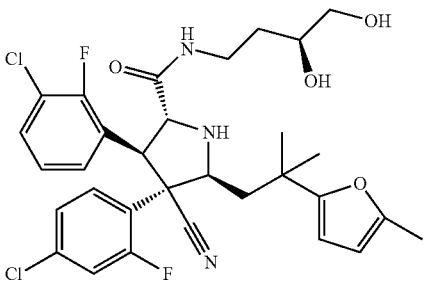

M.W. 620.52
$C_{31}H_{33}Cl_2F_2N_3O_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid trifluoroacetic acid prepared in Example 125c (0.6 g, 0.93 mmol) was reacted with 2-((S)-2,2-dimethyl-[1,3]dioxolan-4-yl)-ethylamine (0.4 g, 2.8 mmol), HATU (0.6 g, 1.7 mmol) and iPr$_2$NEt (0.8 mL, 4.6 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid ((S)-3,4-dihydroxy-butyl)-amide as a white solid (0.16 g, 29%).

HRMS (ES$^+$) m/z Calcd for C$_{31}$H$_{33}$Cl$_2$F$_2$N$_3$O$_4$+H [(M+H)$^+$]: 620.1889 found: 620.1889.

Example 126a

Preparation of intermediate [4-(4-methoxy-phenyl)-3,3-dimethyl-but-(E)-ylideneamino]-acetic acid methyl ester

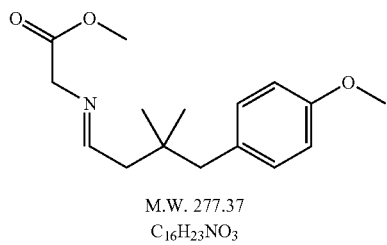 [SMILES: COC(=O)C/N=C/CC(C)(C)Cc1ccc(OC)cc1]

M.W. 277.37
C$_{16}$H$_{23}$NO$_3$

Step A Under Argon, a mixture of NaOH (2.8 g, 70 mmol), tetrabutylammonium iodide (0.6 g, 1.6 mmol) in benzene (8 mL) and H$_2$O (2.8 mL) was heated at 70° C. to form a homogeneous mixture. A mixture of 4-methoxybenzyl chloride (Aldrich) (10 g, 64 mmol) and isobutyraldehyde (5.76 g, 80 mmol) in benzene (22 mL) was added dropwise. The resulting reaction mixture was heated at 70° C. for 3 h. The mixture was cooled, extracted with ethyl acetate. The organic layer was separated, and the aqueous layer was extracted with ethyl acetate. The organic layers were combined, concentrated. The residue was purified by chromatography (EtOAc:hexanes=1:30) to give 2-(4-methoxy-phenyl)-2-methyl-propionaldehyde as a colorless oil (4.1 g, 33%).

Step B To a mixture of methoxymethyl triphenylphosphonium chloride (14.6 g, 42 mmol) in anhydrous tetrahydrofuran (60 mL) at 0° C. was a tetrahydrofuran solution (Aldrich, 1 M) of LiHMDS (42 mL, 42 mmol) dropwise. After the addition was finished, the reaction mixture was stirred at 0° C. for 20 min. Then a tetrahydrofuran solution (40 mL) of 2-(4-methoxy-phenyl)-2-methyl-propionaldehyde (4.1 g, 21 mmol) was added. The reaction mixture was allowed to slowly warmed to room temperature and stirred for 1 h. Water was added to quench the reaction. The mixture was extracted with ethyl acetate twice. The organic layers were combined, concentrated. The residue was purified by chromatography (EtOAc:hexanes=1:30, 1:20) to give a yellow oil (3.5 g). The oil was dissolved into a solution of aqueous HCl solution (2 N, 50 mL, 100 mmol) and tetrahydrofuran (50 mL). The reaction mixture was heated at reflux for 1 h, then cooled to room temperature and concentrated. The residue partitioned between ethyl acetate and water. The organic layer was separated, concentrated. The residue was purified by chromatography (EtOAc:hexanes=1:10, 1:5) to give 3-(4-methoxy-phenyl)-3-methyl-butyraldehyde as a colorless oil (2.1 g, 47%).

Similar transformations have been reported in U.S. Pat. No. 6,531,494 and the procedures described were used without modifications.

Step C In a manner similar to the method described in Example 1a, glycine methyl ester hydrochloride (1.25 g, 10 mmol) was reacted with 3-(4-methoxy-phenyl)-3-methyl-butyraldehyde (2.1 g, 10 mmol and triethylamine (2.2 g, 20 mmol) in CH$_2$Cl$_2$ at room temperature for 5 h to give [4-(4-methoxy-phenyl)-3,3-dimethyl-but-(E)-ylideneamino]-acetic acid methyl ester as a colorless oil (2.7 g, 97%).

Example 126b

Preparation of intermediate rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid methyl ester

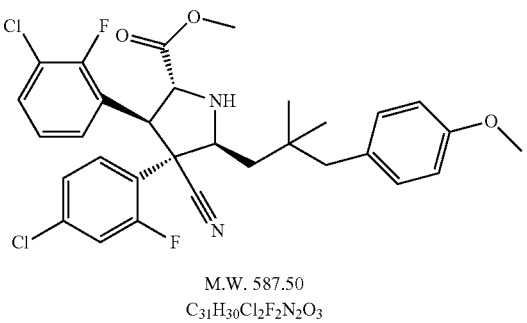 [SMILES: COC(=O)[C@@H]1N[C@@H](CC(C)(C)Cc2ccc(OC)cc2)[C@](C#N)(c2ccc(Cl)cc2F)[C@H]1c1cccc(Cl)c1F]

M.W. 587.50
C$_{31}$H$_{30}$Cl$_2$F$_2$N$_2$O$_3$

In a manner similar to the method described in Example 1c, [4-(4-methoxy-phenyl)-3,3-dimethyl-but-(E)-ylideneamino]-acetic acid methyl ester prepared in Example 126a (2.7 g, 9.7 mmol) was reacted with (Z)-3-(3-chloro-2-fluoro-phenyl)-2-(4-chloro-2-fluoro-phenyl)-acrylonitrile (3.1 g, 10 mmol) prepared in Example 52a, AgF (1.27 g, 10 mmol), and triethylamine (6 g, 60 mmol) in dichloromethane (100 mL) at room temperature for 20 h to give rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid methyl ester as a yellow solid (4 g, 70%).

Example 126c

Preparation of intermediate rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid

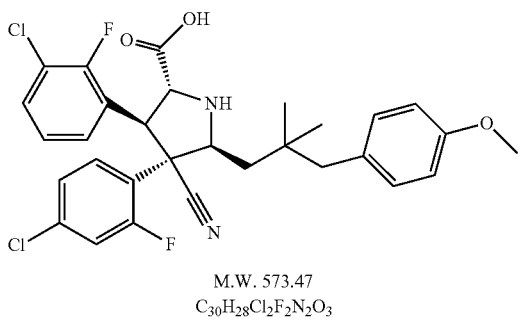 [SMILES: COc1ccc(CC(C)(C)C[C@@H]2N[C@@H](C(=O)O)[C@H](c3cccc(Cl)c3F)[C@@]2(C#N)c2ccc(Cl)cc2F)cc1]

M.W. 573.47
C$_{30}$H$_{28}$Cl$_2$F$_2$N$_2$O$_3$

To rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid methyl ester prepared in Example 126b (4 g, 6.8 mmol) in tetrahydrofuran (60 mL) was added an aqueous solution (1 N) of NaOH (20 mL, 20 mmol) and methanol (20 mL). The reaction mixture was stirred at room temperature for 3 h. The "pH" of the mixture was adjusted to ~4-5 by aqueous HCl solution. The mixture was concentrated. The residue was partitioned between ethyl acetate and water. The organic layer was separated, washed with water, brine, dried over MgSO$_4$, concentrated to give rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid as a light yellow solid (4 g, 100%)

Example 126d

Preparation of rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid ((S)-3,4-dihydroxy-butyl)-amide

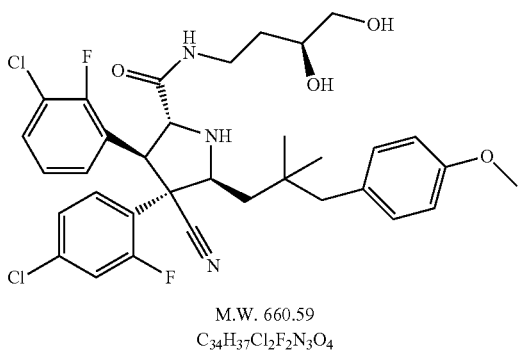 [SMILES: COc1ccc(CC(C)(C)C[C@@H]2N[C@@H](C(=O)NCC[C@H](O)CO)[C@H](c3cccc(Cl)c3F)[C@@]2(C#N)c2ccc(Cl)cc2F)cc1]

M.W. 660.59
$C_{34}H_{37}Cl_2F_2N_3O_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid prepared in Example 126c (0.5 g, 0.87 mmol) was reacted with 2-((S)-2,2-dimethyl-[1,3]dioxolan-4-yl)-ethylamine (0.25 g, 1.7 mmol), HATU (0.6 g, 1.7 mmol) and iPr$_2$NEt (0.45 mL, 2.6 mmol) in CH$_2$Cl$_2$ at room temperature for 20 h, then reacted with aqueous HCl solution in tetrahydrofuran at room temperature to give rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid ((S)-3,4-dihydroxy-butyl)-amide as a white solid (0.16 g, 29%).

HRMS (ES$^+$) m/z Calcd for C$_{34}$H$_{37}$Cl$_2$F$_2$N$_3$O$_4$+H [(M+H)$^+$]: 660.2202. found: 660.2198.

Example 127a

Preparation of intermediate [3-(1-benzyl-1,2,3,6-tetrahydro-pyridin-4-yl)-3-methyl-but-(E)-ylidene-amino]-acetic acid tert-butyl ester

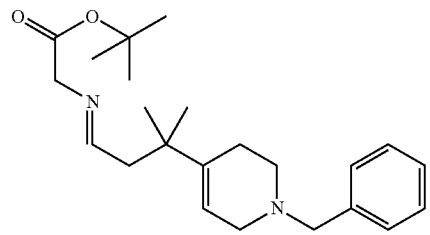

M.W. 370.54
$C_{23}H_{34}N_2O_2$

Step A To a tetrahydrofuran solution (Aldrich, 1.8 M) of LDA (60 mL, 109 mmol) at −50° C. was added isobutyric acid ethyl ester (Alfa) (12.2 mL, 91 mmol) dropwise. The reaction mixture was stirred −50° C. for 1 h, then a tetrahydrofuran solution (10 mL) of 1-benzyl-piperidin-4-one (12 mL, 68 mmol) was added dropwise. The reaction mixture was warmed up to room temperature and stirred for 18 h. Aqueous saturated NH$_4$Cl was added to quench the reaction. The mixture was extracted with ethyl ether. The organic layer was separated, and the aqueous layer was extracted with ethyl ether. The organic layers were combined, washed with brine, water, dried over MgSO$_4$, and concentrated to give 2-(1-benzyl-4-hydroxy-piperidin-4-yl)-2-methyl-propionic acid ethyl ester as an orange oil (18.5 g, 89%).

Step B To a solution of 2-(1-benzyl-4-hydroxy-piperidin-4-yl)-2-methyl-propionic acid ethyl ester (18.5 g, 61 mmol) in chloroform (75 mL) was added thionyl chloride (8.9 mL, 120 mmol) and dimethylformamide (0.17 mL). The reaction mixture was heated at 100° C. for 18 h, then cooled to room temperature and concentrated. To the resulting residue was added aqueous NaOH solution (10 N) to adjust the "pH" of the mixture to basic. The mixture was then extracted with ethyl ether twice. The combined organic extracts were washed with water, brine, dried over MgSO$_4$, and concentrated to give 2-(1-benzyl-1,2,3,6-tetrahydro-pyridin-4-yl)-2-methyl-propionic acid ethyl ester as a brown oil (13 g, 75%).

Step C To a solution of 2-(1-benzyl-1,2,3,6-tetrahydro-pyridin-4-yl)-2-methyl-propionic acid ethyl ester (6 g, 21 mmol) in anhydrous tetrahydrofuran 75 mL) at 0° C. was added a tetrhydrofuran solution (1 M) of LiAlH$_4$ (84 mL, 84 mmol) under nitrogen. The reaction mixture was heated at reflux for 3 h, then cooled to room temperature. Water and aqueous NaOH solution (2N) was added. The mixture was filtered to remove the precipitate, and the filtrate was concentrated. Water was added, and the mixture was extracted with ethyl acetate. The organic layer were separated, washed with water, aqueous HCl solution, brine, dried over MgSO$_4$, and concentrated to give 2-(1-benzyl-1,2,3,6-tetrahydro-pyridin-4-yl)-2-methyl-propan-1-ol as a brown oil (4.73 g, 77%).

Step D To a solution of oxalyl chloride (2.46 mL, 28 mmol) (Aldrich) in dichloromethane (150 mL) at −78° C. was added the solution of dimethyl sulfoxide (4 mL, 56 mmol) in dichloromethane (25 mL) dropwise. After 5 mins, the solution of 2-(1-benzyl-1,2,3,6-tetrahydro-pyridin-4-yl)-2-methyl-propan-1-ol (6.3 g, 25.6 mmol) in dichloromethane (25 mL) was added dropwise. The reaction mixture was stirred at −78° C.

for 15 min. Triethylamine (12.8 mL, 92 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO$_3$, brine, dried over MgSO$_4$, and concentrated to give 2-(1-benzyl-1,2,3,6-tetrahydro-pyridin-4-yl)-2-methyl-propionaldehyde as a brown oil (Yield: 5.6 g, 89%).

Step E To a mixture of methoxymethyl triphenylphosphonium chloride (12.6 g, 37 mmol) in anhydrous tetrahydrofuran (50 mL) at 0° C. was a tetrahydrofuran solution (Aldrich, 1 M) of LiHMDS (46 mL, 46 mmol) dropwise. After the addition was finished, the reaction mixture was stirred at 0° C. for 20 min. Then a tetrahydrofuran solution (40 mL) of 2-(1-benzyl-1,2,3,6-tetrahydro-pyridin-4-yl)-2-methyl-propionaldehyde (5.6 g, 23 mmol) was added. The reaction mixture was stirred at 0° C. for 2 h. Water was added to quench the reaction. The mixture was extracted with ethyl acetate twice. The organic layers were combined, concentrated. The residue was dissolved into a solution of aqueous HCl solution (2 N, 50 mL, 100 mmol) and tetrahydrofuran (50 mL). The reaction mixture was heated at reflux for 30 min, then cooled to room temperature and concentrated. The residue partitioned between ethyl acetate and water. The organic layer was separated, concentrated. The residue was purified by chromatography (EtOAc:hexanes=1:3) to give 3-(1-benzyl-1,2,3,6-tetrahydro-pyridin-4-yl)-3-methyl-butyraldehyde as a yellow oil (1.65 g, 28%).

Step F In a manner similar to the method described in Example 1a, glycine tert-butyl ester (0.84 g, 6.4 mmol) was reacted with 3-(1-benzyl-1,2,3,6-tetrahydro-pyridin-4-yl)-3-methyl-butyraldehyde (1.65 g, 6.4 mmol) in CH$_2$Cl$_2$ at room temperature for 5 h to give [3-(1-benzyl-1,2,3,6-tetrahydro-pyridin-4-yl)-3-methyl-but-(E)-ylideneamino]-acetic acid tert-butyl ester as a yellow oil (2.4 g, 100%).

Example 127b

Preparation of intermediate rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid tert-butyl ester

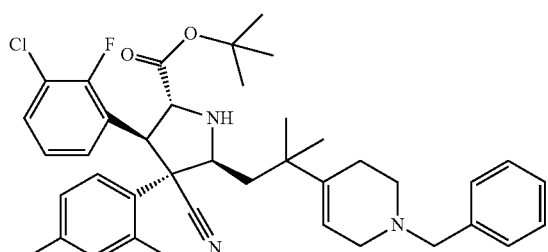

M.W. 680.67
C$_{38}$H$_{41}$Cl$_2$F$_2$N$_3$O$_3$

In a manner similar to the method described in Example 100b, [3-(1-benzyl-1,2,3,6-tetrahydro-pyridin-4-yl)-3-methyl-but-(E)-ylideneamino]-acetic acid tert-butyl ester prepared in Example 127a (2.4 g, 6.4 mmol) was reacted with (Z)-3-(3-chloro-2-fluoro-phenyl)-2-(4-chloro-2-fluoro-phenyl)-acrylonitrile (1.8 g, 6.4 mmol) prepared in Example 52a, AgF (1.3 g, 10 mmol), and triethylamine (2 mL, 14.5 mmol) in dichloromethane (100 mL) at room temperature for 18 h, followed by the reaction with DBU (7 ml) in tert-butanol (30 mL) at 100° C. for 2 h to give rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid tert-butyl ester as a light yellow solid (3.2 g, 81%).

Example 127c

Preparation of intermediate rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid trifluoroacetic acid

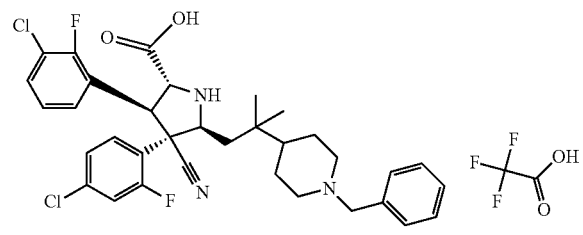

M.W. 626.58
C$_{34}$H$_{35}$Cl$_2$F$_2$N$_3$O$_3$·C$_2$HF$_3$O$_2$

In a manner similar to the method described in Example 25a, rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid tert-butyl ester prepared in Example 127b (1.5 g, 2.2 mmol) was reacted with trifluoroacetic acid in dichloromethane at room temperature to give rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid trifluoroacetic acid as a yellow solid (1.6 g, 98%).

Example 127d

Preparation of intermediate rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide

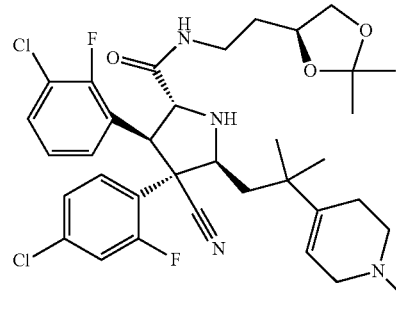

M.W. 751.75
C$_{41}$H$_{46}$Cl$_2$F$_2$N$_4$O$_3$

In a manner similar to the method described in Examples 42c, rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid trifluoroacetic acid prepared in Example 127c (1.6 g, 2.2 mmol) was reacted with 2-((S)-2,2-dimethyl-[1,3]dioxolan-4-yl)-ethylamine (0.94 g, 6.5 mmol), HATU (2.5 g, 6.5 mmol) and iPr$_2$NEt (2.3 mL, 13 mmol) in CH$_2$Cl$_2$ at room temperature for 20 h to give rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide as a light yellow gum (1 g, 83%).

Example 127e

Preparation of rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide

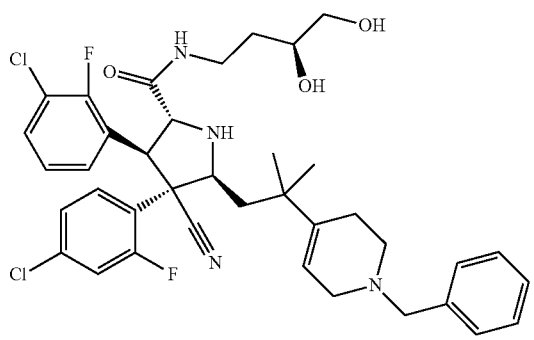

M.W. 711.68
C$_{38}$H$_{42}$Cl$_2$F$_2$N$_4$O$_3$

In a manner similar to the method described in Examples 42d, rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide prepared in Example 127d (1 g, 1.3 mmol) was reacted with aqueous HCl solution (1 N, 5 mL, 5 mol) in tetrahydrofuran (5 mL) at room temperature for 2 h to give rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide as a white solid (0.3 g, 32%).

HRMS (ES$^+$) m/z Calcd for C$_{38}$H$_{42}$Cl$_2$F$_2$N$_4$O$_3$+H [(M+H)$^+$]: 711.2675. found: 711.2675.

Example 128

Preparation of rac-(2R,3S,4R,5S)-5-[2-(1-benzyl-piperidin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide

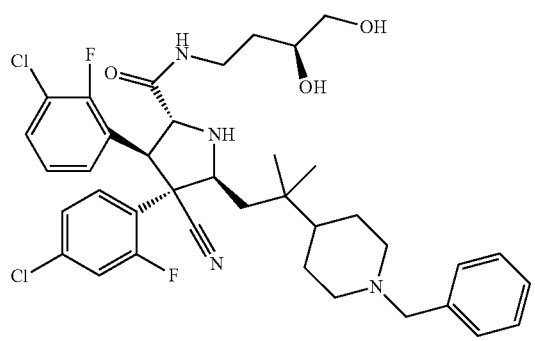

M.W. 713.69
C$_{38}$H$_{44}$Cl$_2$F$_2$N$_4$O$_3$

In a manner similar to the method described in Examples 118a, rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide prepared in Example 127e (60 mg, 0.08 mmol) was treated with PtO$_2$ and H$_2$ in ethyl acetate to give rac-(2R,3S,4R,5S)-5-[2-(1-benzyl-piperidin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide as a off white solid (15 mg, 25%)

HRMS (ES$^+$) m/z Calcd for C$_{38}$H$_{44}$Cl$_2$F$_2$N$_4$O$_3$+H [(M+H)$^+$]: 713.232. found: 713.2837.

Example 129a

Preparation of intermediate [3-(3,6-dihydro-2H-pyran-4-yl)-3-methyl-but-(E)-ylideneamino]-acetic acid tert-butyl ester

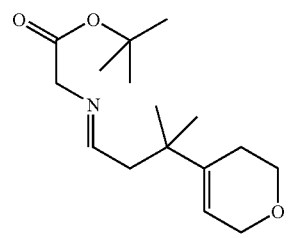

M.W. 281.40
C$_{16}$H$_{27}$NO$_3$

Step A To a hexane solution (Aldrich, 2 M) of LDA (78 mL, 160 mmol) in tetrahydrofuran (100 mL) at −50° C. was added a solution of isobutyric acid ethyl ester (Alfa) (17 mL, 127 mmol) in tetrahydrofuran (20 mL) dropwise. The reaction mixture was stirred −50° C. for 1 h, then a tetrahydrofuran solution (10 mL) of tetrahydro-pyran-4-one (Aldrich) (9.8 g, 98 mmol) was added dropwise. The reaction mixture was warmed up to room temperature and stirred for 18 h. Aqueous saturated NH$_4$Cl was added to quench the reaction. The mixture was extracted with ethyl ether. The organic layer was separated, and the aqueous layer was extracted with ethyl ether. The organic layers were combined, washed with brine, water, dried over MgSO$_4$, and concentrated to give 2-(4-hydroxy-tetrahydro-pyran-4-yl)-2-methyl-propionic acid ethyl ester as a yellow oil (19.5 g, 92%).

Step B To a solution of 2-(4-hydroxy-tetrahydro-pyran-4-yl)-2-methyl-propionic acid ethyl ester (19.5 g, 90 mmol) in chloroform (100 mL) was added thionyl chloride (13.3 mL, 180 mmol) and dimethylformamide (0.28 mL). The reaction mixture was heated at 100° C. for 18 h, then cooled to room temperature and concentrated. To the resulting residue was added aqueous NaOH solution (10 N) to adjust the "pH" of the mixture to basic. The mixture was then extracted with ethyl acetate twice. The combined organic extracts were washed with water, brine, dried over MgSO$_4$, and concentrated to give 2-(3,6-dihydro-2H-pyran-4-yl)-2-methyl-propionic acid ethyl ester as a brown oil (17.6 g, 99%).

Step C To a solution of 2-(3,6-dihydro-2H-pyran-4-yl)-2-methyl-propionic acid ethyl ester (6 g, 30 mmol) in anhydrous tetrahydrofuran (75 mL) at 0° C. was added a tetrahydrofuran solution (1 M) of LiAlH$_4$ (100 mL, 100 mmol) under nitrogen. The reaction mixture was heated at reflux for 3 h, then cooled to room temperature. Water and aqueous NaOH solution (2N) was added. The mixture was filtered to remove the precipitate, and the filtrate was concentrated. Water was added, and the mixture was extracted with ethyl acetate. The organic layer were separated, washed with water, aqueous HCl solution, brine, dried over MgSO$_4$, and concentrated to give 2-(3,6-dihydro-2H-pyran-4-yl)-2-methyl-propan-1-ol as a brown oil (4.63 g, 98%).

Step D To a solution of oxalyl chloride (2.84 mL, 33 mmol) (Aldrich) in dichloromethane (150 mL) at −78° C. was added the solution of dimethyl sulfoxide (4.6 mL, 65 mmol) in dichloromethane (25 mL) dropwise. After 5 mins, the solution of 2-(3,6-dihydro-2H-pyran-4-yl)-2-methyl-propan-1-ol (4.6 g, 29 mmol) in dichloromethane (25 mL) was added dropwise. The reaction mixture was stirred at −78° C. for 15 min. Triethylamine (14.8 mL, 110 mmol) was added and the reaction mixture was slowly warmed up to room temperature and stirred at room temperature for 45 min. Then water was added. The organic layers were separated, and the aqueous layer was extracted with dichloromethane. The organic layers were combined, washed with 10% of HCl, saturated NaHCO$_3$, brine, dried over MgSO$_4$, and concentrated to give 2-(3,6-dihydro-2H-pyran-4-yl)-2-methyl-propionaldehyde as a brown oil (Yield: 5.6 g, 89%).

Step E To a mixture of methoxymethyl triphenylphosphonium chloride (31.3 g, 91 mmol) in anhydrous tetrahydrofuran (150 mL) at 0° C. was a tetrahydrofuran solution (Aldrich, 1 M) of LiHMDS (110 mL, 110 mmol) dropwise. After the addition was finished, the reaction mixture was stirred at 0° C. for 20 min. Then a tetrahydrofuran solution (40 mL) of 2-(3, 6-dihydro-2H-pyran-4-yl)-2-methyl-propionaldehyde (4.4 g, 28.5 mmol) was added. The reaction mixture was stirred at 0° C. for 1 h. Water was added to quench the reaction. The mixture was extracted with ethyl acetate twice. The organic layers were combined, concentrated. The residue was dissolved into a solution of aqueous HCl solution (2 N, 50 mL, 100 mmol) and tetrahydrofuran (50 mL). The reaction mixture was heated at reflux for 30 min, then cooled to room temperature and concentrated. The residue partitioned between ethyl acetate and water. The organic layer was separated, concentrated. The residue was purified by chromatography (EtOAc:hexanes=1:3) to give 3-(3,6-dihydro-2H-pyran-4-yl)-3-methyl-butyraldehyde as a brown oil (2.61 g, 54%).

Step F In a manner similar to the method described in Example 1a, glycine tert-butyl ester (2 g, 15.5 mmol) was reacted with 3-(3,6-dihydro-2H-pyran-4-yl)-3-methyl-butyraldehyde (2.6 g, 15.5 mmol) in CH$_2$Cl$_2$ at room temperature for 5 h to give [3-(3,6-dihydro-2H-pyran-4-yl)-3-methyl-but-(E)-ylideneamino]-acetic acid tert-butyl ester as a yellow oil (4.3 g, 100%).

Example 129b

Preparation of intermediate rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid tert-butyl ester

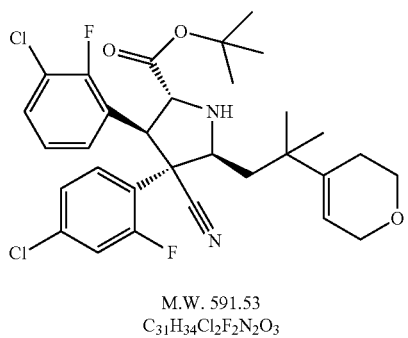 [SMILES: CC(C)(C)OC(=O)[C@@H]1N[C@@H](CC(C)(C)C2=CCOCC2)[C@](C#N)(c2ccc(Cl)cc2F)[C@H]1c1cccc(Cl)c1F]

M.W. 591.53
C$_{31}$H$_{34}$Cl$_2$F$_2$N$_2$O$_3$

In a manner similar to the method described in Example 100b, [3-(3,6-dihydro-2H-pyran-4-yl)-3-methyl-but-(E)-ylideneamino]-acetic acid tert-butyl ester prepared in Example 129a (4.3 g, 15.5 mmol) was reacted with (Z)-3-(3-chloro-2-fluoro-phenyl)-2-(4-chloro-2-fluoro-phenyl)-acrylonitrile (3.8 g, 12.4 mmol) prepared in Example 52a, AgF (2.4 g, 19 mmol), and triethylamine (4.3 mL, 31 mmol) in dichloromethane (100 mL) at room temperature for 18 h, followed by the reaction with DBU (19 ml) in tert-butanol (18 mL) at 100° C. for 2 h to give rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid tert-butyl ester as a yellow gum (5.5 g, 75%).

Example 129c

Preparation of intermediate rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid trifluoroacetic acid

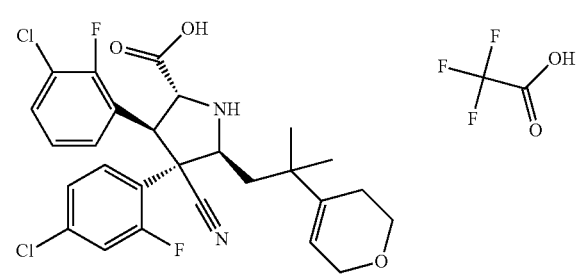

M.W. 535.42
C$_{27}$H$_{26}$Cl$_2$F$_2$N$_3$O$_3$·C$_2$HF$_3$O$_2$

In a manner similar to the method described in Example 25a, rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid tert-butyl ester prepared in Example 129b (5.5 g, 9.29 mmol) was reacted with trifluoroacetic acid in dichloromethane at room temperature to give rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid trifluoroacetic acid as a dark solid (6 g, 99%).

Example 129d

Preparation of intermediate rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid [2-((S)-2,2-dimethyl-[1,3]dioxolan-4-yl)-ethyl]-amide

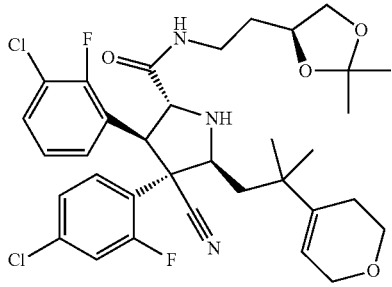

M.W. 662.61
$C_{34}H_{39}Cl_2F_2N_3O_4$

In a manner similar to the method described in Examples 42c, rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid trifluoroacetic acid prepared in Example 129c (0.8 g, 1.2 mmol) was reacted with 2-((S)-2,2-dimethyl-[1,3]dioxolan-4-yl)-ethylamine (0.36 g, 2.5 mmol), HATU (0.84 g, 2.2 mmol) and iPr$_2$NEt (0.64 mL, 3.7 mmol) in CH$_2$Cl$_2$ at room temperature for 20 h to give rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid [2-((S)-2,2-dimethyl-[1,3]dioxolan-4-yl)-ethyl]-amide as a off white gum (0.6 g, 74%).

Example 129e

Preparation of rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid ((S)-3,4-dihydroxy-butyl)-amide

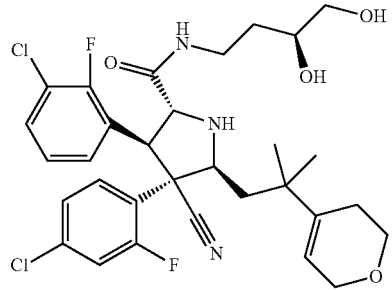

M.W. 622.54
$C_{31}H_{35}Cl_2F_2N_3O_4$

In a manner similar to the method described in Examples 42d, rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid [2-((S)-2,2-dimethyl-[1,3]dioxolan-4-yl)-ethyl]-amide prepared in Example 129d (0.6 g, 0.9 mmol) was reacted with aqueous HCl solution (1 N, 3 mL, 3 mol) in tetrahydrofuran (7 mL) at room temperature for 2 h to give rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid ((S)-3,4-dihydroxy-butyl)-amide as a white solid (0.52 g, 93%).
HRMS (ES$^+$) m/z Calcd for $C_{31}H_{35}Cl_2F_2N_3O_4$+H [(M+H)$^+$]: 622.2046. found: 622.2046.

Example 130

Preparation of rac-(2R,3S,4R,5S)-3-(3-chloro-2-fluoro-phenyl)-4-(4-chloro-2-fluoro-phenyl)-4-cyano-5-[2-methyl-2-(tetrahydro-pyran-4-yl)-propyl]-pyrrolidine-2-carboxylic acid ((S)-3,4-dihydroxy-butyl)-amide

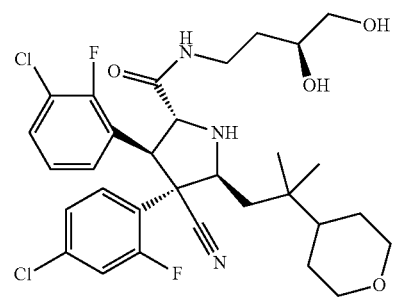

M.W. 624.55
$C_{31}H_{37}Cl_2F_2N_3O_4$

In a manner similar to the method described in Examples 118a, rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid ((S)-3,4-dihydroxy-butyl)-amide prepared in Example 127e (0.28 g, 0.45 mmol) was treated with PtO$_2$ and H$_2$ in ethyl acetate to give rac-(2R,3S,4R,5S)-3-(3-chloro-2-fluoro-phenyl)-4-(4-chloro-2-fluoro-phenyl)-4-cyano-5-[2-methyl-2-(tetrahydro-pyran-4-yl)-propyl]-pyrrolidine-2-carboxylic acid ((S)-3,4-dihydroxy-butyl)-amide as a off white solid (0.15 g, 54%)
HRMS (ES$^+$) m/z Calcd for $C_{31}H_{37}Cl_2F_2N_3O_4$+H [(M+H)$^+$]: 624.2202. found: 624.2207.

Example 131a

Preparation of intermediate 2-((S)-2,2,5,5-tetramethyl-[1,3]dioxolan-4-yl)-ethylamine

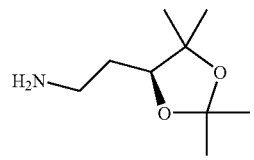

M.W. 173.26
$C_9H_{19}NO_2$

Step A To a suspension of L-(−)-malic acid (Aldrich) (10.3 g, 77 mmol) in 2,2-dimethoxypropane (20 mL) was added p-toluenesulfonic acid monohydrate (0.4 g). The reaction mixture was stirred at room temperature for 30 min. The mixture was partitioned between water and dichloromethane. The organic layer was separated, the aqueous layer was extracted with dichloromethane. The organic layers were combined, washed with water, brine, dried over MgSO$_4$, and concentrated to give ((S)-2,2-dimethyl-5-oxo-[1,3]dioxolan-4-yl)-acetic acid as a white solid (10.1 g, 75%).

Step B To the solution of ((S)-2,2-dimethyl-5-oxo-[1,3]dioxolan-4-yl)-acetic acid (10.1 g, 58 mmol) in anhydrous tetrahydrofuran (20 mL) at 0° C. was added a solution of BH$_3$.THF (1 M, 70 mL, 70 mmol). The reaction mixture was stirred at room temperature for 2 h. Aqueous HCl solution was added, and the mixture was extracted with ethyl acetate. The organic layer was separated, washed with saturated aqueous NaHCO$_3$ solution, brine, dried over MgSO$_4$, and concentrated. The residue was purified by chromatography (EtOAc) to give (S)-5-(2-hydroxy-ethyl)-2,2-dimethyl-[1,3]dioxolan-4-one as a colorless oil (6.8 g, 72%).

Step C A mixture of (S)-5-(2-hydroxy-ethyl)-2,2-dimethyl-[1,3]dioxolan-4-one (6.8 g, 42 mmol) and imidazole (7.5 g, 107 mmol) in dimethylformamide (40 mL) was added tert-butyldimethylchlorosilane (7 g, 45 mmol). The reaction mixture was stirred at room temperature for 18 h. Water was added. The organic layer was separated, the aqueous layer was then extracted with ethyl acetate twice. The combined organic layers were washed with brine, dried over MgSO$_4$, concentrated to give (S)-5-[2-(tert-butyl-dimethyl-silanyloxy)-ethyl]-2,2-dimethyl-[1,3]dioxolan-4-one as a colorless oil (8.6 g, 74%).

Step D To a solution of (S)-5-[2-(tert-butyl-dimethyl-silanyloxy)-ethyl]-2,2-dimethyl-[1,3]dioxolan-4-one (8.5 g, 31 mmol) in diethyl ether (200 mL) at 0° C. was added a diethyl ether (1.6 M) solution of methyllithium (50 mL, 78 mmol) dropwise. The reaction mixture was stirred at 0° C. for 30 min. The mixture was poured into aqueous saturated NH$_4$Cl solution. The organic layer was separated, and the aqueous layer was extracted with ethyl acetate. The organic layers were combined, washed with brine, dried over MgSO$_4$, and concentrated to give (S)-5-(tert-butyl-dimethyl-silanyloxy)-2-methyl-pentane-2,3-diol as a yellow oil (Yield: 6.8 g, 88%).

Step E To a suspension of (S)-5-(tert-butyl-dimethyl-silanyloxy)-2-methyl-pentane-2,3-diol (6.8 g, 27 mmol) in 2,2-dimethoxypropane (35 mL) was added p-toluenesulfonic acid monohydrate (0.2 g). The reaction mixture was stirred at room temperature for 30 min. The mixture was partitioned between water and dichloromethane. The organic layer was separated, the aqueous layer was extracted with dichloromethane. The organic layers were combined, washed with water, brine, dried over MgSO$_4$, and concentrated. The residue was purified by chromatography (EtOAc:hexanes=1:20) to give tert-butyl-dimethyl-[2-((S)-2,2,5,5-tetramethyl-[1,3]dioxolan-4-yl)-ethoxy]-silane as a yellow oil (4.56 g, 58%).

Step F To the solution of tert-butyl-dimethyl-[2-((S)-2,2,5,5-tetramethyl-[1,3]dioxolan-4-yl)-ethoxy]-silane (4.56 g, 15.8 mmol) in tetrahydrofuran (20 mL) at 0° C. was added a solution of tetrabutylammonium fluoride (1 M, 20 mL, 20 mmol). The reaction mixture was stirred at room temperature for 1 h. Water was added, and the mixture was extracted with ethyl acetate. The organic layer was separated, washed with saturated aqueous NaHCO$_3$ solution, brine, dried over MgSO$_4$, and concentrated to give 2-((S)-2,2,5,5-tetramethyl-[1,3]dioxolan-4-yl)-ethanol as a yellow oil (2.7 g, 100%).

Step G To a solution of 2-((S)-2,2,5,5-tetramethyl-[1,3]dioxolan-4-yl)-ethanol (2.7 g, 15.8 mol) and triethylamine (4.6 g, 45 mmol) in dichloromethane (100 mL) at 0° C. was added methanesulfonyl chloride (2.7 g, 24 mmol) dropwise. The reaction mixture was stirred at 0° C. for 1.5 h, then water was added. The organic layer was separated, washed with water, brine, dried over MgSO$_4$, concentrated to give methanesulfonic acid 2-((S)-2,2,5,5-tetramethyl-[1,3]dioxolan-4-yl)-ethyl ester as a yellow oil (2.5 g, 62%).

Step H To a solution of methanesulfonic acid 2-((S)-2,2,5,5-tetramethyl-[1,3]dioxolan-4-yl)-ethyl ester (2.5 g, 9.9 mmol) in N,N-dimethylformamide (50 mL) was added NaN$_3$ (6 g, 70 mmol). The reaction mixture was heated at 95° C. for 4 h. Then the mixture was partitioned between ethyl acetate and water. The organic layer was separated, washed with water, brine several times, dried over MgSO$_4$, concentrated to give (S)-5-(2-azido-ethyl)-2,2,4,4-tetramethyl-[1,3]dioxolane as a yellow oil (1.6 g, 80%).

Step I A suspension of (S)-5-(2-azido-ethyl)-2,2,4,4-tetramethyl-[1,3]dioxolane (1.6 g, 8 mmol) and PtO$_2$ (0.32 g) in ethyl acetate (15 mL) was vigorously shaken in a Parr under atmosphere of H$_2$ (50 psi) for 18 h. The mixture was filtered through a short pad of celite. The filtrate was concentrated to give 2-((S)-2,2,5,5-tetramethyl-[1,3]dioxolan-4-yl)-ethylamine as a colorless oil (1.3 g, 94%).

Example 131b

Preparation of rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide

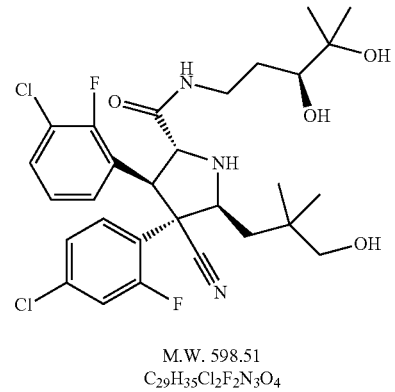 [SMILES: CC(C)(CO)C[C@@H]1N[C@@H](C(=O)NCC[C@H](O)C(C)(C)O)[C@H](c2cccc(Cl)c2F)[C@@]1(C#N)c1ccc(Cl)cc1F]

M.W. 598.51
C$_{29}$H$_{35}$Cl$_2$F$_2$N$_3$O$_4$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid trifluoroacetic acid prepared in Example 105c (0.82 g, 1.37 mmol) was reacted with 2-((S)-2,2,5,5-tetramethyl-[1,3]dioxolan-4-yl)-ethylamine prepared in Example 131a (0.5 g, 2.88 mmol), HATU (0.94 g, 2.5 mmol) and iPr$_2$NEt (1.2 mL, 6.9 mmol) in CH$_2$Cl$_2$ at room temperature for 20 h, then reacted with aqueous HCl solution in tetrahydrofuran at room temperature for 2 h to give rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide as a white solid (0.53 g, 70%).

HRMS (ES$^+$) m/z Calcd for C$_{29}$H$_{35}$Cl$_2$F$_2$N$_3$O$_4$+H [(M+H)$^+$]: 598.2046. found: 598.2047.

Example 131c

Preparation of (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide

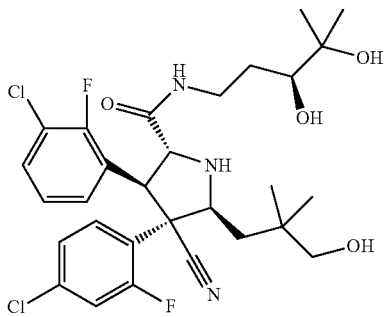

M.W. 598.51
$C_{29}H_{35}Cl_2F_2N_3O_4$

Rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide (0.47 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide as a white solid (0.18 g, 38%) and chiral (2S,3R,4S,5R)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide as a white solid (0.18 g, 38%).

HRMS (ES$^+$) m/z Calcd for $C_{29}H_{35}Cl_2F_2N_3O_4H+H$ [(M+H)$^+$]: 598.2046. found: 598.2045.

Example 132a

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide

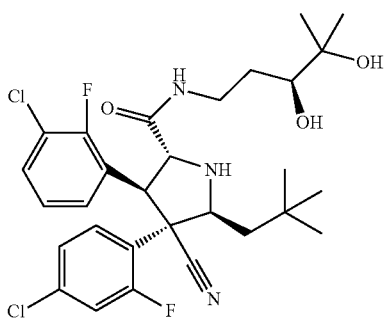

M.W. 582.52
$C_{29}H_{35}Cl_2F_2N_3O_3$

In a manner similar to the method described in Examples 42c, 42d, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.67 g, 1.15 mmol) was reacted with 2-((S)-2,2,5,5-tetramethyl-[1,3]dioxolan-4-yl)-ethylamine prepared in Example 131a (0.4 g, 2.3 mmol), HATU (0.79 g, 2.1 mmol) and iPr$_2$NEt (1 mL, 5.8 mmol) in CH$_2$Cl$_2$ at room temperature for 20 h, then reacted with aqueous HCl solution in tetrahydrofuran at room temperature to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide as a white solid (0.29 g, 43%).

HRMS (ES$^+$) m/z Calcd for $C_{29}H_{35}Cl_2F_2N_3O_3+H$ [(M+H)$^+$]: 582.2097. found: 582.2098.

Example 132b

Preparation of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide

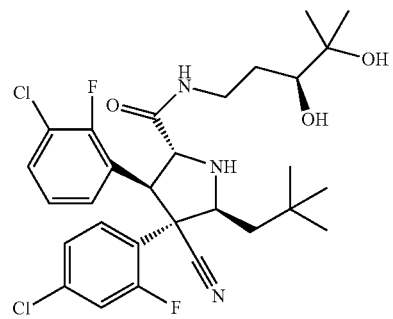

M.W. 582.52
$C_{29}H_{35}Cl_2F_2N_3O_3$

Rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide (0.25 g) was separated by chiral SFC chromatography to provide chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide as a white solid (103 mg, 41%) and chiral-(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide as a white solid (114 mg, 45%).

HRMS (ES$^+$) m/z Calcd for $C_{29}H_{35}Cl_2F_2N_3O_3+H$ [(M+H)$^+$]: 582.2097. found: 582.2098.

Example 133a

Preparation of rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide

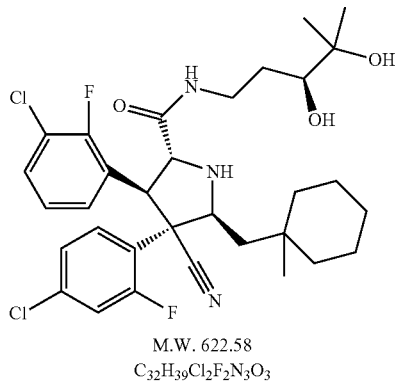 [SMILES: CC1(C[C@@H]2N[C@@H](C(=O)NCC[C@H](O)C(C)(C)O)[C@H](c3cccc(Cl)c3F)[C@@]2(C#N)c2ccc(Cl)cc2F)CCCCC1]

M.W. 622.58
$C_{32}H_{39}Cl_2F_2N_3O_3$

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid trifluoroacetic acid prepared in Example 102c (0.72 g, 1.15 mmol) was reacted with 2-((S)-2,2,5,5-tetramethyl-[1,3]dioxolan-4-yl)-ethylamine prepared in Example 131a (0.4 g, 2.3 mmol), HATU (0.79 g, 2.1 mmol) and iPr₂NEt (1 mL, 5.8 mmol) in CH₂Cl₂ at room temperature for 20 h, then reacted with aqueous HCl solution in tetrahydrofuran at room temperature to give rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide as a white solid (0.25 g, 42%).

HRMS (ES⁺) m/z Calcd for $C_{32}H_{39}Cl_2F_2N_3O_3$+H [(M+H)⁺]: 622.2410. found: 622.2411.

Example 133b

Preparation of (2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide

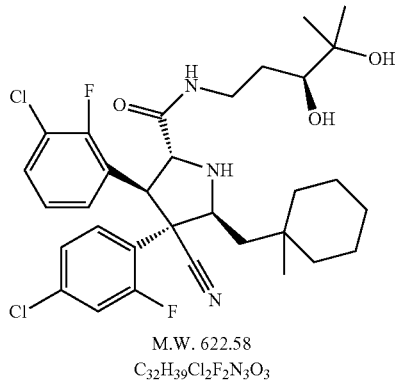 [SMILES: CC1(C[C@@H]2N[C@@H](C(=O)NCC[C@H](O)C(C)(C)O)[C@H](c3cccc(Cl)c3F)[C@@]2(C#N)c2ccc(Cl)cc2F)CCCCC1]

M.W. 622.58
$C_{32}H_{39}Cl_2F_2N_3O_3$

Rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide (0.2 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide as a white solid (61 mg, 32%) and chiral (2S,3R,4S,5R)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide as a white solid (78 mg, 39%).

HRMS (ES⁺) m/z Calcd for $C_{32}H_{39}Cl_2F_2N_3O_3$+H [(M+H)⁺]: 622.2410. found: 622.2412.

Example 134

Preparation of rac-(2S,3R,4S,5R)-4-(3-chloro-2-fluoro-phenyl)-3-(4-chloro-2-fluoro-phenyl)-2-(2,2-dimethyl-propyl)-5-(3-hydroxy-azetidine-1-carbonyl)-pyrrolidine-3-carbonitrile

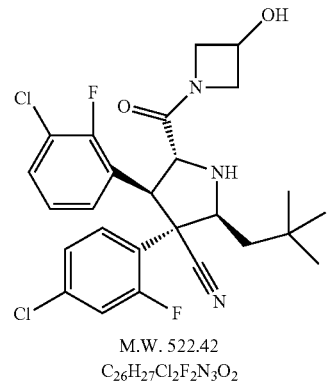 [SMILES: CC(C)(C)C[C@@H]1N[C@@H](C(=O)N2CC(O)C2)[C@H](c2cccc(Cl)c2F)[C@@]1(C#N)c1ccc(Cl)cc1F]

M.W. 522.42
$C_{26}H_{27}Cl_2F_2N_3O_2$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.25 g, 0.43 mmol) was reacted with azetidin-3-ol hydrochloride (Matrix) (0.25 g, 2.7 mmol), HATU (0.4 g, 1 mmol) and iPr₂NEt (0.6 g, 4.6 mmol) in CH₂Cl₂ at room temperature for 20 h to give rac-(2S,3R,4S,5R)-4-(3-chloro-2-fluoro-phenyl)-3-(4-chloro-2-fluoro-phenyl)-2-(2,2-dimethyl-propyl)-5-(3-hydroxy-azetidine-1-carbonyl)-pyrrolidine-3-carbonitrile as a white solid (0.2 g, 89%).

HRMS (ES⁺) m/z Calcd for $C_{26}H_{27}Cl_2F_2N_3O_2$+H [(M+H)⁺]: 522.1521. found: 522.1520.

Example 135a

Preparation of rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1H-pyrazol-3-yl]-amide

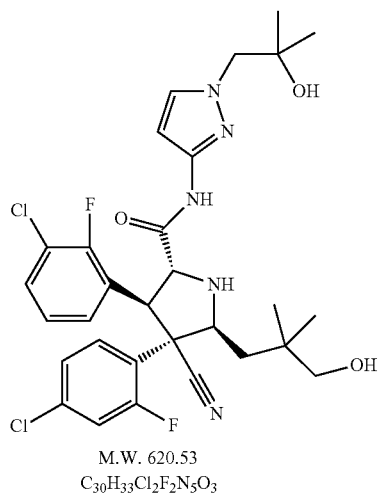 [SMILES: CC(C)(O)Cn1ccc(NC(=O)[C@@H]2N[C@@H](CC(C)(C)CO)[C@](C#N)(c3ccc(Cl)cc3F)[C@H]2c2cccc(Cl)c2F)n1]

M.W. 620.53
$C_{30}H_{33}Cl_2F_2N_5O_3$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid trifluoroacetic acid prepared in Example 105c (0.55 g, 0.92 mmol) was reacted with 1-(3-amino-pyrazol-1-yl)-2-methyl-propan-2-ol (0.17 g, 1.1 mmol), EDCI (0.26 g, 1.38 mmol), HOBT (0.19 g, 1.4 mmol) and NEt₃ (0.26 mL, 1.8 mmol) in CH₂Cl₂ at room temperature for 20 h to give rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1H-pyrazol-3-yl]-amide as a white solid (0.11 g, 20%).

HRMS (ES⁺) m/z Calcd for $C_{30}H_{33}Cl_2F_2N_5O_3+H$ [(M+H)⁺]: 620.2002. found: 620.1997.

Example 135b

Preparation of (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1H-pyrazol-3-yl]-amide

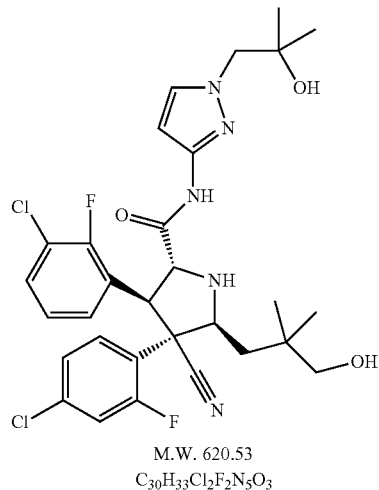 [SMILES: CC(C)(O)Cn1ccc(NC(=O)[C@@H]2N[C@@H](CC(C)(C)CO)[C@](C#N)(c3ccc(Cl)cc3F)[C@H]2c2cccc(Cl)c2F)n1]

M.W. 620.53
$C_{30}H_{33}Cl_2F_2N_5O_3$

Rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1H-pyrazol-3-yl]-amide (0.11 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid (([1-(2-hydroxy-2-methyl-propyl)-1H-pyrazol-3-yl]-amide as a white solid (40 mg, 36%) and chiral (2S,3R,4S,5R)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1H-pyrazol-3-yl]-amide as a white solid (39 mg, 35%).

HRMS (ES⁺) m/z Calcd for $C_{30}H_{33}Cl_2F_2N_5O_3+H$ [(M+H)⁺]: 620.2002. found: 620.1999.

Example 136a

Preparation of rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide

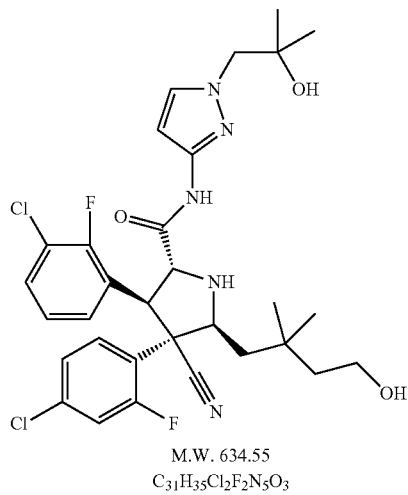 [SMILES: CC(C)(O)Cn1ccc(NC(=O)[C@@H]2N[C@@H](CC(C)(C)CCO)[C@](C#N)(c3ccc(Cl)cc3F)[C@H]2c2cccc(Cl)c2F)n1]

M.W. 634.55
$C_{31}H_{35}Cl_2F_2N_5O_3$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid prepared in Example 116c (0.48 g, 0.78 mmol) was reacted with 1-(3-amino-pyrazol-1-yl)-2-methyl-propan-2-ol (0.15 g, 0.9 mmol), HATU (0.6 g, 1.6 mmol) and iPr₂NEt (0.41 mL, 2.4 mmol) in CH₂Cl₂ at room temperature for 20 h to give rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide as a white solid (0.27 g, 55%).

HRMS (ES⁺) m/z Calcd for $C_{31}H_{35}Cl_2F_2N_5O_3+H$ [(M+H)⁺]: 634.2158 found: 634.2153.

Example 136b

Preparation of (2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide

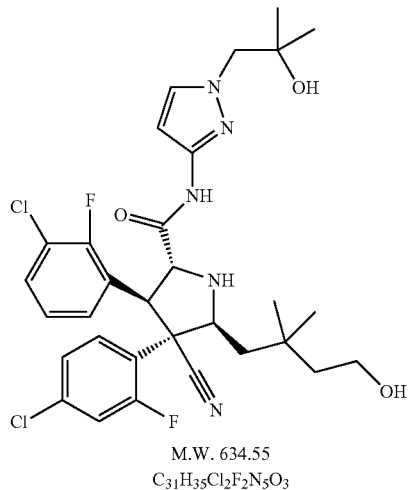 [SMILES: CC(C)(O)Cn1ccc(NC(=O)[C@@H]2N[C@@H](CC(C)(C)CCO)[C@](C#N)(c3ccc(Cl)cc3F)[C@H]2c2cccc(Cl)c2F)n1]

M.W. 634.55
$C_{31}H_{35}Cl_2F_2N_5O_3$

Rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide (0.25 g) was separated by chiral SFC chromatography to provide chiral (2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide as a white solid (105 mg, 42%) and chiral (2S,3R,4S,5R)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide as a white solid (105 mg, 42%).

HRMS (ES$^+$) m/z Calcd for $C_{31}H_{35}Cl_2F_2N_5O_3$+H [(M+H)$^+$]: 634.2158. found: 634.2157.

Example 137

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid amide

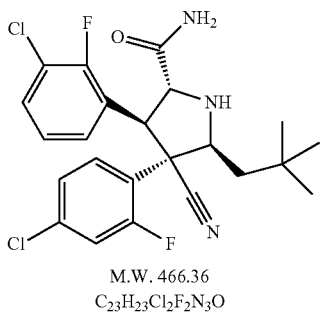 [SMILES: CC(C)(C)C[C@@H]1N[C@@H](C(N)=O)[C@H](c2cccc(Cl)c2F)[C@@]1(C#N)c1ccc(Cl)cc1F]

M.W. 466.36
$C_{23}H_{23}Cl_2F_2N_3O$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.5 g, 0.86 mmol) was reacted with a dioxane solution (0.5 M) of ammonia (2 mL, 1 mmol), HATU (0.38 g, 1 mmol) and iPr$_2$NEt (0.6 g, 4.6 mmol) in CH$_2$Cl$_2$ at room temperature for 20 h to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid amide as a white solid (0.3 g, 75%).

HRMS (ES$^+$) m/z Calcd for $C_{23}H_{23}Cl_2F_2N_3O$+H [(M+H)$^+$]: 466.1259. found: 466.1259.

Example 138

Preparation of rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-nicotinic acid methyl ester

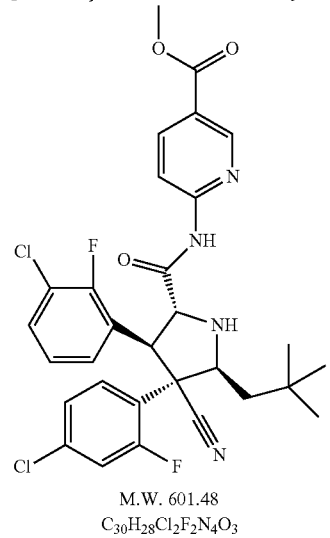

M.W. 601.48
$C_{30}H_{28}Cl_2F_2N_4O_3$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.5 g, 0.86 mmol) was reacted with 6-amino-nicotinic acid methyl ester (Aldrich) (0.3 g, 2 mmol), HATU (0.38 g, 1 mmol) and iPr$_2$NEt (0.6 g, 4.6 mmol) in CH$_2$Cl$_2$ at room temperature for 20 h to give rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-nicotinic acid methyl ester as a white solid (0.3 g, 58%).

HRMS (ES$^+$) m/z Calcd for $C_{30}H_{28}Cl_2F_2N_4O_3$+H [(M+H)$^+$]: 601.1580. found: 601.1578.

Example 139

Preparation of rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-N-(2-hydroxy-1,1-dimethyl-ethyl)-nicotinamide

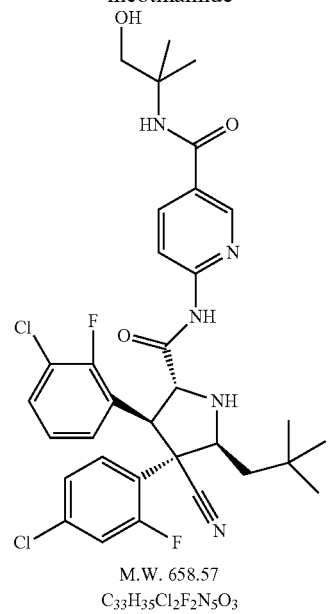

M.W. 658.57
$C_{33}H_{35}Cl_2F_2N_5O_3$

To a solution of rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-nicotinic acid methyl ester prepared in Example 138 (0.2 g, 0.33 mmol) in tetrahydrofuran (3 mL) was added an aqueous solution (1 N) of NaOH (1 mL, 1 mmol) and methanol (1 mL). The reaction mixture was stirred at room temperature for 20 h, and the "pH" of the solution was adjusted to 5-6 by aqueous HCl solution. The mixture was extracted ethyl acetate twice. The combined organic extracts were washed with water, brine, dried over $MgSO_4$, and concentrated to give rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-nicotinic acid as a white foam (0.12 g). In a manner similar to the method described in Examples 1e, rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-nicotinic acid (0.12 g, 0.2 mmol) was reacted with 2-amino-2-methyl-1-propanol (Aldrich) (0.1 g, 1.1 mmol), HATU (0.2 g, 0.5 mmol) and $iPr_2NEt$ (0.3 g, 2.3 mmol) in $CH_2Cl_2$ at room temperature for 20 h to give rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-N-(2-hydroxy-1,1-dimethyl-ethyl)-nicotinamide as a white solid (30 mg, 22%).

HRMS ($ES^+$) m/z Calcd for $C_{33}H_{35}Cl_2F_2N_5O_3$+H [(M+H)$^+$]: 658.2158. found: 658.2155.

Example 140

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-acetylamino-pyridin-3-yl)-amide

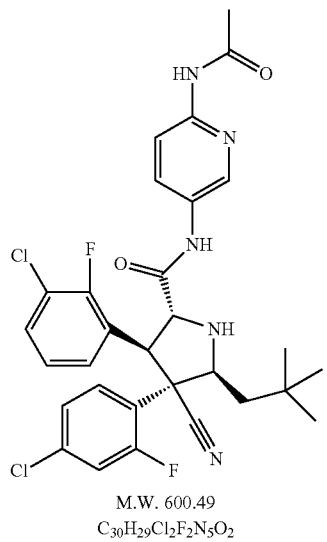 [SMILES: CC(=O)Nc1ccc(NC(=O)[C@@H]2N[C@@H](CC(C)(C)C)[C@](C#N)(c3ccc(Cl)cc3F)[C@H]2c2cccc(Cl)c2F)cn1]

M.W. 600.49
$C_{30}H_{29}Cl_2F_2N_5O_2$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.16 g, 0.28 mmol) was reacted with N-(5-amino-pyridin-2-yl)-acetamide (Aldrich) (0.12 g, 0.79 mmol), HATU (0.1 g, 0.26 mmol) and $iPr_2NEt$ (0.2 g, 1.5 mmol) in $CH_2Cl_2$ at room temperature for 20 h to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-acetylamino-pyridin-3-yl)-amide as a white solid (0.15 g, 89%).

HRMS ($ES^+$) m/z Calcd for $C_{30}H_{29}Cl_2F_2N_5O_2$+H [(M+H)$^+$]: 600.1739. found: 600.1739.

Example 141a

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide

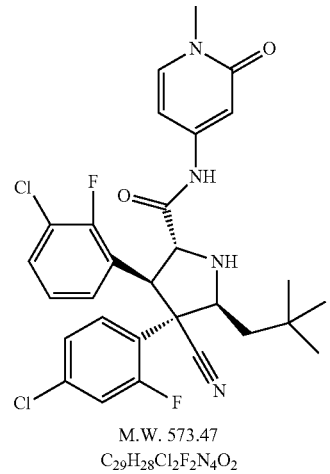 [SMILES: Cn1ccc(NC(=O)[C@@H]2N[C@@H](CC(C)(C)C)[C@](C#N)(c3ccc(Cl)cc3F)[C@H]2c2cccc(Cl)c2F)cc1=O]

M.W. 573.47
$C_{29}H_{28}Cl_2F_2N_4O_2$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.2 g, 0.43 mmol) was vented with 4-amino-1-methyl-1H-pyridin-2-one (Molbridge) (0.11 g, 0.86 mmol), HATU (0.29 g, 0.77 mmol) and $iPr_2NEt$ (0.15 mL, 0.86 mmol) in $CH_2Cl_2$ at room temperature for 20 h to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide as a white solid (35 mg, 14%).

HRMS ($ES^+$) m/z Calcd for $C_{29}H_{28}Cl_2F_2N_4O_2$+H [(M+H)$^+$]: 573.1630. found: 573.1633.

Example 141b

Preparation of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide

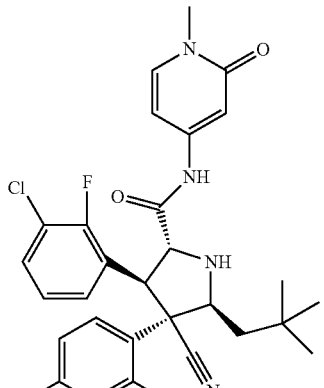

M.W. 573.47
C29H28Cl2F2N4O2

Rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide (68 mg) was separated by chiral SFC chromatography to provide chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide as a white solid (16 mg, 24%) and chiral-(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide as a white solid (16 mg, 24%).

HRMS (ES+) m/z Calcd for $C_{29}H_{28}Cl_2F_2N_4O_2$+H [(M+H)+]: 573.1630. found: 573.1626.

Example 142

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [5-((S)-1,2-dihydroxy-ethyl)-pyrazin-2-yl]-amide

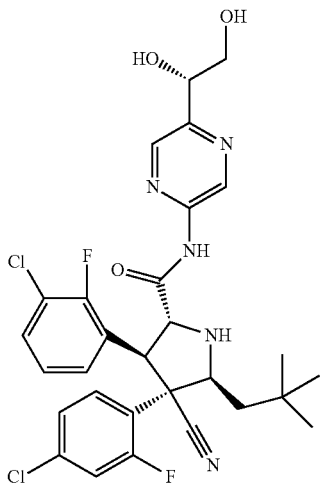

M.W. 604.48
C29H29Cl2F2N5O3

In a manner similar to the method described in Examples 42c and 42d, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.1 g, 0.2 mmol) was reacted with 5-((S)-2,2-dimethyl-[1,3]dioxolan-4-yl)-pyrazin-2-ylamine (46 mg, 0.24 mmol), T3P (Aldrich) (0.32 mL, 0.53 mmol) and iPr2NEt (0.11 mL, 0.64 mmol) in CH2Cl2 at room temperature for 20 h, then reacted with aqueous HCl solution in tetrahydrofuran at room temperature to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [5-((S)-1,2-dihydroxy-ethyl)-pyrazin-2-yl]-amide as a white solid (14 mg, 11%).

HRMS (ES+) m/z Calcd for $C_{29}H_{29}Cl_2F_2N_5O_3$+H [(M+H)+]: 604.1689. found: 604.1687.

Example 143

Preparation of rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid (1-methyl-2-oxo-1,2-dihydro-pyridin-4-yl)-amide

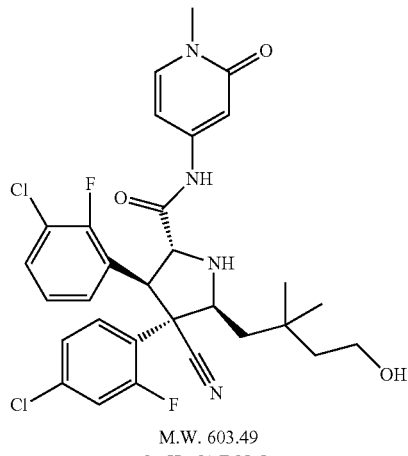

M.W. 603.49
C30H30Cl2F2N4O3

In a manner similar to the method described in Examples 1e, rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid trifluoroacetic acid prepared in Example 116c (0.5 g, 0.8 mmol) was reacted with 4-amino-1-methyl-1H-pyridin-2-one (Molbridge) (0.18 g, 1.5 mmol), HATU (0.62 g, 1.6 mmol) and iPr2NEt (0.71 mL, 4.1 mmol) in CH2Cl2 at room temperature for 20 h to give rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid (1-methyl-2-oxo-1,2-dihydro-pyridin-4-yl)-amide as a white solid (25 mg, 5.1%).

HRMS (ES+) m/z Calcd for $C_{30}H_{30}Cl_2F_2N_4O_3$+H [(M+H)+]: 603.1736. found: 603.1730.

Example 144

Preparation of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid methyl ester

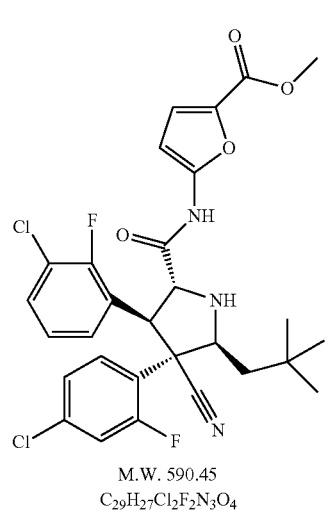 [SMILES: COC(=O)c1ccc(NC(=O)[C@@H]2N[C@@H](CC(C)(C)C)[C@](C#N)(c3ccc(Cl)cc3F)[C@H]2c2cccc(Cl)c2F)o1]

M.W. 590.45
$C_{29}H_{27}Cl_2F_2N_3O_4$

To a solution of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.5 g, 1.07 mmol) in dichloromethane (5 mL) at 0° C. was added oxalyl chloride (0.11 mL, 1.28 mmol) and DMF (0.03 mL). The reaction mixture was stirred at 0° C. for 3 h, then concentrated. The residue was dissolved into dichloromethane (5 mL), triethylamine (0.45 mL, 3.2 mmol) and DMAP (20 mg, 0.14 mmol) were added, followed by the addition of methyl 5-amino-2-furate (Lancaster) (0.38 g, 2.7 mmol). The reaction mixture was stirred at room temperature for 4 h. Water was added, and the mixture was extracted with dichloromethane twice. The organic layers were combined, washed with water, brine, dried over MgSO$_4$, and concentrated. The residue was purified by chromatography (EtOAc:hexanes=1:3) to give rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid methyl ester as a off white solid (0.1 g, 16%).

HRMS (ES$^+$) m/z Calcd for $C_{29}H_{27}Cl_2F_2N_3O_4$+H [(M+H)$^+$]: 590.1420. found: 500.1418.

Example 145

Preparation of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid

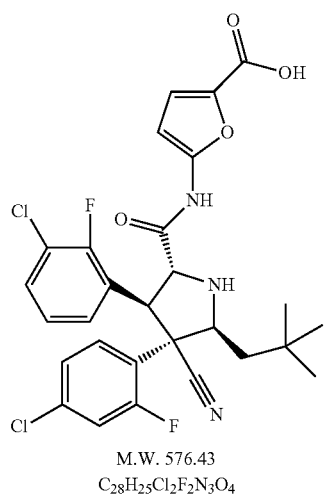 [SMILES: CC(C)(C)C[C@@H]1N[C@@H](C(=O)Nc2ccc(C(=O)O)o2)[C@H](c2cccc(Cl)c2F)[C@@]1(C#N)c1ccc(Cl)cc1F]

M.W. 576.43
$C_{28}H_{25}Cl_2F_2N_3O_4$

To a solution of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid methyl ester prepared in Example 144 (80 mg, 0.14 mmol) in tetrahydrofuran (2 mL) was added an aqueous solution (2 mL) of LiOH (32 mg, 1.35 mmol). The reaction mixture was stirred at room temperature for 66 h, and the "pH" of the solution was adjusted to 5-6 by aqueous HCl solution. The mixture was extracted ethyl acetate twice. The combined organic extracts were washed with water, brine, dried over MgSO$_4$, and concentrated to give rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid as a yellow solid (60 mg, 74%).

HRMS (ES$^+$) m/z Calcd for $C_{28}H_{25}Cl_2F_2N_3O_4$+H [(M+H)$^+$]: 576.1263. found: 576.1264.

Example 146

Preparation of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid amide

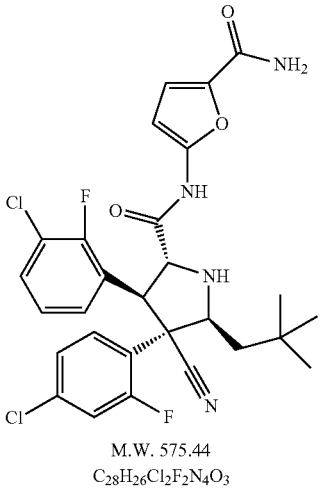 [SMILES: CC(C)(C)C[C@@H]1N[C@@H](C(=O)Nc2ccc(C(N)=O)o2)[C@H](c2cccc(Cl)c2F)[C@@]1(C#N)c1ccc(Cl)cc1F]

M.W. 575.44
$C_{28}H_{26}Cl_2F_2N_4O_3$

To a solution of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid prepared in Example 145 (60 mg, 0.1 mmol) in N,N-dimethylformamide (2 mL) was added NH$_4$Cl (28 mg, 0.5 mmol), EDCI (40 mg, 0.2 mmol), HOBT (28 mg, 0.2 mmol) and NEt$_3$ (0.029 mL, 0.2 mmol). The reaction mixture was heated at 75° C. for 20 h. The mixture was cooled to room temperature, and partitioned between ethyl acetate and water. The organic layer was separated, and the aqueous layer was extracted with ethyl acetate. The organic layers were combined, washed with water, brine, dried over MgSO$_4$, and concentrated. The residue was purified by chromatography (EtOAc) to give rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid amide as a white solid (30 mg, 50%).

HRMS (ES$^+$) m/z Calcd for $C_{28}H_{26}Cl_2F_2N_4O_3$+H [(M+H)$^+$]: 575.1423. found: 575.1425.

Example 147

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-chloro-pyridazin-3-yl)-amide

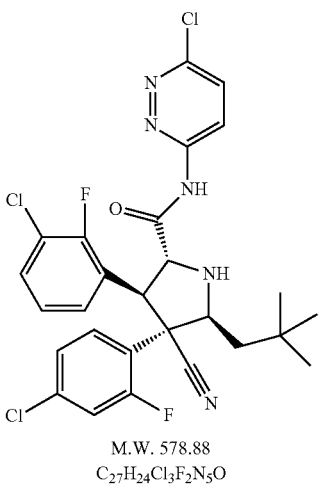 [SMILES: CC(C)(C)C[C@@H]1N[C@@H](C(=O)Nc2ccc(Cl)nn2)[C@H](c2cccc(Cl)c2F)[C@@]1(C#N)c1ccc(Cl)cc1F]

M.W. 578.88
$C_{27}H_{24}Cl_3F_2N_5O$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.3 g, 0.51 mmol) was reacted with 3-amino-6-chloro-pyridazine (Alfa) (0.15 g, 1.2 mmol), HATU (0.2 g, 0.5 mmol) and iPr$_2$NEt (0.6 g, 4.6 mmol) in CH$_2$Cl$_2$ at room temperature for 48 h to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-chloro-pyridazin-3-yl)-amide as a yellow solid (0.15 g, 51%).

Example 148

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-methyl-pyridin-3-yl)-amide

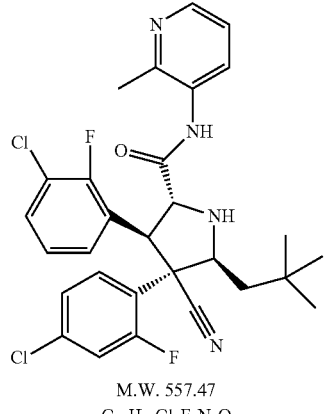

M.W. 557.47
$C_{29}H_{28}Cl_2F_2N_4O$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (0.3 g, 0.52 mmol) was reacted with 3-amino-2-methyl-pyridine (Aldrich) (0.11 g, 1.1 mmol), HATU (0.36 g, 0.94 mmol) and iPr$_2$NEt (0.27 g, 1.6 mmol) in CH$_2$Cl$_2$ at room temperature for 20 h to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-methyl-pyridin-3-yl)-amide as a yellow solid (0.16 g, 55%).

HRMS (ES$^+$) m/z Calcd for $C_{29}H_{28}Cl_2F_2N_4O$+H [(M+H)$^+$]: 557.1681. found: 557.1677.

Example 149a

Preparation of intermediate 2-(4-amino-phenoxy)-ethanol

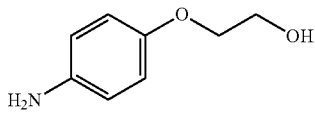

M.W. 153.18
C₈H₁₁NO₂

A suspension of 2-(4-nitrophenoxy)ethanol (Aldrich) (2 g, 10.9 mmol) and Pd/C (Aldrich, 10%, 0.2 g) in methanol (50 mL) was vigorously shaken in a Parr under atmosphere of H$_2$ (50 psi) for 1 h. The mixture was filtered through a short pad of celite. The filtrate was concentrated to give 2-(4-amino-phenoxy)-ethanol as a light yellow solid (1.6 g, 96%).

Example 149b

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide

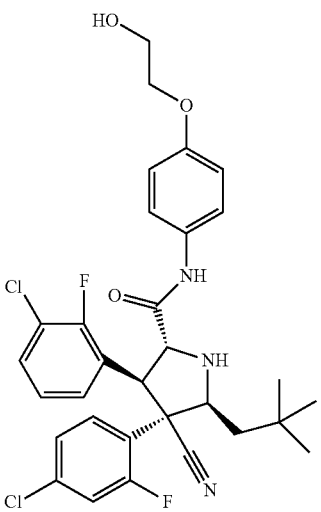

M.W. 602.51
C₃₁H₃₁Cl₂F₂N₃O₃

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.4 g, 0.86 mmol) was reacted with 2-(4-amino-phenoxy)-ethanol (0.24 g, 1.5 mmol), HATU (0.58 g, 1.5 mmol) and iPr₂NEt (0.3 mL, 1.7 mmol) in CH₂Cl₂ (20 mL) at room temperature for 20 h to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide as a white solid (0.4 g, 78%).

HRMS (ES⁺) m/z Calcd for C₃₁H₃₁Cl₂F₂N₃O₃+H [(M+H)⁺]: 602.1784. found: 602.1783.

Example 149c

Preparation of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide

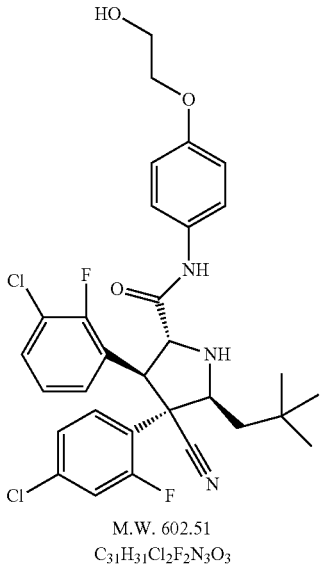 [SMILES: CC(C)(C)C[C@@H]1N[C@@H](C(=O)Nc2ccc(OCCO)cc2)[C@H](c2cccc(Cl)c2F)[C@@]1(C#N)c1ccc(Cl)cc1F]

M.W. 602.51
C₃₁H₃₁Cl₂F₂N₃O₃

Rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide (0.25 g) was separated by chiral SFC chromatography to provide chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide as a white solid (94 mg, 37%) and chiral-(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide as a white solid (100 mg, 40%).

HRMS (ES⁺) m/z Calcd for C₃₁H₃₁Cl₂F₂N₃O₃+H [(M+H)⁺]: 602.1784. found: 602.1784.

Example 150

Preparation of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid methyl ester

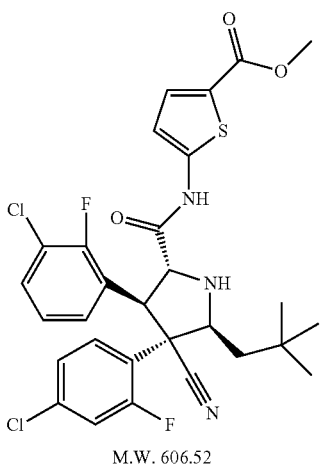

M.W. 606.52
C₂₉H₂₇Cl₂F₂N₃O₃S

In a manner similar to the method described in Examples 144, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.3 g, 0.64 mmol) was reacted with oxalyl chloride (0.12 mL, 1.4 mmol), triethylamine (0.22 mL, 1.6 mmol), DMAP (5 mg), and 5-amino-2-thiophene-carboxylate (Princeton) (0.14 g, 0.96 mmol) to give rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid methyl ester as a yellow solid (0.11 g, 28%).

HRMS (ES$^+$) m/z Calcd for $C_{29}H_{27}Cl_2F_2N_3O_3S$+H [(M+H)$^+$]: 606.1191. found: 606.1191.

Example 151a

Preparation of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid

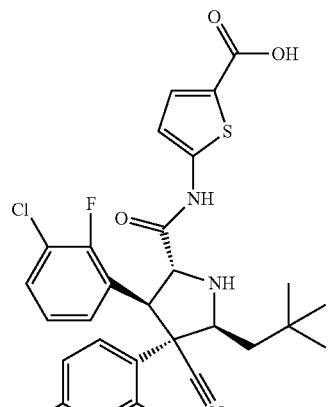

M.W. 592.49
$C_{28}H_{25}Cl_2F_2N_3O_3S$

To a solution of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid methyl ester prepared in Example 150 (90 mg, 0.15 mmol) in tetrahydrofuran (3 mL) was added an aqueous solution (3 mL) of LiOH (36 mg, 1.5 mmol). The reaction mixture was stirred at room temperature for 66 h, and the "pH" of the solution was adjusted to 5 by aqueous HCl solution. The mixture was extracted with ethyl acetate twice. The combined organic extracts were washed with water, brine, dried over MgSO$_4$, and concentrated to give rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid as a yellow solid (60 mg, 74%).

HRMS (ES$^+$) m/z Calcd for $C_{28}H_{25}O_2F_2N_3O_3S$+H [(M+H)$^+$]: 592.1035. found: 592.1035.

Example 151b

Preparation of 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid

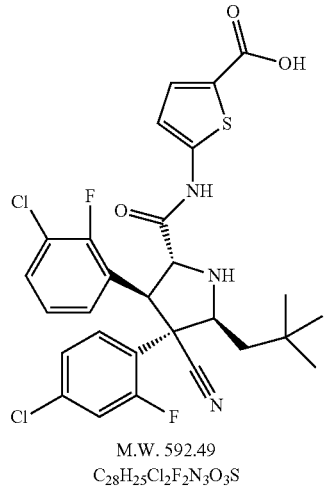 [SMILES: CC(C)(C)C[C@@H]1N[C@@H](C(=O)Nc2ccc(C(=O)O)s2)[C@H](c2cccc(Cl)c2F)[C@@]1(C#N)c1ccc(Cl)cc1F]

M.W. 592.49
$C_{28}H_{25}Cl_2F_2N_3O_3S$

Rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid (50 mg) was separated by chiral SFC chromatography to provide chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid as a white solid (12 mg, 24%) and chiral 5-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid as a white solid (12 mg, 24%).

HRMS (ES$^+$) m/z Calcd for $C_{28}H_{25}Cl_2F_2N_3O_3S$+H [(M+H)$^+$]: 592.1035. found: 592.1035.

Example 152

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-methoxy-pyridin-4-yl)-amide

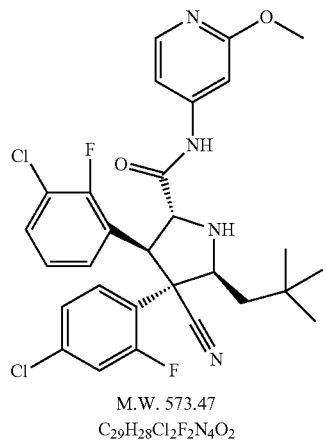 [SMILES: COc1cc(NC(=O)[C@@H]2N[C@@H](CC(C)(C)C)[C@](C#N)(c3ccc(Cl)cc3F)[C@H]2c2cccc(Cl)c2F)ccn1]

M.W. 573.47
$C_{29}H_{28}Cl_2F_2N_4O_2$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.4 g, 0.75 mmol) was reacted with 2-methoxy-pyridin-4-ylamine (Oakwood) (0.1 g, 0.9 mmol), HATU (0.51 g, 1.35 mmol) and iPr$_2$NEt (0.33 mL, 1.9 mmol) in CH$_2$Cl$_2$ at room temperature to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-methoxy-pyridin-4-yl)-amide as a white solid (0.2 g, 47%).

HRMS (ES$^+$) m/z Calcd for C$_{29}$H$_{28}$Cl$_2$F$_2$N$_4$O$_2$S+H [(M+H)$^+$]: 573.1630. found: 573.1633.

Example 153

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-hydroxy-pyridin-4-yl)-amide

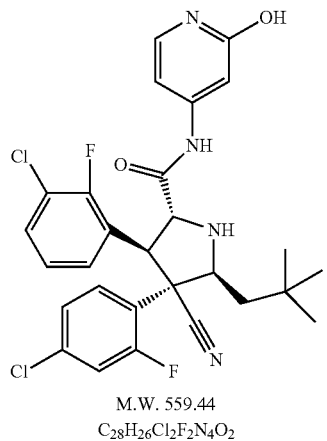 [SMILES: CC(C)(C)C[C@@H]1N[C@@H](C(=O)Nc2ccnc(O)c2)[C@H](c2cccc(Cl)c2F)[C@@]1(C#N)c1ccc(Cl)cc1F]

M.W. 559.44
C$_{28}$H$_{26}$Cl$_2$F$_2$N$_4$O$_2$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.49 g, 1.1 mmol) was reacted with 4-amino-pyridin-2-ol (Molbridge) (0.14 g, 1.3 mmol), HATU (0.72 g, 1.9 mmol) and iPr$_2$NEt (0.46 mL, 2.6 mmol) in CH$_2$Cl$_2$ at room temperature to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-hydroxy-pyridin-4-yl)-amide as a off white solid (20 mg, 3.4%).

HRMS (ES$^+$) m/z Calcd for C$_{28}$H$_{26}$Cl$_2$F$_2$N$_4$O$_2$S+H [(M+H)$^+$]: 559.1474. found: 559.1477.

Example 154

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetyl-phenyl)-amide

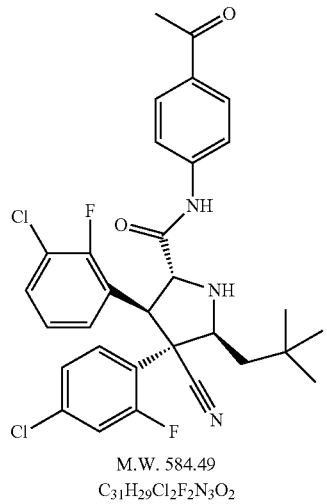 [SMILES: CC(=O)c1ccc(NC(=O)[C@@H]2N[C@@H](CC(C)(C)C)[C@](C#N)(c3ccc(Cl)cc3F)[C@H]2c2cccc(Cl)c2F)cc1]

M.W. 584.49
C$_{31}$H$_{29}$Cl$_2$F$_2$N$_3$O$_2$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.35 g, 0.75 mmol) was reacted with 1-(4-amino-phenyl)-ethanone (Aldrich) (0.12 g, 0.9 mmol), HATU (0.5 g, 1.3 mmol) and iPr$_2$NEt (0.33 mL, 2.6 mmol) in CH$_2$Cl$_2$ at room temperature to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetyl-phenyl)-amide as a white solid (0.12 g, 27%).

HRMS (ES$^+$) m/z Calcd for C$_{31}$H$_{29}$Cl$_2$F$_2$N$_3$O$_2$S+H [(M+H)$^+$]: 584.1678. found: 584.1680.

Example 155

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-bromo-acetyl)-phenyl]-amide

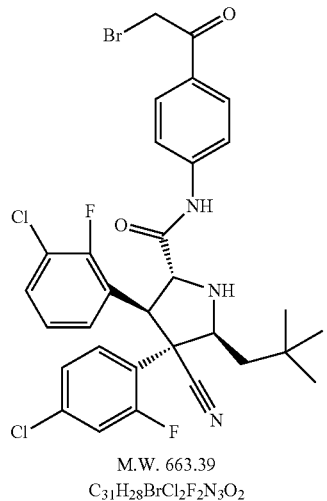 [SMILES: CC(C)(C)C[C@@H]1N[C@@H](C(=O)Nc2ccc(C(=O)CBr)cc2)[C@H](c2cccc(Cl)c2F)[C@@]1(C#N)c1ccc(Cl)cc1F]

M.W. 663.39
C$_{31}$H$_{28}$BrCl$_2$F$_2$N$_3$O$_2$

269

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.35 g, 0.75 mmol) was reacted with 1-(4-amino-phenyl)-2-bromo-ethanone (Astatech) (0.17 g, 0.9 mmol), HATU (0.5 g, 1.3 mmol) and iPr$_2$NEt (0.33 mL, 2.6 mmol) in CH$_2$Cl$_2$ at room temperature to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-bromo-acetyl)-phenyl]-amide as a white solid (36 mg, 7%).

HRMS (ES$^+$) m/z Calcd for C$_{31}$H$_{28}$BrCl$_2$F$_2$N$_3$O$_2$S+H [(M+H)$^+$]: 662.0783. found: 662.0782.

Example 156

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-dimethylamino-acetyl)-phenyl]-amide

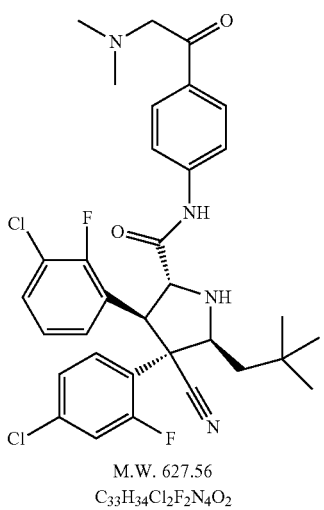 [SMILES: CN(C)CC(=O)c1ccc(NC(=O)[C@@H]2N[C@@H](CC(C)(C)C)[C@](C#N)(c3ccc(Cl)cc3F)[C@H]2c2cccc(Cl)c2F)cc1]

M.W. 627.56
C$_{33}$H$_{34}$Cl$_2$F$_2$N$_4$O$_2$

To the solution of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-bromo-acetyl)-phenyl]-amide (30 mg, 0.045 mmol) in tetrahydrofuran (1 mL) was added a tetrahydrofuran solution (2 M) of dimethylamine (0.057 mL, 0.11 mmol). The reaction mixture was stirred at room temperature for 30 min. The mixture was concentrated, and the residue was partitioned between ethyl acetate and water. The organic layer was separated, washed with water, brine, dried over MgSO$_4$, and concentrated to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-dimethylamino-acetyl)-phenyl]-amide as a yellow solid (10 mg, 35%)

HRMS (ES$^+$) m/z Calcd for C$_{33}$H$_{34}$Cl$_2$F$_2$N$_4$O$_2$S+H [(M+H)$^+$]: 627.2100. found: 627.2102.

270

Example 157

Preparation of 4-chloro-3-fluoro-phenyl)-acetonitrile

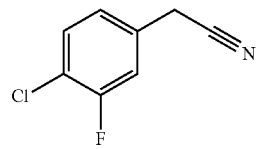 [SMILES: N#CCc1ccc(Cl)c(F)c1]

To a solution of 4-bromo-1-chloro-2-fluoro-benzene in diisopropl ether (50 mL) at −78° C. was added t-butyllithium maintaining the temperature below −70° C. A white precipitate formed. After 30 minutes, zinc chloride was added, maintaining the temperature below −50° C. The resulting mixture was added to a solution of bromoacetonitrile (0.8 mL, 12.1 mmol), nickel(II) acetylacetonate (0.1485 g, 0.578 mmol), and tri-o-tolylphosphine (0.1787 g, 0.578 mmol) in THF (100 mL) and the reaction heated under reflux for 2 hours with pentane removed by distillation. The reaction was concentrated under reduced pressure and partitioned between ethyl acetate and 2N aqueous sodium hydroxide solution. The organic layer was retained and the aqueous layer re-extracted with ethyl acetate. The organic portions were combined, washed with brine, dried over MgSO$_4$, filtered and concentrated under reduced pressure to give a brown oil. Purification by column chromatography, 40 g silica column, (1 to 100% EtOAc/heptane) to yield 4-chloro-3-fluoro-phenyl)-acetonitrile, 0.47 g, 33.6%.

Example 158

Preparation of (Z)-3-(3-chloro-2-fluoro-phenyl)-2-(4-chloro-3-fluoro-phenyl)-acrylonitrile

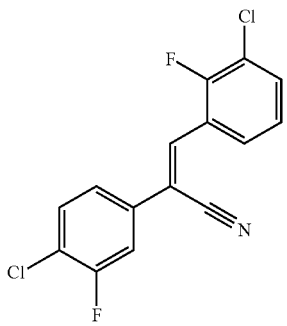 [SMILES: N#C/C(=C\c1cccc(Cl)c1F)c1ccc(Cl)c(F)c1]

A mixture of 4-chloro-3-fluorobenzylcyanide (1.0 g, 5.92 mmol), 3-chloro-2-fluorobenzaldehyde (0.938 g, 5.92 mmol), 2 N NaOH (4 mL) and isopropyl alcohol were stirred at rt. The mixture was stirred for 10 min. to afford a solid ppt that was collected by filtration with multiple water washes. The solid was dried ON under reduced pressure to afford a white solid (Z)-3-(3-chloro-2-fluoro-phenyl)-2-(4-chloro-3-fluoro-phenyl)-acrylonitrile, 1.62 g, 89.3%;

HRMS (ES$^+$) m/z Calcd for C$_{15}$H$_7$Cl$_2$F$_2$N+H [(M+H)$^+$]: 308.9924. found: 308.9926.

Example 159

Preparation of rac-(2S,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid tert-butyl ester and rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid tert-butyl ester

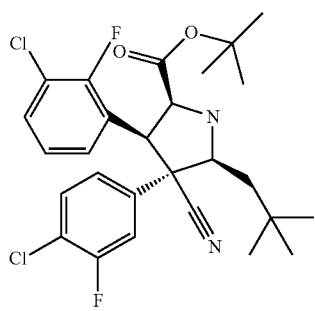

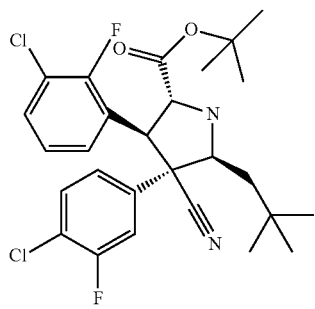

M.W. 523.46
$C_{27}H_{30}Cl_2F_2N_2O_2$

To a solution of (Z)-3-(3-chloro-2-fluoro-phenyl)-2-(4-chloro-3-fluoro-phenyl)-acrylonitrile and [3,3-dimethyl-but-(Z)-ylideneamino]-acetic acid tert-butyl ester in dichloroethane (20 mL) was added TEA (1.46 mL, 10.44 mmol), AgF (0.661 g, 5.22 mmol) and stirred at RT overnight. The mixture was then quenched with NH$_4$Cl (satd) solution and extracted with CH$_2$Cl$_2$. The organic phase was separated, filtered through celite and dried over Na$_2$SO$_4$. the solvent was removed by reduced pressure to yield crude oil that was purified with silica column chromatography (1-20% EtOAc/heptane) to yield two products; rac-(2S,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid tert-butyl ester (0.410 g, 15%) as a yellow solid. HRMS (ES$^+$) m/z Calcd for $C_{27}H_{30}Cl_2F_2N_2O_2S+H$ [(M+H)$^+$]: 523.1725. found: 523.1725. and rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid tert-butyl ester (0.92 g, 33.7%) as an yellow solid. HRMS (ES$^+$) m/z Oiled for $C_{27}H_{30}Cl_2F_2N_2O_2S+H$ [(M+H)$^+$]: 523.1725. found: 523.1722.

Example 160

Preparation of rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid

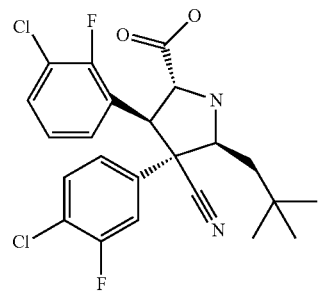

M.W. 467.35
$C_{23}H_{22}Cl_2F_2N_2O_2$

A mixture of rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid tert-butyl ester (0.6 g, 1.15 mmol) was cooled to 0° C., then conc. H$_2$SO$_4$ (2 mL) was added slowly. The reaction was stirred at RT for 2 hours. The mixture was then poured into ice and extracted with EtOAc. The organic phase was separated, dried over Na$_2$SO$_4$, filtered and solvent was removed under reduced pressure to yield a residue that was triturated with ethyl acetate/heptane and the precipitates were collected by filtration and washed with ether to yield the product rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid (0.526 g, 98.1%) as a white solid. HRMS (ES$^+$) m/z Calcd for $C_{23}H_{22}Cl_2F_2N_2O_2S+H$ [(M+H)$^+$]: 467.1099. found: 467.1097.

Example 161

Preparation of rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid [2-((S)-2,2-dimethyl-[1,3]dioxolan-4-yl)-ethyl]-amide

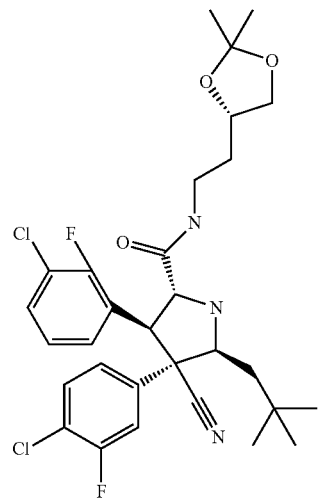

M.W. 594.53
$C_{30}H_{35}Cl_2F_2N_3O_3$

A mixture rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid (125 mg, 0.267 mmol), 2-((S)-2,2-dimethyl-[1,3]dioxolan-4-yl)-ethylamine (0.2 mg, 1.3 mmol), 2-(7-azabenzotriazol-1-yl)-n,n,n',n'-tetramethyluronium hexafluorophosphate (HATU, 114.1 mg, 0.3 mmol) and iPr$_2$NEt (0.3 mL, 3.22 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid [2-((S)-2,2-dimethyl-[1,3]dioxolan-4-yl)-ethyl]-amide (101 mg, 63.5%) as an off-white powder. HRMS (ES$^+$) m/z Calcd for C$_{30}$H$_{35}$Cl$_2$N$_3$O$_3$S+H [(M+H)$^+$]: 594.2097. found: 594.2096.

Example 162

Preparation of rac-(2R,3S,4R,5S)-3-(3-chloro-2-fluoro-phenyl)-4-(4-chloro-3-fluoro-phenyl)-4-cyano-5-(2,2-dimethyl-propyl)-pyrrolidine-2-carboxylic acid ((S)-3,4-dihydroxy-butyl)-amide and rac-(2S,3R,4S,5R)-3-(3-chloro-2-fluoro-phenyl)-4-(4-chloro-3-fluoro-phenyl)-4-cyano-5-(2,2-dimethyl-propyl)-pyrrolidine-2-carboxylic acid ((S)-3,4-dihydroxy-butyl)-amide

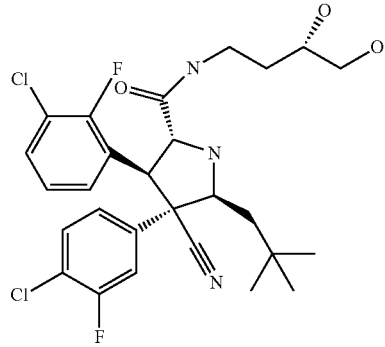

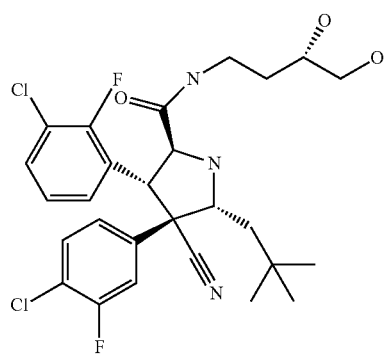

M.W. 554.47
C$_{27}$H$_{31}$Cl$_2$F$_2$N$_3$O$_3$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,2-dimethyl-[1,3]dioxolan-4-ylmethyl)-1H-pyrazol-3-yl]-amide (81 mg, 0.133 mmol), pyridinium p-toluene sulfonic acid (5 mg, 0.0198 mmol) and methanol (4 mL) was microwaved at 120° C. for 5 min. Solvent evaporated and purified by reverse phase chromatography (20-95% of ACN/water) to rac-(2R,3S,4R,5S)-3-(3-Chloro-2-fluoro-phenyl)-4-(4-chloro-3-fluoro-phenyl)-4-cyano-5-(2,2-dimethyl-propyl)-pyrrolidine-2-carboxylic acid ((S)-3,4-dihydroxy-butyl)-amide (20.7 mg, 22%) as a white powder. HRMS (ES$^+$) m/z Calcd for C$_{27}$H$_{31}$Cl$_2$F$_2$N$_3$O$_3$S+H [(M+H)$^+$]: 554.1784. found: 554.1780. rac-(2S,3R,4S,5R)-3-(3-chloro-2-fluoro-phenyl)-4-(4-chloro-3-fluoro-phenyl)-4-cyano-5-(2,2-dimethyl-propyl)-pyrrolidine-2-carboxylic acid ((S)-3,4-dihydroxy-butyl)-amide (18.8 mg, 20%) as a white powder. HRMS (ES$^+$) m/z Calcd for C$_{27}$H$_{31}$Cl$_2$F$_2$N$_3$O$_3$+H [(M+H)$^+$]: 554.1784. found: 554.1781.

Example 163

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1-pyrazol-3-yl]-amide

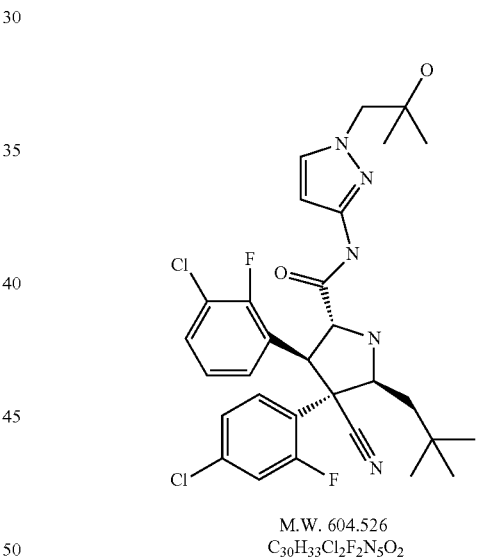

M.W. 604.526
C$_{30}$H$_{33}$Cl$_2$F$_2$N$_5$O$_2$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (86.2 mg, 0.20 mmol), 1-(3-amino-pyrazol-1-yl)-2-methyl-propan-2-ol (62 mg, 0.3 mmol), 2-(7-azabenzotriazol-1-yl)-n,n,n',n'-tetramethyluronium hexafluorophosphate (HATU, 114.06 mg, 0.3 mmol) and iPr$_2$NEt (0.1 mL, 0.6 mmol) in CH$_2$Cl$_2$ (2 mL) was stirred at rt overnight. The mixture was then diluted with CH$_2$Cl$_2$ and washed with water, brine. The organic phase was separated, dried over Na$_2$SO$_4$ and filtered. The mixture was then concentrated and purified by reverse phase chromatography (20-95% of ACN/water) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]- amide (23.1 mg, 20.8%) as an off-white powder. HRMS (ES+) m/z Calcd for $C_{30}H_{33}Cl_2F_2N_5O_2S+H$ [(M+H)+]: 604.2052. found: 604.2052.

Example 164

Preparation of chiral 2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide

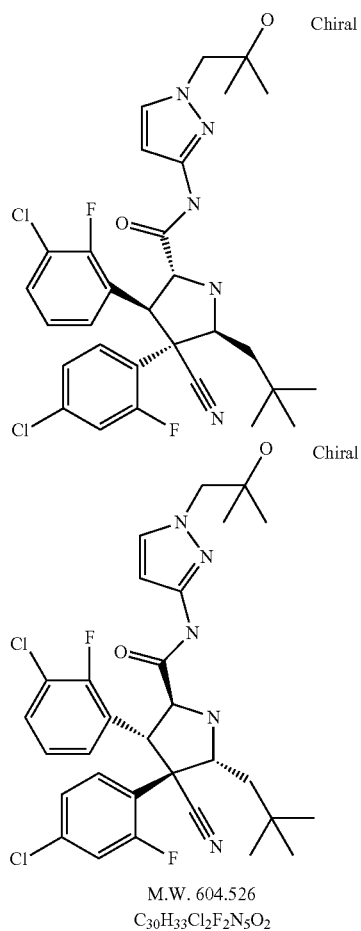

M.W. 604.526
$C_{30}H_{33}Cl_2F_2N_5O_2$

The racemate 2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide (0.25 g) was submitted for SFC purification (30% methanol/water, 100 psi) to afford of chiral 2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide (117 mg, 21%) as an off-white powder. HRMS (ES+) m/z Calcd for $C_{30}H_{33}Cl_2F_2N_5O_2S+H$ [(M+H)+]: 604.2052. found: 604.2051. and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide (110 mg, 19.8%) as an off-white powder. HRMS (ES+) Calcd for $C_{30}H_{33}Cl_2F_2N_5O_2H$ [(M+H)+]: 604.2052. found: 604.2052.

Example 165

Preparation of 1-(3-amino-pyrazol-1-yl)-2-methyl-propan-2-ol

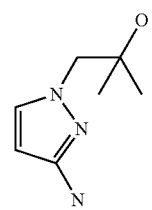

M.W. 155.22
$C_8H_{15}N_2O$

A mixture of 2-methyl-1-(3-nitro-pyrazol-1-yl)-propan-2-ol (0.3 g, 1.6 mmol), Zn dust (0.42 g, 6.5 mmol), ammonium chloride (0.85 g, 16 mmol) and methanol (2 mL) was microwaved at 120° C. for 10 min. The resulting suspension was filtered through celite with methanol and THF washes. Solvent was removed under reduced pressure to yield crude product that was triterated with ethyl acetate and filtered again to get rid of ammonium chloride salt. Product 1-(3-amino-pyrazol-1-yl)-2-methyl-propan-2-ol was a yellow solid (233 mg, 94%).

Example 166

Preparation of 2-methyl-1-(3-nitro-pyrazol-1-yl)-propan-2-ol

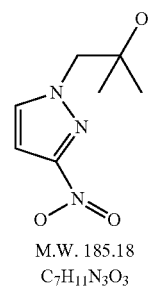

M.W. 185.18
$C_7H_{11}N_3O_3$

A mixture of 3-nitro-1H-pyrazole (10.0 g, 88.43 mmol), 2,2-dimethyl-oxirane (15.7 mL, 176.9 mmol), potassium carbonate (18.2 g, 132 mmol) and DMF (100 mL) was stirred at 100° C. for 1 h, then stirred ON at rt. The mixture was then diluted with ethyl acetate and water, the organic layer was separated, dried over $Na_2SO_4$, and filtered. The resulting mixture was concentrated under reduced pressure to yield the crude product that was purified (50% EtOAc/heptane) to yield the product 2-methyl-1-(3-nitro-pyrazol-1-yl)-propan-2-ol as a waxy solid (4.88 g, 30%).

Example 167

Preparation of 1-[2-methyl-2-((R)-1-oxiranyl-methoxy)-propyl]-3-nitro-1H-pyrazole

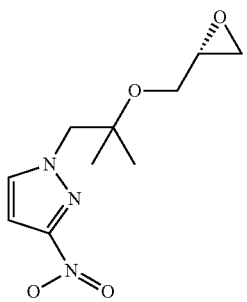

M.W. 241.25
$C_{10}H_{15}N_3O_4$

A mixture of 2-methyl-1-(3-nitro-pyrazol-1-yl)-propan-2-ol (1.31 g, 7.07 mmol), and DMF (60 mL) was stirred at 0° C. for 5 min, then NaH (60% dispersion in oil, 0.85 g, 21.2 mmol) was added and stirred 20 min at 0° C. R-(–)-glycidyl-3-nitrobenzenesulfonate (2.75 g, 10.6 mmol) was added and stirred at 0° C. for 1 h then warmed to rt for 14 h. The mixture was then diluted with NH$_4$Cl(s), ethyl acetate, the organic phase was separated, washed with NaHCO$_3$(satd) dried with Na$_2$SO$_4$, and filtered. The mixture was then concentrated and purified by column chromatography (40-240 g Analogix column, 70% EtoAc/heptane to yield the product 1-[2-methyl-2-((R)-1-oxiranylmethoxy)-propyl]-3-nitro-1H-pyrazole as a white solid (0.7 g, 41%).

Example 168

Preparation of 1-[2-methyl-2-((R)-1-oxiranyl-methoxy)-propyl]-1H-pyrazol-3yl amine

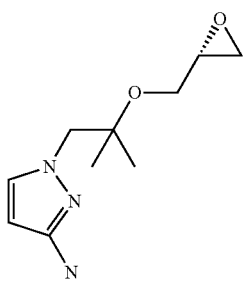

M.W. 211.27
$C_{10}H_{17}N_3O_2$

A mixture of 1-[2-methyl-2-((R)-1-oxiranylmethoxy)-propyl]-3-nitro-1H-pyrazole (0.3 g, 1.24 mmol), and ethyl acetate (15 mL), ethanol (15 mL) was subjected to the H-Cube (Thales Nano) at 1 mL/min at 10° C., 10 psi hydrogen. The first time through not completely reduced. Resubjected and complete reduction of nitro group by NMR. Solvent was removed under reduced pressure to afford 1-[2-methyl-2-((R)-1-oxiranylmethoxy)-propyl]-1H-pyrazol-3ylamine as an oil (0.27 g, 100%).

Example 169

Preparation of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((R)-1-oxiranylmethoxy)-propyl]-1H-pyrazol-3-yl}-amide

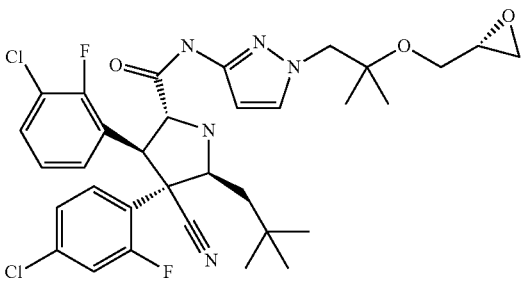

M.W. 660.589
$C_{33}H_{37}Cl_2F_2N_5O_3$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.56 g, 1.2 mmol), 1-[2-methyl-2-((R)-1-oxiranylmethoxy)-propyl]-1H-pyrazol-3ylamine (0.27 g, 1.12 mmol), 2-(7-azabenzotriazol-1-yl)-n,n,n',n'-tetramethyluronium hexafluorophosphate (HATU, 0.912 g, 2.4 mmol) and iPr$_2$NEt (1.5 mL, 8.4 mmol) in CH$_2$Cl$_2$ (50 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by column chromatography (25-80 g Analgix column, 1-100% ethyl acetate/heptane) to give rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((R)-1-oxiranylmethoxy)-propyl]-1H-pyrazol-3-yl}-amide (222 mg, 28%) as an off-white solid. HRMS (ES$^+$) m/z Calcd for $C_{33}H_{37}Cl_2F_2N_5O_3S+H$ [(M+H)$^+$]: 660.2315. found: 660.2312.

Example 170

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((R)-3-amino-2-hydroxy-propoxy)-2-methyl-propyl]-1H-pyrazol-3-yl}-amide

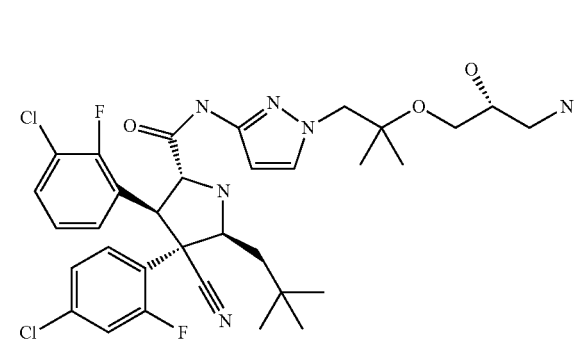

M.W. 677.63
$C_{33}H_{40}Cl_2F_2N_6O_3$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((R)-1-oxiranylmethoxy)-propyl]-1H-pyrazol-3-yl}-amide (43.6 mg, 0.066 mmol), isopropyl alcohol (2 mL), and ammonium hydroxide (1 mL) was microwaved at 130° C. for 15 min. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((R)-3-amino-2-hydroxy-propoxy)-2-methyl-propyl]-1H-pyrazol-3-yl}-amide (11.4 mg, 26%) as an off-white solid. HRMS (ES$^+$) m/z Calcd for C$_{33}$H$_{40}$Cl$_2$F$_2$N$_6$O$_3$+H [(M+H)$^+$]: 677.2580. found: 677.2576.

Example 171

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-{2-[(R)-2-hydroxy-3-(3-hydroxy-propylamino)-propoxy]-2-methyl-propyl}-1H-pyrazol-3-yl)-amide

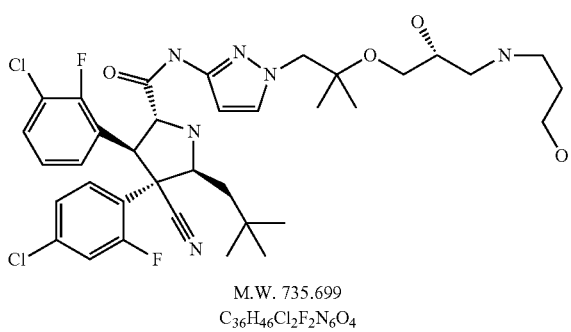 [SMILES: CC(C)(C)C[C@@H]1N[C@@H](C(=O)Nc2ccn(CC(C)(C)OC[C@H](O)CNCCCO)n2)[C@H](c2cccc(Cl)c2F)[C@@]1(C#N)c1ccc(Cl)cc1F]

M.W. 735.699
C$_{36}$H$_{46}$Cl$_2$F$_2$N$_6$O$_4$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((R)-1-oxiranylmethoxy)-propyl]-1H-pyrazol-3-yl}-amide (43.6 mg, 0.066 mmol), isopropyl alcohol (2 mL), diisopropylethyl amine (0.1 mL, 0.56 mmol) and 3-amino-1-propanol (0.1 mL, 1.3 mmol) was microwaved at 130° C. for 15 min. The mixture was then concentrated and purified by reverse phase chromatography (20-95% of ACN/water) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-{2-[(R)-2-hydroxy-3-(3-hydroxy-propylamino)-propoxy]-2-methyl-propyl}-1H-pyrazol-3-yl)-amide (10.1 mg, 20.8%) as an off-white powder. HRMS (ES$^+$) m/z Calcd for C$_{36}$H$_{46}$Cl$_2$F$_2$N$_6$O$_4$S+H [(M+H)$^+$]: 735.2999. found: 735.2998.

Example 172

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-{2-[(R)-2-hydroxy-3-(2-hydroxy-1-hydroxymethyl-ethylamino)-propoxy]-2-methyl-propyl}-1H-pyrazol-3-yl)-amide

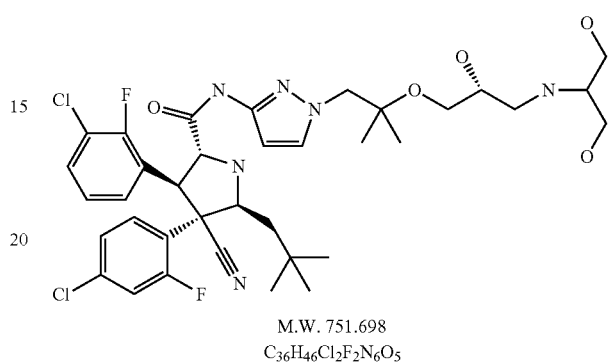

M.W. 751.698
C$_{36}$H$_{46}$Cl$_2$F$_2$N$_6$O$_5$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((R)-1-oxiranylmethoxy)-propyl]-1H-pyrazol-3-yl}-amide (43.6 mg, 0.066 mmol), isopropyl alcohol (2 mL), diisopropylethyl amine (0.1 mL, 0.56 mmol) and serinol (0.1 mL, 1.09 mmol) was microwaved at 130° C. for 15 min. The mixture was then concentrated and purified by reverse phase chromatography (20-95% of ACN/water) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-{2-[(R)-2-hydroxy-3-(2-hydroxy-1-hydroxymethyl-ethylamino)-propoxy]-2-methyl-propyl}-1H-pyrazol-3-yl)-amide (14.2 mg, 28.6%) as an off-white powder. HRMS (ES$^+$) m/z Calcd for C$_{36}$H$_{46}$Cl$_2$F$_2$N$_6$O$_5$S+H [(M+H)$^+$]: 751.2948. found: 751.2943.

Example 173

Preparation of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((5)-1-oxiranylmethoxy)-propyl]-1H-pyrazol-3-yl}-amide

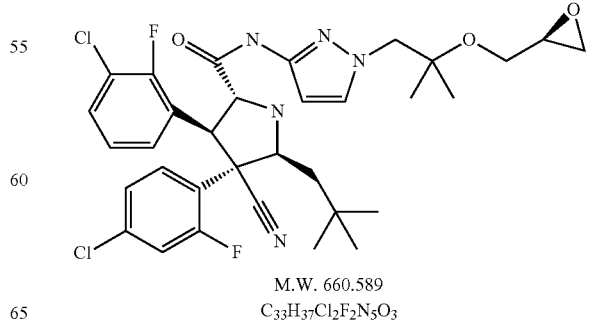

M.W. 660.589
C$_{33}$H$_{37}$Cl$_2$F$_2$N$_5$O$_3$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.12 g, 0.28 mmol), 1-[2-methyl-2-((S)-1-oxiranylmethoxy)-propyl]-1H-pyrazol-3ylamine (52.4 mg, 0.248 mmol), 2-(7-azabenzotriazol-1-yl)-n,n,n',n'-tetramethyluronium hexafluorophosphate (HATU, 0.212 g, 0.56 mmol) and iPr$_2$NEt (0.25 mL, 1.4 mmol) in CH$_2$Cl$_2$ (3 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by column chromatography (4 g column, 1-100% ethyl acetate/heptane) to give rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((5)-1-oxiranylmethoxy)-propyl]-1H-pyrazol-3-yl}-amide (58 mg, 35.4%) as an off-white solid. HRMS (ES$^+$) m/z Calcd for C$_{33}$H$_{37}$Cl$_2$F$_2$N$_5$O$_3$+H [(M+H)$^+$]: 660.2315. found: 660.2316.

Example 174

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-amino-2-hydroxy-propoxy)-2-methyl-propyl]-1H-pyrazol-3-yl}-amide

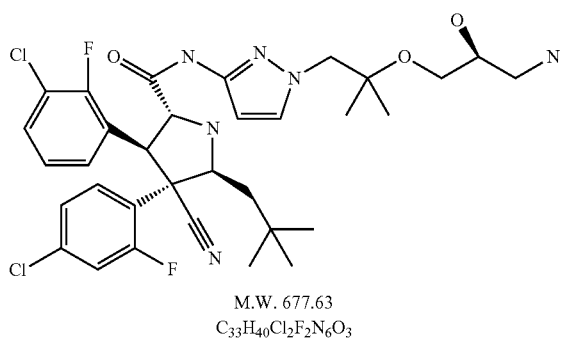 [SMILES: CC(C)(C)C[C@@H]1N[C@@H](C(=O)Nc2ccn(CC(C)(C)OC[C@@H](O)CN)n2)[C@H](c2cccc(Cl)c2F)[C@@]1(C#N)c1ccc(Cl)cc1F]

M.W. 677.63
C$_{33}$H$_{40}$Cl$_2$F$_2$N$_6$O$_3$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((S)-1-oxiranylmethoxy)-propyl]-1H-pyrazol-3-yl}-amide (203 mg, 0.307 mmol), isopropyl alcohol (2 mL), and ammonium hydroxide (2.5 mL) was microwaved at 130° C. for 15 min. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac-(2R,3S,4R,5S)-3-(3-chloro-2-fluoro-phenyl)-4-(4-chloro-2-fluoro-phenyl)-4-cyano-5-(2, 2-dimethyl-propyl)-pyrrolidine-2-carboxylic acid {1-[2-((S)-3-amino-2-hydroxy-propoxy)-2-methyl-propyl]-1H-pyrazol-3-yl}-amide (50.2 mg, 24.1%) as an white powder. HRMS (ES$^+$) m/z Calcd for C$_{33}$H$_{40}$Cl$_2$F$_2$N$_6$O$_3$+H [(M+H)$^+$]: 677.2580. found: 677.2577.

Example 175

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-2,3-dihydroxy-propoxy)-2-methyl-propyl]-1H-pyrazol-3-yl}-amide

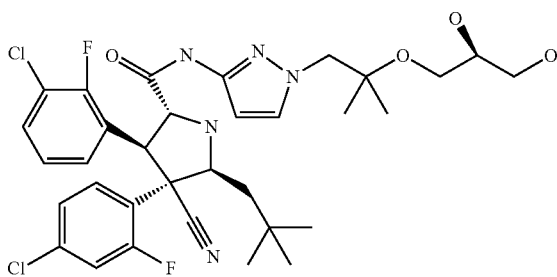

M.W. 678.242
C$_{33}$H$_{39}$Cl$_2$F$_2$N$_5$O$_4$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((S)-1-oxiranylmethoxy)-propyl]-1H-pyrazol-3-yl}-amide (51.2 mg, 0.078 mmol), water (2 mL), and acetone (10 mL) was cooled to 0° C., then a solution of 35% perchloric acid (0.1 mL) was added dropwise. The reaction was stirred an additional 0.5 h. Then an additional 1 mL of the 35% perchloric acid solution was added at 0° C., the reaction was allowed to warm to rt for 12 h. The mixture was then diluted with ethyl acetate and washed with sodium bicarbonate (sat'd). The organic phase was separated, dried over Na$_2$SO$_4$ and filtered. The mixture was then concentrated and purified by reverse phase chromatography (20-95% of ACN/water) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-2,3-dihydroxy-propoxy)-2-methyl-propyl]-1H-pyrazol-3-yl}-amide (22.1 mg, 42%) as an white powder. HRMS (ES$^+$) m/z Calcd for C$_{33}$H$_{39}$Cl$_2$F$_2$N$_5$O$_4$S+H [(M+H)$^+$]: 678.2420. found: 078.2416; C$_{33}$H$_{39}$Cl$_2$F$_2$N$_5$O$_4$+[(Na+H)$^+$]: 700.2239. found: 700.2235.

Example 176

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl)-amide

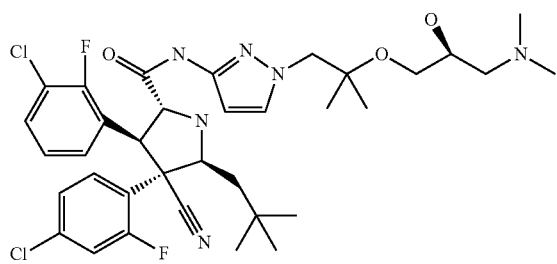

M.W. 705.674
C$_{35}$H$_{44}$Cl$_2$F$_2$N$_6$O$_3$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((S)-1-oxiranylmethoxy)-propyl]-1H-pyrazol-3-yl}-amide (87.5 mg, 0.133 mmol), isopropyl alcohol (2 mL), and dimethylamine (0.133 mL, 0.266 mmol, 2 M in dioxane) was microwaved at 130° C. for 15 min. The mixture was extracted with dichloromethane and water. The organic layer was separated and the solvent evaporated under reduced pressure. The resulting oil was purified by reverse phase chromatography (20-95% of ACN/water) to give rac(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl)-amide (20.6 mg, 20.8%) as a white powder. HRMS (ES+) m/z Calcd for $C_{35}H_{44}Cl_2F_2N_6O_3+H$ [(M+H)+]: 705.2890. found: 705.2893.

Example 177

Preparation of rac-{(S)-3-[2-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-1,1-dimethyl-ethoxy]-2-hydroxy-propylamino}-acetic acid

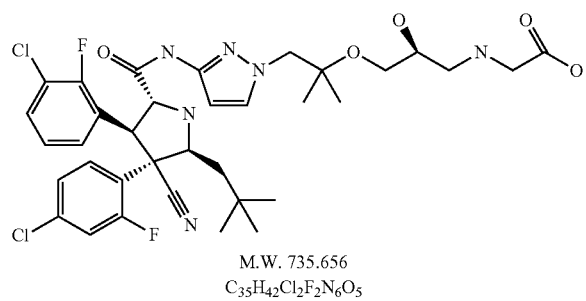 [SMILES: CC(C)(C)C[C@@H]1N[C@@H](C(=O)Nc2ccn(CC(C)(C)OC[C@@H](O)CNCC(=O)O)n2)[C@H](c2cccc(Cl)c2F)[C@@]1(C#N)c1ccc(Cl)cc1F]

M.W. 735.656
$C_{35}H_{42}Cl_2F_2N_6O_5$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((S)-1-oxiranylmethoxy)-propyl]-1H-pyrazol-3-yl}-amide (85.8 mg, 0.133 mmol), isopropyl alcohol (2 mL), and t-butyl glycine (35 mg, 0.266 mmol) was microwaved at 130° C. for 15 min. The solvent evaporated under reduced pressure. The resulting oil was dissolved in dichloromethane (2 mL) and cooled to 0° C.; then TFA (1 mL) was slowly added and stirred for 4 h. The mixture was concentrated under reduced pressure and purified by reverse phase chromatography (20-95% of ACN/water) to give rac-{(S)-3-[2-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-1,1-dimethyl-ethoxy]-2-hydroxy-propylamino}-acetic acid (18.1 mg, 19%) as an off-white powder. HRMS (ES+) m/z Calcd for $C_{35}H_{42}Cl_2F_2N_6O_5S+H$ [(M+H)+]: 735.2635. found: 735.2631

Example 178

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)pyrrolidine-2-carboxylic acid {1-[2-((S)-2-hydroxy-3-methylamino-propoxy)-2-methyl-propyl]-1H-pyrazol-3-yl}-amide

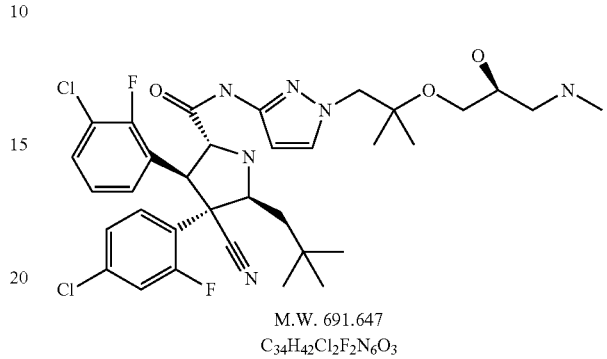

M.W. 691.647
$C_{34}H_{42}Cl_2F_2N_6O_3$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((S)-1-oxiranylmethoxy)-propyl]-1H-pyrazol-3-yl}-amide (87.5 mg, 0.133 mmol), isopropyl alcohol (2 mL), and methylamine (1.0 mL, 2 mmol, 2 M in methanol; old bottle) was microwaved at 130° C. for 15 min. The solvent evaporated under reduced pressure. The resulting oil was purified by reverse phase chromatography (20-95% of ACN/water) to give rac-(2R,3S,4R,5S)-3-(3-chloro-2-fluoro-phenyl)-4-(4-chloro-2-fluoro-phenyl)-4-cyano-5-(2,2-dimethyl-propyl)pyrrolidine-2-carboxylic acid {1-[2-((S)-2-hydroxy-3-methylamino-propoxy)-2-methyl-propyl]-1H-pyrazol-3-yl}-amide (14.9 mg, 16.2%) as an off-white powder. HRMS (ES+) m/z Calcd for $C_{34}H_{42}Cl_2F_2N_6O_3S+H$ [(M+H)+]: 691.2737. found: 691.2731.

Example 179

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((R)-3-dimethylamino-2-hydroxy-propoxy)-2-methyl-propyl]-1H-pyrazol-3-yl)-amide

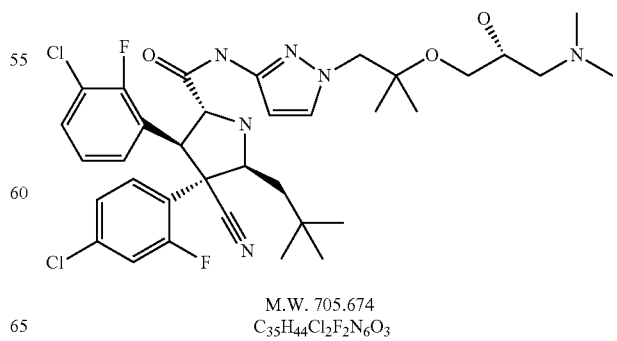

M.W. 705.674
$C_{35}H_{44}Cl_2F_2N_6O_3$

A mixture of rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((R)-1-oxiranylmethoxy)-propyl]-1H-pyrazol-3-yl}-amide (0.69 g, 1.04 mmol), isopropyl alcohol (2 mL), and dimethylamine (1.04 mL, 2.08 mmol, 2 M in THF) was microwaved at 130° C. for 15 min. The mixture was extracted with dichloromethane and water. The organic layer was separated and the solvent evaporated under reduced pressure. The resulting oil was purified by column chromatography (50% ethyl acetate/heptane) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((R)-3-dimethylamino-2-hydroxy-propoxy)-2-methyl-propyl]-1H-pyrazol-3-yl)-amide (147.2 mg, 20.05%) as a white powder. HRMS (ES+) m/z Calcd for $C_{35}H_{44}Cl_2F_2N_6O_3S+H$ $[(M+H)^+]$: 705.2893. found: 705.2893.

Example 180

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid {1-[2-(tert-butyl-dimethyl-silanyloxy)-ethyl]-1H-pyrazol-3-yl}-amide

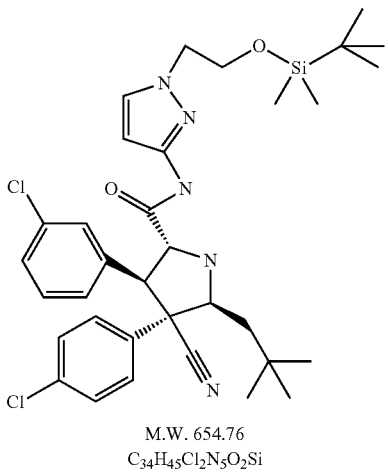 [SMILES: CC(C)(C)C[C@@H]1N[C@@H](C(=O)Nc2ccn(CCO[Si](C)(C)C(C)(C)C)n2)[C@H](c2cccc(Cl)c2)[C@@]1(C#N)c1ccc(Cl)cc1]

M.W. 654.76
$C_{34}H_{45}Cl_2N_5O_2Si$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 1-[2-(tert-Butyl-dimethyl-silanyloxy)-ethyl]-1H-pyrazol-3-ylamine (72.42 mg, 0.3 mmol), 2-(7-azabenzotriazol-1-yl)-n,n,n',n'-tetramethyluronium hexafluorophosphate (HATU, 76 mg, 0.2 mmol) and iPr₂NEt (0.1 mL, 0.55 mmol) in $CH_2Cl_2$ (2 mL) was stirred at rt overnight. The mixture was then diluted with $CH_2Cl_2$ and washed with water, brine. The organic phase was separated, filtered and dried over $Na_2SO_4$. The mixture was then concentrated and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid {1-[2-(tert-butyl-dimethyl-silanyloxy)-ethyl]-1H-pyrazol-3-yl}-amide (77.3 mg, 59%) as an off-white powder. HRMS (ES+) m/z Calcd for $C_{34}H_{45}Cl_2N_5O_2S+H$ $[(M+H)^+]$: 654.2793. found: 654.2790.

Example 181

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,2-dimethyl-[1,3]dioxolan-4-ylmethyl)-1H-pyrazol-3-yl]-amide

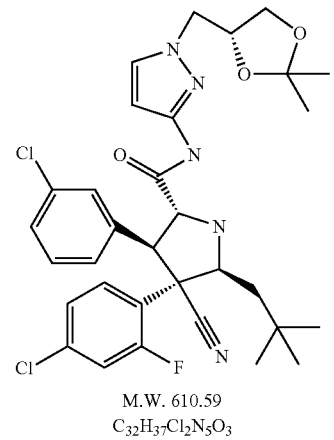 [SMILES: CC(C)(C)C[C@@H]1N[C@@H](C(=O)Nc2ccn(C[C@@H]3COC(C)(C)O3)n2)[C@H](c2cccc(Cl)c2)[C@@]1(C#N)c1ccc(Cl)cc1F]

M.W. 610.59
$C_{32}H_{37}Cl_2N_5O_3$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 1-(2,2-Dimethyl-[1,3]dioxolan-4-ylmethyl)-1H-pyrazol-3-ylamine (59.14 mg, 0.3 mmol), 2-(7-azabenzotriazol-1-yl)-n,n,n',n'-tetramethyluronium hexafluorophosphate (HATU, 76 mg, 0.2 mmol) and iPr₂NEt (0.1 mL, 0.55 mmol) in $CH_2Cl_2$ (2 mL) was stirred at rt overnight. The mixture was then diluted with $CH_2Cl_2$ and washed with water, brine. The organic phase was separated, filtered and dried over $Na_2SO_4$. The mixture was then concentrated and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,2-dimethyl-[1,3]dioxolan-4-ylmethyl)-1H-pyrazol-3-yl]-amide (91.2 mg, 74.68%) as an off-white powder. HRMS (ES+) m/z Calcd for $C_{34}H_{45}Cl_2N_5O_2S+H$ $[(M+H)^+]$: 610.2346. found: 610.2345.

Example 182

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((S)-2,3-dihydroxy-propyl)-amide and rac-(2S,3S,4S,5R)-3-(3-chloro-phenyl)-4-(4-chloro-phenyl)-4-cyano-5-(2,2-dimethyl-propyl)-pyrrolidine-2-carboxylic acid ((S)-2,3-dihydroxy-propyl)-amide Chiral

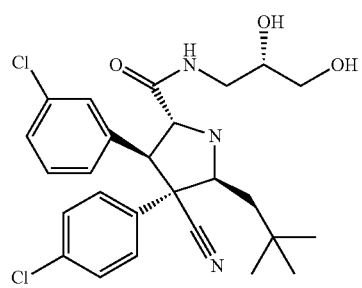

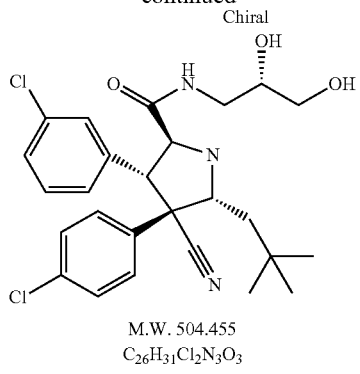

M.W. 504.455
C<sub>26</sub>H<sub>31</sub>Cl<sub>2</sub>N<sub>3</sub>O<sub>3</sub>

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (0.86, 2.0 mmol), (S)-3-amino-propane-1,2-diol (0.27 g, 3.0 mmol), 2-(7-azabenzotriazol-1-yl)-n,n,n',n'-tetramethyluronium hexafluorophosphate (HATU, 0.76 g, 2.0 mmol) and iPr₂NEt (1.0 mL, 5.5 mmol) in CH₂Cl₂ (40 mL) was stirred at rt overnight. The mixture was then diluted with CH₂Cl₂ and washed with water, brine. The organic phase was separated, filtered and dried over Na₂SO₄. The mixture was then concentrated to yield a product that was purified by silica column chromatography (1-100% EtOAc/heptane) to give 1.09 g, 100% two diastereoisomers. The mixture was sent SFC to be separated (35% CH₃OH, 100 barr, 30° C.) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((S)-2,3-dihydroxy-propyl)-amide (187.6 mg, 21.7%) as an off-white powder. HRMS (ES⁺) m/z Calcd for C₂₆H₃₁Cl₂N₃O₃S+H [(M+H)⁺]: 504.455. found: 504.455. and rac-(2S,3S,4S,5R)-3-(3-chloro-phenyl)-4-(4-chloro-phenyl)-4-cyano-5-(2,2-dimethyl-propyl)-pyrrolidine-2-carboxylic acid ((S)-2,3-dihydroxy-propyl)-amide (188.1 mg, 74.68%) as an off-white foam. HRMS (ES⁺) m/z Cabal for C₂₆H₃₁Cl₂N₃O₃S+H [(M+H)⁺]: 504.1815. found: 504.1815.

Example 183

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-(2-hydroxy-ethyl)-1H-pyrazol-3-yl]-amide

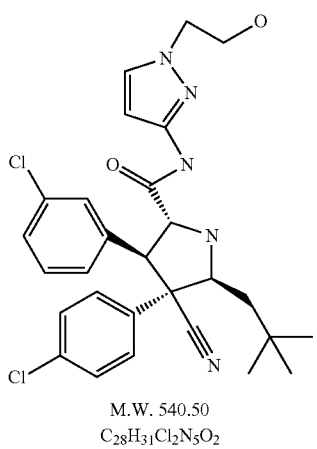 [SMILES: CC(C)(C)C[C@@H]1N[C@@H](C(=O)Nc2ccn(CCO)n2)[C@H](c2cccc(Cl)c2)[C@@]1(C#N)c1ccc(Cl)cc1]

M.W. 540.50
C<sub>28</sub>H<sub>31</sub>Cl<sub>2</sub>N<sub>5</sub>O<sub>2</sub>

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid {1-[2-(tert-butyl-dimethyl-silanyloxy)-ethyl]-1H-pyrazol-3-yl}-amide (65.2 mg, 0.0995 mmol), acetic acid (2.0 mL, 31 mmol), water (1 mL) and stirred at RT over the weekend (48 h). Reaction complete by 50%. The mixture was then diluted with EtOAc and washed with NaHCO₃(s). The organic phase was separated, filtered and dried over Na₂SO₄. The mixture was then concentrated under reduced vacuum and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-(2-hydroxy-ethyl)-1H-pyrazol-3-yl]-amide (21.6 mg, 40.22%) as a white powder.

HRMS (ES⁺) m/z Calcd for C₂₈H₃₁Cl₂N₅O₂S+H [(M+H)⁺]: 540.1928. found: 540.1926.

Example 184

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,3-dihydroxy-propyl)-1H-pyrazol-3-yl]-amide

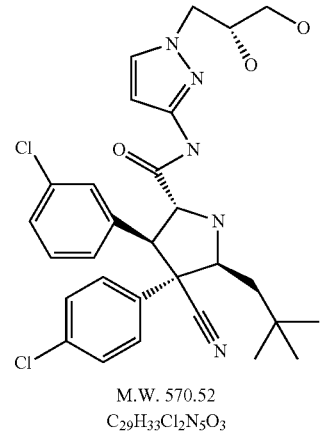 [SMILES: CC(C)(C)C[C@@H]1N[C@@H](C(=O)Nc2ccn(C[C@@H](O)CO)n2)[C@H](c2cccc(Cl)c2)[C@@]1(C#N)c1ccc(Cl)cc1]

M.W. 570.52
C<sub>29</sub>H<sub>33</sub>Cl<sub>2</sub>N<sub>5</sub>O<sub>3</sub>

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,2-dimethyl-[1,3]dioxolan-4-ylmethyl)-1H-pyrazol-3-yl]-amide (81 mg, 0.133 mmol), pyridinium p-toluene sulfonic acid (5 mg, 0.0198 mmol) and methanol (4 mL) was microwaved at 120° C. for 5 min. Solvent evaporated and purified by reverse phase chromatography (20-95% of ACN/water) to rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,3-dihydroxy-propyl)-1H-pyrazol-3-yl]-amide (26.5 mg, 35%) as an off-white powder. HRMS (ES⁺) m/z Calcd for C₂₉H₃₃Cl₂N₅O₃S+H [(M+H)⁺]: 570.2033. found: 570.2032.

Example 185

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 2-trifluoromethyl-benzylamide

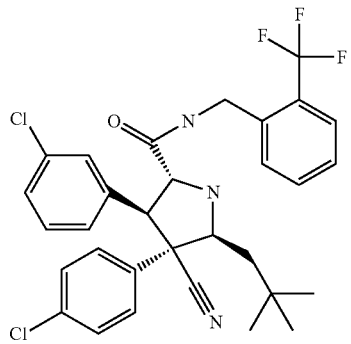

M.W. 588.498
$C_{31}H_{30}Cl_2F_3N_3O$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 2-trifluoromethyl-benzyl amine (52.55 mg, 0.3 mmol), 2-(7-azabenzotriazol-1-yl)-n,n,n',n'-tetramethyluronium hexafluorophosphate (HATU, 76 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac rac-(2R,3R,4R,5S)-3-(3-chloro-phenyl)-4-(4-chloro-phenyl)-4-cyano-5-(2,2-dimethyl-propyl)-pyrrolidine-2-carboxylic acid 2-trifluoromethyl-benzylamide (38 mg, 32.3%) as an off-white powder. HRMS (ES$^+$) m/z Calcd for $C_{31}H_{30}Cl_2F_3N_3O$+H [(M+H)$^+$]: 588.1791. found: 588.1795.

Example 186

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-(2-oxo-pyrrolidin-1-yl)-benzylamide

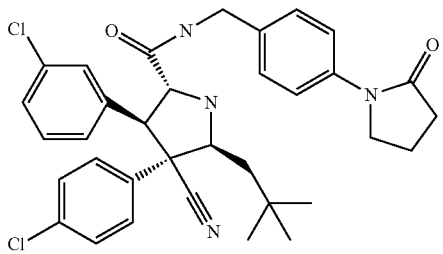

M.W. 603.59
$C_{34}H_{36}Cl_2N_4O_2$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 4-aminomethyl phenyl pyrrolidin-2-one (42.94 mg, 0.3 mmol), 2-(7-azabenzotriazol-1-yl)-n,n,n',n'-tetramethyluronium hexafluorophosphate (HATU, 76 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-(2-oxo-pyrrolidin-1-yl)-benzylamide (48.9 mg, 40.5%) as an off-white powder. HRMS (ES$^+$) m/z Calcd for $C_{34}H_{36}Cl_2N_4O_2S$+H [(M+H)$^+$]: 603.2288. found: 603.2289.

Example 187

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (tetrahydro-pyran-4-ylmethyl)-amide

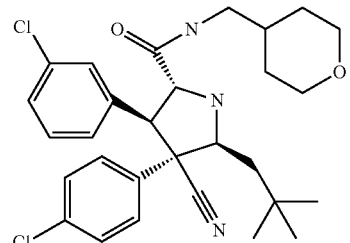

M.W. 528.52
$C_{29}H_{35}Cl_2N_3O_2$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 4-aminomethyl tetrahydropyran (34.5 mg, 0.3 mmol), 2-(7-azabenzotriazol-1-yl)-n,n,n',n'-tetramethyluronium hexafluorophosphate (HATU, 76 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (tetrahydro-pyran-4-ylmethyl)-amide (10.8 mg, 10.2%) as an off-white powder. HRMS (ES$^+$) m/z Calcd for $C_{29}H_{35}Cl_2N_3O_2S$+H [(M+H)$^+$]: 528.2179. found: 528.2180.

Example 188

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-2-hydroxymethyl-propyl)-amide

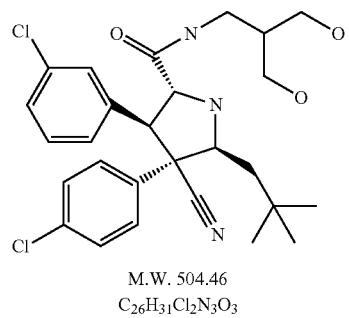 [SMILES: CC(C)(C)C[C@@H]1N[C@@H](C(=O)NCC(CO)CO)[C@H](c2cccc(Cl)c2)[C@@]1(C#N)c1ccc(Cl)cc1]

M.W. 504.46
$C_{26}H_{31}Cl_2N_3O_3$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 2-aminomethyl-propane-1,3-diol (31.5 mg, 0.3 mmol), 2-(7-azabenzotriazol-1-yl)-n,n,n',n'-tetramethyluronium hexafluorophosphate (HATU, 76 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-2-hydroxymethyl-propyl)-amide (31.2 mg, 30.9%) as an off-white powder. HRMS (ES$^+$) m/z Calcd for C$_{26}$H$_{31}$Cl$_2$N$_3$O$_3$S+H [(M+H)$^+$]: 504.455. found: 504.1815.

Example 189

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [2-(2-amino-ethoxy)-ethyl]-amide

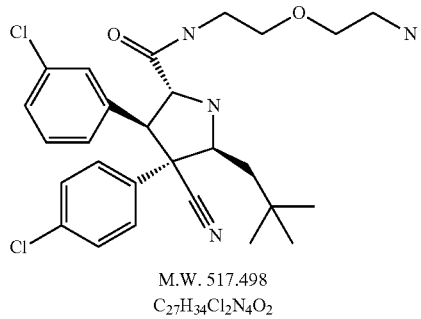 [SMILES: CC(C)(C)C[C@@H]1N[C@@H](C(=O)NCCOCCN)[C@H](c2cccc(Cl)c2)[C@@]1(C#N)c1ccc(Cl)cc1]

M.W. 517.498
$C_{27}H_{34}Cl_2N_4O_2$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 2,2'-oxybis(ethylamine) (31.3 mg, 0.3 mmol), 2-(7-azabenzotriazol-1-yl)-n,n,n',n'-tetramethyluronium hexafluorophosphate (HATU, 76 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid [2-(2-amino-ethoxy)-ethyl]-amide (20.3 mg, 19.6%) as an off-white powder. HRMS (ES$^+$) m/z Calcd for C$_{27}$H$_{34}$Cl$_2$N$_4$O$_2$S+H [(M+H)$^+$]: 517.2132. found: 517.2133.

Example 190

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methane-sulfonyl-propyl)-amide

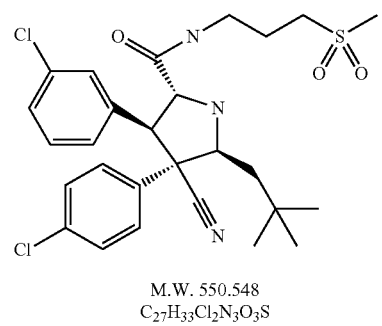 [SMILES: CC(C)(C)C[C@@H]1N[C@@H](C(=O)NCCCS(C)(=O)=O)[C@H](c2cccc(Cl)c2)[C@@]1(C#N)c1ccc(Cl)cc1]

M.W. 550.548
$C_{27}H_{33}Cl_2N_3O_3S$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methylsulfanyl-propyl)-amide (119.2 mg, 0.23 mmol) and dichloromethane (2 mL) was added to a solution of refluxing acetic acid (5 mL, 79.4 mmol) and 30% hydrogen peroxide (2 mL) for 5 min. The reaction mixture was cooled to room temperature and stored in the freezer overnight. The mixture was diluted with water and dichloromethane, the organic layer was separated and solvent removed under reduced pressure. The resulting oil was carried directly to the next step by adding acetic acid (5 mL, 79.4 mmol) and zinc dust (0.85 g, 13 mmol). After stirring at room temperature for 3 h, an additional amount of zinc dust (0.85 g, 13 mmol) was added and stirred for an additional 3 h at room temperature. Reaction worked up by filtration through celite, washing with dichloromethane (50 mL). The filtrate was washed with water (2×) and the organic layer was separated, dried with MgSO$_4$, filtered and the solvent evaporated under reduced pressure to yield crude oil. Purification by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methanesulfonyl-propyl)-amide (36.5 mg, 28.8%) as an off-white powder. HRMS (ES$^+$) m/z Calcd for C$_{27}$H$_{33}$Cl$_2$N$_3$O$_3$S+H [(M+H)$^+$]: 550.1693. found: 550.1692.

Example 191

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-methanesulfonyl-ethyl)-amide

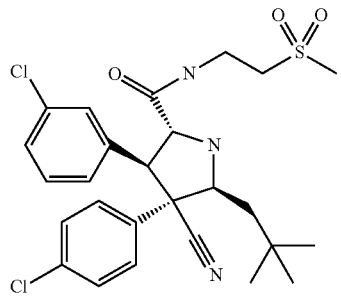

M.W. 536.521
$C_{26}H_{31}Cl_2N_3O_3S$

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 2-methanesulfonyl-ethylamine (54.6 mg, 0.3 mmol), 2-(7-azabenzotriazol-1-yl)-n,n,n',n'-tetramethyluronium hexafluorophosphate (HATU, 76 mg, 0.2 mmol) and iPr$_2$NEt (0.1 mL, 0.55 mmol) in CH$_2$Cl$_2$ (2 mL) was stirred at rt overnight. The mixture was then diluted with CH$_2$Cl$_2$ and washed with water, brine. The organic phase was separated, filtered and dried over Na$_2$SO$_4$. The mixture was then concentrated and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-2-hydroxymethyl-propyl)-amide (65.2 mg, 60.8%) as a white powder. HRMS (ES$^+$) m/z Calcd for $C_{26}H_{31}Cl_2N_3O_3S$+H [(M+H)$^+$]: 536.1536. found: 536.1536.

Example 192

Preparation of rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-cyclohexylamino-1-carboxylic acid tert-butyl ester

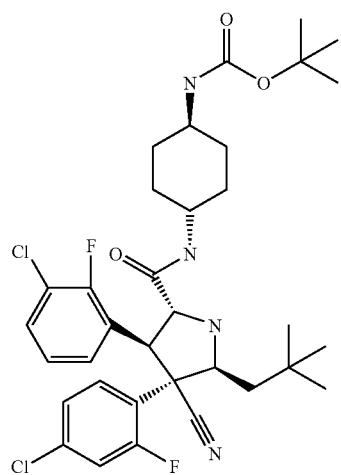

Molecular Weight = 663.64
Molecular Formula = C34H42Cl2F2N4O3

In a manner similar to the method described in Examples 42c, 42d, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 52c (582 mg, 1 mmol) was reacted with 4-Amino-cyclohexylamino-1-carboxylic acid tert-butyl ester (APAC, 429 mg, 2 mmol), HATU (Aldrich, 760.4 mg, 2 mmol) and iPr$_2$NEt (Aldrich, 350 uL, 2 mmol) in CH$_2$Cl$_2$ at room temperature for 1.5 hr. The solvent was reduced and the residue was loaded on 40 g silica gel column and eluted with MeOH/CH$_2$Cl$_2$ (2-5%) to give a white foam. 783 mg HRMS (ES$^+$) m/z Calcd for $C_{34}H_{42}Cl_2F_2N_4O_3S$+H [(M+H)$^+$]: 663.2675. found: 663.2675.

Example 193

Preparation of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoroacetic acid salt

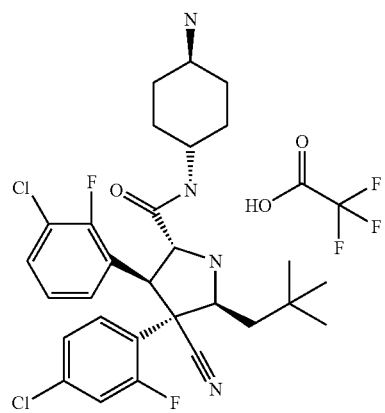

Molecular Weight = 563.52
Molecular Formula = C29H34Cl2F2N4O C2HF3O2

To a stirred solution of trifluoroacetic acid in methylene chloride (3 mL/7 mL) at rt., rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-cyclohexylamino-1-carboxylic acid tert-butyl ester (760 mg) was added and the mixture was stirred for 30 min. The solvent was removed and the residue was treated with ether/hexane. The solid was filtered and washed with hexane to give a white solid. 860 mg. [(M+H)$^+$]: 563.

Example 194

Preparation of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-N-methanesulfonamide

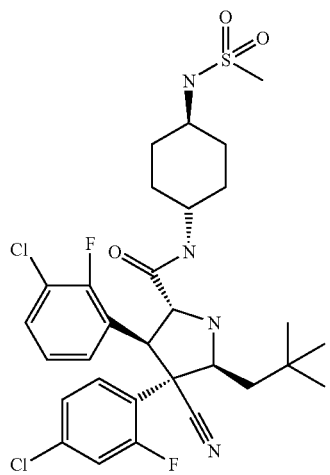

Molecular Weight = 641.61
Molecular Formula = C30H36Cl2F2N4O3S

To a stirred solution of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoroacetic acid salt (80 mg, 0.1 mmol) in methylene chloride (5 mL), Methane sulfonyl chloride (Aldrich, 11.6 uL, 0.15 mmol) was added followed by the addition of triethylamine (70 uL, 0.50 mmol). The mixture was stirred at rt for 1 hr and the reaction was quenched with addition of water. The mixture was extracted with methylene chloride (2×10 mL) and the extracts were dried with magnesium sulfate. The solvent was removed and the residue was chromatographed on ISCO machine (column, 12 g, eluent 5% MeOH/CH2Cl2) to give a white solid. 44 mg.

HRMS (ES$^+$) m/z Calcd: [(M+H)$^+$]: 641.1926. found: 641.1926.

Example 195

Preparation of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-N-methanesulfonamide

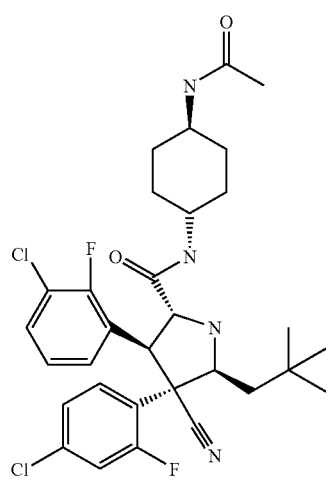

Molecular Weight = 605.56
Molecular Formula = C31H36Cl2F2N4O2

To a stirred solution of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoroacetic acid salt (80 mg, 0.1 mmol) in methylene chloride (5 mL), Acetic anhydride (Aldrich, 16 uL, 0.15 mmol) was added followed by the addition of triethylamine (70 uL, 0.50 mmol). The mixture was stirred at rt for 30 min. and the reaction was quenched with addition of water. The mixture was extracted with methylene chloride (2×10 mL) and the extracts were dried with magnesium sulfate. The solvent was removed and the residue was chromatographed on ISCO machine (column, 12 g, eluent 5% MeOH/CH2Cl2) to give a white solid. 30 mg.

HRMS (ES$^+$) m/z Calcd: [(M+H)$^+$]: 605.2256. found: 605.2259.

Example 196

Preparation of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-(1,1-dioxo)-2-isothiazolidine

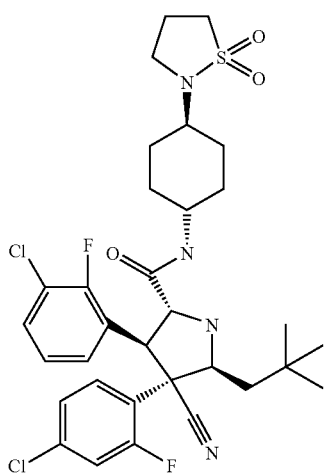

Molecular Weight = 667.65
Molecular Formula = C32H38Cl2F2N4O3S

To a stirred solution of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoroacetic acid salt (200 mg, 0.253 mmol) in methylene chloride (5 mL), 3-chloro-n-propyl sulfonyl chloride (Aldrich, 40 uL, 0.328 mmol) was added followed by the addition of triethylamine (176 uL, 1.265 mmol). The mixture was stirred at rt for 4 hrs and the reaction was quenched with addition of water. The mixture was extracted with methylene chloride (2×10 mL) and the extracts were dried with magnesium sulfate. The solvent was removed and the residue was chromatographed on ISCO machine (column, 12 g, eluent 5% MeOH/CH2Cl2) to give a white solid. 122 mg.

The white solid (80 mg, 0.114 mmol) was dissolved in acetonitrile/water (3:1, 1 mL) and KI (10 mg) and KOAc (55 mg, 0.56 mmol) were added and the mixture was heated on a microwave for 30 min. at 150° C. The mixture was cooled and water was added. The resulting mixture was extracted with ethyl acetate (3×8 mL). The extracts were dried with magnesium sulfate and concentrated. The residue was chromatographed (5% MeOH/CH$_2$Cl$_2$) to give a solid. 46 mg, HRMS (ES$^+$) m/z Calcd: [(M+H)$^+$]: 667.2083. found: 667.2084.

Example 197

Preparation of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-urea

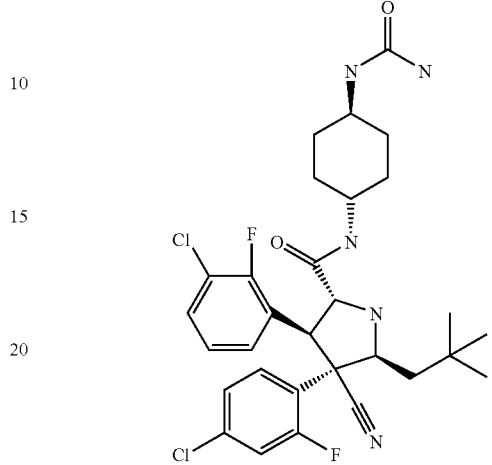

Molecular Weight = 606.55
Molecular Formula = C30H35Cl2F2N5O2

To a stirred solution of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoroacetic acid salt (100 mg, 0.126 mmol) in 1,4-dioxane (5 mL), N-trimethylsilyl isocyanate (Aldrich, 42 uL, 0.316 mmol) was added followed by the addition of triethylamine (44 uL, 0.316 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on a reverse phase HPLC to give a white solid. 39 mg.

HRMS (ES$^+$) m/z Calcd: [(M+H)$^+$]: 606.2209. found: 606.2209.

Example 198

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid N-[1-(2-hydroxy ethyl)-piperidin-4-yl]amide

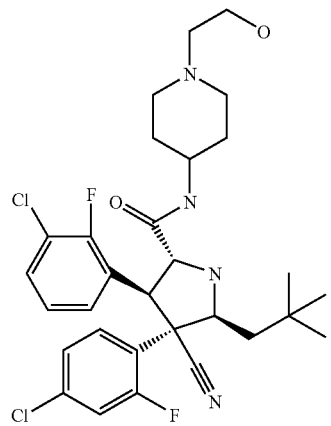

Molecular Weight = 593.55
Molecular Formula = C30H36Cl2F2N4O2

To a stirred solution of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoroacetic acid salt (80 mg, 0.103 mmol) in ethanol (5 mL), 2-bromoethanol (Aldrich, 11 uL, 0.15 mmol) was added followed by the addition of sodium carbonate (106 mg, 1 mmol). The mixture was stirred at reflux overnight. The reaction was quenched with addition of water. The mixture was extracted with EtOAc (2×10 mL) and the extracts were dried with magnesium sulfate. The solvent was removed and the residue was purified on a ISCO machine (12 g column, eluent, 5 MeOH/CH$_2$Cl$_2$) to give a white solid. 22 mg. HRMS (ES$^+$) m/z Calcd: [(M+H)$^+$]: 593.2256. found: 593.2256.

Example 199

Preparation of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-sulfonic acid amide

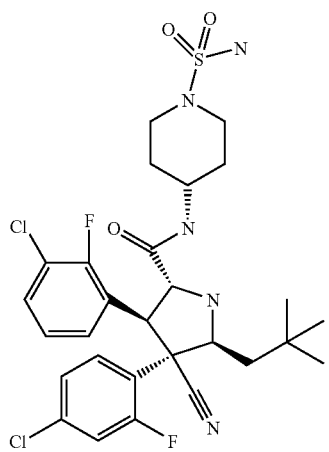

Molecular Weight = 628.57
Molecular Formula = C28H33Cl2F2N5O3S

To a stirred solution of rac-4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoroacetic acid salt (50 mg, 0.091 mmol) in THF (3 mL), sulfamide (Aldrich, 40 mg, 0.416 mmol) was added and the mixture was stirred at 110° C. for 25 min. on microwave oven. The reaction was quenched with addition of water. The mixture was extracted with EtOAc (2×10 mL) and the extracts were dried with magnesium sulfate. The solvent was removed and the residue was purified on a reverse phase HPLC (25-90, acetonitrile/water) to give a white solid. 49 mg.
HRMS (ES$^+$) m/z Calcd: [(M+H)$^+$]: 678.1722. found: 678.1728.

Example 200

Preparation of rac 3-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetic acid

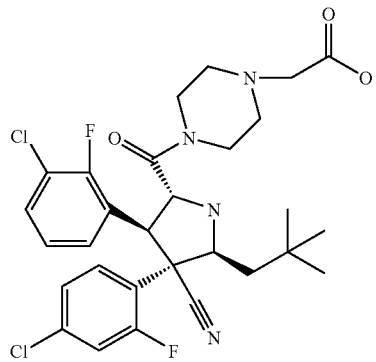

Molecular Weight = 593.5062
Molecular Formula = C29H32Cl2F2N4O3

To a stirred solution of rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid trifluoroacetic acid salt (475 mg, 0.871 mmol) in methylene chloride (5 mL), HATU (Aldrich, 490 mg, 1.29 mmol) was added followed by the addition of DIPEA (0.9 mL, 5.2 mmol) and piperazin-1-yl-acetic acid tert-butyl ester (352 mg, 1.29 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (40 g column, eluent, 50% EtOAc/hexanes) to give a white solid. 525 mg.
The solid (500 mg) was dissolved in 30% TFA/methylene chloride and the solution was stirred for 2 hrs at rt. The solvent was removed at reduced pressure and the residue was triturated with ether and hexane to give a white solid. 560 mg
HRMS (ES$^+$) m/z Calcd: [(M+H)$^+$]: 592.1820. found: 592.1819.

Example 201

Preparation of rac 3-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N,N-bis-(2-methoxy-ethyl)-acetamide

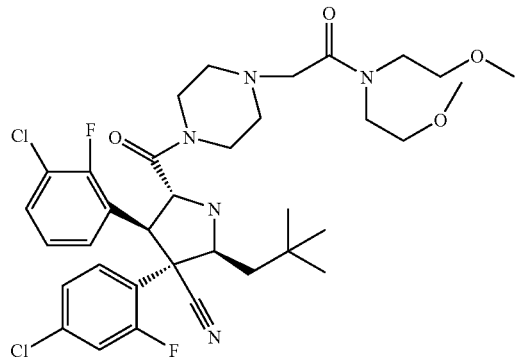

Molecular Weight = 708.6828
Molecular Formula = C35H45Cl2F2N5O4

To a stirred solution of rac 3-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetic acid (80 mg, 0.113 mmol) in methylene chloride (5 mL), HATU (Aldrich, 65 mg, 0.17 mmol) was added followed by the addition of DIPEA (0.06 mL, 0.34 mmol) di-(2-methoxy)-ethylamine (Aldrich, 35 uL, 0.17 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (12 g column, eluent, 20% EtOAc/methylene chloride) to give a white solid. 70 mg.

HRMS (ES+) m/z Calcd: [(M+H)+]: 708.2890. found: 708.2887.

Example 202

Preparation of rac 3-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N,N-bis-(2-hydroxy-ethyl)-acetamide

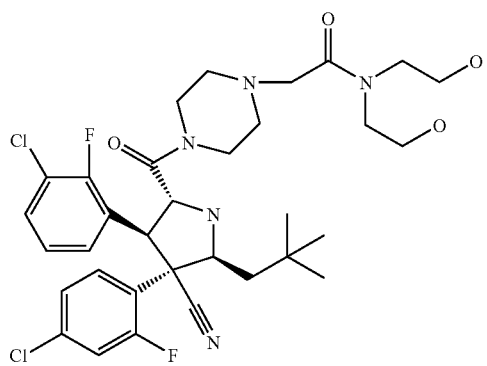

Molecular Weight = 680.6286
Molecular Formula = C33H41Cl2F2N5O4

To a stirred solution of rac 3-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetic acid (80 mg, 0.113 mmol) in methylene chloride (5 mL), HATU (Aldrich, 65 mg, 0.17 mmol) was added followed by the addition of DIPEA (0.06 mL, 0.34 mmol) di-(2-hydroxy)-ethylamine (Across, 35 uL, 0.17 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on a reversed HPLC (10-90%) to give a white solid. 30 mg.

HRMS (ES+) m/z Calcd: [(M+H)+]: 680.2577 found: 680.2575

Example 203

Preparation of rac 3-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N-(3-methoxy-propyl)-acetamide

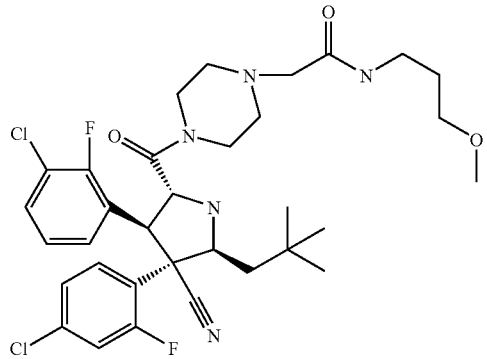

Molecular Weight = 664.6292
Molecular Formula = C33H41Cl2F2N5O3

To a stirred solution of rac 3-{4-[(2R,3S,4R,5S)-3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetic acid (80 mg, 0.113 mmol) in methylene chloride (5 mL), HATU (Aldrich, 65 mg, 0.17 mmol) was added followed by the addition of DIPEA (0.06 mL, 0.34 mmol) and 3-methoxy-propylamine (Aldrich, 0.17 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on a ISCO machine (12 g column, eluent, 20% EtOAc/methylene chloride) to give a white solid. 80 mg.

HRMS (ES+) m/z Calcd: [(M+H)+]: 664.2628. found: 664.2625.

Example 204

Preparation of rac 2-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetamide

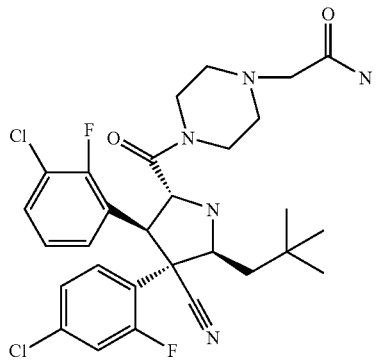

Molecular Weight = 592.5215
Molecular Formula = C29H33Cl2F2N5O2

303

To a stirred solution of rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (80 mg, 0.138 mmol) in methylene chloride (5 mL), HATU (Aldrich, 79 mg, 0.21 mmol) was added followed by the addition of DIPEA (0.145 mL, 0.83 mmol) and 2-piperazin-1-yl-acetamide (Chembridge, 45 mg, 0.21 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on a ISCO machine (12 g column, eluent, 20% EtOAc/methylene chloride) to give a white solid. 87 mg.

HRMS (ES+) m/z Calcd: [(M+H)+]: 592.2052. found: 592.2054.

Example 205

Preparation of rac (2S,3R,4S,5R)-4-(3-chloro-2-fluoro-phenyl)-3-(4-chloro-2-fluoro-phenyl)-2-(2,2-dimethyl-propyl)-5-[4-(2-morpholin-4-yl-2-oxo-ethyl)-piperazine-1-carbonyl]-pyrrolidine-3-carbonitrile

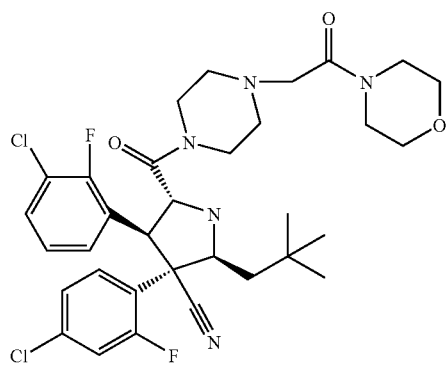

Molecular Weight = 662.6133
Molecular Formula = C33H39Cl2F2N5O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (80 mg, 0.138 mmol) in methylene chloride (5 mL), HATU (Aldrich, 79 mg, 0.21 mmol) was added followed by the addition of DIPEA (0.145 mL, 0.83 mmol) and 1-morpholin-4-yl-2-piperazin-1-yl-ethanone (Oakwood, 44 mg, 0.21 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on a ISCO machine (12 g column, eluent, 20% EtOAc/methylene chloride) to give a white solid. 63 mg.

HRMS (ES+) m/z Calcd: [(M+H)+]: 662.2471. found: 662.2471.

304

Example 206

Preparation of rac 2-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N-[2-((S)-2,2-dimethyl-[1,3]dioxolan-4-yl)-ethyl]-acetamide

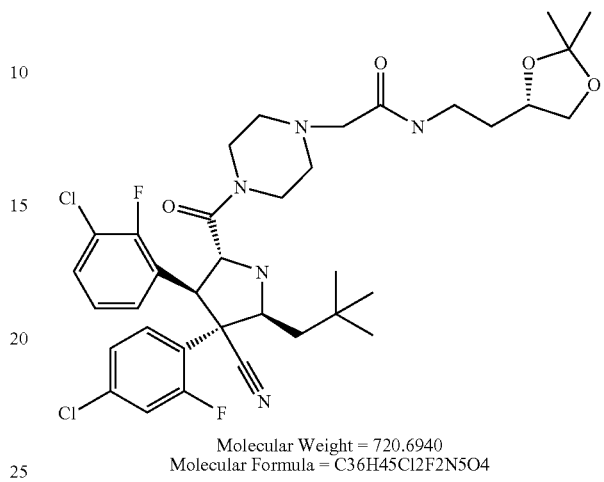

Molecular Weight = 720.6940
Molecular Formula = C36H45Cl2F2N5O4

To a stirred solution of rac 3-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetic acid (80 mg, 0.113 mmol) in methylene chloride (5 mL), HATU (Aldrich, 86 mg, 0.23 mmol) was added followed by the addition of DIPEA (0.06 mL, 0.34 mmol) and 2-((S)-2,2-dimethyl-[1,3]dioxolan-4-yl)-ethylamine (Prepared before, 33 mg, 0.23 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on a reverse phase HPLC (eluent, 40-90% ACN/Water) to give a white solid. 27 mg.

MS (ES+) m/z Calcd: [(M+H)+]: 720. found: 720.

Example 207

Preparation of rac 2-{4-[(2R,3S,4R,5S)-3-(3-Chloro-2-fluoro-phenyl)-4-(4-chloro 2-fluoro-phenyl)-4-cyano-5-(2,2-dimethyl-propyl)-pyrrolidine-2-carbonyl]-piperazin-1-yl}-N—((S)-3,4-dihydroxy-butyl)-acetamide

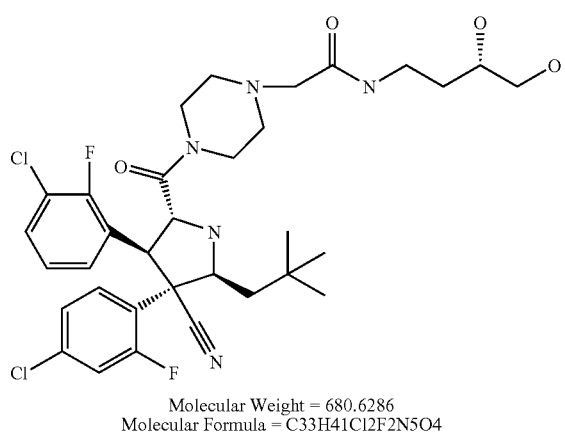 [SMILES: CC(C)(C)C[C@@H]1N[C@@H](C(=O)N2CCN(CC(=O)NCC[C@H](O)CO)CC2)[C@H](c2cccc(Cl)c2F)[C@@]1(C#N)c1ccc(Cl)cc1F]

Molecular Weight = 680.6286
Molecular Formula = C33H41Cl2F2N5O4

To a stirred solution of rac 2-{4-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N-[2-((S)-2,2-dimethyl-[1,3]dioxolan-4-yl)-ethyl]-acetamide (32 mg, 0.0445 mmol) in 1,4-dioxane (5 mL), 4 M HCl (2 mL) was added and the mixture was stirred at rt for 4 hrs. The mixture was concentrated and the residue was dissolved in a mixture of 1,4-dioxane and freeze dried to give a white solid. 31 mg.

MS (ES+) m/z Calcd: [(M+H)+]: 680. found: 680.

Example 208

Preparation of rac {1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid methyl ester

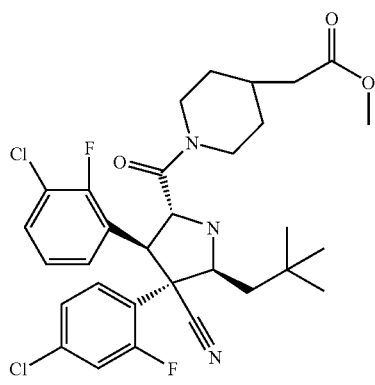

Molecular Weight = 606.5457
Molecular Formula = C31H35Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (581 mg, 1 mmol) in methylene chloride (10 mL), HATU (Aldrich, 500 mg, 1.3 mmol) was added followed by the addition of DIPEA (0.35 mL, 2.2 mmol) and piperidin-4-yl-acetic acid methyl ester (Oakwood, 205 mg, 1.3 mmol). The mixture was stirred at rt for 3 hrs. The reaction was quenched with addition of water. The mixture was extracted with methylene chloride (2×10 mL) and the extracts were dried with magnesium sulfate. The solvent was removed and the residue was purified on a ISCO machine (12 g column, eluent, 20% EtOAc/methylene chloride) to give a white solid. 586 mg.

HRMS (ES+) m/z Calcd: [(M+H)+]: 606.2097. found: 606.2096.

Example 209

Preparation of rac {1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid hydrochloride salt

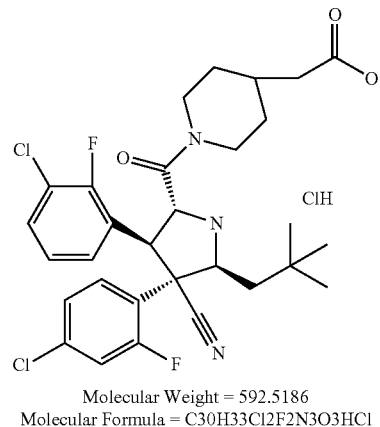 [SMILES: CC(C)(C)C[C@@H]1N[C@@H](C(=O)N2CCC(CC(=O)O)CC2)[C@H](c2cccc(Cl)c2F)[C@@]1(C#N)c1ccc(Cl)cc1F ; Cl]

Molecular Weight = 592.5186
Molecular Formula = C30H33Cl2F2N3O3HCl

To a stirred solution of rac {1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid methyl ester (556 mg, 0.92 mmol) in methanol (8 mL), LiOH.H2O (Aldrich, 80 mg) in 1 mL of water was added. The mixture was stirred at 60° C. overnight. The reaction was quenched with addition of water. The mixture was filtered and the filtrate was concentrated to removed methanol. The aqueous layer was washed with EtOAc (2×5 mL) and acidified with 3N HCl. The mixture was then extracted with EtOAc (3×6 mL). The extracts were combined and dried over sodium sulfate and concentrated to give a white solid. 649 mg.

HRMS (ES+) m/z Calcd: [(M+H)+]: 592.1940. found: 592.1939.

Example 210

Preparation of rac 2-{1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetamide

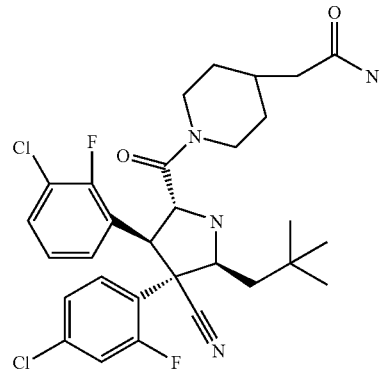

Molecular Weight = 591.5339
Molecular Formula = C30H34Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (80 mg, 0.138 mmol) in methylene chloride (10 mL), HATU (Aldrich, 79 mg, 0.21 mmol) was added followed by the addition of DIPEA (0.145 mL, 0.83 mmol) and piperidin-4-yl-acetamide (Chembridge, 41 mg, 0.21 mmol). The mixture was stirred at rt for 3 hrs then overnight after the addition of 3 mL of DMF. The reaction was quenched with addition of water. The mixture was extracted with methylene chloride (2×10 mL) and the extracts were dried with magnesium sulfate. The solvent was removed and the residue was purified on an ISCO machine (12 g column, eluent, 20% EtOAc/methylene chloride) to give a white solid. 21 mg.

HRMS (ES+) m/z Calcd: [(M+H)+]: 591.2100. found: 591.2100.

Example 211

Preparation of rac 2-{1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-N,N-bis-(2-hydroxy-ethyl)-acetamide

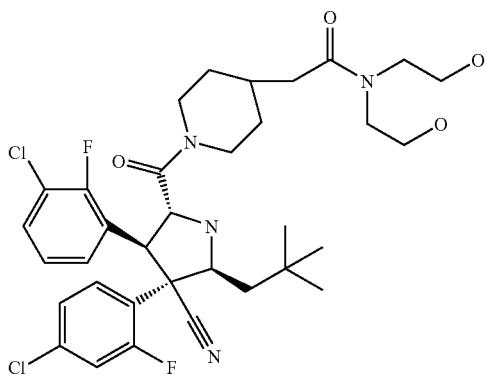

Molecular Weight = 679.6410
Molecular Formula = C34H42Cl2F2N4O4

To a stirred solution of rac {1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid hydrochloride salt (80 mg, 0.127 mmol) in methylene chloride (5 mL), HATU (65 mg, 0.17 mmol) and DIPEA (80 uL, 0.339 mmol) were added followed by 2-(2-hydroxy-ethylamine)-ethanol (Across, 16 uL, 0.17 mmol) and the mixture was stirred at rt overnight. The reaction was quenched with water and the mixture was extracted with methylene chloride (3×10 mL) and the extracts were combined and dried over sodium sulfate. The solvent was removed and the residue was chromatographed on a reverse phase HPLC (acetonitrile/water, 25-85%) to give a white solid. 45 mg.

MS (ES+) m/z Calcd: [(M+H)+]: 679. found: 679.

Example 212

Preparation of rac 2-{1-[(2R,3S,4R,5S)-3-(3-Chloro-2-fluoro-phenyl)-4-(4-chloro 2-fluoro-phenyl)-4-cyano-5-(2,2-dimethyl-propyl)-pyrrolidine-2-carbonyl]-piperidin-4-yl}-N-(2-hydroxy-ethyl)-N-methyl-acetamide

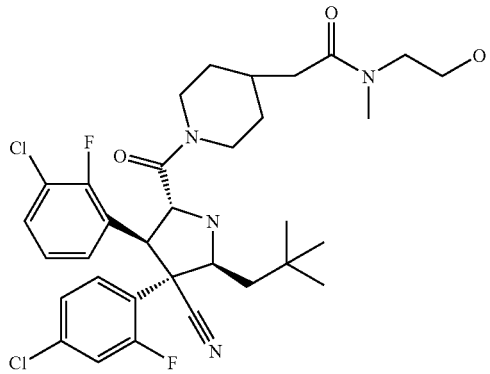

Molecular Weight = 649.6146
Molecular Formula = C33H40Cl2F2N4O3

To a stirred solution of rac {1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid hydrochloride salt (80 mg, 0.127 mmol) in methylene chloride (5 mL), HATU (77 mg, 0.28 mmol) and DIPEA (94 uL, 0.54 mmol) were added followed by 2-hydroxy-ethyl-methyl amine (Oakwood, 20 mg, 0.27 mmol) and the mixture was stirred at rt overnight. The reaction was quenched with water and the mixture was extracted with methylene chloride (3×10 mL) and the extracts were combined and dried over sodium sulfate. The solvent was removed and the residue was chromatographed on a reverse phase HPLC (acetonitrile/water, 25-85%) to give a white solid. 46 mg.

HRMS (ES+) m/z Calcd: [(M+H)+]: 649.2519. found: 645.2518.

Example 213

Preparation of rac 2-{1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-N-(2-hydroxy-propyl)-acetamide

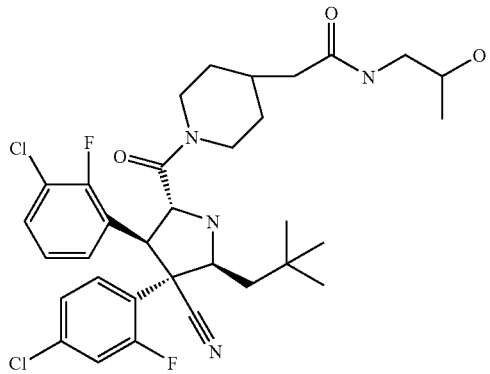

Molecular Weight = 649.6146
Molecular Formula = C33H40Cl2F2N4O3

To a stirred solution of rac {1-[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid hydrochloride salt (80 mg, 0.127 mmol) in methylene chloride (5 mL), HATU (77 mg, 0.28 mmol) and DIPEA (94 uL, 0.54 mmol) were added followed by 2-hydroxy-2-methyl-ethylamine (Aldrich, 20 mg, 0.27 mmol) and the mixture was stirred at rt for hers. The reaction was quenched with water and the mixture was extracted with methylene chloride (3×10 mL) and the extracts were combined and dried over sodium sulfate. The solvent was removed and the residue was chromatographed on a reverse phase HPLC (acetonitrile/water, 25-85%) to give a white solid. 48 mg.

HRMS (ES$^+$) m/z Calcd: [(M+H)$^+$]: 649.2519. found: 645.2519.

Example 214

Preparation of rac {[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-acetic acid tert-butyl ester

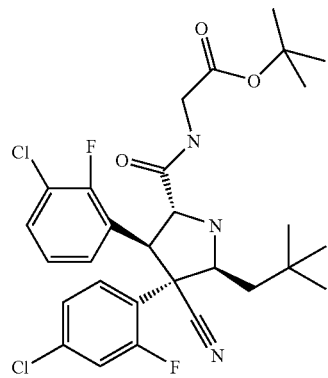

Molecular Weight = 580.5075
Molecular Formula = C29H33Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (515 mg, 1.11 mmol) in methylene chloride (10 mL), HATU (Aldrich, 422 mg, 1.11 mmol) was added followed by the addition of DIPEA (0.5 mL) and 2-amino-t-butyl-acetate (Aldrich, 145 mg, 1.11 mmol). The mixture was stirred at rt for 2 hrs. The reaction was quenched with addition of water. The mixture was extracted with methylene chloride (2×10 mL) and the extracts were dried with magnesium sulfate. The solvent was removed and the residue was purified on an ISCO machine (40 g column, eluent, 30% EtOAc/hexanes chloride) to give a white solid. 510 mg.

HRMS (ES$^+$) m/z Calcd: [(M+H)$^+$]: 579.1867. found: 579.1866.

Example 215

Preparation of rac {[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-acetic aid trifluoro acetic acid salt

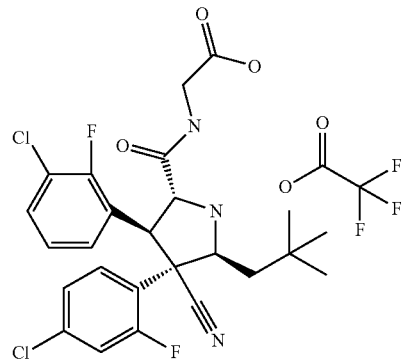

Molecular Weight = 524.3991, 114
Molecular Formula = C25H25Cl2F2N3O3·C2HF3O2

To a stirred solution of {[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-acetic acid tert-butyl ester (500 mg) in methylene chloride (7 mL), TFA (3 mL) was added and the mixture was stirred at rt overnight. The solvent was removed under reduced pressure to give a white solid. 508 mg.

MS (ES$^+$) m/z [(M+H)$^+$]: 524. found: 524.

Example 216

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid carbamoylmethyl-amide

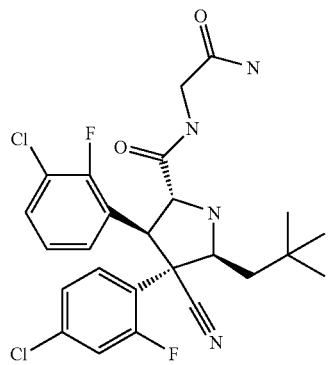

Molecular Weight = 523.4144
Molecular Formula = C25H26Cl2F2N4O2

To a stirred solution of rac {[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-acetic aid trifluoro acetic acid salt. (100 mg, 0.19 mmol) in methylene chloride (10 mL), HATU (Aldrich, 95 mg, 0.25 mmol) was added followed by the addition of DIPEA (0.5 mL) and 4N ammonia in methanol (0.2 mL). The mixture was stirred at rt for 2 hrs. The reaction was quenched with addition of water. The mixture was extracted with methylene chloride (3×7 mL) and the extracts were dried with magnesium sulfate. The solvent was removed and the residue was purified on an ISCO machine (40 g column, eluent, 50% EtOAc/hexanes) to give a white solid. 34 mg.

MS (ES$^+$) m/z Calcd: [(M+H)$^+$]: 523. found: 523.

Example 217

Preparation of {[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-acetic aid trifluoro acetic acid salt

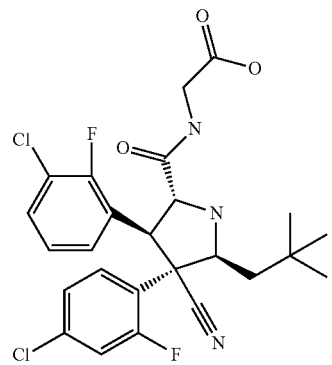

Molecular Weight = 524.3991
Molecular Formula = C25H25Cl2F2N3O3• rac {[(2R,3S,4R,5S)-3-(3-Chloro-2-fluoro-phenyl)-4-(4-chloro-2-fluoro-phenyl)-4 cyano-5-(2,2-dimethyl-propyl)-pyrrolidine-2-carbonyl]-amino}-acetic aid trifluoro acetic acid salt was separate on a sfc machine (30% MeOH, 100 Bar, 30° C.) give the desired enantiomer.

MS (ES$^+$) m/z Calcd: [(M+H)$^+$]: 524. found: 524.

Example 218

Preparation of rac 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester

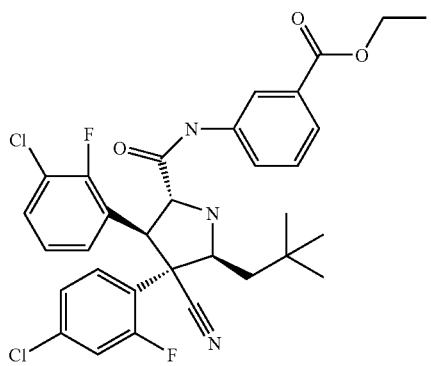

Molecular Weight = 614.5250
Molecular Formula = C32H31Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.172 mmol) in methylene chloride (10 mL), HATU (Aldrich, 98 mg, 0.258 mmol) was added followed by the addition of DIPEA (90 uL, 0.52 mmol) and 3-aminobenzoic acid ethyl ester (Aldrich, 43 mg, 0.26 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (24 g column, eluent, 10% EtOAc/methylene chloride) to give a white solid. 55 mg.

HRMS (ES$^+$) m/z Calcd: [(M+H)$^+$]:614.178d. found: 614.1783.

Example 219

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-carbamoyl-phenyl)-amide

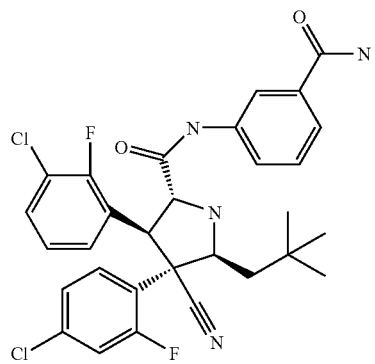

Molecular Weight = 585.4861
Molecular Formula = C30H28Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.172 mmol) in methylene chloride (10 mL), HATU (Aldrich, 98 mg, 0.258 mmol) was added followed by the addition of DIPEA (90 uL, 0.52 mmol) and 3-amino benzamide (Oakwood, 35 mg, 0.26 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (24 g column, eluent, 30% EtOAc/methylene chloride) to give a white solid. 58 mg.

HRMS (ES$^+$) m/z Calcd: [(M+H)$^+$]: 585.1630. found: 585.1629.

Example 220

Preparation of rac 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester

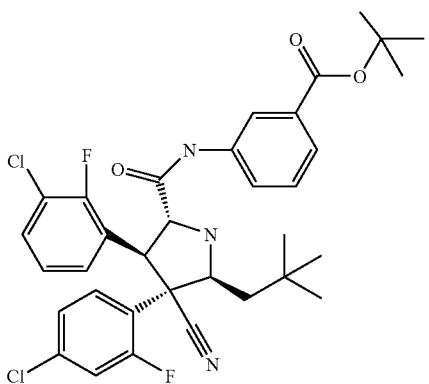

Molecular Weight = 642.5792
Molecular Formula = C34H35Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.172 mmol) in methylene chloride (10 mL), HATU (Aldrich, 98 mg, 0.258 mmol) was added followed by the addition of DIPEA (90 uL, 0.52 mmol) and 3-amino benzoic acid t-butyl ester (Aldrich, 50 mg, 0.26 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (24 g column, eluent, 5% EtOAc/methylene chloride) to give a white solid. 80 mg.

HRMS (ES+) m/z Calcd: [(M+H)+]: 642.2097 found: 642.2101

Example 221

Preparation of rac 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

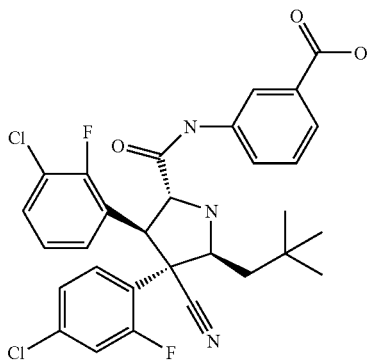

Molecular Weight = 586.4708
Molecular Formula = C30H27Cl2F2N3O3 rac 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid t-butyl ester (20 mg, 0.031 mmol) was treated with 30% TFA/methylene chloride (10 mL) overnight. Removal of solvent and freeze drying of the residue give a white powder. 12 mg.

HRMS (ES+) m/z Calcd: [(M+H)+]: 586.1471. found: 586.1467.

Example 222

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-hydroxymethyl-phenyl)-amide

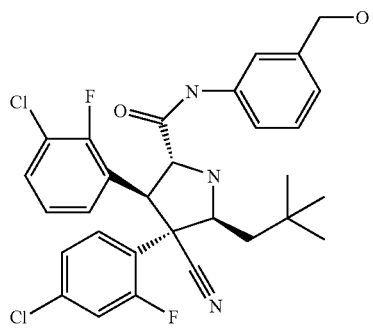

Molecular Weight = 572.4873
Molecular Formula = C30H29Cl2F2N3O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (80 mg, 0.172 mmol) in methylene chloride (10 mL), HATU (Aldrich, 104 mg, 0.27 mmol) was added followed by the addition of DIPEA (80 uL,) and 3-amino benzyl alcohol (Aldrich, 80 uL). The mixture was stirred at rt overnight. The reaction was quenched with addition of water. The mixture was extracted with methylene chloride (2×10 mL) and the extracts were dried with magnesium sulfate. The solvent was removed and the residue was purified reverse phase HPLC (24 g column, eluent, ACN/water, 20-90) to give a white solid. 40 mg.

HRMS (ES+) m/z Calcd: [(M+H)+]: 572.1678. found: 572.1679.

Example 223

Preparation of rac (3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-propyl)-carbamic acid tert-butyl ester

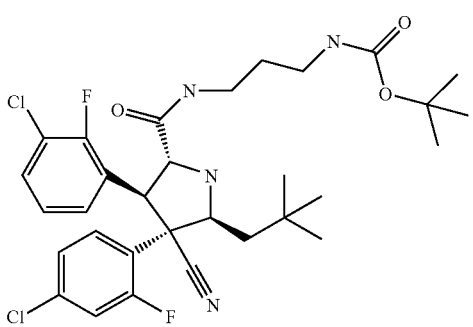

Molecular Weight = 623.5763
Molecular Formula = C31H38Cl2F2N4O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (800 mg, 1.74 mmol) in methylene chloride (10 mL), HATU (Aldrich, 662 mg, 1.74 mmol) was added followed by the addition of DIPEA (1.74 mmol) and (3-amino-propyl)-carbamic acid tert-butyl ester (Aldrich, 1.74 mmol). The mixture was stirred at rt for 1 hr. The reaction was quenched with addition of water. The mixture was extracted with methylene chloride (2×10 mL) and the extracts were dried with magnesium sulfate. The solvent was removed and the residue was purified on an ISCO machine (24 g column, eluent, EtOAc/Hexanes, 20%) to give a white solid. 810 mg.

MS (ES$^+$) m/z Calcd: [(M+H)$^+$]: 623. found: 623.

Example 224

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-amino-propyl)-amide

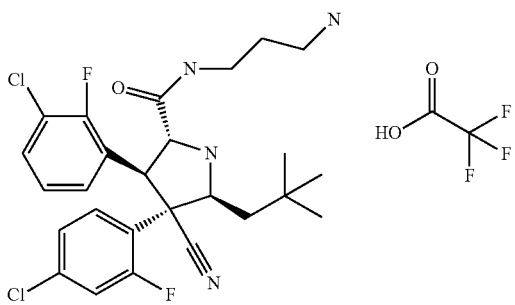

Molecular Weight = 523.4580 114.0243
Molecular Formula = C26H30Cl2F2N4O•C2HF3O2

Rac (3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-propyl)-carbamic acid tert-butyl ester (815 mg) was treated with 30% TFA/methylene chloride (10 mL) overnight. Removal of solvent and freeze drying of the residue give a white powder. 800 mg.

MS (ES$^+$) m/z Calcd: [(M+H)$^+$]: 523. found: 523.

Example 225

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [3-(aminosulfonyl-amino)-propyl]-amide

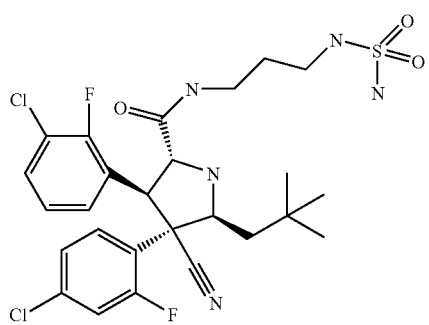

Molecular Weight = 602.5355
Molecular Formula = C26H31Cl2F2N5O3S

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-amino-propyl)-amide (100 mg) in DMF (3 mL), sulfamide (Aldrich, 62 mg) and potassium carbonate (50 mg) were added and the mixture was stirred at 100° C. for 6 hrs. The solvent was removed under reduced pressure and the residue was portioned between EtOAc and water. The organic layer was separated and dried with sodium sulfate. The solvent was removed and the residue was chromatographed on an ISCO machine (70-100% EtOAc/Hexanes) to give a white solid. 25 mg.

MS (ES$^+$) m/z Calcd: [(M+H)$^+$]: 602. found: 602.

Example 226

Preparation of rac 2-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester

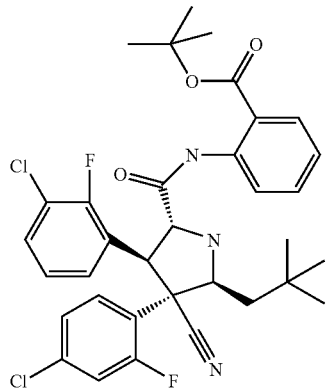

Molecular Weight = 642.5792
Molecular Formula = C34H35Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (120 mg, 0.21 mmol) in methylene chloride (10 mL), HATU (Aldrich, 157 mg, 0.41 mmol) was added followed by the addition of DIPEA (110 uL, 0.62 mmol) and 2-amino benzoic acid t-butyl ester (Aldrich, 80 mg, 0.41 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, eluent, 20% EtOAc/hexanes) to give a white solid. 71 mg.

HRMS (ES$^+$) m/z Calcd: [(M+H)$^+$]: 642.100. found: 642.2009.

Example 227

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester

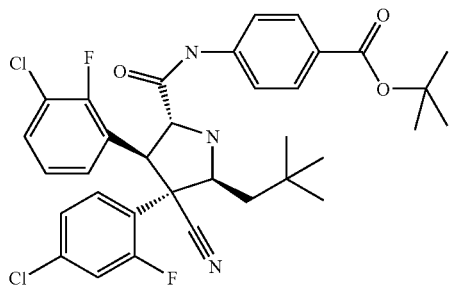

Molecular Weight = 642.5792
Molecular Formula = C34H35Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (120 mg, 0.21 mmol) in methylene chloride (10 mL), HATU (Aldrich, 157 mg, 0.41 mmol) was added followed by the addition of DIPEA (110 uL, 0.62 mmol) and 4-amino benzoic acid t-butyl ester (Aldrich, 80 mg, 0.41 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, eluent, 20% EtOAc/hexanes) to give a white solid. 55 mg.

HRMS (ES$^+$) m/z Calcd: [(M+H)$^+$]: 642.207. found: 642.2100.

Example 228

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester

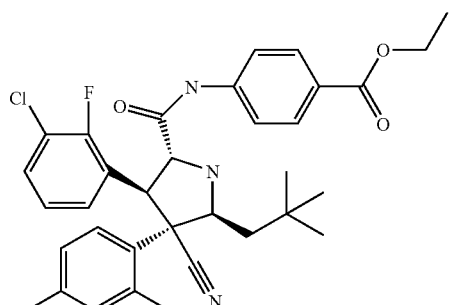

Molecular Weight = 614.5250
Molecular Formula = C32H31Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (90 uL, 0.52 mmol) and 4-amino benzoic acid ethyl ester (43 mg, 0.26 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, eluent, 20% EtOAc/hexanes) to give a white solid. 37 mg.

HRMS (ES$^+$) m/z Calcd: [(M+H)$^+$]: 614.1784. found: 614.1786.

Example 229

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (2-carbamoyl-phenyl)-amide

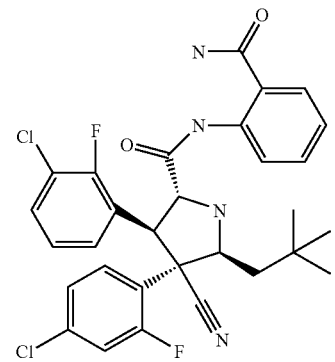

Molecular Weight = 585.4861
Molecular Formula = C30H28Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (90 uL, 0.52 mmol) and 2-amino benzamide (Aldrich, 35 mg, 0.26 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, eluent, 20% EtOAc/hexanes) to give a white solid. 30 mg.

HRMS (ES$^+$) m/z Calcd: [(M+H)$^+$]: 585.1630. found: 585.1628.

Example 230

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide

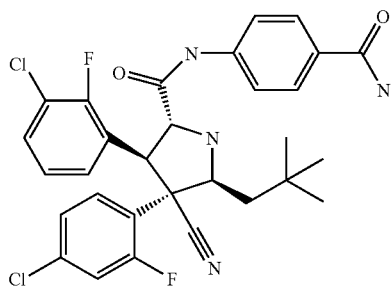

Molecular Weight = 585.4861
Molecular Formula = C30H28Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (90 uL, 0.52 mmol) and 4-amino benzamide (Aldrich, 35 mg, 0.26 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, eluent, 20% EtOAc/hexanes) to give a white solid. 30 mg.

MS (ES$^+$) m/z Calcd: [(M+H)$^+$]: 585. found: 585.

Example 231

Preparation of rac 2-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester

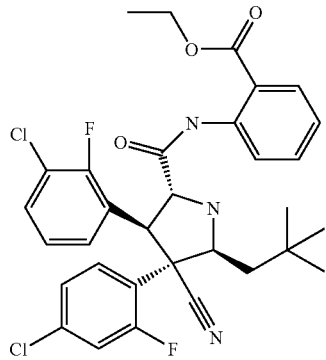

Molecular Weight = 614.5250
Molecular Formula = C32H31Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (90 uL, 0.52 mmol) and 2-amino benzoic acid ethyl ester (Aldrich, 43 mg, 0.26 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, eluent, 20% EtOAc/hexanes) to give a white solid. 13 mg.

HRMS (ES$^+$) m/z Calcd: [(M+H)$^+$]: 614.1784. found: 614.1787.

Example 232

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

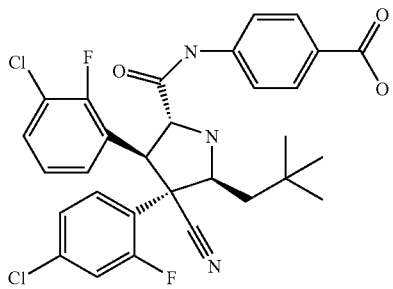

Molecular Weight = 586.4708
Molecular Formula = C30H27Cl2F2N3O3 rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid t-butyl ester (35 mg, 0.031 mmol) was treated with 30% TFA/methylene chloride (10 mL) overnight. Removal of solvent and freeze drying of the residue give a white powder. 31 mg.

HRMS (ES$^+$) m/z Calcd: [(M+H)$^+$]: 586.1471. found: 586.1470.

Example 233

Preparation of rac 2-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

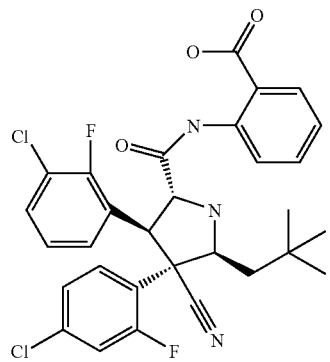

Molecular Weight = 586.4708
Molecular Formula = C30H27Cl2F2N3O3 rac 2-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid t-butyl ester (50 mg, 0.031 mmol) was treated with 30% TFA/methylene chloride (10 mL) overnight. Removal of solvent and freeze drying of the residue give a white powder. 15 mg.

HRMS (ES$^+$) m/z Calcd: [(M+H)$^+$]: 586.1471. found: 586.1473.

Example 234

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-cyano-phenyl)-amide

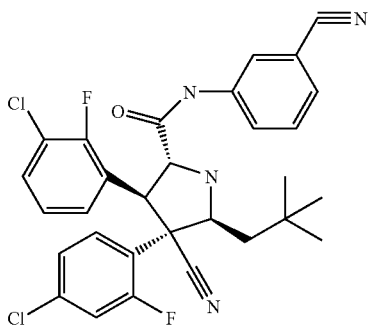

Molecular Weight = 567.4707
Molecular Formula = C30H26Cl2F2N4O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (250 mg, 0.54 mmol) in methylene chloride (10 mL), HATU (Aldrich, 247 mg, 0.65 mmol) was added followed by the addition of DIPEA (0.65 mmol) and 3-amino benzonitrile (Aldrich, 77 mg, 0.65 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, eluent, 35-50% EtOAc/hexanes) to give a white solid. 84 mg.

MS (ES$^+$) m/z Calcd: [(M+H)$^+$]: 567. found: 567.

Example 235

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (2-hydroxy-2-methyl-propyl)-amide

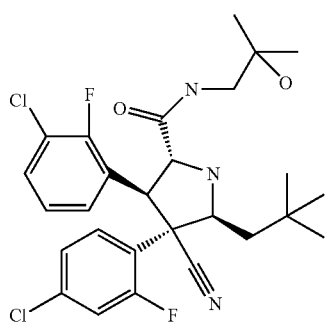

Molecular Weight = 538.4698
Molecular Formula = C27H31Cl2F2N3O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (80 mg, 0.14 mmol) in methylene chloride (10 mL), HATU (Aldrich, 105 mg, 0.28 mmol) was added followed by the addition of DIPEA (0.34 mmol) and 2-hydroxy-2-methyl-propylamine (Matrix, 25 mg, 028 mmol). The mixture was stirred at rt 1 hr. The reaction was quenched with addition of water. The mixture was extracted with methylene chloride (2×10 mL) and the extracts were dried with magnesium sulfate. The solvent was removed and the residue was purified on an ISCO machine (40 g column, eluent, 35-50% EtOAc/hexanes) to give a white solid. 50 mg.

MS (ES$^+$) m/z Calcd: [(M+H)$^+$]: 538.1834. found: 538.1834.

Example 236

Preparation of rac 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid 2-hydroxy-2-methyl-propyl ester

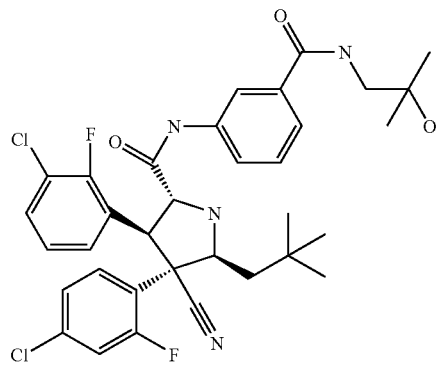

Molecular Weight = 657.5938
Molecular Formula = C34H36Cl2F2N4O3

To a stirred solution rac 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid (80 mg, 0.14 mmol) in methylene chloride (10 mL), HATU (Aldrich, 104 mg, 0.27 mmol) was added followed by the addition of DIPEA (0.41 mmol) and 2-hydroxy-2-methyl-propylamine (Matrix, 24 mg, 027 mmol). The mixture was stirred at rt 1 hr. The reaction was quenched with addition of water. The mixture was extracted with methylene chloride (2×10 mL) and the extracts were dried with magnesium sulfate. The solvent was removed and the residue was purified on an ISCO machine (40 g column, eluent, 35-50% EtOAc/hexanes) to give a white solid. 75 mg.

MS (ES$^+$) m/z Calcd: [(M+H)$^+$]: 657.2206. found: 657.2208.

Example 237

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-methanesulfonylamino-phenyl)-amide

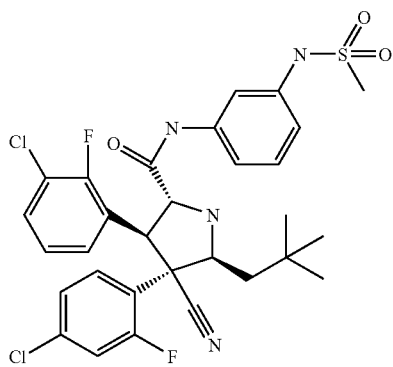

Molecular Weight = 635.5654
Molecular Formula = C30H30Cl2F2N4O3S

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.22 mmol) in methylene chloride (10 mL), HATU (Aldrich, 83 mg, 0.22 mmol) was added followed by the addition of DIPEA (0.20 mL) and 3-aminophenyl-methanesulfonamide (Aldrich, 0.25 mmol). The mixture was stirred at rt 1 hr. The reaction was quenched with addition of water. The mixture was extracted with methylene chloride (2×10 mL) and the extracts were dried with magnesium sulfate. The solvent was removed and the residue was purified on an ISCO machine (40 g column, eluent, 35-80% EtOAc/hexanes) to give a white solid. 64 mg.
MS (ES$^+$) m/z Calcd: [(M+H)$^+$]: 634. found: 634.

Example 238

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (1H-tetrazol-5-ylmethyl)-amide

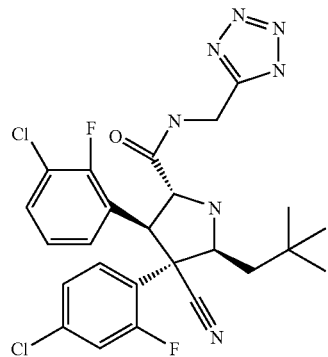

Molecular Weight = 548.4271
Molecular Formula = C25H25Cl2F2N7O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.22 mmol) in methylene chloride (10 mL), HATU (Aldrich, 83 mg, 0.22 mmol) was added followed by the addition of DIPEA (0.20 mL) and 1H-tetrazol-5-yl-methylamine hydrobromide (Aldrich, 54 mg, 0.3 mmol). The mixture was stirred at rt 4.5 hr. The reaction was quenched with addition of water. The mixture was extracted with methylene chloride (2×10 mL) and the extracts were dried with magnesium sulfate. The solvent was removed and the residue was purified on a reverse phase HPLC to give a white solid. 47 mg.
MS (ES$^+$) m/z Calcd: [(M+H)$^+$]: 548. found: 548.

Example 239

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-ureado-propyl)-amide

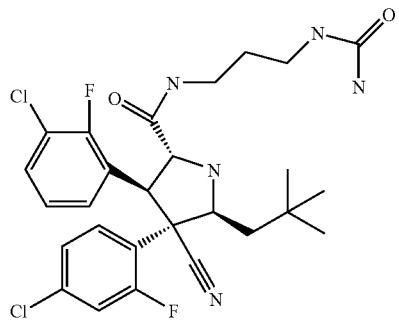

Molecular Weight = 566.4832
Molecular Formula = C27H31Cl2F2N5O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-amino-propyl)-amide (100 mg) in DMF (3 mL), N-trimethylsilyl isocyanate (Aldrich, 0.13 mmol) and isopropylethylamine (Aldrich, 0.15 mL) were added and the mixture was stirred at rt for 2 hrs. The solvent was removed under reduced pressure and the residue was partioned between EtOAc and water. The organic layer was separated and dried with sodium sulfate. The solvent was removed and the residue was chromatographed on an ISCO machine (4-9% MeOH/EtOAc) to give a white solid. 52 mg.
MS (ES$^+$) m/z Calcd: [(M+H)$^+$]: 566. found: 566.

Example 240

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-methylsulfanyl-phenyl)-amide

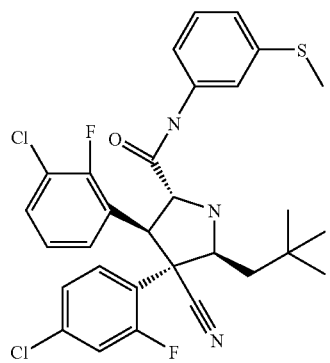

Molecular Weight = 588.5519
Molecular Formula = C30H29Cl2F2N3OS

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (250 mg, 0.44 mmol) in methylene chloride (10 mL), HATU (Aldrich, 332 mg, 0.88 mmol) was added followed by the addition of DIPEA (0.230 mL, 1.31 mmol) and 3-amino-phenyl methyl sulfide (Aldrich, 122 mg, 0.88 mmol). The mixture was stirred at rt for 2 hr. The reaction was quenched with addition of water. The mixture was extracted with methylene chloride (2×10 mL) and the extracts were dried with magnesium sulfate. The solvent was removed and the residue was purified on an ISCO machine (50 g column, eluent EtOAc/Hexanes, 5-10%) to give a white solid. 178 mg.

HRMS (ES$^+$) m/z Calcd: [(M+H)$^+$]: 588.1449. found: 588.1450.

Example 241

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-methanesulfonyl-phenyl)-amide

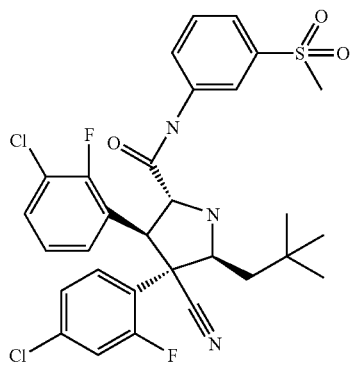

Molecular Weight = 620.5507
Molecular Formula = C30H29Cl2F2N3O3S

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-methylsulfanyl-phenyl)-amide (32 mg, 0.0544 mmol) in methylene chloride (5 mL) at rt, McPBA (Aldrich, 77%, 20.6 mg, 0.12 mmol) was added and the mixture was stirred for 2 hrs. The reaction was quenched with aqueous thiosulfate and the layers were separated. The organic layer was washed with 10% sodium carbonate (10 mL) and dried with sodium sulfate. The solvent was removed and the residue was loaded onto a silica gel column (12 g, 10% EtOAc/methylene chloride) to give a white solid. 28 mg.

HRMS (ES$^+$) m/z Calcd: [(M+H)$^+$]: 620.1348. found: 620.1347.

Example 242

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-methanesulfinyl-phenyl)-amide

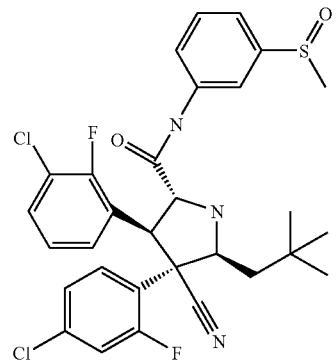

Molecular Weight = 604.5513
Molecular Formula = C30H29Cl2F2N3O2S

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-methylsulfanyl-phenyl)-amide (12 mg, 0.02 mmol) in methylene chloride (5 mL) at rt, McPBA (Aldrich, 77%, 6 mg, 0.026 mmol) was added and the mixture was stirred for 1.5 hrs. The reaction was quenched with aqueous sodium thiosulfate and the layers were separated. The organic layer was washed with 10% sodium carbonate (10 mL) and dried with sodium sulfate. The solvent was removed and the residue was loaded onto a silica gel column (12 g, 10% EtOAc/methylene chloride) to give a white solid. 6 mg.

HRMS (ES$^+$) m/z Calcd: [(M+H)$^+$]: 604.1399. found: 604.1399.

2 mg of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-methanesulfonyl-phenyl)-amide was also obtained.

Example 243

Preparation of 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

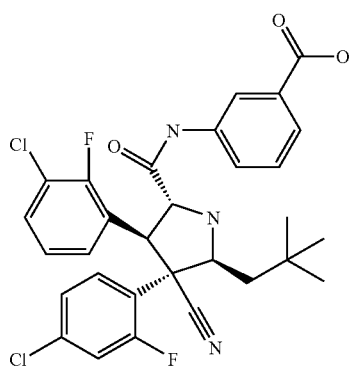

Molecular Weight = 586.4708
Molecular Formula = C30H27Cl2F2N3O3 rac 3-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid t-butyl ester (26 mg, 0.411 mmol) was treated with 50% TFA/methylene chloride (10 mL) overnight. Removal of solvent and freeze drying of the residue give a white powder. 250 mg. The solid was resolved on a Berger SFC system on a Whelk column under 100 bar, 30° C., and 45% of methanol to give two peaks: Peak 1, undesired enantiomer, 78 mg; Peak 2, 77 mg as white solid.

HRMS (ES+) m/z Calcd: [(M+H)+]: 586.1471. found: 586.1467.

Example 244

Preparation of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-carbamoyl-phenyl)-amide

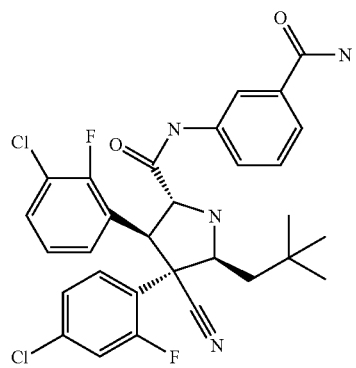

Molecular Weight = 585.4861
Molecular Formula = C30H28Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.172 mmol) in methylene chloride (10 mL), HATU (Aldrich, 98 mg, 0.258 mmol) was added followed by the addition of DIPEA (90 uL, 0.52 mmol) and 3-amino benzamide (Oakwood, 35 mg, 0.26 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (24 g column, eluent, 30% EtOAc/methylene chloride) to give a white solid. 58 mg. The solid was resolved on a Berger SFC system on a Whelk column under 100 bar, 30° C., and 35% of methanol to give two peaks: Peak 1, undesired enantiomer, 19 mg; Peak 2, 21 mg as white solid.

HRMS (ES+) m/z Calcd: [(M+H)+]: 585.1630. found: 585.1620.

Example 245

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide

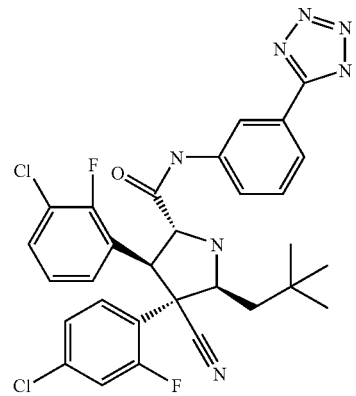

Molecular Weight = 610.4988
Molecular Formula = C30H27Cl2F2N7O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.172 mmol) in methylene chloride (10 mL), HATU (Aldrich, 130 mg, 0.344 mmol) was added followed by the addition of DIPEA (90 uL, 0.52 mmol) and 3-(1H-tetrazol-5-yl)-phenylamine (Alfa, 55 mg, 0.344 mmol). The mixture was stirred at rt for 2 hrs. The reaction was quenched with addition of water. The mixture was extracted with methylene chloride (2×10 mL) and the extracts were dried with magnesium sulfate. The solvent was removed and the residue was purified on a reverse phase HPLC (24 g column, eluent, 30% EtOAc/methylene chloride) to give a yellow solid. 21 mg.

HRMS (ES+) m/z Calcd: [(M+H)+]: 610.1695. found: 610.1698.

Example 246

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide

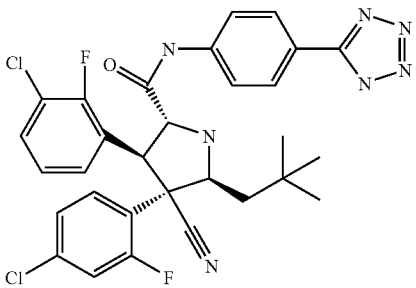

Molecular Weight = 610.4988
Molecular Formula = C30H27Cl2F2N7O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.172 mmol) in methylene chloride (10 mL), HATU (Aldrich, 130 mg, 0.344 mmol) was added followed by the addition of DIPEA (90 uL, 0.52 mmol) and 4-(1H-tetrazol-5-yl)-phenylamine (Alfa, 55 mg, 0.344 mmol). The mixture was stirred at rt for 2 hrs. The reaction was quenched with addition of water. The mixture was extracted with methylene chloride (2×10 mL) and the extracts were dried with magnesium sulfate. The solvent was removed and the residue was purified on a reverse phase HPLC (24 g column, eluent, 30% EtOAc/methylene chloride) to give a yellow solid. 21 mg.

HRMS (ES$^+$) m/z Calcd: [(M+H)$^+$]: 610.1695. found: 610.1696.

Example 247

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-amino-phenyl)-amide

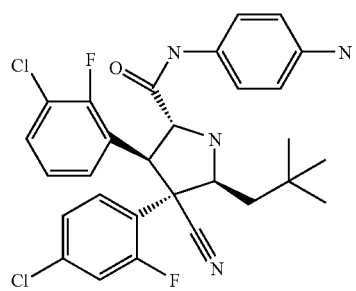

Molecular Weight = 557.4755
Molecular Formula = C29H28Cl2F2N4O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (300 mg, 0.66 mmol) in methylene chloride (10 mL), HATU (Aldrich, 266 mg, 0.66 mmol) was added followed by the addition of DIPEA (0.30 mL) and 4-amino-aniline (Aldrich, 143 mg, 1.32 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (24 g column, eluent, 40-85% EtOAc/hexanes) to give an off-white solid. 298 mg.

MS (ES$^+$) m/z Calcd: [(M+H)$^+$]: 557. found: 557.

Example 248

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide

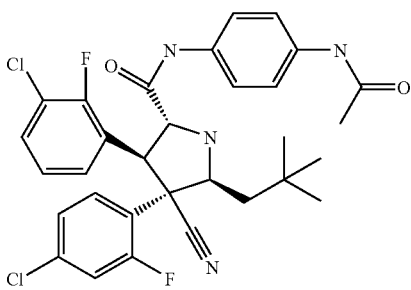

Molecular Weight = 599.5132
Molecular Formula = C31H30Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-amino-phenyl)-amide (40 mg, 0.072 mmol) in methylene chloride (5 mL), acetic anhydride (0.072 mmol) was added at room temperature followed by triethylamine (0.10 mL). The mixture was stirred at for 1 hr. and then chromatographed on an ISCO machine (12 g, 40-85% EtOAc/Hexanes) to give a white solid. 34 mg.

MS (ES$^+$) m/z Calcd: [(M+H)$^+$]: 599. found: 599.

Example 249

Preparation of rac 2-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-thiazole-4-carboxylic acid ethyl ester

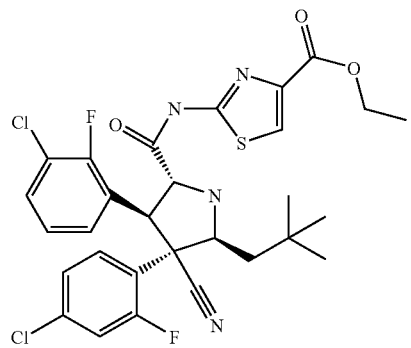

Molecular Weight = 621.5383
Molecular Formula = C29H28Cl2F2N4O3S

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.22 mmol) in methylene chloride (10 mL), HATU (Aldrich, 83 mg, 0.25 mmol) was added followed by the addition of DIPEA (100 uL) and 2-amino-thiazole-4-carboxylic acid ethyl ester (Oakwood, 43 mg, 0.25 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (24 g column, eluent, 40-80% EtOAc/hexanes) to give a solid. 32 mg.

MS (ES$^+$) m/z Calcd: [(M+H)$^+$]: 621. found: 621.

Example 250

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (1,3-dioxo-2,3-dihydro-1H-isoindol-5-yl)-amide

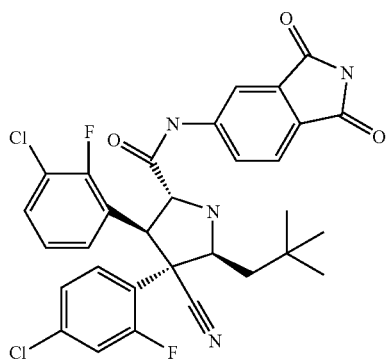

Molecular Weight = 611.4807
Molecular Formula = C31H26Cl2F2N4O3

To a stirred solution of thionyl chloride (2 mL), rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (110 mg, 0.24 mmol) was added and the mixture was stirred at rt for 2 hrs. The excess thionyl chloride was removed and the residue was dissolved in methylene chloride (5 mL) and 5-amino-isoindole-1,3-dione (Aldrich, 0.30 mmol) was added followed by the addition of triethylamine (0.2 mL). The mixture was stirred overnight. The solvent was removed and the residue was purified on an ISCO machine (24 g column, eluent, 40-80% EtOAc/hexanes) to give a pale yellow solid. 10 mg.

MS (ES$^+$) m/z Calcd: [(M+H)$^+$]: 611. found: 611.

Example 251

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide

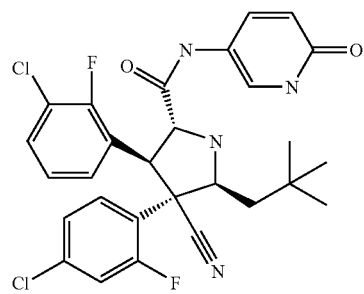

Molecular Weight = 559.4478
Molecular Formula = C28H26Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (200 mg, 0.44 mmol) in methylene chloride (8 mL), HATU (Aldrich, 166 mg, 0.50 mmol) was added followed by the addition of DIPEA (200 uL) and 5-amino-2-pyridinone (Alfa, 97 mg, 0.88 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (24 g column, eluent, 40-80% EtOAc/hexanes) to give a solid. 168 mg.

MS (ES$^+$) m/z Calcd: [(M+H)$^+$]: 559. found: 559.

Example 252

Preparation of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide

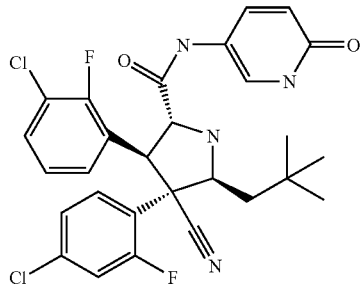

Molecular Weight = 559.4478
Molecular Formula = C28H26Cl2F2N4O2

(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide (168 mg) was resolved on a Berger SFC machine under 100 bar, 30° C. with 40% of methanol at a rate of 2 mL/min give two separated peaks. Peak 1, 62 mg, peak 2, 64 mg (desired).

MS (ES$^+$) m/z Calcd: [(M+H)$^+$]: 559. found: 559.

Example 253

Preparation of rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methylsulfanyl-phenyl)-amide

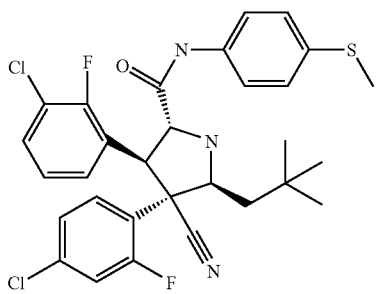

Molecular Weight = 588.5519
Molecular Formula = C30H29Cl2F2N3OS

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (250 mg, 0.44 mmol) in methylene chloride (10 mL), HATU (Aldrich, 332 mg, 0.88 mmol) was added followed by the addition of DIPEA (0.230 mL, 1.31 mmol) and 4-amino-phenyl methyl sulfide (Aldrich, 122 mg, 0.88 mmol). The mixture was stirred at rt for 2 hr. The reaction was quenched with addition of water. The mixture was extracted with methylene chloride (2×10 mL) and the extracts were dried with magnesium sulfate. The solvent was removed and the residue was purified on an ISCO machine (50 g column, eluent EtOAc/Hexanes, 5-10%) to give a white solid. 135 mg.

HRMS (ES$^+$) m/z Calcd: [(M+H)$^+$]: 588.1449. found: 588.1452.

Example 254

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide

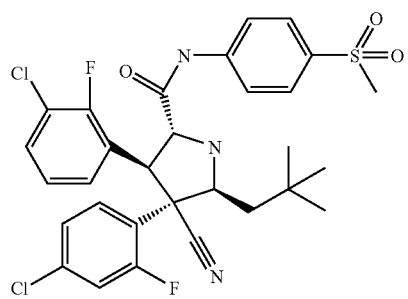

Molecular Weight = 620.5507
Molecular Formula = C30H29Cl2F2N3O3S

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-methylsulfanyl-phenyl)-amide (41 mg, 0.085 mmol) in methylene chloride (5 mL) at rt, MCPBA (Aldrich, 77%, 32 mg, 0.187 mmol) was added and the mixture was stirred for 2 hrs. The reaction was quenched with aqueous sodium thiosulfate and the layers were separated. The organic layer was washed with 10% sodium carbonate (10 mL) and dried with sodium sulfate. The solvent was removed and the residue was loaded onto a silica gel column (12 g, 10% EtOAc/methylene chloride) to give a white solid. 38 mg.

HRMS (ES$^+$) m/z Calcd: [(M+H)$^+$]: 620.1348. found: 620.1348.

Example 255

Preparation of 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester

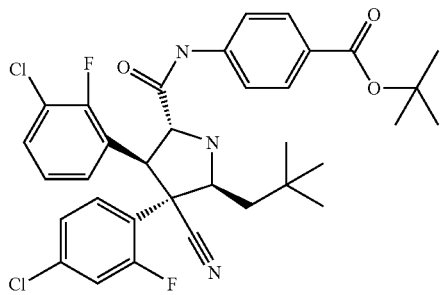

Molecular Weight = 642.5792
Molecular Formula = C34H35Cl2F2N3O3

Racemic 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester (670 mg) was resolved on a Berger SFC system under 30° C., 100 Bar, 20% MeOH on a O.D. column to give two peaks. Peak 1, desired, 267 mg, white solid; Peak 2, the other enantiomer, undesired, 267 mg, white solid;

HRMS (ES$^+$) m/z Calcd: [(M+H)$^+$]: 42. found: 642.

Example 256

Preparation of 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

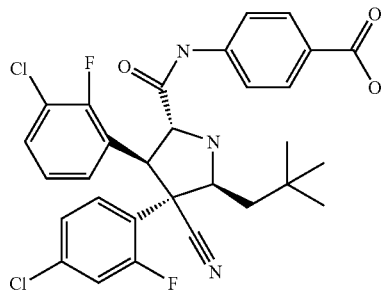

Molecular Weight = 586.4708
Molecular Formula = C30H27Cl2F2N3O3

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid t-butyl ester (255 mg, 0.397 mmol) was treated with 50% TFA/methylene chloride (10 mL) overnight. Removal of solvent and treating the residue with acetonitrile and water gave a white solid after filtration and drying. 236 mg.

HRMS (ES$^+$) m/z Calcd: [(M+H)$^+$]: 586.1471 found: 586.1467

Example 257

Preparation of 4-{[(2S,3R,4S,5R)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

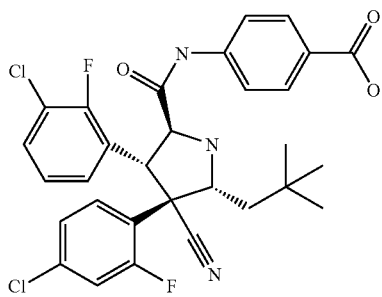

Molecular Weight = 586.4708
Molecular Formula = C30H27Cl2F2N3O3

4-{[(2S,3R,4S,5R)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid t-butyl ester (made above, 255 mg, 0.397 mmol) was treated with 50% TFA/methylene chloride (10 mL) overnight. Removal of solvent and treating the residue with acetonitrile and water gave a white solid after filtration and dying. 239 mg.

HRMS (ES$^+$) m/z Calcd: [(M+H)$^+$]: 586.1471. found: 586.1467.

Example 258

Preparation of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide

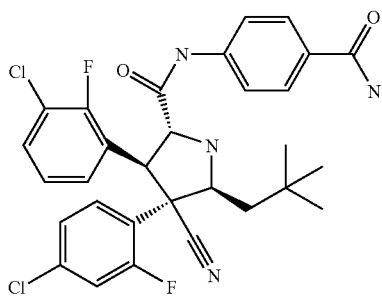

Molecular Weight = 585.4861
Molecular Formula = C30H28Cl2F2N4O2

Rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide (475 mg) was resolved on Berger SFC system under 30° C., 100 Bar, 35% MeOH on a O.D. Column to give two peaks. Peak 1, desired, 38 mg white solid; Peak 2, undesired, 38 mg white solid;

MS (ES$^+$) m/z Calcd: [(M+H)$^+$]: 585. found: 585.

Example 259

Preparation of (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide

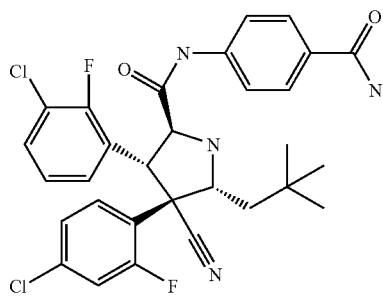

Molecular Weight = 585.4861
Molecular Formula = C30H28Cl2F2N4O2

Rac (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide (475 mg) was resolved on Berger SFC system under 30° C., 100 Bar, 35% MeOH on a O.D. Column to give two peaks. Peak 1, undesired, 38 mg white solid; Peak 2, desired, 38 mg white solid;

MS (ES$^+$) m/z Calcd: [(M+H)$^+$]: 585. found: 585.

Example 260

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylamino-phenyl)-amide

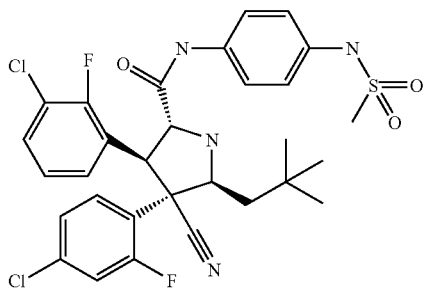

Molecular Weight = 635.5654
Molecular Formula = C30H30Cl2F2N4O3S

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-amino-phenyl)-amide (made above, 40 mg, 0.072 mmol) in methylene chloride (5 mL), methanesulfonic anhydride (Aldrich, 0.072 mmol) was added at room temperature followed by triethylamine (0.10 mL). The mixture was stirred at for 1 hr. and then chromatographed on an ISCO machine (12 g, 40-85% EtOAc/Hexanes) to give a white solid. 31 mg.

MS (ES$^+$) m/z Calcd: [(M+H)$^+$]: 635. found: 635.

Example 261

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-trifluoro-methanesulfonylamino-phenyl)-amide

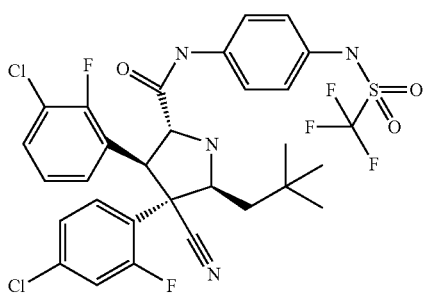

Molecular Weight = 689.5367
Molecular Formula = C30H27Cl2F5N4O3S

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-amino-phenyl)-amide (80 mg, 0.15 mmol) in methylene chloride (5 mL) at 0° C., trifluoromethanesulfonic anhydride (Aldrich, 0.15 mmol) was added at room temperature followed by triethylamine (0.10 mL). The mixture was stirred at for 1 hr. and then chromatographed on an ISCO machine (12 g, 40-85% EtOAc/Hexanes) to give a white solid. 64 mg.

MS (ES$^+$) m/z Calcd: [(M+H)$^+$]: 689. found: 689.

Example 262

Preparation of rac (2R,3R,4R,5S)-4-(4-Chloro-2-fluoro-phenyl)-3-(3-chloro-2-methyl-phenyl)-4-cyano-5-(2,2-dimethyl-propyl)-pyrrolidine-2-carboxylic acid [3-(1-methyl-1H-tetrazol-5-yl)-phenyl]-amide

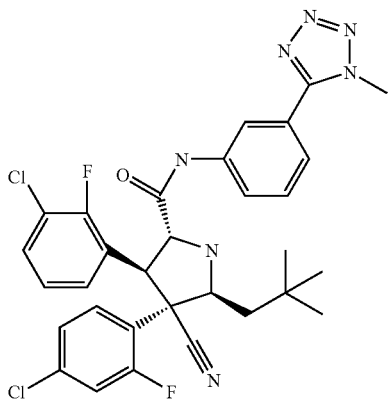

Molecular Weight = 624.5259
Molecular Formula = C31H29Cl2F2N7O

To a stirred solution of rac (2R,3R,4R,5S)-4-(4-Chloro-2-fluoro-phenyl)-3-(3-chloro-2-methyl-phenyl)-4-cyano-5-(2,2-dimethyl-propyl)-pyrrolidine-2-carboxylic acid [3-(1H-tetrazol-5-yl)-phenyl]-amide (44 mg, 0.172 mmol) in acetone (5 mL), sodium bicarbonate (84 mg, 1 mmol) and dimethyl sulfate (30 uL, 0.22 mmol) was added and the mixture was stirred at rt for 5 hrs. The solvent was removed and the residue was suspended in 3 mL of methylene chloride. The mixture was filtered and the filtrate was loaded on a silica gel column. Eluting with 35-70% EtOAc/Hexanes on an ISCO machine gave the desired product (12 mg) and the other regioisomer (26 mg).

MS (ES$^+$) m/z Calcd: [(M+H)$^+$]: 624. found: 624.

Example 263

Preparation of rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [3-(2-methyl-1H-tetrazol-5-yl)-phenyl]-amide

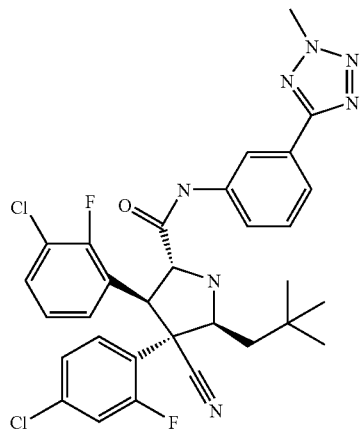

Molecular Weight = 624.5259
Molecular Formula = C31H29Cl2F2N7O

To a stirred solution of rac (2R,3R,4R,5S)-4-(4-Chloro-2-fluoro-phenyl)-3-(3-chloro-2-methyl-phenyl)-4-cyano-5-(2,2-dimethyl-propyl)-pyrrolidine-2-carboxylic acid [3-(1H-tetrazol-5-yl)-phenyl]-amide (44 mg, 0.172 mmol) in acetone (5 mL), sodium bicarbonate (84 mg, 1 mmol) and dimethyl sulfate (30 uL, 0.22 mmol) was added and the mixture was stirred at rt for 5 hrs. The solvent was removed and the residue was suspended in 3 mL of methylene chloride. The mixture was filtered and the filtrate was loaded on a silica gel column. Eluting with 35-70% EtOAc/Hexanes on an ISCO machine gave the desired product (26 mg) and the other regioisomer (12 mg).

MS (ES$^+$) m/z Calcd: [(M+H)$^+$]: 624. found: 624.

Example 264

Preparation of (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide

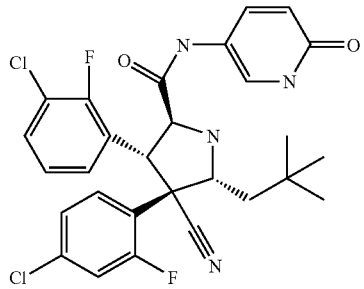

Molecular Weight = 559.4478
Molecular Formula = C28H26Cl2F2N4O2

Rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide (168 mg) was resolved on a Berger SFC machine under 100 bar, 30° C. with 40% of methanol at a rate of 2 mL/min give two separated peaks. Peak 1, 62 mg (desired), peak 2, 64 mg (undesired).

MS (ES$^+$) m/z Calcd: [(M+H)$^+$]: 559 found: 559.

Example 265

Preparation of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide

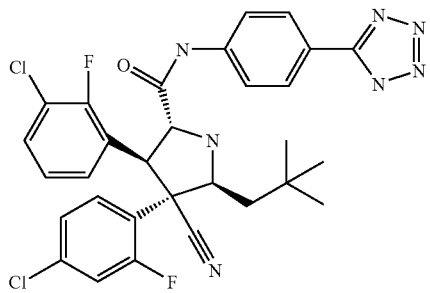

Molecular Weight = 610.4988
Molecular Formula = C30H27Cl2F2N7O

Rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide (522 mg) was resolved on a Berger SFC machine under 100 bar, 30° C. with 35% of methanol on an O.D. column gave two separated peaks. Peak 1, 186 mg (desired), peak 2, 185 mg (undesired).

MS (ES$^+$) m/z Calcd: [(M+H)$^+$]: 610. found: 610.

Example 266

Preparation of (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide

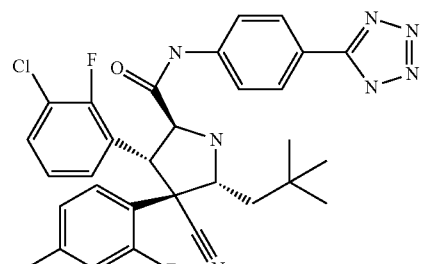

Molecular Weight = 610.4988
Molecular Formula = C30H27Cl2F2N7O

Rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide (522 mg) was resolved on a Berger SFC machine under 1000 bar, 30° C. with 35% of methanol on an O.D. column gave two separated peaks. Peak 1, 186 mg (undesired), peak 2, 185 mg (desired).

MS (ES$^+$) m/z Calcd: [(M+H)$^+$]: 610. found: 610.

Example 267

Preparation of rac (2R,3R,4R,5S)-4-(4-Chloro-2-fluoro-phenyl)-3-(3-chloro-2-methyl-phenyl)-4-cyano-5-(2,2-dimethyl-propyl)-pyrrolidine-2-carboxylic acid [4-(2-methyl-1H-tetrazol-5-yl)-phenyl]-amide

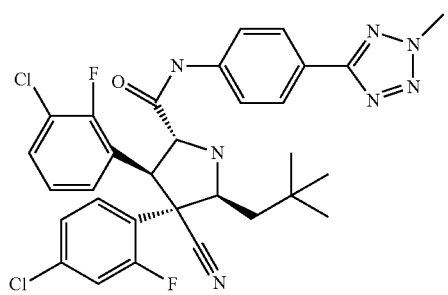

Molecular Weight = 624.5259
Molecular Formula = C31H29Cl2F2N7O

To a stirred solution of rac (2R,3R,4R,5S)-4-(4-Chloro-2-fluoro-phenyl)-3-(3-chloro-2-methyl-phenyl)-4-cyano-5-(2,2-dimethyl-propyl)-pyrrolidine-2-carboxylic acid [4-(1H-tetrazol-5-yl)-phenyl]-amide (32 mg, 0.0524 mmol) in acetone (5 mL), sodium bicarbonate (45 mg, 0.6 mmol) and dimethyl sulfate (0.11 mmol) was added and the mixture was stirred at rt for 5 hrs. The solvent was removed and the residue was suspended in 3 mL of methylene chloride. The mixture was filtered and the filtrate was loaded on a silica gel column. Eluting with 35-70% EtOAc/Hexanes on an ISCO machine gave the desired product (18 mg) and the other regioisomer (3 mg).

MS (ES$^+$) m/z Calcd: [(M+H)$^+$]: 624. found: 624.

Example 268

Preparation of rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [4-(1-methyl-1H-tetrazol-5-yl)-phenyl]-amide

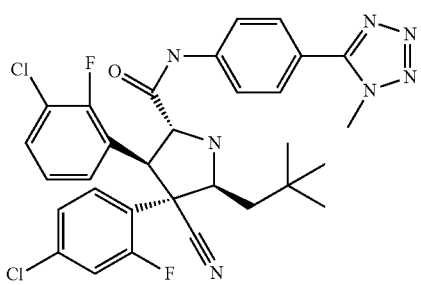

Molecular Weight = 624.5259
Molecular Formula = C31H29Cl2F2N7O

To a stirred solution of rac (2R,3R,4R,5S)-4-(4-Chloro-2-fluoro-phenyl)-3-(3-chloro-2-methyl-phenyl)-4-cyano-5-(2,2-dimethyl-propyl)-pyrrolidine-2-carboxylic acid [4-(1H-tetrazol-5-yl)-phenyl]-amide (32 mg, 0.0524 mmol) in acetone (5 mL), sodium bicarbonate (45 mg, 0.6 mmol) and dimethyl sulfate (0.11 mmol) was added and the mixture was stirred at rt for 5 hrs. The solvent was removed and the residue was suspended in 3 mL of methylene chloride. The mixture was filtered and the filtrate was loaded on a silica gel column. Eluting with 35-70% EtOAc/Hexanes on an ISCO machine gave the desired product (3 mg) and the other regioisomer (18 mg).

MS (ES$^+$) m/z Calcd: [(M+H)$^+$]: 624 found: 624.

Example 269

Preparation of rac 5-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid ethyl ester

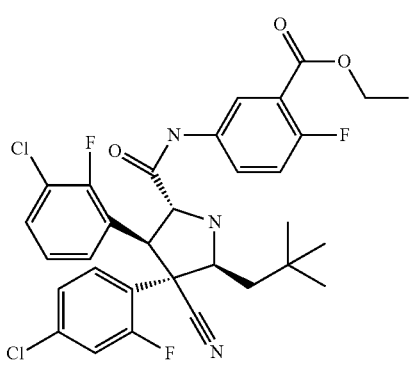

Molecular Weight = 632.5154
Molecular Formula = C32H30Cl2F3N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (0.150 mL, 0.855 mmol) and 5-amino-2-fluoro-benzoic acid ethyl ester (Oakwood, 63 mg, 0.34 mmol). The mixture was stirred at rt for 1.5 hr. The reaction was quenched with addition of water. The mixture was extracted with methylene chloride (2×10 mL) and the extracts were dried with magnesium sulfate. The solvent was removed and the residue was purified on an ISCO machine (50 g column, eluent EtOAc/Hexanes, 5-20%) to give a white solid. 64 mg.

MS (ES$^+$) m/z Calcd: [(M+H)$^+$]: 632. found: 632.

Example 270

Preparation of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide

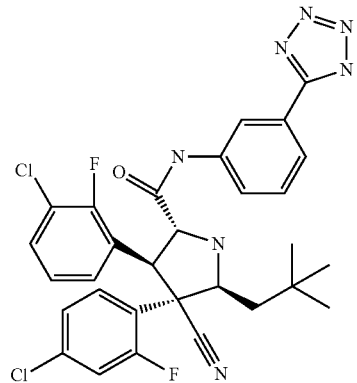

Molecular Weight = 610.4988
Molecular Formula = C30H27Cl2F2N7O

Rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide (690 mg) was resolved on a Berger SFC machine under 100 bar, 30° C. with 10% of methanol on an O.D. column gave two separated peaks. Peak 1, 256 mg (desired), peak 2, 186 mg (undesired).

MS (ES$^+$) m/z Calcd: [(M+H)$^+$]: 610; found: 610.

Example 271

Preparation of (2S,3R,4S,5R)-3-(3-Chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide

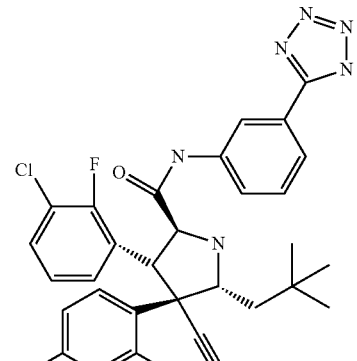

Molecular Weight = 610.4988
Molecular Formula = C30H27Cl2F2N7O

Rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide (690 mg) was resolved on a Berger SFC machine under 100 bar, 30° C. with 10% of methanol on an O.D. column gave two separated peaks. Peak 1, 256 mg (undesired), peak 2, 186 mg (desired).

MS (ES$^+$) m/z Calcd: [(M+H)$^+$]: 610 found: 610.

Example 272

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-3-chloro-phenyl)-amide

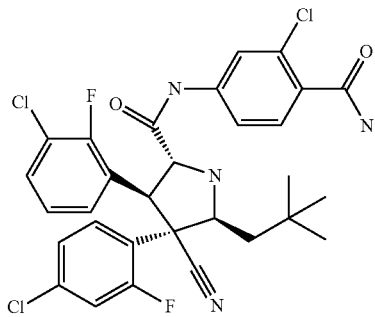

Molecular Weight = 619.9311
Molecular Formula = C30H27Cl3F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (0.150 mL, 0.855 mmol) and 4-amino-2-chloro-benzamide (Chembridge, 58 mg, 0.34 mmol). The mixture was stirred at rt for 1.5 hr. The reaction was quenched with addition of water. The mixture was extracted with methylene chloride (2×10 mL) and the extracts were dried with magnesium sulfate. The solvent was removed and the residue was purified on a reverse phase HPLC to give a white solid. 6 mg.
MS (ES$^+$) m/z Calcd: [(M+H)$^+$]: 619. found: 619.

Example 273

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [3-chloro-4-(1H-tetrazol-5-yl)-phenyl]-amide

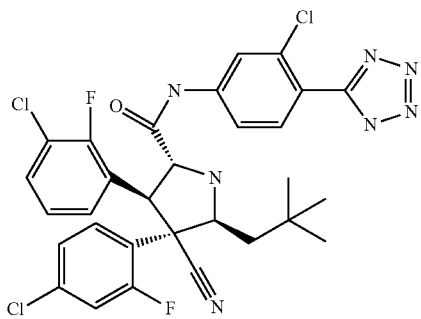

Molecular Weight = 644.9438
Molecular Formula = C30H26Cl3F2N7O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (0.150 mL, 0.855 mmol) and 3-chloro-4-(1H-tetrazol-5-yl) aniline (made below, 67 mg, 0.34 mmol). The mixture was stirred at rt for 1.5 hr. The reaction was quenched with addition of water. The mixture was extracted with methylene chloride (2×10 mL) and the extracts were dried with magnesium sulfate. The solvent was removed and the residue was purified on a reverse phase HPLC to give a white solid. 52 mg.
MS (ES$^+$) m/z Calcd: [(M+H)$^+$]: 644. found: 644.

Example 274

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-fluoro-phenyl)-amide

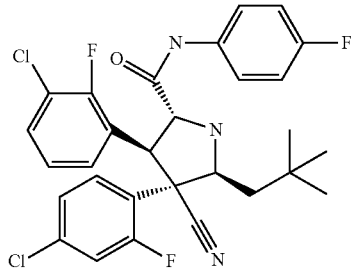

Molecular Weight = 560.4513
Molecular Formula = C29H26Cl2F3N3O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (0.150 mL, 0.855 mmol) and 4-fluoro-aniline (Aldrich, 38 mg, 0.32 mmol). The mixture was stirred at rt for 1.5 hr. The reaction was quenched with addition of water. The mixture was extracted with methylene chloride (2×10 mL) and the extracts were dried with magnesium sulfate. The solvent was removed and the residue was purified on an ISCO machine (20 g column, 0-10% EtOAc/methylene chloride) to give a white solid. 67 mg.
MS (ES$^+$) m/z Calcd: [(M+H)$^+$]: 560. found: 560.

Example 275

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-fluoro-phenyl)-amide

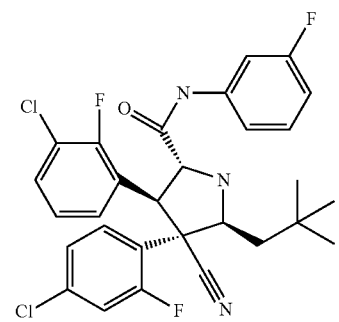

Molecular Weight = 560.4513
Molecular Formula = C29H26Cl2F3N3O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (0.150 mL, 0.855 mmol) and 3-fluoro-aniline (Aldrich, 38 mg, 0.32 mmol). The mixture was stirred at rt for 1.5 hr. The reaction was quenched with addition of water. The mixture was extracted with methylene chloride (2×10 mL) and the extracts were dried with magnesium sulfate. The solvent was removed and the residue was purified on an ISCO machine (20 g column, 0-10% EtOAc/methylene chloride) to give a white solid. 60 mg.

MS (ES$^+$) m/z Calcd: [(M+H)$^+$]: 560. found: 560.

Example 276

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (3-chloro-phenyl)-amide

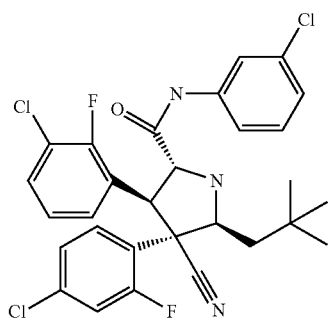

Molecular Weight = 576.9059
Molecular Formula = C29H26Cl3F2N3O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 98 mg, 0.26 mmol) was added followed by the addition of DIPEA (0.150 mL, 0.855 mmol) and 3-chloro-aniline (Aldrich, 44 mg, 0.32 mmol). The mixture was stirred at rt for 1.5 hr. The reaction was quenched with addition of water. The mixture was extracted with methylene chloride (2×10 mL) and the extracts were dried with magnesium sulfate. The solvent was removed and the residue was purified on an ISCO machine (20 g column, 0-10% EtOAc/methylene chloride) to give a white solid. 48 mg.

MS (ES$^+$) m/z Calcd: [(M+H)$^+$]: 576, found: 576.

Example 277

Preparation of rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (5-iodo-pyridin-2-yl)-amide

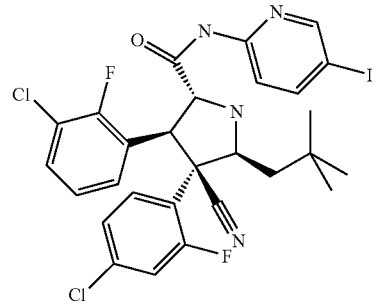

Molecular Weight = 669.3449
Molecular Formula = C28H25Cl2F2IN4O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid, TFA salt (200 mg, 0.34 mmol) in methylene chloride (3 mL), HATU (Aldrich, 235 mg, 0.62 mmol) was added followed by the addition of DIPEA (0.3 mL, 1.72 mmol) and 5-Iodo-pyridin-2-ylamine (Aldrich, 138 mg, 0.69 mmol). The mixture was stirred at RT overnight. The reaction was quenched with water. The mixture was extracted with methylene chloride (2×10 mL) and the extracts were dried with sodium sulfate. The solvent was removed and the residue was purified by flash chromatography (0-8% EtOAc/methylene chloride) to give the title compound as a white solid (95 mg, 41% yield).

MS (ES$^+$) m/z Calcd: [(M+H)$^+$]: 669, found: 669.

Example 278

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid tert-butyl ester

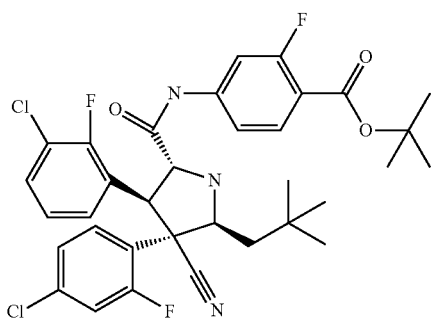

Molecular Weight = 660.5696
Molecular Formula = C34H34Cl2F3N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (150 mg, 0.26 mmol) in methylene chloride (10 mL), HATU (Aldrich, 147 mg, 0.39 mmol) was added followed by the addition of DIPEA (0.225 mL, 1.29 mmol) and 4-amino-2-fluoro-benzoic acid t-butyl ester (Aldrich, 44 mg, 0.32 mmol). The mixture was stirred at rt for 5.5 hr. The reaction was quenched with addition of water. The mixture was extracted with methylene chloride (2×10 mL) and the extracts were dried with magnesium sulfate. The solvent was removed and the residue was purified on an ISCO machine (40 g column, 0-15% EtOAc/hexanes) to give a white solid. 19 mg.

MS (ES$^+$) m/z Calcd: [(M+H)$^+$]: 660. found: 660.

Example 279

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-ethylcarbamoyl-phenyl)-amide

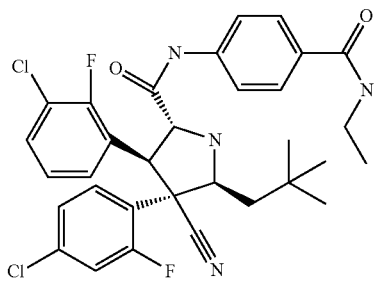

Molecular Weight = 613.5402
Molecular Formula = C32H32Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (150 mg, 0.26 mmol) in methylene chloride (10 mL), HATU (Aldrich, 147 mg, 0.39 mmol) was added followed by the addition of DIPEA (0.225 mL, 1.29 mmol) and 4-amino-ethyl-benzamide (made by reducing the corresponding nitro precursor, 56 mg, 0.34 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (40 g column, 0-15% EtOAc/hexanes) to give a white solid. 42 mg.

MS (ES$^+$) m/z Calcd: [(M+H)$^+$]: 613. found: 613.

Example 280

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid

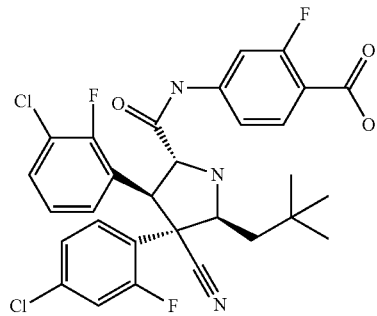

Molecular Weight = 604.4612
Molecular Formula = C30H26Cl2F3N3O3 rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid tert-butyl ester (35 mg, 0.053 mmol) was treated with 50% TFA/methylene chloride (10 mL) overnight. Removal of solvent and treating the residue with acetonitrile and water gave a white solid after filtration and dying. 29 mg.

HRMS (ES$^+$) m/z Calcd: [(M+H)$^+$]: 604.1376. found: 604.1376.

Example 281

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (6-methoxy-pyridin-3-yl)-amide

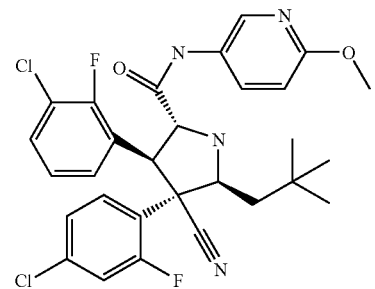

Molecular Weight = 573.4749
Molecular Formula = C29H28Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.217 mmol) in methylene chloride (10 mL), HATU (Aldrich, 118 mg, 0.31 mmol) was added followed by the addition of DIPEA (0.15 mL, 0.86 mmol) and 3-amino-6-methoxy-pyridine (Aldrich, 43 mg, 0.34 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (40 g column, 0-5% MeOH/methylene chloride) to give a white solid. 73 mg.

MS (ES+) m/z Calcd: [(M+H)+]: 573.1630. found: 573.1630.

Example 281

Preparation of rac 3-({[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid methyl ester

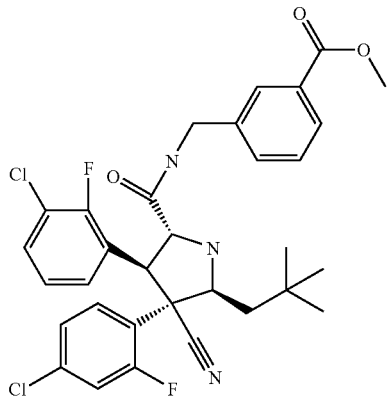

Molecular Weight = 614.5250
Molecular Formula = C32H31Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (150 mg, 0.26 mmol) in methylene chloride (10 mL), HATU (Aldrich, 177 mg, 0.46 mmol) was added followed by the addition of DIPEA (0.36 mL, 2.06 mmol) and 3-aminomethyl-benzoic acid methyl ester hydrochloride salt (Aldrich, 104 mg, 0.52 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (40 g column, 5-15% EtOAc/hexanes) to give a white solid. 118 mg.

MS (ES+) m/z Calcd: [(M+H)+]: 614. found: 614.

Example 282

Preparation of rac 4-({[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid methyl ester

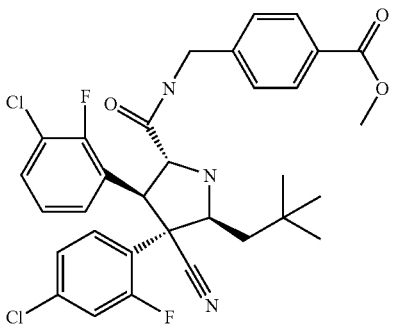

Molecular Weight = 614.5250
Molecular Formula = C32H31Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (150 mg, 0.26 mmol) in methylene chloride (10 mL), HATU (Aldrich, 177 mg, 0.46 mmol) was added followed by the addition of DIPEA (0.36 mL, 2.06 mmol) and 4-aminomethyl-benzoic acid methyl ester hydrochloride salt (Aldrich, 104 mg, 0.52 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (40 g column, 5-15% EtOAc/hexanes) to give a white solid. 119 mg.

MS (ES+) m/z Calcd: [(M+H)+]: 614, found: 614.

Example 283

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide

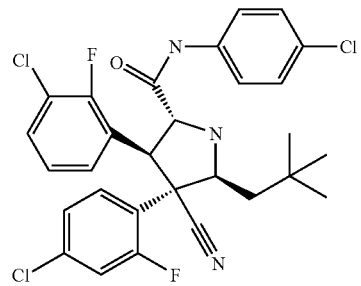

Molecular Weight = 576.9059
Molecular Formula = C29H26Cl3F2N3O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (200 mg, 0.34 mmol) in methylene chloride (10 mL), HATU (Aldrich, 234 mg, 0.62 mmol) was added followed by the addition of DIPEA (0.30 mL, 1.71 mmol) and 4-chloro-aniline (Aldrich, 88 mg, 0.68 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (40 g column, 5-15% EtOAc/hexanes) to give a white solid. 105 mg.

MS (ES+) m/z Calcd: [(M+H)+]: 576, found: 576.

Example 284

Preparation of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide

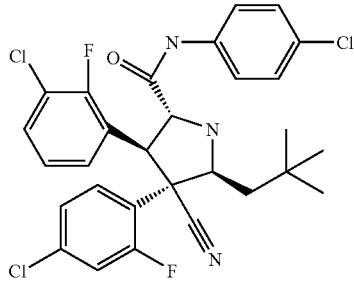

Molecular Weight = 576.9059
Molecular Formula = C29H26Cl3F2N3O rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide (100 mg) was separated on a Berger SFC machine under 100 bar, 30° C., and 45% of MeOH through a Whelk column to give a white solid (peak 2, 41 mg)

MS (ES$^+$) m/z Calcd: [(M+H)$^+$]: 576, found: 576.

Example 285

Preparation of (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide

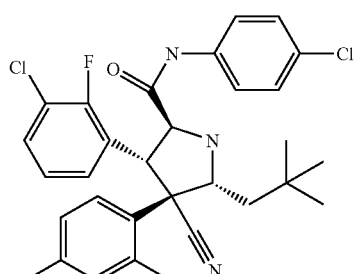

Molecular Weight = 576.9059
Molecular Formula = C29H26Cl3F2N3O rac (2S,3R,4S,5R)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide (100 mg) was separated on a Berger SFC machine under 100 bar, 30° C., and 45% of MeOH through a Whelk column to give a white solid (peak 1, 40 mg)

MS (ES$^+$) m/z Calcd: [(M+H)$^+$]: 576. found: 576.

Example 286

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid methyl ester

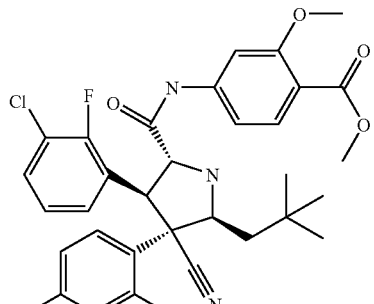

Molecular Weight = 630.5244
Molecular Formula = C32H31Cl2F2N3O4

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (100 mg, 0.17 mmol) in methylene chloride (10 mL), HATU (Aldrich, 118 mg, 0.31 mmol) was added followed by the addition of DIPEA (0.15 mL, 0.86 mmol) and 4-amino-2-methoxy-benzoic acid (Avocado, 62 mg, 0.34 mmol). The mixture was stirred at rt for overnight. The reaction was quenched with addition of water. The mixture was extracted with methylene chloride (2×10 mL) and the extracts were dried with magnesium sulfate. The solvent was removed and the residue was purified on an ISCO machine (40 g column, 5-15% EtOAc/methylene chloride) to give a white solid. 29 mg.

MS (ES$^+$) m/z Calcd: [(M+H)$^+$]: 630.1733. found: 630.1732.

Example 287

Preparation of rac 3-({[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid

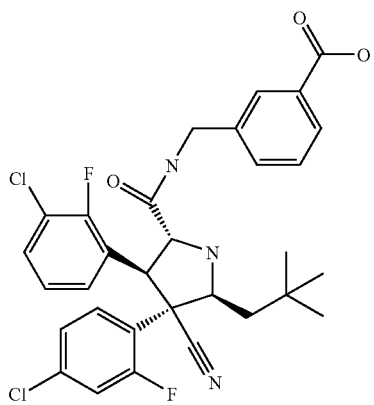

Molecular Weight = 600.4979
Molecular Formula = C31H29Cl2F2N3O3 rac 3-({[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid methyl ester (40 mg) was dissolved in MeOH (10 mL) with help of slight heating. To the stirred solution was added NaOH (1N, 2 mL) and the mixture was stirred for 1.5 hrs. The solvent was removed and the residue was treated with 1 N HCl to make the mixture acidic. The white suspension was extracted with EtOAc (3×10 mL) and the extracts combined and dried with sodium sulfate. The solvent was removed and the residue was freeze dried to give a white powder. 38 mg.

MS (ES+) m/z Calcd: [(M+H)+]: 600. found: 600.

Example 288

Preparation of rac 4-({[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid

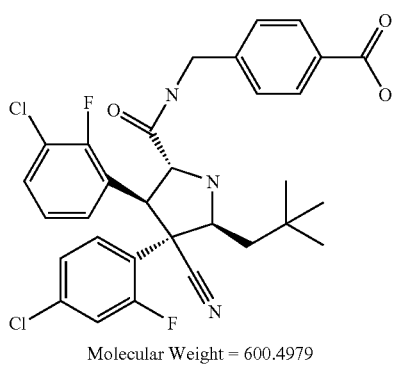

Molecular Weight = 600.4979
Molecular Formula = C31H29Cl2F2N3O3 rac 4-({[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid methyl ester (40 mg) was dissolved in MeOH (10 mL) with help of slight heating. To the stirred solution was added NaOH (1N, 2 mL) and the mixture was stirred for 1.5 hrs. The solvent was removed and the residue was treated with 1 N HCl to make the mixture acidic. The white suspension was extracted with EtOAc (3×10 mL) and the extracts combined and dried with sodium sulfate. The solvent was removed and the residue was freeze dried to give a white powder. 38 mg.

MS (ES+) m/z Calcd: [(M+H)+]: 600. found: 600.

Example 289

Preparation of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide

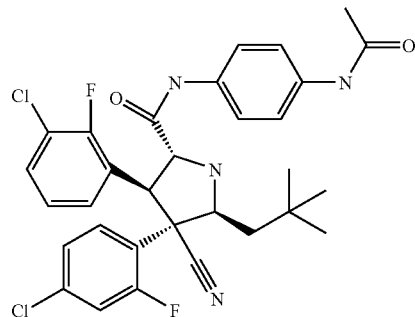

Molecular Weight = 599.5132
Molecular Formula = C31H30Cl2F2N4O2 rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide (360 mg) was separated on a Berger SFC machine under 100 bar, 30° C., and 45% of MeOH through an OJ column to give a white solid (peak 1, 103 mg)

MS (ES+) m/z Calcd: [(M+H)+]: 599. found: 599.

Example 290

Preparation of (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide

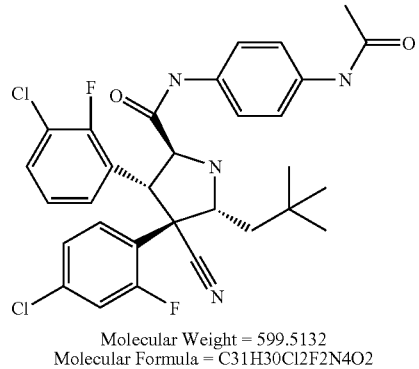 [SMILES: CC(=O)Nc1ccc(NC(=O)[C@H]2N[C@H](CC(C)(C)C)[C@@](C#N)(c3ccc(Cl)cc3F)[C@@H]2c2cccc(Cl)c2F)cc1]

Molecular Weight = 599.5132
Molecular Formula = C31H30Cl2F2N4O2 rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide (360 mg) was separated on a Berger SFC machine under 100 bar, 30° C., and 45% of MeOH through a OJ column to give a white solid (peak 2, 100 mg)

MS (ES+) m/z Calcd: [(M+H)+]: 599. found: 599.

Example 291

Preparation of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide

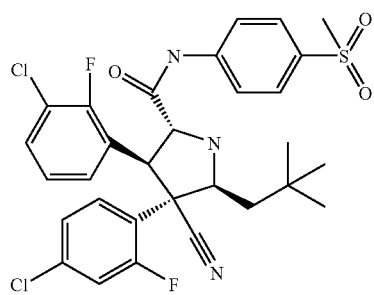

Molecular Weight = 620.5507
Molecular Formula = C30H29Cl2F2N3O3S rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide (165 mg) was separated on a Berger SFC machine under 100 bar, 30° C., and 20% of MeOH to give a white solid (peak 1, 90 mg)

MS (ES$^+$) m/z Calcd: [(M+H)$^+$]: 620. found: 620.

Example 292

Preparation of (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide

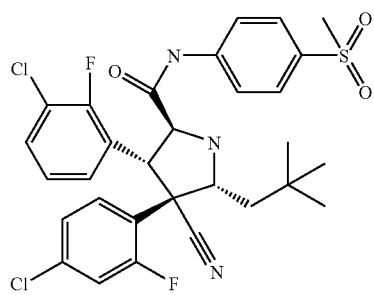

Molecular Weight = 620.5507
Molecular Formula = C30H29Cl2F2N3O3S rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide (165 mg) was separated on a Berger SFC machine under 100 bar, 30° C., and 20% of MeOH to give a white solid (peak 2, 90 mg)

MS (ES$^+$) m/z Calcd: [(M+H)$^+$]: 620. found: 620.

Example 293

Preparation of rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid

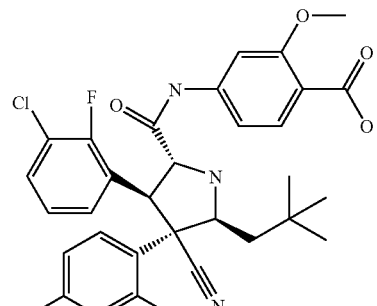

Molecular Weight = 616.4973
Molecular Formula = C31H29Cl2F2N3O4 rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid ester (40 mg) was dissolved in MeOH (10 mL) with help of slight heating. To the stirred solution was added NaOH (1N, 2 mL) and the mixture was stirred for 4 hrs at 50° C. The solvent was removed and the residue was treated with 1 N HCl to make the mixture acidic. The white suspension was extracted with EtOAc (3×10 mL) and the extracts combined and dried with sodium sulfate. The solvent was removed and the residue was freeze dried to give a white powder. 27 mg.

MS (ES$^+$) m/z Calcd: [(M+H)$^+$]: 616. found: 616.

Example 294

Preparation of rac 5-bromo-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid methyl ester

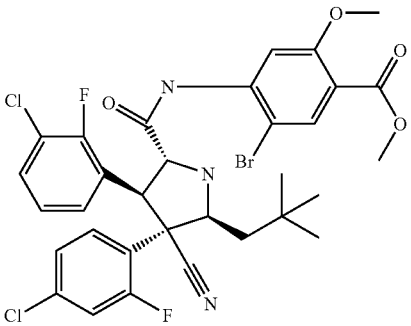

Molecular Weight = 709.4204
Molecular Formula = C32H30BrCl2F2N3O4

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (200 mg, 0.34 mmol) in methylene chloride (10 mL), HATU (Aldrich, 235 mg, 0.62 mmol) was added followed by the addition of DIPEA (0.30 mL, 1.72 mmol) and 4-amino-5-bromo-2-methoxy-benzoic acid (Aldrich, 179 mg, 0.69 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, 5-15% EtOAc/methylene chloride) to give a white solid. 7.3 mg.

MS (ES$^+$) m/z Calcd: [(M+H)$^+$]: 709. found: 709.

Example 295

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-methyl-benzoic acid methyl ester

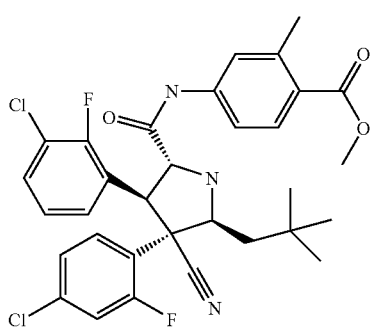

Molecular Weight = 614.5250
Molecular Formula = C32H31Cl2F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (200 mg, 0.34 mmol) in methylene chloride (10 mL), HATU (Aldrich, 235 mg, 0.62 mmol) was added followed by the addition of DIPEA (0.30 mL, 1.72 mmol) and 4-amino-2-methyl-benzoic acid (Aldrich, 114 mg, 0.69 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, 5-15% EtOAc/methylene chloride) to give a white solid. 102 mg.

MS (ES$^+$) m/z Calcd: [(M+H)$^+$]: 614. found: 614.

Example 296

Preparation of 4-amino-2-chlorobenzoic acid methyl ester

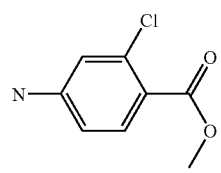

A solution of 4-nitro-2-chlorobenzoic acid methyl ester (Aldrich, 700 mg, 3.24 mmol) in ethyl acetate (50 mL) was treated with 10% Pd/C (50 mg) and hydrogenated at 1 atmosphere for 3 hrs. The mixture was filtered and concentrated to give a light yellow solid which was directly used for the next step.

Example 297

Preparation of rac 2-Chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester

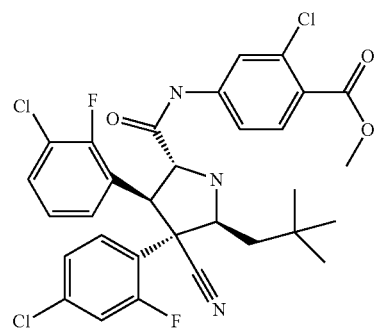

Molecular Weight = 634.9429
Molecular Formula = C31H28Cl3F2N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (200 mg, 0.34 mmol) in methylene chloride (10 mL), HATU (Aldrich, 235 mg, 0.62 mmol) was added followed by the addition of DIPEA (0.30 mL, 1.72 mmol) and 4-amino-2-chloro-benzoic acid (made above, 128 mg, 0.69 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, 5-15% EtOAc/methylene chloride) to give a white solid. 74 mg.

MS (ES$^+$) m/z Calcd: [(M+H)$^+$]: 634. found: 634.

Example 298

Preparation of 4-amino-2-trifluoromethyl benzoic acid methyl ester

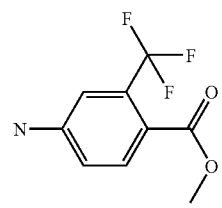

A solution of 4-nitro-2-trifluoromethyl benzoic acid methyl ester (Aldrich, 700 mg, 3.24 mmol) in ethyl acetate (50 mL) was treated with 10% Pd/C (50 mg) and hydrogenated at 1 atmosphere for 3 hrs. The mixture was filtered and concentrated to give a light yellow solid which was directly used for the next step.

Example 299

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-trifluoromethyl-benzoic acid methyl ester

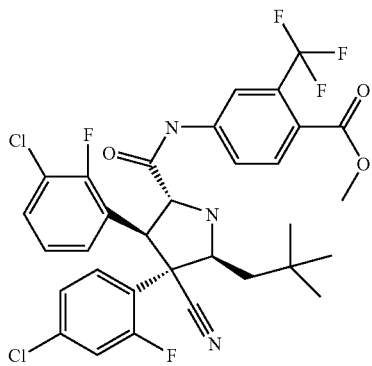

Molecular Weight = 668.4963
Molecular Formula = C32H28Cl2F5N3O3

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (166 mg, 0.29 mmol) in methylene chloride (10 mL), HATU (Aldrich, 195 mg, 0.54 mmol) was added followed by the addition of DIPEA (0.25 mL, 1.425 mmol) and 4-amino-2-trifluoromethyl-benzoic acid (made above, 125 mg, 0.57 mmol). The mixture was stirred at rt overnight. The reaction was quenched with addition of water. The mixture was extracted with methylene chloride (2×10 mL) and the extracts were dried with magnesium sulfate. The solvent was removed and the residue was purified on an ISCO machine (40 g column, 5-15% EtOAc/methylene chloride) to give a white solid. 40 mg.

MS (ES+) m/z Calcd: [(M+H)+]: 668. found: 668.

Example 300

Preparation of rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-methyl-benzoic acid

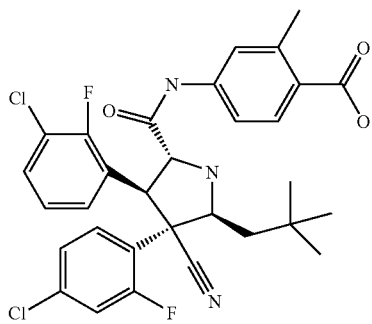

Molecular Weight = 600.4979
Molecular Formula = C31H29Cl2F2N3O3 rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-methyl-benzoic acid methyl ester (82 mg) was dissolved in MeOH (10 mL) with help of slight heating. To the stirred solution was added NaOH (1N, 2 mL) and the mixture was stirred for 3 hrs at 50° C. The solvent was removed and the residue was treated with 1 N HCl to make the mixture acidic. The white suspension was extracted with EtOAc (3×10 mL) and the extracts combined and dried with sodium sulfate. The solvent was removed and the residue was freeze dried to give a white powder. 67 mg.

MS (ES+) m/z Calcd: [(M+H)+]: 600. found: 600.

Example 301

Preparation of rac 2-Chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

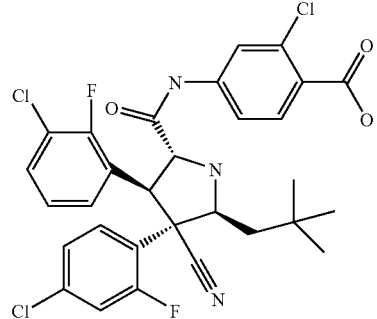

Molecular Weight = 620.9158
Molecular Formula = C30H26Cl3F2N3O3 rac 4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-chloro-benzoic acid methyl ester (54 mg) was dissolved in MeOH (10 mL) with help of slight heating. To the stirred solution was added NaOH (1N, 2 mL) and the mixture was stirred for 1 hrs at 55° C. The solvent was removed and the residue was treated with 1 N HCl to make the mixture acidic. The white suspension was extracted with EtOAc (3×10 mL) and the extracts combined and dried with sodium sulfate. The solvent was removed and the residue was freeze dried to give a white powder. 40 mg.

MS (ES+) m/z Calcd: [(M+H)+]: 620. found: 620.

Example 302

Preparation of 4-nitro-benzimidic acid methyl ester hydrochloride

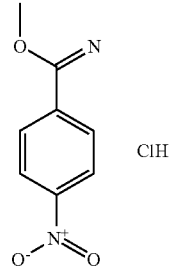

Molecular Weight = 180.1646 36.4610
Molecular Formula = C8H8N2O3•HCl

To a stirred solution of 4-nitro-benzonitrile (Aldrich, 17 g) in methanol (200 mL) was added 0.53 g of sodium methoxide. The solution was stirred for 12 hrs and another 1.5 g of sodium methoxide was added and the mixture was stirred for 6 hrs. The solution was cooled to 0° C. and HCl gas was bubbled in until a white solid forms. The solvent was reduced to about 100 mL and the solid was filtered and dried under vacuum to give a white solid. 12.1 g.

Example 303

Preparation of 5-(4-nitro-phenyl)-1H-[1,2,4]triazole

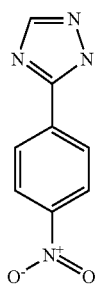

Molecular Weight = 190.1626
Molecular Formula = C8H6N4O2

4-Nitro-benzimidic acid methyl ester hydrochloride (635 mg, 2.93 mmol) was suspended in pyridine (7 mL) and formic hydrazide (Aldrich, 178 mg, 2.95 mmol) was added and the mixture was stirred at rt for 1 hr. The solvent was removed and the residue was dissolved in toluene (10 mL) and the mixture was stirred at reflux for 1.5 hrs. the mixture was cooled and water was added. The organic layer was separated and dried over sodium sulfate. The solvent was removed and the residue was suspended in 25% EtOAc/Hexanes and the solid was filtered to give a solid. 510 mg.
MS (ES$^+$) m/z Calcd: [(M+H)$^+$]: 191. found: 191.

Example 304

Preparation of
5-(4-amino-phenyl)-1H-[1,2,4]triazole

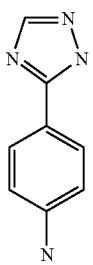

Molecular Weight = 160.1798
Molecular Formula = C8H8N4

5-(4-Nitro-phenyl)-1H-[1,2,4]triazole (510 mg) was suspended in 50 mL of ethyl acetate and 56 mg of 10% Pd/C was added. The mixture was hydrogenated under 50 Psi for 100 min. The mixture was filtered and the filtrate was concentrate to give a solid. 497 mg
MS (ES$^+$) m/z Calcd: [(M+H)$^+$]: 161. found: 161.

Example 305

Preparation of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid [4-(2H-[1,2,4]triazol-3-yl)-phenyl]-amide

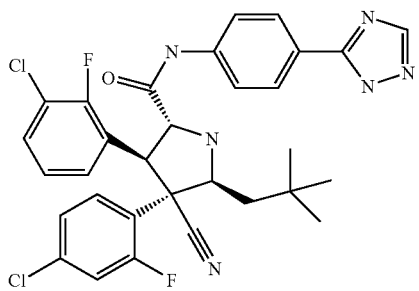

Molecular Weight = 609.5112
Molecular Formula = C31H28Cl2F2N6O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (150 mg, 0.32 mmol) in methylene chloride (5 mL), HATU (Aldrich, 152 mg, 0.4 mmol) was added followed by the addition of DIPEA (0.1 mL) and 5-(4-amino-phenyl)-1H-[1,2,4]triazole (made above, 64 mg, 0.4 mmol). The mixture was stirred at rt for 2 hrs. The reaction was quenched with addition of water. The mixture was extracted with methylene chloride (2×10 mL) and the extracts were dried with magnesium sulfate. The solvent was removed and the residue was purified on an ISCO machine (40 g column, 70% EtOAc/hexanes) to give a white solid. 140 mg.
MS (ES$^+$) m/z Calcd: [(M+H)$^+$]: 609. found: 609.

Example 306

Preparation of N'-[imino-(4-nitro-phenyl)-methyl]-hydrazinecarboxylic acid tert-butyl ester

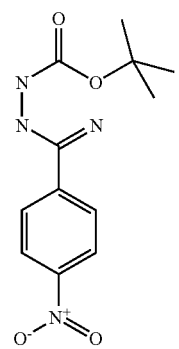

Molecular Weight = 280.2857
Molecular Formula = C12H16N4O4

To a stirred solution of 4-nitro-benzimidic acid methyl ester hydrochloride (500 mg, 2.31 mmol) in ethanol (8 mL), hydrazinecarboxylic acid tert-butyl ester (305 mg, 2.31 mmol) was added followed by triethylamine. The mixture was stirred at rt over night. The solvent was removed and the residue was suspended in methylene chloride (10 mL). The mixture was filtered and the filtrate was concentrated to about 4 mL and loaded on a 20 g silica gel column. Eluting with 40-90% EtOAc/Hexanes on an ISCO machine gave a yellow solid. 410 mg. Which was directly used for the next step.

Example 307

Preparation of 5-(4-Nitro-phenyl)-1,2-dihydro-[1,2,4]triazol-3-one

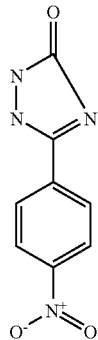

Molecular Weight = 206.1620
Molecular Formula = C8H6N4O3

N'-[Imino-(4-nitro-phenyl)-methyl]-hydrazinecarboxylic acid tert-butyl ester (made above, 410 mg) was suspended in 3 mL of acetonitrile and the mixture was heated at 200° C. for 5 min. The mixture was cooled and the solid was filtered and dried. 341 mg.
MS (ES$^+$) m/z Calcd: [(M+H)$^+$]: 207. found: 207.

Example 308

Preparation of 544-amino-phenyl)-1,2-dihydro-[1,2,4]triazol-3-one

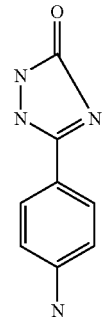

Molecular Weight = 176.1792
Molecular Formula = C8H8N4O 5-(4-amino-phenyl)-1,2-dihydro-[1,2,4]triazol-3-one (made above, 340 mg) was suspended in a mixture of THF and EtOAc (10 mL each). 10% Pd/C (100 mg) was added and the mixture was hydrogenated under 50 psi for 4 hrs. Filtered and the filtrate was concentrated to give a white solid. 217 mg.
MS (ES$^+$) m/z Calcd: [(M+H)$^+$]: 177. found: 177.

Example 309

Preparation of rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(5-oxo-2,5-dihydro-1H-[1,2,4]triazol-3-yl)-phenyl]-amide

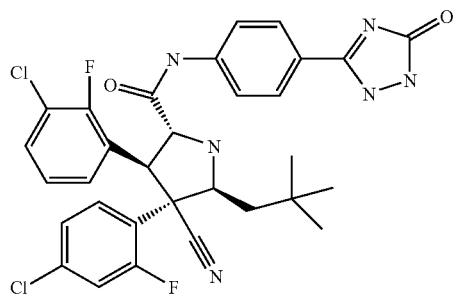

Molecular Weight = 625.5106
Molecular Formula = C31H28Cl2F2N6O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid (264 mg, 0.56 mmol) in DMF (5 mL), HATU (Aldrich, 213 mg, 0.56 mmol) was added followed by the addition of DIPEA (0.1 mL) and 5-(4-amino-phenyl)-1,2-dihydro-[1,2,4]triazol-3-one (made above, 100 mg, 0.56 mmol). The mixture was stirred at rt for 4 hrs. The reaction was quenched with addition of water. The mixture was extracted with methylene chloride (2×10 mL) and the extracts were dried with magnesium sulfate. The solvent was removed and the residue was purified on an ISCO machine (40 g column, 5% MeOH/methylene chloride) to give a white solid. 47 mg.
MS (ES$^+$) m/z Calcd: [(M+H)$^+$]: 625. found: 625.

Example 310

Preparation of 3-chloro-4-(1H-tetrazol-5-yl)-phenylamine

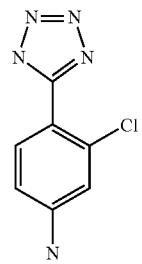

Molecular Weight = 195.6124
Molecular Formula = C7H6ClN5

To a stirred solution of 4-amino-2-chloro-benzonitrile (Aldrich, 765 mg, 5 mmol) in toluene (10 mL), sodium azide (423 mg, 6.5 mmol) and triethylamine hydrochloride (895 mg, 6.5 mmol) was added and the mixture was stirred vigorously at 115° C. overnight. The mixture was cooled and poured into water. The aqueous layer was adjusted to PH=5 by the addition of 6 N HCl and the solid formed was filtered and dried. 175 mg, MS (ES$^+$) m/z Calcd: [(M+H)$^+$]: 196. found: 196.

Example 311

Preparation of rac-(5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-4H-[1,2,4]triazol-3-yl)-acetic acid

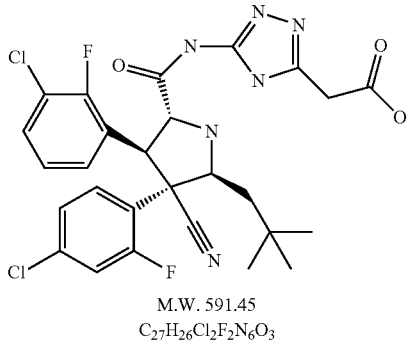 [SMILES: CC(C)(C)C[C@@H]1N[C@@H](C(=O)Nc2nnc(CC(=O)O)[nH]2)[C@H](c2cccc(Cl)c2F)[C@@]1(C#N)c1ccc(Cl)cc1F]

M.W. 591.45
$C_{27}H_{26}Cl_2F_2N_6O_3$

A mixture of rac-(5-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-4H-[1,2,4]triazol-3-yl)-acetic acid methyl ester (20 mg, 0.033 mmol) was dissolved in THF (0.6 mL) and methanol (0.2 mL), then 2N LiOH (0.2 mL) was added and stirred at room temperature for 3 hours. The mixture was concentrated and diluted with water and ethyl acetate. The organic phase was separated then concentrated to yield rac-(5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-4H-[1,2,4]triazol-3-yl)-acetic acid (6.7 mg, 34%) as an off-white powder. HRMS (ES$^+$) m/z Calcd for $C_{27}H_{26}Cl_2F_2N_6O_3$+H [(M+H)$^+$]: 591.1485. found: 591.1483.

Example 312

Preparation of rac-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-acetic acid

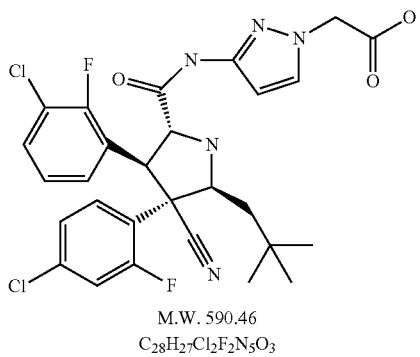 [SMILES: CC(C)(C)C[C@@H]1N[C@@H](C(=O)Nc2ccn(CC(=O)O)n2)[C@H](c2cccc(Cl)c2F)[C@@]1(C#N)c1ccc(Cl)cc1F]

M.W. 590.46
$C_{28}H_{27}Cl_2F_2N_5O_3$

A mixture of rac-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-acetic acid tert-butyl ester (25 mg, 0.039 mmol) was chilled to 0° C. Then concentrated sulfuric acid (1 mL) was added and the reaction was stirred for 2 hours. Ice and water added all at once, crystals filtered and washed with water. The crystals were azeotroped three times with toluene then treated to high vacuum overnight to yield rac-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-acetic acid as an off white powder (12.1 mg, 53%). HRMS (ES$^+$) m/z Calcd for $C_{28}H_{27}Cl_2F_2N_5O_3$+H [(M+H)$^+$]: 590.1532. found: 590.1531.

Example 313

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1H-imidazol-4-ylmethyl)-amide

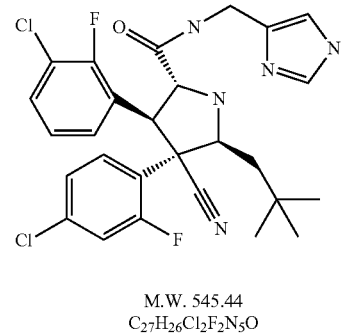

M.W. 545.44
$C_{27}H_{26}Cl_2F_2N_5O$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.43 mmol), 1H-(imidazoyl-4-yl)methylamine (62 mg, 0.64 mmol), 2-(7-azabenzotriazol-1-yl)-n,n,n',n'-tetramethyluronium hexafluorophosphate (HATU, 243.3 mg, 0.64 mmol) and iPr$_2$NEt (0.22 mL, 1.2 mmol) in CH$_2$Cl$_2$ (10 mL) was stirred at rt overnight. The mixture was then diluted with CH$_2$Cl$_2$ and washed with water, brine. The organic phase was separated, dried over Na$_2$SO$_4$ and filtered. The mixture was then concentrated and purified by reverse phase chromatography (15-95% of ACN/water) to rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1H-imidazol-4-ylmethyl)-amide (6.2 mg, 2.6%) as an off-white powder. HRMS (ES$^+$) m/z Calcd for $C_{27}H_{26}Cl_2F_2N_5O$+H [(M+H)$^+$]: 546.1634. found: 546.1632.

Example 314

Preparation of rac-(2S,3R,4S,5R)-4-(3-chloro-2-fluoro-phenyl)-3-(4-chloro-2-fluoro-phenyl)-2-(2,2-dimethyl-propyl)-5-(2-oxa-6-aza-spiro[3.3]heptane-6-carbonyl)-pyrrolidine-3-carbonitrile

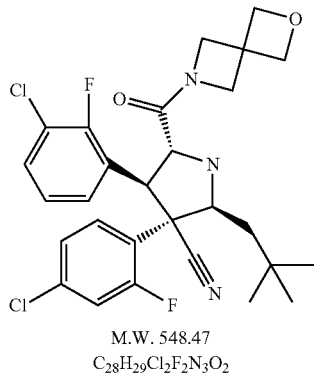 [SMILES: CC(C)(C)C[C@@H]1N[C@@H](C(=O)N2CC3(COC3)C2)[C@H](c2cccc(Cl)c2F)[C@@]1(C#N)c1ccc(Cl)cc1F]

M.W. 548.47
$C_{28}H_{29}Cl_2F_2N_3O_2$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.43 mmol), 2-oxa-6-aza-spiro[3.3]heptane oxylate salt (123 mg, 0.65 mmol), 2-(7-azabenzotriazol-1-yl)-n,n,n',n'-tetramethyluronium hexafluorophosphate (HATU, 243.3 mg, 0.64 mmol) and iPr₂NEt (0.22 mL, 1.2 mmol) in CH₂Cl₂ (10 mL) was stirred at rt overnight. The mixture was then diluted with CH₂Cl₂ and washed with water, brine. The organic phase was separated, dried over Na₂SO₄ and filtered. The mixture was then concentrated and purified by reverse phase chromatography (20-95% of ACN/water) to rac-(2S,3R,4S,5R)-4-(3-chloro-2-fluoro-phenyl)-3-(4-chloro-2-fluoro-phenyl)-2-(2,2-dimethyl-propyl)-5-(2-oxa-6-aza-spiro[3.3]heptane-6-carbonyl)-pyrrolidine-3-carbonitrile (78 mg, 33.3%) as an off-white powder. HRMS (ES⁺) m/z Calcd for $C_{28}H_{29}Cl_2F_2N_3O_2$+H [(M+H)⁺]: 548.1678. found: 548.1678.

Example 316

Preparation of rac-1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-azetidine-3-carboxylic acid

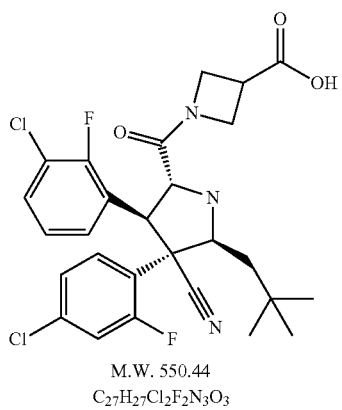 [SMILES: CC(C)(C)C[C@@H]1N[C@@H](C(=O)N2CC(C(=O)O)C2)[C@H](c2cccc(Cl)c2F)[C@@]1(C#N)c1ccc(Cl)cc1F]

M.W. 550.44
$C_{27}H_{27}Cl_2F_2N_3O_3$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.43 mmol), azetidine-3-carboxylate methyl ester hydrochloride (200 mg, 1.32 mmol), 2-(7-azabenzotriazol-1-yl)-n,n,n',n'-tetramethyluronium hexafluorophosphate (HATU, 243.3 mg, 0.64 mmol) and iPr₂NEt (0.22 mL, 1.2 mmol) in CH₂Cl₂ (10 mL) was stirred at rt overnight. The mixture was then diluted with CH₂Cl₂ and washed with water, brine. The organic phase was separated, dried over Na₂SO₄ and filtered. The mixture was then concentrated and purified by reverse phase chromatography (20-95% of ACN/water) to yield 1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-azetidine-3-carboxylic acid methyl ester (26 mg, 10.7%). The ester was taken directly to the hydrolysis step by dissolved in THF (0.6 mL) and methanol (0.2 mL), then 2N LiOH (0.2 mL) was added and stirred at room temperature for 3 hours. The mixture was concentrated and diluted with water and ethyl acetate. The organic phase was separated then concentrated to rac-1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-azetidine-3-carboxylic acid (11.8 mg, 46.6%) as an off-white powder. HRMS (ES⁺) m/z Calcd for $C_{27}H_{27}Cl_2F_2N_3O_3$+H [(M+H)⁺]: 550.1471. found: 550.1471.

Example 317

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-[1,2,3]triazol-1-yl-ethyl)-amide

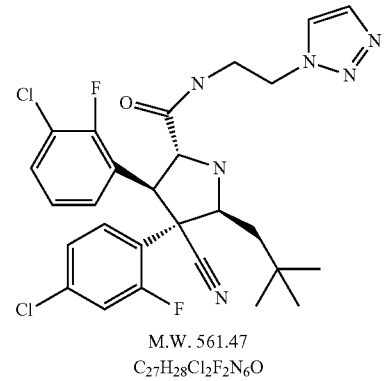 [SMILES: CC(C)(C)C[C@@H]1N[C@@H](C(=O)NCCn2ccnn2)[C@H](c2cccc(Cl)c2F)[C@@]1(C#N)c1ccc(Cl)cc1F]

M.W. 561.47
$C_{27}H_{28}Cl_2F_2N_6O$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.43 mmol), 2-[1,2,3]triazol-1-yl ethylamine (200 mg, 1.78 mmol), 2-(7-azabenzotriazol-1-yl)-n,n,n',n'-tetramethyluronium hexafluorophosphate (HATU, 243.3 mg, 0.64 mmol) and iPr₂NEt (0.22 mL, 1.2 mmol) in CH₂Cl₂ (10 mL) was stirred at rt overnight. The mixture was then diluted with CH₂Cl₂ and washed with water, brine. The organic phase was separated, dried over Na₂SO₄ and filtered. The mixture was then concentrated and purified by reverse phase chromatography (15-95% of ACN/water) rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-[1,2,3]triazol-1-yl-ethyl)-amide (83.7 mg, 34.7%) as an off-white powder. HRMS ES⁺) m/z Calcd for C₂₇H₂₈Cl₂F₂N₆O+H [(M+H)⁺]: 561.1743. found: 561.1741.

Example 318

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-carbamoylmethyl-1H-pyrazol-3-yl)-amide

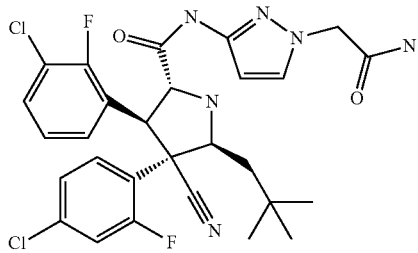

M.W. 589.48
C₂₈H₂₈Cl₂F₂N₆O₂

A mixture of rac-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-acetic acid (85 mg, 0.144 mmol), ammonia (0.57 mL, 0.288 mmol, 0.5 M in dioxane), 2-(7-azabenzotriazol-1-yl)-n,n,n',n'-tetramethyluronium hexafluorophosphate (HATU, 109 mg, 0.288 mmol) and iPr₂NEt (0.1 mL, 0.43 mmol) in CH₂Cl₂ (10 mL) was stirred at rt overnight. The mixture was then diluted with CH₂Cl₂ and washed with water, brine. The organic phase was separated, dried over Na₂SO₄ and filtered. The mixture was then concentrated and purified by reverse phase chromatography (20-95% of ACN/water) rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-[1,2,3]triazol-1-yl-ethyl)-amide (12.3 mg, 14.5%) as an off-white powder. HRMS (ES⁺) m/z Calcd for C₂₈H₂₈Cl₂F₂N₆O₂+H [(M+H)⁺]: 589.1692. found: 589.1693.

Example 319

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-(2-hydroxy-2-methyl-propyl)-1H-pyrazol-3-yl]-amide

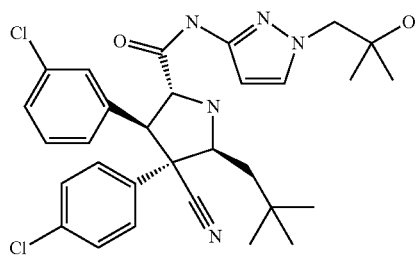

M.W. 568.545
C₃₀H₃₅Cl₂N₅O₂

A mixture of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (86.2 mg, 0.20 mmol), 1-(3-amino-pyrazol-1-yl)-2-methyl-propan-2-ol (93.12 mg, 0.3 mmol), 2-(7-azabenzotriazol-1-yl)-n,n,n',n'-tetramethyluronium hexafluorophosphate (HATU, 76 mg, 0.2 mmol) and iPr₂NEt (0.1 mL, 0.55 mmol) in CH₂Cl₂ (2 mL) was stirred at rt overnight. The mixture was then diluted with CH₂Cl₂ and washed with water, brine. The organic phase was separated, filtered and dried over Na₂SO₄. The mixture was then concentrated and purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-(2-hydroxy-2-methyl-propyl)-1H-pyrazol-3-yl]-amide (54.1 mg, 47.6%) as an off-white powder. HRMS (ES⁺) m/z Calcd for C₃₀H₃₅Cl₂N₅O₂+H [(M+H)⁺]: 568.2241. found: 568.2246.

Example 320

Preparation of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methanesulfonylamino-propyl)-amide

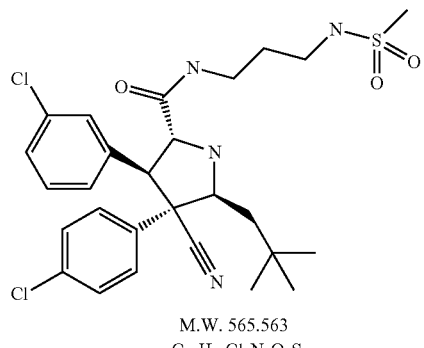

M.W. 565.563
C₂₇H₃₄Cl₂N₄O₃S

A mixture of rac (2R,3R,4R,5S)-3-(3-chloro-phenyl)-4-(4-chloro-phenyl)-4-cyano-5-(2,2-dimethyl-propyl)-pyrrolidine-2-carboxylic acid (3-amino-propyl)-amide (120 mg, 0.24 mmol), methane sulfonyl chloride (49 µL, 0.6 mmol) and dimethylaminopyridine (97.6 mg, 0.8 mmol) in CH₂Cl₂ (8 mL) was stirred for 5 h at rt. The mixture was then extracted with NaHCO₃(s), water and the organic layer dried with MgSO₄, filtered and the solvent was evaporated under reduced pressure. diluted with CH₂Cl₂ and washed with water, brine. The organic phase was separated, filtered and dried over Na₂SO₄. The mixture was then purified by reverse phase chromatography (20-95% of ACN/water) to give rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methanesulfonylamino-propyl)-amide (112.1 mg, 80.5%) as an off-white powder. HRMS (ES⁺) m/z Calcd for C₂₇H₃₄Cl₂N₄O₃S+H [(M+H)⁺]: 565.1802. found: 565.1800.

Example 321

Preparation of chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide

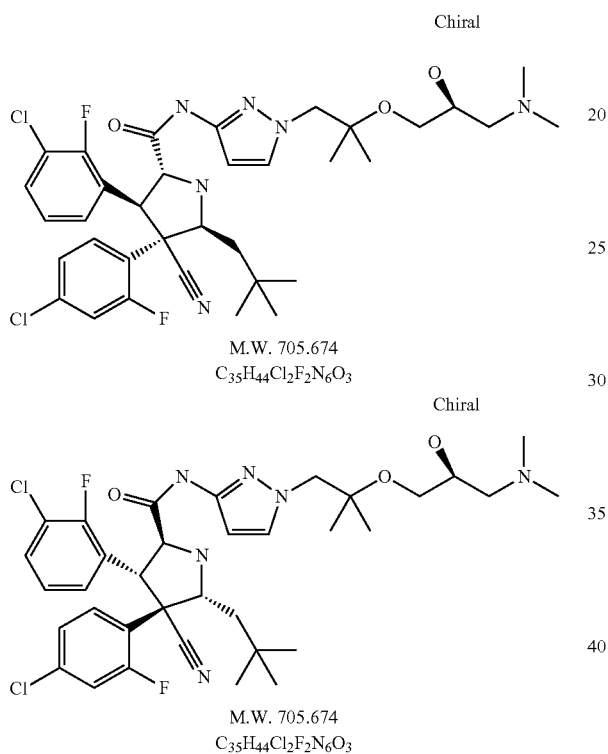

M.W. 705.674
$C_{35}H_{44}Cl_2F_2N_6O_3$

M.W. 705.674
$C_{35}H_{44}Cl_2F_2N_6O_3$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (86.2 mg, 0.20 mmol), (S)-1-[2-(3-amino-pyrazol-1-yl)-1,1-dimethyl-ethoxy]-3-dimethylamino-propan-2-ol (370 mg, 1.44 mmol), 2-(7-azabenzotriazol-1-yl)-n,n,n',n'-tetramethyluronium hexafluorophosphate (HATU, 950 mg, 2.5 mmol) and iPr₂NEt (1.4 mL, 8 mmol) in CH₂Cl₂ (50 mL) was stirred at rt overnight. The mixture was then diluted with CH₂Cl₂ and washed with water, brine. The organic phase was separated, dried over Na₂SO₄ and filtered. The mixture was then concentrated and purified by reverse phase chromatography (15-95% of ACN/water) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide (255 mg, 18%) as an off-white powder. The racemate mixture was submitted for SFC purification to of chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide (85.1 mg, 6.1%) as an white powder. HRMS (ES⁺) m/z Calcd for $C_{35}H_{44}Cl_2F_2N_6O_3+H$ [(M+H)⁺]: 705.2893. found: 705.2891. and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide (23.1 mg, 20.8%) as an off-white powder. HRMS (ES⁺) m/z Calcd for $C_{35}H_{44}Cl_2F_2N_6O_3+H$ [(M+H)⁺]: 705.2893. found: 705.2889.

Example 322

Preparation of (S)-1-[2-(3-Amino-pyrazol-1-yl)-1,1-dimethyl-ethoxy]-3-dimethylamino-propan-2-ol

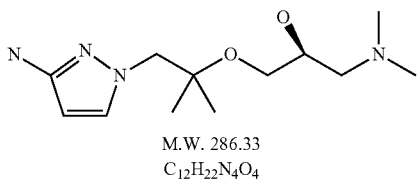

M.W. 286.33
$C_{12}H_{22}N_4O_2$

Compound (S)-1-dimethylamino-3-[1,1-dimethyl-2-(3-nitro-pyrazol-1-yl)-ethoxy]-propan-2-ol was prepared by reacting 1-[2-methyl-2-((S)-1-oxiranylmethoxy)-propyl]-3-nitro-1H-pyrazole (0.39 g, 1.62 mmol), isopropyl alcohol (6 mL), and dimethylamine (3 mL, 6 mmol, 2 M in dioxane) under microwave conditions at 130° C. for 15 min. The mixture was extracted with dichloromethane and water. The organic layer was separated and the solvent evaporated under reduced pressure to yield (S)-1-dimethylamino-3-[1,1-dimethyl-2-(3-nitro-pyrazol-1-yl)-ethoxy]-propan-2-ol (0.4 g, 87%). This compound was reduced under the following conditions. The mixture of (S)-1-dimethylamino-3-[1,1-dimethyl-2-(3-nitro-pyrazol-1-yl)-ethoxy]-propan-2-ol (0.39 g, 1.66 mmol), ethyl acetate (30 mL), ethanol (30 mL) was added to a Parr bottle with 10% Pd/C (0.22 g) and subjected hydrogen gas (20 psi) for 2 h under the Parr Shaker Apparatus conditions. Work up by filtration via a glass membrane filter paper, solvent was removed under reduced pressure to afford (S)-1-[2-(3-amino-pyrazol-1-yl)-1,1-dimethyl-ethoxy]-3-dimethylamino-propan-2-ol as an oil (0.37 g, 97.5%).

Example 323

Preparation of 1-[2-methyl-2-((S)-1-oxiranylmethoxy)-propyl]-3-nitro-1H-pyrazole

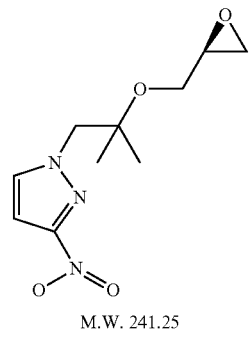

M.W. 241.25
$C_{10}H_{15}N_3O_4$

A mixture of 2-methyl-1-(3-nitro-pyrazol-1-yl)-propan-2-ol (0.64 g, 3.46 mmol), and DMF (30 mL) was stirred at 0° C. for 5 min, then NaH (60% dispersion in oil, 0.415 g, 17.3 mmol) was added and stirred 20 min at 0° C. S-(+)-glycidyl-3-nitrobenzenesulfonate (1.79 g, 6.92 mmol) was added and stirred at 0° C. for 1 h then warmed to 25° C. for 3 h. The mixture was then diluted with NH$_4$Cl(s), ethyl acetate, the organic phase was separated, washed with NaHCO$_3$(satd) dried with Na$_2$SO$_4$, and filtered. The mixture was then concentrated and purified by column chromatography (40-120 g Analogix column, 80% EtOAc/heptane to yield the product 1-[2-methyl-2-((S)-1-oxiranylmethoxy)-propyl]-3-nitro-1H-pyrazole as a white solid (0.36 g, 43.1%).

Example 324

Preparation of chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid

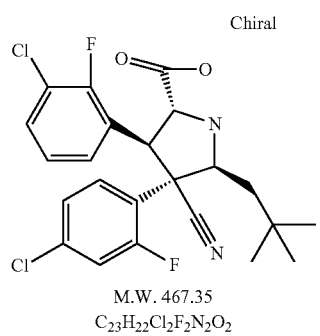

M.W. 467.35
C$_{23}$H$_{22}$Cl$_2$F$_2$N$_2$O$_2$

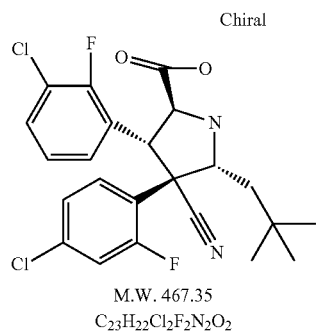

M.W. 467.35
C$_{23}$H$_{22}$Cl$_2$F$_2$N$_2$O$_2$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid was synthesized by the Synthesis group (Lot#40476-42-2, 84 g). A portion was submitted (20.5 g, 40526-055-1) for SFC Separation CH#3978; AD column method #05200916, 2 mL/min; 10% methanol, 100 bar, 30° C. to afford chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid as a white solid (10.12 g) HRMS (ES$^+$) m/z Calcd C$_{23}$H$_{22}$Cl$_2$F$_2$N$_2$O$_2$+H [(M+H)$^+$]: 467.1099. Found: 467.1099 and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid as a white solid (9.6 g) HRMS (ES$^+$) m/z Calcd C$_{23}$H$_{22}$Cl$_2$F$_2$N$_2$O$_2$+H [(M+H)$^+$]: 467.1099. Found: 467.1099.

Example 325

Preparation of rac-1-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-cyclopropane carboxylic acid

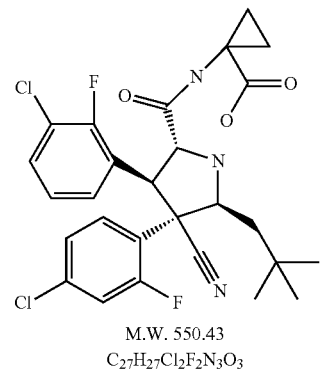 [SMILES: CC(C)(C)C[C@@H]1N[C@@H](C(=O)NC2(C(=O)O)CC2)[C@H](c2cccc(Cl)c2F)[C@@]1(C#N)c1ccc(Cl)cc1F]

M.W. 550.43
C$_{27}$H$_{27}$Cl$_2$F$_2$N$_3$O$_3$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.43 mmol), 1-amino-cyclopropanecarboxylic acid methyl ester hydrochloride (100 mg, 0.86 mmol), 2-(7-azabenzotriazol-1-yl)-n,n,n',n'-tetramethyluronium hexafluorophosphate (HATU, 243.3 mg, 0.64 mmol) and iPr$_2$NEt (0.22 mL, 1.2 mmol) in CH$_2$Cl$_2$ (20 mL) was stirred at rt overnight. The mixture was then diluted with CH$_2$Cl$_2$ and washed with water, brine. The organic phase was separated, dried over Na$_2$SO$_4$ and filtered. The mixture was then concentrated and purified flash column chromatography (1-100% ethyl acetate/heptane) to afford rac-1-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-cyclopropanecarboxylic acid methyl ester as a white powder (120 mg, 49.6%). HRMS (ES$^+$) m/z Calcd for C$_{28}$H$_{29}$Cl$_2$F$_2$N$_3$O$_3$+H [(M+H)$^+$]: 564.1627. found: 564.1627.

The ester was taken directly to the hydrolysis step by dissolved in THF (3 mL) and methanol (1 mL), then 2N LiOH (1 mL) was added and stirred at room temperature for 3 hours. The mixture was diluted with water and ethyl acetate, the organic phase was separated then concentrated under reduced pressure to rac-1-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-cyclopropanecarboxylic acid (65.2 mg, 67.2%) as an off-white powder. HRMS (ES$^+$) m/z Calcd for C$_{27}$H$_{27}$Cl$_2$F$_2$N$_3$O$_3$+H [(M+H)$^+$]: 550.1471. found: 550.1471.

Example 326

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(4-hydroxy-piperidin-4-ylmethyl)-1H-pyrazol-3-yl]-amide

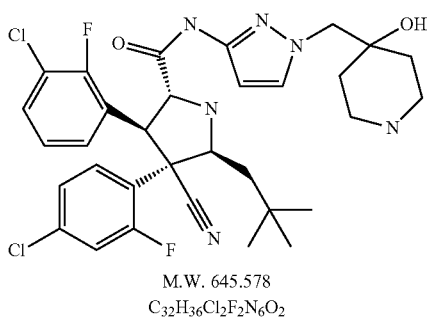 [SMILES: CC(C)(C)C[C@@H]1N[C@@H](C(=O)Nc2ccn(CC3(O)CCNCC3)n2)[C@H](c2cccc(Cl)c2F)[C@@]1(C#N)c1ccc(Cl)cc1F]

M.W. 645.578
C₃₂H₃₆Cl₂F₂N₆O₂

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (500 mg, 1.0 mmol), 4-(3-amino-pyrazol-1-ylmethyl)-4-hydroxy-piperidine-1-carboxylic acid tert-butyl ester (592 mg, 2.0 mmol), 2-(7-azabenzotriazol-1-yl)-n,n,n',n'-tetramethyluronium hexafluorophosphate (HATU, 593 mg, 1.5 mmol) and iPr₂NEt (0.718 mL, 4 mmol) in CH₂Cl₂ (50 mL) was stirred at rt overnight. The mixture was then diluted with CH₂Cl₂ and washed with water, brine. The organic phase was separated, dried over Na₂SO₄ and filtered. The mixture was then concentrated and purified flash column chromatography (1-100% ethyl acetate/heptane) to afford rac-4-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-ylmethyl)-4-hydroxy-piperidine-1-carboxylic acid tert-butyl ester as a white powder (480 mg, 64.4%).

The compound was taken directly to the deprotection step by dissolved in a solution of 30% TFA in dichloromethane (3 mL) and stirred at room temperature for 3 hours. The mixture was diluted with NaHCO₃(s) and dichloromethane and the organic phase was separated then concentrated under reduced pressure to afford an oil that was purified via tritaration with ethyl acetate and heptane to afford a white foam rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(4-hydroxy-piperidin-4-ylmethyl)-1H-pyrazol-3-yl]-amide (370 mg, 64.3%). HRMS (ES⁺) m/z Calcd for $C_{32}H_{36}Cl_2F_2N_6O_2$+H [(M+H)⁺]: 645.2318. found: 645.2315.

Example 327

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-acetyl-thiophen-3-yl)-amide

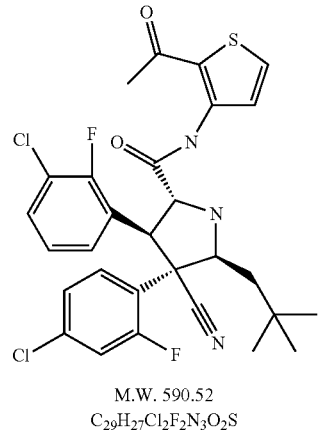 [SMILES: CC(=O)c1sccc1NC(=O)[C@@H]1N[C@@H](CC(C)(C)C)[C@](C#N)(c2ccc(Cl)cc2F)[C@H]1c1cccc(Cl)c1F]

M.W. 590.52
C₂₉H₂₇Cl₂F₂N₃O₂S

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.43 mmol), 1-(3-aminothiophen-2-yl)ethanone (140 mg, 0.98 mmol), 2-(7-azabenzotriazol-1-yl)-n,n,n',n'-tetramethyluronium hexafluorophosphate (HATU, 243.3 mg, 0.64 mmol) and iPr₂NEt (0.3 mL, 1.67 mmol) in CH₂Cl₂ (5 mL) was stirred at rt overnight. The mixture was then diluted with CH₂Cl₂ and washed with water, brine. The organic phase was separated, dried over Na₂SO₄ and filtered. The mixture was then concentrated and purified flash column chromatography (1-100% ethyl acetate/heptane) to afford rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-acetyl-thiophen-3-yl)-amide as a off white powder (40 mg, 15.8%). HRMS (ES⁺) m/z Calcd for $C_{29}H_{27}Cl_2F_2N_3O_2S$+H [(M+H)⁺]: 590.1242. found: 590.1244.

Example 328

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-carbamoyl-thiophen-3-yl)-amide

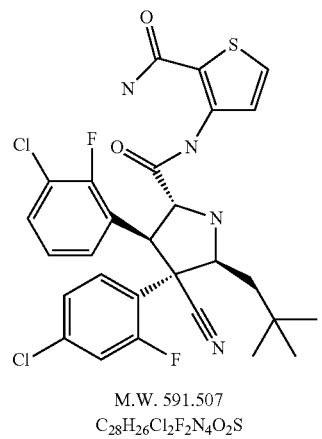 [SMILES: CC(C)(C)C[C@@H]1N[C@@H](C(=O)Nc2ccsc2C(N)=O)[C@H](c2cccc(Cl)c2F)[C@@]1(C#N)c1ccc(Cl)cc1F]

M.W. 591.507
C₂₈H₂₆Cl₂F₂N₄O₂S

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.43 mmol), 3-aminothiophene-2-carboxylic acid amide (160 mg, 1.1 mmol), 2-(7-azabenzotriazol-1-yl)-n,n,n',n'-tetramethyluronium hexafluorophosphate (HATU, 243.3 mg, 0.64 mmol) and iPr$_2$NEt (0.3 mL, 1.67 mmol) in CH$_2$Cl$_2$ (5 mL) was stirred at rt overnight. The mixture was then diluted with CH$_2$Cl$_2$ and washed with water, brine. The organic phase was separated, dried over Na$_2$SO$_4$ and filtered. The mixture was then concentrated and purified flash column chromatography (1-100% ethyl acetate/heptane) to afford rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-carbamoyl-thiophen-3-yl)-amide as a off white powder (15.8 mg, 6.2%). HRMS (ES$^+$) m/z Calcd for C$_{28}$H$_{26}$Cl$_2$F$_2$N$_4$O$_2$S+H  [(M+H)$^+$]: 501.1195.  found: 591.1191.

Example 329

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-((S)-3-dimethylamino-2-hydroxy-propyl)-1H-pyrazol-3-yl]-amide

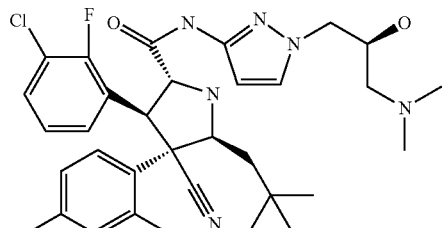

M.W. 633.57
C$_{31}$H$_{36}$Cl$_2$F$_2$N$_6$O$_2$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.43 mmol), (S)-1-(3-amino-pyrazol-1-yl)-3-dimethylamino-propan-2-ol (158 mg, 0.86 mmol), 2-(7-azabenzotriazol-1-yl)-n,n,n',n'-tetramethyluronium hexafluorophosphate (HATU, 243.3 mg, 0.64 mmol) and iPr$_2$NEt (0.3 mL, 1.67 mmol) in CH$_2$Cl$_2$ (10 mL) was stirred at rt overnight. The mixture was then diluted with CH$_2$Cl$_2$ and washed with water, brine. The organic phase was separated, dried over Na$_2$SO$_4$ and filtered. The mixture was then concentrated and purified flash column chromatography (1-100% ethyl acetate/heptane) to afford rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-((S)-3-dimethylamino-2-hydroxy-propyl)-1H-pyrazol-3-yl]-amide as an off white powder (63.2 mg, 43.6%). HRMS (ES m/z Calcd. for C$_{31}$H$_{36}$Cl$_2$F$_2$N$_6$O$_2$+H  [(M+H)$^+$]: 633.2318.  found: 633.2313.

Example 330

Preparation of (S)-1-(3-amino-pyrazol-1-yl)-3-dimethylamino-propan-2-ol

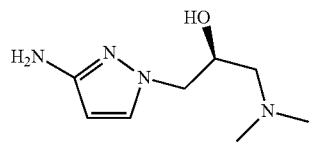

M.W. 184.24
C$_8$H$_{16}$N$_4$O

Compound ((S)-1-dimethylamino-3-(3-nitro-pyrazol-1-yl)-propan-2-ol was prepared by reacting 3-nitro-1-(R)-1-oxiranylmethyl-1H-pyrazole (0.8 g, 4.73 mmol), isopropyl alcohol (6 mL), and dimethylamine (4 mL, 8 mmol, 2 M in dioxane) under microwave conditions at 130° C. for 15 min. The mixture was extracted with dichloromethane and water. The organic layer was separated and the solvent evaporated under reduced pressure to yield (S)-1-dimethylamino-3-[1,1-dimethyl-2-(3-nitro-pyrazol-1-yl)-ethoxy]-propan-2-ol (0.76 g, 75.2%). This compound was reduced under the following conditions.

The mixture of (S)-1-dimethylamino-3-[1,1-dimethyl-2-(3-nitro-pyrazol-1-yl)-ethoxy]-propan-2-ol (0.76 g, 3.54 mmol), ethyl acetate (30 mL), ethanol (30 mL) was added to a Parr bottle with 10% Pd/C (0.14 g) and subjected hydrogen gas (20 psi) for 2 h under the Parr Shaker Apparatus conditions. Work up by filtration via a glass membrane filter paper, solvent was removed under reduced pressure to afford (S)-1-(3-amino-pyrazol-1-yl)-3-dimethylamino-propan-2-ol as an oil (0.62 g, 96.1%).

Example 331

Preparation of
3-nitro-1-(R)-1-oxiranylmethyl-1H-pyrazole

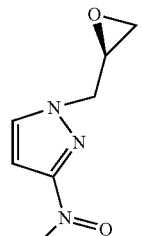

M.W. 169.14
C$_6$H$_7$N$_3$O$_3$

A mixture of 3-nitro-1H-pyrazole (0.76 g, 6.72 mmol), (S)-(+)-glycidyl-3-nitrobenzenesulfonate (2 g, 7.72 mmol), cesium carbonate (5.6 g, 17.16 mmol) and DMF (30 mL) were stirred at 25° C. for 16 hours. The mixture was then diluted with ethyl acetate and water (3×), the organic phase

Example 332

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-hydroxycarbamoyl-phenyl)-amide

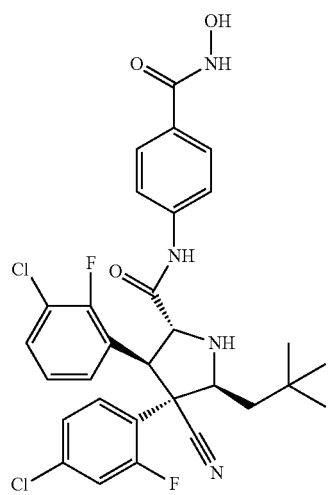

M.W. 601.48
$C_{30}H_{28}Cl_2F_2N_4O_3$

To a solution of rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid prepared in Example 232 (50 mg, 0.09 mmol) in N,N-dimethylformamide (2 mL) was added. $NH_2OH \cdot HCl$ (18 mg, 0.26 mmol), EDCI (33 mg, 0.17 mmol), HOBT (21 mg, 0.15 mmol) and $NEt_3$ (0.036 mL, 0.26 mmol). The reaction mixture was heated at 80° C. for 48 h. The mixture was cooled to room temperature, and partitioned between ethyl acetate and water. The organic layer was separated, and the aqueous layer was extracted with ethyl acetate. The organic layers were combined, washed with water, brine, dried over $MgSO_4$, and concentrated. The residue was purified by prep-HPLC to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-hydroxycarbamoyl-phenyl)-amide as a white solid (24 mg, 47%).

HRMS (ES$^+$) m/z Calcd for $C_{30}H_{28}Cl_2F_2N_4O_3$+H [(M+H)$^+$]: 601.1580. found: 601.1577.

Example 333

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylaminocarbonyl-phenyl)-amide

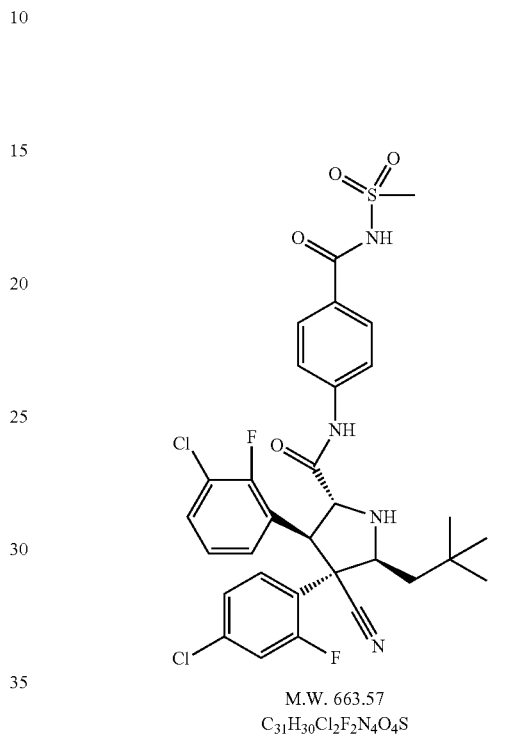

M.W. 663.57
$C_{31}H_{30}Cl_2F_2N_4O_4S$

A solution of rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid prepared in Example 232 (0.14 g, 0.24 mmol) and CDI (97 mg, 0.6 mmol) in N,N-dimethylformamide (5 mL) was heated at 60° C. for 2 h, then to this solution was added a mixture of methanesulfonamide (0.14 g, 1.43 mmol) and NaH (60% in mineral oil, 63 mg, 1.58 mmol), which had been stirred at room temperature for 2 h. The resulting mixture was stirred at room temperature for 1 h, then poured into water. The mixture was acidified to "pH" 1-2 by addition of aqueous HCl solution, then partitioned between ethyl acetate and water. The organic layer was separated, and the aqueous layer was extracted with ethyl acetate. The organic layers were combined, washed with water, brine, dried over $MgSO_4$, and concentrated. The residue was purified by chromatography (EtOAc) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylaminocarbonyl-phenyl)-amide as a white solid (11 mg, 7%).

HRMS (ES$^+$) m/z Calcd for $C_{31}H_{30}Cl_2F_2N_4O_4S$+H [(M+H)$^+$]: 663.1406. found: 663.107.

Example 336

Preparation of rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester

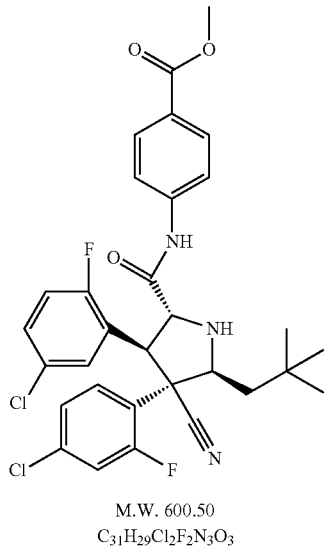 [SMILES: COC(=O)c1ccc(NC(=O)[C@@H]2N[C@@H](CC(C)(C)C)[C@](C#N)(c3ccc(Cl)cc3F)[C@H]2c2cc(Cl)ccc2F)cc1]

M.W. 600.50
$C_{31}H_{29}Cl_2F_2N_3O_3$

In a manner similar to the method described in Examples 1e, rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 98c (0.5 g, 0.89 mmol) was reacted with methyl 4-aminobenzoate (0.24 g, 1.6 mmol), HATU (0.61 g, 1.6 mmol) and iPr$_2$NEt (0.39 mL, 2.2 mmol) in CH$_2$Cl$_2$ at room temperature to give rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester as a white solid (0.14 g, 27%).

HRMS (ES$^+$) m/z Calcd for $C_{31}H_{29}Cl_2F_2N_3O_3$+H [(M+H)$^+$]: 600.1627. found: 600.1626.

Example 337

Preparation of rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

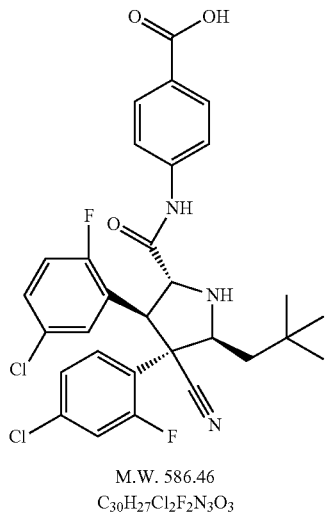 [SMILES: CC(C)(C)C[C@@H]1N[C@@H](C(=O)Nc2ccc(C(=O)O)cc2)[C@H](c2cc(Cl)ccc2F)[C@@]1(C#N)c1ccc(Cl)cc1F]

M.W. 586.46
$C_{30}H_{27}Cl_2F_2N_3O_3$

To a solution of rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester prepared in Example 336 (125 mg, 0.21 mmol) in tetrahydrofuran (3 mL) was added an aqueous solution (1 N) of NaOH (3 mL, 3 mmol) and methanol (1 mL). The reaction mixture was heated at 80° C. for 2 h, and the "pH" of the solution was adjusted to 5 by aqueous HCl solution. The mixture was extracted ethyl acetate twice. The combined organic extracts were washed with water, brine, dried over MgSO$_4$, and concentrated to give rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid as a white solid (90 mg, 73%). HRMS (ES$^+$) m/z Calcd for $C_{30}H_{27}Cl_2F_2N_3O_3$+H [(M+H)$^+$]: 586.1471. found: 586.1473.

Example 338

Preparation of rac-4-{[(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester

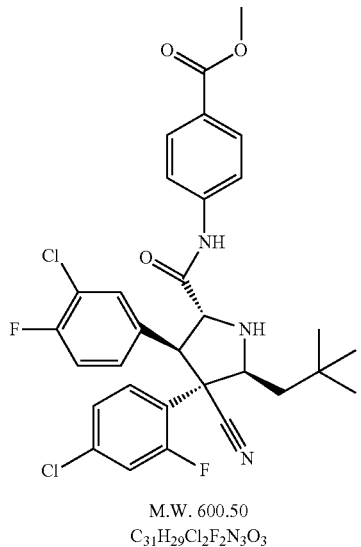 [SMILES: COC(=O)c1ccc(NC(=O)[C@@H]2N[C@@H](CC(C)(C)C)[C@](C#N)(c3ccc(Cl)cc3F)[C@H]2c2ccc(F)c(Cl)c2)cc1]

M.W. 600.50
$C_{31}H_{29}Cl_2F_2N_3O_3$

In a manner similar to the method described in Examples 1e, rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid trifluoroacetic acid prepared in Example 69c (0.25 g, 0.43 mmol) was reacted with methyl 4-aminobenzoate (0.12 g, 0.8 mmol), HATU (0.29 g, 0.43 mmol) and iPr$_2$NEt (0.19 mL, 1.1 mmol) in CH$_2$Cl$_2$ at room temperature to give rac-4-{[(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester as a white solid (0.125 g, 48%).

HRMS (ES$^+$) m/z Calcd for $C_{31}H_{29}Cl_2F_2N_3O_3$+H [(M+H)$^+$]: 600.1627. found: 600.1627.

Example 339

Preparation of rac-4-{[(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carbonyl]-amino}-benzoic acid

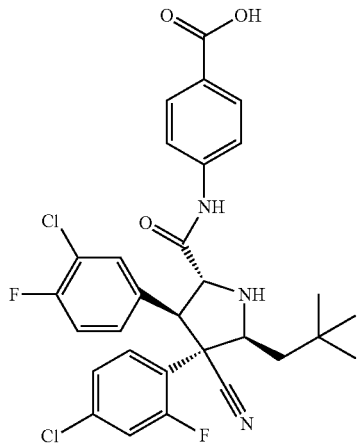

M.W. 586.46
$C_{30}H_{27}Cl_2F_2N_3O_3$

To a solution of rac-4-{[(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester prepared in Example 338 (0.11 g, 0.18 mmol) in tetrahydrofuran (9 mL) was added an aqueous solution (1 N) of NaOH (9 mL, 9 mmol) and methanol (3 mL). The reaction mixture was heated at 80° C. for 2 h, and the "pH" of the solution was adjusted to 5 by aqueous HCl solution. The mixture was extracted ethyl acetate twice. The combined organic extracts were washed with water, brine, dried over MgSO$_4$, and concentrated to give rac-4-{[(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carbonyl]-amino}-benzoic acid as a white solid (0.1 g, 94%).

HRMS (ES$^+$) m/z Calcd for $C_{30}H_{27}Cl_2F_2N_3O_3$+H [(M+H)$^+$]: 586.1471. found: 586.1472.

Example 340

Preparation of rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid methyl ester

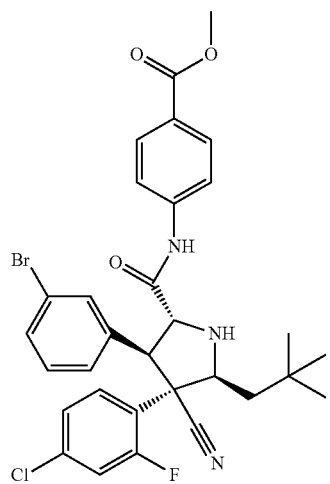

M.W. 626.95
$C_{31}H_{30}BrClFN_3O_3$

In a manner similar to the method described in Examples 1e, rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid trifluoroacetic acid prepared in Example 66c (0.44 g, 0.74 mmol) was reacted with methyl 4-aminobenzoate (0.1 g, 1.32 mmol), HATU (0.3 g, 0.4 mmol) and iPr$_2$NEt (0.32 mL, 1.8 mmol) in CH$_2$Cl$_2$ at room temperature to give rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid methyl ester as a white solid (0.17 g, 37%).

HRMS (ES$^+$) m/z. Calcd for $C_{31}H_{30}BrClFN_3O_3$+H [(M+H)$^+$]: 626.1216. found: 626.1218.

Example 341

Preparation of rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid

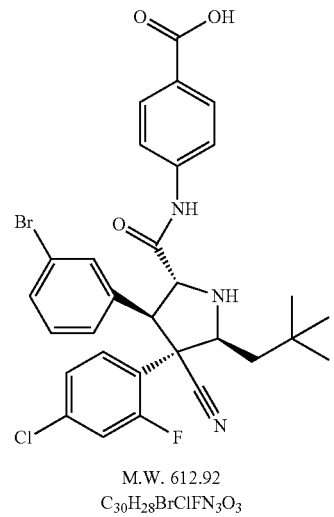 [SMILES: CC(C)(C)C[C@@H]1N[C@@H](C(=O)Nc2ccc(C(=O)O)cc2)[C@H](c2cccc(Br)c2)[C@@]1(C#N)c1ccc(Cl)cc1F]

M.W. 612.92
$C_{30}H_{28}BrClFN_3O_3$

To a solution of rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid methyl ester prepared in Example 340 (0.15 g, 0.25 mmol) in tetrahydrofuran (9 mL) was added an aqueous solution (1 N) of NaOH (9 mL, 9 mmol) and methanol (3 mL). The reaction mixture was heated at 80° C. for 2 h, and the "pH" of the solution was adjusted to 5 by aqueous HCl solution. The mixture was extracted ethyl acetate twice. The combined organic extracts were washed with water, brine, dried over MgSO$_4$, and concentrated to give rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid as a white solid (90 mg, 60%).

HRMS (ES$^+$) Calcd for $C_{30}H_{28}BrClFN_3O_3$+H [(M+H)$^+$]: 612.1060, found: 612.1062

Example 342

Preparation of rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid methyl ester

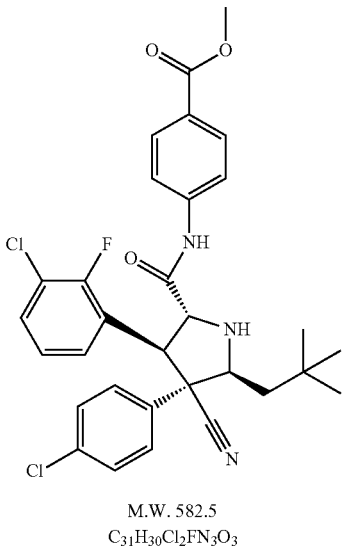 [SMILES: COC(=O)c1ccc(NC(=O)[C@@H]2N[C@@H](CC(C)(C)C)[C@](C#N)(c3ccc(Cl)cc3)[C@H]2c2cccc(Cl)c2F)cc1]

M.W. 582.5
$C_{31}H_{30}Cl_2FN_3O_3$

In a manner similar to the method described in Examples 1e, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid trifluoroacetic acid prepared in Example 26c (0.38 g, 0.55 mmol) was reacted with methyl 4-aminobenzoate (0.33 g, 2.2 mmol), HATU (0.38 g, 1 mmol) and iPr$_2$NEt (0.29 mL, 1.7 mmol) in CH$_2$Cl$_2$ at room temperature to give rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid methyl ester as a white solid (0.11 g, 34%).

HRMS (ES$^+$) m/z Calcd for $C_{31}H_{30}Cl_2FN_3O_3$+H [(M+H)$^+$]: 582.1721 found: 582.1721.

Example 343

Preparation of rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid

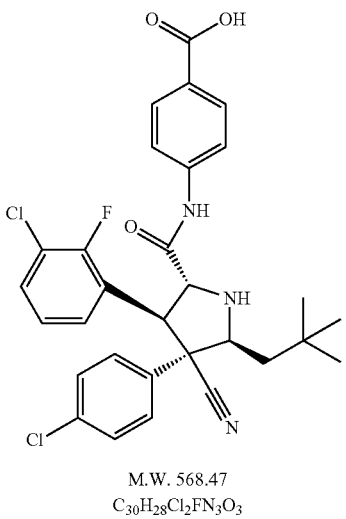 [SMILES: CC(C)(C)C[C@@H]1N[C@@H](C(=O)Nc2ccc(C(=O)O)cc2)[C@H](c2cccc(Cl)c2F)[C@@]1(C#N)c1ccc(Cl)cc1]

M.W. 568.47
$C_{30}H_{28}Cl_2FN_3O_3$

To a solution of rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid methyl ester prepared in Example 342 (95 mg, 0.16 mmol) in tetrahydrofuran (6 mL) was added an aqueous solution (1 N) of NaOH (6 mL, 6 mmol) and methanol (2 mL). The reaction mixture was heated at 80° C. for 2 h, and the "pH" of the solution was adjusted to 5 by aqueous HCl solution. The mixture was extracted ethyl acetate twice. The combined organic extracts were washed with water, brine, dried over MgSO$_4$, and concentrated to give rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid as a white solid (80 mg, 86%).

HRMS (ES$^+$) m/z Calcd for $C_{30}H_{28}Cl_2FN_3O_3$+H [(M+H)$^+$]: 568.1565. found: 568.1561.

Example 344

Preparation of rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid methyl ester

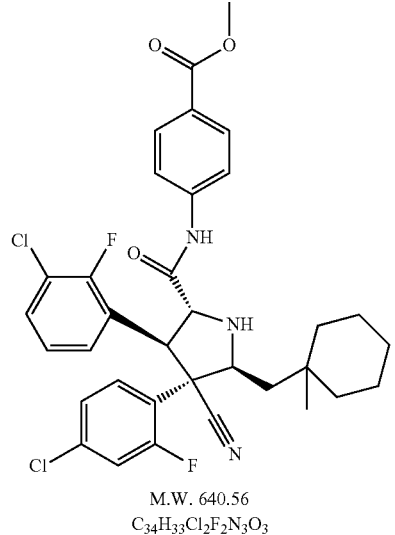 [SMILES: COC(=O)c1ccc(NC(=O)[C@@H]2N[C@@H](CC3(C)CCCCC3)[C@](C#N)(c3ccc(Cl)cc3F)[C@H]2c2cccc(Cl)c2F)cc1]

M.W. 640.56
$C_{34}H_{33}Cl_2F_2N_3O_3$

In a manner similar to the method described in Examples 1e, rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid trifluoroacetic acid prepared in Example 102c (0.41 g, 0.66 mmol) was reacted with methyl 4-aminobenzoate (0.2 g, 1.3 mmol), HATU (0.45 g, 1.2 mmol) and iPr$_2$NEt (0.29 mL, 1.7 mmol) in CH$_2$Cl$_2$ at room temperature to give rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid methyl ester as a white solid (0.17 g, 41%).

HRMS (ES$^+$) m/z Calcd for $C_{34}H_{33}Cl_2F_2N_3O_3$+H [(M+H)$^+$]: 640.1940. found: 640.1938.

Example 345

Preparation of rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid

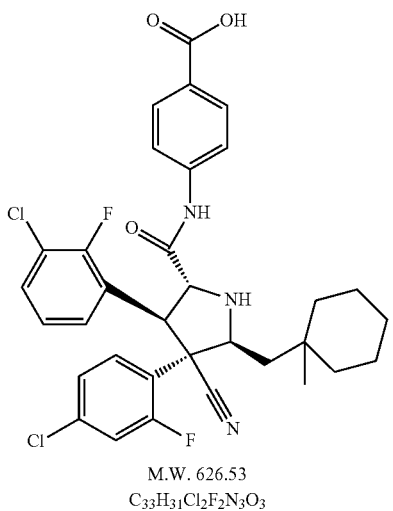 [SMILES: CC1(C[C@@H]2N[C@@H](C(=O)Nc3ccc(C(=O)O)cc3)[C@H](c3cccc(Cl)c3F)[C@@]2(C#N)c2ccc(Cl)cc2F)CCCCC1]

M.W. 626.53
$C_{33}H_{31}Cl_2F_2N_3O_3$

To a solution of rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid methyl ester prepared in Example 344 (0.16 g, 0.24 mmol) in tetrahydrofuran (3 mL) was added an aqueous solution (1 N) of NaOH (3 mL, 3 mmol) and methanol (1 mL). The reaction mixture was heated at 80° C. for 2 h, and the "pH" of the solution was adjusted to 5 by aqueous HCl solution. The mixture was extracted ethyl acetate twice. The combined organic extracts were washed with water, brine, dried over MgSO₄, and concentrated to give rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid as a white solid (0.14 g, 90%).

HRMS ES) m/z Calcd for $C_{33}H_{31}Cl_2F_2N_3O_3+H$ [(M+H)⁺]: 626.1784. found: 626.1788.

Example 346

Preparation of rac-[4-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-ylmethyl)-4-hydroxy-piperidin-1-yl]-acetic acid

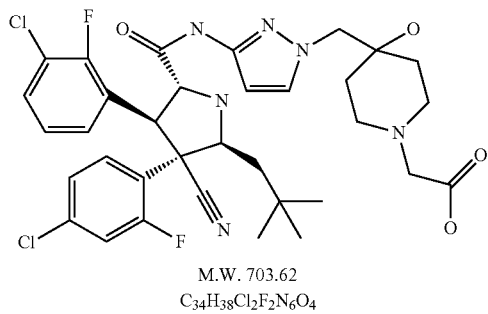 [SMILES: CC(C)(C)C[C@@H]1N[C@@H](C(=O)Nc2ccn(CC3(O)CCN(CC(=O)O)CC3)n2)[C@H](c2cccc(Cl)c2F)[C@@]1(C#N)c1ccc(Cl)cc1F]

M.W. 703.62
$C_{34}H_{38}Cl_2F_2N_6O_4$

A mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(4-hydroxy-piperidin-4-ylmethyl)-1H-pyrazol-3-yl]-amide (80 mg, 0.12 mmol) was dissolved in DMF (3 mL) with cesium carbonate (100 mg, 0.31 mmol) then t-butyl acetate (0.1 mL, 0.677 mmol) was added stirred 16 hours at 25° C. The reaction mixture was diluted with ethyl acetate and separated with water (3×), the organic layer was dried with Na₂SO₄, filtered and concentrated under reduced pressure. The mixture was purified by reverse phase column chromatography (20-95% acetonitrile/water) to yield compound rac-[4-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-ylmethyl)-4-hydroxy-piperidin-1-yl]-acetic acid tert-butyl ester (68 mg, 74.7%).

The compound was taken directly to the deprotection step by dissolved in a solution of 30% TFA in dichloromethane (3 mL) and stirred at room temperature for 16 hours. The mixture was concentrated under reduced pressure then taken up in ethyl acetate and NaHCO₃(s), separated the organic layer, concentrated under reduced pressure to yield compound rac-[4-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-ylmethyl)-4-hydroxy-piperidin-1-yl]-acetic acid as an off-white foam (41.2 mg, 65.4%). HRMS (ES⁺) m/z Calcd for $C_{34}H_{38}Cl_2F_2N_6O_4+H$ [(M+H)⁺]: 703.2373. found: 703.2376.

Example 347

Preparation of 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid

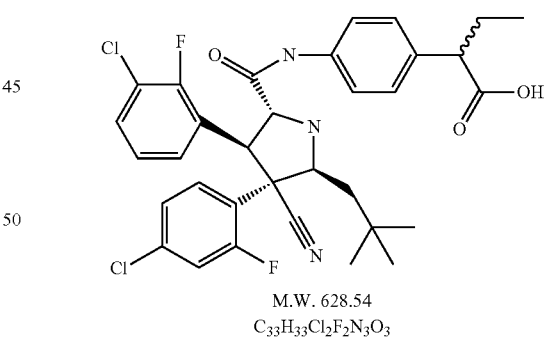

M.W. 628.54
$C_{33}H_{33}Cl_2F_2N_3O_3$

A mixture of 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid methyl ester (23 mg, 0.036 mmol) was dissolved in THF (0.9 mL) and methanol (0.3 mL), then 2N LiOH (1 mL) was added and stirred at room temperature for 2 hours. The mixture was diluted with water and ethyl acetate. The organic phase was separated then concentrated to yield 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid (16.4 mg,

Example 348

Preparation of chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid

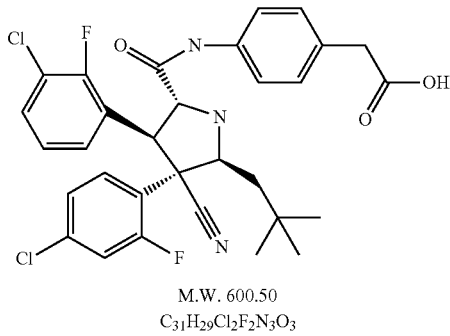 [SMILES: CC(C)(C)C[C@@H]1N[C@@H](C(=O)Nc2ccc(CC(=O)O)cc2)[C@H](c2cccc(Cl)c2F)[C@@]1(C#N)c1ccc(Cl)cc1F]

M.W. 600.50
$C_{31}H_{29}Cl_2F_2N_3O_3$

A mixture of (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid methyl ester (72 mg, 0.117 mmol) was dissolved in THF (3 mL) and methanol (1 mL), then 2N LiOH (1 mL) was added and stirred at room temperature for 2 hours. The mixture was concentrated and diluted with water and ethyl acetate. The organic phase was separated then concentrated to yield chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid (37 mg, 52.6%) as an white powder. HRMS (ES$^+$) m/z Calcd for $C_{31}H_{29}Cl_2F_2N_3O_3+H$ [(M+H)$^+$]: 600.1627. found: 600.1626.

Example 349

Preparation of chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid methyl ester

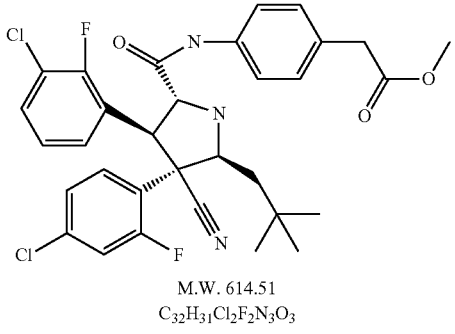 [SMILES: COC(=O)Cc1ccc(NC(=O)[C@@H]2N[C@@H](CC(C)(C)C)[C@](C#N)(c3ccc(Cl)cc3F)[C@H]2c2cccc(Cl)c2F)cc1]

M.W. 614.51
$C_{32}H_{31}Cl_2F_2N_3O_3$

A mixture of chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (228 mg, 0.488 mmol), methyl 2-(4-aminophenyl)acetate (200 mg, 1.21 mmol), 2-(7-azabenzotriazol-1-yl)-n,n,n',n'-tetramethyluronium hexafluorophosphate (HATU, 241 mg, 0.634 mmol) and iPr$_2$NEt (0.4 mL, 2.29 mmol) in CH$_2$Cl$_2$ (10 mL) was stirred at rt overnight. The mixture was then diluted with CH$_2$Cl$_2$ and washed with water, brine. The organic phase was separated, then concentrated and purified by column chromatography (1-100% of EtOAc/heptane, 12 g Analogix column) to afford chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid methyl ester (209 mg, 69.7%) as an white powder. LCMS (ES$^+$) m/z Calcd for $C_{32}H_{31}Cl_2F_2N_3O_3+H$ [M+H)$^+$]: 613.17. found: 614.2.

Example 350

Preparation of 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid methyl ester

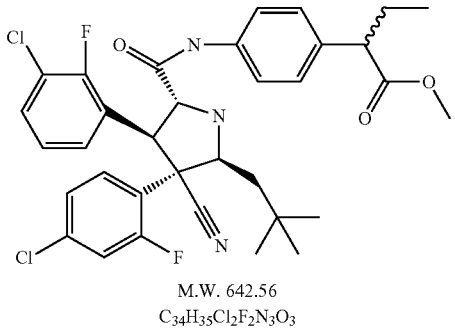 [SMILES: CCC(C(=O)OC)c1ccc(NC(=O)[C@@H]2N[C@@H](CC(C)(C)C)[C@](C#N)(c3ccc(Cl)cc3F)[C@H]2c2cccc(Cl)c2F)cc1]

M.W. 642.56
$C_{34}H_{35}Cl_2F_2N_3O_3$

A mixture of chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid methyl ester (22 mg, 0.036 mmol) was dissolved in THF (1 mL) and cooled to −78° C., then LHMDS (1 mL, 1M in THF) was added and the mixture stirred 15 min at −78° C. Ethyl iodide (0.1 mL, 0.107 mmol) was added and stirred for 1 h at −78° C., then warmed to 1 h at room temperature. The mixture was diluted with sat'd ammonium chloride solution extracted with ethyl acetate, the organic layer was separated then concentrated under reduced pressure to afford an oil that was purified by silica column chromatography (4 g Analogix column, 1-100% EtOAc/heptane) to afford 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid methyl ester as a light yellow foam (12.4 mg, 53.9%). LCMS (ES$^+$) m/z Calcd for $C_{34}H_{35}Cl_2F_2N_3O_3+H$ [(M+H)$^+$]: 641.20. found: 642.2.

Example 351

Preparation of (4-nitro-phenyl)-acetic acid methyl ester

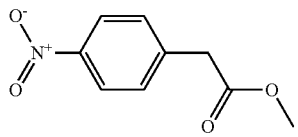

M.W. 195.18
$C_9H_9NO_4$

Page continues with: 72.9%) as an off-white powder. HRMS (ES$^+$) m/z Calcd for $C_{33}H_{33}Cl_2F_2N_3O_3+H$ [(M+H)$^+$]: 628.1940. found: 628.1939.

To a mixture of 2-(4-nitrophenyl)acetic acid (1 g, 5.52 mmol) dissolved in methanol (100 mL) cooled to 0° C., was added thionyl chloride (1.31 mL, 11 mmol) dropwise slowly. The mixture was stirred at 0° C. for 30 min then 25° C. for 1 h. TLC $R_f$=0.5 PDT (50% EtOAc/heptane; Rf=0.2 for SM). The mixture was concentrated under reduced pressure to afford (4-nitro-phenyl)-acetic acid methyl ester (1.1 g, 100%). $^1$H NMR (CDCl$_3$) δ 8.2 (d, 1H), 7.5 (d, 1H), 3.79 (s, 2H), 3.78 (s, 3H).

Example 352

Preparation of (4-amino-phenyl)-acetic acid methyl ester

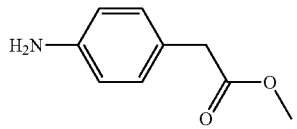

M.W. 165.19
C$_9$H$_{11}$NO$_2$ (4-Nitro-phenyl)-acetic acid methyl ester (1.08 g, 5.52 mmol) was dissolved in methanol (50 mL) and EtOAc (50 mL), then added to a Parr bottle containing 10% Pd/C (0.42 g), the vessel was subjected to hydrogen atmosphere (40 psi) for 2 h under the Parr Shaker Apparatus conditions. Workup with filtration via a glass membrane filter paper, solvent was removed under reduced pressure to afford (4-amino-phenyl)-acetic acid methyl ester as an oil (0.9 g, 98.7%). $^1$H NMR (CDCl$_3$) δ 7.05 (d, 1H), 6.62 (d, 1H), 3.63 (s, 3H), 3.6 (bs, 2H) 3.5 (s, 2H).

Example 353

Preparation of 2-((2R,3S,4R,5S)-3-(3-chloro-2-fluorophenyl)-4-(4-chloro-2-fluorophenyl)-4-cyano-5-neopentylpyrrolidine-2-carboxamido)thiazole-5-carboxylic acid triethylamine salt

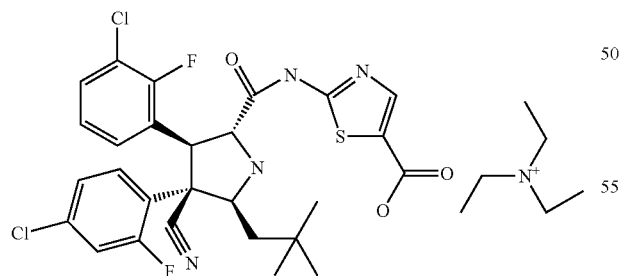

Molecular Weight = 593.4841 102.2011
Molecular Formula = C27H24Cl2F2N4O3S•C6H16N Racemic 2-((2R,3S,4R,5S)-3-(3-chloro-2-fluorophenyl)-4-(4-chloro-2-fluorophenyl)-4-cyano-5-neopentylpyrrolidine-2-carboxamido)thiazole-5-carboxylic acid was separated on a Berger SFC machine under 2 ml/m of 40% MeOH+ TEAM, 100 bar at 30° C. with a Whelko column to give the desired product (peak 1) as a white solid. 32 mg. MS (ES$^+$) m/z Calcd: [(M+H)$^+$]: 593. found: 593.

Example 354

Preparation of rac 6-((2R,3S,4R,5S)-3-(3-chloro-2-fluorophenyl)-4-(4-chloro-2-fluorophenyl)-4-cyano-5-neopentylpyrrolidine-2-carboxamido)-2-naphthoic acid

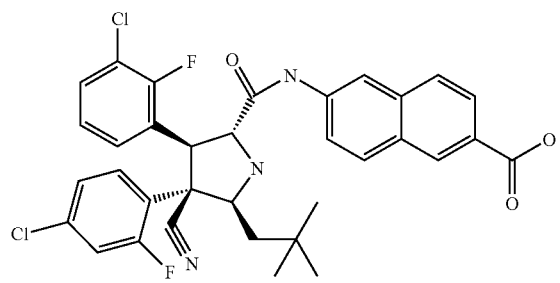

Molecular Weight = 636.5313
Molecular Formula = C34H29Cl2F2N3O3

To a stirred solution of methyl 6-((2R,3S,4R,5S)-3-(3-chloro-2-fluorophenyl)-4-(4-chloro-2-fluorophenyl)-4-cyano-5-neopentylpyrrolidine-2-carboxamido)-2-naphthoate (120 mg, 0.184 mmol) in methylene chloride 10 ml), aluminum bromide (295 mg, 1.11 mmol) and dimethyl sulfide (150 ul, 2.03 mmol) were added and the mixture was stirred at rt for overnight. LC/mass indicates complete reaction.

The solvent was removed and the residue was suspended in 6 ml of acetonitrile, 15 ml of water was added and the mixture was extracted with ethyl acetate (3×10 ml). The extracts were combined and dried with sodium sulfate. Removal of solvent at reduced pressure gave a white solid, 111 mg. MS (ES$^+$) m/z Calcd: [(M+H)$^+$]: 636. found: 636.

Example 355

Preparation of rac 6-((2R,3S,4R,5S)-3-(3-chloro-2-fluorophenyl)-4-(4-chloro-2-fluorophenyl)-4-cyano-5-neopentylpyrrolidine-2-carboxamido)-2-naphthoic acid methyl ester

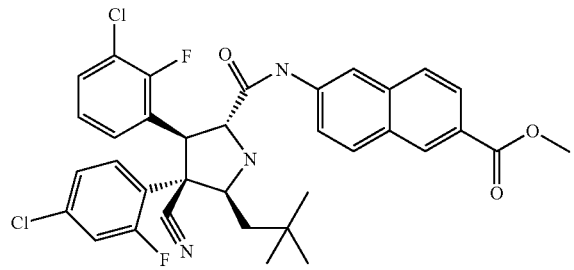

Molecular Weight = 650.5584
Molecular Formula = C35H31Cl2F2N3O3

(2R,3S,4R,5S)-3-(3-chloro-2-fluorophenyl)-4-(4-chloro-2-fluorophenyl)-4-cyano-5-neopentylpyrrolidine-2-carboxylic acid (233.5 mg, 0.50 mmol), HATU (190 mg, 0.50 mmol), methyl 6-amino-2-naphthoate (208 mg, 1 mmol) and DIPEA (0.2 mL) were combined with methylene chloride (10 ml) and the mixture was stirred at rt overnight.
The solvent was reduced to 4 ml and the residue was loaded onto a silica gel column (40 g) and eluted with 15-34% EtOAC/Hexanes to give a white solid. 210 mg. MS (ES$^+$) m/z Calcd: [(M+H)$^+$]: 650. found: 650.

Example 356

Preparation of rac methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methylbenzoate

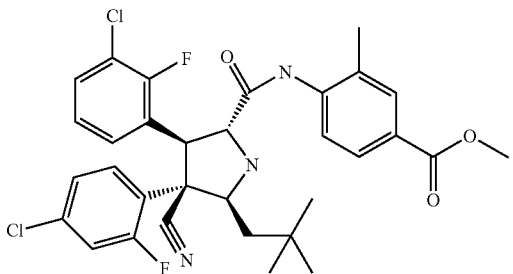

Molecular Weight = 614.5250
Molecular Formula = C32H31Cl2F2N3O3

In a round bottom flask containing (2R,3S,4R,5S)-3-(3-chloro-2-fluorophenyl)-4-(4-chloro-2-fluorophenyl)-4-cyano-5-neopentylpyrrolidine-2-carboxylic acid (133 mg) was combined with methylene chloride (10 ml), methyl 4-amino-3-methylbenzoate and DiPea. The mixture was stirred at rt for 2 hrs and another 100 mg of (2R,3S,4R,5S)-3-(3-chloro-2-fluorophenyl)-4-(4-chloro-2-fluorophenyl)-4-cyano-5-neopentylpyrrolidine-2-carboxylic acid was added and the mixture was stirred for another 2 hrs. The mixture was pardoned between water (10 ml) and methylene chloride (10 ml) and the organic layer was dried and concentrated to give a solid, which was treated with 3 ml of acetonitrile. The mixture was stirred and filtered. the solid was dried to give a white solid, 102 mg as the desired product. The filtrate was chromatographed on a reverse phase column (40 g, 30-100% acetonitrile) to give another 34 mg of desired product after removal of solvent. combined product: 102+34=136 mg. MS (ES$^+$) m/z Calcd: [(M+H)$^+$]: 614. found: 614.

Example 357

Preparation of rac 14-((2R,3S,4R,5S)-3-(3-chloro-2-fluorophenyl)-4-(4-chloro-2-fluorophenyl)-4-cyano-5-neopentylpyrrolidine-2-carboxamido)-3-methylbenzoic acid

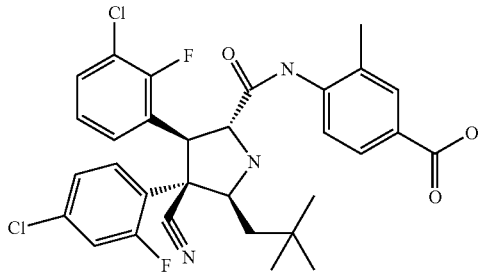

Molecular Weight = 600.4979
Molecular Formula = C31H29Cl2F2N3O3

To a stirred solution of methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methylbenzoate (26 mg, 42.3 µmol) in methylene chloride (10 ml) at rt, aluminum bromide (100 mg, 375 µmol) was added followed by dimethyl sulfide (60 mg, 966 µmol) and the mixture was stirred at rt overnight.
LC/Mass indicated complete reaction. The reaction was quenched with 1 N HCl (6 ml) and the mixture was extracted with methylene chloride (4×8 ml). The extracts were combined and dried with sodium sulfate. Removal of solvent gave a white solid. 11 mg. MS (ES$^+$) m/z Calcd: [(M+H)$^+$]: 600. found: 600.

Example 358

Preparation of rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-3,5-dimethyl-phenyl)-amide

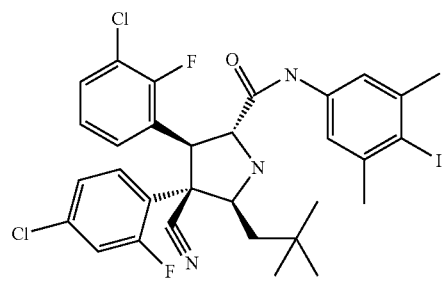

Molecular Weight = 696.4115
Molecular Formula = C31H30Cl2F2IN3O

To a stirred solution of 3 ml CH$_2$Cl$_2$ at r.t. was added 100 mg of the (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid, TFA salt and ⅓ amount of DIPEA under nitrogen. To this was added all of 4-iodo-3, 5-dimethylaniline (0.255 g, 1.03 mmol), followed by 128 mg of HATU. The reaction was stirred for 30 minutes. To the reaction was added another 0.15 ml of the DIPEA, followed by a solid mixture of 100 mg of the starting acid and 128 mg of the HATU. This was stirred for 30 minutes and then the rest of the starting material and the reagents were added the same way. The reaction was stirred for overnight. LCMS (z9808672/ZQ) indicated clean Rxn. The reaction was diluted with CH$_2$Cl$_2$ (10 ml), washed with 0.5 N aqueous HCl solution, dried with MgSO$_4$, filtered and concentrated to give a yellow oil and this was purified by a 40 g flash silica gel column, eluted with a stepwise gradient of Hexanes to 25% EtOAc/Hexanes. Obtained the product as a white solid. 60 mg. MS (ES$^+$) m/z Calcd: [(M+H)$^+$]: 696, found: 696.

Example 359

Preparation of rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,6-dimethyl-benzoic acid

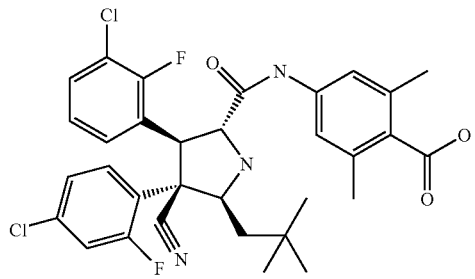

Molecular Weight = 614. 5250
Molecular Formula = C32H31Cl2F2N3O3

In a 50 ml pressure tube, (2R,3S,4R,5S)-3-(3-chloro-2-fluorophenyl)-4-(4-chloro-2-fluorophenyl)-4-cyano-N-(5-iodopyridin-2-yl)-5-neopentylpyrrolidine-2-carboxamide (60 mg, 86.2 µmol, Eq: 1.00) was combined with DMF (3 ml) and water (200 µl). potassium carbonate (23.8 mg, 172 µmol, Eq: 2) was added. The mixture was bubbled with nitrogen and then palladium(II) acetate (3 mg, 12.9 µmol, Eq: 0.15) was added. The tube was subjected to CO atmosphere at 50 PSI and stirred for 3 hours at 70° C. LCMS (z9809424, 50% ACN) indicated little desired product (RT 1.41, M+1 614), reduction product (RT 2.21, 570), and sm (RT 2.62, 696). The reaction was continued for 5 days.

The reaction was filtered through celite, washed with DMF, water and EtOAC. The filtrate was acidified with 0.5N HC and was extracted with EtOAC 3×. The EtOAC solution washed with water, dried over Na2SO4, and concentrated to give a residue. The residue was dissolved in DMSO and ACN and was purified by preparative HPLC (60-100% ACN/water). The first peak was concentrated and freezed dried to give a white foam, 2.2 mg desired product.

MS (ES$^+$) m/z Calcd: [(M+H)$^+$]:614, found: 614.

Example 360

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-methoxy-benzoic acid

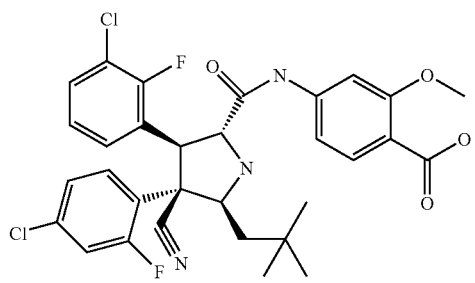

Molecular Weight = 616.4973
Molecular Formula = C31H29Cl2F2N3O4

Racemic 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-methoxy-benzoic acid was separated on a SFC machine with whelk column under a flow rate of 50% (MeOH) to give two products. The desired isomer came out as the second peak.

MS (ES$^+$) m/z Calcd: [(M+H)$^+$]: 616. found: 616.

Example 361

Preparation of rac 4-{[(2R,3S,4R,5S)-4-(4-Chloro-2-fluoro-phenyl)-3-(3-chloro-2-fluoro-phenyl)-4-cyano5(2,2-dimethyl-propyl)-pyrrolidine-2-carbonyl]-amino}-2-trifluoromethyl-benzoic acid

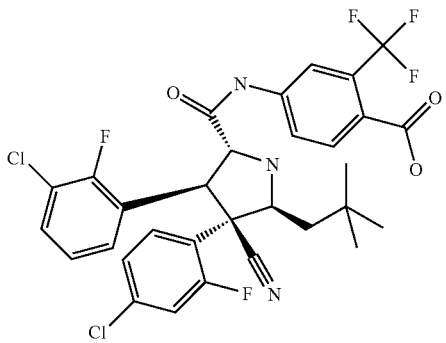

Molecular Weight = 654.4692
Molecular Formula = C31H26Cl2F5N3O3

Rac 4 {[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-trifluoromethyl-benzoic acid methyl ester (36 mg) was dissolved in MeOH (10 mL). To the stirred solution was added NaOH (1N, 3 mL) and the mixture was stirred at 50° C. for 3 hrs. The solvent was removed and the residue was treated with 1 N HCl to make the mixture acidic. The white suspension was filtered to collect the white solid as the title compound (29 mg, 82% yield).

HRMS (ES$^+$) m/z Calcd for $C_{31}H_{26}Cl_2F_5N_3O_3$+H [(M+H)$^+$]: 654.1344 found: 654.1343

Example 362

Preparation of rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-bromo-2-methoxy-phenyl)-amide

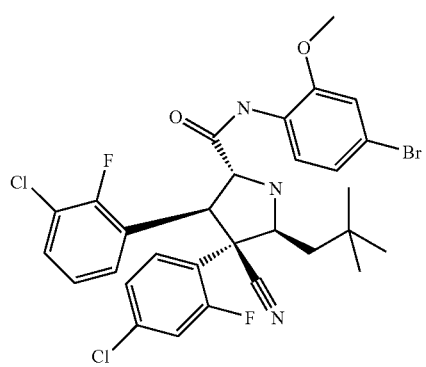

Molecular Weight = 651.3834
Molecular Formula = C30H28BrCl2F2N3O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid, TFA salt (300 mg, 0.52 mmol) in methylene chloride (3 mL), HATU (Aldrich, 352 mg, 0.93 mmol) was added followed by the addition of DIPEA (0.360 mL, 2.07 mmol) and 4-Bromo-2-methoxy-phenylamine (Oakwood, 210 mg, 1.04 mmol). The mixture was stirred at rt for 1.5 h. The reaction was quenched with addition of water. The mixture was extracted with methylene chloride (2×10 mL) and the extracts were dried with magnesium sulfate. The solvent was removed and the residue was purified by flash chromatography (0-20% EtOAc/hexanes) to give the title compound as a white solid (295 mg, 88% yield).

MS (ES$^+$) m/z Calcd: [(M+H)$^+$]: 650, found: 650.

Example 363

Preparation of rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylcarbamoyl-phenyl)-amide

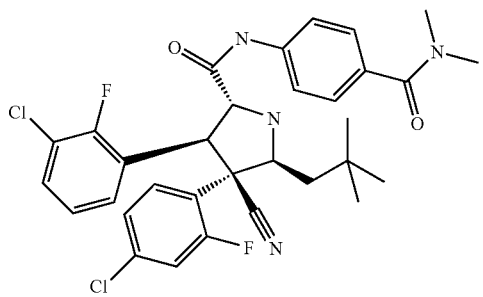

Molecular Weight = 613.5402
Molecular Formula = C32H32Cl2F2N4O2

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid, TFA salt (150 mg, 0.26 mmol) in methylene chloride (3 mL), HATU (Aldrich, 176 mg, 0.46 mmol) was added followed by the addition of DIPEA (0.225 mL, 1.29 mmol) and 4-Amino-N,N-dimethyl-benzamide (Alfa, 85 mg, 0.52 mmol). The mixture was stirred at rt for 3 h. The reaction was quenched with addition of water. The mixture was extracted with methylene chloride (2×10 mL) and the extracts were dried with magnesium sulfate. The solvent was removed and the residue was purified by flash chromatography (0-5% MeOH/CH$_2$Cl$_2$) and recrystallized from CH$_2$Cl$_2$/Hexanes/EtOAc to give the title compound as a white solid (50.5 mg, 32% yield).

MS (ES$^+$) m/z Calcd: [(M+H)$^+$]: 613. found: 613.

Example 364

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-methyl-benzoic acid

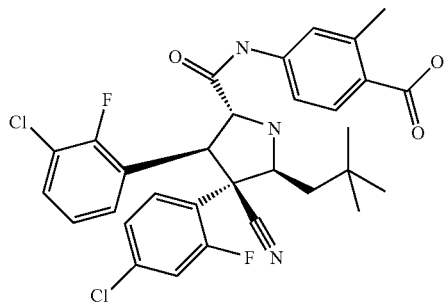

Molecular Weight = 600.4979
Molecular Formula = C31H29Cl2F2N3O3

Rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-methyl-benzoic acid (65 mg) was resolved on a Berger SFC machine using whelk column under 100 bar, 30° C. with 50% of methanol at a rate of 2 mL/min to give two separated peaks. Peak 1 (20 mg, 31% yield) (RO5488609-000) and peak 2, (desired product, 20 mg, 31% yield) (RO5488610-000)

MS (ES$^+$) m/z Calcd: [(M+H)$^+$]: 600. found: 600.

Example 365

Preparation of intermediate rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-2,5-dimethyl-phenyl)-amide

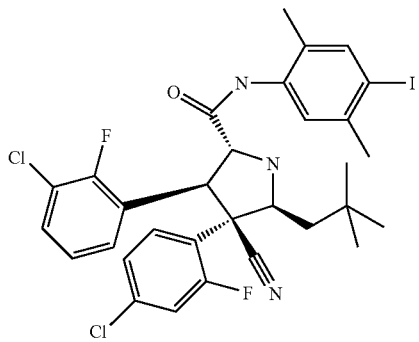

Molecular Weight = 696.4115
Molecular Formula = C31H30Cl2F2IN3O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid, TFA salt (250 mg, 0.43 mmol) in methylene chloride (3 mL), HATU (Aldrich, 294 mg, 0.77 mmol) was added followed by the addition of DIPEA (0.375 mL, 2.15 mmol) and 4-Iodo-2,5-dimethyl-phenylamine (Spectra Group, 248 mg, 0.86 mmol). The mixture was stirred at RT for 1 h. The reaction was quenched with addition of 1N HCl (1.5 ml). The mixture was extracted with methylene chloride (2×10 mL) and the extracts were dried with magnesium sulfate. The solvent was removed and the residue was purified by flash chromatography (0-15% EtOAc/Hexanes) to give the title compound as a light yellow solid (175 mg, 63% pure, 37% yield).

MS (ES$^+$) m/z Calcd: [(M+H)$^+$]: 696. found: 696.

Example 366

Preparation of rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,5-dimethyl-benzoic acid

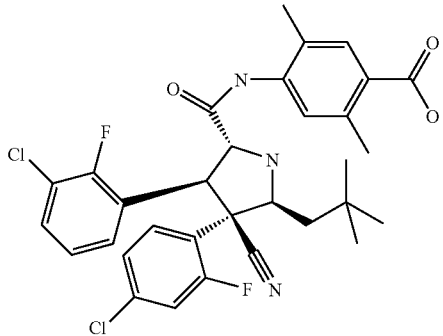

Molecular Weight = 614.5250
Molecular Formula = C32H31Cl2F2N3O3

To a solution of rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-2,5-dimethyl-phenyl)-amide (Example 365, 149 mg, 0.214 mmol) in DMF (5 ml) was added water (0.2 ml), and potassium carbonate (60 mg, 0.428 mmol). The mixture was bubbled with nitrogen and palladium acetate (5 mg, 0.021 mmol) was added. The mixture was subjected to carbon monoxide atmosphere at 50 psi and was heated at 70° C. for 3 h. The mixture was then filtered through celite, acidified with HOAc and extracted with EtOAc (3×10 ml). The organic solution was concentrated and was purified by reverse phase HPLC using acetonitrile and water. Obtained the title compound as a white powder, (45 mg, 35% yield).

MS (ES$^+$) m/z Calcd: [(M+H)$^+$]: 614. found: 614.

Example 367

Preparation of intermediate rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (2-fluoro-4-iodo-phenyl)-amide

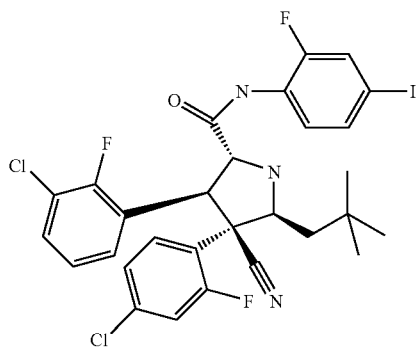

Molecular Weight = 686.3477
Molecular Formula = C29H25Cl2F3IN3O

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid, TFA salt (250 mg, 0.43 mmol) in methylene chloride (3 mL), HATU (Aldrich, 294 mg, 0.77 mmol) was added followed by the addition of DIPEA (0.375 mL, 2.15 mmol) and 2-Fluoro-4-iodo-phenylamine (Aldrich, 204 mg, 0.86 mmol). The mixture was stirred at RT for 5 h. The reaction was quenched with 0.5 N HCl (2 ml). The mixture was extracted with methylene chloride (2×10 mL) and the extracts were dried with magnesium sulfate. The solvent was removed and the residue was purified by flash chromatography (0-20% EtOAc/Hexanes) to give the title compound as a white solid (100 mg, 60% pure, 20% yield).

MS (ES$^+$) m/z Calcd: [(M+H)$^+$]: 686. found: 686.

Example 368

Preparation rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-fluoro-benzoic acid

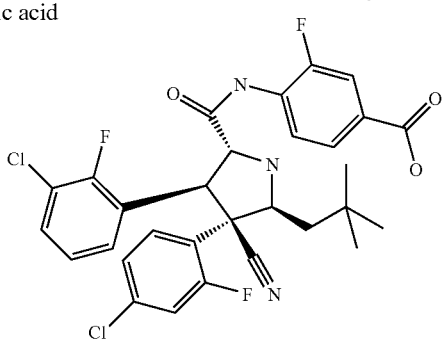

Molecular Weight = 604.4612
Molecular Formula = C30H26Cl2F3N3O3

To a solution of rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (2-fluoro-4-iodo-phenyl)-amide (Example 367, 95 mg, 0.138 mmol) in DMF (3 ml) was added water (0.2 ml), and potassium carbonate (38 mg, 0.27 mmol). The mixture was bubbled with nitrogen and palladium acetate (3 mg, 0.014 mmol) was added. The mixture was subjected to carbon monoxide atmosphere at 50 psi and was heated at 70° C. for 3 h. The mixture was then filtered through celite. The filtrate was acidified with HOAc and was extracted with EtOAc (3×10 ml). The organic solution was concentrated and purified by reverse phase HPLC using acetonitrile and water. Obtained the title compound as a white solid (28 mg, 34% yield).

MS (ES$^+$) m/z Calcd: [(M+H)$^+$]: 604. found: 604.

Example 369

Preparation of rac (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (6-iodo-pyridin-3-yl)-amide

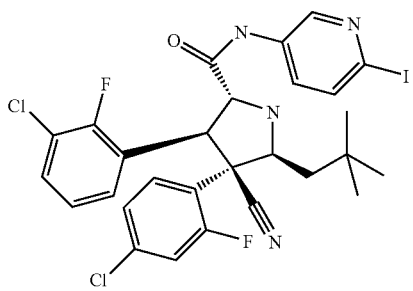

Molecular Weight = 669.3449
Molecular Formula = C28H25Cl2F2IN4O

401

To a stirred solution of rac (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid, TFA salt (200 mg, 0.34 mmol) in methylene chloride (3 mL), HATU (Aldrich, 235 mg, 0.62 mmol) was added followed by the addition of DIPEA (0.3 mL, 1.72 mmol) and 6-Iodo-pyridin-3-ylamine (Lancaster, 138 mg, 0.69 mmol). The mixture was stirred at RT for 4 h. The reaction was quenched with water. The mixture was extracted with methylene chloride (2×10 mL) and the extracts were dried with sodium sulfate. The solvent was removed and the residue was purified by flash chromatography (0-8% EtOAc/methylene chloride) to give the title compound as a white solid (95 mg, 41% yield).

MS (ES$^+$) m/z Calcd: [(M+H)$^+$]: 669, found: 669.

Example 370

Preparation of 2-Chloro-4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-benzoic acid methyl ester

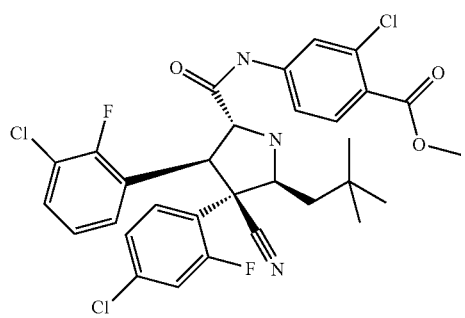

Molecular Weight = 634.9429
Molecular Formula = C31H28Cl3F2N3O3

To a stirred solution of (2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carboxylic acid, TFA salt (200 mg, 0.34 mmol) in methylene chloride (3 mL), HATU (Aldrich, 235 mg, 0.62 mmol) was added followed by the addition of DIPEA (0.3 mL, 1.72 mmol) and 4-Amino-2-chloro-benzoic acid methyl ester (Example 296, 128 mg, 0.69 mmol). The mixture was stirred at RT for 2 h. The reaction was quenched with water. The mixture was extracted with methylene chloride (2×10 mL) and the extracts were dried with sodium sulfate. The solvent was removed and the residue was purified by flash chromatography (0-25% EtOAc/Hexanes) to give the title compound as a white solid (72 mg, 33% yield).

MS (ES$^+$) m/z Calcd: [(M+H)$^+$]: 634. found 634

Example 371

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-trifluoromethyl-phenyl)-amide

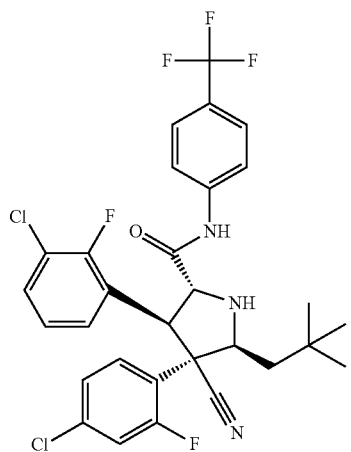

M.W. 610.45
C$_{30}$H$_{26}$Cl$_2$F$_5$N$_3$O

In a manner similar to the method described in Examples 1e, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.2 g, 0.43 mmol) was reacted with 4-aminobenzotrifluoride (Alfa) (0.14 g, 0.86 mmol), HATU (0.29 g, 0.77 mmol) and iPr$_2$NEt (0.15 mL, 0.86 mmol) in CH$_2$Cl$_2$ at room temperature to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-trifluoromethyl-phenyl)-amide as a white solid (38 mg, 15%).

HRMS (ES$^+$) m/z Calcd for C$_{30}$H$_{26}$Cl$_2$F$_5$N$_3$O+H [(M+H)$^+$]: 610.1446. found: 610.1448.

Example 372a

Preparation of intermediate 1-(4-amino-phenyl)-2-(tert-butyl-dimethyl-silanyloxy)-ethanone

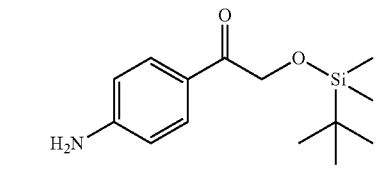

M.W. 265.43
C$_{14}$H$_{23}$NO$_2$Si

Step A To a solution of 2-hydroxy-1-(4-nitrophenyl)ethanone (1 g, 5.52 mmol) in DMF (25 ml) was added imidazole (564 mg, 8.28 mmol), followed by the addition of tert-butyl-chlorodimethylsilane (915 mg, 6.07 mmol). The reaction mixture was stirred at room temperature for 3 h. The mixture was poured into H₂O (25 mL) and extracted with ethyl acetate (3×25 mL). The organic layers were combined, washed with H₂O (5×25 mL), brine (1×25 mL), dried over MgSO₄ and concentrated in vacuo to give 2-(tert-butyldimethylsilyloxy)-1-(4-nitrophenyl)ethanone as a yellow solid (1.6 g, 98%).

Step B To a solution of 2-(tert-butyldimethylsilyloxy)-1-(4-nitrophenyl)ethanone (0.54 g, 1.83 mmol) in methanol (60 mL) was added an aqueous solution (15 mL) of ammonium chloride (0.98 g, 18.3 mmol), followed by the addition of Zinc (1.2 g, 18.3 mmol). The reaction mixture was stirred at room temperature for 1 h. The mixture was filtered through a short pad of celite. The filtrate was concentrated to a small volume, then when partitioned between ethyl acetate and water. The organic layer was separated, the aqueous layer was extracted with ethyl acetate. The organic layers were combined, washed with water, brine, dried over MgSO₄, and concentrated to give 1-(4-amino-phenyl)-2-(tert-butyl-dimethyl-silanyloxy)-ethanone as a white foam (0.4 g, 82%)

Example 372b

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-acetyl)-phenyl]-amide

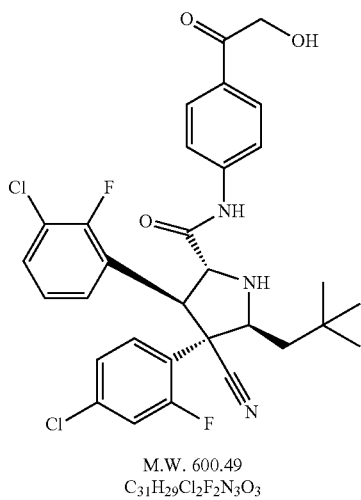 [SMILES: CC(C)(C)C[C@@H]1N[C@@H](C(=O)Nc2ccc(C(=O)CO)cc2)[C@H](c2cccc(Cl)c2F)[C@@]1(C#N)c1ccc(Cl)cc1F]

M.W. 600.49
$C_{31}H_{29}Cl_2F_2N_3O_3$

To a solution of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.35 g, 0.749 mmol) in dichloromethane (25 ml) was added iPr₂NEt (242 mg, 1.87 mmol) was added, followed by the addition of HATU (513 mg, 1.35 mmol) and 1-(4-aminophenyl)-2-(tert-butyldimethylsilyloxy)ethanone (398 mg, 1.5 mmol). The reaction mixture was stirred at room temperature for 3 h. The reaction mixture was poured into H₂O (50 mL) and extracted with dichloromethane (3×25 mL). The organic layers were combined, washed with H₂O (1×50 mL), brine (50 mL), dried over MgSO₄ and concentrated in vacuo. The residue was dissolved in THF (25 mL) and then an aqueous solution (1 N) of HCl (10 mL) was added. The reaction mixture was stirred at room temperature for 30 min. The mixture was concentrated in vacuo. The residue was poured into 20 mL saturated aqueous NaHCO₃ and extracted with ethyl acetate (3×25 mL). The organic layers were combined, washed with H₂O (25 mL), brine (25 mL), dried over MgSO₄ and concentrated. The residue was purified by flash chromatography (silica gel, 40 g, 20% to 100% EtOAc in hexanes) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-acetyl)-phenyl]-amide as a light yellow solid (0.17 g, 38%).

LCMS (ES⁺) m/z Calcd for $C_{31}H_{29}Cl_2F_2N_3O_3$+H [(M+H)⁺]: 600. found: 600.

Example 373

Preparation of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylaminocarbonyl-phenyl)-amide

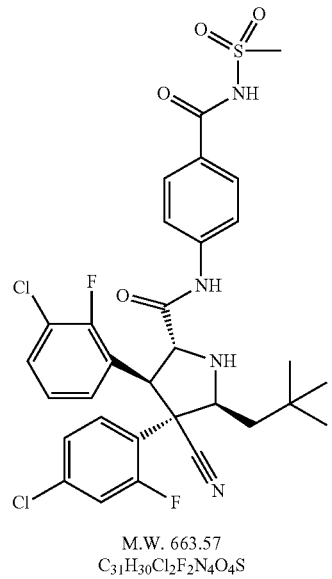 [SMILES: CC(C)(C)C[C@@H]1N[C@@H](C(=O)Nc2ccc(C(=O)NS(C)(=O)=O)cc2)[C@H](c2cccc(Cl)c2F)[C@@]1(C#N)c1ccc(Cl)cc1F]

M.W. 663.57
$C_{31}H_{30}Cl_2F_2N_4O_4S$

Rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylaminocarbonyl-phenyl)-amide (63 mg) was separated by chiral SFC chromatography to provide chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylaminocarbonyl-phenyl)-amide as a white solid (25 mg, 40%) and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylaminocarbonyl-phenyl)-amide as a white solid (24 mg, 38%).

Example 374a

Preparation of intermediate 4-amino-1-[2-(tert-butyl-dimethyl-silanyloxy)-ethyl]-1H-pyridin-2-one

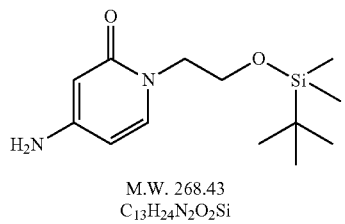 [SMILES: CC(C)(C)[Si](C)(C)OCCn1ccc(N)cc1=O]

M.W. 268.43
$C_{13}H_{24}N_2O_2Si$

To a solution of 4-aminopyridin-2(1H)-one (Molbridge) (0.9 g, 8.17 mmol) in DMF (30 mL) was added NaH (60%, 490 mg, 12.3 mmol). The mixture was stirred at room temperature for 30 min before (2-bromoethoxy) (tert-butyl)dimethylsilane (2.15 g, 8.99 mmol) was added. The reaction mixture was heated at 78° C. for 15 h. The mixture was cooled and poured into H$_2$O (100 mL) and extracted with ethyl acetate (3×50 mL). The organic layers were combined, washed with H$_2$O (5×50 mL), brine (50 mL), dried over MgSO$_4$ and concentrated. The residue was purified by flash chromatography (silica gel, 40+S, 0% to 10% MeOH in EtOAc) to give 4-amino-1-[2-(tert-butyl-dimethyl-silanyloxy)-ethyl]-1H-pyridin-2-one as a white solid (0.9 g, 41%).

Example 374b

Preparation of intermediate rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-(tert-butyl-dimethyl-silanyloxy)-ethyl]-2-oxo-1,2-dihydro-pyridin-4-yl)-amide

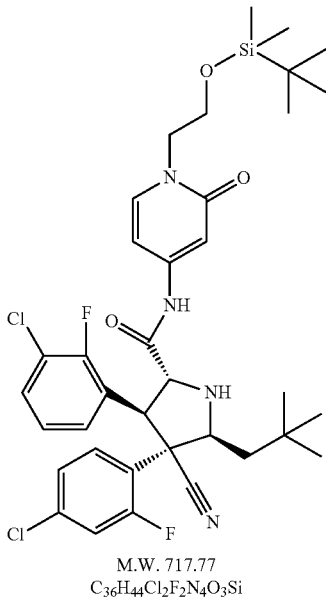 [SMILES: CC(C)(C)C[C@@H]1N[C@@H](C(=O)Nc2ccn(CCO[Si](C)(C)C(C)(C)C)c(=O)c2)[C@H](c2cccc(Cl)c2F)[C@@]1(C#N)c1ccc(Cl)cc1F]

M.W. 717.77
C$_{36}$H$_{44}$Cl$_2$F$_2$N$_4$O$_3$Si

To a mixture of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (0.2 g, 0.428 mmol) in dichloromethane (20 mL) was added iPr$_2$NEt (138 mg, 1.07 mmol), followed by the addition of diphenylphosphinic chloride (Aldrich) (203 mg, 0.856 mmol). The mixture was stirred at room temperature for 30 min, then 4-amino-1-(2-(tert-butyldimethylsilyloxy)ethyl)pyridin-2(1H)-one (115 mg, 428 µmol) was added. The reaction mixture was stirred at room temperature for 3 h, then concentrated. The residue was purified by flash chromatography (silica gel, 40 g, 5% to 80% EtOAc in hexanes) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-(tert-butyl-dimethyl-silanyloxy)-ethyl]-2-oxo-1,2-dihydro-pyridin-4-yl)-amide as a white solid (35 mg, 11%).

Example 374c

Preparation of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-ethyl)-2-oxo-1,2-dihydro-pyridin-4-yl]-amide

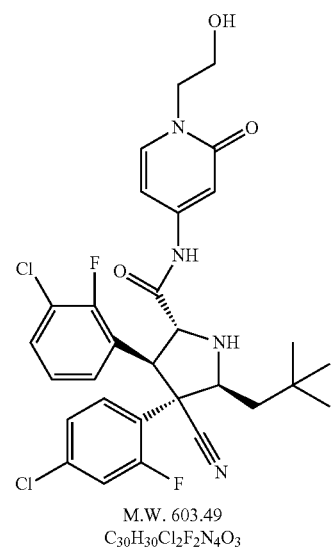 [SMILES: CC(C)(C)C[C@@H]1N[C@@H](C(=O)Nc2ccn(CCO)c(=O)c2)[C@H](c2cccc(Cl)c2F)[C@@]1(C#N)c1ccc(Cl)cc1F]

M.W. 603.49
C$_{30}$H$_{30}$Cl$_2$F$_2$N$_4$O$_3$

To a solution of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-(tert-butyl-dimethyl-silanyloxy)-ethyl]-2-oxo-1,2-dihydro-pyridin-4-yl)-amide (35 mg, 0.049 mmol) in THF (5 ml) was added an aqueous solution (1 N) of HCl (5 mL). The reaction mixture was stirred at room temperature for 30 min. The mixture was concentrated and the residue was partitioned between aqueous saturated Na$_2$SO$_4$ and ethyl acetate. The organic layer was collected and washed with H$_2$O (25 mL), brine (25 mL), dried over MgSO$_4$ and concentrated. The residue was purified by flash chromatography (silica gel, 12 g, 20% to 100% EtOAc in hexanes) to give rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-ethyl)-2-oxo-1,2-dihydro-pyridin-4-yl]-amide as a white solid (12 mg, 41%).

Example 375

Preparation of 4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid

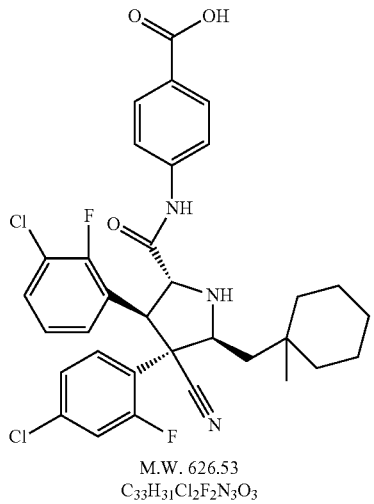 [SMILES: CC1(C[C@@H]2N[C@@H](C(=O)Nc3ccc(C(=O)O)cc3)[C@H](c3cccc(Cl)c3F)[C@@]2(C#N)c2ccc(Cl)cc2F)CCCCC1]

M.W. 626.53
$C_{33}H_{31}Cl_2F_2N_3O_3$

Rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid (110 mg) was separated by chiral SFC chromatography to provide chiral 4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid as a white solid (48 mg, 44%) and chiral 4-{[(2S,3R,4S,5R)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid as a white solid (48 mg, 44%).

Example 376

Preparation of chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid

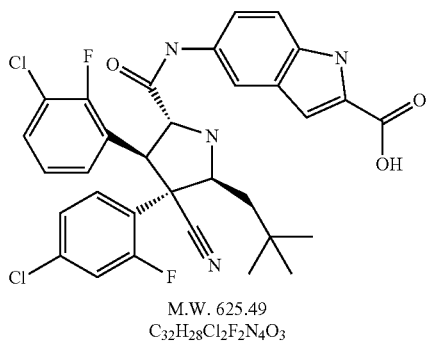 [SMILES: CC(C)(C)C[C@@H]1N[C@@H](C(=O)Nc2ccc3[nH]c(C(=O)O)cc3c2)[C@H](c2cccc(Cl)c2F)[C@@]1(C#N)c1ccc(Cl)cc1F]

M.W. 625.49
$C_{32}H_{28}Cl_2F_2N_4O_3$

A chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid ethyl ester (33 mg, 0.051 mmol) was dissolved in ethanol (15 mL), then 2N KOH (5 mL) was added and stirred 2 hours @ 50° C., then the temperature was warmed to 65° C. for 2 h, after cooling to 25° C., the reaction was diluted with water and extracted with ethyl acetate (3×). The organic phase was separated then concentrated under reduce pressure to chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid (24 mg, 76%) as a white powder. HRMS (ES$^+$) m/z Calcd for $C_{32}H_{28}Cl_2F_2N_4O_3$+H [(M+H)$^+$]: 625.1580 found: 625.1580.

Example 377

Preparation of chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid ethyl ester

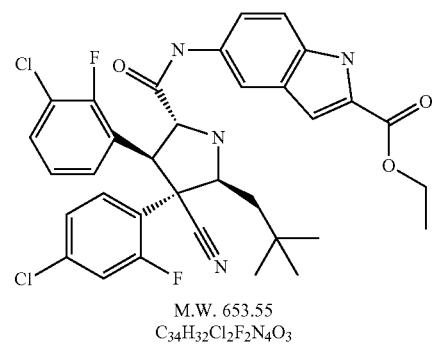 [SMILES: CCOC(=O)c1cc2cc(NC(=O)[C@@H]3N[C@@H](CC(C)(C)C)[C@](C#N)(c4ccc(Cl)cc4F)[C@H]3c3cccc(Cl)c3F)ccc2[nH]1]

M.W. 653.55
$C_{34}H_{32}Cl_2F_2N_4O_3$

A mixture of chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (150 mg, 0.321 mmol), ethyl 5-amino-1H-indole-2-carboxylate (114 mg, 0.558 mmol), 2-(7-azabenzotriazol-1-yl)-n,n,n',n'-tetramethyluronium hexafluorophosphate (HATU, 159 mg, 0.417 mmol) and iPr$_2$NEt (0.4 mL, 2.29 mmol) in CH$_2$Cl$_2$ (10 mL) was stirred at rt overnight. The mixture was then diluted with CH$_2$Cl$_2$ and washed with water, brine. The organic phase was separated, then concentrated and purified by RP-HPLC chromatography (20-95% acetonitrile/water) to afford 5-{[(2R,3S,4R,5S)-3-(3-Chloro-2-fluoro-phenyl)-4-(4-chloro-2-fluoro-phenyl)-4-cyano-5-(2,2-dimethyl-propyl) pyrrolidine-2-carbonyl]-amino}-1H-indole-2-carboxylic acid ethyl ester (37 mg, 17.6%) as an off-white powder. LCMS (ES$^+$) m/z Calcd for $C_{34}H_{32}Cl_2F_2N_4O_3$+H [(M+H)$^+$]: 652.18. found: 6512.

Example 378

Preparation of 5-Amino-1H-indole-2-carboxylic acid ethyl ester

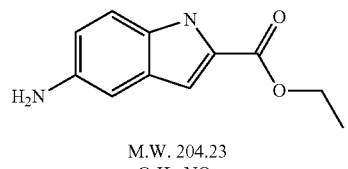

M.W. 204.23
$C_9H_{11}NO_2$

5-Amino-1H-indole-2-carboxylic acid ethyl ester (150 mg, 0.64 mmol) was dissolved in ethanol (10 mL) and EtOAc (10 mL), then subjected to the H-Cube (ThalesNano) with a 10% Pd/C cartridge at the 10° C. setting at 10 psi. The solution was concentrated under reduced pressure to afford 5-amino-1H-indole-2-carboxylic acid ethyl ester as a yellow solid (0.114 g, 87.2%). $^1$H NMR (DMSO-d$_6$) δ 11.4 (bs, 1H), 7.18 (d, 1H), 6.8 (s, 1H), 6.62 (m, 2H), 34.65 (bs, 2H), 4.3 (q, 2H), 1.3 (t, 3H).

Example 379

Preparation of rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid methyl ester

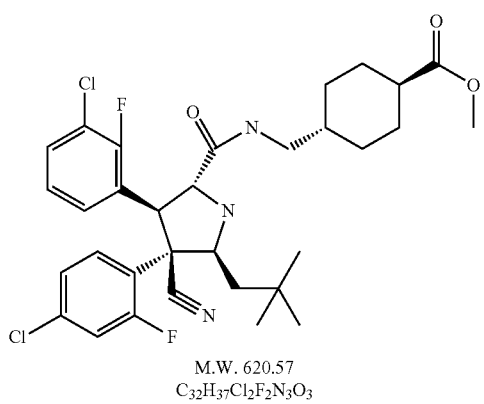 [SMILES: COC(=O)[C@H]1CC[C@H](CNC(=O)[C@@H]2N[C@@H](CC(C)(C)C)[C@](C#N)(c3ccc(Cl)cc3F)[C@H]2c2cccc(Cl)c2F)CC1]

M.W. 620.57
C$_{32}$H$_{37}$Cl$_2$F$_2$N$_3$O$_3$

To a stirred solution of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (61 mg, 0.13 mmol) in N,N-dimethyl formamide (5 mL) was added diisopropylethylamine (126.1 mg, 0.976 mmol), HOBt (35.3 mg, 0.262 mmol), HBTU (97.8 mg, 0.258 mmol) and methyl-trans-4-aminomethyl-cyclohexane carboxylic acid HCl (56.2 mg, 0.256 mmol, AK Scientific). After it was stirred at rt for 2.5 hrs, the solvent was removed and the reaction mixture was extracted with EtOAc and washed with 1N NaOH (2×), water, and saturated NaCl. The organic phase was separated and dried over Na$_2$SO$_4$. The reaction mixture was then purified by flash column to give rac 4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid methyl ester (64.0 mg, 79%) and a white solid foam. HRMS (ES$^+$) m/z Calcd C$_{32}$H$_{37}$Cl$_2$F$_2$N$_3$O$_3$+H [(M+H): 620.2253. Found: 620.2253.

Example 380

Preparation of rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid

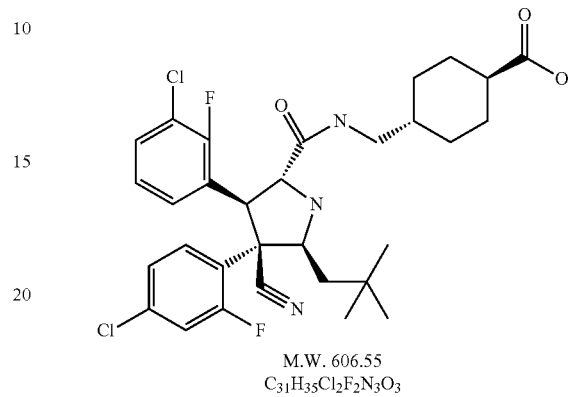

M.W. 606.55
C$_{31}$H$_{35}$Cl$_2$F$_2$N$_3$O$_3$

To a solution of rac 4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid methyl ester (54.3 mg, 0.0875 mmol, example XC-1) in THF (5 mL) was added a solution of LiOH (27.8 mg, 0.662 mmol, Aldrich) in water (2.5 mL) and the reaction mixture was stirred at rt for 22 hrs. The reaction mixture was partly concentrated and quenched with 1 N HCl (pH 6), extracted with EtOAc, and washed with water, saturated NaCl. The organic phase was separated, and dried over Na$_2$SO$_4$. The mixture was then concentrated to give rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid (52.1 mg, 98%). HRMS (ES$^+$) m/z Calcd C$_{31}$H$_{35}$Cl$_2$F$_2$N$_3$O$_3$+H [(M+H): 606.2097. Found: 606.2097.

Example 381

Preparation of rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid methyl ester

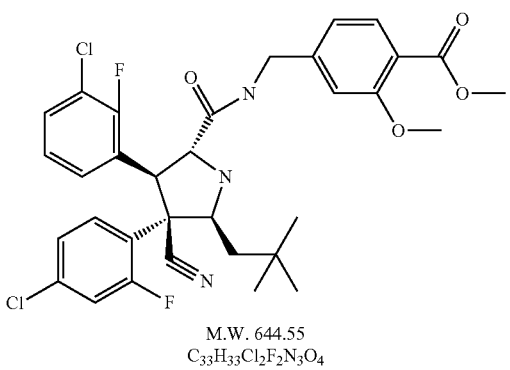 [SMILES: COC(=O)c1ccc(CNC(=O)[C@@H]2N[C@@H](CC(C)(C)C)[C@](C#N)(c3ccc(Cl)cc3F)[C@H]2c2cccc(Cl)c2F)cc1OC]

M.W. 644.55
C$_{33}$H$_{33}$Cl$_2$F$_2$N$_3$O$_4$

A solution of 4-cyano-2-methoxy benzoic acid (1.0 g, 5.65 mmol, Biogene) in methanol was reacted with p-toluenesulfonic acid monohydrate (285.6 mg, 1.479 mmol) and heated to reflux for 16 hrs. The solvent was removed and the reaction residue was extracted with EtOAc, and washed with saturated sodium carbonate, water, and saturated NaCl, and dried over $Na_2SO_4$ to give 4-Cyano-2-methoxy-benzoic acid methyl ester (1.04 g, 96%). This ester (1.01 g, 5.28 mmol) in methanol (50 mL) was reacted with Raney Ni (3 spatula tips full, exact amount unknown, Aldrich) under 50 psi $H_2$ in a Parr apparatus for 16 hrs. After filtering through Celite and concentrating, the crude mixture was purified by silica gel chromatography using methanol and methylene chloride to give 4-aminomethyl-2-methoxy-benzoic acid methyl ester (385.7 mg, 37%).

In a manner similar to the method described in Example 379, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (64 mg, 0.137 mmol) and 4-aminomethyl-2-methoxy-benzoic acid methyl ester (55 mg, 0.282 mmol) in N,N-dimethyl formamide (5 mL) were reacted with DIPEA (111.3 mg, 0.861 mmol), HOBt (38.8 mg, 0.287 mmol) and HBTU (107.6 mg, 0.284 mmol) at room temperature to give rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid methyl ester (91.8 mg, ~100%). HRMS ($ES^+$) m/z Calcd $C_{33}H_{33}Cl_2F_2N_3O_4$+H [(M+H): 644.1889. Found: 644.1885.

Example 382

Preparation of rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid

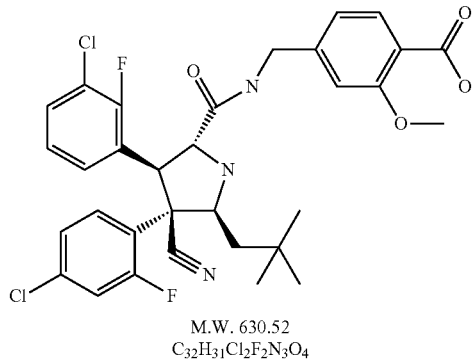 [SMILES: COc1cc(CNC(=O)[C@@H]2N[C@@H](CC(C)(C)C)[C@](C#N)(c3ccc(Cl)cc3F)[C@H]2c2cccc(Cl)c2F)ccc1C(=O)O]

M.W. 630.52
$C_{32}H_{31}Cl_2F_2N_3O_4$

In a manner similar to the method described in Example 380, rac-4-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid methyl ester (75.2 mg, 0.117 mmol), was combined with THF (7 ml) and lithium hydroxide hydrate (33.5 mg, 0.798 mmol) in water (3.5 mL). It was stirred at room temperature to give rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid as a white lyophilized solid (66.6 mg, 89%).

HRMS ($ES^+$) m/z Calcd $C_{32}H_{31}Cl_2F_2N_3O_4$+H [(M+H): 630.1733. Found: 630.1729.

Example 383

Preparation of rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid methyl ester

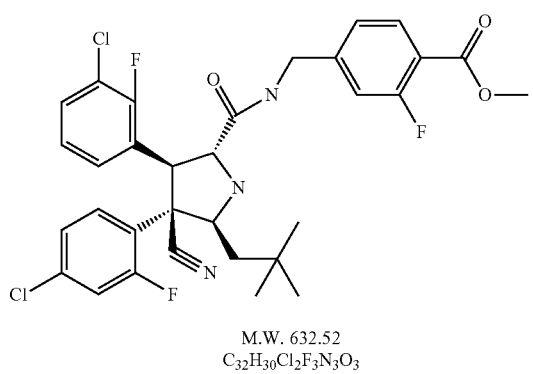

M.W. 632.52
$C_{32}H_{30}Cl_2F_3N_3O_3$

Preparation of methyl 4-(aminomethyl)-2-fluorobenzoate: A solution of 4-cyano-2-fluorobenzoic acid (4.02 g, 24.36 mmol, Aldrich) in methanol (50 mL) was treated with p-toluenesulfonic acid monohydrate (0.46 g, 2.43 mmol) and heated to reflux overnight. The solvent was removed and the reaction residue was extracted with EtOAc, washed with saturated $Na_2CO_3$, brine and dried over $Na_2SO_4$ to give Methyl 4-cyano-2-fluorobenzoate (4.46 g, 95%). This Methyl ester (1.03 g, 5.77 mmol) was combined with methanol (60 mL) and Raney Ni (2 spatula tip fulls were added after washing with methanol under argon). It was then put under Hydrogen at 50 PSI on a PARR shaker for 18 hrs. The reaction was filtered through celite and washed with methanol while being kept under $N_2$. It was then purified by silica gel chromatography with methanol and methylene chloride to give methyl 4-(aminomethyl)-2-fluorobenzoate (247.6 mg, 23%) as off-white solid.

In a manner similar to the method described in Example 379, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (66.1 mg, 0.141 mmol) and methyl 4-(aminomethyl)-2-fluorobenzoate (51.0 mg, 0.278 mmol in N,N-dimethyl formamide (5 mL) were reacted with DIPEA (111 mg, 0.857 mmol), HOBt (37.6 mg, 0.277 mmol) and HBTU (104.9 mg, 0.275 mmol) at room temperature to give rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid methyl ester (88.5 mg, 98%). HRMS ($ES^+$) m/z Calcd $C_{32}H_{30}Cl_2F_3N_3O_3$+H [(M+H):632.1689. Found: 632.1692.

Example 384

Preparation of rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid

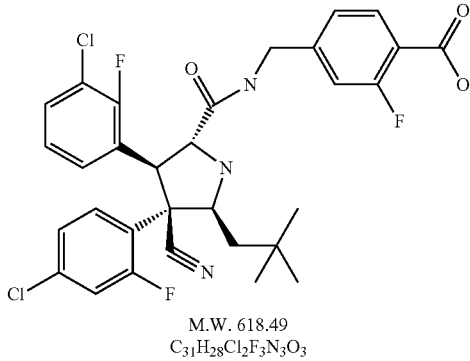 [SMILES: CC(C)(C)C[C@@H]1N[C@@H](C(=O)NCc2ccc(C(=O)O)c(F)c2)[C@H](c2cccc(Cl)c2F)[C@@]1(C#N)c1ccc(Cl)cc1F]

M.W. 618.49
C$_{31}$H$_{28}$Cl$_2$F$_3$N$_3$O$_3$

In a manner similar to the method described in Example 380, rac-4-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid methyl ester (80.3 mg, 0.127 mmol) in THF (9 ml) was reacted with lithium hydroxide hydrate (37.6 mg, 0.896 mmol) in water (4.5 mL) to give rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid as a white lyophilized solid (76.5 mg, 97%). HRMS (ES$^+$) m/z Calcd C$_{31}$H$_{28}$Cl$_2$F$_3$N$_3$O$_3$+H [(M+H): 618.1533. Found: 618.1533.

Example 385

Preparation of chiral 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid methyl ester

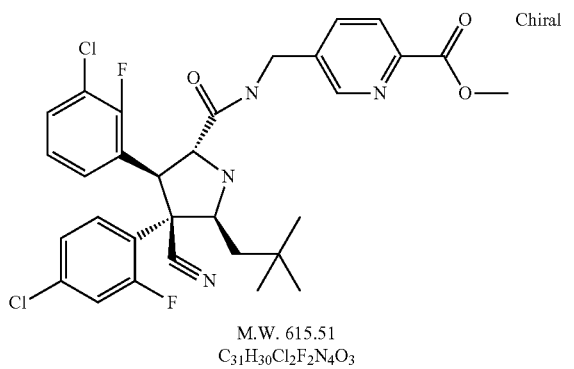

M.W. 615.51
C$_{31}$H$_{30}$Cl$_2$F$_2$N$_4$O$_3$

Ethyl 5-cyanopicolinate 1.0387 g, 5.9 mmol, BioNet) was combined with methanol (60 mL) and Raney Ni (2 spatula tip fulls were added after washing with methanol under argon). It was then put under Hydrogen at 50PSI on a PARR shaker for 18 hrs. The reaction was filtered through celite and washed with methanol while being kept under N$_2$. It was then purified by silica gel chromatography with methanol and methylene chloride to give methyl 4-(aminomethyl)-2-fluorobenzoate (738.1 mg, 69%) as an off-white solid which was used immediately.

In a manner similar to the method described in Example 379, a mixture of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (59.2 mg, 0.127 mmol) and methyl 5-(aminomethyl)picolinate (64.4 mg, 0.388 mmol) in N,N-dimethyl formamide (5 mL) were treated with DIPEA (119 mg, 0.916 mmol), HOBt (34.2 mg, 0.253 mmol) and HBTU (96.1 mg, 0.253 mmol) at room temperature to give 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid methyl ester (30.7 mg, 39%). HRMS (ES$^+$) m/z Calcd C$_{31}$H$_{30}$Cl$_2$F$_2$N$_4$O$_3$+H [(M+H): 615.1736. Found: 615.1731.

Example 386

Preparation of chiral 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid

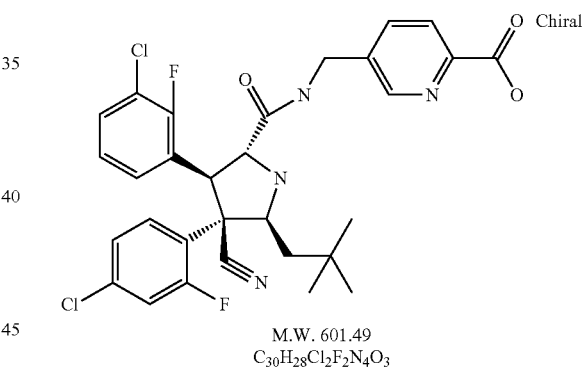

M.W. 601.49
C$_{30}$H$_{28}$Cl$_2$F$_2$N$_4$O$_3$

In a manner similar to the method described in Example 380, chiral 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid methyl ester (24.9 mg, 0.0405 mmol) in THF (3 ml) was treated with lithium hydroxide hydrate (12.0 mg, 0.286 mmol) in water (1.5 mL). It was stirred at room temperature to give chiral 5-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid as a white lyophilized solid (25.4 mg, 100). RMS (ES$^+$) m/z Calcd C$_{30}$H$_{28}$Cl$_2$F$_2$N$_4$O$_3$+H [(M+H):601.1580. Found: 601.1579.

Example 387

Preparation of chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid ethyl ester

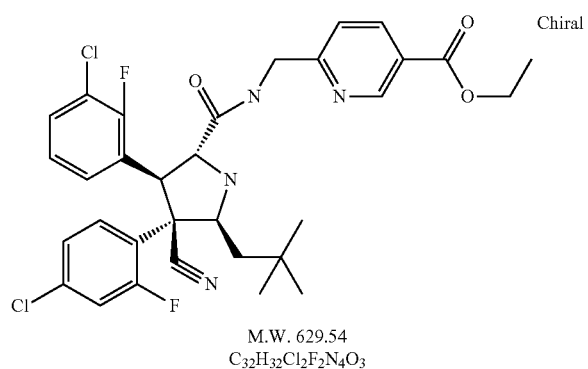

M.W. 629.54
$C_{32}H_{32}Cl_2F_2N_4O_3$

In a manner similar to the method described in Example 379, chiral 2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (60.9 mg, 0.130 mmol) in N,N-dimethyl formamide (5 mL) were reacted with DIPEA (134 mg, 1.03 mmol), 5-(ethoxycarbonyl)pyridin-2-yl) methanaminium chloride (68.5 mg, 0.316 mmol, Chem-Impex), HOBt (34.0 mg, 0.252 mmol) and HBTU (93.5 mg, 0.247 mmol) at room temperature to give chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid ethyl ester as a white solid, (81.3 mg, 99%). HRMS (ES$^+$) m/z Calcd $C_{32}H_{32}Cl_2F_2N_4O_3$+H [(M+H): 629.1893. Found: 629.1896.

Example 388

Preparation of chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid

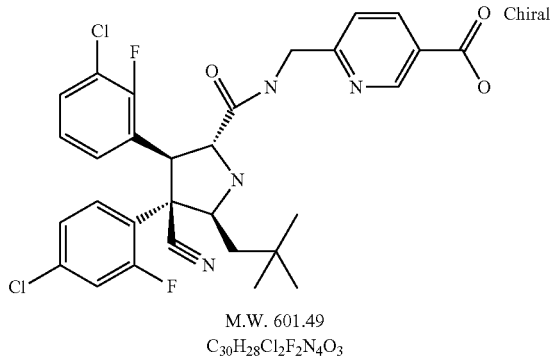

M.W. 601.49
$C_{30}H_{28}Cl_2F_2N_4O_3$

In a manner similar to the method described in Example 380, chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid ethyl ester (73.8 mg, 0.117 mmol) in THF (8 ml) was combined with lithium hydroxide hydrate (35.9 mg, 0.855 mmol) in water (4 mL). It was stirred at room temperature to give chiral 6-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid as a white lyophilized solid (71.3 mg, 100%). HRMS (ES$^+$) m/z Calcd $C_{30}H_{28}Cl_2F_2N_4O_3$+H [(M+H): 601.1580. Found: 601.1581.

Example 389

Preparation of rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-ethoxy-benzoic acid

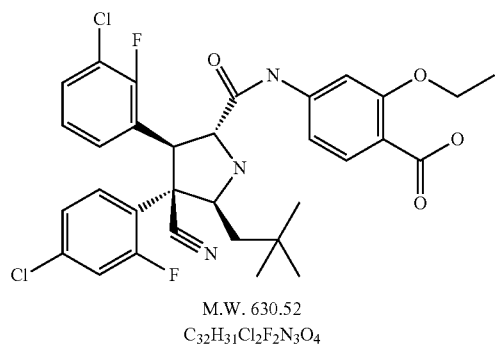 [SMILES: CCOc1cc(NC(=O)[C@@H]2N[C@@H](CC(C)(C)C)[C@](C#N)(c3ccc(Cl)cc3F)[C@H]2c2cccc(Cl)c2F)ccc1C(=O)O]

M.W. 630.52
$C_{32}H_{31}Cl_2F_2N_3O_4$

A solution of 2-ethoxy-4-nitrobenzoic acid (2.035 g, 9.45 mmol, Aldrich) in methanol (40 ml) was treated with p-toluenesulfonic acid monohydrate (583.3 mg, 3.07 mmol) and heated at reflux under argon for 17 hrs. The solvent was removed and the residue was dissolved in ethyl acetate, washed with saturated $Na_2CO_3$, water and saturated NaCl and dried over $Na_2SO_4$, filtered and concentrated to give methyl 2-ethoxy-4-nitrobenzoate (2.15 g, 101%) as a yellow solid.

A mixture of methyl 2-ethoxy-4-nitrobenzoate (2.038 g, 9.05 mmol) and palladium on carbon (583 mg, 10 wt %, Aldrich) in methanol (62 ml) was reacted with hydrogen at 40 psi for 18 hrs on the PARR shaker. It was filtered through celite and washed with methanol under N2 and the filtrate was concentrated to give methyl 4-amino-2-ethoxybenzoate (1.672 g, 94%) as a light brown solid.

To a solution of rac-(2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carboxylic acid (60.8 mg, 0.13 mmol) in dichloromethane (3 mL) were added DIPEA (89.0 mg, 0.69 mmol), methyl 4-amino-2-ethoxybenzoate (50.9 mg, 0.26 mmol) and HATU (90.8 mg, 0.24 mmol). (The acid, DIPEA, and HATU were added in thirds at 20 min intervals). After 90 min, the reaction was diluted with dichloromethane, washed with water and saturated sodium chloride and purified by silica gel chromatography with ethyl acetate and hexanes to give racemic methyl 4-((2R,3S,4R,5S)-3-(3-chloro-2-fluorophenyl)-4-(4-chloro-2-fluorophenyl)-4-cyano-5-neopentylpyrrolidine-2-carboxamido)-2-ethoxybenzoate (90 mg, with minor impurity) as a light brown oil.

In a manner similar to Example 380, a solution of the above methyl 4-((2R,3S,4R,5S)-3-(3-chloro-2-fluorophenyl)-4-(4-chloro-2-fluorophenyl)-4-cyano-5-neopentylpyrrolidine-2-carboxamido)-2-ethoxybenzoate (89.7 mg, ~0.13 mmol) in THF (8 ml) was treated with lithium hydroxide hydrate (40.9 mg, 0.974 mmol) in water (4 mL) and heated at 70° C. for 3 hrs and then stirred at room temperature to give rac 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-ethoxy-benzoic acid as a white lyophilized solid (33.5 mg., 38%) after HPLC purification.

HRMS (ES$^+$) m/z Calcd C$_{32}$H$_{31}$Cl$_2$F$_2$N$_3$O$_4$+H [(M+H): 630.1733. Found: 630.1733.

Example 390

Preparation of chiral (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-hydrazinocarbonyl-phenyl)-amide

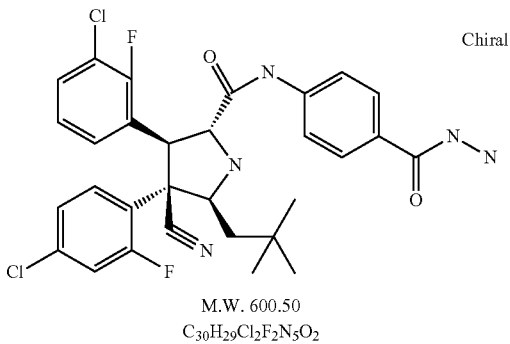 [SMILES: CC(C)(C)C[C@@H]1N[C@@H](C(=O)Nc2ccc(C(=O)NN)cc2)[C@H](c2cccc(Cl)c2F)[C@@]1(C#N)c1ccc(Cl)cc1F]

M.W. 600.50
C$_{30}$H$_{29}$Cl$_2$F$_2$N$_5$O$_2$

To a solution of chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (52.7 mg, 0.113 mmol) in dichloromethane (3 mL) were added DIPEA (71.2 mg, 0.55 mmol), 4-aminobenzhydrazide (33.1 mg, 0.22 mmol, Aldrich) and HATU (72.3 mg, 0.19 mmol). (The acid, DIPEA, and HATU were added in thirds at 20 min intervals). After 90 minutes the reaction was diluted with dichloromethane, washed with water and saturated sodium chloride and purified by HPLC with acetonitrile and water (with TFA 0.1% VAT) to give chiral (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-hydrazinocarbonyl-phenyl)-amide (45.7 mg., 67.5%) as a white solid. HRMS (ES$^+$) m/z Calcd C$_{30}$H$_{29}$Cl$_2$F$_2$N$_5$O$_2$+H [(M+H): 600.1739. Found: 600.1737.

Example 391

Preparation of chiral [2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-ethyl]-carbamic acid tent-butyl ester

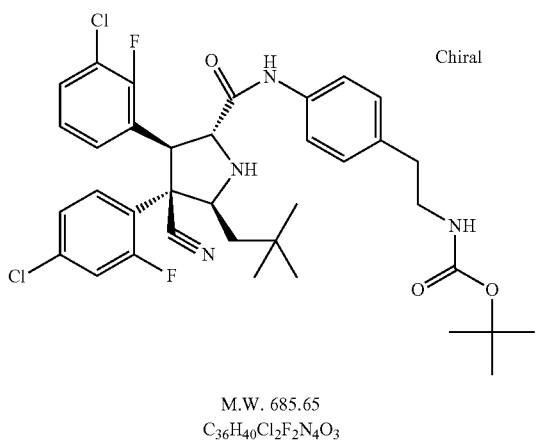 [SMILES: CC(C)(C)C[C@@H]1N[C@@H](C(=O)Nc2ccc(CCNC(=O)OC(C)(C)C)cc2)[C@H](c2cccc(Cl)c2F)[C@@]1(C#N)c1ccc(Cl)cc1F]

M.W. 685.65
C$_{36}$H$_{40}$Cl$_2$F$_2$N$_4$O$_3$

To a solution of chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (51.1 mg, 0.11 mmol) in dichloromethane (3 mL) were added DIPEA (71.2 mg, 0.55 mmol), [2-(4-AMINO-PHENYL)-ETHYL]-CARBAMIC ACID TERT-BUTYL ESTER (52.3 mg., 0.22 mmol, Chem-Impex) and HATU (77.8 mg, 0.20 mmol) (The acid, DIPEA, and HATU were added in thirds at 20 min intervals). After 90 mins, the reaction was diluted with dichloromethane, washed with water and saturated sodium chloride and purified by silica gel chromatography with ethyl acetate and n-hexanes to give chiral [2-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-ethyl]-carbamic acid tent-butyl ester (40.6 mg., 54.2%) as a white lyophilized solid. HRMS (ES$^+$) m/z Calcd C$_{36}$H$_{40}$Cl$_2$F$_2$N$_4$O$_3$+H [(M+H): 685.2519. Found: 685.2517.

Example 392

Preparation of chiral (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-amino-ethyl)-phenyl]-amide

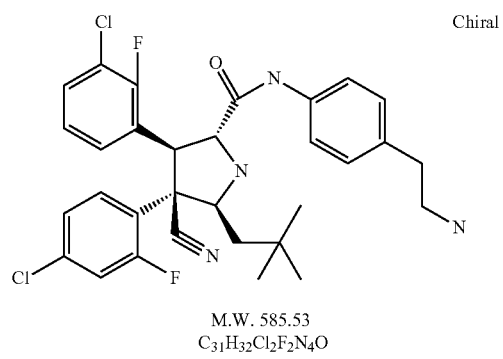 [SMILES: CC(C)(C)C[C@@H]1N[C@@H](C(=O)Nc2ccc(CCN)cc2)[C@H](c2cccc(Cl)c2F)[C@@]1(C#N)c1ccc(Cl)cc1F ; "Chiral"]

M.W. 585.53
C$_{31}$H$_{32}$Cl$_2$F$_2$N$_4$O

A solution of tert-butyl 4-((2R,3S,4R,5S)-3-(3-chloro-2-fluorophenyl)-4-(4-chloro-2-fluorophenyl)-4-cyano-5-neopentylpyrrolidine-2-carboxamido)phenethylcarbamate (77.3 mg, 0.113 mmol) in dichloromethane (3 ml) was treated with trifluoroacetic acid (2.23 g, 19.6 mmol) and stirred under argon. After 1.5 hrs, the reaction mixture was concentrated and the residue diluted with ethyl acetate, washed with saturated sodium carbonate, water and brine to give chiral (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(2-amino-ethyl)-phenyl]-amide (40.6 mg, 54.2%) as a white lyophilized solid.

MS (ES$^+$) m/z Calcd: [(M+H)$^+$]: 585.19. found: 585.1.

Example 393

Preparation of chiral 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyrazine-2-carboxylic acid

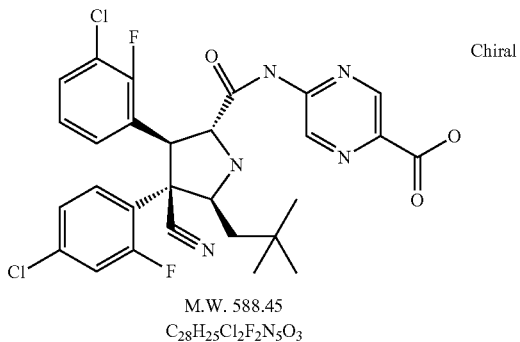 [SMILES: CC(C)(C)C[C@@H]1N[C@@H](C(=O)Nc2cnc(C(=O)O)cn2)[C@H](c2cccc(Cl)c2F)[C@@]1(C#N)c1ccc(Cl)cc1F]

M.W. 588.45
C28H25Cl2F2N5O3

A solution of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (79.9 mg, 0.171 mmol) in dichloromethane (3 ml) was treated with DIPEA (89.0 mg, 0.685 mmol) and DIPHENYLPHOSPHINIC CHLORIDE (103 mg, 0.428 μmol, Aldrich) and stirred for 30 mins under argon before 5-AMINO-PYRAZINE-2-CARBOXYLIC ACID ETHYL ESTER (30.4 mg, 0.173 mmol, Ark Pharm) was added and the reaction was stirred overnight. The reaction mixture was diluted with dichloromethane and extracted with H2O. The organic layer was washed with sat NaHCO₃, H₂O, and sat NaCl and purified by flash chromatography using ethyl acetate and n-hexanes to give ethyl 5-((2R,3S,4R,5S)-3-(3-chloro-2-fluorophenyl)-4-(4-chloro-2-fluorophenyl)-4-cyano-5-neopentylpyrrolidine-2-carboxamido)pyrazine-2-carboxylate (27.6 mg, 26%) which was used in the next step.

To a solution of ethyl 5-((2R,3S,4R,5S)-3-(3-chloro-2-fluorophenyl)-4-(4-chloro-2-fluorophenyl)-4-cyano-5-neopentylpyrrolidine-2-carboxamido)pyrazine-2-carboxylate (27.6 mg, 0.0448 mmol) in dichloromethane (2 ml) were added DIMETHYL SULFIDE (846 mg, 0.0136 mmol) and ALUMINUM BROMIDE (64.5 mg, 0.242 mmol). The mixture was stirred under argon for 5 hrs. The reaction mixture was diluted with acetonitrile (2 ml), EtOAc (10 ml) and water (10 ml) and stirred for several minutes. After more ethyl acetate (50 ml) was added, the organic layer was separated and washed with saturated ammonium chloride (10 ml), water (10 ml) and sat. sodium chloride (10 ml). The organic layers were dried over Na₂SO₄ and concentrated and purified by silica gel chromatography with methanol and dichloromethane to give chiral 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyrazine-2-carboxylic acid as an off-white lyophilized solid (19.7 mg, 74%). MS (ES⁺) m/z Calcd: [(M+H)⁺]: 588.13. found: 588.0

Example 394

Preparation of chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-methoxybenzoic acid and chiral-4-({[(2S,3R,4R,5R)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxybenzoic acid

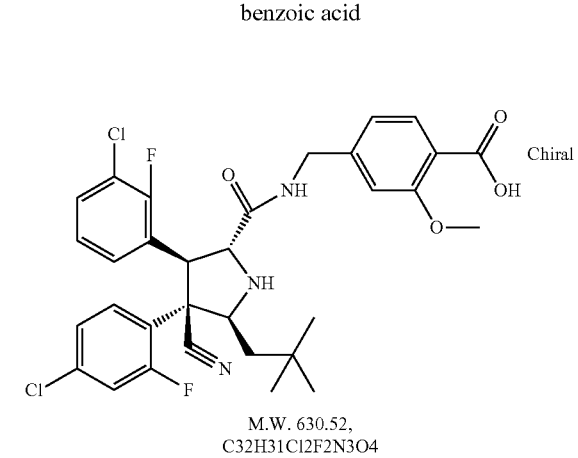

M.W. 630.52,
C32H31Cl2F2N3O4

M.W 630.52,
C32H31Cl2F2N3O4

The mixture of rac-4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid (60 mg. 0.095 mmol) was separated by SFC, 25% CH₃OH on a Diacel AD prep column to give chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-methoxybenzoic acid (24.1 mg., 40.2%) as a white lyophilized solid. MS (ES⁺) m/z Calcd: [(M+H)⁺]: 630.17. found: 630.2 and chiral-4-({[(2S,3R,4R,5R)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid (23.5 mg., 39.2%) as a white lyophilized solid. MS (ES⁺) m/z Calcd: [(M+H)⁺]:630.17. found: 630.2

Example 395

Preparation of chiral methyl 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoate

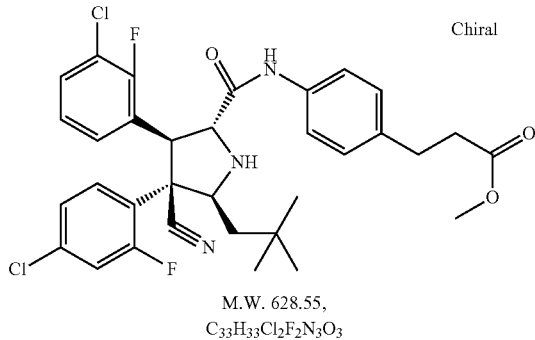 [SMILES: COC(=O)CCc1ccc(NC(=O)[C@@H]2N[C@@H](CC(C)(C)C)[C@](C#N)(c3ccc(Cl)cc3F)[C@H]2c2cccc(Cl)c2F)cc1]

M.W. 628.55,
$C_{33}H_{33}Cl_2F_2N_3O_3$

Thionyl chloride (2.5 mL, 4.08 g, 34.3 mmol) was added to stirred anhydrous methanol (10 mL) at 0° C. After 20 mins, 3-(4-AMINOPHENYL)PROPIONIC ACID (1.7 g, 10.3 mmol, Trans World Chemicals) was added and the mixture was stirred at rt for 16 hrs. The reaction mixture was concentrated and the residue dissolved in ethyl acetate, washed with sat. NaHCO3, water, and sat. NaCl, dried over $Na_2SO_4$ and concentrated to give methyl 3-(4-aminophenyl)propanoate (1.80 g, 97%) as a light brown solid.

To a solution of chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (80.6 mg, 0.172 mmol) in dichloromethane (3 ml) were added DIPEA (89.0 mg, 0.685 mmol) and DIPHENYLPHOSPHINIC CHLORIDE (106 mg, 0.437 mmol). The mixture was stirred for 20 mins under argon before methyl 3-(4-aminophenyl) propanoate (33.4 mg, 0.186 mmol) was added. After 2 hrs, the reaction mixture was diluted with dichloromethane, washed with sat. NaHCO3, water and brine. After drying over $Na_2SO_4$ the crude material was purified by silica gel chromatography with ethyl acetate and n-hexanes to give chiral methyl 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoate (104.2 mg, 96%) as a white solid. MS (ES+) m/z Calcd: [(M+H)+]: 628.19. found: 628.1.

Example 396

Preparation of chiral 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoic acid

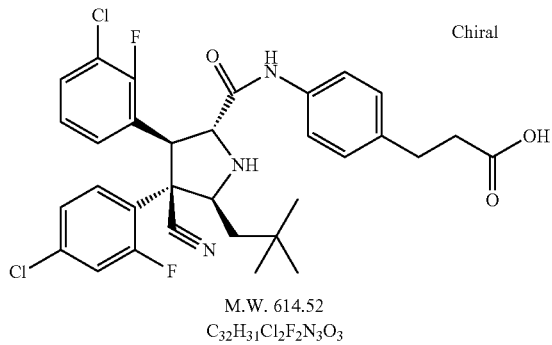 [SMILES: CC(C)(C)C[C@@H]1N[C@@H](C(=O)Nc2ccc(CCC(=O)O)cc2)[C@H](c2cccc(Cl)c2F)[C@@]1(C#N)c1ccc(Cl)cc1F]

M.W. 614.52
$C_{32}H_{31}Cl_2F_2N_3O_3$

A solution of chiral methyl 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoate (58.8 mg, 0.0936 mmol) in THF (5 ml) was treated with LITHIUM HYDROXIDE MONOHYDRATE (15.7 mg, 0.374 mmol) in water (2.5 ml) and stirred at rt overnight. The mixture was then treated with 1 N HCl to pH 3-4, extracted with ethyl acetate. The organic extracts were washed with water and brine, dried over sodium sulfate and concentrated to give chiral 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoic acid (57.7 mg, 100%) as a white solid. MS (ES+) m/z Calcd: [(M+H)+]: 614.17. found: 614.2.

Example 397

Preparation of chiral-4-(((2S,3R,4S,5R)-3-(3-chloro-2-fluorophenyl)-4-(4-chloro-2-fluorophenyl)-4-cyano-5-neopentylpyrrolidine-2-carboxamido)methyl)-2-fluorobenzoic acid and chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-fluorobenzoic acid

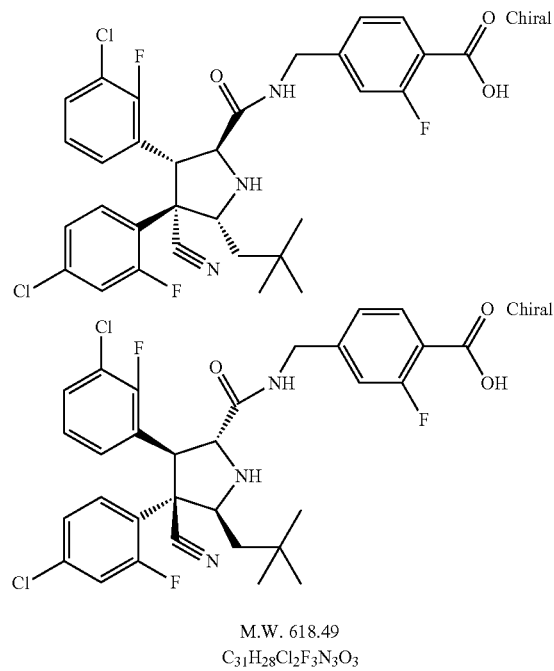

M.W. 618.49
$C_{31}H_{28}Cl_2F_3N_3O_3$

The mixture 4-({[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid (71.1 mg. 0.115 mmol) was separated by SFC, 40% $CH_3OH$ on a Whelk-01 R,R prep column to give chiral-4-(((2S,3R,4S,5R)-3-(3-chloro-2-fluorophenyl)-4-(4-chloro-2-fluorophenyl)-4-cyano-5-neopentylpyrrolidine-2-carboxamido)methyl)-2-fluorobenzoic acid (29.4 mg., 41.4%) as a white lyophilized solid. MS (ES+) m/z Calcd: [(M+H)+]: 618.15. found: 618.2 and chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-fluorobenzoic acid (29.7 mg., 41.8%) as a white lyophilized solid. MS (ES+) m/z Calcd: [(M+H)+]: 618.15. found: 618.2.

Example 398

Preparation of chiral (2R,3S,4R,5S)-3-(3-chloro-2-fluorophenyl)-4-(4-chloro-2-fluorophenyl)-4-cyano-N-(2-morpholinopyrimidin-5-yl)-5-neopentylpyrrolidine-2-carboxamide

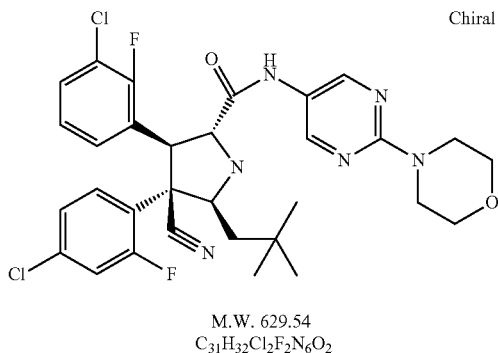 [SMILES: CC(C)(C)C[C@@H]1N[C@@H](C(=O)Nc2cnc(N3CCOCC3)nc2)[C@H](c2cccc(Cl)c2F)[C@@]1(C#N)c1ccc(Cl)cc1F ; "Chiral"]

M.W. 629.54
C₃₁H₃₂Cl₂F₂N₆O₂

A solution of chiral (2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carboxylic acid (59.9 mg, 0.128 mmol) in dichloromethane (3 ml) was treated with DIPEA (66.8 mg, 0.514 mmol) and DIPHENYLPHOSPHINIC CHLORIDE (75.8 mg, 0.314 mmol) and stirred for 20 min under argon. 2-MORPHOLIN-4-YLPYRIMIDIN-5-AMINE (23.4 mg, 0.130 mmol, Atlantic Research) was added. After stirred 2.5 hrs, the reaction mixture was diluted with dichloromethane, washed with sat. NaHCO3, water and brine. After dried over Na2SO4, the crude material was purified by silica gel chromatography with ethyl acetate and n-hexanes to give chiral (2R,3S,4R,5S)-3-(3-chloro-2-fluorophenyl)-4-(4-chloro-2-fluorophenyl)-4-cyano-N-(2-morpholinopyrimidin-5-yl)-5-neopentylpyrrolidine-2-carboxamide (78.4 mg., 97.2%) as a white solid. MS (ES⁺) m/z Calcd: [(M+H)⁺]: 629.19. found: 629.2.

Example 399

Preparation of chiral (2R,3S,4R,5S)-3-(3-chloro-2-fluorophenyl)-4-(4-chloro-2-fluorophenyl)-4-cyano-5-neopentyl-N-(pyrimidin-5-yl)pyrrolidine-2-carboxamide

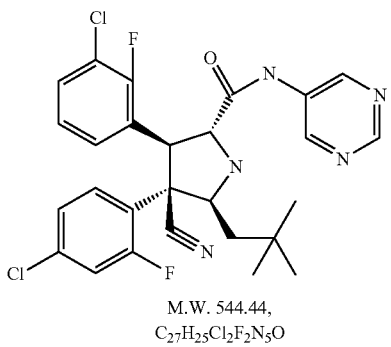

M.W. 544.44,
C₂₇H₂₅Cl₂F₂N₅O

A solution of chiral-(2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carboxylic acid (39.4 mg, 84.3 mmol) in dichloromethane (3 ml) was reacted with DIPEA (44.5 mg, 0.343 mmol) and DIPHENYLPHOSPHINIC CHLORIDE (49.7 mg, 0.210 mmol) and stirred for 20 min under argon. PYRIMIDIN-5-AMINE (8.3 mg, 0.0829 mmol, Ark Pharm) was added and stirred 2.5 hrs. The reaction mixture was diluted with dichloromethane, washed with water then with sat. NaHCO3, water, and sat. NaCl. After drying over Na₂SO₄ the crude material was purified by silica gel chromatography with ethyl acetate and n-hexanes giving chiral (2R,3S,4R,5S)-3-(3-chloro-2-fluorophenyl)-4-(4-chloro-2-fluorophenyl)-4-cyano-5-neopentyl-N-(pyrimidin-5-yl)pyrrolidine-2-carboxamide (35.7 mg., 77%) as a white lyophilized solid. MS (ES⁺) m/z Calcd: [(M+H)⁺]: 544.14. found: 544.0.

Example 400

Preparation of chiral (2S,3R,4S,5R)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide and (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide

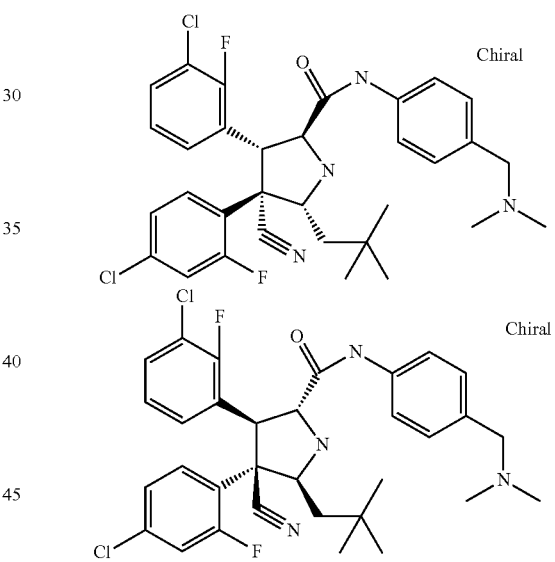

M.W. 544.44
C₃₂H₃₄Cl₂F₂N₄O

The mixture of rac-(2R,3S,4R,5S)-3-(3-chloro-2-fluorophenyl)-4-(4-chloro-2-fluorophenyl)-4-cyano-N-(4-((dimethylamino)methyl)phenyl)-5-neopentylpyrrolidine-2-carboxamide (41 mg. 0.0684 mmol) was separated by SFC, 55% CH₃OH on a Whelk-01 R,R prep column to give chiral (2S,3R,4S,5R)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide (17.3 mg., 42.2%) as a light yellow lyophilized solid, MS (ES⁺) m/z Calcd: [(M+H)⁺]: 599.21. found: 599.2. and (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide (15.9 mg., 38.8%) as a light yellow lyophilized solid, MS (ES⁺) m/z Calcd: [(M+H)⁺]: 599.21. found: 599.2.

Example 401

Preparation of chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylate

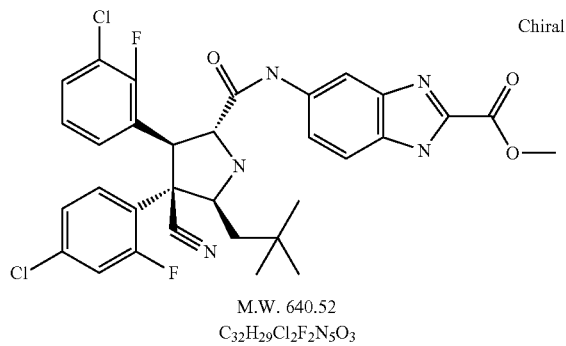 [SMILES: COC(=O)c1nc2cc(NC(=O)[C@@H]3N[C@@H](CC(C)(C)C)[C@](C#N)(c4ccc(Cl)cc4F)[C@H]3c3cccc(Cl)c3F)ccc2[nH]1]

M.W. 640.52
$C_{32}H_{29}Cl_2F_2N_5O_3$

A solution of chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (60.3 mg, 0.129 mmol) in dichloromethane (3 ml) was reacted with DIPEA (66.8 mg, 0.514 mmol) and DIPHENYLPHOSPHINIC CHLORIDE (75.7 mg, 0.320 mmol) and stirred for 20 min under argon. 5-AMINO-1H-BENZOIMIDAZOLE-2-CARBOXYLIC ACID METHYL ESTER (25.7 mg, 0.134 mmol, Biofine) was added and stirred 2.5 hrs. The reaction mixture was diluted with dichloromethane and extracted with water then with sat'd NaHCO3, water, and brine. After drying over $Na_2SO_4$ the crude material was purified by silica gel chromatography with ethyl acetate and n-hexanes giving a white lyophilized solid, chiral methyl 542R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylate (43 mg, 52%). MS (ES$^+$) m/z Calcd: [(M+H)$^+$]: 640.16. found: 640.1.

Example 402

Preparation of chiral-5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylic acid

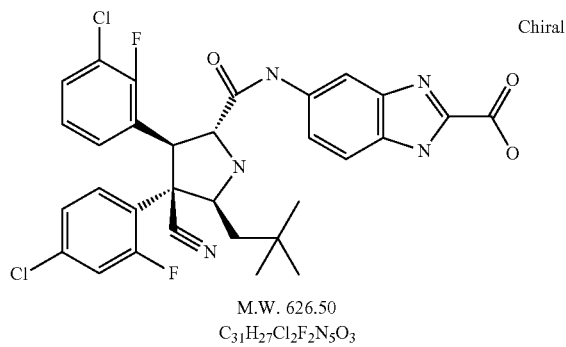 [SMILES: CC(C)(C)C[C@@H]1N[C@@H](C(=O)Nc2ccc3[nH]c(C(=O)O)nc3c2)[C@H](c2cccc(Cl)c2F)[C@@]1(C#N)c1ccc(Cl)cc1F]

M.W. 626.50
$C_{31}H_{27}Cl_2F_2N_5O_3$

A solution of chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylate (84.4 mg, mmol) in THF (6 ml) was reacted with LITHIUM HYDROXIDE MONOHYDRATE (22.9 mg, 0.545 mmol) in water (3 ml) and stirred at rt overnight. The reaction mixture was treated with 1 N HCl (0.37 ml, pH 3-4) and extracted with ethyl acetate. The organic extract was washed with water and brine, dried with sodium sulfate, filtered and lyophilized to give chiral-5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylic acid (36 mg, 43.6%) a white solid, MS (ES$^+$) m/z Calcd: [(M+H)$^+$]: 626.15. found: 626.0.

Example 403

Preparation of chiral-methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylate

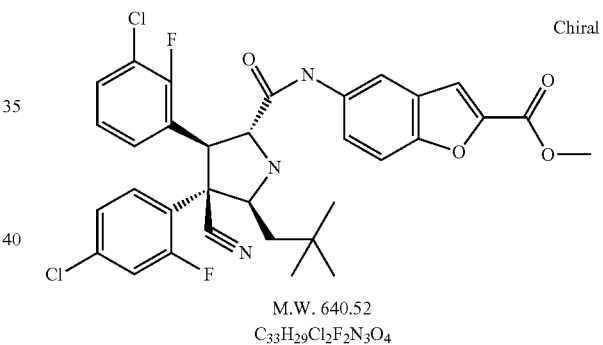

M.W. 640.52
$C_{33}H_{29}Cl_2F_2N_3O_4$

A solution of chiral-(2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carboxylic acid (60.9 mg, 0.130 mmol) in dichloromethane (3 ml) was reacted with DIPEA (66.8 mg, 0.517 mmol) and DIPHENYLPHOSPHINIC CHLORIDE (75.8 mg, 0.320 mmol) and stirred for 20 min under argon. 5-AMINO-BENZOFURAN-2-CARBOXYLIC ACID METHYL ESTER (26.0 mg, 0.136 mmol, Biofine,) was added and stirred 2.5 hrs. The reaction mixture was diluted with dichloromethane and washed with water, sat. NaHCO3 and brine. After drying over $Na_2SO_4$ the crude material was purified by silica gel chromatography with ethyl acetate and n-hexanes giving chiral-methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylate (46.2 mg., 55.4%) as a white solid. MS (ES$^+$) m/z Calcd: [(M+H)$^+$]: 640.15. found: 640.0.

Example 404

Preparation of chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylic acid

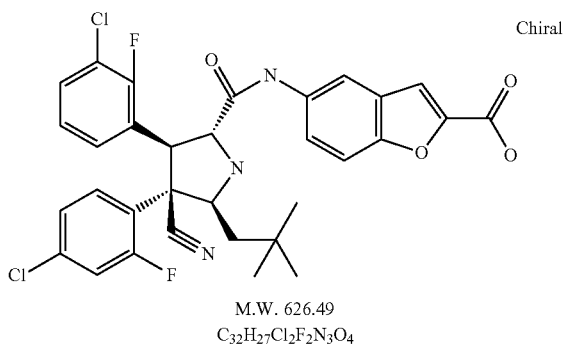 [SMILES: CC(C)(C)C[C@@H]1N[C@@H](C(=O)Nc2ccc3oc(C(=O)O)cc3c2)[C@H](c2cccc(Cl)c2F)[C@@]1(C#N)c1ccc(Cl)cc1F]

M.W. 626.49
$C_{32}H_{27}Cl_2F_2N_3O_4$

A solution of chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylate (80.7 mg, 0.126 mmol) in THF (6 ml) was reacted with LITHIUM HYDROXIDE MONOHYDRATE (222.3 mg, 0.531 mmol) in water (3 ml) and stirred at rt for 3 hrs. The reaction treated with 1 N HCl (pH 3-4) and extracted with ethyl acetate. The organic extracts were washed with water and brine, dried with sodium sulfate, filtered and lyophilized to give chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylic acid (74.3 mg, 94.1%) as a white solid. MS (ES$^+$) m/z Calcd: [(M+H)$^+$]: 626.13. found: 626.2.

Example 405

Preparation of chiral methyl 4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoate

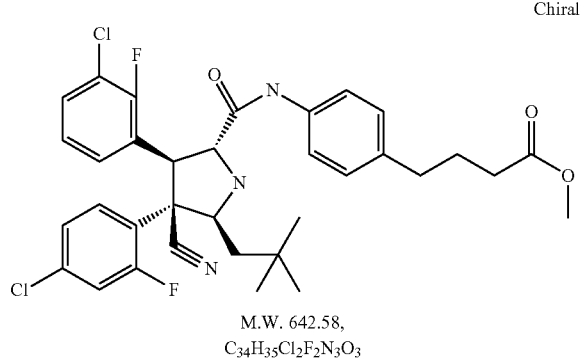 [SMILES: COC(=O)CCCc1ccc(NC(=O)[C@@H]2N[C@@H](CC(C)(C)C)[C@](C#N)(c3ccc(Cl)cc3F)[C@H]2c2cccc(Cl)c2F)cc1]

M.W. 642.58,
$C_{34}H_{35}Cl_2F_2N_3O_3$

Thionyl chloride (2.5 mL, 4.08 g, 34.3 mmol) was added to stirred anhydrous methanol (10 mL) at 0° C. After 20 mins, 4-(4-AMINOPHENYL)BUTYRIC ACID (1.85 g, 10.3 mmol, Aldrich) was added and the mixture was stirred at rt for 16 hrs. The reaction mixture was concentrated and the residue dissolved in ethyl acetate, washed with sat. NaHCO3, water, and sat. NaCl, dried over $Na_2SO_4$ and concentrated to give methyl 4-(4-aminophenyl)butanoate (1.88 g, 94%) as a light brown solid.

A solution of chiral (2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carboxylic acid (60.9 mg, 0.130 mmol) in dichloromethane (3 ml) were added DIPEA (66.8 mg, 0.514 mmol) and DIPHENYLPHOSPHINIC CHLORIDE (78.2 mg, 0.324 mmol). The mixture was stirred for 20 mins under argon before methyl 4-(4-aminophenyl)butanoate (24.7 mg, 0.128 mmol) was added. After 2 hrs, the reaction mixture was diluted with dichloromethane and extracted with water then with sat. NaHCO3, water, and sat. NaCl. After drying over $Na_2SO_4$ the crude material was purified by silica gel chromatography with ethyl acetate and n-hexanes giving chiral methyl 4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoate (79.2 mg., 96%) as a white solid. MS (ES$^+$) m/z Calcd: [(M+H)$^+$]: 642.2. found: 642.1.

Example 406

Preparation of chiral-4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoic acid

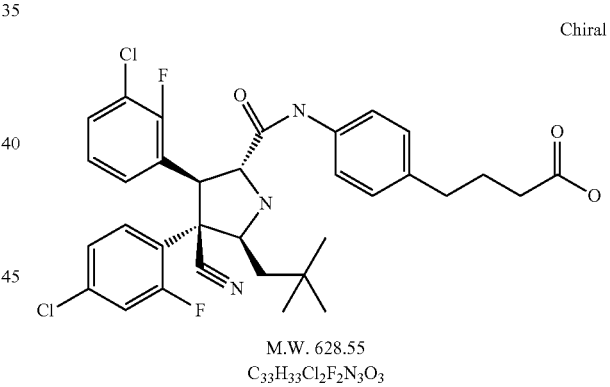

M.W. 628.55
$C_{33}H_{33}Cl_2F_2N_3O_3$

A solution of chiral methyl 4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoate (70.5 mg, 0.110 mmol) in THF (5 ml) was treated with LITHIUM HYDROXIDE MONOHYDRATE (18.5 mg, 0.441 mmol) in water (2.5 ml) and stirred at rt for 16 hrs. The reaction was treated with 1 N HCl (pH 5) and extracted with ethyl acetate, washed with water then sat'd sodium chloride, dried with sodium sulfate, filtered and lyophilized to give chiral-4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoic acid (67 mg, 97.2%) as a white lyophilized solid. MS (ES$^+$) m/z Calcd: [(M+H)$^+$]: 628.19. found: 628.1.

Example 407

Preparation of chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylate

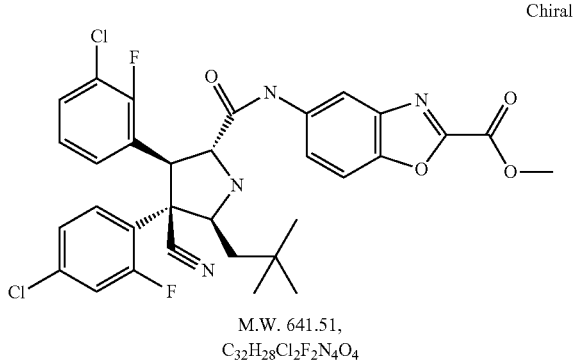 [SMILES: COC(=O)c1nc2cc(NC(=O)[C@@H]3N[C@@H](CC(C)(C)C)[C@](C#N)(c4ccc(Cl)cc4F)[C@H]3c3cccc(Cl)c3F)ccc2o1]

M.W. 641.51,
$C_{32}H_{28}Cl_2F_2N_4O_4$

A solution of chiral (2R,3S,4R,5S)-3-(3-chloro-2-fluorophenyl)-4-(4-chloro-2-fluoro-phenyl)-4-cyano-5-(2,2-dimethyl-propyl)-pyrrolidine-2-carboxylic acid (59.8 mg, 0.128 mmol) in dichloromethane (3 ml) was treated with DIPEA (66.8 mg, 0.517 mmol) and DIPHENYLPHOSPHINIC CHLORIDE (80.7 mg, 0.341 mmol) and stirred for 20 min under argon. 5-AMINO-BENZOOXAZOLE-2-CARBOXYLIC ACID METHYL ESTER (25.8 mg, 134 µmol, JW PharmLab) was added and stirred 2 hrs. The reaction mixture was diluted with dichloromethane and washed with water, sat'd NaHCO3, water and brine. After drying over $Na_2SO_4$ the crude material was purified by silica gel chromatography with ethyl acetate and n-hexanes giving chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylate (73.7 mg., 89.8%) as a white lyophilized solid. MS (ES+) m/z Calcd: [(M+H)+]: 641.15. found: 641.2.

Example 408

Preparation of chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylic acid and chiral-(2R,3S,4R,5S)—N-(benzo[d]oxazol-5-yl)-3-(3-chloro-2-fluorophenyl)-4-(4-chloro-2-fluorophenyl)-4-cyano-5-neopentylpyrrolidine-2-carboxamide

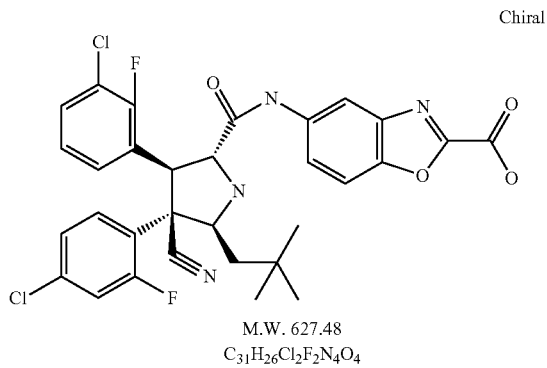

M.W. 627.48
$C_{31}H_{26}Cl_2F_2N_4O_4$

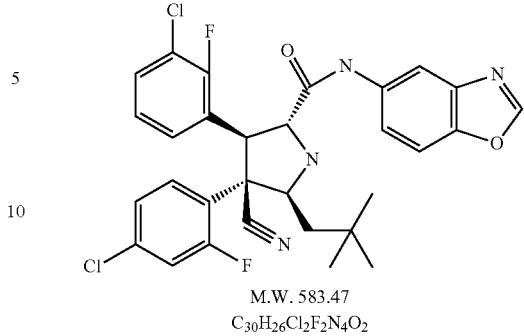

M.W. 583.47
$C_{30}H_{26}Cl_2F_2N_4O_2$

A solution of chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylate (64.5 mg, 0.101 mµmol) in THF (5 ml) was reacted with LITHIUM HYDROXIDE MONOHYDRATE (17.1 mg, 0.407 mmol) in water (2.5 ml) and stirred at rt for 4.5 hrs. The reaction mixture was treated with 1 N HCl (pH 5-6) and extracted with ethyl acetate. The organic extracts were washed with water, brine, dried with sodium sulfate, filtered and purified by silica gel chromatography with methylene chloride and methanol to give chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylic acid (7.8 mg., 12.4%) a white lyophilized solid. MS (ES+) m/z Calcd: [(M+H)+]: 627.13. found: 627.2. and chiral (2R,3S,4R,5S)—N-(benzo[d]oxazol-5-yl)-3-(3-chloro-2-fluorophenyl)-4-(4-chloro-2-fluorophenyl)-4-cyano-5-neopentylpyrrolidine-2-carboxamide (38.3 mg., 65.3%) as a white lyophilized solid. MS (ES+) m/z Calcd: [(M+H)+]: 583.14. found: 583.2.

Example 409

Preparation of rac-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-benzyl)-carbamic acid tert-butyl ester

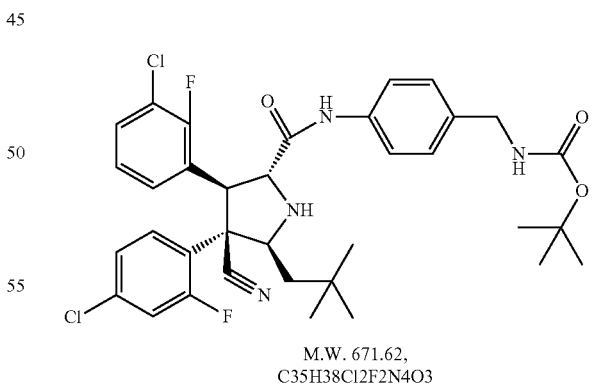

M.W. 671.62,
$C_{35}H_{38}Cl2F_2N_4O_3$

To a stirred solution of rac-(2R,3S,4R,5S)-3-(3-chloro-2-fluorophenyl)-4-(4-chloro-2-fluorophenyl)-4-cyano-5-neopentylpyrrolidine-2-carboxylic acid (20.0 mg) in dichloromethane (5 ml) were added N,N-DIISOPROPYLETHYLAMINE (33 mg) and tert-butyl 4-aminobenzylcarbamate (57.0 mg, 0.256 mmol, Array) followed by N,N,N',N'-tetramethyl-O-(7-aza-benzotriazol-1- yl)uranium hexafluorophosphate (HATU) (29 mg, Chem-Impex) and the reaction mixture was stirred for 30 min; Another portion of N,N-DIISOPROPYLETHYLAMINE (33 mg), rac-(2R,3S,4R,5S)-3-(3-chloro-2-fluorophenyl)-4-(4-chloro-2-fluorophenyl)-4-cyano-5-neopentylpyrrolidine-2-carboxylic acid (20.0 mg) and HATU (29 mg) was added and stirring was continued for 30 min before the addition of the last portion of N,N-DIISOPROPYLETHYLAMINE (33 mg), (2R,3S,4R,5S)-3-(3-chloro-2-fluorophenyl)-4-(4-chloro-2-fluorophenyl)-4-cyano-5-neopentylpyrrolidine-2-carboxylic acid (20.0 mg) and HATU (29 mg). 1 hr later, the reaction mixture was diluted with $CH_2Cl_2$ (80 mL), washed with sat Na2CO3 (2×15 mL), water (2×15 mL) and evaporated. The crude material was purified by flash chromatography (silica gel, 4 g, 4% to 50% EtOAc in hexanes) to give rac-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-benzyl)-carbamic acid tert-butyl ester as off-white solid (82.8 mg, 96%). HRMS (ES$^+$) m/z Calcd for C35H39Cl2F2N4O3 [(M+H)$^+$]: 671.2362. found: 671.2360.

Example 410

Preparation of rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-aminomethyl-phenyl)-amide

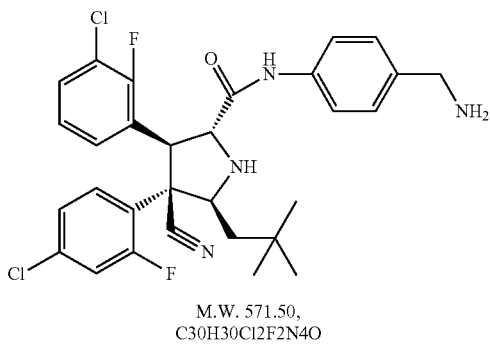 [SMILES: CC(C)(C)C[C@@H]1N[C@@H](C(=O)Nc2ccc(CN)cc2)[C@H](c2cccc(Cl)c2F)[C@@]1(C#N)c1ccc(Cl)cc1F]

M.W. 571.50,
C30H30Cl2F2N4O

To a solution of rac tert-butyl 4-((2R,3S,4R,5S)-3-(3-chloro-2-fluorophenyl)-4-(4-chloro-2-fluorophenyl)-4-cyano-5-neopentylpyrrolidine-2-carboxamido)benzylcarbamate (64 mg, example XC31) in $CH_2Cl_2$ (4 ml) was added TRIFLUOROACETIC ACID (5.92 g, 4 mL) and the reaction was stirred at 0 C for 1.5 hrs. The crude reaction mixture was concentrated in vacuo and the taken up in CH2Cl2 (80 mL) and washed with sat Na2CO3 (2×15 mL), water (2×15 mL) and concentrated to give rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-aminomethyl-phenyl)-amide as a white solid (54.3 mg, 99%). HRMS (ES$^+$) m/z Calcd for C30H31Cl2F2N4O [(M+H)$^+$]: 571.1838. found: 571.1837.

Example 411

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(methanesulfonylamino-methyl)-phenyl]-amide

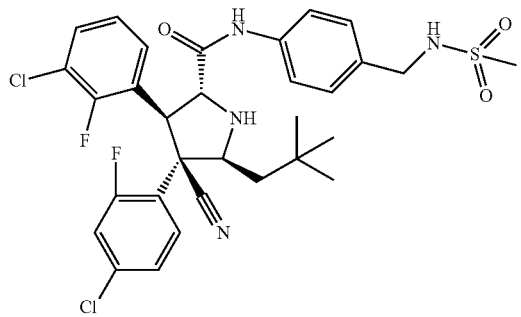

M.W. 649.59,
C31H32Cl2F2N4O3S

To a solution of rac-(2R,3S,4R,5S)—N-(4-(aminomethyl)phenyl)-3-(3-chloro-2-fluorophenyl)-4-(4-chloro-2-fluorophenyl)-4-cyano-5-neopentylpyrrolidine-2-carboxamide (21.0 mg, 0.0367 mmol, example XJ-2) in CH2Cl2 (4 ml) was treated with METHANESULFONYL CHLORIDE (8.5 mg, 5.78 µl, 0.0742 µmol) and the reaction was stirred at 0 C for 1 hr. The reaction mixture was diluted with CH2Cl2 (80 mL), washed with sat Na2CO3 (2×15 mL), water (2×15 mL) and evaporated. The crude material was purified by flash chromatography (silica gel, 4 g, 1% to 10% MeOH/CH2Cl2) to give rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid [4-(methanesulfonylamino-methyl)-phenyl]-amide as off-white solid (17.6 mg, 73%). MS (ES$^+$) m/z Calcd: [(M+H)$^+$]: 649. found: 649.

Example 412

Preparation of 1-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid ethyl ester

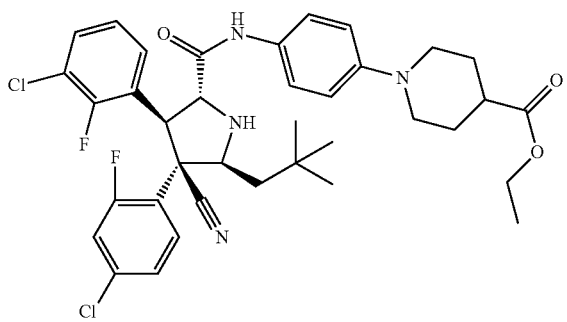

M.W. 697.66,
C37H40Cl2F2N4O3

433

To a stirred solution of (2R,3S,4R,5S)-3-(3-chloro-2-fluorophenyl)-4-(4-chloro-2-fluorophenyl)-4-cyano-5-neopentylpyrrolidine-2-carboxylic acid (20.0 mg) in dichloromethane (5 ml) were added N,N-DIISOPROPYL-ETHYLAMINE (33 mg) and ethyl 1-(4-aminophenyl)piperidine-4-carboxylate (63.8 mg, 0.257 mmol, Bionet Research Intermediates) followed by N,N,N',N'-tetramethyl-O-(7-azabenzotriazol-1-yl)uranium hexafluorophosphate (HATU) (29 mg, Chem-Impex) and the reaction mixture was stirred for 30 min; Another portion of N,N-DIISOPROPYLETHYLAMINE (33 mg), (2R,3S,4R,5S)-3-(3-chloro-2-fluorophenyl)-4-(4-chloro-2-fluorophenyl)-4-cyano-5-neopentylpyrrolidine-2-carboxylic acid (20.0 mg) and HATU (29 mg) was added and stirring was continued for 30 min before the addition of the last portion of N,N-DIISOPROPYLETHYLAMINE (33 mg), (2R,3S,4R,5S)-3-(3-chloro-2-fluorophenyl)-4-(4-chloro-2-fluorophenyl)-4-cyano-5-neopentylpyrrolidine-2-carboxylic acid (20.0 mg) and HATU (29 mg). 1 hr later, the reaction mixture was diluted with $CH_2Cl_2$ (80 mL), washed with sat Na2CO3 (2×15 mL), water (2×15 mL) and evaporated. The crude material was purified by flash chromatography (silica gel, 4 g, 4% to 50% EtOAc in hexanes) to give 1-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid ethyl ester as off-white solid (86.9 mg, 97%). MS (ES+) m/z Calcd: [(M+H)+]: 697. found: 697.

Example 413

Preparation of 1-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid

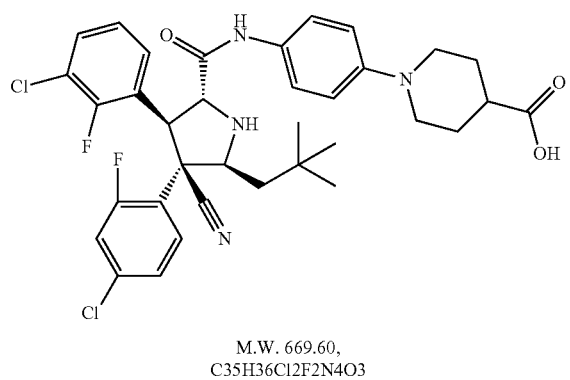 [SMILES: CC(C)(C)C[C@@H]1N[C@@H](C(=O)Nc2ccc(N3CCC(C(=O)O)CC3)cc2)[C@H](c2cccc(Cl)c2F)[C@@]1(C#N)c1ccc(Cl)cc1F]

M.W. 669.60,
C35H36Cl2F2N4O3

To a solution of ethyl 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)piperidine-4-carboxylate (75 mg, 0.108 mmol) in THF (4 mL) was added a solution of LITHIUM HYDROXIDE monohydrate (19.2 mg, 0.458 mmol) in Water (2 mL) dropwise. The reaction mixture was stirred at rt for 2 hrs before it was neutralized with 1N HCl. it was then diluted with EtOAc, washed with water (2×10 mL), brine (2×10 mL), dried and evaporated to give 1-(4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid as a white solid (76 mg, 100%). MS (ES+) m/z Calcd: [(M+H)+]: 669. found: 669.

Example 414

Preparation of rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide

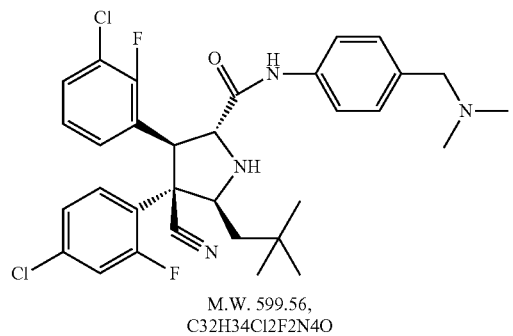 [SMILES: CN(C)Cc1ccc(NC(=O)[C@@H]2N[C@@H](CC(C)(C)C)[C@](C#N)(c3ccc(Cl)cc3F)[C@H]2c2cccc(Cl)c2F)cc1]

M.W. 599.56,
C32H34Cl2F2N4O

To a stirred solution of rac-(2R,3S,4R,5S)-3-(3-chloro-2-fluorophenyl)-4-(4-chloro-2-fluorophenyl)-4-cyano-5-neopentylpyrrolidine-2-carboxylic acid (60 mg, 0.128 mmol) in dichloromethane (5.00 ml) were added N,N-DIISOPROPYLETHYLAMINE (100 mg) and 4-((dimethylamino)methyl)aniline (29.8 mg, 0.198 mmol) followed by N,N,N',N'-tetramethyl-O-(7-aza-benzotriazol-1-yl)uranium hexafluorophosphate (HATU) (90.3 mg, 0.237 mmol, Chem-Impex) and the reaction mixture was stirred for 1 hr. The reaction mixture was diluted with CH2Cl2 (80 mL), washed with sat Na2CO3 (2×15 mL), water (2×15 mL) and evaporated. The crude material was purified by flash chromatography (silica gel, 4 g, 4% to 50% EtOAc in hexanes) to give rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide as white solid (54.1 mg, 70%). MS (ES+) m/z Calcd: [(M+H)+]: 599. found: 599.

Example 415

Preparation of rac-5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-pyrrolidin-1-yl-benzoic acid

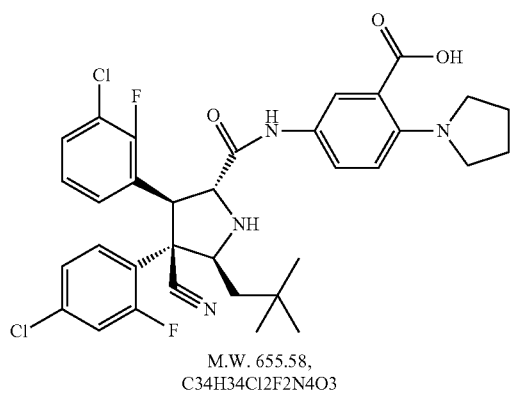 [SMILES: CC(C)(C)C[C@@H]1N[C@@H](C(=O)Nc2ccc(N3CCCC3)c(C(=O)O)c2)[C@H](c2cccc(Cl)c2F)[C@@]1(C#N)c1ccc(Cl)cc1F]

M.W. 655.58,
C34H34Cl2F2N4O3

To a stirred solution of rac-(2R,3S,4R,5S)-3-(3-chloro-2-fluorophenyl)-4-(4-chloro-2-fluorophenyl)-4-cyano-5-neopentylpyrrolidine-2-carboxylic acid (60 mg, 0.128 mmol) in dichloromethane (5.00 ml) were added N,N-DIISOPROPYLETHYLAMINE (99.6 mg, 0.770 mmol) and N,N,N',N'-tetramethyl-O-(7-aza-benzotriazol-1-yl)uranium hexafluorophosphate (HATU) (90.3 mg, 0.237 mmol, Chem-Impex) followed by 5-amino-2-(pyrrolidin-1-yl)benzoic acid (38.5 mg, 0.187 mmol, Array). The reaction mixture was stirred for 2 hr. The reaction mixture was diluted with CH$_2$Cl$_2$ (80 mL), washed with sat Na2CO3 (2×15 mL), water (2×15 mL) and evaporated. The crude material was purified by flash chromatography (silica gel, 8 g, 0.5% to 5% MeOH in CH2Cl2) to give rac-5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-pyrrolidin-1-yl-benzoic acid as white solid (14.6 mg, 15.4%). MS (ES$^+$) m/z Calcd: [(M+H)$^+$]: 655. found: 655.

Example 416

Preparation of rac-4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-4-methyl-piperidine-1-carboxylic acid tert-butyl ester

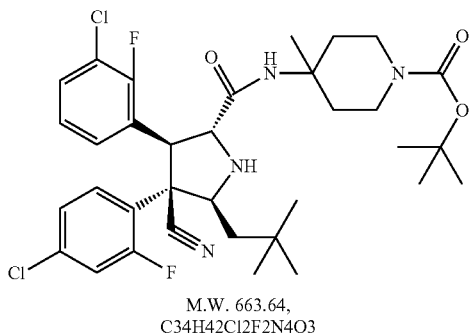 [SMILES: CC(C)(C)C[C@@H]1N[C@@H](C(=O)NC2(C)CCN(C(=O)OC(C)(C)C)CC2)[C@H](c2cccc(Cl)c2F)[C@@]1(C#N)c1ccc(Cl)cc1F]

M.W. 663.64,
C34H42Cl2F2N4O3

To a stirred solution of racemic-(2R,3S,4R,5S)-3-(3-chloro-2-fluorophenyl)-4-(4-chloro-2-fluorophenyl)-4-cyano-5-neopentylpyrrolidine-2-carboxylic acid (48.2 mg, 0.103 mmol) in dichloromethane (8 ml) were added N,N-DIISOPROPYLETHYLAMINE (72.7 mg, 98.3 µl, 563 µmol, Eq: 6) and N,N,N',N'-tetramethyl-O-(7-aza-benzotriazol-1-yl)uranium hexafluorophosphate (HATU) (64.2 mg, 0.169 mmol) followed by tert-butyl 4-amino-4-methylpiperidine-1-carboxylate (20.1 mg, 0.0938 mmol, Astatech). The reaction mixture was stirred from 2:00 PM for 2 hrs. The reaction mixture was diluted with CH$_2$Cl$_2$ (80 mL), washed with sat Na2CO3 (15 mL), water (2×15 mL) and evaporated. The crude material was purified by flash chromatography (silica gel, 4 g, 5% to 70% EtOAc in hexanes) to give rac-4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-4-methyl-piperidine-1-carboxylic acid tert-butyl ester as a white solid. MS (ES$^+$) m/z Calcd: [(M+H)$^+$]: 663. found: 663.

Example 417

Preparation of rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-methyl-piperidin-4-yl)-amide

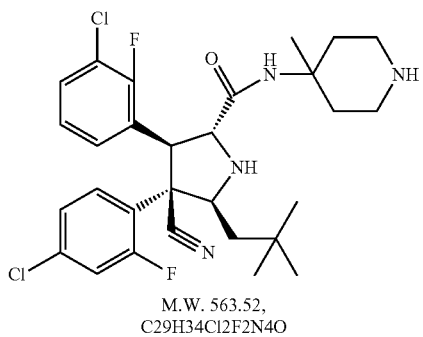 [SMILES: CC(C)(C)C[C@@H]1N[C@@H](C(=O)NC2(C)CCNCC2)[C@H](c2cccc(Cl)c2F)[C@@]1(C#N)c1ccc(Cl)cc1F]

M.W. 563.52,
C29H34Cl2F2N4O

To a stirred solution of racemic tert-butyl 4-((2R,3S,4R,5S)-3-(3-chloro-2-fluorophenyl)-4-(4-chloro-2-fluorophenyl)-4-cyano-5-neopentylpyrrolidine-2-carboxamido)-4-methylpiperidine-1-carboxylate (27.0 mg, 0.0407 mmol, example 386) in dichloromethane (3 mL) was added TRIFLUOROACETIC ACID (4.44 g, 3 mL) and the reaction mixture was stirred at 0~5 C for 2.5 hrs. The solvent was removed in vacuum and residue was dissolved in CH2Cl2 (80 mL), washed with sat Na2CO3 (15 mL), water (2×15 mL) and evaporated to give rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-methyl-piperidin-4-yl)-amide as a white solid. MS (ES$^+$) m/z Calcd: [(M+H)$^+$]: 563. found: 563.

Example 418

Preparation of rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (1-methanesulfonyl-4-methyl-piperidin-4-yl)-amide

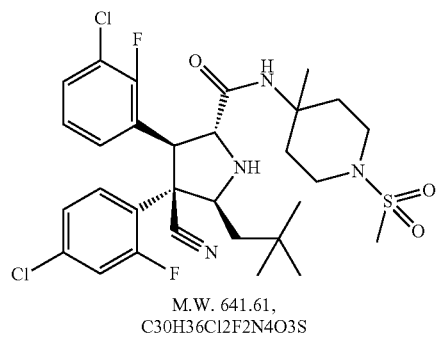 [SMILES: CC(C)(C)C[C@@H]1N[C@@H](C(=O)NC2(C)CCN(S(C)(=O)=O)CC2)[C@H](c2cccc(Cl)c2F)[C@@]1(C#N)c1ccc(Cl)cc1F]

M.W. 641.61,
C30H36Cl2F2N4O3S

A solution of racemic (2R,3S,4R,5S)-3-(3-chloro-2-fluorophenyl)-4-(4-chloro-2-fluorophenyl)-4-cyano-N-(4-methylpiperidin-4-yl)-5-neopentylpyrrolidine-2-carboxamide (20.5 mg, 0.0364 µmol, example 387) was treated with TRIETHYLAMINE (24.8 mg, 0.245 mmol) followed by METHANESULFONYL CHLORIDE (8.5 mg, 0.0742 mmol). The reaction was stirred at 0 C for 2 hrs. The reaction mixture was diluted with CH₂Cl₂ (80 mL), washed with sat. Na2CO3 (2×15 mL), water (2×15 mL) and evaporated. The crude material was purified by flash chromatography (silica gel, 4 g, 10% to 100% EtOAc/hexane) to give rac-(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (1-methanesulfonyl-4-methyl-piperidin-4-yl)-amide a white solid (20.5 mg, 88%). MS (ES⁺) m/z Calcd: [(M+H)⁺]: 641. found: 641.

Example 419

Preparation of methyl 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylate

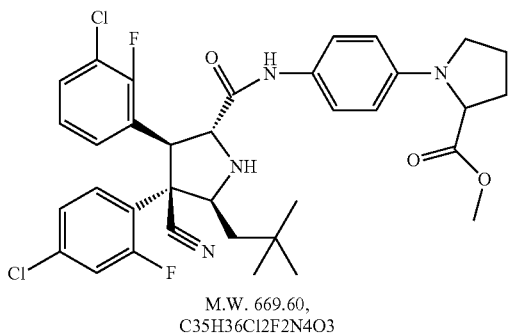 [SMILES: COC(=O)C1CCCN1c1ccc(NC(=O)[C@@H]2N[C@@H](CC(C)(C)C)[C@](C#N)(c3ccc(Cl)cc3F)[C@H]2c2cccc(Cl)c2F)cc1]

M.W. 669.60,
C35H36Cl2F2N4O3

To a stirred solution of (2R,3S,4R,5S)-3-(3-chloro-2-fluorophenyl)-4-(4-chloro-2-fluorophenyl)-4-cyano-5-neopentylpyrrolidine-2-carboxylic acid (60 mg, 0.128 mmole) in dichloromethane (6 ml) were added N,N-DIISOPROPYLETHYLAMINE (104 mg, 140 µl, 0.802 mmol) and methyl 1-(4-aminophenyl)pyrrolidine-2-carboxylate hydrochloride (50.2 mg, 0.196 mmol, Beta Pharma) followed by N,N,N',N'-tetramethyl-O-(7-aza-benzotriazol-1-yl)uranium hexafluorophosphate (HATU) (90.3 mg, 0237 mmole, Chem-Impex) and the reaction mixture was stirred at rt for 1 hr. The reaction mixture was diluted with CH₂Cl₂ (80 mL), washed with sat Na2CO3 (2×15 mL), water (2×15 mL) and evaporated. The crude material was purified by flash chromatography (silica gel, 4 g, 5% to 100% EtOAc in hexanes) to give methyl 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylate (72.4 mg, 84%) as a white solid. MS (ES⁺) m/z Calcd: [(M+H)⁺]: 669. found: 669.

Example 420

Preparation of 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylic acid

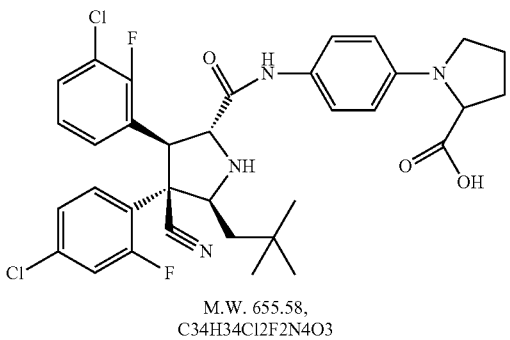 [SMILES: CC(C)(C)C[C@@H]1N[C@@H](C(=O)Nc2ccc(N3CCCC3C(=O)O)cc2)[C@H](c2cccc(Cl)c2F)[C@@]1(C#N)c1ccc(Cl)cc1F]

M.W. 655.58,
C34H34Cl2F2N4O3

To a solution of methyl 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylate (61.2 mg, 0.091.4 mmol, example 11) in THF (4.00 ml) was added a solution of LITHIUM HYDROXIDE monohydrate (22.6 mg, 0.539 mmol) in Water (2.00 ml) dropwise. The reaction mixture was stirred at rt for 2 hrs before it was neutralized with 1N HCl. it was then diluted with EtOAc, washed with water (2×10 mL), brine (2×10 mL), dried and evaporated to give 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylic acid as a white solid. MS (ES⁺) m/z Calcd: [(M+H)⁺]: 655. found: 655.

Example 421

Preparation of chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid

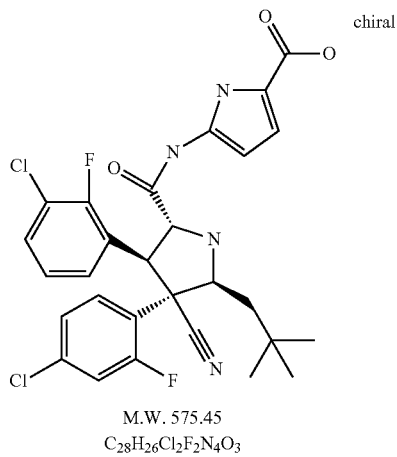 [SMILES: CC(C)(C)C[C@@H]1N[C@@H](C(=O)Nc2ccc(C(=O)O)[nH]2)[C@H](c2cccc(Cl)c2F)[C@@]1(C#N)c1ccc(Cl)cc1F]

M.W. 575.45
C28H26Cl2F2N4O3

A mixture of chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid ethyl ester (38 mg, 0.036 mmol) was dissolved in EtOH (4 mL) and 2N KOH (2 mL) was added and stirred 3 hours at 60° C., then increased heat to 80° C. for 12 h. The mixture was diluted with water and ethyl acetate. The organic phase was separated then concentrated under reduced pressure. The compound was purified by RP-HPLC (20%-95% of acetonitrile/water) to afford chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid trifluoroacetate salt (5 mg, 13.8%) as an off-white powder. HRMS (ES$^+$) m/z Calcd for $C_{28}H_{26}Cl_2F_2N_4O_3$+H [(M+H)$^+$]: 575.1423. found: 575.1427.

Example 422

Preparation of chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid ethyl ester

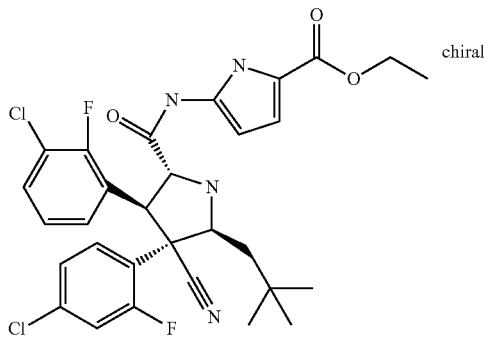

M.W. 603.50
$C_{30}H_{30}Cl_2F_2N_4O_3$

A mixture of chiral-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (200 mg, 0.428 mmol), ethyl 5-amino-1H-pyrrole-2-carboxylate (180 mg, 1.17 mmol), 2-(7-azabenzotriazol-1-yl)-n,n,n',n'-tetramethyluronium hexafluorophosphate (HATU, 200 mg, 0.526 mmol) and iPr$_2$NEt (0.4 mL, 2.29 mmol) in CH$_2$Cl$_2$ (4 mL) and THF (4 mL) was stirred at 25° C. for 16 hours. The mixture was then diluted with CH$_2$Cl$_2$ and washed with water. The organic phase was separated, then concentrated under reduced pressure. The compound was purified by RP-HPLC (20%-95% of acetonitrile/water) to afford chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid ethyl ester (42 mg, 16.3%) as an off-white powder. HRMS (ES) m/z Calcd for $C_{30}H_{30}Cl_2F_2N_4O_3$+H [(M+H)$^+$]: 603 736. found: 603.1736.

Example 423

Preparation of chiral (R)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid and chiral (S)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid

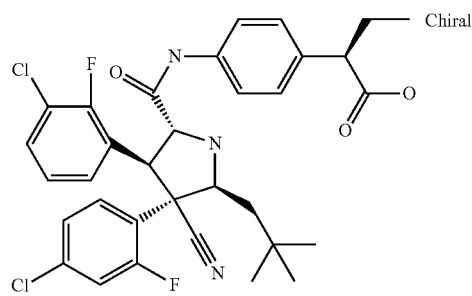

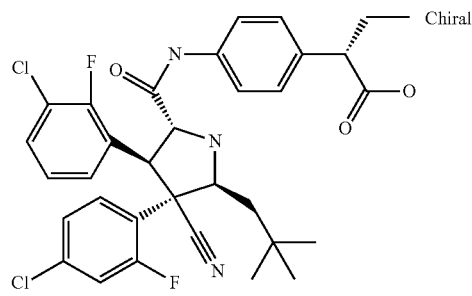

M.W. 628.55
$C_{33}H_{33}Cl_2F_2N_3O_3$

A mixture of diasteromeric 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid methyl esters (370 mg, 0.576 mmol) was dissolved in THF (15 mL) and methanol (5 mL), then 2N LiOH (5 mL) was added and stirred at room temperature for 2 hours. The mixture was diluted with water and extracted with ethyl acetate (2×). The organic phase was separated then concentrated under reduced pressure to afford crude product. Purified by SFC (30% MeOH, 100 bar, 30° C., 2 mL/min) to afford chiral (R)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid as a off-white solid (80.5 mg, 22.2%) HRMS (ES$^+$) m/z Calcd for $C_{33}H_{33}Cl_2F_2N_3O_3$+H [(M+H)$^+$]: 628.1940. found: 628.1942. and chiral (S)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid (50.1 mg, 16.0%) as an off-white powder. HRMS (ES$^+$) m/z Calcd for $C_{33}H_{33}Cl_2F_2N_3O_3$+H [(M+H)$^+$]:628.1940. found: 628.1944.

Example 424

Preparation of chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester and chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester

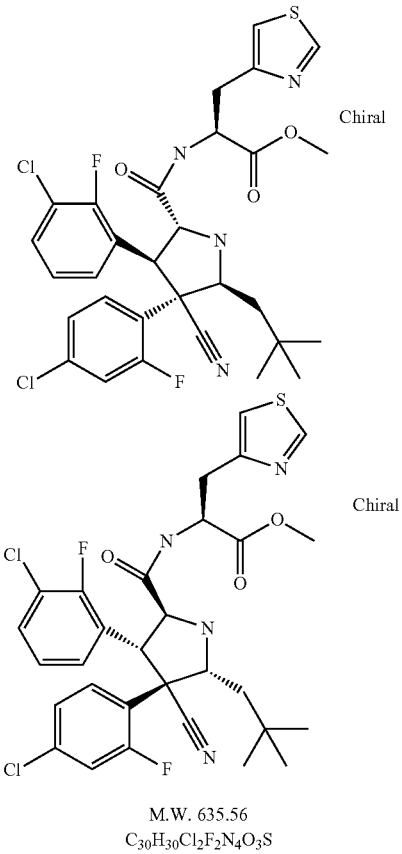

M.W. 635.56
$C_{30}H_{30}Cl_2F_2N_4O_3S$

Regeant (S)-methyl 2-amino-3-(thiazol-4-yl)propanoate (655 mg, 2.94 mmol), was dissolved in dichloromethane (30 mL) then iPr$_2$NEt (2.41 mL, 13.9 mmol) was added and stirred at 25° C. In three portions racemic (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (701 mg, 1.5 mmol) and 2-(7-azabenzotriazol-1-yl)-n,n,n',n'-tetramethyluronium hexafluorophosphate (HATU, 741 mg, 1.95 mmol) was added in 30 min intervals. The reaction mixture was stirred at 25° C. for 14 hours. The mixture was then diluted with CH$_2$Cl$_2$ and washed with water. The organic phase was separated, then concentrated under reduced pressure. The diasteromers were purified by RP-HPLC (20%-95% acetonitrile/water) to afford chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester trifluoroacetate salt as a white powder (122 mg, 12.8%) HRMS (ES$^+$) m/z Calcd for $C_{30}H_{30}Cl_2F_2N_4O_3S$+H [(M+H)$^+$]: 635.1457. found: 635.1456 and chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester trifluoroacetate salt as a white powder (37 mg, 4%). HRMS (ES$^+$) m/z Calcd for $C_{30}H_{30}Cl_2F_2N_4O_3S$+H [(M+H)$^+$]: 635.1457. found: 635.1456.

Example 425

Preparation of chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid

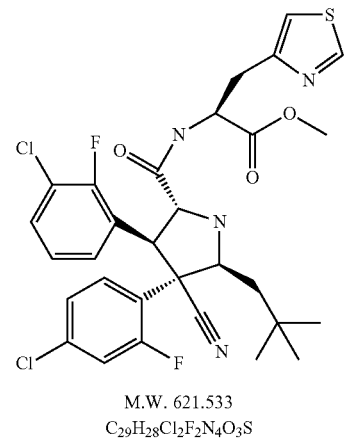 [SMILES: COC(=O)[C@H](Cc1cscn1)NC(=O)[C@@H]1N[C@@H](CC(C)(C)C)[C@](C#N)(c2ccc(Cl)cc2F)[C@H]1c1cccc(Cl)c1F]

M.W. 621.533
$C_{29}H_{28}Cl_2F_2N_4O_3S$

A mixture of chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester trifluoroacetate salt (112 mg, 0.176 mmol) was dissolved in THF (3 mL) and methanol (1 mL), then 2N LiOH (1 mL) was added and stirred at room temperature for 2 hours. The mixture was diluted with water and extracted with ethyl acetate (2×), the organic phase was separated then concentrated under reduced pressure to afford the crude product that was purified by RP-HPLC (20-95% acetonitrile/water). The solvent was evaporated under reduced pressure to afford chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid trifluoroacetate salt as a white powder (41 mg, 37.9%). HRMS (ES$^+$) m/z Calcd for $C_{29}H_{28}Cl_2F_2N_4O_3S$+H [(M+H)$^+$]: 621.1300. found: 621.1298.

Example 426

Preparation of chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid

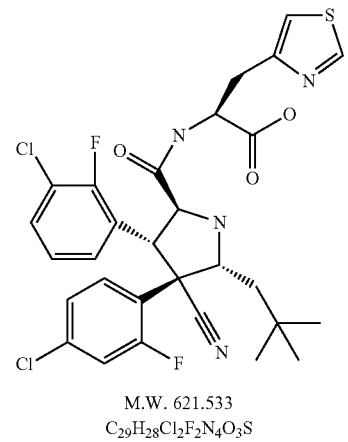 [SMILES: CC(C)(C)C[C@H]1N[C@H](C(=O)N[C@@H](Cc2cscn2)C(=O)O)[C@@H](c2cccc(Cl)c2F)[C@]1(C#N)c1ccc(Cl)cc1F]

M.W. 621.533
$C_{29}H_{28}Cl_2F_2N_4O_3S$

A mixture of chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester trifluoroacetate salt (31 mg, 0.48.8 mmol) was dissolved in THF (1.5 mL) and methanol (0.5 mL), then 2N LiOH (0.5 mL) was added and stirred at room temperature for 2 hours. The mixture was diluted with water and extracted with ethyl acetate (2×), the organic phase was separated then concentrated under reduced pressure to afford crude product that was purified by RP-HPLC (20-95% acetonitrile/water) solvent evaporated from pure fraction under reduced pressure to afford the trifluoroacetate salt. This was free based with EtOAc and NaHCO$_3$(s), the organic layer was separated and concentrated under reduced pressure to afford chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid as a white powder (21 mg, 68.3%). HRMS (ES$^+$) m/z Calcd for $C_{29}H_{28}Cl_2F_2N_4O_3S$+H [(M+H)$^+$]: 621.1300. found: 621.1298.

Example 427

Preparation of chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid

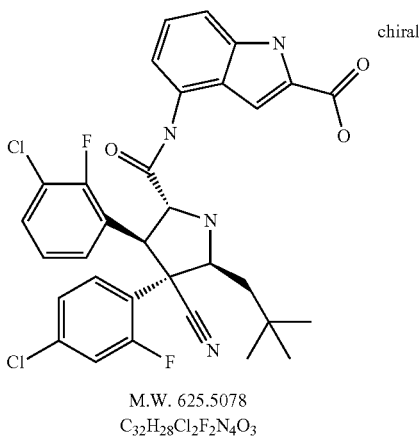 [SMILES: CC(C)(C)C[C@@H]1N[C@@H](C(=O)Nc2cccc3[nH]c(C(=O)O)cc23)[C@H](c2cccc(Cl)c2F)[C@@]1(C#N)c1ccc(Cl)cc1F]

M.W. 625.5078
$C_{32}H_{28}Cl_2F_2N_4O_3$

A mixture of chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid ethyl ester (168 mg, 0.257 mmol) was dissolved in EtOH (4 mL) and 2N KOH (2 mL) was added and stirred 3 hours at 70° C., then cooled to 25° C. The mixture was diluted with water and ethyl acetate. The organic phase was separated then concentrated under reduced pressure. The compound was purified by RP-HPLC (20%-95% of acetonitrile/water) to afford the trifluoroacetate salt. Compound was very insoluble, used iPA with EtOAc and NaHCO$_3$(s) to free base, the organic layer was separated and concentrated under reduced pressure to afford chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid (84.5 mg, 52.6%) as an off-white solid. HRMS (ES$^+$) m/z Calcd for $C_{32}H_{28}Cl_2F_2N_4O_3$+H [(M+H)$^+$]:625.1580. found: 625.1580.

Example 428

Preparation of rac (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (5-iodo-pyridin-2-yl)-amide

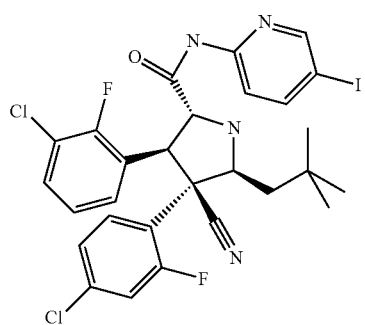

Molecular Weight = 669.3449
Molecular Formula = C28H25Cl2F2IN4O

To a stirred solution of rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid, TFA salt (200 mg, 0.34 mmol) in methylene chloride (3 mL), HATU (Aldrich, 235 mg, 0.62 mmol) was added followed by the addition of DIPEA (0.3 mL, 1.72 mmol) and 6-Iodo-pyridin-3-ylamine (Lancaster, 138 mg, 0.69 mmol). The mixture was stirred at RT for 4 h. The reaction was quenched with water. The mixture was extracted with methylene chloride (2×10 mL) and the extracts were dried with sodium sulfate. The solvent was removed and the residue was purified by flash chromatography (0-8% EtOAc/methylene chloride) to give the title compound as a white solid (95 mg, 41% yield).
MS (ES$^+$) m/z Calcd: [(M+H)$^+$]: 669. found: 669.

Example 429

Preparation of 2-chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid

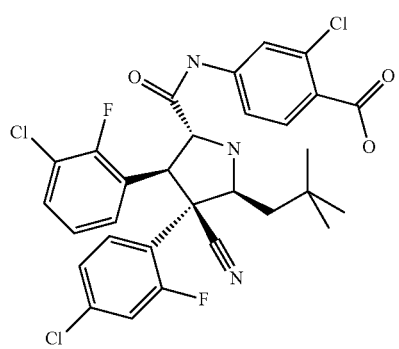

Molecular Weight = 620.9158
Molecular Formula = C30H26Cl3F2N3O3

4-{[(2R,3S,4R,5S)-3-(3-Chloro-2-fluoro-phenyl)-4-(4-chloro-2-fluoro-phenyl)-4-cyano-5-(2,2-dimethyl-propyl)-pyrrolidine-2-carbonyl]-amino}-2-chloro-benzoic acid methylester (54 mg) was dissolved in MeOH (10 mL) with help of slight heating. To the stirred solution was added NaOH (1N, 2 mL) and the mixture was stirred for 1 hr. at 55° C. The solvent was removed and the residue was treated with 1 N HCl to make the mixture acidic. The white suspension was extracted with EtOAc (3×10 mL) and the extracts combined and dried with sodium sulfate. The solvent was removed and the residue was freeze dried to give a white powder. 40 mg. MS (ES+) m/z Calcd: [(M+H)+]: 620. found: 620.

Example 430

Preparation of 6-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid

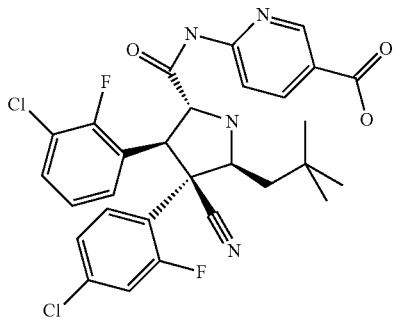

Molecular Weight = 587.4584
Molecular Formula = C29H26Cl2F2N4O3

In a 50 ml pressure tube, (2R,3S,4R,5S)-3-(3-chloro-2-fluorophenyl)-4-(4-chloro-2-fluorophenyl)-4-cyano-N-(5-iodopyridin-2-yl)-5-neopentylpyrrolidine-2-carboxamide (87 mg, 130 μmol, Eq: 1.00) was combined with DMF (3.48 ml) and water (174 μl). Potassium carbonate (35.9 mg, 260 μmol, Eq: 2) was added. The mixture was bubbled with nitrogen and then palladium (II) acetate (3.48 mg, 15.5 μmol, Eq: 0.119) was added. The tube was subjected to CO atmosphere at 40 PSI and stirred for 3 hours at 70° C.

The mixture was cooled to rt and filtered through celite. The filtrate was acidified with 1NHCl to PH 5 and was extracted with 5 ml EtOAc three times. The combined organic was dried over $Na_2SO_4$, concentrated to give a residue.

The residue was dissolved in DMSO and was purified by HPLC using acetonitrile/Water. The peak one was concentrated and freeze dried to give an off-white foam, 8.7 mg, MS (ES+) m/z Calcd: [(M+H)+]: 587. found: 587.

Example 431

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-2-ylamide

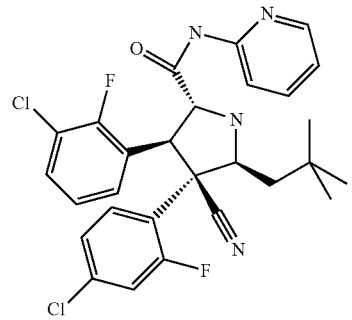

Molecular Weight = 543.4484
Molecular Formula = C28H26Cl2F2N4O

In a 50 ml pressure tube, (2R,3S,4R,5S)-3-(3-chloro-2-fluorophenyl)-4-(4-chloro-2-fluorophenyl)-4-cyano-N-(5-iodopyridin-2-yl)-5-neopentylpyrrolidine-2-carboxamide (87 mg, 130 μmol, Eq: 1.00) was combined with DMF (3.48 ml) and water (174 μl). Potassium carbonate (35.9 mg, 260 μmol, Eq: 2) was added. The mixture was bubbled with nitrogen and then palladium (II) acetate (3.48 mg, 15.5 μmol, Eq: 0.119) was added. The tube was subjected to CO atmosphere at 40 PSI and stirred for 3 hours at 70° C.

The mixture was cooled to rt and filtered through celite. The filtrate was acidified with 1NHCl to PH 5 and was extracted with 5 ml EtOAc three times. The combined organic was dried over Na2SO4, concentrated to give a residue.

The residue was dissolved in DMSO and was purified by HPLC using acetonitrile/Water. The peak two was concentrated and freeze dried to give an off-white foam, 13.8 mg, MS (ES+) m/z Calcd: [(M+H)+]: 543. found: 543.

Example 432

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-4-ylamide

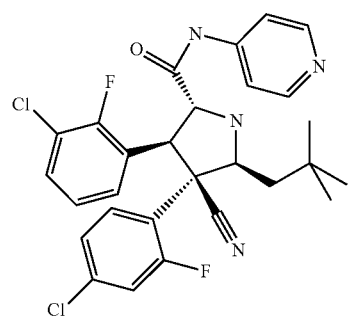

Molecular Weight = 543.4484
Molecular Formula = C28H26Cl2F2N4O

To 2 ml of CH$_2$Cl$_2$ at r.t. was added 1/3 amount of the (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid, TFA salt (66.67 mg) and 1/3 amount of DIPEA (100 uL) under nitrogen. To this was added ⅓ amount of HATU (80 mg). A solution of 4-amionpyridine in DCM 1 ml/DMF 0.5 ml was then added. The reaction was stirred for 30 minutes. To the reaction was added ⅓ of the DIPEA (100 uL), followed by a solid mixture of ⅓ amount of the starting acid (66.67 mg) and ⅓ amount of the HATU (80 mg). The mixture was stirred for 30 minutes and then the rest of the starting material and the reagents were added the same way. The reaction was stirred for overnight. The reaction was then diluted with CH$_2$Cl$_2$ (10 ml), dried with MgSO$_4$, filtered and concentrated to give a residue. The residue was dissolved in DMSO (10 ml) and was purified by RP HPLC using 50-100% acetonitrile/water. 44.3 mg MS (ES+) m/z Calcd: [(M+H)+]: 543. found: 543.

Example 433

Preparation of 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid

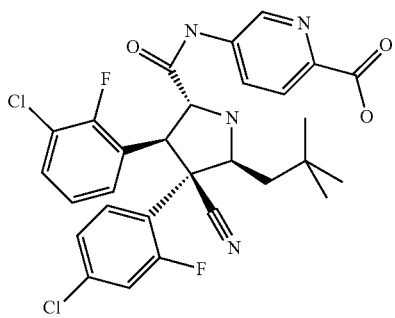

Molecular Weight = 587.4584
Molecular Formula = C29H26Cl2F2N4O3

In a 50 ml pressure tube, (2R,3S,4R,5S)-3-(3-chloro-2-fluorophenyl)-4-(4-chloro-2-fluorophenyl)-4-cyano-N-(5-iodopyridin-2-yl)-5-neopentylpyrrolidine-2-carboxamide (100 mg, 149 μmol, Eq: 1.00) was combined with DMF (4 ml) and water (200 μl). Potassium carbonate (41.3 mg, 299 μmol, Eq: 2) was added. The mixture was bubbled with nitrogen and then palladium(II) acetate (4 mg, 17.8 μmol, Eq: 0.119) was added. The tube was subjected to CO atmosphere at 40 PSI and stirred overnight at 70° C.

The reaction was filtered through celite. The filtrate diluted with water and was extracted with EtOAc (2×10 mL). The aqueous layer was acidified with 1N HCl to PH 5 to give a light suspension. This was filtered to give an orange solid. The EtOAc wash still contained the desired product. This was dried over Na$_2$SO$_4$, concentrated to give a residue. The solid and the residue were combined and the mixture was dissolved in DMSO and was purified by HPLC using 50-100% ACETONITRILE/Water. The clean fraction was concentrated and freeze dried to give a white foam, 8.7 mg, MS (ES+) m/z Calcd: 1587. found: 587.

Example 434

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid pyridin-3-ylamide

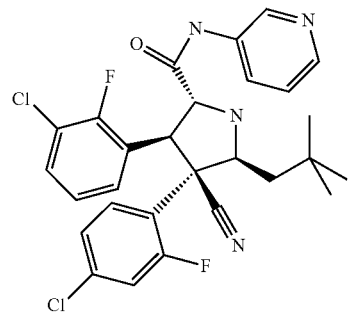

Molecular Weight = 543.4484
Molecular Formula = C28H26Cl2F2N4O

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid compound with 2,2,2-trifluoroacetic acid (1:1) (200 mg, 344 μmol, Eq: 1.00), was combined with CH$_2$Cl$_2$ (3 ml) to give a colorless solution. DIPEA (240 μl, 1.38 mmol, Eq: 4) and diphenylphosphinic chloride (244 mg, 1.03 mmol, Eq: 3) were added and the reaction was stirred at RT for 20 minutes. 3-Amino-pyridine (38.9 mg, 413 μmol, Eq: 1.2) was added and the reaction mixture was stirred at RT overnight. The crude reaction mixture was concentrated in vacuum. The crude material was purified by flash chromatography (silica gel, 40 g, 2% to 5% MeOH in DCM) to give a white solid as the product. 185 mg. MS (ES+) m/z Calcd: [(M+H)+]: 543. found: 543.

Example 435

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-3,5-dimethyl-phenyl)-amide

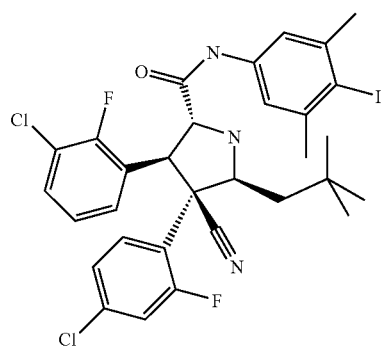

Molecular Weight = 696.4115
Molecular Formula = C31H30Cl2F2IN3O

To 3 ml of CH₂Cl₂ at r.t. was added ⅓ amount of the (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic 1) under nitrogen. To acid, TFA salt (100 mg) and ⅓ amount of DIPEA (111 this was added all of 4-iodo-3,5-dimethylaniline (0.255 g, 1.03 mmol), followed by ⅓ amount of HATU (117.7 mg). The reaction was stirred for 30 minutes. To 1), followed by a solid the reaction was added another ⅓ of the DIPEA (111 mixture of ⅓ amount of the starting acid (100 mg) and ⅓ amount of the HATU (117.7 mg). This was stirred for 30 minutes and then the rest of the starting material and the reagents were added the same way. The reaction was stirred for overnight. The reaction was diluted with CH₂Cl₂ (10 ml), washed with 0.5 N aqueous HCl solution, dried with MgSO₄, filtered and concentrated to give a yellow oil and this was purified by a 40 g flash silica gel column, eluted with a stepwise gradient of Hexanes to 25% EtOAc/Hexanes. Obtained was the product as a white solid. 60 mg. MS (ES+) m/z Calcd: [(M+H)+]: 696. found: 696.

Example 436

Preparation of 4-{[(2R,3S,4R,5S)-4-(4-Chloro-2-fluoro-phenyl)-3-(3-chloro-2 fluoro-phenyl)-4-cyano-5-(2,2-dimethyl-propyl)-pyrrolidine-2-carbonyl]-amino}-2-fluoro-benzoic acid tert-butyl ester

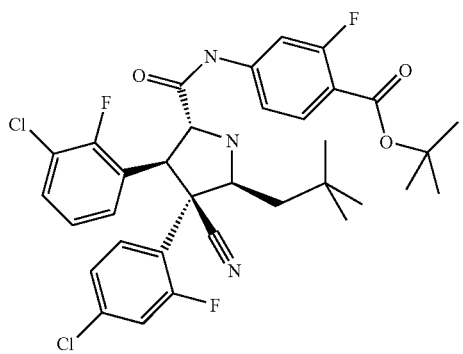

Molecular Weight = 660.5696
Molecular Formula = C34H34Cl2F3N3O3

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid compound with 2,2,2-trifluoroacetic acid (1:1) (200 mg, 344 μmol, Eq: 1.00), was combined with CH₂Cl₂ (4.5 ml) to give a yellow solution. DIPEA (178 mg, 1.38 mmol, Eq: 4) and diphenylphosphinic chloride (244 mg, 1.03 mmol, Eq: 3) were added and the reaction was stirred at RT for 20 minutes. Tert-butyl 4-amino-2-fluorobenzoate (72.7 mg, 344 μmol, Eq: 1.00) was added and the reaction mixture was stirred at RT overnight. The crude reaction mixture was concentrated under vacuum. The crude material was purified by flash chromatography (silica gel, 40 g, 10% to 20% EtOAc in hexanes) to give a white solid as the product. 215 mg. MS (ES⁺) m/z Calcd: [(M+H)+]: 660, fund: 660.

Example 437

Preparation of 4-{[(2R,3S,4R,5S)-4-(4-Chloro-2-fluoro-phenyl)-3-(3-chloro-2 fluoro-phenyl)-4-cyano-5-(2,2-dimethyl-propyl)-pyrrolidine-2-carbonyl]-amino}-2-fluoro-benzoic acid

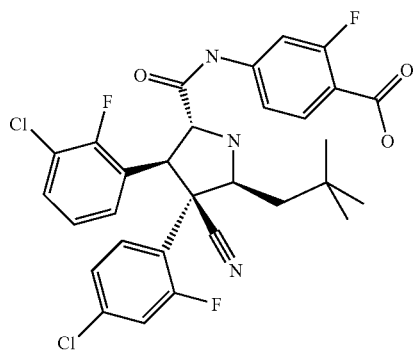

Molecular Weight = 604.4612
Molecular Formula = C30H26Cl2F3N3O3

In a 50 mL round-bottomed flask, tert-butyl 4-((2R,3S,4R,5S)-3-(3-chloro-2-fluorophenyl)-4-(4-chloro-2-fluorophenyl)-4-cyano-5-neopentylpyrrolidine-2-carboxamido)-2-fluorobenzoate (170 mg, 257 μmol, Eq: 1.00) was combined with CH₂Cl₂ (3 mL) to give a colorless solution. TFA (3 ml) was added and the reaction was stirred for 6 hours. The crude reaction mixture was concentrated in vacuum, added DCM and concentrated again. Recrystallization from diethyl ether and hexanes afforded a white solid (148 mg, 93% yield). MS (ES+) m/z Calcd: [(M+H)+]: 604. found: 604.

Example 438

Preparation of 4-{[(2R,3S,4R,5S)-4-(4-Chloro-2-fluoro-phenyl)-3-(3-chloro-2 fluoro-phenyl)-4-cyano-5-(2,2-dimethyl-propyl)-pyrrolidine-2-carbonyl]-amino}-3-fluoro-benzoic acid

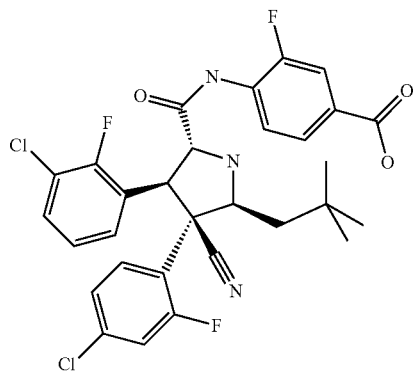

Molecular Weight = 604.4612
Molecular Formula = C30H26Cl2F3N3O3

In a 50 ml pressure tube, (2R,3S,4R,5S)-3-(3-chloro-2-fluorophenyl)-4-(4-chloro-2-fluorophenyl)-4-cyano-N-(5-iodopyridin-2-yl)-5-neopentylpyrrolidine-2-carboxamide (100 mg, 149 µmol, Eq: 1.00) was combined with DMF (4 ml) and water (200 µl). Potassium carbonate (41.3 mg, 299 µmol, Eq: 2) was added. The mixture was bubbled with nitrogen and then palladium(II) acetate (4 mg, 17.8 µmol Eq: 0.119) was added. The tube was subjected to CO atmosphere at 40 PSI and stirred for 3 hours at 60° C. The reaction temperature was raised to 70° C., charged CO to 50 psi, stirred for 5 hours, and another 5 hours.

The reaction was filtered through celite. The filtrate diluted with 5% Na$_2$CO$_3$ solution and was extracted with EtOAc (3×). The EtOAc solution was acidified with 0.5N HCl, washed with water, dried over Na$_2$SO$_4$, and concentrated to give a residue. The residue was dissolved in methylene chloride and was purified by a 23 g silica gel column, eluted with methylene chloride to 5% MeOH in methylene chloride. The clean fraction was concentrated and the residue recrystallized from DCM/ether/hexanes. Obtained was desired product as a white solid, 165 mg.

MS (ES+) m/z Calcd: [(M+H)+]: 604. found: 604.

Example 439

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-trifluoromethyl-benzoic acid

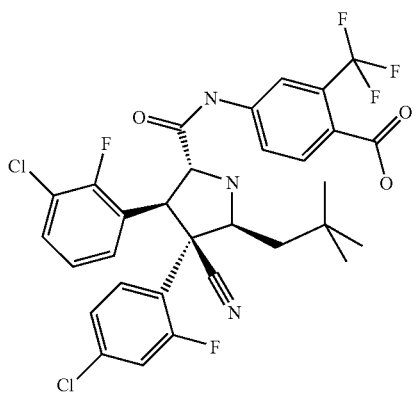

Molecular Weight = 654.4692
Molecular Formula = C31H26Cl2F5N3O3

In a 50 mL round-bottomed flask, methyl 4-((2R,3S,4R,5S)-3-(3-chloro-2-fluorophenyl)-4-(4-chloro-2-fluorophenyl)-4-cyano-5-neopentylpyrrolidine-2-carboxamido)-2-(trifluoromethyl)benzoate (290 mg, 434 µmol, Eq: 1.00) was combined with THF (8 ml) and MeOH (8.00 ml) to give a colorless solution. 1.5 M NaOH (3 ml, 4.5 mmol, Eq: 10.4) was added. The reaction mixture was heated to 50° C. and stirred for 3 h. The reaction mixture was acidified with 1N HCl and was extracted with EtOAc (3×15 mL). The organic layers were combined, washed with saturated NaCl (1×10 mL), dried over Na$_2$SO$_4$ and concentrated in vacuum. The crude material was dissolved in DMSO and purified by preparative HPLC (70-100% ACETONITRILE/water). Obtained was a white solid (130 mg, 46% yield). MS (ES+) m/z Calcd: [(M+H)+]: 654. found: 654.

Example 440

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-iodo-2-trifluoromethoxy-phenyl)-amide

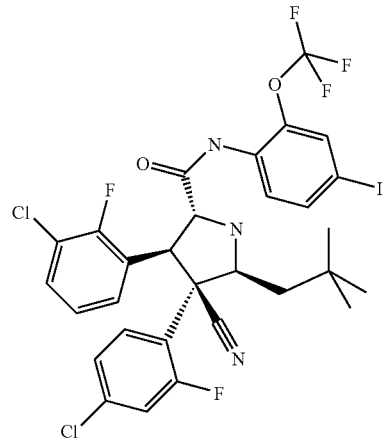

Molecular Weight = 752.3551
Molecular Formula = C30H25Cl2F5IN3O2

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid compound with 2,2,2-trifluoroacetic acid (1:1) (200 mg, 344 µmol, Eq: 1.00), was combined with CH$_2$Cl$_2$ (5 ml) to give a clear solution. DIPEA (178 mg, 1.38 mmol, Eq: 4) and diphenylphosphinic chloride (244 mg, 1.03 mmol, Eq: 3) were added and the reaction was stirred at RT for 30 minutes. 4-Iodo-2-(trifluoromethoxy) aniline (136 mg, 447 µmol, Eq: 1.3) was added and the reaction mixture was stirred at RT overnight. The crude reaction mixture was concentrated in vacuum. The crude material was purified by flash chromatography (silica gel, 40 g, 0% to 20% EtOAc/Hexanes) to give the desired product as a white solid. 255 mg. (ES+) m/z Calcd: [(M+)+]: 752. found: 752.

Example 441

Preparation 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-trifluoromethoxy-benzoic acid methyl ester

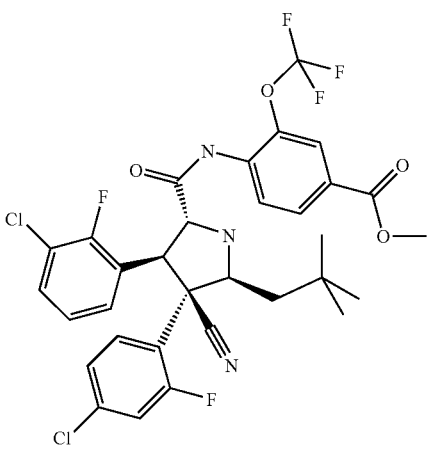

Molecular Weight = 684.4957
Molecular Formula = C32H28Cl2F5N3O4

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid compound with 2,2,2-trifluoroacetic acid (1:1) (300 mg, 516 µmol, Eq: 1.00), was combined with $CH_2Cl_2$ (8 ml) to give a clear solution. DIPEA (267 mg, 361 µl, 2.06 mmol, Eq: 4) and diphenylphosphenic chloride (366 mg, 1.55 mmol, Eq: 3) were added and the reaction was stirred at RT for 20 minutes. Methyl 4-amino-2-(trifluoromethyl)benzoate (136 mg, 619 µmol, Eq: 1.2) was added and the reaction mixture was stirred at RT overnight.

The crude reaction mixture was concentrated in vacuum. The crude material was purified by flash chromatography (silica gel, 40 g, 5% to 25% EtOAc/Hexanes) to give the desired product as a white solid (340 mg, 98.6% yield). (ES+) m/z Calcd: [(M+H)+]: 684. found: 684.

Example 442

Preparation 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-trifluoromethoxy-benzoic acid

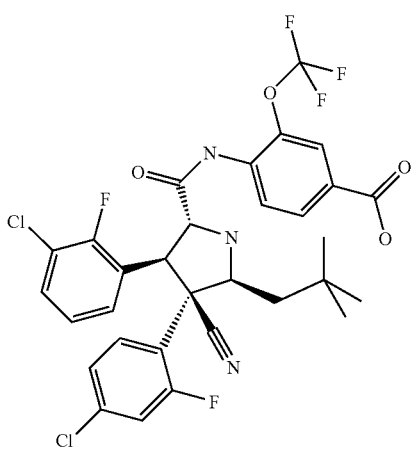

Molecular Weight = 670.4686
Molecular Formula = C31H26Cl2F5N3O4

In a 50 ml pressure tube, (2R,3S,4R,5S)-3-(3-chloro-2-fluorophenyl)-4-(4-chloro-2-fluorophenyl)-4-cyano-N-(4-iodo-2-(trifluoromethoxy)phenyl)-5-neopentylpyrrolidine-2-carboxamide (200 mg, 266 µmol, Eq: 1.00) was combined with DMF (5 ml) and water (0.5 ml) to give a colorless solution. Potassium carbonate (83 mg, 601 µmol, Eq: 2.26) was added. The mixture was bubbled with nitrogen and then palladium (II) acetate (10 mg, 44.5 µmol, Eq: 0.168) was added. The tube was subjected to CO atmosphere at 50 PSI and stirred for overnight at 70° C.

The reaction was filtered through celite, washed with DMF, water and EtOAc. The filtrate was acidified with 1 NHC and was extracted with EtOAc (3×8 ml). The combined EtOAc solution was washed with water, dried over $Mg_2SO_4$, and concentrated to give a white solid. This was triturated with diethyl ether (2×15 ml) to give a white solid as desired product (172 mg, 97% yield). (ES+) m/z Calcd: [(M+H)+]: 670. found: 670.

Example 443

Preparation of 6-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid

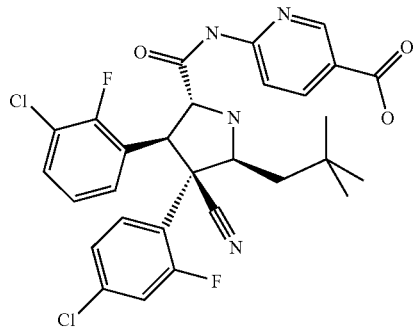

Molecular Weight = 587.4584
Molecular Formula = C29H26Cl2F2N4O3

In a 50 mL round-bottomed flask, methyl 6-((2R,3S,4R,5S)-3-(3-chloro-2-fluorophenyl)-4-(4-chloro-2-fluorophenyl)-4-cyano-5-neopentylpyrrolidine-2-carboxamido)nicotinate (25 mg, 41.6 µmol, Eq: 1.00) was dissolved in methylene chloride (8 ml) to give a colorless solution. Aluminum bromide (66.5 mg, 249 µmol, Eq: 6) and dimethyl sulfide (25.8 mg, 30.7 µl, 416 µmol, Eq: 10) were added and the mixture was stirred at rt for overnight. The solvent was removed and the residue was suspended in 3 ml of acetonitrile, 3 ml of water was added and the mixture was extracted with ethyl acetate (3×8 ml). The extracts were combined and dried with sodium sulfate. Removal of solvent at reduced pressure gave a yellow solid, 30 mg.

The crude material was purified by preparative HPLC, (60-100% ACETONITRILE/water). The product peak was concentrated and freeze dried to give the desire product as a white foam. (10.1 mg, 41% yield). (ES+) m/z Calcd: [(M+H)+]: 587. found: 587.

Example 444

Preparation of 6-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid methyl ester

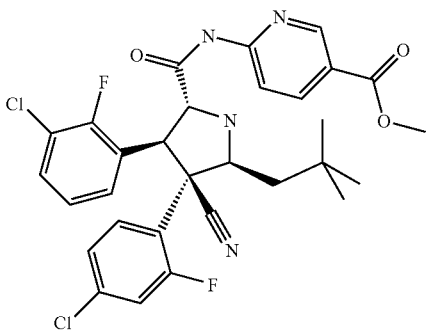

Molecular Weight = 601.4855
Molecular Formula = C30H28Cl2F2N4O3

In a 50 ml pressure tube, (2R,3S,4R,5S)-3-(3-chloro-2-fluorophenyl)-4-(4-chloro-2-fluorophenyl)-4-cyano-N-(5-iodopyridin-2-yl)-5-neopentylpyrrolidine-2-carboxamide (185 mg, 276 μmol, Eq: 1.00) and DIPEA (0.29 ml, 1.67 mmol) were combined with DMF (5 ml) and MeOH (3.96 g, 5 ml, 124 mmol, Eq: 447) to give a colorless solution. The mixture was bubbled with nitrogen and palladium(II) acetate (6.21 mg, 27.7 mmol) was added. The tube was subjected to CO atmosphere at 50 PSI and stirred for overnight at 70° C.

The reaction was filtered through celite, concentrated somewhat to remove MeOH. The mixture was acidified with 1N HCl (3 ml) and was extracted with EtOAc (3×5 ml). The EtOAc solution was washed with water, dried over $Na_2SO_4$, and concentrated. The crude material was purified by flash chromatography (silica gel, 24 g, 5% to 15% EtOAc in DCM). Obtained was a white solid as desired product (113 mg, 68% yield). (ES+) m/z Calcd: [(M+H)+]: 601. found: 601.

Example 445

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (6-iodo-pyridin-3-yl)-amide

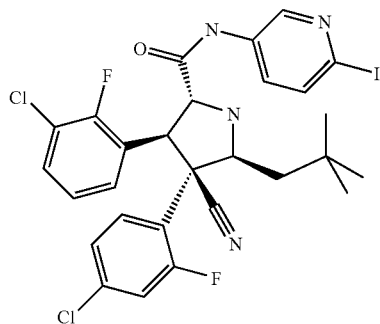

Molecular Weight = 669.3449
Molecular Formula = C28H25Cl2F2IN4O

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid (300 mg, 642 μmol, Eq: 1.00), was combined with $CH_2Cl_2$ (8 ml) to give a clear solution. DIPEA (332 mg, 448 μl, 2.57 mmol, Eq: 4) and diphenylphosphinic chloride (456 mg, 368 μl, 1.93 mmol, Eq: 3) were added and the reaction was stirred at RT for 30 minutes. 5-Amino-2-iodopyridine (141 mg, 642 μmol, Eq: 1) was added and the reaction mixture was stirred at RT overnight.

The crude reaction mixture was concentrated in vacuum. The crude material was purified by flash chromatography (silica gel, 40 g, 5% to 20% EtOAc/$CH_2Cl_2$) to give the desired product as a white solid (409 mg, 93% yield). (ES+) m/z Calcd: [(M+H)+]: 669. found: 669.

Example 446

Preparation of 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid methyl ester

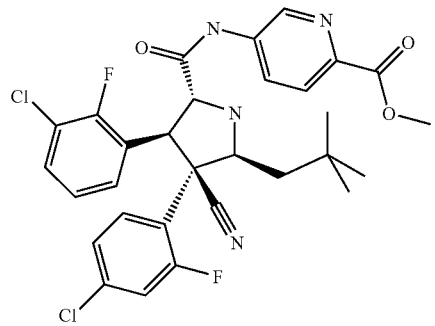

Molecular Weight = 601.4855
Molecular Formula = C30H28Cl2F2N4O3

In a 50 ml pressure tube, (2R,3S,4R,5S)-3-(3-chloro-2-fluorophenyl)-4-(4-chloro-2-fluorophenyl)-4-cyano-N-(6-iodopyridin-3-yl)-5-neopentylpyrrolidine-2-carboxamide (358 mg, 535 μmol, Eq: 1.00) and DIPEA (0.29 ml, 1.67 mmol) were combined with DMF (10 ml) and MeOH (10 ml) to give a colorless solution. The mixture was bubbled with nitrogen and palladium(II) acetate (25 mg, 111 μmol, Eq: 0.208) was added. The tube was subjected to CO atmosphere at 50 PSI and stirred for two days at 70° C.

The reaction mixture was filtered through celite, concentrated somewhat to remove MeOH and was extracted with EtOAc (3×5 ml). The EtOAc solution was washed with water, dried over $Na_2SO_4$, and concentrated. The crude material was purified by flash chromatography (silica gel, 40 g, 5% to 25% EtOAc in DCM). obtained was a white solid as desired product (265 mg, 82% yield). (ES+) m/z Calcd: [(M+H)+]: 601. found: 601.

Example 447

Preparation of 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid methyl ester

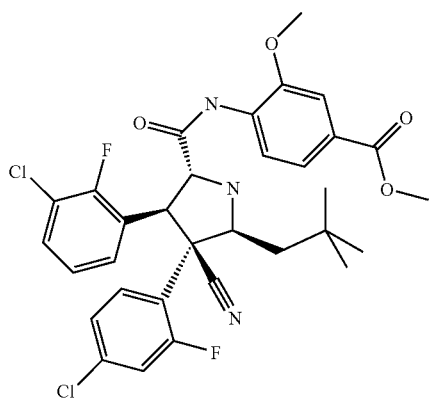

Molecular Weight =630.5244
Molecular Formula = C32H31Cl2F2N3O4

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid (250 mg, 535 µmol), was combined with CH₂Cl₂ (5 ml). DIPEA (277 mg, 374 µl, 2.14 mmol) and dipenylphospenic chloride (380 mg, 306 µl, 1.6 mmol) were added and the reaction was stirred at RT for 20 minutes. Methyl 4-amino-3-methoxybenzoate (100 mg, 552 µmol) was added and the reaction mixture was stirred at RT overnight.

The crude reaction mixture was concentrated in vacuum. The crude material was purified by flash chromatography (silica gel, 40 g, 5% to 25% EtOAc/Hexanes) to give the desired product as a white solid (275 mg, 81% yield).

Example 448

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid

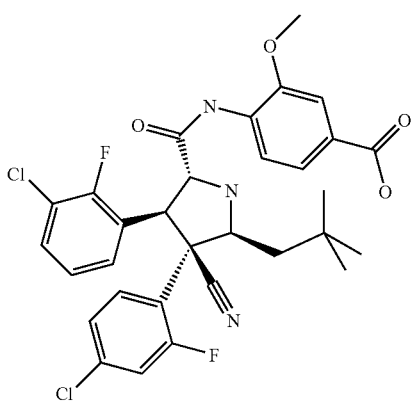

Molecular Weight = 616.4973
Molecular Formula = C31H29Cl2F2N3O4

In a 25 mL round-bottomed flask, methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (150 mg, 238 µmol, Eq: 1.00) was combined with CH₂Cl₂ (2 ml) to give a colorless solution. Aluminum bromide (Aldrich, 254 mg, 952 µmol, Eq: 4) and dimethyl sulfide (1.69 g, 2 mL, 27.2 mmol, Eq: 114) were added. The reaction mixture was stirred for overnight.

The reaction mixture was diluted with CH₃CN (6 ml), EtOAc (10 ml) and water (10 ml), stirred and layers separated. The aqueous layer was extracted with EtOAc (2×10 mL). The organic layers were combined, washed with saturated NaCl (1×15 mL), dried over MgSO₄ and concentrated in vacuum.

The crude material was dissolved in DMSO (4 ml) and was purified by preparative HPLC (70-100% ACETONITRILE/water). The fractions were combined, concentrated and freeze dried to give a white powder as desired product (75 mg, 51% yield). (ES+) m/z Calcd: [(M+H)+]: 616. found: 616.

Alternatively, the title compound could be prepared by the following method.

In a 500 mL round-bottomed flask, methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoate (3.74 g, 5.93 mmol, Eq: 1.00) was combined with THF (140 ml) and MeOH (160 ml) at 50° C. to give a colorless solution. 1 N NaOH (23.7 ml, 23.7 mmol, Eq: 4) was added. The reaction mixture was stirred at 40° C. for 18 hrs.

The reaction mixture was concentrated to remove about ½ of the solvent, filtered to removed the insoluble, acidified with 1N HCl to PH=4-5 and the resulting solid was collected by filtration and was washed with water, small amount of MeOH and diethyl ether. It was then dried in vacuum oven (60° C.) overnight. Obtained was a white solid as the desired product (2.96 g, 80.5% yield). H¹NMR and LC/MASS data were the same as that in the above procedure.

Example 449

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (6-carbamoyl-naphthalen-2-yl)-amide

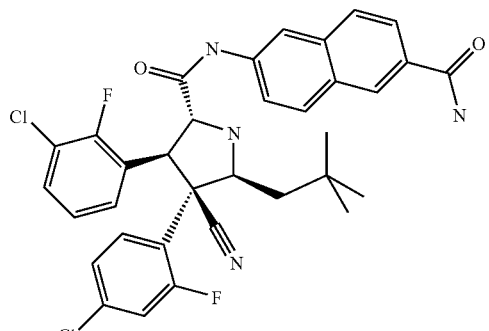

Molecular Weight = 635.5466
Molecular Formula = C34H30Cl2F2N4O2

To a stirred solution of 6-((2R,3S,4R,5S)-3-(3-chloro-2-fluorophenyl)-4-(4-chloro-2-fluorophenyl)-4-cyano-5-neopentylpyrrolidine-2-carboxamido)-2-naphthoic acid (58 mg, 0.091 mmol) in methylene chloride (8 ml), HATU (35 mg, 0.091 mmol) was added followed by DIPEA (0.15 ml). The solution was stirred for 5 minutes and then ammonia in methanol (2M in methanol, 1.0 ml) was added and the mixture was stirred at rt for 3 hrs. The solvent was reduced to 4 ml and loaded onto a silica gel column and eluted with 5% Methanol/methylene chloride on a combifalsh machine to give a white solid. 49 mg, 84.5%. (ES⁺) m/z Calcd: [(M+H)+]: 635. found: 635.

Example 450

Preparation (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-chloro-phenyl)-amide

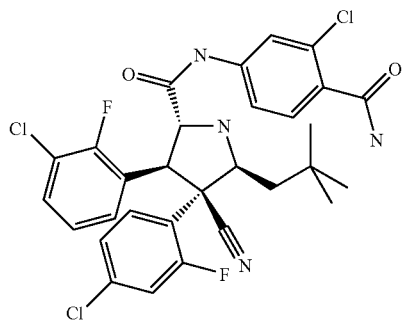

Molecular Weight = 619.9311
Molecular Formula = C30H27Cl3F2N4O2

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid (150 mg, 321 µmol, Eq: 1.00), was combined with CH$_2$Cl$_2$ (5 ml) to give a clear solution. DIPEA (145 mg, 196 µl, 1.12 mmol, Eq: 3.5) and diphenylphospenic chloride (Aldrich, 190 mg, 153 µl, 802 µmol, Eq: 2.5) were added and the reaction was stirred at RT for 20 minutes. 4-Amino-2-chlorobenzamide (53.1 mg, 311 µmol, Eq: 0.97) was added and the reaction mixture was stirred at RT overnight.

The crude reaction mixture was concentrated under vacuum. The crude material was purified by preparative HPLC (70-100% ACETONITRILE/water) to give the desired product as a white solid (62 mg, 31% yield). (ES+) m/z Calcd: [(M+H)+]: 619. found: 619.

Example 451

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-trifluoromethyl-phenyl)-amide

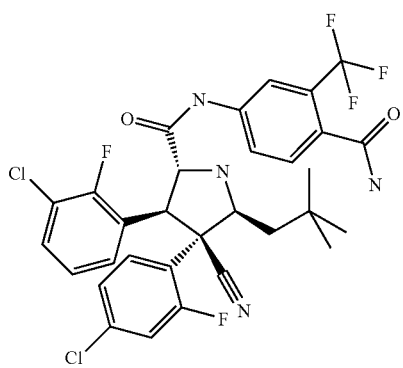

Molecular Weight = 653.4844
Molecular Formula = C31H27Cl2F5N4O2

In a 25 mL round-bottomed flask, 4-((2R,3S,4R,5S)-3-(3-chloro-2-fluorophenyl)-4-(4-chloro-2-fluorophenyl)-4-cyano-5-neopentylpyrrolidine-2-carboxamido)-2-(trifluoromethyl)benzoic acid (42 mg, 64.2 µmol, Eq: 1.00) was combined with DMF (2.50 ml) to give a colorless solution. HATU (36.6 mg, 96.3 µmol, Eq: 1.5) and DIPEA (41.5 mg, 56.0 µl, 321 µmol, Eq: 5) were added. The reaction was stirred for 5 minutes and ammonia hydrochloride (34.3 mg, 642 µmol, Eq: 10) was added. The reaction mixture was stirred for overnight. The reaction mixture was poured into 10 mL of H$_2$O and extracted with EtOAc (3×10 mL). The organic layers were combined, washed with H$_2$O (1×10 mL), saturated NaCl (1×10 mL), dried over Na$_2$SO$_4$ and concentrated in vacuum. The crude material was purified by preparative HPLC (65-100% ACETONITRILE/water). The fractions were combined and freeze dried and triturated with CH$_2$Cl$_2$/hexanes to give a white foam (12 mg, 26% yield). (ES+) m/z Calcd: [(M+H)+]: 653. found: 653.

Example 452

Preparation of 5-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid

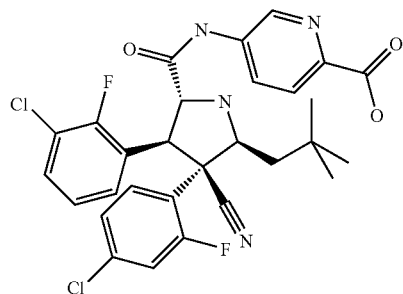

Molecular Weight = 587.4584
Molecular Formula = C29H26Cl2F2N4O3

In a 25 mL round-bottomed flask, methyl 5-((2R,3S,4R,5S)-3-(3-chloro-2-fluorophenyl)-4-(4-chloro-2-fluorophenyl)-4-cyano-5-neopentylpyrrolidine-2-carboxamido)picolinate (230 mg, 382 µmol, Eq: 1.00) was combined with CH$_2$Cl$_2$ (MeI) to give a colorless solution. Aluminum bromide (408 mg, 1.53 mmol, Eq: 4) and dimethyl sulfide (1.69 g, 2 ml, 27.2 mmol, Eq: 71.1) were added. The reaction mixture was stirred for overnight. The reaction mixture was diluted with ACETONITRILE (5 ml), EtOAc (10 ml) and water (10 ml), stirred and layers separated. The aqueous layer was extracted with EtOAc (2×10 mL). The organic layers were combined, washed with H2O (1×15 mL), sat NaCl (1×15 mL), dried over Na$_2$SO$_4$ and concentrated under vacuum.

The crude material was purified by preparative HPLC (with TFA). Obtained was a white solid after freeze drying (16.3 mg, 7% yield). (ES+) m/z Calcd: [(M+H)+]: 587. found: 587.

Example 453

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-fluoro-benzoic acid methyl ester

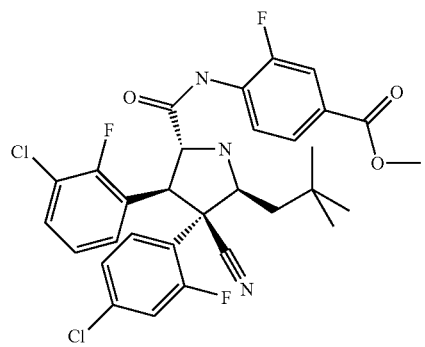

Molecular Weight = 618.4883
Molecular Formula = C31H28Cl2F3N3O3

In a 50 ml pressure tube, (2R,3S,4R,5S)-3-(3-chloro-2-fluorophenyl)-4-(4-chloro-2-fluorophenyl)-4-cyano-N-(2-fluoro-4-iodophenyl)-5-neopentylpyrrolidine-2-carboxamide (1.42 g, 2.07 mmol, Eq: 1.00) and DIPEA (0.29 ml, 1.67 mmol) were combined with DMF (15 ml) and MeOH (11.9 g, 15 ml, 371 mmol, Eq: 179) to give a colorless solution. The mixture was bubbled with nitrogen and palladium(II) acetate (40 mg, 178 μmol, Eq: 0.0861) was added. The tube was subjected to CO atmosphere at 50 PSI and stirred for two days at 70° C.

The reaction mixture was filtered through celite, concentrated somewhat to remove MeOH and was extracted with EtOAc (3×5 ml). The EtOAc solution was washed with water, dried over $Na_2SO_4$, and concentrated. The crude material was purified by flash chromatography (silica gel, 40 g, 5% to 25% EtOAc in hexanes). Obtained was a white solid as desired product (845 mg, 65% yield). (ES+) m/z Calcd: [(M+H)+]: 618. found: 6.

Example 454

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid methyl ester

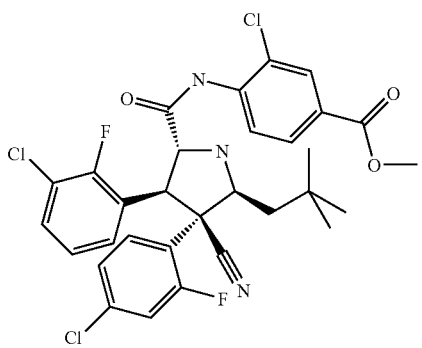

Molecular Weight = 634.9429
Molecular Formula = C31H28Cl3F2N3O3

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid (150 mg, 321 μmol, Eq: 1.00), was combined with $CH_2Cl_2$ (5 ml) to give a clear solution. DIPEA (145 mg, 196 μl, 1.12 mmol, Eq: 3.5) and diphenyphophenic chloride (Aldrich, 190 mg, 153 μl, 802 μmol, Eq: 2.5) were added and the reaction was stirred at RT for 10 minutes. Methyl-4-amino-3-chloro-benzoate (62.6 mg, 337 μmol, Eq: 1.05) was added and the reaction mixture was stirred at RT overnight.

The crude reaction mixture was concentrated under vacuum. The crude material was purified by flash chromatography (silica gel, 40 g, 8% to 20% EtOAc in hexanes) to give a white solid which still contains the aniline.

The mixture was purified again by flash chromatography (silica gel, 40 g, 10% to 18% EtOAc in hexanes) to give the desired product as a white solid (60 mg, 30% yield). (ES+) m/z Calcd: [(M+H)+]: 634. found: 634.

Example 455

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid

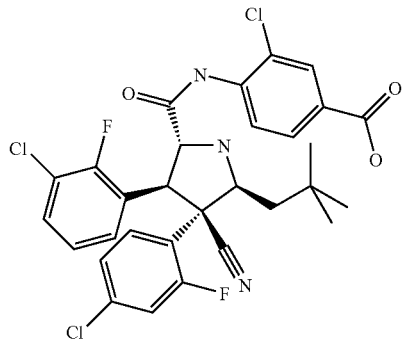

Molecular Weight = 620.9158
Molecular Formula = C30H26Cl3F2N3O3

To a stirred solution of aluminum bromide (250 mg, 937 μmol, Eq: 7.00) in dimethyl sulfide (1.01 g, 1.2 ml, 16.2 mmol, Eq: 121) was added a solution of methyl 3-chloro-4-((2R,3S,4R,5S)-3-(3-chloro-2-fluorophenyl)-4-(4-chloro-2-fluorophenyl)-4-cyano-5-neopentylpyrrolidine-2-carboxamido)benzoate (85 mg, 134 μmol, Eq: 1.00) in $CH_2Cl_2$ (2 ml). The reaction mixture was stirred for 3 hours.

The reaction mixture was diluted with $CH_3CN$ (3 ml), EtOAc (6 ml) and water (6 ml), stirred and layers separated. The aqueous layer was extracted with EtOAc (2×6 ml). The organic layers were combined, washed with water (1×6 ml), sat NaCl (1×8 ml), dried over MgSO4 and concentrated under vacuum.

The crude material was purified by flash chromatography (silica gel, 12 g, 3% to 5% MeOH in DCM). The fractions were combined, concentrated, and was triturated with $CH_2Cl_2$/hexanes to give a white powder as desired product (52 mg, 56% yield). (ES+) m/z Calcd: [(M++H)+]: 620. found: 620.

Example 456

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-fluoro-phenyl)-amide

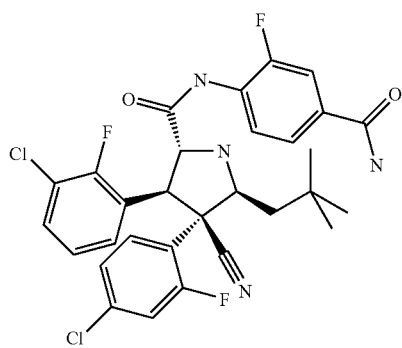

Molecular Weight = 603.4765
Molecular Formula = C30H27Cl2F3N4O2

In a 10 mL round-bottomed flask, 4-((2R,3S,4R,5S)-3-(3-chloro-2-fluorophenyl)-4-(4-chloro-2-fluorophenyl)-4-cyano-5-neopentylpyrrolidine-2-carboxamido)-3-fluorobenzoic acid (70 mg, 116 μmol, Eq: 1.00) was combined with CH₂Cl₂ (5.43 ml) to give a suspension. DIPEA (18.0 mg, 24.3 μl, 139 μmol, Eq: 1.2) and HATU (48.4 mg, 127 μmol, Eq: 1.1) were added. The reaction was stirred for 2 minutes and 2M ammonia (290 μl, 579 μmol, Eq: 5) in Methanol was added. The reaction mixture was stirred for overnight.

The crude material was purified by flash chromatography (silica gel, 40 g, 2% to 5% MeOH in DCM). The fractions were combined and concentrated to give a white solid (68 mg, 95% yield). (ES+) m/z Calcd: [(M+H)+]: 603. found: 603.

Example 457

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-methoxy-phenyl)-amide

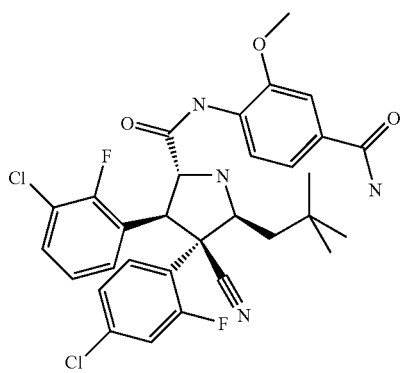

Molecular Weight = 615.5125
Molecular Formula = C31H30Cl2F2N4O3

In a 10 mL round-bottomed flask, 4-((2R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (200 mg, 324 μmol, Eq: 1.00) was combined with CH₂Cl₂ (5.43 ml) to give a suspension. DIPEA (50.3 mg, 68.0 μl, 389 μmol, Eq: 1.2) and HATU (136 mg, 357 μmol, Eq: 1.1) were added. The reaction was stirred for 2 minutes and 2M ammonia (811 μl, 1.62 mmol, Eq: 5) in methanol was added. The reaction mixture was stirred for 4 h.

The crude material was dissolved in CH₂Cl₂/methanol, purified by flash chromatography (silica gel, 40 g, 2% to 30% EtOAc in DCM). The pure fractions were combined and triturated with CH₂Cl₂/Hexanes to give a white solid (66 mg). Some later fractions were combined and purified by HPLC to give a white foam (14.9 mg). 81 mg. yield, 40.5%. (ES+) m/z Calcd: [(M+H)+]: 615. found: 615.

Example 458

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,5-difluoro-benzoic acid methyl ester

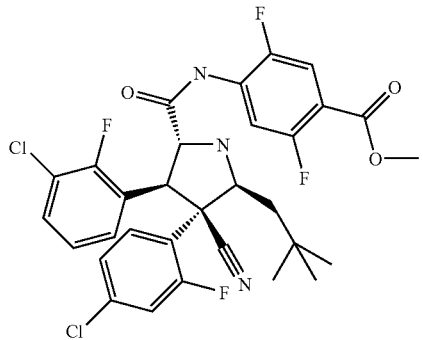

Molecular Weight = 636.4787
Molecular Formula = C31H27Cl2F4N3O3

To a stirred solution of (2R,3S,4R,5S)-3-(3-chloro-2-fluorophenyl)-4-(4-chloro-2-fluorophenyl)-4-cyano-5-neopentylpyrrolidine-2-carboxylic acid (300 mg, 0.64 mmol) in methylene chloride (5 mL), DIPEA (Aldrich, 2.57 mmol, 0.45 ml) was added followed by diphenylphosphinic chloride (Aldrich, 1.93 mmol, 0.37 ml). The mixture was stirred for 5 min. and 4-amino-2,5-difluoro-benzoic acid methyl ester (Prepared by methylation of the corresponding acid. 201 mg, 0.76 mmol) was added and the mixture was stirred overnight. The reaction was quenched with 10% sodium carbonate (6 mL) and the mixture was stirred for 15 min. The organic layer was separated and the solvent was reduced to about 3 ml. The solution was loaded onto a 40 g silica gel column and eluted with 2% EtOAc/CH₂Cl₂ to give a mixture of the desired product and aniline. The crude was again chromatographed on a reverse phase column and eluted with 50-95% acetonitrile/water to give a white solid. 82 mg. (ES+) m/z Calcd: [(M+H)+]: 636. found: 636.

Example 459

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,5-difluoro-benzoic acid

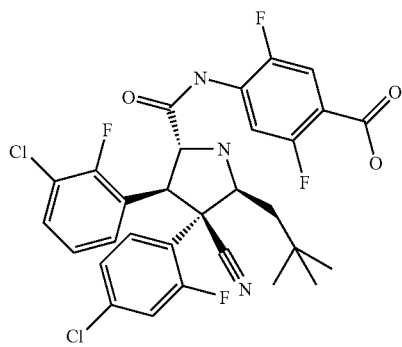

Molecular Weight = 622.4516
Molecular Formula = C30H25Cl2F4N3O3

To a stirred solution of methyl 4-((2R,3S,4R,5S)-3-(3-chloro-2-fluorophenyl)-4-(4-chloro-2-fluorophenyl)-4-cyano-5-neopentylpyrrolidine-2-carboxamido)-2,5-difluorobenzoate (75 mg, 0.118 mmol) in methylene chloride (10 ml), AlBr$_3$ (Aldrich, 59 mg, 0.94 mmol) was added followed by dimethyl sulfide (Aldrich, 0.2 ml, 0.63 mmol). The mixture was stirred at rt for 2 hrs. The solvent was removed and the residue was treated with 3 ml of acetonitrile and 10 ml of water. The mixture was then extracted with ethyl acetate. Removal of solvent gave an off white solid. 72 mg. (ES+) m/z Calcd: [(M+H)+]: 622. found: 622.

Example 460

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (3,5-difluoro-4-iodo-phenyl)-amide

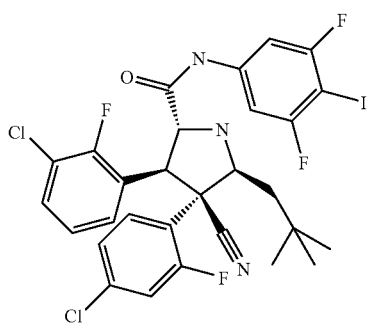

Molecular Weight = 704.3381
Molecular Formula = C29H24Cl2F4IN3O

In a 25 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid, 2,2,2-trifluoroacetic acid salt (1:1) (400 mg, 688 µmol, Eq: 1.00) was combined with CH$_2$Cl$_2$ (3 ml) to give a clear solution. N-ethyl-N-isopropylpropan-2-amine (Aldrich, 356 mg, 479 µl, 2.75 mmol, Eq: 4) and diphenylphosphinic chloride (Aldrich, 407 mg, 328 µl, 1.72 mmol, Eq: 2.5) were added and the reaction was stirred at RT for 5 minutes. 3,5-Difluoro-4-iodoaniline (Aldrich, 175 mg, 688 µmol, Eq: 1.00) was added and the reaction mixture was stirred at RT overnight.

The reaction mixture was diluted with DCM (10 ml), washed with 0.5 M HCl (2×5 ml) and sat. NaHCO$_3$ (1×10 ml), dried over Na$_2$SO$_4$ and concentrated under vacuum. The crude material was purified by flash chromatography (silica gel, 40 g, 5% to 25% EtOAc/Hexanes). The pure fractions were combined to give the desired product as a white solid (345 mg, 71% yield).

(ES$^+$) m/z Calcd: [(M+H)+]: 704. found: 704.

Example 461

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2,6-difluoro-benzoic acid

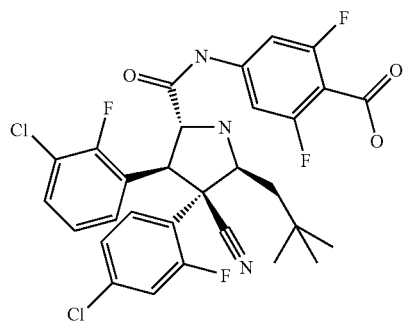

Molecular Weight = 622.4516
Molecular Formula = C30H25Cl2F4N3O3

In a 100 mL round-bottomed flask, methyl 4-((2R,3S,4R,5S)-3-(3-chloro-2-fluorophenyl)-4-(4-chloro-2-fluorophenyl)-4-cyano-5-neopentylpyrrolidine-2-carboxamido)-2,6-difluorobenzoate (270 mg, 424 µmol, Eq: 1.00) was combined with THF (5 ml) and MeOH (5.00 ml) to give a colorless solution. NaOH (1.06 ml, 2.12 mmol, Eq: 5) was added. The reaction mixture was heated to 40° C. and stirred for 3 h.

The crude reaction mixture was concentrated under vacuum to remove half of the solvent and the residue was diluted with water. Some solid came out and was removed by filtration (dimer, M+1=899). The filtrate was acidified with 1N HCl to pH 2-3 and was extracted with EtOAc (3×10 mL). The organic layers were dried over Na$_2$SO$_4$ and concentrated under vacuum to give a yellow foam. This was recrystallized from DCM/Hexanes to give a white solid as desired product (27 mg, 10% yield). (ES$^+$) m/z Calcd: [(M+H)+]: 622. found: 622.

Example 462

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-3-hydroxy-benzoic acid

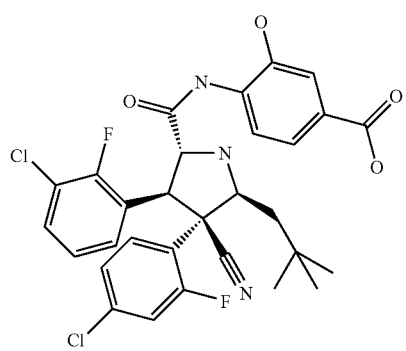

Molecular Weight = 602.4702
Molecular Formula = C30H27Cl2F2N3O4

In a 25 mL round-bottomed flask, 442R,3S,4R,5S)-3-(3-chloro-2-fluorophenyl)-4-(4-chloro-2-fluorophenyl)-4-cyano-5-neopentylpyrrolidine-2-carboxamido)-3-methoxybenzoic acid (200 mg, 324 µmol, Eq: 1.00) was combined with CH$_2$Cl$_2$ (5 ml) to give a suspension. Boron tribromide (Aldrich, 1.3 ml, 1.3 mmol, Eq: 4) was added dropwise to give a brown solution. The reaction mixture was stirred for overnight (72% conversion after 4 hours) at rt. To the reaction mixture was added CH$_3$CN (3 mL). Then were added CH$_2$Cl$_2$ (10 ml) and water (10 ml) with stirring. Layers were separated, the aqueous layer was extracted with CH$_2$Cl2$_2$ (2×10 ml). The organic layers were combined, washed with H$_2$O (1×15 mL), sat NaCl (1×15 mL), dried over Na$_2$SO$_4$ and concentrated under vacuum. To it was added DCM (3 mL). The solid was collected by filtration and washed with DCM. Obtained was a white solid as desired product (140 mg, 72% yield). (ES+) m/z Calcd: [(M+H)+]: 602. found: 602.

Example 463

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-methoxy-phenyl)-amide

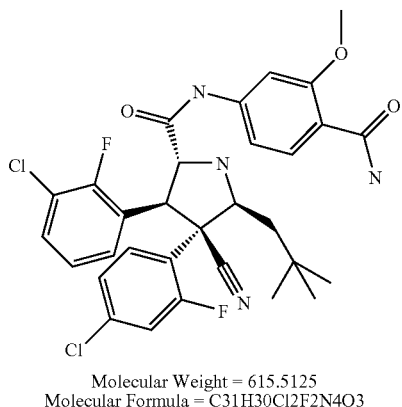 [SMILES: COc1cc(NC(=O)[C@@H]2N[C@@H](CC(C)(C)C)[C@](C#N)(c3ccc(Cl)cc3F)[C@H]2c2cccc(Cl)c2F)ccc1C(N)=O]

Molecular Weight = 615.5125
Molecular Formula = C31H30Cl2F2N4O3

To a stirred solution of 4-((2R,3S,4R,5S)-3-(3-chloro-2-fluorophenyl)-4-(4-chloro-2-fluorophenyl)-4-cyano-5-neopentylpyrrolidine-2-carboxamido)-2-methoxybenzoic acid (250 mg, 0.41 mmol) in methylene chloride (8 ml), HATU (154 mg, 0.41 mmol) and DIPEA (0.1 ml, 0.57 mmol) were added. The mixture was stirred for 5 min. at rt and ammonia in methanol (2N, 2 ml) was added and the mixture was stirred overnight. The solvent was reduced to 3 ml and loaded onto a silica gel column, eluted with 3% methanol and methylene chloride to give 230 mg desired product. (ES+) m/z Calcd: [(M+H)+]: 615. found: 615.

Example 464

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-trifluoromethoxy-phenyl)-amide

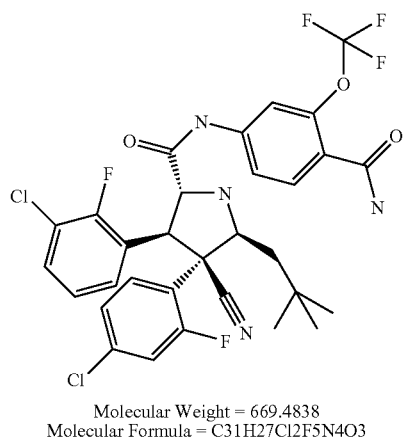 [SMILES: CC(C)(C)C[C@@H]1N[C@@H](C(=O)Nc2ccc(C(N)=O)c(OC(F)(F)F)c2)[C@H](c2cccc(Cl)c2F)[C@@]1(C#N)c1ccc(Cl)cc1F]

Molecular Weight = 669.4838
Molecular Formula = C31H27Cl2F5N4O3

In a 20 mL round-bottomed flask, 442R,3S,4R,5S)-3-(3-chloro-2-fluorophenyl)-4-(4-chloro-2-fluorophenyl)-4-cyano-5-neopentylpyrrolidine-2-carboxamido)-3-(trifluoromethoxy)benzoic acid (80 mg, 119 µmol, Eq: 1.00) was combined with CH$_2$Cl$_2$ (7 ml) to give a suspension. DIPEA (20.0 mg, 27.1 µl, 155 µmol, Eq: 1.3) and HATU (49.9 mg, 131 µmol, Eq: 1.1) were added. The reaction was stirred for 5 minutes and 2M ammonia (298 µl, 597 µmol, Eq: 5) in methanol was added. The reaction mixture was stirred for overnight.

The crude material was dissolved in CH$_2$Cl$_2$/methanol, purified by flash chromatography (silica gel, 24 g, 2% to 5% MeOH in DCM). The pure fractions were combined and concentrated and triturated with 15% EtOAc/Hexanes to give a white solid as desired product (75 mg, 91% yield). (ES+) m/z Calcd: [(M+H)+]: 669. found: 669.

Example 465

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-fluoro-phenyl)-amide

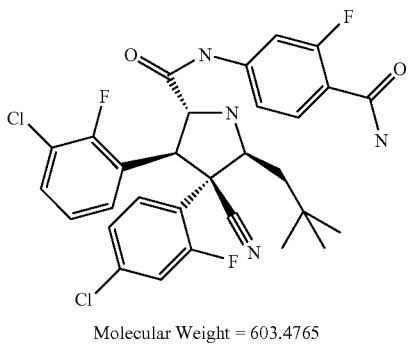

Molecular Weight = 603.4765
Molecular Formula = C30H27Cl2F3N4O2

In a 20 mL round-bottomed flask, 442R,3S,4R,5S)-3-(3-chloro-2-fluorophenyl)-4-(4-chloro-2-fluorophenyl)-4-cyano-5-neopentylpyrrolidine-2-carboxamido)-2-fluorobenzoic acid (60 mg, 99.3 μmol, Eq: 1.00) was combined with CH₂Cl₂ (5 ml) to give a suspension. DIPEA (16.7 mg, 22.5 μl, 129 μmol, Eq: 1.3) and HATU (42 mg, 110 μmol, Eq: 1.11) were added. The reaction was stirred for 5 minutes and 2M ammonia (248 μl, 496 μmol, Eq: 5) in Methanol was added. The reaction mixture was stirred for overnight.

The crude material was dissolved in CH₂Cl₂/methanol, purified by flash chromatography (silica gel, 24 g, 2% to 5% MeOH in DCM). The pure fractions were combined and concentrated and triturated with 15% EtOAc/Hexanes to give a white solid as desired product (54 mg, 88% yield). (ES+) m/z Calcd: [(M+H)+]: 603. found: 603.

Example 466

Preparation of (2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-chloro-phenyl)-amide

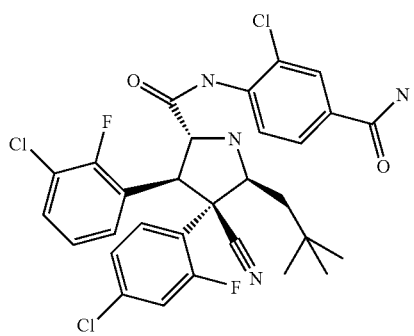

Molecular Weight = 619.9311
Molecular Formula = C30H27Cl3F2N4O2

In a 20 mL round-bottomed flask, 3-chloro-4-((2R,3S,4R,5S)-3-(3-chloro-2-fluorophenyl)-4-(4-chloro-2-fluorophenyl)-4-cyano-5-neopentylpyrrolidine-2-carboxamido)benzoic acid (215 mg, 346 μmol, Eq: 1.00) was combined with CH₂Cl₂ (8 ml) to give a suspension. DIPEA (58.2 mg, 78.6 μl, 450 μmol, Eq: 1.3) and HATU (145 mg, 381 μmol, Eq: 1.1) were added. The reaction was stirred for 5 minutes and 2M ammonia (866 μl, 1.73 mmol, Eq: 5) in methanol was added. The reaction mixture was stirred over weekend.

The crude material was dissolved in CH₂Cl₂/methanol, purified by flash chromatography (silica gel, 24 g, 2% to 5% MeOH in DCM). The pure fractions were combined and concentrated to give a white solid as desired product (155 mg, 71% yield). (ES+) m/z Calcd: [(M+H)+]: 619. found: 619.

Example 467

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-fluoro-5-methoxy-benzoic acid methyl ester

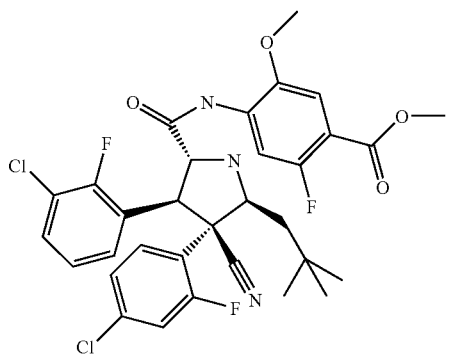

Molecular Weight = 648.5148
Molecular Formula = C32H30Cl2F3N3O4

In a 15 mL round-bottomed flask, (2R,3S,4R,5S)-3-(3-chloro-2-fluorophenyl)-4-(4-chloro-2-fluorophenyl)-4-cyano-5-neopentylpyrrolidine-2-carboxylic acid (250 mg, 535 μmol, Eq: 1.00), was combined with CH₂Cl₂ (3 ml) to give a clear solution. DIPEA (242 mg, 327 μl, 1.87 mmol, Eq: 3.5) and diphenylphosphenic chloride (316 mg, 255 μl, 1.34 mmol, Eq: 2.5) were added and the reaction was stirred at RT for 5 minutes. Methyl 4-amino-2-fluoro-5-methoxybenzoate (107 mg, 535 μmol, Eq: 1.00) was added and the reaction mixture was stirred at RT overnight.

The crude reaction mixture was diluted with CH₂Cl₂ and washed with 0.5 M HCl (1×5 ml), dried over MgSO₄, filtered and concentrated to give a yellow oil.

The oil was dissolved in CH₂Cl₂, purified by flash chromatography (silica gel, 24 g, 5% to 20% EtOAc in hexanes). The fractions were combined, concentrated and triturated with CH₂Cl₂/Hexanes. Obtained was an off white solid (220 mg, 63% yield). (ES+) m/z Calcd: [(M+H)+]: 648. found: 648.

Example 468

Preparation of 4-{[(2R,3S,4R,5S)-4-(4-Chloro-2-fluoro-phenyl)-3-(3-chloro-2-fluoro-phenyl)-4-cyano-5-(2,2-dimethyl-propyl)-pyrrolidine-2-carbonyl]-amino}-2-fluoro-5-methoxy-benzoic acid

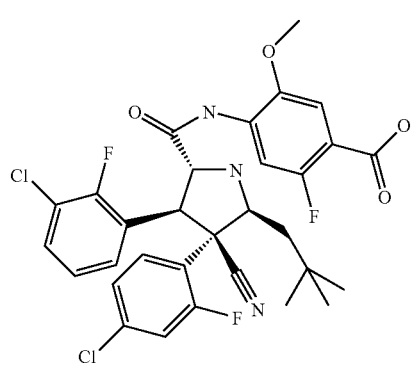

Molecular Weight = 634.4877
Molecular Formula = C31H28Cl2F3N3O4

In a 25 mL round-bottomed flask, methyl 4-((2R,3S,4R,5S)-3-(3-chloro-2-fluorophenyl)-4-(4-chloro-2-fluorophenyl)-4-cyano-5-neopentylpyrrolidine-2-carboxamido)-2-fluoro-5-methoxybenzoate (80 mg, 123 μmol, Eq: 1.00) was combined with THF (2 ml) and MeOH (4 ml) at 45° C. to give a colorless solution. 1 N NaOH (0.5 ml, 1.00 mmol, Eq: 8.11) was added. The reaction mixture was stirred at 40° C. for 2 hr.

The reaction mixture was concentrated to remove about ½ of the solvent, acidified with 1N HCl to PH 2-3, diluted with water (10 ml) and EtOAc (15 ml). The layers were separated and the aqueous was extracted with EtOAc (2×15 ml). The organic layers were combined, washed with sat NaCl (1×15 mL), dried over MgSO$_4$ and concentrated under vacuum. Triturating with CH$_2$Cl$_2$ gave a white solid (60 mg, 73% yield). (Calcd: [(M+H)+]: 634. found: 634.

Example 469

Preparation of 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-4-methyl-pentanoic acid

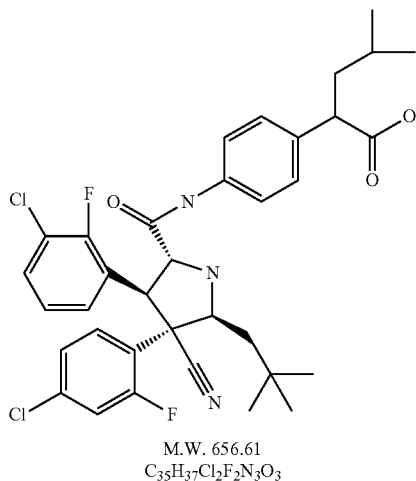 [SMILES: CC(C)CC(C(=O)O)c1ccc(NC(=O)[C@@H]2N[C@@H](CC(C)(C)C)[C@](C#N)(c3ccc(Cl)cc3F)[C@H]2c2cccc(Cl)c2F)cc1]

M.W. 656.61
C$_{35}$H$_{37}$Cl$_2$F$_2$N$_3$O$_3$

A mixture of 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-4-methyl-pentanoic acid methyl ester (14 mg, 0.0209 mmol) was dissolved in THF (15 mL) and methanol (5 mL), then 2N LiOH (5 mL) was added and stirred at room temperature for 2 hours. The mixture was diluted with water and extracted with ethyl acetate (2×). The organic phase was separated then concentrated under reduced pressure to afford the crude mixture. The compound was purified by RP-HPLC (20%-95% acetonitrile/water) to afford of 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-4-methyl-pentanoic acid trifluoroacetate salt (8.2 mg, 51.0%) as a light brown solid. HRMS (ES$^+$) m/z Calcd C$_{35}$H$_{37}$Cl$_2$F$_2$N$_3$O$_3$+H [(M+H)$^+$]: 656.2253. found: 656.1254.

Example 470

Preparation of chiral 2-(4-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid methyl ester

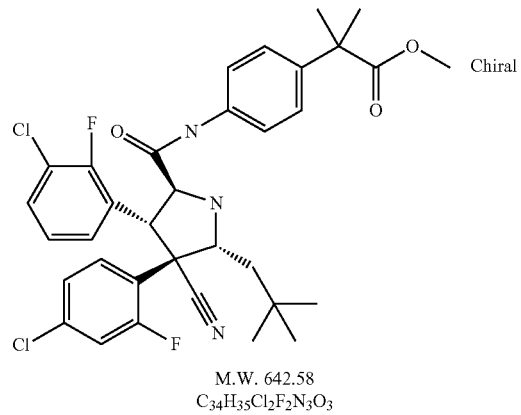 [SMILES: COC(=O)C(C)(C)c1ccc(NC(=O)[C@H]2N[C@H](CC(C)(C)C)[C@@](C#N)(c3ccc(Cl)cc3F)[C@@H]2c2cccc(Cl)c2F)cc1]

M.W. 642.58
C$_{34}$H$_{35}$Cl$_2$F$_2$N$_3$O$_3$

Methyl 2-(4-aminophenyl)-2-methyl propanoate hydrochloride (100 mg, 0.435 mmol) was dissolved in dichloromethane (30 mL) then iPr$_2$NEt (0.5 mL, 2.86 mmol) was added and stirred at 25° C. In three portions chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (100 mg, 0.214 mmol) and 2-(7-azabenzotriazol-1-yl)-n,n,n',n'-tetramethyluronium hexafluorophosphate (HATU, 106 mg, 0.278 mmol) was added in 30 min intervals. The reaction mixture was stirred at 25° C. for 5 hours. Reaction not complete by LCMS, additional methyl 2-(4-aminophenyl)-2-methyl propanoate hydrochloride (30 mg, 0.13 mmol) was added to the reaction and stirred an additional 1 hr. The mixture was diluted with CH$_2$Cl$_2$ and washed with water. The organic phase was separated, then concentrated under reduced pressure. The compound was purified by column chromatography (8 g silica column, Analogix, 1-100% EtOAc/heptane) to afford chiral 2-(4-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid methyl ester as a light yellow foam (26 mg, 18.9%) LCMS (ES$^+$) m/z Calcd for C$_{34}$H$_{35}$Cl$_2$F$_2$N$_3$O$_3$+H [(M+H)$^+$]: 642.58. found: 642.1.

Example 471

Preparation of chiral 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid

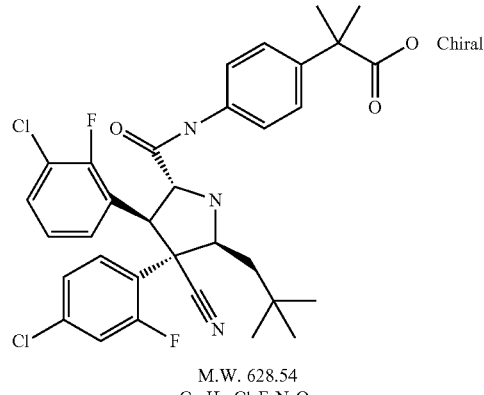

M.W. 628.54
C$_{33}$H$_{33}$Cl$_2$F$_2$N$_3$O$_3$

A mixture of chiral 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid methyl ester (21 mg, 0.0327 mmol) was dissolved in THF (3 mL) and methanol (1 mL), followed by 2N LiOH (1 mL). The reaction mixture was stirred at room temperature for 14 hours. The mixture was diluted with water and extracted with ethyl acetate (2×). The organic phase was separated then concentrated under reduced pressure to afford crude product. The compound was purified by RP-HPLC (30%-95% of acetonitrile/water) to afford of chiral 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid (12 mg, 58.4%) as an off-white solid. HRMS (ES$^+$) m/z Calcd for $C_{33}H_{33}Cl_2F_2N_3O_3$+H [(M+H)$^+$]: 628.1940. found: 628.1937.

Example 472

Preparation of chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-methyl-1-methylcarbamoyl-ethyl)-phenyl]-amide

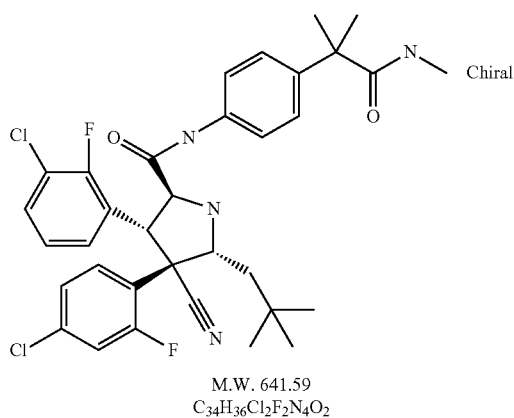 [SMILES: CNC(=O)C(C)(C)c1ccc(NC(=O)[C@H]2N[C@H](CC(C)(C)C)[C@@](C#N)(c3ccc(Cl)cc3F)[C@@H]2c2cccc(Cl)c2F)cc1]

M.W. 641.59
$C_{34}H_{36}Cl_2F_2N_4O_2$

Reagent 2-(4-amino-phenyl)-N-methyl-isobutyramide (130 mg, 0.676 mmol) was dissolved in dichloromethane (4 mL) then iPr$_2$NEt (0.375 mL, 2.15 mmol) was added and stirred at 25° C. In three portions chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (100 mg, 0.214 mmol) and 2-(7-azabenzotriazol-1-yl)-n,n,n',n'-tetramethyluronium hexafluorophosphate (HATU, 106 mg, 0.278 mmol) was added in 30 min intervals. The reaction mixture was stirred at 25° C. for 5 hours, complete by LCMS. The mixture was then diluted with CH$_2$Cl$_2$ and washed with water. The organic phase was separated, then concentrated under reduced pressure. The compound was purified by RP-HPLC (30-95% acetonitrile/water) to afford chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-methyl-1-methylcarbamoyl-ethyl)-phenyl]-amide as an off-white solid (56 mg, 40.8%) HRMS (ES$^+$) m/z Calcd for $C_{34}H_{36}Cl_2F_2N_4O_2$+H [(M+H)$^+$]: 641.2256. found: 641.2256.

Example 473

Preparation of chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {4-[1-(3-hydroxy-propylcarbamoyl)-1-methyl-ethyl]-phenyl}amide

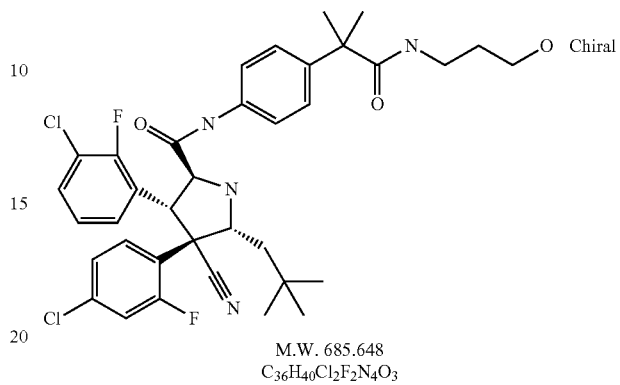

M.W. 685.648
$C_{36}H_{40}Cl_2F_2N_4O_3$

Reagent 2-(4-aminophenyl)-N-(3-hydroxylpropyl)-2-propanamide (130 mg, 0.550 mmol) was dissolved in dichloromethane (4 mL) then iPr$_2$NEt (0.375 mL, 2.15 mmol) was added and stirred at 25° C. In three portions chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (100 mg, 0.214 mmol) and 2-(7-azabenzotriazol-1-yl)-n,n,n',n'-tetramethyluronium hexafluorophosphate (HATU, 106 mg, 0.278 mmol) was added in 30 min intervals. The reaction mixture was stirred at 25° C. for 5 hours. The mixture was then diluted with CH$_2$Cl$_2$ and washed with water. The organic phase was separated, then concentrated under reduced pressure. The compound was purified by RP-HPLC (30-95% acetonitrile/water) to afford chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {4-[1-(3-hydroxy-propylcarbamoyl)-1-methyl-ethyl]-phenyl}amide as an off-white solid (75 mg, 51.1%) HRMS (ES$^+$) m/z Calcd for $C_{36}H_{40}Cl_2F_2N_4O_3$+H [(M+H)$^+$]: 685.2519. found: 685.2523.

Example 474

Preparation of chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-carbamoyl-1-methyl-ethyl)-phenyl]-amide

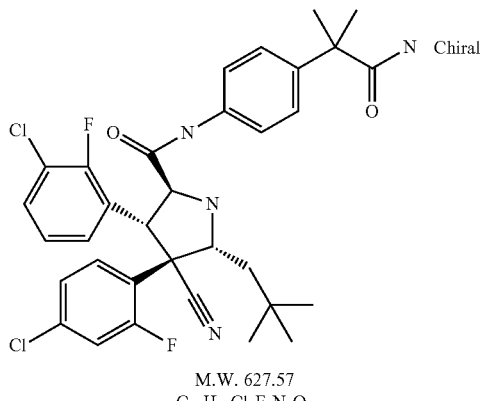

M.W. 627.57
$C_{33}H_{34}Cl_2F_2N_4O_2$

Reagent 2-(4-amino-phenyl)isobutyramide (80 mg, 0.171 mmol) was dissolved in dichloromethane (5 mL) then iPr$_2$NEt (0.1 mL, 0.573 mmol) was added and stirred at 25° C. Chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (50 mg, 0.107 mmol) and 2-(7-azabenzotriazol-1-yl)-n,n,n',n'-tetramethyluronium hexafluorophosphate (HATU, 60 mg, 0.158 mmol) was added and the reaction mixture was stirred at 25° C. for 2 hours. The mixture was then diluted with CH$_2$Cl$_2$ and washed with water. The organic phase was separated, then concentrated under reduced pressure. The compound was purified by RP-HPLC (30-95% acetonitrile/water) to afford chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-carbamoyl-1-methyl-ethyl)-phenyl]-amide [4-(1-methyl-1-methylcarbamoyl-ethyl)-phenyl]-amide as an solid (32.5 mg, 48.4%)

LCMS (ES$^+$) m/z Calcd for C$_{33}$H$_{34}$Cl$_2$F$_2$N$_4$O$_2$+H [(M+H)$^+$]: 627.2. found: 627.0.

Example 475

In Vitro Activity Assay

The ability of the compounds to inhibit the interaction between p53 and MDM2 proteins was measured by an HTRF (homogeneous time-resolved fluorescence) assay in which recombinant GST-tagged MDM2 binds to a peptide that resembles the MDM2-interacting region of p53 (Lane et al.), Binding of GST-MDM2 protein and p53-peptide (biotinylated on its N-terminal end) is registered by the FRET (fluorescence resonance energy transfer) between Europium (Eu)-labeled anti-GST antibody and streptavidin-conjugated Allophycoeyanin (APC).

Test is performed in black flat-bottom 384-well plates (Costar) in a total volume of 40 uL containing: 90 nM biotinylate peptide, 160 ng/ml GST-MDM2, 20 nM streptavidin-APC (PerkinElmerWallac), 2 nM Eu-labeled anti-GST-antibody (PerkinElmerWallac), 0.2% bovine serum albumin (BSA), 1 mM dithiothreitol (DTT) and 20 mM Tris-borate saline (TBS) buffer as follows: Add 10 uL of GST-MDM2 (640 ng/ml working solution) in reaction buffer to each well. Add 10 uL diluted compounds (1:5 dilution in reaction buffer) to each well, mix by shaking. Add 20 uL biotinylated p53 peptide (180 nM working solution) in reaction buffer to each well and mix on shaker. Incubate at 37° C. for 1 h. Add 20 uL streptavidin-APC and Eu-anti-GST antibody mixture (6 nM Eu-anti-GST and 60 nM streptavidin-APC working solution) in TBS buffer with 0:2% BSA, shake at room temperature for 30 minutes and read using a TRF-capable plate reader at 665 and 615 nm (Victor 5, Perkin ElmerWallac). If not specified, the reagents were purchased from Sigma. Chemical Co.

Activity data for some of the Example compounds expressed as IC$_{50}$:bsa:0.02% are as follows:

| Example Number | IC$_{50}$: bsa: 0.02% |
|---|---|
| 7 | 0.309 |
| 14 | 2.38 |
| 43d | 0.603 |
| 69d | 0.192 |
| 83d | 0.165 |

What is claimed is:
1. A compound of the formula

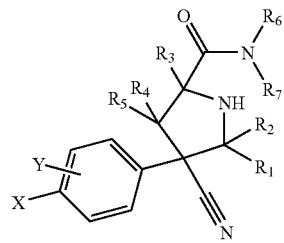

wherein
X is selected from the group consisting of H, F, Cl, Br, I, cyano, nitro, ethynyl, cyclopropyl, methyl, ethyl, isopropyl, vinyl and methoxy,
Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, hetereoaryl, hetereocycle, COOR', OCOR', CONR'R", NR'COR", NR"SO$_2$R', SO$_2$NR'R" and NR'R" wherein
R' and R" is independently selected from H or substituted or unsubstituted lower alkyl, substituted or unsubstituted lower cycloalkyl, substituted or unsubstituted lower alkenyl, substituted or unsubstituted lower cycloalkenyl, substituted or unsubstituted aryl, substituted or unsubstituted hetereoaryl or substituted or unsubstituted hetereocycle, and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle,
one of R$_1$ and R$_2$ is selected from the group consisting of lower alkyl,
substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl and the other is hydrogen or lower alkyl,
R$_3$ is H or lower alkyl,
one of R$_4$ and R$_5$ is selected from the group consisting of lower alkyl, substituted lower alkyl, lower alkenyl, substituted lower alkenyl, aryl, substituted aryl,
heteroaryl, substituted heteroaryl, heterocycle, substituted heterocycle, cycloalkyl, substituted cycloalkyl, cycloalkenyl, and substituted cycloalkenyl and the other is hydrogen,
R$_6$ and R$_7$ are selected from the group consisting of (CH$_2$)$_n$—R', (CH$_2$)$_n$—NR'R", (CH$_2$)$_n$—NR'COR", (CH$_2$)$_n$—NR'SO$_2$R", (CH$_2$)$_n$—COON, (CH$_2$)$_n$—COOR', (CH$_2$)$_n$—CONR' R", (CH$_2$)$_n$—OR', (CH$_2$)$_n$—SR', (CH$_2$)$_n$—SOR', (CH$_2$)$_n$—SO$_2$R', (CH$_2$)$_n$—COR', (CH$_2$)$_n$—SO$_3$H, (CH$_2$)$_n$—SONR' R", (CH$_2$)$_n$—SO$_2$NR'R", (CH$_2$CH$_2$O)$_m$—(CH$_2$)$_n$—R', (CH$_2$CH$_2$O)$_m$—(CH$_2$)$_n$—OH, (CH$_2$CH$_2$O)$_m$—(CH$_2$)$_n$—OR', (CH$_2$CH$_2$O)$_m$—(CH$_2$)$_n$—NR'R", (CH$_2$CH$_2$O)$_m$—(CH$_2$)$_n$—NR'COR", (CH$_2$CH$_2$O)$_m$—(CH$_2$)$_n$—NR'SO$_2$R", (CH$_2$CH$_2$O)$_m$—(CH$_2$)$_n$—COOH, (CH$_2$CH$_2$O)$_m$—(CH$_2$)$_n$—COOR', (CH$_2$CH$_2$O)$_m$—(CH$_2$)$_n$—CONR'R", (CH$_2$CH$_2$O)$_m$—(CH$_2$)$_n$—SO$_2$R', (CH$_2$CH$_2$O)$_m$—(CH$_2$)$_n$—COR', (CH$_2$CH$_2$O)$_m$—

(CH₂)ₙ—SONR'R", (CH₂CH₂O)ₘ—(CH₂)ₙ—SO₂NR'R", (CH₂)ₚ—(CH₂CH₂O)ₘ—(CH₂)ₙ—R', (CH₂)ₚ—(CH₂CH₂O)ₘ—(CH₂)ₙ—OH, (CH₂)ₚ—(CH₂CH₂O)ₘ—(CH₂)ₙ—OR', (CH₂)ₚ—(CH₂CH₂O)ₘ—(CH₂)ₙ—NR'R", (CH₂)ₚ—(CH₂CH₂O)ₘ—(CH₂)ₙ—NR'COR", (CH₂)ₚ—(CH₂CH₂O)ₘ—(CH₂)ₙ—NR'SO₂R", (CH₂)ₚ—(CH₂CH₂O)ₘ—(CH₂)ₙ—COOH, (CH₂)ₚ—(CH₂CH₂O)ₘ—(CH₂)ₙ—COOR', (CH₂)ₚ—(CH₂CH₂O)ₘ—(CH₂)ₙ—CONR'R", (CH₂)ₚ—(CH₂CH₂O)ₘ—(CH₂)ₙ—SO₂R', (CH₂)ₚ—(CH₂CH₂O)ₘ—(CH₂)ₙ—COR', (CH₂)ₚ—(CH₂CH₂O)ₘ—(CH₂)ₙ—SONR'R", (CH₂)ₚ—(CH₂CH₂O)ₘ—(CH₂)ₙ—SO₂NR'R", —COR', —SOR' and SO₂R' wherein R' and R" are the same definitions as above, m, n and p are independently 0 to –6 and the pharmaceutically acceptable salts and esters thereof.

2. A compound of claim 1 of the formula

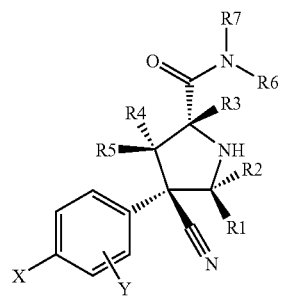

II wherein

X is selected from the group consisting of H, F, Cl, Br, I, cyano, nitro, ethynyl, cyclopropyl, methyl, ethyl, isopropyl, vinyl and methoxy, Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, hetereoaryl, hetereocycle, COOR', OCOR', CONR'R", NR'COR", NR"SO₂R', SO₂NR'R" and NR'R" wherein R' and R" are independently selected from H or substituted or unsubstituted lower alkyl, substituted or unsubstituted lower cycloalkyl, substituted or unsubstituted lower alkenyl, substituted or unsubstituted lower cycloalkenyl, substituted or unsubstituted aryl, substituted or unsubstituted hetereoaryl or substituted or unsubstituted hetereocycle, and wherein R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, R₁ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, R₂ is hydrogen or lower alkyl, R₃ is H or lower alkyl, R₅ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, R₄ is hydrogen, R₆ and R₇ are selected from the group consisting of (CH₂)ₙ—R', (CH₂)ₙ—NR'R", (CH₂)ₙ—NR'COR", (CH₂)ₙ—NR'SO₂R", (CH₂)ₙ—COOH, (CH₂)ₙ—COOR', (CH₂)ₙ—CONR'R", (CH₂)ₙ—OR', (CH₂)ₙ—SR', (CH₂)ₙ—SOR', (CH₂)ₙ—SO₂R', (CH₂)ₙ—COR', (CH₂)ₙ—SO₃H, (CH₂)ₙ—SONR'R", (CH₂)ₙ—SO₂NR'R", (CH₂CH₂O)ₘ—(CH₂)ₙ—R', (CH₂CH₂O)ₘ—(CH₂)ₙ—OH, (CH₂CH₂O)ₘ—(CH₂)ₙ—OR', (CH₂CH₂O)ₘ—(CH₂)ₙ—NR'R", (CH₂CH₂O)ₘ—(CH₂)ₙ—NR'COR", (CH₂CH₂O)ₘ—(CH₂)ₙ—NR'SO₂R", (CH₂CH₂O)ₘ—(CH₂)ₙ—COOH, (CH₂CH₂O)ₘ—(CH₂)ₙ—COOR', (CH₂CH₂O)ₘ—(CH₂)ₙ—CONR'R", (CH₂CH₂O)ₘ—(CH₂)ₙ—SO₂R', (CH₂CH₂O)ₘ—(CH₂)ₙ—COR', (CH₂CH₂O)ₘ—(CH₂)ₙ—SONR'R", (CH₂CH₂O)ₘ—(CH₂)ₙ—SO₂NR'R", (CH₂)ₚ—(CH₂CH₂O)ₘ—(CH₂)ₙ—R', (CH₂)ₚ—(CH₂CH₂O)ₘ—(CH₂)ₙ—OH, (CH₂)ₚ—(CH₂CH₂O)ₘ—(CH₂)ₙ—OR', (CH₂)ₚ—(CH₂CH₂O)ₘ—(CH₂)ₙ—NR'R", (CH₂)ₚ—(CH₂CH₂O)ₘ—(CH₂)ₙ—NR'COR", (CH₂)ₚ—(CH₂CH₂O)ₘ—(CH₂)ₙ—NR'SO₂R", (CH₂)ₚ—(CH₂CH₂O)ₘ—(CH₂)ₙ—COOH, (CH₂)ₚ—(CH₂CH₂O)ₘ—(CH₂)ₙ—COOR', (CH₂)ₚ—(CH₂CH₂O)ₘ—(CH₂)ₙ—CONR'R", (CH₂)ₚ—(CH₂CH₂O)ₘ—(CH₂)ₙ—SO₂R', (CH₂)ₚ—(CH₂CH₂O)ₘ—(CH₂)ₙ—COR', (CH₂)ₚ—(CH₂CH₂O)ₘ—(CH₂)ₙ—SONR'R", (CH₂)ₚ—(CH₂CH₂O)ₘ—(CH₂)ₙ—SO₂NR'R", —COR', —SOR' and SO₂R' wherein R' and R" are the same definitions as above, m, n, and p are independently 0 to-6 and the pharmaceutically acceptable salts and esters thereof.

3. The compound of claim 2 wherein

X is F, Cl or Br,

Y is one to two group(s) independently selected from the group consisting of H, F, Cl, Br, I, CN, OH, nitro, lower alkyl, cycloalkyl, lower alkoxy, lower alkenyl, lower cycloalkenyl and lower alkynyl, R₁ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl and substituted cycloalkenyl, R₂ is hydrogen, R₃ is H, R₅ is selected from the group consisting of aryl, substituted aryl, heteroaryl and substituted heteroaryl, R₄ is hydrogen, R₆ and R₇ are selected from the group consisting of (CH₂)ₙ—R', (CH₂)ₙ—NR'R", (CH₂)ₙ—NR'COR", (CH₂)ₙ—NR'SO₂R", (CH₂)ₙ—COOH, (CH₂)ₙ—COOR', (CH₂)ₙ—CONR' R", (CH₂)ₙ—OR', (CH₂)ₙ—SR', (CH₂)ₙ—SOR', (CH₂)ₙ—SO₂R', (CH₂)ₙ—COR', (CH₂)ₙ—SO₃H, (CH₂)ₙ—SONR' R", (CH₂)ₙ—SO₂NR'R", (CH₂CH₂O)ₘ—(CH₂)ₙ—R', (CH₂CH₂O)ₘ—(CH₂)ₙ—OH, (CH₂CH₂O)ₘ—(CH₂)ₙ—OR', (CH₂CH₂O)ₘ—(CH₂)ₙ—NR'R", (CH₂CH₂O)ₘ—(CH₂)ₙ—NR'COR", (CH₂CH₂O)ₘ—

(CH₂)ₙ—NR'SO₂R", (CH₂CH₂O)ₘ—(CH₂)ₙ—COOH, (CH₂CH₂O)ₘ—(CH₂)ₙ—COOR', (CH₂CH₂O)ₘ—(CH₂)ₙ—CONR'R", (CH₂CH₂O)ₘ—(CH₂)ₙ—SO₂R', (CH₂CH₂O)ₘ—(CH₂)ₙ—COR', (CH₂CH₂O)ₘ—(CH₂)ₙ—SONR'R", (CH₂CH₂O)ₘ—(CH₂)ₙ—SO₂NR'R", (CH₂)ₚ—(CH₂CH₂O)ₘ—(CH₂)ₙ—R', (CH₂)ₚ—(CH₂CH₂O)ₘ—(CH₂)ₙ—OH, (CH₂)ₚ—(CH₂CH₂O)ₘ—(CH₂)ₙ—OR', (CH₂)ₚ—(CH₂CH₂O)ₘ—(CH₂)ₙ—NR'R", (CH₂)ₚ—(CH₂CH₂O)ₘ—(CH₂)ₙ—NR'COR", (CH₂)ₚ—(CH₂CH₂O)ₘ—(CH₂)ₙ—NR'SO₂R", (CH₂)ₚ—(CH₂CH₂O)ₘ—(CH₂)ₙ—COOH, (CH₂)ₚ—(CH₂CH₂O)ₘ—(CH₂)ₙ—COOR', (CH₂)ₚ—(CH₂CH₂O)ₘ—(CH₂)ₙ—CONR'R", (CH₂)ₚ—(CH₂CH₂O)ₘ—(CH₂)ₙ—SO₂R', (CH₂)ₚ—(CH₂CH₂O)ₘ—(CH₂)ₙ—COR', (CH₂)ₚ—(CH₂CH₂O)ₘ—(CH₂)ₙ—SONR'R", (CH₂)ₚ—(CH₂CH₂O)ₘ—(CH₂)ₙ—SO₂NR'R", —COR', —SOR' and SO₂R' wherein R' and R" are independently selected from H or substituted or unsubstituted lower alkyl, substituted or unsubstituted lower cycloalkyl, substituted or unsubstituted lower alkenyl, substituted or unsubstituted lower cycloalkenyl, substituted or unsubstituted aryl, substituted or unsubstituted hetereoaryl or substituted or unsubstituted hetereocycle, and wherein R' and R" may also independently link to form a cyclic structure selected from substituted or unsubstituted cycloalkyl, substituted or unsubstituted cycloalkenyl, substituted or unsubstituted heteroaryl or substituted or unsubstituted heterocycle, m, n and p are independently 0 to-6 and the pharmaceutically acceptable salts and esters thereof.

4. The compound of claim 2 wherein

X is F, Cl or Br,

Y is a mono-substituting group selected from H or F and

R₁ is selected from the group consisting of lower alkyl, substituted lower alkyl, lower alkenyl, substituted lower alkenyl, heterocycle, substituted heterocycle, cycloalkyl, substituted cycloalkyl, cycloalkenyl and substituted cycloalkenyl.

5. The compound of claim 2 wherein

R₁ is a substituted lower alkyl of the formula

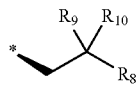

where R₈, R₉ are both methyl or linked to form a cyclopropyl, cyclobutyl, cyclopentyl or a cyclohexyl group, R₁₀ is (CH₂)ₘ—R₁₁, m is 0, 1 or 2, R₁₁ is selected from hydrogen, hydroxyl, lower alkyl, lower alkoxy, aryl, substituted aryl, hetereoaryl, substituted heteroaryl, heterocycle or substituted heterocycle, R₂ is H, R₃ is H, R₅ is a substituted phenyl selected from

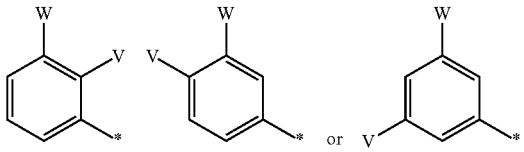

W is F, Cl or Br,

V is H or F,

R₄ is hydrogen, one of R₆ and R₇ is hydrogen and the other is (CH₂)ₙ—R', n is 0 or 1 and R' is selected from aryl, substituted aryl, hetereoaryl, substituted heteroaryl, heterocycle or substituted heterocycle.

6. A compound of claim 1 selected from the group consisting of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-morpholin-4-yl-ethyl)-amide, (2R,3R,4R,5S)-3-(3-chloro-phenyl)-4-(4-chloro-phenyl)-4-cyano-5-(2,2-dimethyl-propyl)-pyrrolidine-2-carboxylic acid (2-morpholin-4-yl-ethyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid dimethylamide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide, (2R,3R,4R,5S)-3-(3-chloro-phenyl)-4-(4-chloro-phenyl)-4-cyano-5-(2,2-dimethyl-propyl)-pyrrolidine-2-carboxylic acid ((S)-3,4-dihydroxy-butyl)-amide, rac-(2S,3R,4R,5R)-4-(3-chloro-phenyl)-3-(4-chloro-phenyl)-2-(2,2-dimethyl-propyl)-5-[4-(2-morpholin-4-yl-2-oxo-ethyl)-piperazine-1-carbonyl]-pyrrolidine-3-carbonitrile, rac-(2S,3R,4R,5R)-4-(3-chloro-phenyl)-3-(4-chloro-phenyl)-2-(2,2-dimethyl-propyl)-5-[4-(2-oxo-2-pyrrolidin-1-yl-ethyl)-piperazine-1-carbonyl]-pyrrolidine-3-carbonitrile, rac-(2S,3R,4R,5R)-4-(3-chloro-phenyl)-3-(4-chloro-phenyl)-2-(2,2-dimethyl-propyl)-5-[4-(2-hydroxy-ethyl)-piperazine-1-carbonyl]-pyrrolidine-3-carbonitrile, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (4-hydroxy-butyl)-amide, and rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-pyrrolidin-1-yl-ethyl)-amide.

7. A compound of claim 1 selected from the group consisting of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-piperazin-1-yl-ethyl)-amide, (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid methyl ester, (S)-2-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-3-methyl-butyric acid, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (1-hydroxymethyl-cyclopropylmethyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (1-hydroxymethyl-cyclobutylmethyl)-amide, rac-(2R,3R,4R,5S)-3-(3-chloro-phenyl)-4-(4-chloro-phenyl)-4-cyano-5-(2,2-dimethyl-propyl)pyrrolidine-2-carboxylic acid (3,3-dimethyl-butyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2,2-dimethyl-propyl)-amide, (2S,3R,4R,5R)-4-(3-chloro-phenyl)-3-(4-chloro-phenyl)-2-(2,2-dimethyl-propyl)-5-((S)-2-hydroxymethyl-pyrrolidine-1-carbonyl)pyrrolidine-3-carbonitrile and rac-(2R,3R,4R,5S)-3-(3-chloro-phenyl)-4-(4-chloro-phenyl)-4-cyano-5-(2,2-dimethyl-propyl)-pyrrolidine-2-carboxylic acid 2-(3,4-dimethoxy-phenyl)ethyl amide.

8. A compound of claim 1 selected from the group consisting of (2S,3S,4S,5R)-3-(3-chloro-phenyl)-4-(4-chloro-phenyl)-4-cyano-5-(2,2-dimethyl-propyl)-pyrrolidine-2-carboxylic acid ((R)-1-hydroxymethyl-3-methyl-butyl) amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-propyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid [2-(cis-2,6-dimethyl-morpholin-4-yl)-ethyl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-cyclopropyl-ethyl)-amide, rac-(3-{[(2R,3R,4R,5S)-3-(3-chloro-phenyl)-4-(4-chloro-phenyl)-4-cyano-5-(2,2-dimethyl-propyl)-pyrrolidine-2-carbonyl]-amino}-propyl)-carbamic acid tert-butyl ester, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-amino-propyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [3-(1-acetyl-piperidin-4-ylamino)-propyl]-amide, rac-(2R,3R,4R,5S)-3-(3-chloro-phenyl)-4-(4-chloro-phenyl)-4-cyano-5-isobutyl-pyrrolidine-2-carboxylic acid (3-hydroxy-propyl)-amide, rac-(2R,3R,4R,5R)-5-(3-chloro-phenyl)-4-(4-chloro-phenyl)-4-cyano-3-(2,2-dimethyl-propyl)-pyrrolidine-2-carboxylic acid (3-hydroxy-propyl)-amide and rac-(2R,3R,4R,5S)-3-(3-chloro-phenyl)-4-(4-chloro-phenyl)-4-cyano-5-(2,2-dimethyl-propyl)-2-methyl-pyrrolidine-2-carboxylic acid (3-hydroxy-propyl)-amide.

9. A compound of claim 1 selected from the group consisting of rac-(2R,3S,4R,5S)-3-(3-chloro-2-fluoro-phenyl)-4-(4-chloro-phenyl)-4-cyano-5-cyclopentylmethyl-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (2-hydroxy-1,1-dimethyl-ethyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (3-hydroxy-2,2-dimethyl-propyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid [2-(2-hydroxy-ethoxy)-ethyl]-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (2-acetylamino-ethyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid (3-imidazol-1-yl-propyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((R)-4-hydroxy-3-methyl-butyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid cyclopropylmethoxy-amide, rac-(2R,3R,4R,5S)-3,5-bis-(3-chloro-phenyl)-4-(4-chloro-phenyl)-4-cyano-pyrrolidine-2-carboxylic acid [2-((S)-2,2-dimethyl-[1,3]dioxolan-4-yl)-ethyl]-amide, rac-(2R,3R,4R,5S)-3,5-bis-(3-chloro-phenyl)-4-(4-chloro-phenyl)-4-cyano-pyrrolidine-2-carboxylic acid ((S)-3,4-dihydroxy-butyl)-amide and rac-(2R,3R,4R,5S)-3-(3-chloro-phenyl)-4-(4-chloro-phenyl)-4-cyano-5-(1-ethyl-propyl)-pyrrolidine-2-carboxylic acid ((S)-3,4-dihydroxy-butyl)-amide.

10. A compound of claim 1 selected from the group consisting of rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-3-(3-chloro-phenyl)-4-(4-chloro-phenyl)-4-cyano-5-isobutyl-pyrrolidine-2-carboxylic acid ((S)-3,4-dihydroxy-butyl)-amide, rac-(2R,3R,4R,5R)-3-(3-chloro-phenyl)-4-(4-chloro-phenyl)-4-cyano-5-isobutyl-pyrrolidine-2-carboxylic acid ((S)-3,4-dihydroxy-butyl)-amide, rac-(2R,3R,4R,5R)-3-(3-chloro-phenyl)-4-(4-chloro-phenyl)-4-cyano-5-(1-ethyl-propyl)-pyrrolidine-2-carboxylic acid ((S)-3,4-dihydroxy-butyl)-amide, rac-(2R,3R,4R)-3-(3-chloro-phenyl)-4-(4-chloro-phenyl)-4-cyano-5,5-diethyl-pyrrolidine-2-carboxylic acid ((S)-3,4-dihydroxy-butyl)-amide, rac-(2R,3R,4R,5S)-3-(3-chloro-phenyl)-4-(4-chloro-phenyl)-4-cyano-5-isopropyl-pyrrolidine-2-carboxylic acid ((S)-3,4-dihydroxy-butyl)-amide, rac-(2R,3R,4R,5S)-3-(3-chloro-phenyl)-4-(4-chloro-phenyl)-4-cyano-5-cyclohexyl-pyrrolidine-2-carboxylic acid ((S)-3,4-dihydroxy-butyl)-amide, rac-(2R,3S,4R,5S)-5-tert-butyl-3-(3-chloro-2-fluoro-phenyl)-4-(4-chloro-phenyl)-4-cyano-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-fluoro-phenyl)-4-cyano-5-(2,2-dimethyl-propyl)-pyrrolidine-2-carboxylic acid ((S)-3,4-dihydroxy-butyl)-amide and (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide.

11. A compound of claim 1 selected from the group consisting of rac-(2S,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3S,4R,5S)-4-(4-bromo-phenyl)-3-(3-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-cyano-5-(2,2-dimethyl-propyl)-4-(4-fluoro-phenyl)-pyrrolidine-2-carboxylic acid ((S)-3,4-dihydroxy-butyl)-amide, rac-(2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide, (2R,3S,4R,5S)-3-(3-chloro-2-fluoro-phenyl)-4-cyano-4-(2,4-dichloro-phenyl)-5-(2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-methyl-phenyl)-4-cyano-5-(2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-phenyl)-4-cyano-5-cyclohexylmethyl-pyrrolidine-2-carboxylic acid ((S)-3,4-dihydroxy-butyl)-amide, rac-(2S,3S,4R,5S)-3-(3-chloro-2-fluoro-phenyl)-4-(4-chloro-phenyl)-4-cyano-5-cyclohexylmethyl-pyrrolidine-2-carboxylic acid ((S)-3,4-dihydroxy-butyl)-amide, rac-(2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide, (2R,3S,4R,5S)-4-(4-chloro-2-fluoro-phenyl)-4-cyano-3-(2,3-difluoro-phenyl)-5-(2,2-dimethyl-propyl)-pyrrolidine-2-carboxylic acid ((S)-3,4-dihydroxy-butyl)-amide, rac-(2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide and (2R,3S,4R,5S)-3-(3-bromo-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide.

12. A compound of claim 1 selected from the group consisting of rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide, (2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-4-(4-chloro-2-fluoro-phenyl)-4-cyano-5-(2,2-dimethyl-propyl)-3-(3-fluoro-phenyl)-pyrrolidine-2-carboxylic acid ((S)-3,4-dihydroxy-butyl)-amide, rac-(2R,3R,4R,5S)-3-(3-bromo-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2S,3R,4R,5S)-3-(3-bromo-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-4-(4-chloro-2-fluoro-phenyl)-4-cyano-3-(3,4-dichloro-phenyl)-5-(2,2-dimethyl-propyl)-pyrrolidine-2-carboxylic acid ((S)-3,4-dihydroxy-butyl)-amide rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, (2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-3-(4-bromo-thiophen-2-yl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, (2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide, (2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide, rac-(2R,3R,4R,5S)-4-(4-chloro-2-fluoro-phenyl)-3-(3-chloro-phenyl)-4-cyano-5-(2,2-dimethyl-propyl)-pyrrolidine-2-carboxylic acid ((R)-3,4-dihydroxy-butyl)-amide, rac-(2R,3S,4R,5S)-3-(3-chloro-2-fluoro-phenyl)-4-(4-chloro-phenyl)-4-cyano-5-(2,2-dimethyl-propyl)-pyrrolidine-2-carboxylic acid ((R)-3,4-dihydroxy-butyl)-amide and rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((R)-3,4-dihydroxy-butyl)-amide.

13. A compound of claim 1 selected from the group consisting of rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2,3-trimethyl-butyl)-pyrrolidine-2-carboxylic acid ((R)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-dimethyl-but-3-enyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-dimethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2-methyl-2-phenyl-propyl)-pyrrolidine-2-carboxylic acid ((S)-3,4-dihydroxy-butyl)-amide, rac-(2R,3S,4R,5S)-4-(4-chloro-2-fluoro-phenyl)-3-(5-chloro-2-methoxy-phenyl)-4-cyano-5-(2,2-dimethyl-propyl)-pyrrolidine-2-carboxylic acid ((S)-3,4-dihydroxy-butyl)-amide, rac(2R,3R,4R,5S)-3-(3-chloro-phenyl)-4-(4-chloro-phenyl)-4-cyano-5-(2,2-dimethyl-propyl)-pyrrolidine-2-carboxylic acid (quinolin-3-ylmethyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-hydroxy-benzylamide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-ethyl-butyl)-amide, rac-(2R,3R,4R,5S)-3-(3-chloro-5-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide, rac-(2R,3S,4R,5S)-4-(4-chloro-2-fluoro-phenyl)-3-[5-chloro-2-(2-hydroxy-ethoxy)-phenyl]-4-cyano-5-(2,2-dimethyl-propyl)-pyrrolidine-2-carboxylic acid ((S)-3,4-dihydroxy-butyl)-amide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-carboxylic acid tert-butyl ester, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid piperidin-4-ylamide trifluoroacetic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methanesulfonylpiperidin-4-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-carbonyl-piperidin-4-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-benzoyl-piperidin-4-yl)-amide and rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-carboxylic acid isopropylamide.

14. A compound of claim 1 selected from the group consisting of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide, chiral 2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-2-methyl-propyl)-1H-pyrazol-3-yl]-amide, rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((R)-1-oxiranylmethoxy)-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((R)-3-amino-2-hydroxy-propoxy)-2-methyl-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-{2-[(R)-2-hydroxy-3-(3-hydroxy-propylamino)-propoxy]-2-methyl-propyl}-1H-pyrazol-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-{2-[(R)-2-hydroxy-3-(2-hydroxy-1-hydroxymethyl-ethylamino)-propoxy]-2-methyl-propyl}-1H-pyrazol-3-yl)-amide, rac-(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carboxylic acid {1-[2-methyl-2-((S)-1-oxiranylmethoxy)-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-amino-2-hydroxy-propoxy)-2-methyl-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-2,3-dihydroxy-propoxy)-2-methyl-propyl]-1H-pyrazol-3-yl}-amide and of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl)amide.

15. A compound of claim 1 selected from the group consisting of rac-{(S)-3-[2-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-1,1-dimethyl-ethoxy]-2-hydroxy-propylamino}-acetic acid, rac-(2R,3S,4R,5S)-3-(3-chloro-2-fluoro-phenyl)-4-(4-chloro-2-fluoro-phenyl)-4-cyano-5-(2,2-dimethyl-propyl)pyrrolidine-2-carboxylic acid {1-[2-((S)-2-hydroxy-3-methylamino-propoxy)-2-methyl-propyl]-1H-pyrazol-3-yl}-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((R)-3-dimethylamino-2-hydroxy-propoxy)-2-methyl-propyl]-1H-pyrazol-3-yl)amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,3-dihydroxy-propyl)-1H-pyrazol-3-yl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-(2-hydroxy-ethyl)-1H-pyrazol-3-yl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid ((S)-2,3-dihydroxy-propyl)-amide, rac-(2S,3S,4S,5R)-3-(3-chloro-phenyl)-4-(4-chloro-phenyl)-4-cyano-5-(2,2-dimethyl-propyl)-pyrrolidine-2-carboxylic acid ((S)-2,3-dihydroxy-propyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-((R)-2,2-dimethyl-[1,3]dioxolan-4-ylmethyl)-1H-pyrazol-3-yl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid 2-trifluoromethyl-benzylamide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid 4-(2-oxo-pyrrolidin-1-yl)-benzylamide and rac-(2R,3R,4R,5S)-3-(3-chloro-phenyl)-4-(4-chloro-phenyl)-4-cyano-5-(2,2-dimethyl-propyl)-pyrrolidine-2-carboxylic acid (tetrahydro-pyran-4-ylmethyl)-amide.

16. A compound of claim 1 selected from the group consisting of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-hydroxy-2-hydroxymethyl-propyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid [2-(2-amino-ethoxy)-ethyl]-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methanesulfonyl-propyl)-amide, rac-(2R,3R,4R,5S)-3-(3-chloro-phenyl)-4-(4-chloro-phenyl)-4-cyano-5-(2,2-dimethyl-propyl)-pyrrolidine-2-carboxylic acid (2-methanesulfonyl-ethyl)-amide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-cyclohexylamino-1-carboxylic acid tert-butyl ester, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexylamine trifluoroacetic acid salt, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-N-methanesulfonamide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-N-methanesulfonamide, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-(1,1-dioxo)-2-isothiazolidine, rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-trans-cyclohexyl-urea and rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid N-[1-(2-hydroxyethyl)-piperidin-4-yl]amide.

17. A compound of claim 1 selected from the group consisting of rac-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-piperidine-1-sulfonic acid amide, rac 3-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetic acid, rac 3-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N,N-bis-(2-methoxy-ethyl)-acetamide, rac 3-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N,N-bis-(2-hydroxy-ethyl)-acetamide, rac 3-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N-(3-methoxy-propyl)-acetamide, rac 2-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-acetamide, rac (2S,3R,4S,5R)-4-(3-chloro-2-fluoro-phenyl)-3-(4-chloro-2-fluoro-phenyl)-2-(2,2-dimethyl-propyl)-5-[4-(2-morpholin-4-yl-2-oxo-ethyl)-piperazine-1-carbonyl]-pyrrolidine-3-carbonitrile, rac 2-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N-[2-((S)-2,2-dimethyl-[1,3]dioxolan-4-yl)-ethyl]-acetamide, rac 2-{4-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperazin-1-yl}-N—((S)-3,4-dihydroxy-butyl)-acetamide, rac {1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid methyl ester and rac {1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetic acid hydrochloride salt.

18. A compound of claim 1 selected from the group consisting of rac 2-{1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-acetamide, rac 2-{1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-N,N-bis-(2-hydroxy-ethyl)-acetamide, rac 2-{1-[(2R,3S,4R,5S)-3-(3-chloro-2-fluoro-phenyl)-4-(4-chloro 2-fluoro-phenyl)-4-cyano-5-(2,2-dimethyl-propyl)-pyrrolidine-2-carbonyl]-piperidin-4-yl}-N-(2-hydroxy-ethyl)-N-methyl-acetamide, rac 2-{1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-piperidin-4-yl}-N-(2-hydroxy-propyl)-acetamide, rac {[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-acetic acid tert-butyl ester, rac {[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-acetic aid trifluoro acetic acid salt, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid carbamoylmethyl-amide, {[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-acetic aid trifluoro acetic acid salt, rac 3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-carbamoyl-phenyl)-amide and rac 3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester.

19. A compound of claim 1 selected from the group consisting of rac 3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-hydroxymethyl-phenyl)-amide, rac (3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-propyl)-carbamic acid tert-butyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-amino-propyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-(aminosulfonyl-amino)-propyl]-amide, rac 2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester, rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-carbamoyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide and rac 2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid ethyl ester.

20. A compound of claim 1 selected from the group consisting of rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac 2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-cyano-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-hydroxy-2-methyl-propyl)-amide, rac 3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid 2-hydroxy-2-methyl-propyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-methanesulfonyl-amino-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1H-tetrazol-5-ylmethyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-ureado-propyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-methylsulfanyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-methanesulfonyl-phenyl)-amide and rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-methanesulfinyl-phenyl)-amide.

21. A compound of claim 1 selected from the group consisting of

3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-carbamoyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-amino-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide, rac 2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiazole-4-carboxylic acid ethyl ester, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1,3-dioxo-2,3-dihydro-1H-isoindol-5-yl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide and rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methylsulfanyl-phenyl)-amide.

22. A compound of claim 1 selected from the group consisting of rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide, 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid tert-butyl ester, 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, 4-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylamino-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-trifluoro-methanesulfonylamino-phenyl)-amide, rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [3-(1-methyl-1H-tetrazol-5-yl)-phenyl]-amide, rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [3-(2-methyl-1H-tetrazol-5-yl)-phenyl]-amide and (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-oxo-1,6-dihydro-pyridin-3-yl)-amide.

23. A compound of claim 1 selected from the group consisting of (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1H-tetrazol-5-yl)-phenyl]-amide, rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [4-(2-methyl-1H-tetrazol-5-yl)-phenyl]-amide, rac (2R,3R,4R,5S)-4-(4-chloro-2-fluoro-phenyl)-3-(3-chloro-2-methyl-phenyl)-4-cyano-5-(2,2-dimethyl-propyl)-pyrrolidine-2-carboxylic acid [4-(1-methyl-1H-tetrazol-5-yl)-phenyl]-amide, rac 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid ethyl ester, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide, (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-(1H-tetrazol-5-yl)-phenyl]-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-carbamoyl-3-chloro-phenyl)-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [3-chloro-4-(1H-tetrazol-5-yl)-phenyl]-amide, rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-fluoro-phenyl)-amide and rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-fluoro-phenyl)-amide.

24. A compound of claim 1 selected from the group consisting of
- rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (3-chloro-phenyl)-amide,
- rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid tert-butyl ester,
- (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (5-iodo-pyridin-2-yl)-amide,
- rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-ethylcarbamoyl-phenyl)-amide,
- rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-fluoro-benzoic acid,
- rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-methoxy-pyridin-3-yl)-amide,
- rac 3-({[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid methyl ester,
- rac 4-({[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid methyl ester,
- rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide,
- (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide and
- (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-chloro-phenyl)-amide.

25. A compound of claim 1 selected from the group consisting of
- rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid methyl ester,
- rac 3-({[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid,
- rac 4-({[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-methyl)-benzoic acid,
- (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide,
- (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetylamino-phenyl)-amide,
- (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide,
- (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonyl-phenyl)-amide,
- rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid,
- rac 5-bromo-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methoxy-benzoic acid methyl ester,
- rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methyl-benzoic acid methyl ester and
- rac 2-chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester.

26. A compound of claim 1 selected from the group consisting of
- rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-trifluoromethyl-benzoic acid methyl ester,
- rac 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-2-methyl-benzoic acid,
- rac 2-chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid,
- rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2H-[1,2,4]triazol-3-yl)-phenyl]-amide,
- rac (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(5-oxo-2,5-dihydro-1H-[1,2,4]thiazol-3-yl)-phenyl]-amide,
- rac-(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-butyl)-amide,
- rac-(2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide,
- (2R,3S,4R,5S)-3-(3-chloro-2-fluoro-phenyl)-4-(4-chloro-2-fluoro-phenyl)-4-cyano-5-(2-cyclopropyl-2-methyl-propyl)-pyrrolidine-2-carboxylic acid ((S)-3,4-dihydroxy-butyl)-amide,
- rac-(2R,3S,4R,5S)-3-(3-chloro-2-fluoro-phenyl)-4-(4-chloro-3-methyl-phenyl)-4-cyano-5-(2,2-dimethyl-propyl)-pyrrolidine-2-carboxylic acid ((S)-3,4-dihydroxy-butyl)-amide,
- rac-(2R,3S,4R,5S)-3-(3-chloro-2-fluoro-phenyl)-4-(4-chloro-2-fluoro-phenyl)-4-cyano-5-(tetrahydro-pyran-4-ylmethyl)-pyrrolidine-2-carboxylic acid ((S)-3,4-dihydroxy-butyl)-amide and rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide.

27. A compound of formula 1 selected from the group consisting of (2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-butyl)-amide, rac-(2R,3S,4R,5S)-5-(2-benzyloxycarbonyl-2-methyl-propyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2-methoxycarbonyl-2-methyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2,2-diethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(2-ethyl-2-methyl-butyl)-pyrrolidine-2-carboxylic acid ((S)-3,4-dihydroxy-butyl)-amide, rac-(2R,3R,4R,5S)-4-(4-chloro-2,6-difluoro-phenyl)-3-(3-chloro-phenyl)-4-cyano-5-(2,2-dimethyl-propyl)-pyrrolidine-2-carboxylic acid ((S)-3,4-dihydroxy-butyl)-amide, rac-(2R,3R,4R,5S)-4-(4-chloro-2,5-difluoro-phenyl)-3-(3-chloro-phenyl)-4-cyano-5-(2,2-dimethyl-propyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide and (2R,3S,4R,5S)-3-(3-chloro-2-fluoro-phenyl)-4-(4-chloro-2-fluoro-phenyl)-4-cyano-5-(3-methoxy-2,2-dimethyl-propyl)-pyrrolidine-2-carboxylic acid ((S)-3,4-dihydroxy-butyl)-amide.

28. A compound of claim 1 selected from the group consisting of rac-(2R,3S,4R,5S)-3-(3-chloro-2-fluoro-phenyl)-4-(4-chloro-2-fluoro-phenyl)-4-cyano-5-(2-ethyl-2-hydroxymethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-methyl-oxetan-3-ylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-ethyl-oxetan-3-ylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(1-hydroxymethyl-cyclopropylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(1-hydroxymethyl-cyclobutylmethyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide, (2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(1-hydroxymethyl-cyclohex-3-enylmethyl)-pyrrolidine-2-carboxylic acid ((S)-3,4-dihydroxy-butyl)-amide and rac-(2R,3S,4R,5S)-3-(3-chloro-2-fluoro-phenyl)-4-(4-chloro-2-fluoro-phenyl)-4-cyano-5-(1-hydroxymethyl-cyclohexylmethyl)-pyrrolidine-2-carboxylic acid ((S)-3,4-dihydroxy-butyl)-amide.

29. A compound of claim 1 selected from the group consisting of rac-(2R,3S,4R,5S)-3-(3-chloro-2-fluoro-phenyl)-4-(4-chloro-2-fluoro-phenyl)-4-cyano-5-[4-(2-hydroxy-ethoxy)-2,2-dimethyl-butyl]-pyrrolidine-2-carboxylic acid ((S)-3,4-dihydroxy-butyl)-amide, rac-(2R,3S,4R,5S)-5-(4-azido-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-5-(4-amino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-5-(4-acetylamino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(4-methanesulfonylamino-2,2-dimethyl-butyl)-pyrrolidine-2-carboxylic acid ((S)-3,4-dihydroxy-butyl)-amide, rac-(2R,3S,4R,5S)-5-(4-benzoylamino-2,2-dimethyl-butyl)-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-[2-methyl-2-(5-methyl-furan-2-yl)-propyl]-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-[3-(4-methoxy-phenyl)-2,2-dimethyl-propyl]-pyrrolidine-2-carboxylic acid ((S)-3,4-dihydroxy-butyl)-amide, rac-(2R,3S,4R,5S)-5-[2-(1-benzyl-1,2,3,6-tetrahydro-pyridin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide, rac-(2R,3S,4R,5S)-5-[2-(1-benzyl-piperidin-4-yl)-2-methyl-propyl]-3-(3-chloro-2-fluoro-phenyl)-4-(4-chloro-2-fluoro-phenyl)-4-cyano-pyrrolidine-2-carboxylic acid ((S)-3,4-dihydroxy-butyl)-amide and rac-(2R,3S,4R,5S)-3-(3-chloro-2-fluoro-phenyl)-4-(4-chloro-2-fluoro-phenyl)-4-cyano-5-[2-(3,6-dihydro-2H-pyran-4-yl)-2-methyl-propyl]-pyrrolidine-2-carboxylic acid ((S)-3,4-dihydroxy-butyl)-amide.

30. A compound of claim 1 selected from the group consisting of rac-(2R,3S,4R,5S)-3-(3-chloro-2-fluoro-phenyl)-4-(4-chloro-2-fluoro-phenyl)-4-cyano-5-[2-methyl-2-(tetrahydro-pyran-4-yl)-propyl]-pyrrolidine-2-carboxylic acid ((S)-3,4-dihydroxy-butyl)-amide, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide, (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid ((S)-3,4-dihydroxy-4-methyl-pentyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((S)-3,4-dihydroxy-4-methyl-pentyl)-amide, rac-(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide, (2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carboxylic acid ((S)-3,4-dihydroxy-4-methyl-pentyl)-amide, rac-(2S,3R,4S,5R)-4-(3-cloro-2-fluoro-phenyl)-3-(4-chloro-2-fluoro-phenyl)-2-(2,2-dimethyl-propyl)-5-(3-hydroxy-azetidine-1-carbonyl)-pyrrolidine-3-carbonitrile, rac-(2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1H-pyrazol-3-yl]-amide and (2R,3S,4R,5S)-3-(3-chloro-2-fluoro-phenyl)-4-(4-chloro-2-fluoro-phenyl)-4-cyano-5-(3-hydroxy-2,2-dimethyl-propyl)-pyrrolidine-2-carboxylic acid [1-(2-hydroxy-2-methyl-propyl)-1H-pyrazol-3-yl]-amide.

31. A compound of claim 1 selected from the group consisting of rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide, (2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid [1-(2-hydroxy-2-methyl-propyl)-1H-pyrazol-3-yl]-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid amide, rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-nicotinic acid methyl ester, of rac-6-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-N-(2-hydroxy-1,1-dimethyl-ethyl)-nicotinamide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-acetylamino-pyridin-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-methyl-2-oxo-1,2-dihydro-pyridin-4-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [5-((S)-1,2-dihydroxy-ethyl)-pyrazin-2-yl]-amide, rac-(2R,3S,4R,5S)-3-(3-chloro-2-fluoro-phenyl)-4-(4-chloro-2-fluoro-phenyl)-4-cyano-5-(4-hydroxy-2,2-dimethyl-butyl)-pyrrolidine-2-carboxylic acid (1-methyl-2-oxo-1,2-dihydro-pyridin-4-yl)-amide and rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid methyl ester.

32. A compound of claim 1 selected from the group consisting of rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid, rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-furan-2-carboxylic acid amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (6-chloro-pyridazin-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-methyl-pyridin-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-ethoxy)-phenyl]-amide, rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid methyl ester, rac-5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid, 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-thiophene-2-carboxylic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-methoxy-pyridin-4-yl)-amide and rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-hydroxy-pyridin-4-yl)-amide.

33. A compound of claim 1 selected from the group consisting of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-acetyl-phenyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-bromo-acetyl)-phenyl]-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-dimethylamino-acetyl)-phenyl]-amide, rac-(5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-4H-[1,2,4]triazol-3-yl)-acetic acid, rac-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-yl)-acetic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1H-imidazol-4-ylmethyl)-amide, rac-(2S,3R,4S,5R)-4-(3-chloro-2-fluoro-phenyl)-3-(4-chloro-2-fluoro-phenyl)-2-(2,2-dimethyl-propyl)-5-(2-oxa-6-aza-spiro[3.3]heptane-6-carbonyl)-pyrrolidine-3-carbonitrile, rac-1-[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-azetidine3-carboxylic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-[1,2,3]triazol-1-yl-ethyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-carbamoyl methyl-1H-pyrazol-3-yl)-amide and rac-(2R,3R,4R,5S)-3-(3-chloro-phenyl)-4-(4-chloro-phenyl)-4-cyano-5-(2,2-dimethyl-propyl)-pyrrolidine-2-carboxylic acid [1-(2-hydroxy-2-methyl-propyl)-1H-pyrazol-3-yl]-amide.

34. A compound of claim 1 selected from the group consisting of rac-(2R,3R,4R,5S)-3-(3-chloro-phenyl)-4-(4-chloro-phenyl)-4-cyano-5-(2,2-dimethyl-propyl)-pyrrolidine-2-carboxylic acid (3-methanesulfonylamino-propyl)-amide, chiral (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {1-[2-((S)-3-dimethylamino-2-hydroxy-propoxy)-2-methyl-propyl]-1H-pyrazol-3-yl}-amide, rac-1-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-cyclopropane carboxylic acid, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(4-hydroxy-piperidin-4-ylmethyl)-1H-pyrazol-3-yl]-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-acetyl-thiophen-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (2-carbamoyl-thiophen-3-yl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-((S)-3-dimethylamino-2-hydroxy-propyl)-1H-pyrazol-3-yl]-amide, rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid and rac-[4-(3-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-pyrazol-1-ylmethyl)-4-hydroxy-piperidin-1-yl]-acetic acid.

35. A compound of claim 1 selected from the group consisting of rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid, rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester, rac-4-{[(2R,3S,4R,5S)-3-(5-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, rac-4-{[(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carbonyl]-amino}-benzoic acid methyl ester, rac-4-{[(2R,3R,4R,5S)-3-(3-chloro-4-fluoro-phenyl)-4-(4-chloro-2-fluoro-phenyl)-4-cyano-5-(2,2-dimethyl-propyl)-pyrrolidine-2-carbonyl]-amino}-benzoic acid, rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid methyl ester, rac-4-{[(2R,3R,4R,5S)-3-(3-bromo-phenyl)-4-(4-chloro-2-fluoro-phenyl)-4-cyano-5-(2,2-dimethyl-propyl)-pyrrolidine-2-carbonyl]-amino}-benzoic acid, rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid methyl ester, rac-4-{[(2R,3S,4R,5S)-3-(3-chloro-2-fluoro-phenyl)-4-(4-chloro-phenyl)-4-cyano-5-(2,2-dimethyl-propyl)-pyrrolidine-2-carbonyl]-amino}-benzoic acid and rac-4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid methyl ester.

36. A compound of claim 1 selected from the group consisting of rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-trifluoromethyl-phenyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(2-hydroxy-acetyl)-phenyl]-amide, (2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (4-methanesulfonylaminocarbonyl-phenyl)-amide, rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid [1-(2-hydroxy-ethyl)-2-oxo-1,2-dihydro-pyridin-4-yl]-amide, 4-{[(2R,3S,4R,5S)-3-(3-chloro-2-fluoro-phenyl)-4-(4-chloro-2-fluoro-phenyl)-4-cyano-5-(1-methyl-cyclohexylmethyl)-pyrrolidine-2-carbonyl]-amino}-benzoic acid, 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid, chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid, chiral (4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-acetic acid methyl ester, 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid methyl ester, 2-((2R,3S,4R,5S)-3-(3-chloro-2-fluorophenyl)-4-(4-chloro-2-fluorophenyl)-4-cyano-5-neopentylpyrrolidine-2-carboxamido)thiazole-5-carboxylic acid triethylamine salt and rac 6-((2R,3S,4R,5S)-3-(3-chloro-2-fluorophenyl)-4-(4-chloro-2-fluorophenyl)-4-cyano-5-neopentylpyrrolidine-2-carboxamido)-2-naphthoic acid.

37. A compound of claim 1 selected from the group consisting of rac 6-((2R,3S,4R,5S)-3-(3-chloro-2-fluorophenyl)-4-(4-chloro-2-fluorophenyl)-4-cyano-5-neopentylpyrrolidine-2-carboxamido)-2-naphthoic acid methyl ester, rac methyl 4-((2R,3S,4R,5S)-3-(3-chloro-2-fluorophenyl)-4-(4-chloro-2-fluorophenyl)-4-cyano-5-neopentylpyrrolidine-2-carboxamido)-3-methylbenzoate, rac 1 4-((2R,3S,4R,5S)-3-(3-chloro-2-fluorophenyl)-4-(4-chloro-2-fluorophenyl)-4-cyano-5-neopentylpyrrolidine-2-carboxamido)-3-methylbenzoic acid, rac (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-iodo-3,5-dimethyl-phenyl)-amide, rac 4-{[(2R,3S,4R,5S)-4-(4-chloro-2-fluoro-phenyl)-3-(3-chloro-2-fluoro-phenyl)-4-cyano-5-(2,2-dimethylpropyl)-pyrrolidine-2-carbonyl]-amino}-2,6-dimethylbenzoic acid, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2-methoxy-benzoic acid, rac 4-{[(2R,3S,4R,5S)-4-(4-chloro-2-fluoro-phenyl)-3-(3-chloro-2-fluoro-phenyl)-4-cyano5(2,2-dimethylpropyl)-pyrrolidine-2-carbonyl]-amino}-2-trifluoromethyl-benzoic acid, rac (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-bromo-2-methoxy-phenyl)-amide, rac (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-dimethylcarbamoyl-phenyl)-amide and 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2-methyl-benzoic acid.

38. A compound of claim 1 selected from the group consisting of rac 4-{[(2R,3S,4R,5S)-4-(4-chloro-2-fluoro-phenyl)-3-(3-chloro-2-fluoro-phenyl)-4-cyano-5-(2,2-dimethylpropyl)-pyrrolidine-2-carbonyl]-amino}-2,5-dimethylbenzoic acid, rac 4-{[(2R,3S,4R,5S)-4-(4-chloro-2-fluoro-phenyl)-3-(3-chloro-2-fluoro-phenyl)-4-cyano-5-(2,2-dimethylpropyl)-pyrrolidine-2-carbonyl]-amino}-3-fluoro-benzoic acid, rac (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (6-iodo-pyridin-3-yl)-amide, 2-chloro-4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-benzoic acid methyl ester, chiral 5-{[(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carbonyl]-amino}-1H-indole-2-carboxylic acid, chiral 5-{[(2R,3S,4R,5S)-3-(3-chloro-2-fluoro-phenyl)-4-(4-chloro-2-fluoro-phenyl)-4-cyano-5-(2,2-dimethylpropyl)-pyrrolidine-2-carbonyl]-amino}-1H-indole-2-carboxylic acid ethyl ester, rac-4-({[(2R,3S,4R,5S)-4-(4-chloro-2-fluoro-phenyl)-3-(3-chloro-2-fluoro-phenyl)-4-cyano-5-(2,2-dimethylpropyl)-pyrrolidine-2-carbonyl]-amino}-methyl)-cyclohexanecarboxylic acid methyl ester, rac-4-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-cyclohexanecarboxylic acid,
rac-4-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid methyl ester,
rac-4-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid,
rac-4-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid methyl ester and
rac-4-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-fluoro-benzoic acid.

39. A compound of claim 1 selected from the group consisting of
chiral 5-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid methyl ester,
chiral 5-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-pyridine-2-carboxylic acid,
chiral 6-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid ethyl ester,
chiral 6-({[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-nicotinic acid,
rac 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2-ethoxy-benzoic acid,
chiral (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-hydrazinocarbonyl-phenyl)-amide,
chiral [2-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-ethyl]-carbamic acid tert-butyl ester,
chiral (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid [4-(2-amino-ethyl)-phenyl]-amide,
chiral 5-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-pyrazine-2-carboxylic acid,
chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-methoxybenzoic acid and chiral-4-({[(2S,3R,4S,5R)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-methyl)-2-methoxy-benzoic acid.

40. A compound of claim 1 selected from the group consisting of
chiral methyl 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoate,
chiral 3-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)propanoic acid,
chiral-4-(((2S,3R,4S,5R)-3-(3-chloro-2-fluorophenyl)-4-(4-chloro-2-fluorophenyl)-4-cyano-5-neopentylpyrrolidine-2-carboxamido)methyl)-2-fluorobenzoic acid,
chiral 4-(((2R,3S,4R,5S)-3-(3-chloro-2-fluorophenyl)-4-(4-chloro-2-fluorophenyl)-4-cyano-5-neopentylpyrrolidine-2-carboxamido)methyl)-2-fluorobenzoic acid,
chiral (2R,3S,4R,5S)-3-(3-chloro-2-fluorophenyl)-4-(4-chloro-2-fluorophenyl)-4-cyano-N-(2-morpholinopyrimidin-5-yl)-5-neopentylpyrrolidine-2-carboxamide,
chiral (2R,3S,4R,5S)-3-(3-chloro-2-fluorophenyl)-4-(4-chloro-2-fluorophenyl)-4-cyano-5-neopentyl-N-(pyrimidin-5-yl)pyrrolidine-2-carboxamide,
chiral (2S,3R,4S,5R)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide,
chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylate,
chiral-5-((2R,3S,4R,5S)-3-(3-chloro-2-fluorophenyl)-4-(4-chloro-2-fluorophenyl)-4-cyano-5-neopentylpyrrolidine-2-carboxamido)-1H-benzo[d]imidazole-2-carboxylic acid,
chiral-methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylate and
chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzofuran-2-carboxylic acid.

41. A compound of claim 1 selected from the group consisting of
chiral-methyl 4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoate,
chiral-4-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)butanoic acid,
chiral methyl 5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylate,
chiral-5-((2R,3S,4R,5S)-3-(3-chloro-2-fluorophenyl)-4-(4-chloro-2-fluorophenyl)-4-cyano-5-neopentylpyrrolidine-2-carboxamido)benzo[d]oxazole-2-carboxylic acid,
chiral-(2R,3S,4R,5S)—N-(benzo[d]oxazol-5-yl)-3-(3-chloro-2-fluorophenyl)-4-(4-chloro-2-fluorophenyl)-4-cyano-5-neopentylpyrrolidine-2-carboxamide,
rac-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-benzyl)-carbamic acid tert-butyl ester, rac-(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-aminomethyl-phenyl)-amide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid [4-(methanesulfonylamino-methyl)-phenyl]-amide, 1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid ethyl ester, 1-(4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-phenyl)-piperidine-4-carboxylic acid, rac-(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-dimethylaminomethyl-phenyl)-amide and rac-5-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2-pyrrolidin-1-yl-benzoic acid.

42. A compound of claim 1 selected from the group consisting of rac-4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-4-methyl-piperidine-1-carboxylic acid tert-butyl ester, rac-(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-methyl-piperidin-4-yl)-amide, rac-(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (1-methanesulfonyl-4-methyl-piperidin-4-yl)-amide, methyl 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylate, 1-(4-((2R,3S,4R,5S)-3-(3-chloro-2-fluorophenyl)-4-(4-chloro-2-fluorophenyl)-4-cyano-5-neopentylpyrrolidine-2-carboxamido)phenyl)pyrrolidine-2-carboxylic acid, chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid, chiral 5-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-pyrrole-2-carboxylic acid ethyl ester, chiral (R)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid, chiral (S)-2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-butyric acid, chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester and chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid methyl ester.

43. A compound of claim 1 selected from the group consisting of chiral (S)-2-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid, chiral (S)-2-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-3-thiazol-4-yl-propionic acid, chiral 4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-1H-indole-2-carboxylic acid, rac (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (5-iodo-pyridin-2-yl)-amide, 2-chloro-4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-benzoic acid, 6-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid pyridin-2-ylamide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid pyridin-4-ylamide, 5-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid pyridin-3-ylamide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-iodo-3,5dimethyl-phenyl)-amide and 4-{[(2R,3S,4R,5S)-4-(4-chloro-2-fluoro-phenyl)-3-(3-chloro-2 fluoro-phenyl)-4-cyano-5-(2,2-dimethyl-propyl)-pyrrolidine-2-carbonyl]-amino}-2-fluoro-benzoic acid tert-butyl ester.

44. A compound of claim 1 selected from the group consisting of

4-{[(2R,3S,4R,5S)-4-(4-chloro-2-fluoro-phenyl)-3-(3-chloro-2 fluoro-phenyl)-4-cyano-5-(2,2-dimethyl-propyl)-pyrrolidine-2-carbonyl]-amino}-2-fluoro-benzoic acid, 4-{[(2R,3S,4R,5S)-4-(4-chloro-2-fluoro-phenyl)-3-(3-chloro-2 fluoro-phenyl)-4-cyano-5-(2,2-dimethyl-propyl)-pyrrolidine-2-carbonyl]-amino}-3-fluoro-benzoic acid, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2-trifluoromethyl-benzoic acid, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-iodo-2-trifluoromethoxy-phenyl)-amide, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-trifluoromethoxy-benzoic acid methyl ester, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-trifluoromethoxy-benzoic acid, 6-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid, 6-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-nicotinic acid methyl ester, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (6-iodo-pyridin-3-yl)-amide, 5-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid methyl ester, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid methyl ester and 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid.

45. A compound of claim 1 selected from the group consisting of (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (6-carbamoyl-naphthalen-2-yl)-amide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-chloro-phenyl)-amide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-trifluoromethyl-phenyl)-amide, 5-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-pyridine-2-carboxylic acid, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-fluoro-benzoic acid methyl ester, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid methyl ester, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-fluoro-phenyl)-amide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-methoxy-phenyl)-amide, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2,5-difluoro-benzoic acid methyl ester, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2,5-difluoro-benzoic acid and (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (3,5-difluoro-4-iodo-phenyl)-amide.

46. A compound of claim 1 selected from the group consisting of

4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2,6-difluoro-benzoic acid, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-hydroxy-benzoic acid, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-methoxy-phenyl)-amide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-trifluoromethoxy-phenyl)-amide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-fluoro-phenyl)-amide, (2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-2-chloro-phenyl)-amide, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2-fluoro-5-methoxy-benzoic acid methyl ester, 4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-2-fluoro-5-methoxy-benzoic acid, 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-4-methyl-pentanoic acid, chiral 2-(4-{[(2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid methyl ester, chiral 2-(4-{[(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carbonyl]-amino}-phenyl)-2-methyl-propionic acid, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-methyl-1-methylcarbamoyl-ethyl)-phenyl]-amide, chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid {4-[1-(3-hydroxy-propylcarbamoyl)-1-methyl-ethyl]-phenyl}amide and chiral (2S,3R,4S,5R)-3-(3-chloro-2-fluoro-phenyl)-4-(4-chloro-2-fluoro-phenyl)-4-cyano-5-(2,2-dimethyl-propyl)-pyrrolidine-2-carboxylic acid [4-(1-carbamoyl-1-methyl-ethyl)-phenyl]-amide.

47. A pharmaceutical formulation comprising a compound of the formula

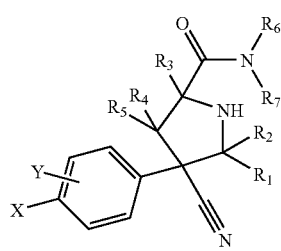

wherein

X is selected from the group consisting of H, F, Cl, Br, I, cyano, nitro, ethynyl, cyclopropyl, methyl, ethyl, isopropyl, vinyl and methoxy Y is one to four group(s) independently selected from the group consisting of H, F, Cl, Br, I, CN, OH, nitro, lower alkyl, cycloalkyl, lower alkoxy, lower alkenyl, cycloalkenyl, lower alkynyl, aryl, hetereoaryl, hetereocycle, COOR', OCOR', CONR'R", NR'COR", NR"SO$_2$R', SO$_2$NR'R" and NR'R" wherein R' and R" is independently selected from H or substituted or unsubstituted lower alkyl, substituted or unsubstituted lower cycloalkyl, substituted or unsubstituted lower alkenyl, substituted or unsubstituted lower cycloalkenyl, substituted or unsubstituted aryl, substituted or unsubstituted hetereoaryl or substituted or unsubstituted hetereocycle, and in the case of R' and R" may independently link to form a cyclic structure selected from substituted or unsubstituted cycloalkyl, substituted or unsubstituted cycloalkenyl, substituted or unsubstituted heteroaryl or substituted or unsubstituted heterocycle, one of R$_1$ and R$_2$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen or lower alkyl, R$_3$ is H or lower alkyl, one of R$_4$ and R$_5$ is selected from the group consisting of lower alkyl, substituted lower alkyl, lower alkenyl, substituted lower alkenyl, aryl, substituted aryl, heteroaryl, substituted heteroaryl, heterocycle, substituted heterocycle, cycloalkyl, substituted cycloalkyl, cycloalkenyl, and substituted cycloalkenyl and the other is hydrogen, R$_6$ and R$_7$ are selected from the group consisting of $(CH_2)_n$—R', $(CH_2)_n$—NR'R", $(CH_2)_n$—NR'COR", $(CH_2)_n$—NR'SO$_2$R", $(CH_2)_n$—COOH, $(CH_2)_n$—COOR', $(CH_2)_n$—CONR'R", $(CH_2)_n$—OR', $(CH_2)_n$—SR', $(CH_2)_n$—SOR', $(CH_2)_n$—SO$_2$R', $(CH_2)_n$—COR', $(CH_2)_n$—SO$_3$H, $(CH_2)_n$—SONR'R", $(CH_2)_n$—SO$_2$NR'R", $(CH_2CH_2O)_m$—$(CH_2)_n$—R', $(CH_2CH_2O)_m$—$(CH_2)_n$—OH, $(CH_2CH_2O)_m$—$(CH_2)_n$—OR', $(CH_2CH_2O)_m$—$(CH_2)_n$—NR'R", $(CH_2CH_2O)_m$—$(CH_2)_n$—NR'COR", $(CH_2CH_2O)_m$—$(CH_2)_n$—NR'SO$_2$R", $(CH_2CH_2O)_m$—$(CH_2)_n$—COOH, $(CH_2CH_2O)_m$—$(CH_2)_n$—COOR', $(CH_2CH_2O)_m$—$(CH_2)_n$—CONR'R", $(CH_2CH_2O)_m$—$(CH_2)_n$—SO$_2$R', $(CH_2CH_2O)_m$—$(CH_2)_n$—COR', $(CH_2CH_2O)_m$—$(CH_2)_n$—SONR'R", $(CH_2CH_2O)_m$—$(CH_2)_n$—SO$_2$NR'R", $(CH_2)_p$—$(CH_2CH_2O)_m$—$(CH_2)_n$—R', $(CH_2)_p$—$(CH_2CH_2O)_m$—$(CH_2)_n$—OH, $(CH_2)_p$—$(CH_2CH_2O)_m$—$(CH_2)_n$—OR', $(CH_2)_p$—$(CH_2CH_2O)_m$—$(CH_2)_n$—NR'R", $(CH_2)_p$—$(CH_2CH_2O)_m$—$(CH_2)_n$—NR'COR", $(CH_2)_p$—$(CH_2CH_2O)_m$—$(CH_2)_n$—NR'SO$_2$R", $(CH_2)_p$—$(CH_2CH_2O)_m$—$(CH_2)_n$—COOH, $(CH_2)_p$—$(CH_2CH_2O)_m$—$(CH_2)_n$—COOR', $(CH_2)_p$—$(CH_2CH_2O)_m$—$(CH_2)_n$—CONR'R", $(CH_2)_p$—$(CH_2CH_2O)_m$—$(CH_2)_n$—SO$_2$R', $(CH_2)_p$—$(CH_2CH_2O)_m$—$(CH_2)_n$—COR', $(CH_2)_p$—$(CH_2CH_2O)_m$—$(CH_2)_n$—SONR'R", $(CH_2)_p$—$(CH_2CH_2O)_m$—$(CH_2)_n$—SO$_2$NR'R", —COR', —SOR' and SO$_2$R' wherein R' and R" are the same definitions as above, m, n and p are independently 0 to –6 and the pharmaceutically acceptable salts and esters thereof together with a pharmaceutically acceptable excipient or carrier.

48. A compound of the formula:
4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-methoxy-benzoic acid.

49. A compound of the formula:
(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carboxylic acid (4-carbamoyl-3-chloro-phenyl)-amide.

50. A compound of the formula:
4-{[(2R,3S,4R,5S)-4-(4-chloro-2-fluoro-phenyl)-3-(3-chloro-2-fluoro-phenyl)-4-cyano-5-(2,2-dimethyl-propyl)-pyrrolidine-2-carbonyl]-amino}-3-chloro-benzoic acid methyl ester.

51. A compound of the formula:
rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid ((R)-3,4-dihydroxy-butyl)-amide.

52. A compound of the formula:
rac-(2R,3S,4R,5S)-3-(3-chloro-2-fluoro-phenyl)-4-(4-chloro-2-fluoro-phenyl)-4-cyano-5-(2,2-dimethyl-propyl)-pyrrolidine-2-carboxylic acid (1-carbamoyl methyl-1H-pyrazol-3-yl)-amide.

* * * * *